(12) United States Patent
Whitten et al.

(10) Patent No.: US 7,612,063 B2
(45) Date of Patent: Nov. 3, 2009

(54) SUBSTITUTED QUINOBENZOXAZINE ANALOGS

(75) Inventors: Jeffrey P. Whitten, Santee, CA (US); Michael Schwaebe, San Diego, CA (US); Adam Siddiqui-Jain, San Diego, CA (US); Terence Moran, San Diego, CA (US)

(73) Assignee: Cylene Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 12/013,961

(22) Filed: Jan. 14, 2008

(65) Prior Publication Data

US 2008/0261963 A1 Oct. 23, 2008

Related U.S. Application Data

(62) Division of application No. 11/390,810, filed on Mar. 28, 2006, now Pat. No. 7,326,702, which is a division of application No. 10/821,243, filed on Apr. 7, 2004, now Pat. No. 7,141,565.

(60) Provisional application No. 60/461,271, filed on Apr. 7, 2003, provisional application No. 60/463,171, filed on Apr. 15, 2003, provisional application No. 60/519,535, filed on Nov. 12, 2003, provisional application No. 60/532,727, filed on Dec. 23, 2003.

(51) Int. Cl.
*A61K 31/5365* (2006.01)
(52) U.S. Cl. .................. 514/229.5; 544/61; 544/73; 544/99
(58) Field of Classification Search ............... 514/229.5
See application file for complete search history.

(56) References Cited

U.S. PATENT DOCUMENTS

| | | | |
|---|---|---|---|
| 4,533,663 A | 8/1985 | Chu | |
| 4,559,157 A | 12/1985 | Smith et al. | |
| 4,607,032 A | 8/1986 | Chu et al. | |
| 4,608,392 A | 8/1986 | Jacquet et al. | |
| 4,725,595 A | 2/1988 | Schriewer et al. | |
| 4,820,508 A | 4/1989 | Wortzman | |
| 4,938,949 A | 7/1990 | Borch et al. | |
| 4,992,478 A | 2/1991 | Geria | |
| 5,225,418 A | 7/1993 | Miller | |
| 5,318,965 A | 6/1994 | Chu | |
| 5,624,924 A | 4/1997 | Chu et al. | |
| 5,703,055 A | 12/1997 | Felgner | |
| 6,214,560 B1 | 4/2001 | Yguerabide et al. | |
| 6,528,517 B1 | 3/2003 | Hurley et al. | |
| 6,645,981 B2 | 11/2003 | Ledoussal et al. | |
| 6,750,224 B1 | 6/2004 | Patel et al. | |
| 6,900,224 B2 | 5/2005 | Ledoussal et al. | |
| 7,141,565 B1 | 11/2006 | Whitten et al. | |
| 7,354,916 B2 * | 4/2008 | Whitten et al. ............ | 514/229.5 |
| 7,381,720 B2 * | 6/2008 | Whitten et al. ............ | 514/229.5 |
| 2002/0049223 A1 | 4/2002 | Elmore et al. | |
| 2003/0232818 A1 | 12/2003 | Anderson et al. | |
| 2004/0029882 A1 | 2/2004 | Ledoussal et al. | |
| 2004/0072817 A1 | 4/2004 | Anderson et al. | |
| 2005/0159423 A1 | 7/2005 | Anderson et al. | |

FOREIGN PATENT DOCUMENTS

| | | |
|---|---|---|
| EP | 0 160 284 | 11/1985 |
| EP | 0 162 333 | 11/1985 |
| EP | 0 229 635 | 7/1987 |
| JP | 02040379 | 2/1990 |
| WO | WO-92/03136 | 3/1992 |
| WO | WO-99/40093 | 8/1999 |
| WO | WO-2004/014893 | 2/2004 |
| WO | WO-2004/091504 | 10/2004 |
| WO | WO-2004/091627 | 10/2004 |

OTHER PUBLICATIONS

Anantha et al., Biochemistry (1998) 37:2709-2714.
Ansell et al., Current Opinion in Biotechnology (1996) 7:89-94.
Banker et al., "Modern Pharmaceutics, 3$^{rd}$ ed." Marcel Dekker, New York (1996) pp. 451-596.
Berge et al., J. Pharm. Sci. (1977) 66:1-19.
Cecil Textbook of Medicine (20$^{th}$ Edition, vol. 2, 1996, pp. 1739-1747).
Datta et al., JACS (2001) 123:9612-9619.
Dermer, Bio/Technology (1994) 12:320.
Freshney, "Culture of Animal Cells, A Manual of Basic Technique" Alan R. Liss, Inc., (1983) New York, p. 4.
Gibson et al., Genome Res. (1996) 6:995-1001.
Han et al., Nucl. Acids Res. (1999) 27:537-542.
Han et al., Trends Pharm. Sci. (2000) 21:136-142.
He et al., Science (1998) 281:1509-1512.
Heid et al., Genome Res. (1996) 6:986-994.

(Continued)

*Primary Examiner*—Kahsay T Habte
(74) *Attorney, Agent, or Firm*—Morrison & Foerster LLP

(57) ABSTRACT

The present invention relates to quinobenzoxazines analogs having the general formula:

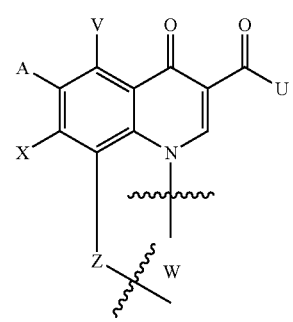

(1)

and pharmaceutically acceptable salts, esters and prodrugs thereof;
wherein A, U, V, W, X and Z are substituents.

The present invention also relates to methods for using such compounds.

28 Claims, 2 Drawing Sheets

OTHER PUBLICATIONS

Henegariu et al., Nature Biotech (2000) 18:345-348.
Jin and Pike, Mol. Endocrinol. (1996) 10:196-205.
Kim et al., J. of Medicinal Chemistry (2003) 46(4):571-583.
Kriz et al., Analytical Chemistry (1995) 67:2142-2144.
Qu and Chaires, Methods Enzymol (2000) 321:353-369.
Shea, Trends in Polymer Science (1994) 2:166-173.
Tomita et al., J. Med. Chem. (2002) 45:5564-5575.
Vaickus, Crit. Rev. in Oncol./Hemotol. (1991) 11:267-297.
Vlatakis et al., Nature (1993) 361:645-647.
Wang et al., Methods Cell Sci (1996) 18:249-255.
Weitzmann et al., J. Biol. Chem (1996) 271:20958-20964.
Wolff, "Burger's Medicinal Chemistry, $5^{th}$ ed., Part 1" John Wiley & Sons, 1995, pp. 975-977.
Zeng et al., J. Med. Chem. (1998) 41:4273-4278.
International Search Report for PCT/US2005/026977, mailed on Jul. 3, 2006, 5 pages.
Supplementary Partial European Search Report for EP 04759406.4, mailed on Nov. 14, 2006, 5 pages.
Supplementary European Search Report for EP 04 75 9406, mailed on Mar. 19, 2007, 5 pages.

* cited by examiner

SEQUENCE LISTING

<160> NUMBER OF SEQ ID NOS: 20

<210> SEQ ID NO 1
<211> LENGTH: 27
<212> TYPE: DNA
<213> ORGANISM: Homo sapiens

<400> SEQUENCE: 1
tggggagggt ggggagggtg gggaagg                                    27

<210> SEQ ID NO 2
<211> LENGTH: 37
<212> TYPE: DNA
<213> ORGANISM: Homo sapiens

<400> SEQUENCE: 2
gggggggggg gggcgggggc ggggcgggg gaggggc                          37

<210> SEQ ID NO 3
<211> LENGTH: 57
<212> TYPE: DNA
<213> ORGANISM: Homo sapiens

<400> SEQUENCE: 3 gggggggac gcgggagctg ggggagggct tggggccagg gcggggcgct taggggg    57

<210> SEQ ID NO 4
<211> LENGTH: 28
<212> TYPE: DNA
<213> ORGANISM: Homo sapiens

<400> SEQUENCE: 4
aggaagggga gggccggggg gaggtggc                                   28

<210> SEQ ID NO 5
<211> LENGTH: 22
<212> TYPE: DNA
<213> ORGANISM: Homo sapiens

<400> SEQUENCE: 5
aggggcgggg cggggcgggg gc                                         22

<210> SEQ ID NO 6
<211> LENGTH: 25
<212> TYPE: DNA
<213> ORGANISM: Homo sapiens

<400> SEQUENCE: 6
gggaggaagg gggcgggagc ggggc                                      25

<210> SEQ ID NO 7
<211> LENGTH: 32
<212> TYPE: DNA
<213> ORGANISM: Homo sapiens

<400> SEQUENCE: 7 gggggcggg ggcgggcgca gggggagggg gc                               32

<210> SEQ ID NO 8
<211> LENGTH: 23
<212> TYPE: DNA

```
<400> SEQUENCE: 8
cggggcgggg cggggcggg ggc                                              23

<210> SEQ ID NO 9
<211> LENGTH: 46
<212> TYPE: DNA
<213> ORGANISM: Homo sapiens

<400> SEQUENCE: 9
agaggaggag gaggtcacgg aggaggagga gaaggaggag gaggaa                    46

<210> SEQ ID NO 10
<211> LENGTH: 12
<212> TYPE: DNA
<213> ORGANISM: Homo sapiens

<400> SEQUENCE: 10
ggaggaggag ga                                                         12

<210> SEQ ID NO 11
<211> LENGTH: 38
<212> TYPE: DNA
<213> ORGANISM: Homo sapiens

<400> SEQUENCE: 11
agagaagagg ggaggaggag gaggagagga ggaggcgc                             38

<210> SEQ ID NO 12
<211> LENGTH: 13
<212> TYPE: DNA
<213> ORGANISM: Homo sapiens

<400> SEQUENCE: 12 ggaggggag ggg                                                         13

<210> SEQ ID NO 13
<211> LENGTH: 27
<212> TYPE: DNA
<213> ORGANISM: Homo sapiens

<400> SEQUENCE: 13
aggagaagga ggaggtggag gaggagg                                         27

<210> SEQ ID NO 14
<211> LENGTH: 33
<212> TYPE: DNA
<213> ORGANISM: Homo sapiens

<400> SEQUENCE: 14
aggaggagga gaatgcgagg aggagggagg aga                                  33

<210> SEQ ID NO 15
<211> LENGTH: 36
<212> TYPE: DNA
<213> ORGANISM: Homo sapiens

<400> SEQUENCE: 15
ggggcgggcc gggggcgggg tcccggcggg gcggag                               36

<210> SEQ ID NO 16
<211> LENGTH: 27
<212> TYPE: DNA
```

```
<213> ORGANISM: Homo sapiens

<400> SEQUENCE: 16
cgggaggagg aggaaggagg aagcgcg                                27

<210> SEQ ID NO 17
<211> LENGTH: 15
<212> TYPE: DNA
<213> ORGANISM: Homo sapiens

<400> SEQUENCE: 17
tccaactatg tatac                                             15

<210> SEQ ID NO 18
<211> LENGTH: 35
<212> TYPE: DNA
<213> ORGANISM: Homo sapiens

<400> SEQUENCE: 18
ttagcgacac gcaattgcta tagtgagtcg tatta                       35

<210> SEQ ID NO 19
<211> LENGTH: 45
<212> TYPE: DNA
<213> ORGANISM: Artificial Sequence
<220> FEATURE:
<223> OTHER INFORMATION: Primer

<400> SEQUENCE: 19
agtctgactg actgtacgta gctaatacga ctcactatag caatt            45

<210> SEQ ID NO 20
<211> LENGTH: 99
<212> TYPE: DNA
<213> ORGANISM: Homo sapiens

<400> SEQUENCE: 20
tccaactatg tatactgggg agggtgggga gggtgggggaa ggttagcgac acgcaattgc    60
tatagtgagt cgtattagct acgtacagtc agtcagact                           99
```

SUBSTITUTED QUINOBENZOXAZINE ANALOGS

CROSS-REFERENCE TO RELATED APPLICATIONS

This application is a divisional of U.S. patent application Ser. No. 11/390,810, filed Mar. 28, 2006, which is a divisional of U.S. patent application Ser. No. 10/821,243, filed Apr. 7, 2004, which claims the benefit of U.S. provisional application 60/461,271, filed Apr. 7, 2003; U.S. provisional application 60/463,171, filed Apr. 15, 2003; U.S. provisional application 60/519,535, filed Nov. 12, 2003; and U.S. provisional application 60/532,727, filed Dec. 23, 2003. The contents of these documents are incorporated herein by reference in their entirety.

Reference to Sequence Listing Submitted Via EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
|---|---|---|
| 532232001114Seqlist.txt | May 1, 2008 | 3,380 bytes |

FIELD OF THE INVENTION

The invention relates to substituted quinobenzoxazines analogs, and methods of using such compounds.

BACKGROUND

Quadruplexes can form in certain purine-rich strands of nucleic acids. In duplex nucleic acids, certain purine rich strands are capable of engaging in a slow equilibrium between a typical duplex helix structure and in unwound and non-B-form regions. These unwound and non-B forms can be referred to as "paranemic structures." Some forms are associated with sensitivity to S1 nuclease digestion, which can be referred to as "nuclease hypersensitivity elements" or "NHEs." A quadruplex is one type of paranemic structure and certain NHEs can adopt a quadruplex structure. Considerable circumstantial evidence suggests that quadruplex structures can exist in vivo in specific regions of the genome, including the telomeric ends of chromosomes and oncogene regulatory regions. (Han, et al., *Trends Pharm. Sci.* (2000) 21:136-142). Thus, quadruplex forming regions of DNA may be used as molecular targets for anticancer agents.

SUMMARY OF THE INVENTION

Compounds described herein interact with regions of DNA that can form quadruplexes and act as tumor suppression agents with reduced side effects. Such compounds reduce expression of highly proliferate genes and are utilized for treating cancers. Furthermore, the compounds may also exhibit antibacterial or antiviral activity, and may be used for treating bacterial and viral infections.

Various embodiments of the present invention are described below. The present invention encompasses other compounds having formula 1, with substituents independently selected from compounds in Tables 1-3. Thus, the present invention is not limited to the specific combination of substituents described in various embodiments below.

The compounds have the general formula:

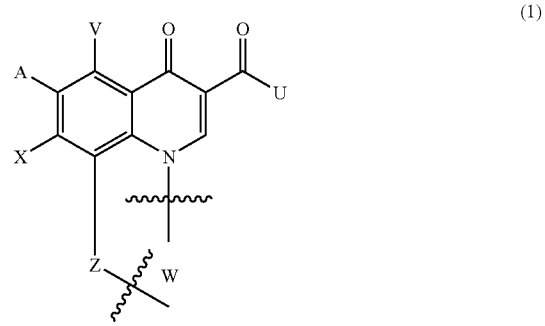

and pharmaceutically acceptable salts, esters and prodrugs thereof;

wherein V is H, halo, or $NR^1R^2$;

A is H, fluoro, or $NR^1{}_2$;

Z is O, S, $NR^1$ or $CH_2$;

U is $OR^2$ or $NR^1R^2$;

X is $OR^2$, $NR^1R^2$, halo, azido, or $SR^2$;

n is 1-3;

wherein in $NR^1R^2$, $R^1$ and $R^2$ may form a double bound or a ring, each of which is optionally substituted;

$R^1$ is H or a $C_{1-6}$ alkyl;

$R^2$ is H or a $C_{1-10}$ alkyl or $C_{2-10}$ alkenyl optionally containing one or more non-adjacent heteroatoms selected from N, O, and S, and optionally substituted with a carbocyclic or heterocyclic ring; or $R^2$ is an optionally substituted heterocyclic ring, aryl or heteroaryl;

W is selected from the group consisting of

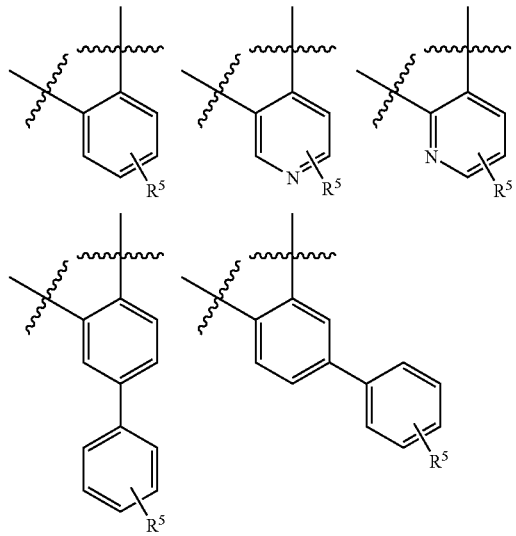

-continued
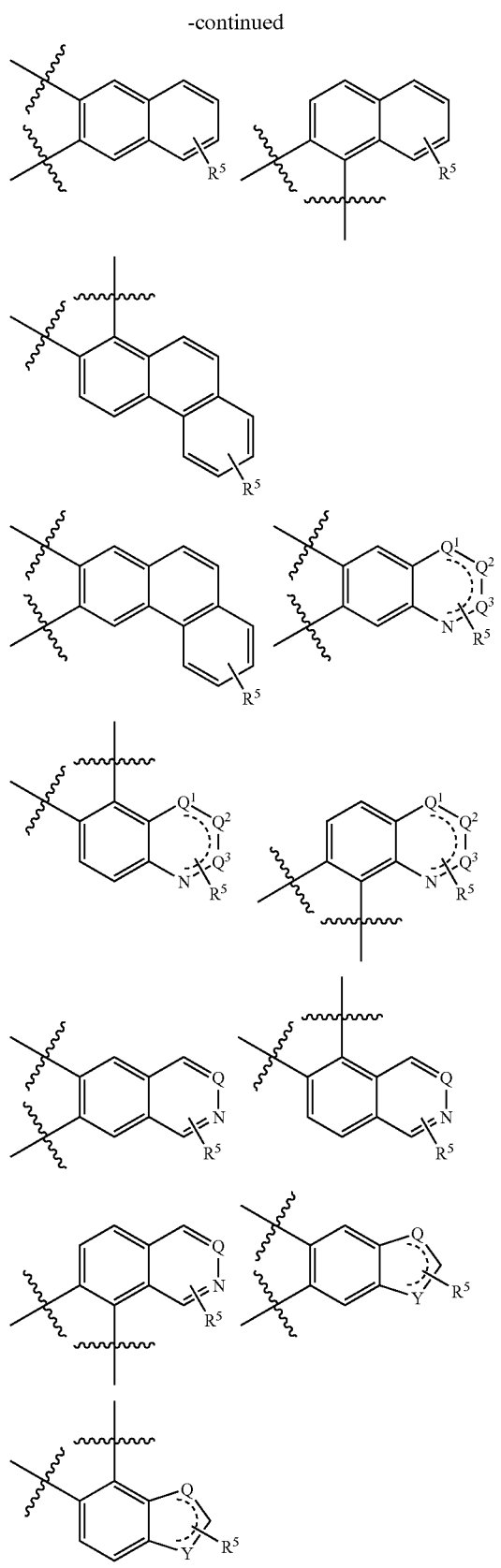
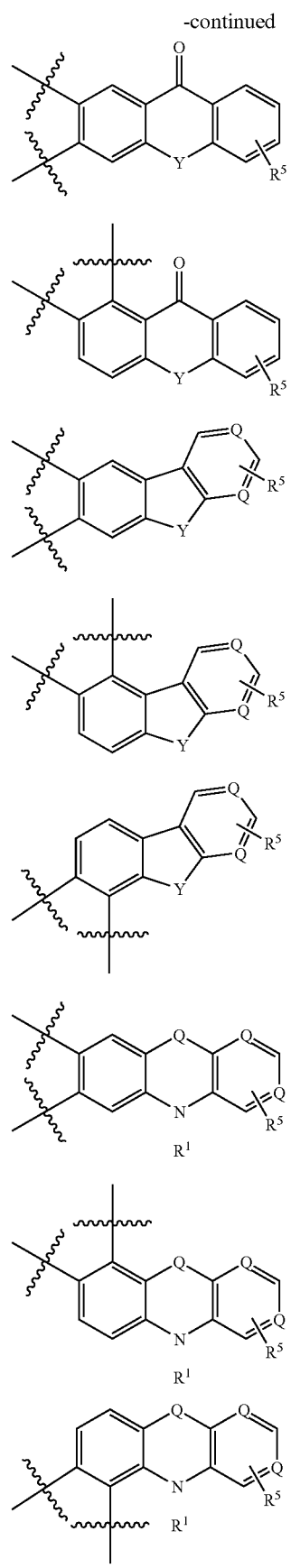

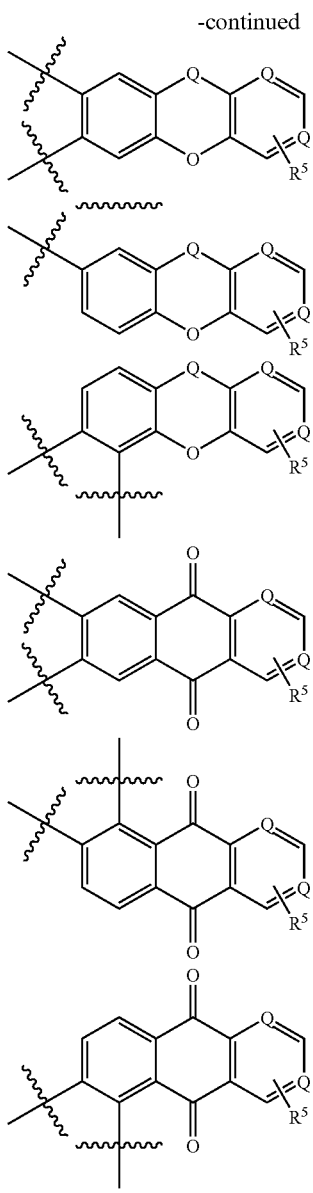

wherein Q, Q¹, Q², and Q³ are independently CH or N;

Y is independently O, CH, =O or NR¹;

and R⁵ is a substituent at any position on the fused ring; and is H, OR², C$_{1-6}$ alkyl, C$_{2-6}$ alkenyl, each optionally substituted by halo, =O or one or more heteroatoms; or R⁵ is an inorganic substituent; or two adjacent R⁵ is linked to obtain a 5-6 membered substituted or unsubstituted carbocyclic or heterocyclic ring, optionally fused to an additional substituted or unsubstituted carbocyclic or heterocyclic ring;

provided that U is not OR¹ when X is pyrrolidinyl; A is F; Z is O; and W is naphthalenyl or phenylene;

U is not morpholinyl or 2,4-difluoroaniline when X is F or pyrrolidinyl; A is F; Z is O; and W is phenylene; and further provided that if U is OH, then W represents multiple fused aromatic rings and X is not halo; and X is NH₂, or a moiety that does not contain N, or contains more than 6 carbons.

In the above formula 1, A and X may independently be halo. In one example, A and X may independently be fluoro.

In the above formula, V may be H. Alternatively, V may be NH₂ or a compound having the formula NR¹—(CR¹₂)$_n$—NR³R⁴;

wherein R¹ and R³ are independently H or C$_{1-6}$ alkyl;

n is 1-6; and

R⁴ is H, C$_{1-6}$ alkyl optionally substituted with a carbocyclic or heterocyclic ring, or aryl; and wherein in NR³R⁴, R³ and R⁴ may form an optionally substituted ring.

In the above formula 1, U and X may independently be NR¹R². In one example, R¹ is H and R² is a C$_{1-10}$ alkyl optionally containing one or more heteroatoms, and optionally substituted with a C$_{3-6}$ cycloalkyl, aryl or a 5-14 membered heterocyclic ring containing one or more N, O or S. In another example, R¹ is H and R² is an aryl or a 5-14 membered heterocyclic ring containing one or more N, O or S, each optionally substituted with an amino or another heterocyclic ring. In yet another example, R¹ and R² in NR¹R² form an optionally substituted 5-14 membered ring containing one or more N, O or S. In particular examples, NR¹R² is morpholine, thiomorpholine, piperazine, piperidine or diazepine.

In the above formula 1, U and X may independently have the formula

wherein R¹ and R³ are independently H or C$_{1-6}$ alkyl;

n is 1-6; and

R⁴ is H or a C$_{1-10}$ alkyl or C$_{2-10}$ alkenyl optionally containing one or more non-adjacent heteroatoms selected from N, O and S, and optionally substituted with a carbocyclic or heterocyclic ring; and wherein in NR³R⁴, R³ and R⁴ may form an optionally substituted ring.

In the above formula 2, n may be 2-3. In one example, NR³R⁴ is an acyclic amine, or guanidinyl or a tautomer thereof; or R³ and R⁴ optionally form a substituted ring containing one or more N, O or S. In particular examples, NR³R⁴ is morpholine, thiomorpholine, imidazole, pyrrolidine, piperazine, pyridine or piperidine.

In the above formula 1, X may be NR¹R²; and U has the formula

wherein R¹ and R² are as defined in claim 1;

R³ is H or C$_{1-6}$ alkyl;

n is 1-6; and

R⁴ is H or a Cl$_{1-10}$ alkyl or C$_{2-10}$ alkenyl optionally containing one or more non-adjacent heteroatoms selected from N, O and S, and optionally substituted with a carbocyclic or heterocyclic ring; and wherein in NR¹R² and NR³R⁴, R¹ and R², and R³ and R⁴ each independently may form a substituted ring.

In the above formula, where X is NR¹R² and U has the formula NR¹—(CR¹₂)$_n$—NR³R⁴ (2), R¹ and R² in NR¹R², and R³ and R⁴ in NR³R⁴ each may independently form a substituted ring containing one or more N, O or S. For example, X is optionally substituted with amino, carbamate, a C$_{1-10}$ alkyl containing one or more non-adjacent N, O or S, and optionally substituted with a heterocyclic ring; aryl or a saturated or unsaturated heterocyclic ring, each of which is optionally substituted. In one example, X and NR³R⁴ are independently morpholine, thiomorpholine, imidazole, pyrrolidine, piperazine, pyridine or piperidine. In one example, X and NR³R⁴ are independently pyrrolidine. In another example, X is pyrrolidine substituted with pyrazine. In this example, V is H; A is fluoro; and W is naphthalenyl.

Examples of 5-6 membered heterocyclic rings include but are not limited to tetrahydrofuran, 1,3-dioxolane, 2,3-dihydrofuran, tetrahydropyran, benzofuran, isobenzofuran, 1,3-dihydro-isobenzofuran, isoxazole, 4,5-dihydroisoxazole, piperidine, pyrrolidine, pyrrolidin-2-one, pyrrole, pyridine, pyrimidine, octahydro-pyrrolo[3,4-b]pyridine, piperazine, pyrazine, morpholine, thiomorpholine, imidazole, imidazolidine-2,4-dione, benzimidazole, 1,3-dihydrobenzimidazol-2-one, indole, thiazole, benzothiazole, thiadiazole, thiophene, tetrahydro-thiophene 1,1-dioxide, diazepine, triazole, guanidine, diazabicyclo[2.2.1]heptane, 2,5-diazabicyclo[2.2.1]heptane, and 2,3,4,4a,9,9a-hexahydro-1H-β-carboline.

In the above formula 1, W may be benzene, pyridine, biphenyl, naphthalene, phenanthrene, quinoline, isoquinoline, quinazoline, cinnoline, phthalazine, quinoxaline, indole, benzimidazole, benzoxazole, benzthiazole, benzofuran, anthrone, xanthone, acridone, fluorenone, carbazolyl, pyrimido[4,3-b]furan, pyrido[4,3-b]indole, pyrido[2,3-b]indole, dibenzofuran, acridine or acridizine.

In the above formula 1, U may be $OR^2$ and $R^2$ is a $C_{1-6}$ alkyl optionally substituted with a carbocyclic or heterocyclic ring.

In the above formula 1, each optionally substituted moiety is substituted with one or more halo, $OR^2$, $NR^1R^2$, carbamate, $C_{1-10}$ alkyl, $C_{2-10}$ alkenyl, each optionally substituted by halo, =O, aryl or one or more heteroatoms; inorganic substituents, aryl, carbocyclic or a heterocyclic ring.

The compounds of the present invention may be chiral. As used herein, a chiral compound is a compound that is different from its mirror image, and has an enantiomer. Methods of synthesizing chiral compounds and resolving a racemic mixture of enantiomers are well known to those skilled in the art. See, e.g., March, "*Advanced Organic Chemistry*," John Wiley and Sons, Inc., New York, (1985), which is incorporated herein by reference.

The present invention also provides pharmaceutical compositions comprising compounds having formula 1, and a pharmaceutically acceptable excipient.

Furthermore, the present invention provides methods for ameliorating a cell proliferative disorder, comprising administering to a subject in need thereof an effective amount of a compound having formula 1 or a pharmaceutical composition thereof, thereby ameliorating said cell-proliferative disorder. In one example, the cell proliferative disorder is cancer. In another example, cell proliferation is reduced, or cell death is induced. The subject may be human or animal.

The present invention also provides methods for reducing cell proliferation or inducing cell death, comprising contacting a system with an effective amount of a compound having formula 1 or a pharmaceutical composition thereof, thereby reducing cell proliferation or inducing cell death in said system. The system may be a cell or tissue.

The present invention further provides methods for reducing microbial titers, comprising contacting a system with an effective amount of a compound having formula 1 or a pharmaceutical composition thereof, thereby reducing microbial titers. The system may be a cell or tissue. In one example, the microbial titers are viral, bacterial or fungal titers.

Further, the present invention provides methods for ameliorating a microbial infection, comprising administering to a subject in need thereof an effective amount of a compound having formula 1 or a pharmaceutical composition thereof, thereby ameliorating said microbial infection. The subject may be human or animal. In one example, the microbial infection is viral, bacterial or fungal.

DESCRIPTION OF THE INVENTION

Figure 1:
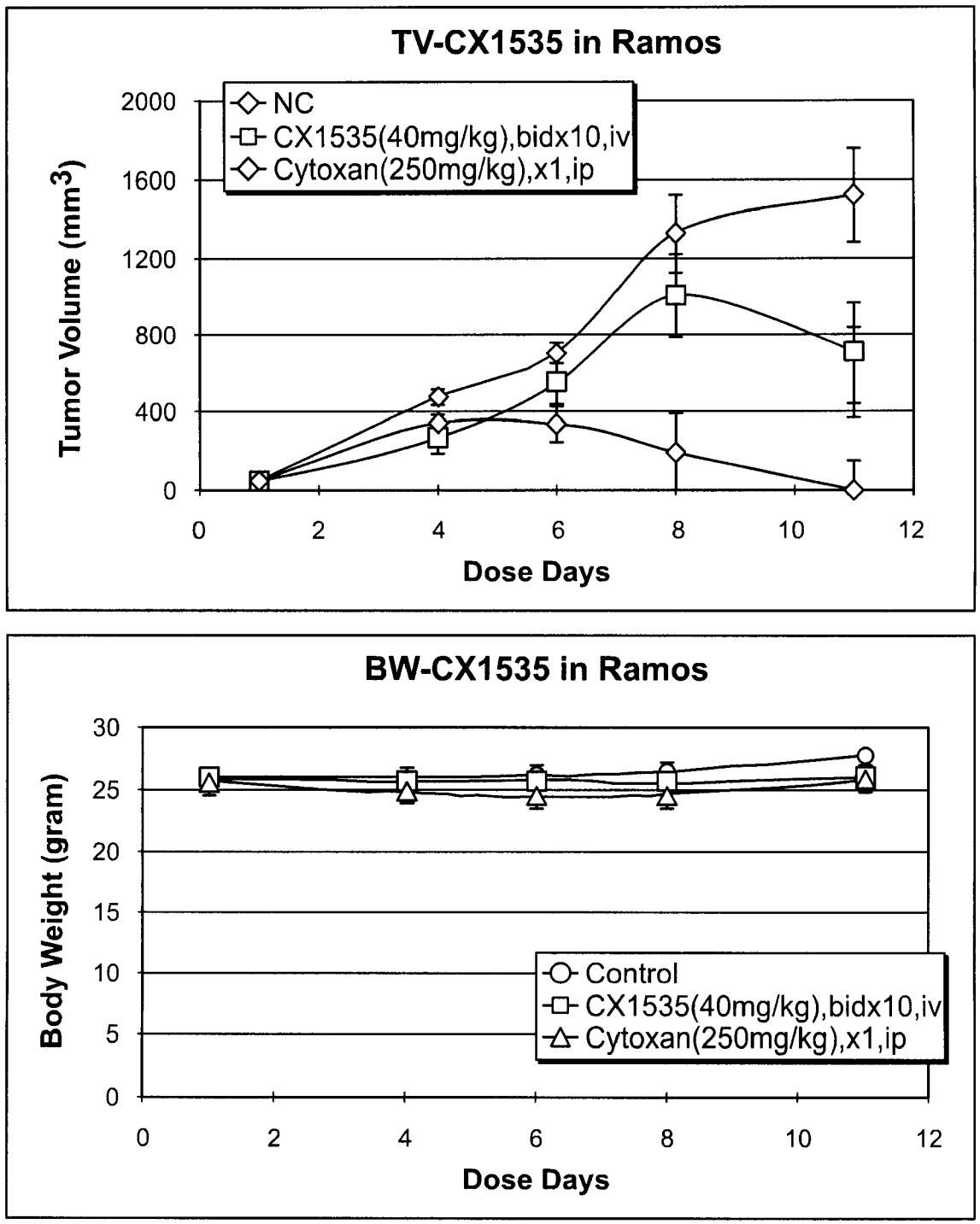
FIG. 1 shows antitumor activity of a compound having formula 1 tested in a Ramos xenograft model.

The present invention relates to quinoline derivatives having formula 1, and pharmaceutically acceptable salts, esters, and prodrugs thereof. In particular embodiments, the compounds interact with regions of DNA that can form quadruplexes. The present invention also relates to methods for treating cancer, bacterial and viral infections using such compounds.

Because regions of DNA that can form quadruplexes are regulators of biological processes such as oncogene transcription, modulators of quadruplex biological activity can be utilized as cancer therapeutics. Molecules that interact with regions of DNA that can form quadruplexes can exert a therapeutic effect on certain cell proliferative disorders and related conditions. Particularly, abnormally increased oncogene expression can cause cell proliferative disorders and quadruplex structures typically down-regulate oncogene expression. Examples of oncogenes include but are not limited to MYC, HIF, VEGF, ABL, TGF, PDGFA, MYB, SPARC, HUMTEL, HER, VAV, RET, H-RAS, EGF, SRC, BCL1, BCL2, and other oncogenes known to one of skill in the art.

Molecules that bind to regions of DNA that can form quadruplexes can exert a biological effect according to different mechanisms, which include for example, stabilizing a native quadruplex structure, inhibiting conversion of a native quadruplex to duplex DNA by blocking strand cleavage, and stabilizing a native quadruplex structure having a quadruplex-destabilizing nucleotide substitution and other sequence specific interactions. Thus, compounds that bind to regions of DNA that can form quadruplexes described herein may be administered to cells, tissues, or organisms for the purpose of down-regulating oncogene transcription and thereby treating cell proliferative disorders. The terms "treatment" and "therapeutic effect" as used herein refer to reducing or stopping a cell proliferation rate (e.g., slowing or halting tumor growth) or reducing the number of proliferating cancer cells (e.g., removing part or all of a tumor).

Determining whether the biological activity of native DNA that can form quadruplexes is modulated in a cell, tissue, or organism can be accomplished by monitoring quadruplex biological activity. Quadruplex forming regions of DNA biological activity may be monitored in cells, tissues, or organisms, for example, by detecting a decrease or increase of gene transcription in response to contacting the quadruplex forming DNA with a molecule. Transcription can be detected by directly observing RNA transcripts or observing polypeptides translated by transcripts, which are methods well known in the art.

Molecules that interact with quadruplex forming DNA and quadruplex forming nucleic acids can be utilized to treat many cell proliferative disorders. Cell proliferative disorders include, for example, colorectal cancers and hematopoietic neoplastic disorders (i.e., diseases involving hyperplastic/neoplastic cells of hematopoietic origin such as those arising from myeloid, lymphoid or erythroid lineages, or precursor cells thereof). The diseases can arise from poorly differentiated acute leukemias, e.g., erythroblastic leukemia and acute megakaryoblastic leukemia. Additional myeloid disorders include, but are not limited to, acute promyeloid leukemia (APML), acute myelogenous leukemia (AML) and chronic myelogenous leukemia (CML) (Vaickus, Crit. Rev. in Oncol./Hemotol. 11:267-297 (1991)). Lymphoid malignancies include, but are not limited to acute lymphoblastic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease. Cell proliferative disorders also include cancers of the colorectum, breast, lung, liver, pancreas, lymph node, colon, prostate, brain, head and neck, skin, liver, kidney, and heart. Compounds that interact with regions of DNA that can form quadruplexes also can be utilized to target cancer related processes and conditions, such as increased angiogenesis, by inhibiting angiogenesis in a subject.

The present invention provides a method for reducing cell proliferation or for treating or alleviating cell proliferative disorders, comprising contacting a system having a DNA capable of forming a quadruplex with a compound having formula 1. The system may be a group of cells or one or more tissues. In one embodiment, the system is a subject in need of a treatment of a cell proliferative disorder (e.g., a mammal such as a mouse, rat, monkey, or human). The present invention also provides a method for treating colorectal cancer by administering a compound that interacts with a c-MYC quadruplex forming region to a subject in need thereof, thereby reducing the colorectal cancer cell proliferation. Furthermore, the present invention provides a method for inhibiting angiogenesis and optionally treating a cancer associated with angiogenesis, comprising administering a compound that interacts with a vascular endothelial growth factor (VEGF) quadruplex forming region to a subject in need thereof, thereby reducing angiogenesis and optionally treating a cancer associated with angiogenesis.

As used herein, the term "alkyl" refers to a carbon-containing compound, and encompasses compounds containing one or more heteroatoms. The term "alkyl" also encompasses compounds substituted with one or more non-interfering substituents. Examples of non-interfering substituents include but are not limited to $OR^1$, amino, amido, halo, =O, aryl, heterocyclic groups, or inorganic substituents, and other substituents that do not interfere with the activity of the compound.

As used herein, the term "carbocycle" refers to a cyclic compound containing only carbon atoms in the ring.

As used herein, the term "heterocycle" refers to a cyclic compound comprising a heteroatom, including monocyclic or bicyclic heterocycles. As used herein, the term "heteroatom" refers to any atom that is not carbon or hydrogen, such as nitrogen, oxygen or sulfur. Examples of heterocycles include but are not limited to oxirane, oxetane, pyran, tetrahydropyran, dioxane, lactones, aziridine, azetidine, pyrrolidine, piperidine, morpholine, lactams, and tetrahydrofuran.

As used herein, the term "bicyclic compound" refers to a compound having two rings which share a pair of bridgehead carbon atoms. Examples of bicyclic compounds include but are not limited to decalin, norbornane, camphor, and diazabicyclo[2.2.1]heptane.

As used herein, the terms "heteroaryl" or "heteroaromatic" refer to an aromatic heterocycle. Examples of heteroaryls include but are not limited to furan, pyrrole, pyridine, pyrimidine, imidazole, or triazole.

The terms "treat," "treatment" and "therapeutic effect" as used herein refer to reducing or stopping a cell proliferation rate (e.g., slowing or halting tumor growth) or reducing the number of proliferating cancer cells (e.g., removing part or all of a tumor). These terms also are applicable to reducing a titre of a microorganism in a system (i.e., cell, tissue, or subject) infected with a microorganism, reducing the rate of microbial propagation, reducing the number of symptoms or an effect of a symptom associated with the microbial infection, and/or removing detectable amounts of the microbe from the system. Examples of microorganism include but are not limited to virus, bacterium and fungus.

Compounds that interact with quadruplex forming regions of DNA can also be used to reduce a microbial infection, such as a viral infection. Retroviruses offer a wealth of potential targets for G-quadruplex targeted therapeutics. G-quadruplex structures have been implicated as functional elements in at least two secondary structures formed by either viral RNA or DNA in HIV, the dimer linker structure (DLS) and the central DNA flap (CDF). Additionally, DNA aptamers which are able to adopt either inter- or intramolecular quadruplex structures are able to inhibit viral replication. In one example, DNA aptamers are able to inhibit viral replication by targeting the envelope glycoprotein (putatively). In another example, DNA aptamers inhibit viral replication by targeting the HIV-integrase respectively, suggesting the involvement of native quadruplex structures in interaction with the integrase enzyme.

Dimer linker structures, which are common to all retroviruses, serve to bind two copies of the viral genome together by a non-covalent interaction between the two 5' ends of the two viral RNA sequences. The genomic dimer is stably associated with the gag protein in the mature virus particle. In the case of HIV, the origin of this non-covalent binding may be traced to a 98 base-pair sequence containing several runs of at least two consecutive guanines (e.g., the 3' for the formation of RNA dimers in vitro). An observed cation (potassium) dependence for the formation and stability of the dimer in vitro, in addition to the failure of an antisense sequence to effectively dimerize, has revealed the most likely binding structure to be an intermolecular G-quadruplex.

Prior to integration into the host genome, reverse transcribed viral DNA forms a pre-integration complex (PIC) with at least two major viral proteins, integrase and reverse transcriptase, which is subsequently transported into the nucleus. The Central DNA Flap (CDF) refers to 99-base length single-stranded tail of the +strand, occurring near the center of the viral duplex DNA, which is known to a play a role in the nuclear import of the PIC. Oligonucleotide mimics of the CDF have been shown to form intermolecular G-quadruplex structures in cell-free systems.

Thus, compounds that recognize quadruplex forming regions can be used to stabilize the dimer linker structure and thus prevent de-coupling of the two RNA strands. Also, by binding to the quadruplex structure formed by the CDF, protein recognition and/or binding events for nuclear transport of the PIC may be disrupted. In either case, a substantial advantage can exist over other anti-viral therapeutics. Current Highly Active Anti-Retroviral Therapeutic (HAART) regimes rely on the use of combinations of drugs targeted towards the HIV protease and HIV integrase. The requirement for multi-drug regimes is to minimize the emergence of resistance, which will usually develop rapidly when agents are used in isolation. The source of such rapid resistance is the infidelity of the reverse transcriptase enzyme which makes a mutation approximately once in every 10,000 base pairs. An advantage of targeting viral quadruplex structures over protein targets, is that the development of resistance is slow or is impossible. A point mutation of the target quadruplex can compromise the integrity of the quadruplex structure and lead to a non-functional copy of the virus. A single therapeutic agent based on this concept may replace the multiple drug regimes currently employed, with the concomitant benefits of reduced costs and the elimination of harmful drug/drug interactions.

compound. While background signals may be assessed each time a new molecule is probed by the assay, detecting the background signal is not required each time a new molecule is assayed.

Examples of quadruplex forming nucleic acid sequences are set forth in the following Table A:

TABLE A

| SEQUENCE | SEQ ID NO | ORIGIN |
|---|---|---|
| TG$_4$AG$_3$TG$_4$AG$_3$TG$_4$AAGG | 1 | CMYC |
| GGGGGGGGGGGGGCGGGGGCGGGGCGGGGAGGGC | 2 | PDGFA |
| G$_8$ACGCG$_3$AGCTG$_5$AG$_3$CTTG$_4$CCAG$_3$CG$_4$CGCTTAG$_5$ | 3 | PDGFB/c-sis |
| AGGAAGGGGAGGGCCGGGGGGAGGTGGC | 4 | CABL |
| AGGGGCGGGGCGGGGCGGGGC | 5 | RET |
| GGGAGGAAGGGGCGGGAGCGGGGC | 6 | BCL-2 |
| GGGGGGCGGGGCGGGCGCAGGGGGAGGGGGC | 7 | Cyclin D1/BCL-1 |
| CGGGGCGGGGCGGGGCGGGGC | 8 | H-RAS |
| AGAGGAGGAGGAGGTCACGGAGGAGGAGGAGAAGGAGGAGGAGGAA | 9 | CMYB |
| (GGA)$_4$ | 10 | VAV |
| AGAGAAGAGGGGAGGAGGAGGAGGAGAGGAGGAGGCGC | 11 | HMGA2 |
| GGAGGGGAGGGG | 12 | CPIM |
| AGGAGAAGGAGGAGGTGGAGGAGGAGG | 13 | HER2/neu |
| AGGAGGAGGAGAATGCGAGGAGGAGGGAGGAGA | 14 | EGFR |
| GGGGCGGGCCGGGGCGGGGTCCCGGCGGGGCGGAG | 15 | VEGF |
| CGGGAGGAGGAGGAAGGAGGAAGCGCG | 16 | CSRC |

The present invention provides a method for reducing a microbial titer in a system, comprising contacting a system having a native DNA quadruplex forming region with a compound having formula 1. The system may be one or more cells or tissues. Examples of microbial titers include but are not limited to viral, bacterial or fungal titers. In a particular embodiment, the system is a subject in need of a treatment for a viral infection (e.g., a mammal such as a mouse, rat, monkey, or human). Examples of viral infections include infections by a hepatitis virus (e.g., hepatitis B or C), human immunodeficiency virus (HIV), rhinovirus, herpes-zoster virus (VZV), herpes simplex virus (e.g., HSV-1 or HSV-2), cytomegalovirus (CMV), vaccinia virus, influenza virus, encephalitis virus, hantavirus, arbovirus, West Nile virus, human papilloma virus (HPV), Epstein-Barr virus, and respiratory syncytial virus. The present invention also provides a method for treating HIV infection by administering a compound having formula 1 to a subject in need thereof, thereby reducing the HIV infection.

Identifying Compounds that can Bind to Quadruplex Forming Regions of DNA

Compounds described herein are identified as compounds that can bind to quadruplex forming regions of DNA where a biological activity of this region, often expressed as a "signal," produced in a system containing the compound is different than the signal produced in a system not containing the compound.

In addition to determining whether a test molecule or test nucleic acid gives rise to a different signal, the affinity of the interaction between the nucleic acid and the compound may be quantified. $IC_{50}$, $K_d$, or $K_i$ threshold values may be compared to the measured $IC_{50}$ or $K_d$ values for each interaction, and thereby identify a test molecule as a quadruplex interacting molecule or a test nucleic acid as a quadruplex forming nucleic acid. For example, $IC_{50}$ or $K_d$ threshold values of 10 µM or less, 1 µM or less, and 100 nM or less are often utilized. In another example, threshold values of 10 nM or less, 1 nM or less, 100 pM or less, and 10 pM or less may be utilized to identify quadruplex interacting molecules and quadruplex forming nucleic acids.

Many assays are available for identifying compounds that have affinity for quadruplex forming regions of DNA. In some of these assays, the biological activity is the quadruplex nucleic acid binding to a compound and binding is measured as a signal. In other assays, the biological activity is a polymerase arresting function of a quadruplex and the degree of arrest is measured as a decrease in a signal. In certain assays, the biological activity is transcription and transcription levels can be quantified as a signal. In another assay, the biological activity is cell death and the number of cells undergoing cell death is quantified. Another assay monitors proliferation rates of cancer cells. Examples of assays are fluorescence binding assays, gel mobility shift assays (see, e.g., Jin & Pike, Mol.

*Endocrinol.* (1996) 10:196-205), polymerase arrest assays, transcription reporter assays, cancer cell proliferation assays, and apoptosis assays (see, e.g., Amersham Biosciences (Piscataway, N.J.)), and embodiments of such assays are described hereafter. Also, topoisomerase assays can be utilized to determine whether the quadruplex interacting molecules have a topoisomerase pathway activity (see, e.g. Topo-GEN, Inc. (Columbus, Ohio)).

Gel Electrophoretic Mobility Shift Assay (EMSA)

An EMSA is useful for determining whether a nucleic acid forms a quadruplex and whether a nucleotide sequence is quadruplex-destabilizing. EMSA is conducted as described previously (Jin & Pike, *Mol. Endocrinol.* 10: 196-205 (1996)) with minor modifications. Generally, synthetic single-stranded oligonucleotides are labeled in the 5'-terminus with T4-kinase in the presence of $[\gamma\text{-}^{32}P]$ ATP (1,000 mCi/mmol, Amersham Life Science) and purified through a sephadex column. $^{32}$P-labeled oligonucleotides (~30,000 cpm) are then incubated with or without various concentrations of a testing compound in 20 µl of a buffer containing 10 mM Tris pH 7.5, 100 mM KCl, 5 mM dithiothreitol, 0.1 mM EDTA, 5 mM $MgCl_2$, 10% glycerol, 0.05% Nonedit P-40, and 0.1 mg/ml of poly(dI-dC) (Pharmacia). After incubation for 20 minutes at room temperature, binding reactions are loaded on a 5% polyacrylamide gel in 0.25× Tris borate-EDTA buffer (0.25× TBE, 1×TBE is 89 mM Tris-borate, pH 8.0, 1 mM EDTA). The gel is dried and each band is quantified using a phosphoimager.

DMS Methylation Protection Assay

Chemical footprinting assays are useful for assessing quadruplex structure. Quadruplex structure is assessed by determining which nucleotides in a nucleic acid are protected or unprotected from chemical modification as a result of being inaccessible or accessible, respectively, to the modifying reagent. A DMS methylation assay is an example of a chemical footprinting assay. In such an assay, bands from EMSA are isolated and subjected to DMS-induced strand cleavage. Each band of interest is excised from an electrophoretic mobility shift gel and soaked in 100 mM KCl solution (300 µl) for 6 hours at 4° C. The solutions are filtered (microcentrifuge) and 30,000 cpm (per reaction) of DNA solution is diluted further with 100 mM KCl in 0.1×TE to a total volume of 70 µl (per reaction). Following the addition of 1 µl salmon sperm DNA (0.1 µg/µl), the reaction mixture is incubated with 1 µl DMS solution (DMS ethanol; 4:1; v:v) for a period of time. Each reaction is quenched with 18 µl of stop buffer (b-mercaptoathanol:water:NaOAc (3 M); 1:6:7; v:v:v). Following ethanol precipitation (twice) and piperidine cleavage, the reactions are separated on a preparative gel (16%) and visualized on a phosphoimager.

Polymerase Arrest Assay

An arrest assay includes a template nucleic acid, which may comprise a quadruplex forming sequence, and a primer nucleic acid which hybridizes to the template nucleic acid 5' of the quadruplex-forming sequence. The primer is extended by a polymerase (e.g., Taq polymerase), which advances from the primer along the template nucleic acid. In this assay, a quadruplex structure can block or arrest the advance of the enzyme, leading to shorter transcription fragments. Also, the arrest assay may be conducted at a variety of temperatures, including 45° C. and 60° C., and at a variety of ion concentrations.

An example of the Taq polymerase stop assay is described in Han, et al., *Nucl. Acids Res.* (1999) 27:537-542, which is a modification of that used by Weitzmann, et al., *J. Biol. Chem.* (1996) 271:20958-20964. Briefly, a reaction mixture of template DNA (50 nM), Tris.HCl (50 mM), $MgCl_2$ (10 mM), DTT (0.5 mM), EDTA (0.1 mM), BSA (60 ng), and 5'-end-labeled quadruplex nucleic acid (~18 nM) is heated to 90° C. for 5 minutes and allowed to cool to ambient temperature over 30 minutes. Taq Polymerase (1 µl) is added to the reaction mixture, and the reaction is maintained at a constant temperature for 30 minutes. Following the addition of 10 µl stop buffer (formamide (20 ml), 1 M NaOH (200 µl), 0.5 M EDTA (400 µl), and 10 mg bromophenol blue), the reactions are separated on a preparative gel (12%) and visualized on a phosphoimager. Adenine sequencing (indicated by "A" at the top of the gel) is performed using double-stranded DNA Cycle Sequencing System from Life Technologies. The general sequence for the template strands is TCCAACTATG-TATAC(SEQ ID NO:17)-INSERT-TTAGCGACACGCAAT-TGCTATAGTGAGTCGTATTA (SEQ ID NO:18), where "INSERT" refers to a nucleic acid sequence comprising a quadruplex forming sequence (See e.g., Table A). Bands on the gel that exhibit slower mobility are indicative of quadruplex formation.

High Throughput Polymerase Arrest Assay

A high throughput polymerase arrest assay has been developed. The assay comprises contacting a template nucleic acid, often DNA, with a primer, which also is often DNA; contacting the primer/template complex with a compound described herein (also referred to as a "test compound"); contacting the primer/template complex with a polymerase; and separating reaction products. The assay often includes the step of denaturing the primer/template complex mixture and then renaturing the complex, which often is carried out before a test molecule is added to the system. Multiple assays often are carried out using varying concentrations of a test compound, such that an $IC_{50}$ value can be obtained, for example. The reaction products often include extended primers of different lengths. Where a test compound does not significantly interact with a quadruplex structure in the template, the primer often is extended to the end of the template.

Where a test compound significantly interacts with a quadruplex structure in the template, the primer often is extended only to the quadruplex structure in the template and no further. Thus, the reaction mixture often includes at least two reaction products when a test compound interacts with a quadruplex structure in the template, one having a completely extended primer and one having an incompletely extended primer, and these two reaction products are separated. The products may be separated using any convenient separation method, such as mass spectrometry and in one embodiment, capillary electrophoresis.

The reaction products often are identified by detecting a detectable label linked to the primer. The detectable label may be non-covalently linked to the 5' end of the primer (e.g., a biotin molecule covalently linked to the 5' end of the primer which is non-covalently linked to an avidin molecule joined to a detectable label). The detectable label may be joined to the primer at any stage of the assay, sometimes before the primer is added to the system, after the primer is extended, or after the products are separated. The detectable label often is covalently linked to the primer using a procedure selected based upon the nature of the chemical groups in the detectable label.

Many methods for covalently linking detectable labels to nucleic acids are available, such as chemically coupling an allylamine-derivatized nucleotide to a succinimidyl-ester derivative of a detectable label, and then generating a primer using the labeled nucleotide. (See, e.g., *Nature Biotech* (2000) 18:345-348 and http address info.med.yale.edu/genetics/ward/tavi/n_coupling.html). A spacer (often between 5-16 carbon atoms long) sometimes is incorporated between the detectable label and the nucleotide. Any convenient detectable label may be utilized, including but not limited to a radioactive isotope (e.g., $^{125}$I, $^{131}$I, $^{35}$S, $^{32}$P, $^{14}$C or $^{3}$H); a light scattering label (e.g., a spherical gold or silver label; Genicon Sciences Corporation, San Diego, Calif. and U.S. Pat. No. 6,214,560); an enzymic or protein label (e.g., GFP or peroxidase); or another chromogenic label or dye sometimes is utilized. Often, a fluorescent label is utilized (e.g., aminomethyl coumarin (AMCA); diethyl aminomethyl coumarin (DEAC); cascade blue (CB); fluorescein isothiocyanate (FITC); Oregon green (OG); Alexa 488 (A488); rhodamine green (RGr); lanthanide chelate (e.g., europium), carboxyrhodamine 6G (R6G); tetramethyl rhodamine (TAMRA); Texas Red (TxR); Cy3; Cy3.5; Cy5, Cy5.5 and carboxynaphtofluorescein (CNF), digoxigenin (DIG); and 2,4-dinitrophenyl (DNP)). Other fluorophores and attendant excitation and emission wavelengths are described in Anantha, et al., *Biochemistry* (1998) 37:2709-2714 and Qu & Chaires, *Methods Enzymol* (2000) 321:353-369).

In an embodiment, a primer oligonucleotide covalently linked to a fluorescent label is contacted with template DNA. The resulting complex is contacted with a test molecule and then contacted with a polymerase capable of extending the primer. The reaction products then are separated and detected by capillary electrophoresis. A longer primer sequence was used for practicing this embodiment as compared to embodiments where the primer includes no covalently-linked fluorophore or where capillary electrophoresis is not utilized for separation. Deoxynucleotides are added at any stage of the assay before the separation, often when the primer is contacted with the template DNA. The template DNA/primer complex often is denatured (e.g., by increasing the temperature of the system) and then renatured (e.g., by cooling the system) before a test compound is added).

The following is a specific example of the assay embodiment. A 5'-fluorescent-labeled (FAM) primer (P45, 15 nM) was mixed with template DNA (15 nM) in a Tris-HCL buffer (15 mM Tris, pH 7.5) containing 10 mM MgCl$_2$, 0.1 mM EDTA and 0.1 mM mixed deoxynucleotide triphosphates (dNTP's). The FAM-P45 primer (5'-6FAM-AGTCTGAC TGACTGTACGTAGCTAATACGACTCAC-TATAGCAATT-3')(SEQ ID NO:19) and the template DNA (5'-TCCAACTATGTATACTGGGGAGGGTGGG-GAGGGTGGGGAAGGTT AGCGACACGCAATTGC-TATAGTGAGTCGTATTAGCTACGTA-CAGTCAGTCAGACT-3') (SEQ ID NO:20) were synthesized and HPLC purified by Applied Biosystems. The mixture was denatured at 95° C. for 5 minutes and, after cooling down to room temperature, was incubated at 37° C. for 15 minutes.

After cooling down to room temperature, 1 mM KCl$_2$ and the test compound (various concentrations) were added and the mixture incubated for 15 minutes at room temperature. The primer extension was performed by adding 10 mM KCl and Taq DNA Polymerase (2.5 U/reaction, Promega) and incubating at 70° C. for 30 minutes. The reaction was stopped by adding 1 µl of the reaction mixture to 10 µl Hi-Di Formamide mixed and 0.25 µl LIZ120 size standard. Hi-Di Formamide and LIZ120 size standard were purchased from Applied Biosystems. The partially extended quadruplex arrest product was between 61 or 62 bases long and the full-length extended product was 99 bases long. The products were separated and analyzed using capillary electrophoresis. Capillary electrophoresis was performed using an ABI PRISM 3100-Avant Genetic Analyzer. The assay was performed using compounds described above and results are shown in Table 1. µM concentrations reported in Table 1 are concentrations at which 50% of the DNA was arrested in the assay (i.e., the ratio of shorter partially extended DNA (arrested DNA) to full-length extended DNA is 1:1).

Transcription Reporter Assay

In a transcription reporter assay, test quadruplex DNA is coupled to a reporter system, such that a formation or stabilization of a quadruplex structure can modulate a reporter signal. An example of such a system is a reporter expression system in which a polypeptide, such as luciferase or green fluorescent protein (GFP), is expressed by a gene operably linked to the potential quadruplex forming nucleic acid and expression of the polypeptide can be detected. As used herein, the term "operably linked" refers to a nucleotide sequence which is regulated by a sequence comprising the potential quadruplex forming nucleic acid. A sequence may be operably linked when it is on the same nucleic acid as the quadruplex DNA, or on a different nucleic acid. An exemplary luciferase reporter system is described herein.

A luciferase promoter assay described in He, et al., *Science* (1998) 281:1509-1512 often is utilized for the study of quadruplex formation. Specifically, a vector utilized for the assay is set forth in reference 11 of the He, et al., document. In this assay, HeLa cells are transfected using the lipofectamin 2000-based system (Invitrogen) according to the manufacturer's protocol, using 0.1 µg of pRL-TK (Renilla luciferase reporter plasmid) and 0.9 µg of the quadruplex-forming plasmid. Firefly and Renilla luciferase activities are assayed using the Dual Luciferase Reporter Assay System (Promega) in a 96-well plate format according to the manufacturer's protocol.

Circular Dichroism Assay

Circular dichroism (CD) is utilized to determine whether another molecule interacts with a quadruplex nucleic acid. CD is particularly useful for determining whether a PNA or PNA-peptide conjugate hybridizes with a quadruplex nucleic acid in vitro. PNA probes are added to quadruplex DNA (5 µM each) in a buffer containing 10 mM potassium phosphate (pH 7.2) and 10 or 250 mM KCl at 37° C. and then allowed to stand for 5 minutes at the same temperature before recording spectra. CD spectra are recorded on a Jasco J-715 spectropolarimeter equipped with a thermoelectrically controlled single cell holder. CD intensity normally is detected between 220 nm and 320 nm and comparative spectra for quadruplex DNA alone, PNA alone, and quadruplex DNA with PNA are generated to determine the presence or absence of an interaction (see, e.g., Datta, et al., *JACS* (2001) 123:9612-9619). Spectra are arranged to represent the average of eight scans recorded at 100 nm/min.

Fluorescence Binding Assay

An example of a fluorescence binding assay is a system that includes a quadruplex nucleic acid, a signal molecule, and a test molecule. The signal molecule generates a fluorescent signal when bound to the quadruplex nucleic acid (e.g., N-methylmesoporphyrin IX (NMM)), and the signal is altered when a test compound competes with the signal molecule for binding to the quadruplex nucleic acid. An alteration in the signal when test molecule is present as compared to when test compound is not present identifies the test compound as a quadruplex interacting compound.

50 µl of quadruplex nucleic acid or a nucleic acid not capable of forming a quadruplex is added in 96-well plate. A test compound also is added in varying concentrations. A typical assay is carried out in 100 µl of 20 mM HEPES buffer, pH 7.0, 140 mM NaCl, and 100 mM KCl. 50 µl of the signal molecule NMM then is added for a final concentration of 3 µM. NMM is obtained from Frontier Scientific Inc, Logan, Utah. Fluorescence is measured at an excitation wavelength of 420 nm and an emission wavelength of 660 nm using a FluoroStar 2000 fluorometer (BMG Labtechnologies, Durham, N.C.). Fluorescence often is plotted as a function of concentration of the test compound or quadruplex-targeted nucleic acid and maximum fluorescent signals for NMM are assessed in the absence of these molecules.

Cell Proliferation Assay

In a cancer cell proliferation assay, cell proliferation rates are assessed as a function of different concentrations of test compounds added to the cell culture medium. Any cancer cell type can be utilized in the assay. In one embodiment, colon cancer cells are cultured in vitro and test compounds are added to the culture medium at varying concentrations. A useful colon cancer cell line is colo320, which is a colon adenocarcinoma cell line deposited with the National Institutes of Health as accession number JCRB0225. Parameters for using such cells are available at the http address cellbank.nihs.gojp/cell/data/jcrb0225.htm.

Formulation of Compounds

As used herein, the term "pharmaceutically acceptable salts, esters and amides" includes but are not limited to carboxylate salts, amino acid addition salts, esters and amides of the compounds, as well as the zwitterionic forms thereof, which are known to those skilled in the art as suitable for use with humans and animals. (See, e.g., Gerge, S. M., et al., "Pharmaceutical Salts," *J. Pharm. Sci.* (1977) 66:1-19, which is incorporated herein by reference.)

Any suitable formulation of the compounds described herein can be prepared. In cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts. Pharmaceutically acceptable salts are obtained using standard procedures well known in the art, for example by reacting a sufficiently basic compound such as an amine with a suitable acid affording a physiologically acceptable anion. Alkali metal (e.g., sodium, potassium or lithium) or alkaline earth metal (e.g., calcium) salts of carboxylic acids also are made.

A compound may be formulated as a pharmaceutical composition and administered to a mammalian host in need of such treatment. In one embodiment, the mammalian host is human. Any suitable route of administration may be used, including but not limited to oral, parenteral, intravenous, intramuscular, topical and subcutaneous routes.

In one embodiment, a compound is administered systemically (e.g., orally) in combination with a pharmaceutically acceptable vehicle such as an inert diluent or an assimilable edible carrier. They may be enclosed in hard or soft shell gelatin capsules, compressed into tablets, or incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may be varied and may conveniently be between about 2 to about 60% of the weight of a given unit dosage form. The amount of active compound in such therapeutically useful compositions is such that an effective dosage level will be obtained.

Tablets, troches, pills, capsules, and the like also may contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Any material used in preparing any unit dosage form is pharmaceutically acceptable and substantially non-toxic in the amounts employed. In addition, the active compound may be incorporated into sustained-release preparations and devices.

The active compound also may be administered intravenously or intraperitoneally by infusion or injection. Solutions of the active compound or its salts may be prepared in a buffered solution, often phosphate buffered saline, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms. The compound is sometimes prepared as a polymatrix-containing formulation for such administration (e.g., a liposome or microsome). Liposomes are described for example in U.S. Pat. No. 5,703,055 (Felgner, et al) and Gregoriadis, Liposome Technology vols. I to III (2nd ed. 1993).

The pharmaceutical dosage forms suitable for injection or infusion can include sterile aqueous solutions or dispersions or sterile powders comprising the active ingredient that are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in liquid form. Compounds often are administered as compositions or formulations, in combination with a dermatologically acceptable carrier, which may be a solid or a liquid. Examples of useful dermatological compositions used to deliver compounds to the skin are known (see, e.g., Jacquet, et al. (U.S. Pat. No. 4,608,392), Geria (U.S. Pat. No. 4,992,478), Smith, et al. (U.S. Pat. No. 4,559,157) and Wortzman (U.S. Pat. No. 4,820,508).

Compounds may be formulated with a solid carrier, which include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Generally, the concentration of the compound in a liquid composition often is from about 0.1 wt % to about 25 wt %, sometimes from about 0.5 wt % to about 10 wt %. The concentration in a semi-solid or solid composition such as a gel or a powder often is about 0.1 wt % to about 5 wt %, sometimes about 0.5 wt % to about 2.5 wt %. A compound composition may be prepared as a unit dosage form, which is prepared according to conventional techniques known in the pharmaceutical industry. In general terms, such techniques include bringing a compound into association with pharmaceutical carrier(s) and/or excipient(s) in liquid form or finely divided solid form, or both, and then shaping the product if required. The compound composition may be formulated into any dosage form, such as tablets, capsules, gel capsules, liquid syrups, soft gels, suppositories, and enemas. The compositions also may be formulated as suspensions in aqueous, non-aqueous, or mixed media. Aqueous suspensions may further contain substances which increase viscosity, including for example, sodium carboxymethylcellulose, sorbitol, and/or dextran. The suspension may also contain one or more stabilizers.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

A useful compound dosage often is determined by assessing its in vitro activity in a cell or tissue system and/or in vivo activity in an animal system. For example, methods for extrapolating an effective dosage in mice and other animals to humans are known to the art (see, e.g., U.S. Pat. No. 4,938,949). Such systems can be used for determining the $LD_{50}$ (the dose lethal to 50% of the population) and the $ED_{50}$ (the dose therapeutically effective in 50% of the population) of a compound. The dose ratio between a toxic and therapeutic effect is the therapeutic index and it can be expressed as the ratio $ED_{50}/LD_{50}$. The compound dosage often lies within a range of circulating concentrations for which the $ED_{50}$ is associated with little or no toxicity. The dosage may vary within this range depending upon the dosage form employed and the route of administration utilized. For any compounds used in the methods described herein, the therapeutically effective dose can be estimated initially from cell culture assays. A dose sometimes is formulated to achieve a circulating plasma concentration range covering the $IC_{50}$ (i.e., the concentration of the test compound which achieves a half-maximal inhibition of symptoms) as determined in in vitro assays, as such information often is used to more accurately determine useful doses in humans. Levels in plasma may be measured, for example, by high performance liquid chromatography.

Another example of effective dose determination for a subject is the ability to directly assay levels of "free" and "bound" compound in the serum of the test subject. Such assays may utilize antibody mimics and/or "biosensors" generated by molecular imprinting techniques. The compound is used as a template, or "imprinting molecule", to spatially organize polymerizable monomers prior to their polymerization with catalytic reagents. Subsequent removal of the imprinted molecule leaves a polymer matrix which contains a repeated "negative image" of the compound and is able to selectively rebind the molecule under biological assay conditions (see, e.g., Ansell, et al., *Current Opinion in Biotechnology* (1996) 7:89-94 and in Shea, *Trends in Polymer Science* (1994) 2:166-173). Such "imprinted" affinity matrixes are amenable to ligand-binding assays, whereby the immobilized monoclonal antibody component is replaced by an appropriately imprinted matrix (see, e.g., Vlatakis, et al., *Nature* (1993) 361:645-647). Through the use of isotope-labeling, "free" concentration of compound can be readily monitored and used in calculations of $IC_{50}$. Such "imprinted" affinity matrixes can also be designed to include fluorescent groups whose photon-emitting properties measurably change upon local and selective binding of compound. These changes can be readily assayed in real time using appropriate fiberoptic devices, in turn allowing the dose in a test subject to be quickly optimized based on its individual $IC_{50}$. An example of such a "biosensor" is discussed in Kriz, et al., *Analytical Chemistry* (1995) 67:2142-2144.

Exemplary doses include milligram or microgram amounts of the compound per kilogram of subject or sample weight, for example, about 1 microgram per kilogram to about 500 milligrams per kilogram, about 100 micrograms per kilogram to about 5 milligrams per kilogram, or about 1 microgram per kilogram to about 50 micrograms per kilogram. It is understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid described herein, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The following examples are offered to illustrate but not to limit the invention.

EXAMPLES

The following are exemplary procedures for synthesizing substituted quinobenzoxazines analogs.

Example 1

Preparation of Substituted Quinobenzoxazine Analogs

The general synthetic scheme for the preparation of substituted quinobenzoxazines analogs is shown in Scheme 1.

Ethyl-(2',3',4',5'-tetrafluorobenzoyl)-ethanoate

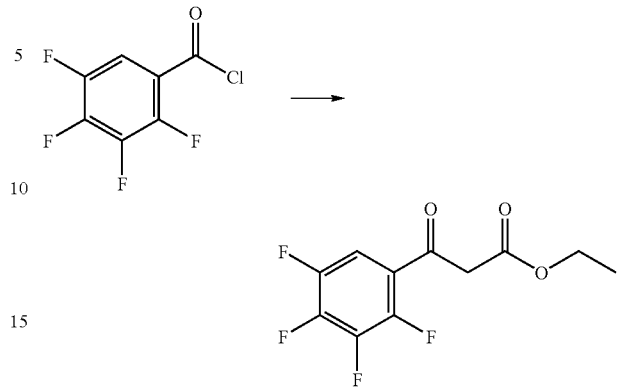

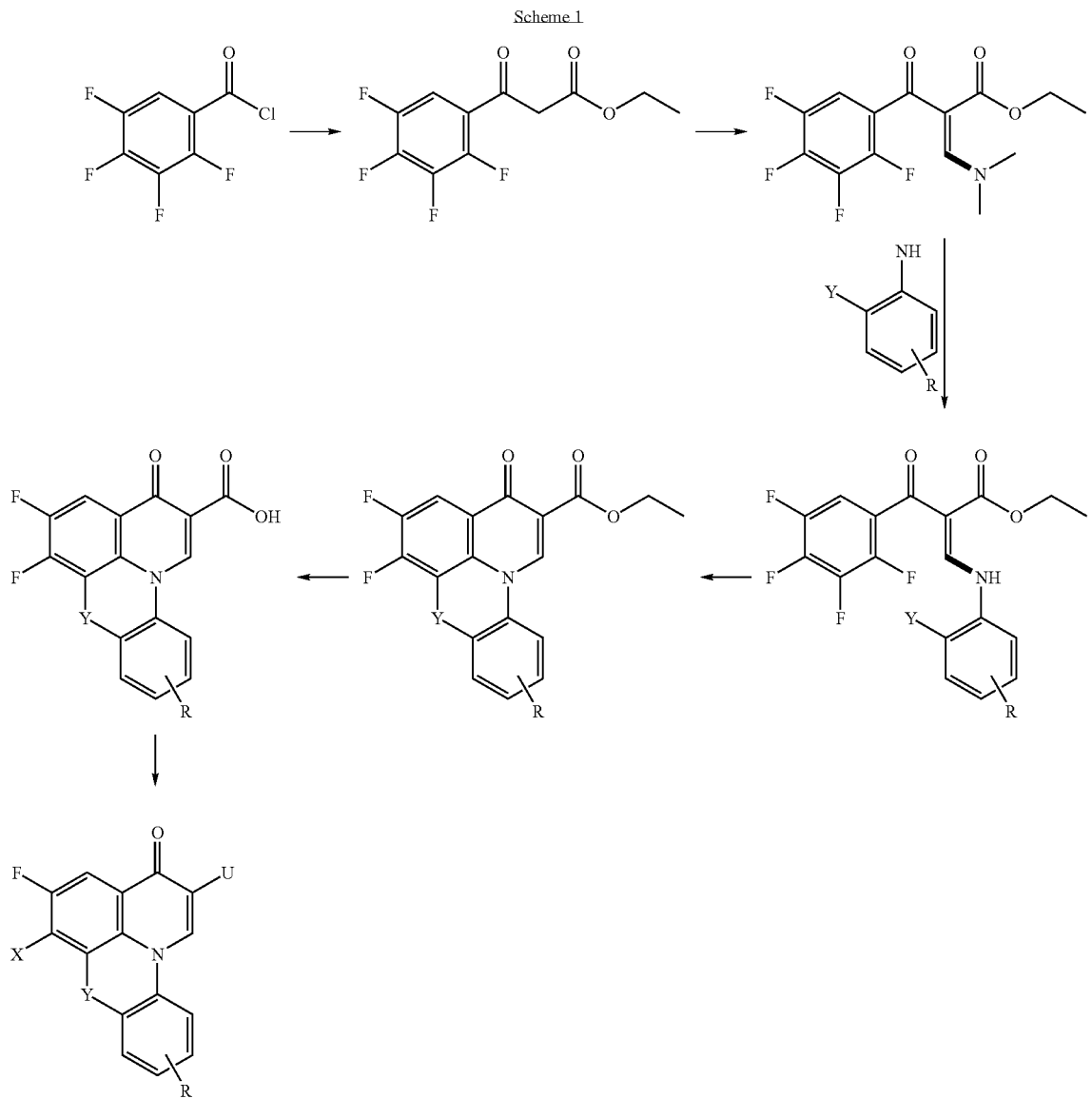

Potassium ethyl malonate (3.66 g, 21.5 mmol), MgCl₂ (2.44 g, 25.7 mmol) and TEA (2.05 g, 20.3 mmol) were mixed in acetonitrile (70 ml) at 10-15° C. for 2.5 hr. 2,3,4,5-tetrafluorobenzoyl chloride (2.00 g, 10.3 mmol) in acetonitrile (10 ml) was added at 0° C. over 15 min followed by a second addition of TEA (0.23 g, 2.3 mmol). After allowing to warm to RT, the mixture was stirred for 16 hr. After removal of volatiles in vaccuo Toluene (30 ml) was added and removed in vacuo. Following the addition of toluene (60 ml), HCl 1.5 M (40 ml) was added cautiously, ensuring the temperature did not exceed 25° C. The organic fraction was washed with HCl 1.5 M (2×25 ml) and water (2×25 ml), dried over MgSO₄ and reduced to a light orange oil in vacuo ([M+1]⁺ 265, 98%).

Ethyl-2-(2',3',4',5'-tetrafluorobenzoyl-)-3-(dimethylamino)-prop-2-enoate

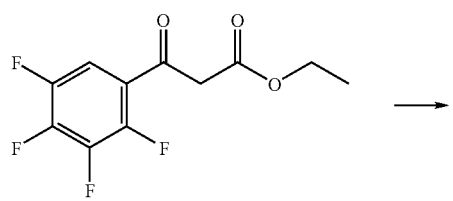

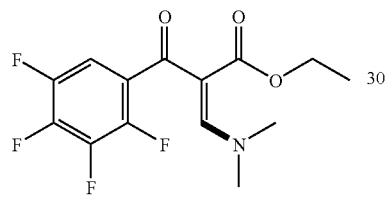

Dimethyl acetal dimethyl formamide (0.61 g, 5.1 mmol) was added dropwise to ethyl-(2',3',4',5'-tetrafluorobenzoyl)-ethanoate (0.9 g, 3.41 mmol) dissolved in acetic anhydride (2 ml), under argon. After 30 min solvent was removed in vacuo to leave the product as an orange oil in a quantitative yield ([M+1⁺] 320).

Ethyl 1,2-Difluoro-4-oxo-4H-pyrido[3,2,1-kl]-8-phenyl-phenoxazine-5-carboxylate

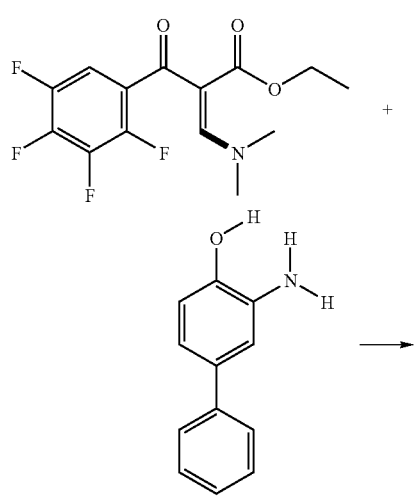

-continued

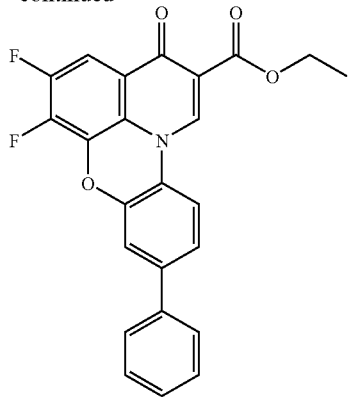

Ethyl-2-(2',3',4',5'-tetrafluorobenzoyl-)-3-(dimethylamino)-prop-2-enoate (3.4 g, 8.0 mmol) and 2-amino-4-phenyl-phenol (1.5 g, 8.0 mmol) in 20 DMSO (20 ml) was stirred under vacuum at 60° C. for 30 min. K2CO3 (5 g) and MeCN (20 ml) was added and the suspension was heated at 80° C. for 1 hr. After cooling to RT, the mixture was poured into a slight excess of dilute sulfuric acid and filtered. The product was recovered as a yellow-brown solid ([M+1]⁺ 420, 65%).

Example 2

Preparation of 1,2-Difluoro-4-oxo-4H-pyrido[3,2,1-kl]-8-phenyl-phenoxazine-5-carboxylic acid

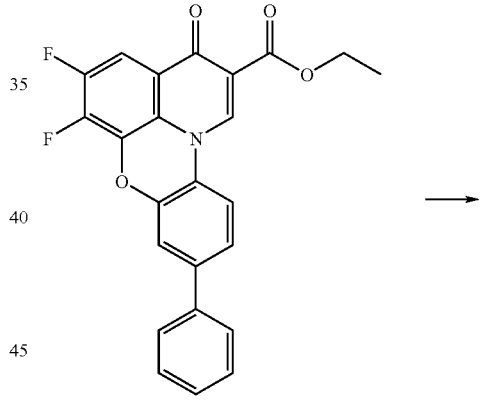

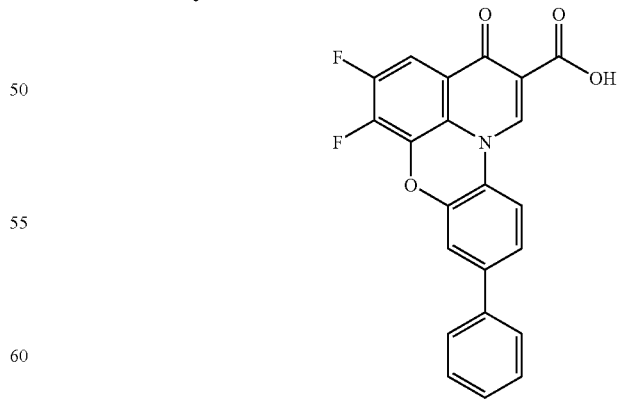

Ethyl 1,2-Difluoro-4-oxo-4H-pyrido[3,2,1-kl]-8-phenyl-phenoxazine-5-carboxylate (2.2 g, 5.3 mmol) was refluxed in a mixture of conc. HCl and acetic acid (20 ml each) for 2 hr. After cooling to room temperature cold water (40 ml) was added to the reaction mixture and the resulting precipitate filtered and washed with ether to afford the product as a yellow-brown solid 90% ([M+1]⁺ 392).

Example 3

Preparation of Ethyl-2-(2',3',4',5'-tetrafluorobenzoyl-)-3-(napthyl-2",3"-diamino)-prop-2-enoate

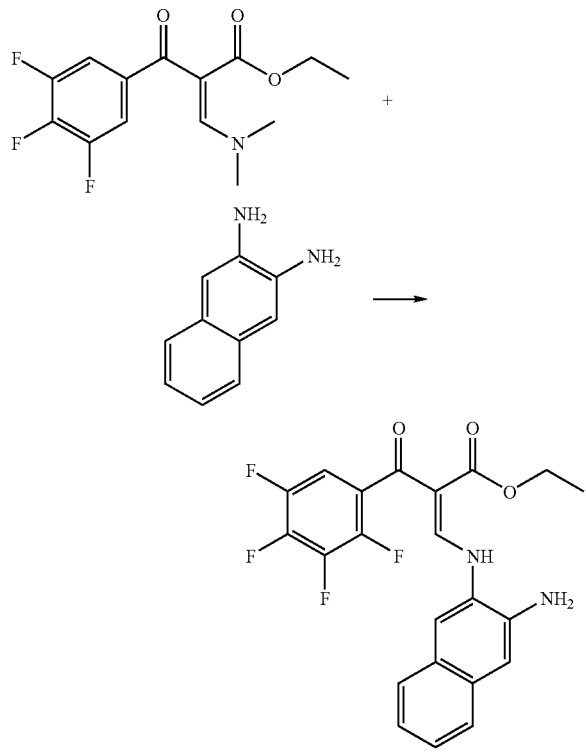

Ethyl-2-(2',3',4',5'-tetrafluorobenzoyl-)-3-(dimethylamino)-prop-2-enoate (10.53 g, 33 mmol) in acetonitrile (50 ml) was added to a solution of 2,3-diaminonapthalene (5.22 g, 33 mmol) in acetonitrile (150 ml), maintained at 50° C. under argon. After 3 hours, volatiles were removed in vacuo and the residue was subjected to chromatography over silica (15% EtOAc/Hexane) to yield the product as a yellow solid ([M+1]⁺ 433) (55%).

Example 4

Preparation of Ethyl 1,2-Difluoro-4-oxo-4H-pyrido [3,2,1-kl]benzo[g]-phendiazine-5-carboxylate

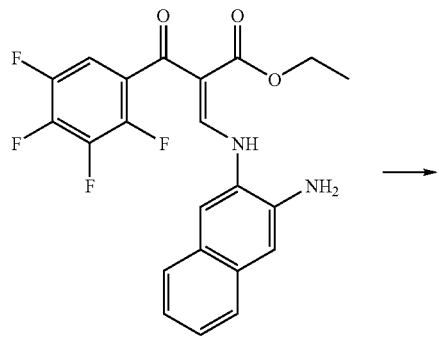

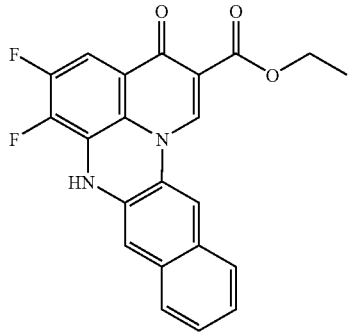

Ethyl-2-(2',3',4',5'-tetrafluorobenzoyl-)-3-(napthyl-2", 3"diamino)-prop-2-enoate (600 mg 1.4 mmol) was dissolved in a slurry of K₂CO₃ in DMF (500 ml), The mixture was stirred vigorously at 100° C. for 1 hour, then allowed to cool to RT. The K₂CO₃ was removed by filtration and the DMF removed in vacuo to leave a yellow-brown solid in quantitative yield. ([M+1]⁺ 393).

Example 5

Preparation of 1,2-Difluoro-4-oxo-4H-pyrido[3,2,1-kl]benzo[g]-phendiazine-5-carboxylic acid

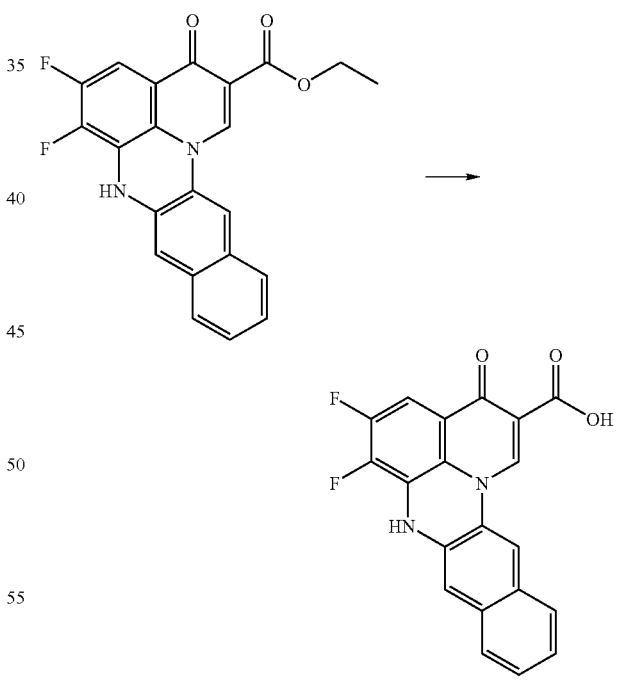

KOH solution (1N, 2.54 ml, 2.56 mmol) was added to a solution of ethyl 1,2-difluoro-4-oxo-4H-pyrido[3,2,1-kl] benzo[g]-phendiazine-5-carboxylate (500 mg, 1.28 mmol) in ethanol (400 ml), heated under reflux. After 2 hours the reaction mixture was allowed to cool to RT, then neutralized with HCl solution (1N). The product was collected by filtration as a yellow solid, 89%. ([M+1]⁺ 365).

Example 6

Preparation of Ethyl 1,2-Difluoro-4-oxo-4H-pyrido[3,21-kl]-phenthiazine-5-carboxylate Ethyl-2-(2',3',4',5'-tetrafluorobenzoyl-)-3-(N-aminobenzyldisulfide)-prop-2-enoate

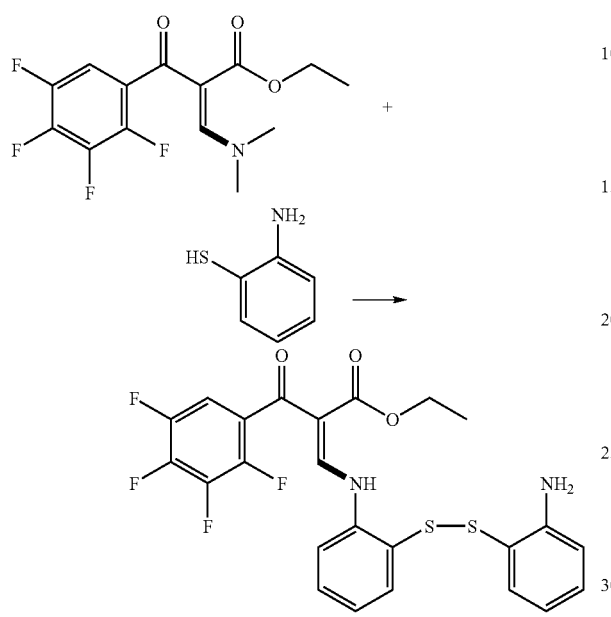

Ethyl-2-(2',3',4',5'-tetrafluorobenzoyl-)-3-(dimethylamino)-prop-2-enoate (17.7 g, 55.3 mmol) in acetonitrile (10 ml) was added to a solution of 1,2-aminothiophenol dimer (5.22 g, 33 mmol) in acetonitrile (100 ml). After 3 hours, volatiles were removed in vacuo and the residue was subjected to chromatography over silica (1% MeOH/DCM) to yield the product as a yellow solid ([M+1]$^+$ 523) (50%).

Ethyl 1,2-Difluoro-4-oxo-4H-pyrido[3,2,1-kl]-phenthiazine-5-carboxylate

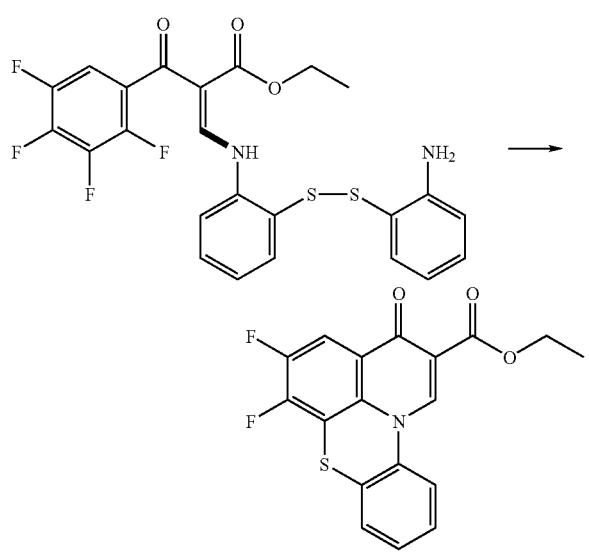

Ethyl-2-(2',3',4',5'-tetrafluorobenzoyl-)-3-(N-aminobenzyldisulfide)-prop-2-enoate (2.5 g 3.2 mmol) was dissolved in DMF (120 ml) and heated under reflux for six hours. Removal of DMF in vacuo gave the product as a yellow solid 90% ([M+1]$^+$ 360).

Example 7

Preparation of 1,2-Difluoro-4-oxo-4H-pyrido[3,2,1-k]1-phenthiazine-5-carboxylic acid

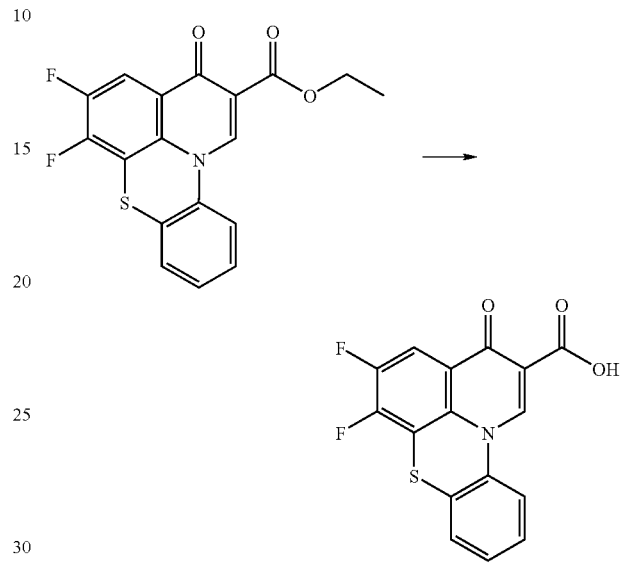

KOH solution (1N, 3.0, 3.0 mmol) was added to a solution of ethyl 1,2-difluoro-4-oxo-4H-pyrido[3,2,1-kl]-phenthiazine-5-carboxylate (1000 mg, 2.5 mmol) in ethanol (400 ml), heated under reflux. After 2 hours the reaction mixture was allowed to cool to RT, then neutralized with HCl solution (1N). The product was collected by filtration as a yellow solid, ([M+1]$^+$ 332, 95%)

Example 8

Preparation of 5,6-Difluoro-9-hydroxy-3-oxo-3H-pyrido[3,2,1-kl]pyrimido[g]phenoxazine-2-carboxylic acid 7-nitroquinazoline-4,6-diol

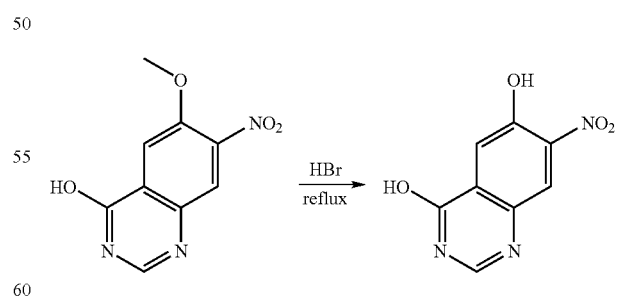

To a solution containing 20 ml of 48% aqueous HBr and 20 ml of AcOH was added 6-methoxy-7-nitro-3,4-dihydroquinazolin-4-one (1.4 g, 6.3 mmol) and the mixture was refluxed overnight. The resulting solution was evaporated to afford the crude phenol as a residue and was used without further purification (1.2 g, 5.8 mmol) (M+1, 208).

7-aminoquinazoline-4,6-diol

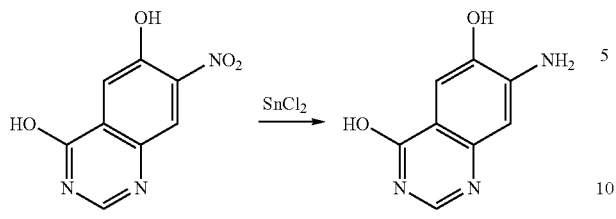

The crude product from above (1.0 g, 5.8 mmol) was diluted with 40 ml water and 3 g of Tin II chloride dihydrate was added and the reaction was stirred at room temperature. After 1 h the reaction was neutralized with $K_2CO_3$, and extracted with EtOAc (3×50 mL). The combined organic extracts were dried over sodium sulfate and the solvent was removed in vacuo to afford the crude amino alcohol (1.0 g, 5.6 mmol) (M+1, 178).

Ethyl; 5,6-difluoro-9-hydroxy-3-oxo-3H-pyrido[3,2,1-kl]pyrimido[g]phenoxazine-2-carboxylate

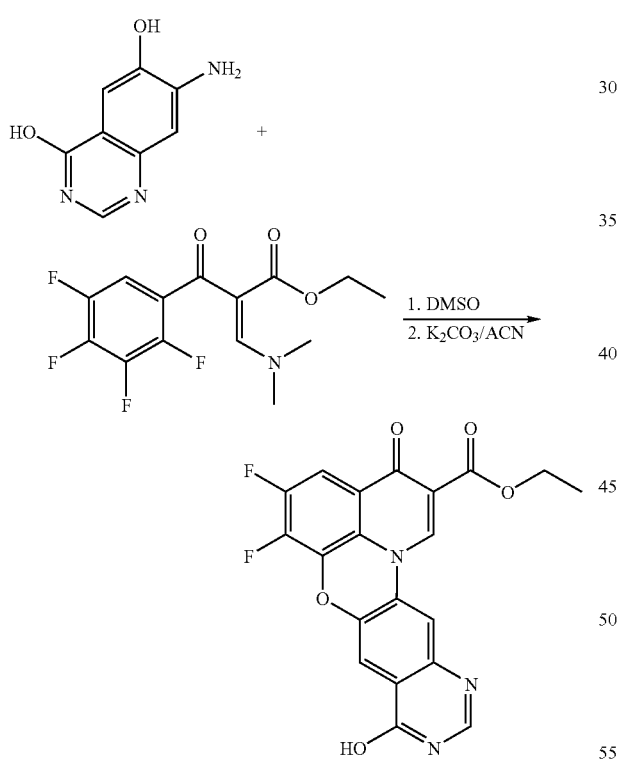

To a solution of the tetrafluoroenamine (2.2 g, 6.9 mmol) in DMSO (3 mL) was added the aminophenol (1.0 g, 5.6 mmol) and the reaction mixture was stirred under vacuum (rotary evaporator) at 60° C. for 20 minutes. The reaction mixture was allowed to cool to room temperature and was diluted with acetonitrile (200 mL) and potassium carbonate was added. The mixture was heated to reflux for 5 hours and poured into dilute HOAc/water. The solid product was collected by vacuum filtration and dried to afford the difluoroester as a tan solid (1.3 g, 3.2 mmol) (M+1, 412).

5,6-Difluoro-9-hydroxy-3-oxo-3H-pyrido[3,2,1-kl]pyrimido[g]phenoxazine-2-carboxylic acid

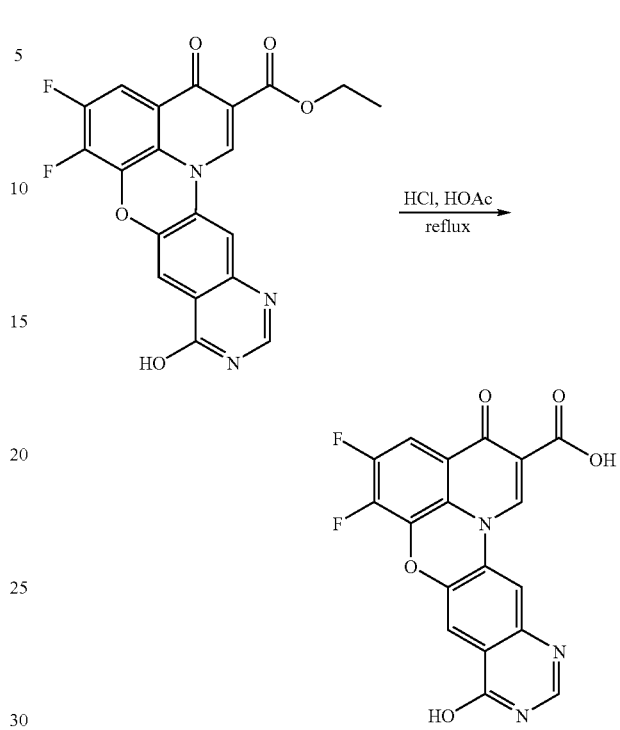

The difluoroester (1.3 g, 3.2 mmol) was dissolved in a 1:1 mixture of glacial acetic acid and 12 M HCl (20 mL) and refluxed for 30 min. The mixture was then cooled to room temperature and poured into water. The solid product was then collected by vacuum filtration and dried to afford the difluoroacid as a tan solid (0.98 g, 2.5 mmol) ([M+1]$^+$ 392).

Example 9

Preparation of 2-(2-(Ethoxycarbonyl)-5,6-difluoro-3-oxo-3H-pyrido[3,2,1-kl]phenoxazin-9-yloxy)acetic acid Ethyl 5,6-difluoro-9-hydroxy-3-oxo-3H-pyrido[3,2,1-kl]phenoxazine-2-carboxylate

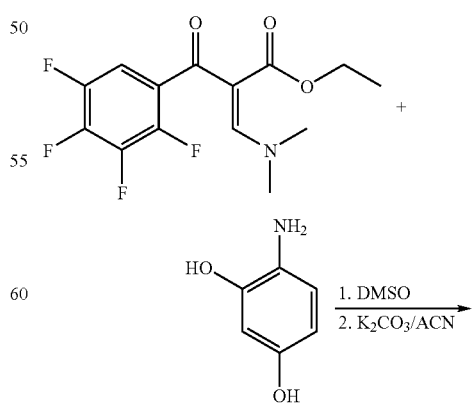

-continued

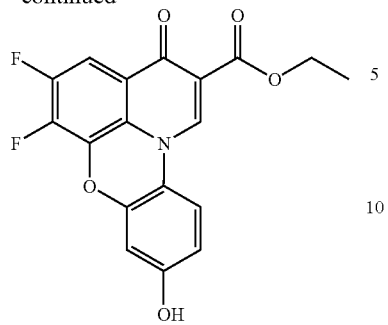

To a solution of the tetrafluoroenamine (5.8 g, 18.2 mmol), dissolved in DMSO (12 mL), was added 2,4-dihydroxyaniline hydrochloride (2.5 g, 15.5 mmol) and the mixture was heated to 60° C. under vacuum (rotary evaporator) for 20 minutes. The reaction mixture was then diluted with acetonitrile (100 mL) and potassium carbonate (3 g) was added and the mixture was refluxed overnight. The mixture was allowed to cool to room temperature and the solvent was removed in vacuo. A slight excess of 2 M HCl was added to rapidly dissolve the carbonate, and the solid precipitate was filtered and dried to afford the difluoroester as a tan solid (5.0 g, 13.9 mmol) (M+1, 360).

2-(2-(Ethoxycarbonyl)-5,6-difluoro-3-oxo-3H-pyrido[3,2,1-kl]phenoxazin-9-yloxy)acetic acid

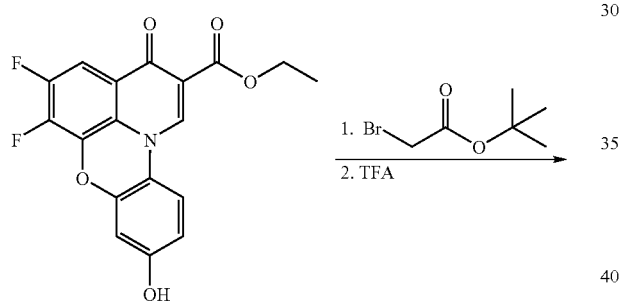

To a solution of the difluoroester (2.1 g, 5.8 mmol) and tert-butylbromoacetate (2.0 g, 10.3 mmol) in DMF (30 mL) was added potassium carbonate (2.0 g) and the mixture was heated to 60° C. for 1 hour. The reaction was allowed to cool and poured into water (500 mL) and extracted with ethyl acetate (3×100 mL), washed with brine, dried over magnesium sulfate and filtered over a pad of silica gel (30×50 mm), eluting with ethyl acetate. The solvent was removed in vacuo and the resulting material was triturated with hexanes and dried to afford the tert-butyl ester as a tan solid (2.8 g, 5.8 mmol). This material was dissolved in trifluoroacetic acid (40 mL) and stirred at room temperature for 30 minutes. The solvent was removed in vacuo to afford the acid as a tan solid (2.4 g, 5.7 mmol) (M+1, 418).

Example 10

Preparation of 9-(Carboxymethoxy)-5,6-difluoro-3-oxo-3H-pyrido[3,2,1-kl]phenoxazine-2-carboxylic acid

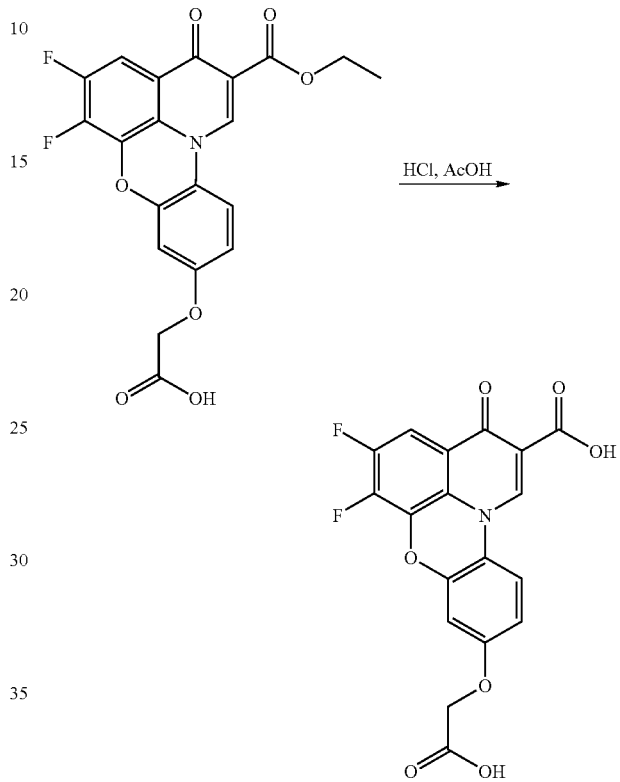

The difluoroester (2.4 g, 5.7 mmol) was dissolved in a 1:1 mixture of glacial acetic acid and 12 M HCl (40 mL) and refluxed for 1 hour. The mixture was then cooled to room temperature and poured into water. The solid product was then collected by vacuum filtration and dried to afford the difluoroacid as a tan solid (2.0 g, 5.1 mmol) (M+1, 390).

Example 11

Preparation of Ethyl 1,2,3-trifluoro-4-oxo-4H-pyrido[3,2,1-kl]benzo[g]-phenoxazine-5-carboxylate

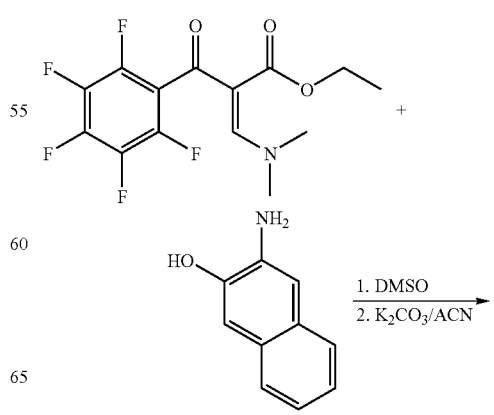

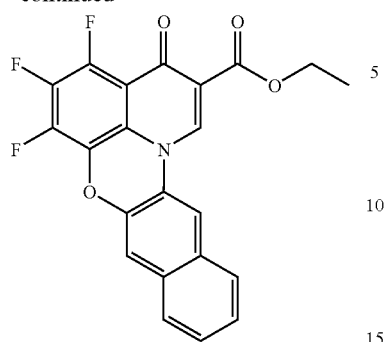

To a solution of pentafluoroenamine (8 g, 23.7 mmol), prepared by a similar procedure as for the tetrafluoroenamine dissolved in DMSO (12 mL) was added 3-amino-2-naphthol (3.5 g, 21.9 mmol) and the mixture was heated to 60° C. under vacuum (rotary evaporator) for 2 hours. The reaction mixture was then diluted with acetonitrile (200 mL) and potassium carbonate (8.0 g) was added and the mixture was refluxed overnight. The mixture was allowed to cool to room temperature and the solvent was removed in vacuo. A slight excess of 2 M HCl was added to rapidly dissolve the carbonate, and the solid precipitate was filtered and dried to afford the difluoroester as a tan solid (1.3 g, 3.2 mmol) (M+1, 412).

Example 12

Preparation of 1,2,3-Trifluoro-4-oxo-4H-pyrido[3,2,1-kl]benzo[g]-phenoxazine-5-carboxylic acid

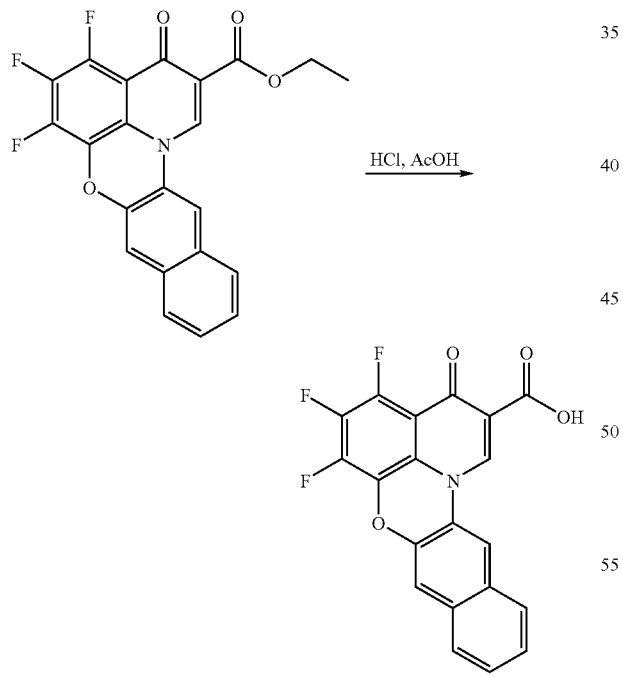

The trifluoroester (1.3 g, 3.2 mmol) was dissolved in acetic acid (5 mL) and 12 M HCl was added (5 mL) and the reaction mixture was heated to reflux for 2 hours. The mixture was then cooled to room temperature, poured into water and the solid product was collected by vacuum filtration and dried to afford the trifluoroacid as a pale solid (1.0 g, 2.6 mmol) (M+1, 384).

Example 13

Preparation of Ethyl 1,2-difluoro-4-oxo-4H-pyrido[3,2,1-kl]benzo[g]-phenoxazine-5-carboxylate

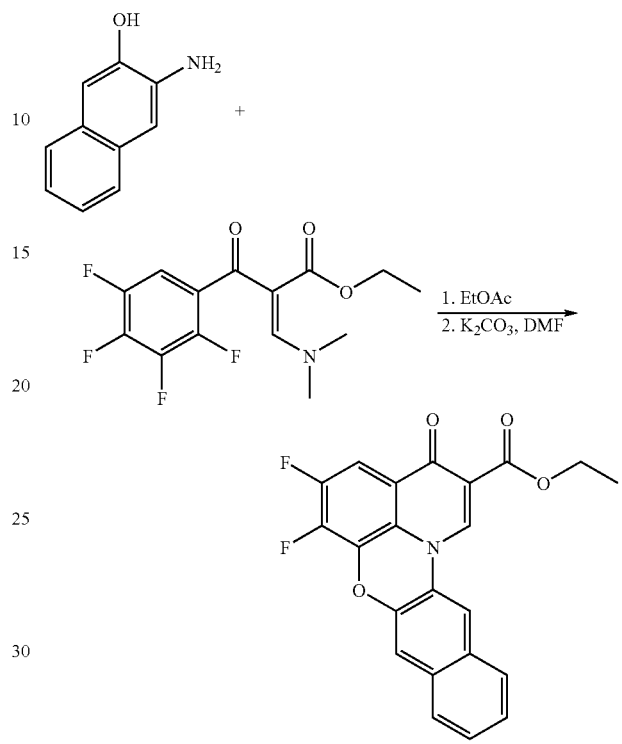

To a solution of the enamine (30 g, 94 mmol) in ethyl acetate (100 mL) was added 3-amino-2-naphthol (10 g, 63 mmol) at room temperature and the mixture was immediately placed on a rotary evaporator and the solvent was removed over 2 hours at a temperature below 0° C. (ice formed on the flask) to produce a yellow solid. To this solid was added ether (200 mL) and the slurry was filtered to afford a yellow solid. This solid was then dissolved in DMF (200 mL) and potassium carbonate was added (16.5 g, 120 mmol) and the mixture was heated to 90° C. for 1 hour. The mixture was allowed to cool to room temperature and water was added (500 mL) and the resulting solid was filtered, washed with water and dried to afford the difluoroester as a tan solid (12.2 g, 30.8 mmol) (M+1, 394).

Example 14

Preparation of 1,2-Difluoro-4-oxo-4H-pyrido[3,2,1-kl]benzo[g]-phenoxazine-5-carboxylic acid

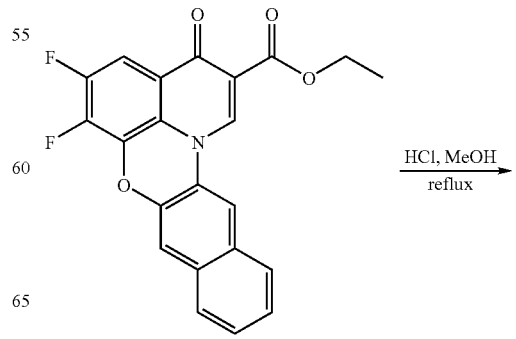

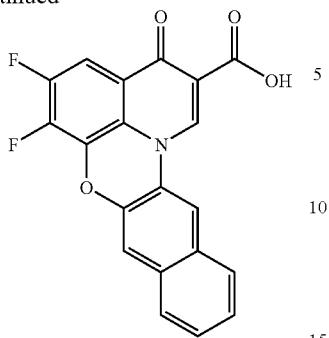

The difluoroester (5 g, 12.7 mmol) was dissolved in methanol (50 mL) and conc HCl was added (20 mL) and the mixture was refluxed for 12 hours. The mixture was allowed to cool to room temperature and the solid was collected by vacuum filtration, washing with methanol to afford the difluoroacid as a light tan powder (3.6 g, 9.9 mmol) (M+1, 366).

Example 15

Preparation of Ethyl 1-fluoro-4-oxo-4H-pyrido[3,2,1-kl]benzo[g]-phenoxazine-5-carboxylate

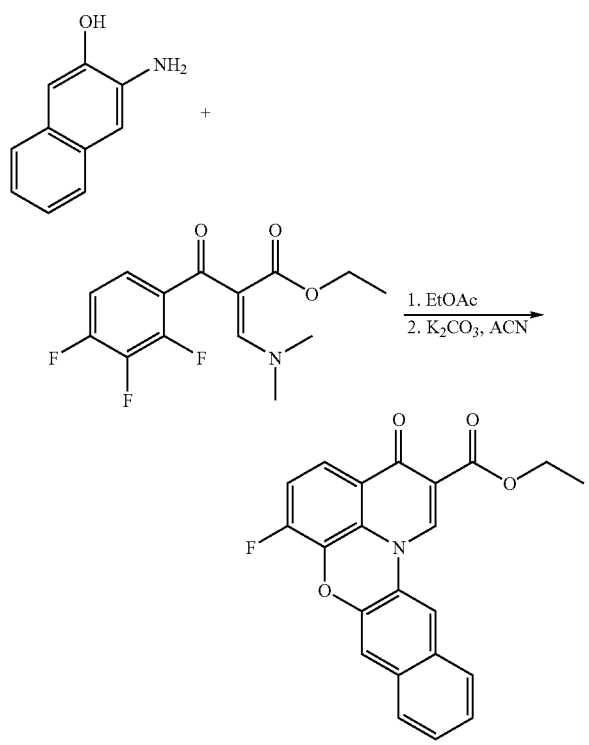

To a solution of the enamine, similarly prepared as the tetrafluoroenamine (14 g, 46.3 mmol) in ethyl acetate (100 mL) was added 3-Amino-2-naphthol (5.0 g, 31.2 mmol) at room temperature and the mixture was immediately placed on a rotary evaporator and the solvent was removed over 2 hours at a temperature below 0° C. (ice formed on the flask) to produce a yellow solid. To this solid was added methanol (200 mL) and the slurry was filtered to afford a yellow solid. This solid was then dissolved in acetonitrile (200 mL) and potassium carbonate was added (10.0 g, 72.5 mmol) and the mixture was heated to 80° C. for 1 hour. The mixture was allowed to cool to room temperature and water was added (500 mL) and the resulting solid was filtered, washed with water and dried to afford the fluoroester as a tan solid (6.0 g, 16.0 mmol) (M+1, 376).

Example 16

Preparation of 1-Fluoro-4-oxo-4H-pyrido[3,2,1-kl]benzo[g]-phenoxazine-5-carboxylic acid

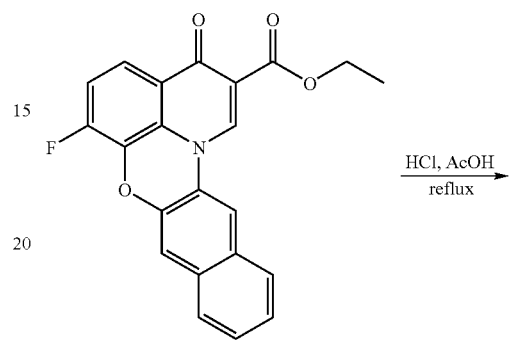

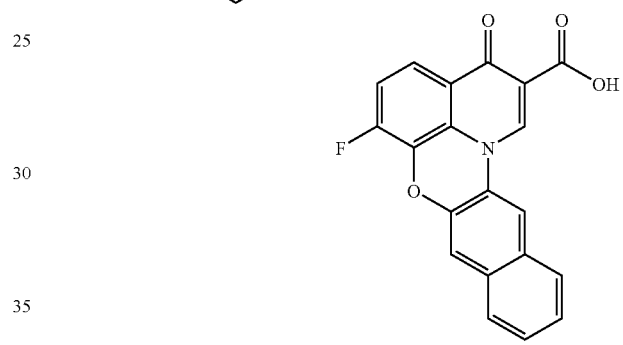

The fluoroester (6.0 g, 16.0 mmol) was dissolved in acetic acid (10 mL) and 12 M HCl was added (10 mL) and the reaction mixture was heated to reflux for 2 hours. The mixture was then cooled to room temperature, poured into water and the solid product was collected by vacuum filtration and dried to afford the fluoroacid as a pale solid (4.8 g, 13.8 mmol) (M+1, 348).

Example 17

Preparation of Ethyl 9-chloro-5,6-difluoro-3-oxo-3H-pyrido[3,2,1-kl]phenoxazine-2-carboxylate

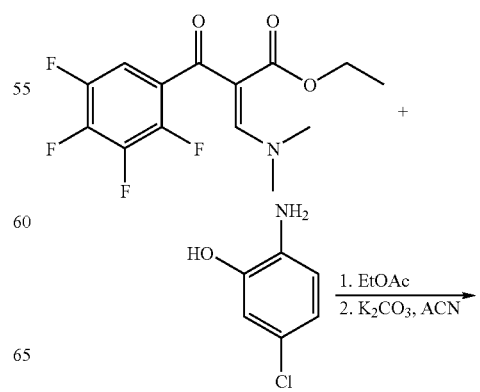

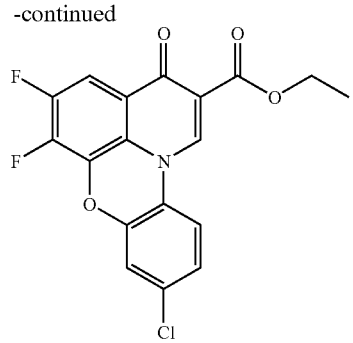

To a solution of the enamine (14.4 g, 45.3 mmol) in ethyl acetate (200 mL) was added 5-chloro-2-aminophenol (5.0 g, 34.8 mmol) and the solvent was removed in vacuo with a rotary evaporator over 2 hours without heating. Methanol was added and the resulting phenolic enamine was isolated by vacuum filtration. The resulting solid (7.0 g) was dissolved in acetonitrile and potassium carbonate was added and the resulting mixture was heated to reflux for 2 hours. The mixture was then allowed to cool to room temperature and poured into Dilute HCl. The resulting solid was collected by vacuum filtration and dried to afford the difluoroester as a pale yellow solid (5.0 g, 13.3 mmol) (M+1, 378).

Example 18

Preparation of 9-Chloro-5,6-difluoro-3-oxo-3H-pyrido[3,2,1-kl]phenoxazine-2-carboxylic acid

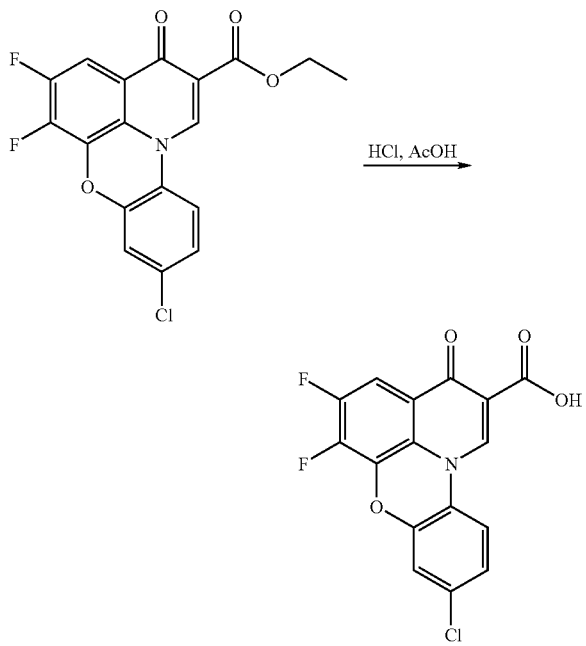

The difluoroester (5.0 g, 13.3 mmol) was dissolved in acetic acid (45 mL) and 12 M HCl was added (30 mL) and the reaction mixture was heated to reflux for 2 hours. The mixture was then cooled to room temperature, poured into water and the solid product was collected by vacuum filtration and dried to afford the difluoroacid as a pale solid (4.0 g, 10.6 mmol) (M+1, 350).

Example 19

Preparation of Ethyl 10-chloro-5,6-difluoro-3-oxo-3H-pyrido[3,2,1-kl]phenoxazine-2-carboxylate

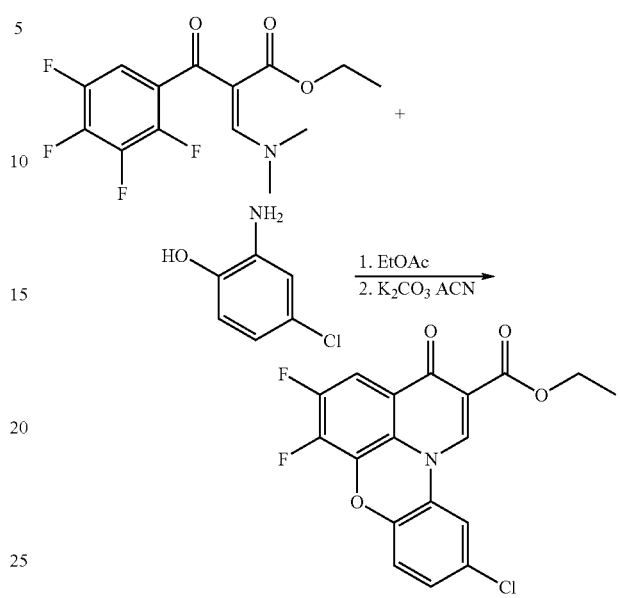

To a solution of the enamine (14.4 g, 45.3 mmol) in ethyl acetate (200 mL) was added 4-chloro-2-aminophenol (5.0 g, 34.8 mmol) and the solvent was removed in vacuo with a rotary evaporator over 2 hours without heating. Methanol was added and the resulting phenolic enamine was isolated by vacuum filtration. The resulting solid (7.5 g) was dissolved in acetonitrile and potassium carbonate was added and the resulting mixture was heated to reflux for 2 hours. The mixture was then allowed to cool to room temperature and poured into Dilute HCl. The resulting solid was collected by vacuum filtration and dried to afford the difluoroester as a pale yellow solid (5.0 g, 13.3 mmol) (M+1, 378).

Example 20

Preparation of 10-Chloro-5,6-difluoro-3-oxo-3H-pyrido[3,2,1-kl]phenoxazine-2-carboxylic acid

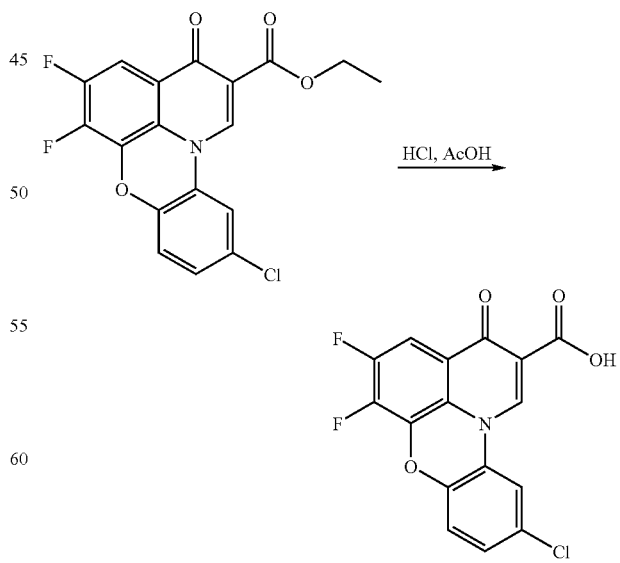

The difluoroester (2.5 g) was dissolved in acetic acid (25 mL) and 12 M HCl was added (20 mL) and the reaction mixture was heated to reflux for 2 hours. The mixture was then cooled to room temperature, poured into water and the solid product was collected by vacuum filtration and dried to afford the difluoroacid as a pale solid (2.0 g, 5.3 mmol) (M+1, 350).

Example 21

Preparation of Ethyl 5,6-Difluoro-3-oxo-3H-pyrido[3,2,1-kl]phenoxazine-2-carboxylate

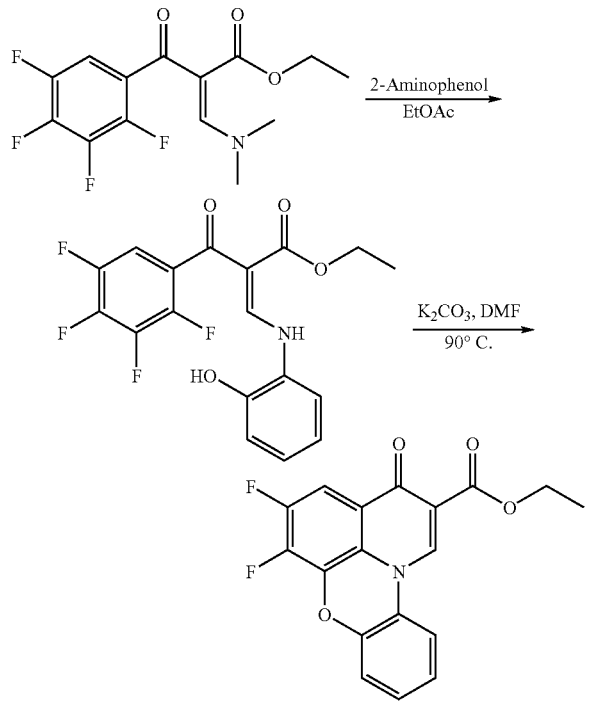

To a solution of the enamine (5.7 g, 17.9 mmol) in ethyl acetate (50 mL) was added 2-aminophenol (1.9 g, 17.43 mmol) at room temperature and the mixture was immediately placed on a rotary evaporator and the solvent was removed over 2 hours at a temperature below 0° C. (ice formed on the flask) to produce a yellow solid. To this solid was added ether (25 mL) and the slurry was filtered to afford a yellow solid. This solid was then dissolved in DMF (20 mL) and potassium carbonate was added (2.9 g, 21 mmol) and the mixture was heated to 90° C. for 1 hour. The mixture was allowed to cool to room temperature and water was added (200 mL) and the resulting solid was filtered, washed with water and dried to afford the phenoxazine as a tan solid (2.9 g, 8.45 mmol) (M+1, 344).

Example 22

Preparation of 5,6-Difluoro-3-oxo-3H-pyrido[3,2,1-kl]phenoxazine-2-carboxylic acid

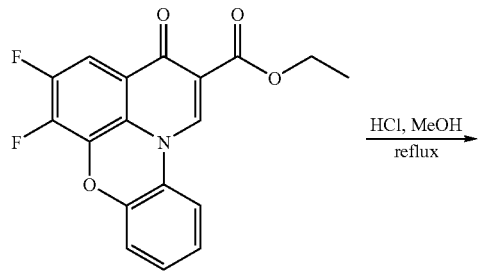

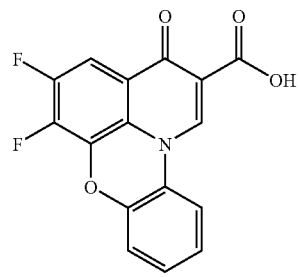

The difluoroester (5.0 g, 14 mmol) was dissolved in methanol (50 mL) and conc HCl was added (20 mL) and the mixture was refluxed for 2 hours. The mixture was allowed to cool to room temperature and the solid was collected by vacuum filtration, washing with methanol to afford the difluoroacid as a light tan powder (4.2 g, 13.3 mmol, 91%) (M+1,316).

Example 23

Preparation of Ethyl 1,2-Difluoro-4-oxo-4H-pyrido[3,2,1-kl]benzo[h]-phenoxazine-5-carboxylate

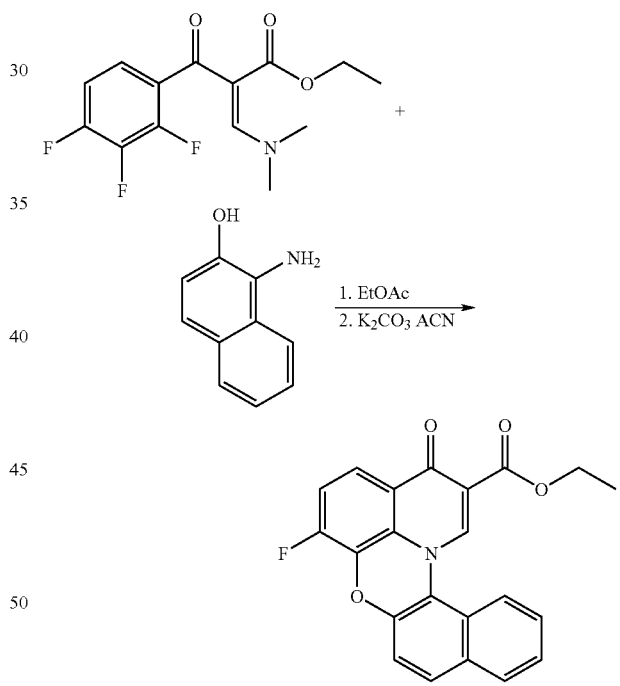

To a solution of the enamine (14.0 g, 45.3 mmol) in ethyl acetate (200 mL) was added 1-amino-2-naphthol (5.0 g, 31.3 mmol) and the solvent was removed in vacuo with a rotary evaporator over 2 hours without heating. Methanol was added and the resulting phenolic enamine was isolated by vacuum filtration. The solid was dissolved in acetonitrile and potassium carbonate (10 g) was added and the mixture was heated to reflux for 2 hours. The mixture was then allowed to cool to room temperature and poured into Dilute HCl. The resulting solid was collected by vacuum filtration and dried to afford the difluoroester as a pale yellow solid (5.0 g, 13.3 mmol) (M+1, 376).

Example 24

Preparation of 1,2-Difluoro-4-oxo-4H-pyrido[3,2,1-kl]benzo[h]-phenoxazine-5-carboxylic acid

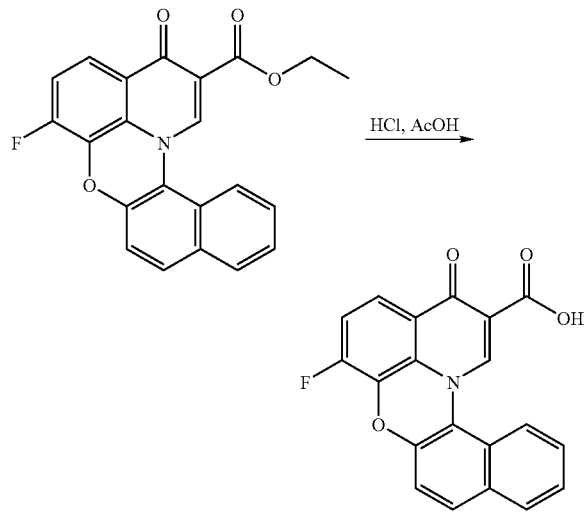

The difluoroester (5.5 g) was dissolved in acetic acid (25 mL) and 12 M HCl was added (20 mL) and the reaction mixture was heated to reflux for 2 hours. The mixture was then cooled to room temperature, poured into water and the solid product was collected by vacuum filtration and dried to afford the difluoroacid as a pale solid (5.0 g, 14.4 mmol) (M+1, 348).

Example 25

Preparation of Ethyl 1,2-Difluoro-4-oxo-4H-pyrido[3,2,1-kl]benzo[f]-phenoxazine-5-carboxylate

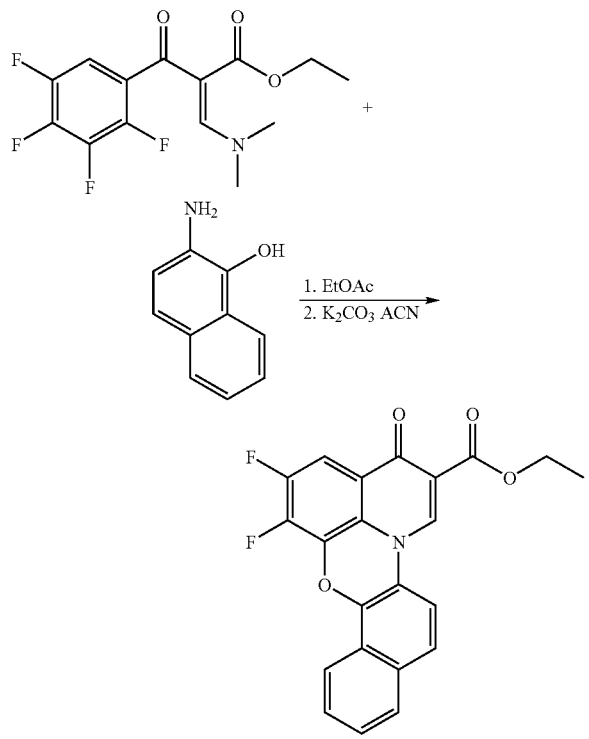

To a solution of the enamine (45 g, 141 mmol) in ethyl acetate (500 mL) was added 2-amino-1-naphthol (15.0 g, 93.8 mmol) and the solvent was removed in vacuo with a rotary evaporator over 2 hours without heating. Methanol was added and the phenolic enamine was isolated by vacuum filtration. The resulting solid was dissolved in acetonitrile (400 mL) and potassium carbonate (25 g) was added and the mixture was heated to reflux for 2.5 hours. The mixture was then allowed to cool to room temperature and poured into Dilute HCl. The resulting solid was collected by vacuum filtration and dried to afford the difluoroester as a pale yellow solid (19.69 g, 50.1 mmol) (M+1, 394).

Example 26

Preparation of 1,2-Difluoro-4-oxo-4H-pyrido[3,2,1-kl]benzo[f]-phenoxazine-5-carboxylic acid

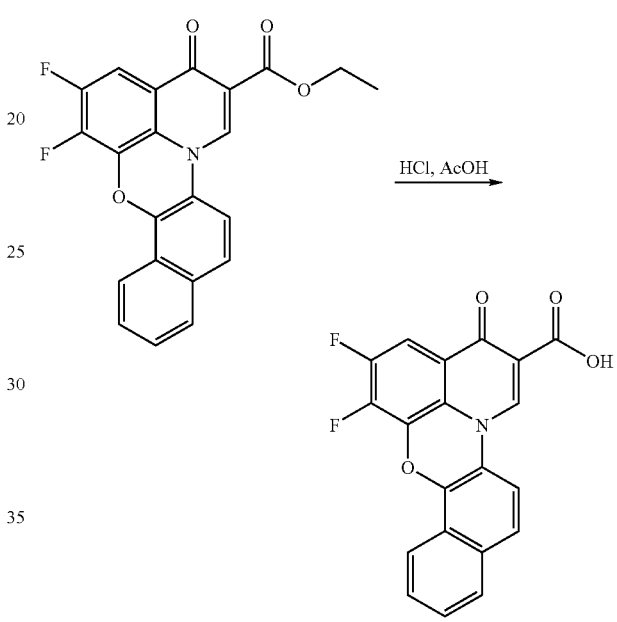

The difluoroester (15.0 g, 38.1 mmol) was dissolved in acetic acid (60 mL) and 12M HCl was added (60 mL) and the reaction mixture was heated to reflux for 2 hours. The mixture was then cooled to room temperature, poured into water and the solid product was collected by vacuum filtration and dried to afford the difluoroacid as a pale solid (11.7 g, 32 mmol) (M+1, 366).

Example 27

Preparation of Ethyl 1,2-Difluoro-4-oxo-4H-pyrido[3,2,1-kl]benzo[b]furan[2,3-g]-phenoxazine-5-carboxylate 3-Aminodibenzofuran-2-ol

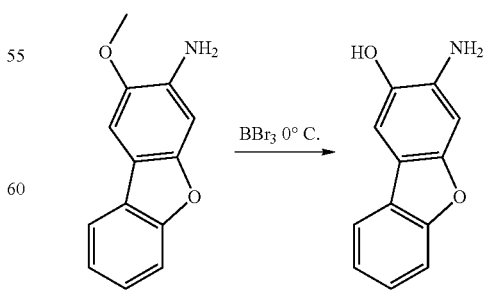

To a solution of the dibenzofuran (15 g, 70.4 mmol) dissolved in methylene chloride (500 mL) at 0° C. was added BBr$_3$ (200 mL, 1 M in CH$_2$Cl$_2$) via addition funnel. After the addition was complete, the mixture was allowed to come to room temperature over 1 hour and then quenched with water followed by potassium carbonate (40 g). The resulting solid was recovered by vacuum filtration and dried to afford the hydroxyl dibenzofuran as a white solid (13.2 g, 199 mmol) (M+1, 200).

Ethyl 1,2-Difluoro-4-oxo-4H-pyrido[3,2,1-kl]benzo[b]furan[2,3-g]-phenoxazine-5-carboxylate

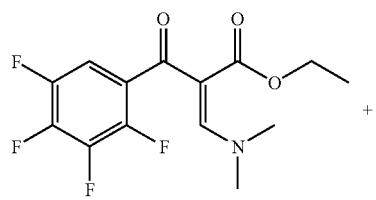

+

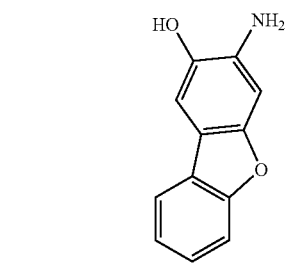

1. DMSO
2. K₂CO₃, ACN

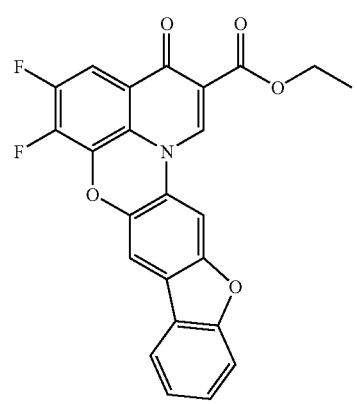

To a solution of the tetrafluoroenamine (15.0 g, 47 mmol) dissolved in DMSO (30 mL) was added the hydroxyl dibenzofuran (12.0 g, 60 mmol) and the mixture was heated to 60° C. under vacuum (rotary evaporator) for 20 minutes. The reaction mixture was then diluted with acetonitrile (200 mL) and potassium carbonate (17 g) was added and the mixture was refluxed for 2.5 hours. The mixture was allowed to cool to room temperature and the solvent was removed in vacuo. A slight excess of 2 M HCl was added to rapidly dissolve the carbonate, and the solid precipitate was filtered and dried to afford the difluoroester as a tan solid (15.0 g, 34.6 mmol) (M+1, 434).

Example 28

Preparation of 1,2-Difluoro-4-oxo-4H-pyrido[3,2,1-kl]benzo[b]furan[2,3-g]-phenoxazine-5-carboxylic acid

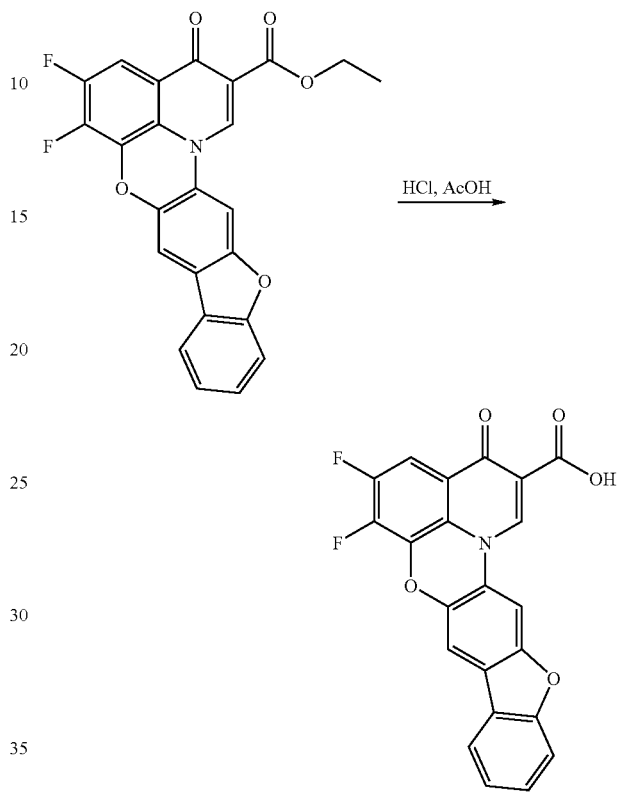

The difluoroester (15.0 g, 34.6 mmol) was dissolved in acetic acid (60 mL) and 12 M HCl was added (60 mL) and the reaction mixture was heated to reflux for 2 hours. The mixture was then cooled to room temperature, poured into water and the solid product was collected by vacuum filtration and dried to afford the difluoroacid as a pale solid (13.7 g, 34 mmol) (M+1, 406).

Example 29

Preparation of Ethyl 2-(ethoxycarbonyl)-5,6-difluoro-3-oxo-3H-pyrido[3,2,1-kl]phenoxazine-10-carboxylate

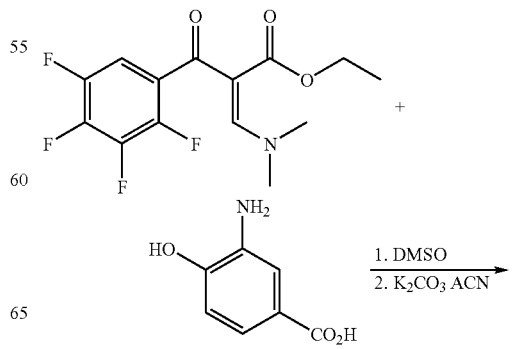

1. DMSO
2. K₂CO₃ ACN

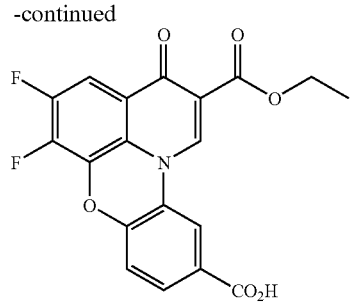

To a solution of the tetrafluoroenamine (7.0 g, 21.9 mmol) dissolved in DMSO (25 mL) was added 4-hydroxy-3-amino benzoic acid (3.0 g, 19.6 mmol) and the mixture was heated to 60° C. under vacuum (rotary evaporator) for 2 hours. The reaction mixture was then diluted with acetonitrile (200 mL) and potassium carbonate (8.0 g) was added and the mixture was refluxed overnight. The mixture was allowed to cool to room temperature and the solvent was removed in vacuo. A slight excess of 2 M HCl was added to rapidly dissolve the carbonate, and the solid precipitate was filtered and dried to afford the difluoroester as a tan solid (6.2 g, 16.0 mmol) (M+1, 388).

Example 30

Preparation of 2-(Ethoxycarbonyl)-5,6-difluoro-3-oxo-3H-pyrido[3,2,1-kl]phenoxazine-10-carboxylic acid

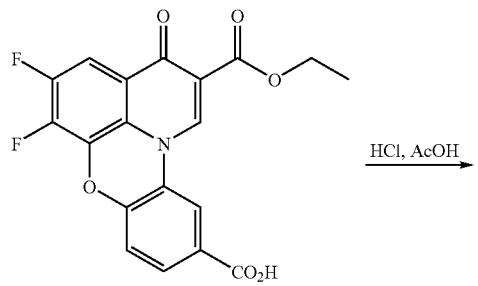

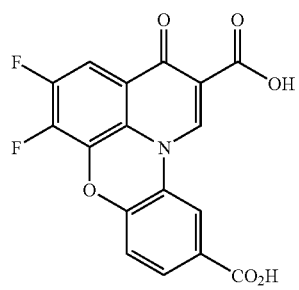

The difluoroester (6.2, 16.0 mmol g) was dissolved in acetic acid (25 mL) and 12 M HCl was added (20 mL) and the reaction mixture was heated to reflux for 2 hours. The mixture was then cooled to room temperature, poured into water and the solid product was collected by vacuum filtration and dried to afford the difluorodi-acid as a pale solid (5.3 g, 14.8 mmol) (M+1, 360).

Example 31

Preparation of Ethyl 5,6-difluoro-10-nitro-3-oxo-3H-pyrido[3,2,1-kl]phenoxazine-2-carboxylate

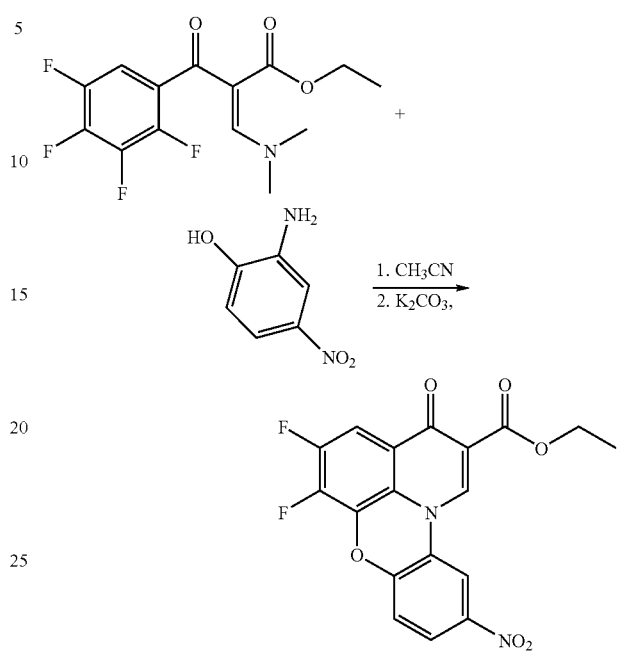

A solution of the enamine (6.0 g, 18.7 mmol) and 2-amino-4-nitrophenol (3.5 g, 23.3 mmol) in acetonitrile was heated to 80° C. for 15 minutes. Potassium carbonate was then added (8.0 g) and the mixture was heated to reflux overnight. The reaction mixture was then filtered hot and the solvent was removed in vacuo to afford the crude nitroester (5.0 g, 12.8 mmol) (M+1, 389).

Example 32

Preparation of 5,6-Difluoro-10-nitro-3-oxo-3H-pyrido[3,2,1-kl]phenoxazine-2-carboxylic acid

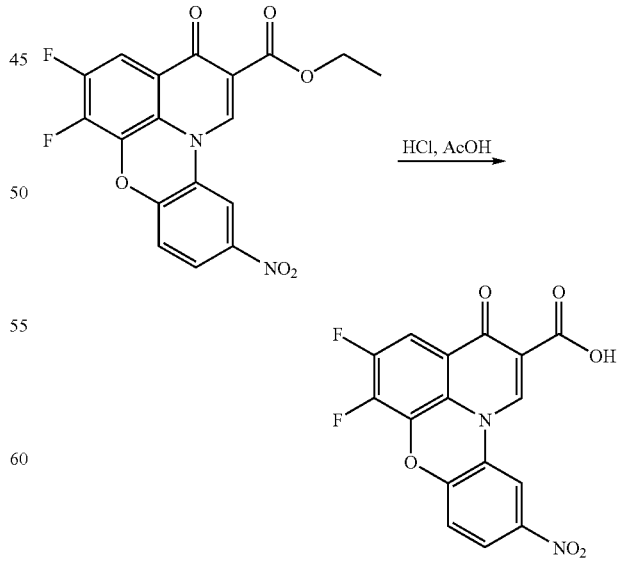

The crude difluoroester (5.0 g, 12.8 mmol) was dissolved in acetic acid (25 mL) and 12 M HCl was added (20 mL) and the reaction mixture was heated to reflux for 2 hours. The mixture was then cooled to room temperature, poured into water and the solid product was collected by vacuum filtration and dried to afford the difluoroacid as a pale solid (2.0 g, 5.5 mmol) (M+1, 361).

Example 33

Preparation of Ethyl 5,6-difluoro-3-oxo-10-phenyl-3H-pyrido[3,2,1-kl]phenoxazine-2-carboxylate

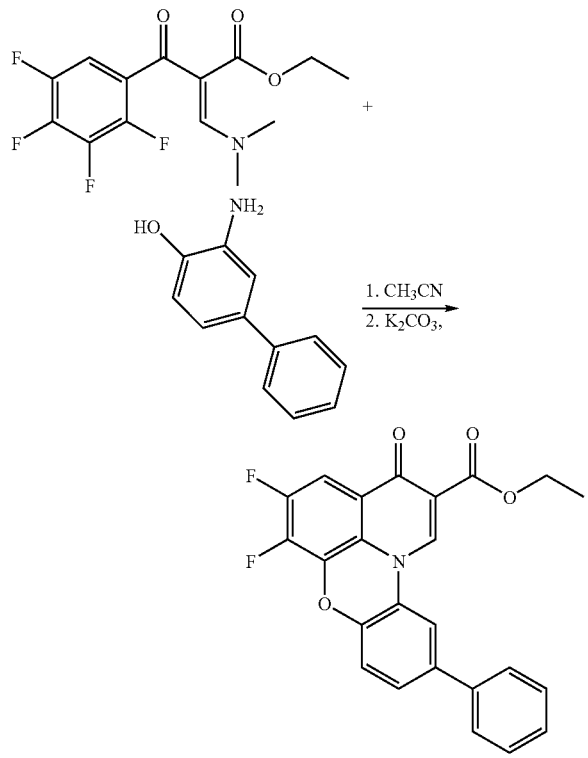

A solution of the enamine (5.4 g, 16.9 mmol) and 3-amino-4-hydroxybiphenyl (3.5 g, 18.9 mmol) in acetonitrile was heated to 80° C. for 90 minutes. Potassium carbonate was then added (8.0 g) and the mixture was heated to reflux overnight. The reaction mixture was then filtered hot and the solvent was removed in vacuo to afford the crude difluoroester (3.9 g, 9.3 mmol) (M+1, 420).

Example 34

Preparation of 5,6-Difluoro-3-oxo-10-phenyl-3H-pyrido[3,2,1-kl]phenoxazine-2-carboxylic acid

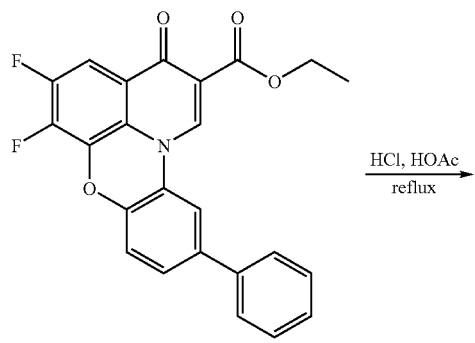

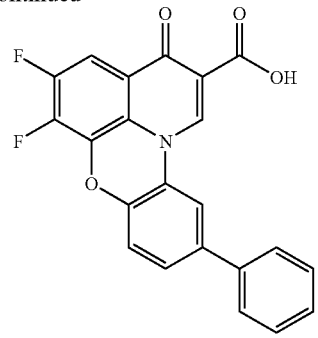

The crude difluoroester (3.6 g, 8.6 mmol) was dissolved in acetic acid (10 mL) and 12 M HCl was added (10 mL) and the reaction mixture was heated to reflux for 2 hours. The mixture was then cooled to room temperature, poured into water and the solid product was collected by vacuum filtration and dried to afford the difluoroacid as a pale solid (2.6 g, 6.6 mmol) (M+1,392).

Example 35

Preparation of Ethyl 1,2-Difluoro-4-oxo-4H-11-sulfonic-acid-pyrido[3,2,1-kl]benzo[h]-phenoxazine-5-carboxylate

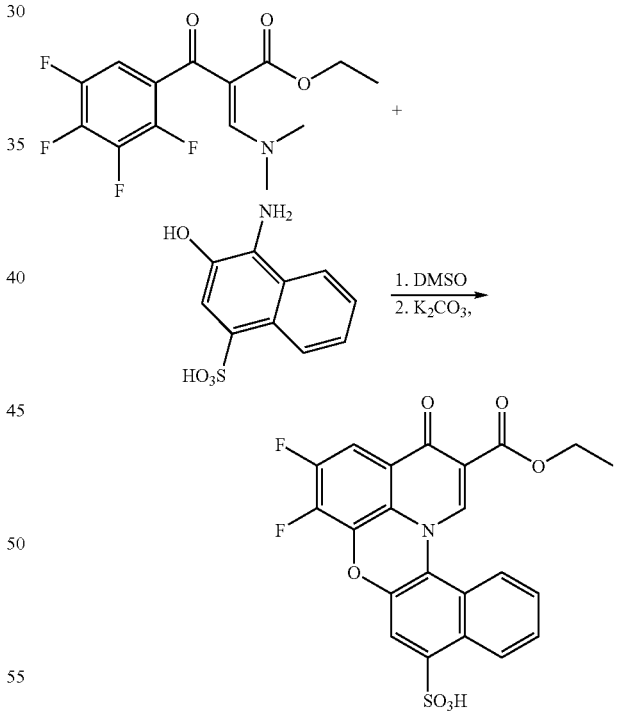

To a solution of the tetrafluoroenamine (5.4 g, 16.9 mmol) dissolved in DMSO (30 mL) was added 1-amino-2-hydroxy-4-naphthalenesulfonic acid (4.8 g, 20 mmol) and the mixture was heated to 60° C. under vacuum (rotary evaporator) for 2 hours. To the reaction mixture was added potassium carbonate (10.0 g) and the mixture was heated to 60° C. for 1 hour. The mixture was allowed to cool to room temperature and a slight excess of 2 M HCl was added to rapidly dissolve the carbonate. The aqueous layer was decanted and the remaining organic residue was dissolved in methanol (100 mL) and precipitated with ethyl acetate (200 mL) and the solid precipitate was filtered and dried to afford the sulfonic acid as a brown solid (3.1 g, 6.5 mmol) (M+1, 474).

Example 36

Preparation of 1,2-Difluoro-4-oxo-4H-11-sulfonic-pyrido[3,2,1-kl]benzo[h]-phenoxazine-5-carboxylic acids

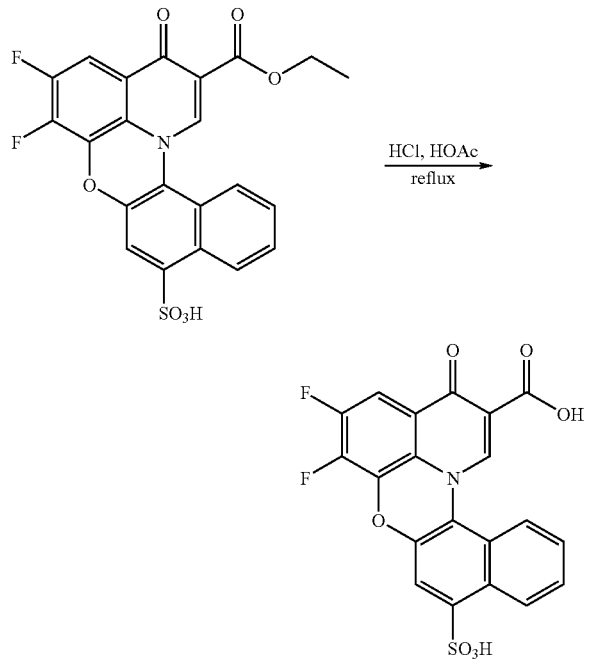

The crude difluoroester (1.5 g, 3.2 mmol) was dissolved in acetic acid (10 mL) and 12 M HCl was added (10 mL) and the reaction mixture was heated to reflux for 30 minutes. The solvent was removed in vacuo to afford the sulfonic acid as a brown solid (1.1 g, 2.5 mmol) (M+1, 446)

Example 37

Preparation of 2-(Ethoxycarbonyl)-5,6-difluoro-3-oxo-3H-pyrido[3,2,1-kl]phenoxazine-9-carboxylic acid

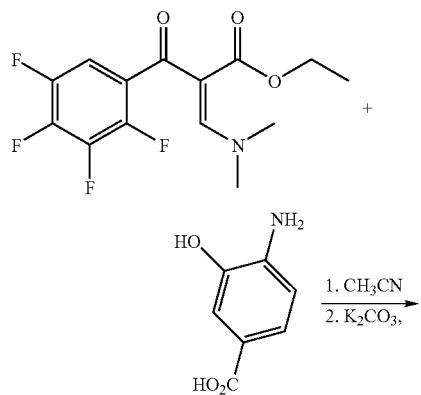

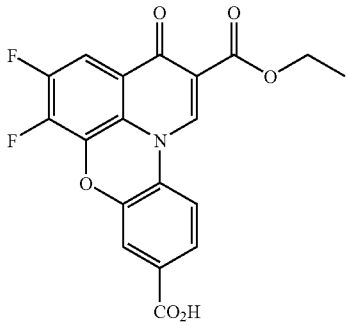

A solution of the difluoroenamine (5.2 g, 16.3 mmol) and 4-amino-3-hydroxybenzoic acid (4.0 g, 26.1 mmol) in DMSO was stirred at room temperature for 1.5 hours. Potassium carbonate (8 g) was then added and the reaction mixture was stirred under vacuum (rotary evaporator) for 1 hour. The mixture was then heated to 100° C. for 1 hour and then allowed to cool to room temperature. The reaction mixture was then poured into 1 M $H_2SO_4$ (500 mL) and the solids were recovered by vacuum filtration. The resulting solid was dried to afford the crude difluoroacid as a tan solid (5.0 g, 12.9 mmol) (M+1, 388).

Example 38

Preparation of 5,6-Difluoro-3-oxo-3H-pyrido[3,2,1-kl]phenoxazine-2,9-dicarboxylic acid

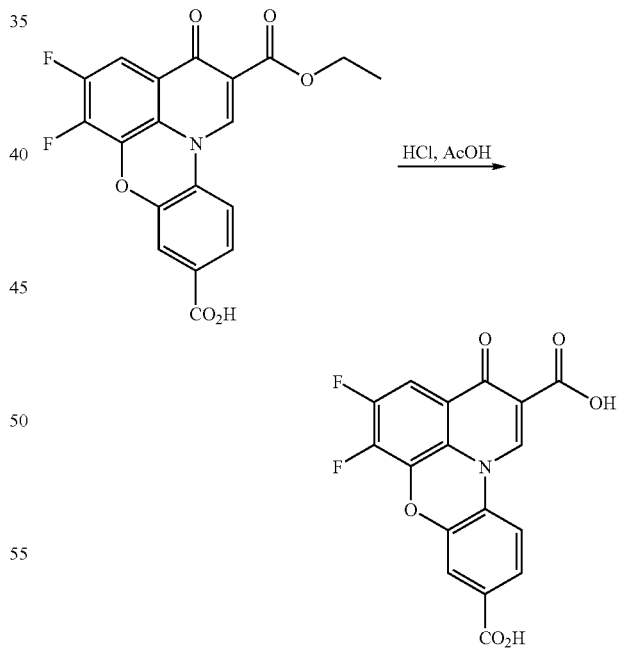

The crude difluoroester (5.0 g, 12.9 mmol) was dissolved in acetic acid (20 mL) and 12 M HCl was added (20 mL) and the reaction mixture was heated to reflux for 1 hour. The reaction was allowed to cool to room temperature and water was added. The resulting solid was collected by vacuum filtration and dried overnight to afford the di-acid as a tan solid (1.9 g, 5.3 mmol) (M+1, 360).

Example 39

Preparation of Ethyl 1,2-Difluoro-4-oxo-4H-pyrido[3,2,1-kl]-8-fluorenone-5-carboxylate 3-Nitro-2-hydroxyfluorenone

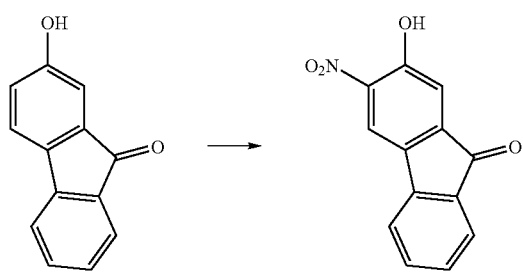

A solution of $NO_2BF_4$ (3.52 g, 25.5 mmol) in acetonitrile (100 ml) was added dropwise to a solution of 2-hydroxyfluorenone (5 g, 25.5 mmol) in acetonitrile (400 ml) at ambient temperature. The reaction mixture was then cooled to 0° C. and water (100 ml) was added to precipitate impurities. After filtration, water (200 ml) was added and the precipitate filtered off as a red solid (68%) (M+1, 242).

3-amino-2-hydroxyfluorenone

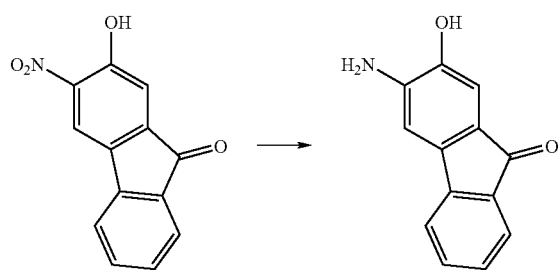

A mixture of 3-nitro-2-hydroxyfluorenone (1.6 g, 6.6 mmol) and $SnCl_2$ (3 g, 6.6 mmol) was refluxed in 100 ml acetic acid:conc. HCl (1:1) for 1 hour. The mixture was allowed to cool to room temperature and neutralized with ammonium hydroxide. After extracting with EtOAc (3×100 ml), combined organic fractions were dried over magnesium sulfate and evaporated to leave the product as a brown solid (65%) (M+1, 212).

Ethyl 1,2-Difluoro-4-oxo-4H-pyrido[3,2,1-kl]-8-fluorenone-5-carboxylate

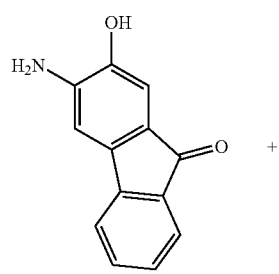

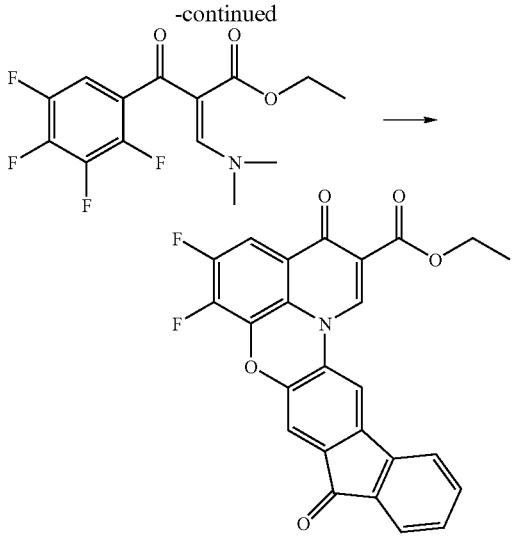

A mixture of 3-amino-2-hydroxyfluorenone (0.9 g, 4.26 mmol) and ethyl-2-(2',3',4',5'-tetrafluorobenzoyl-)-3-(dimethylamino)-prop-2-enoate (1.36 g, 4.26 mmol) were heated in DMSO (50 ml) under vacuum for 18 hr. The product was extracted using EtOAc/Brine and the organic layers combined and dried to give the product as a red solid. The solid was dissolved in DMSO (40 ml) containing a large excess of $K_2CO_3$ and heated at 100° C. for 30 min. After cooling to room temperature, brine (30 ml) was added and the precipitated product collected as a yellow solid (60% over two steps) (M+1, 446).

Example 40

Preparation of 1,2-Difluoro-4-oxo-4H-pyrido[3,2,1-kl]-8-fluorenone-5-carboxylic acid

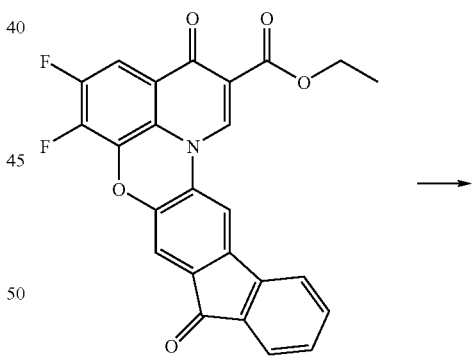

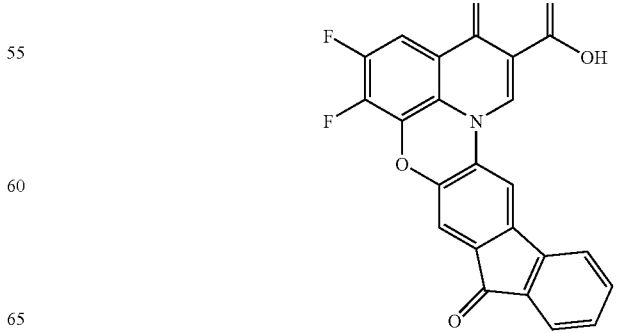

A mixture of ethyl 1,2-difluoro-4-oxo-4H-pyrido[3,2,1-kl]-8-fluorenone-5-carboxylate in acetic acid:conc. HCl (1:1) (50 ml each) was heated at reflux for 2 hr. After cooling to room temperature, water (50 ml) was added and the product collected as yellow solid (94%) (M+1, 418).

Example 41

Preparation of Ethyl 1,2-Difluoro-4-oxo-4H-pyrido[3,2,1-kl]-8-anthraquinone-5-carboxylate

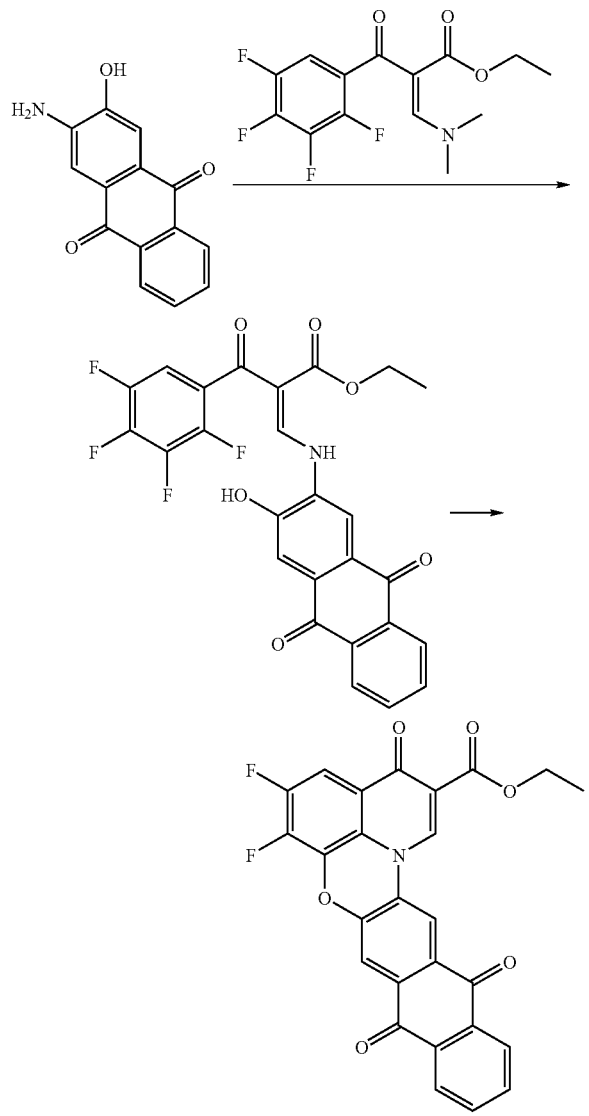

A mixture of 3-amino-2-hydroxyanthraquinone (5.54 g, 23.2 mmol) and ethyl-2-(2',3',4',5'-tetrafluorobenzoyl-)-3-(dimethylamino)-prop-2-enoate (8.7 g, 34.8 mmol) were heated in a minimum of DMSO (~10 ml) under vacuum for 24 hr. The product was precipitated by the addition of water (50 ml). The solid was dried overnight in a vacuum oven and dissolved in DMSO (40 ml) containing a large excess of K₂CO₃ and heated at 100° C. for 30 min. After cooling to room temperature, brine (30 ml) was added and the precipitated product collected as a yellow solid (60% over two steps) (M+1, 474).

Example 42

Preparation of 1,2-Difluoro-4-oxo-4H-pyrido[3,2,1-kl]-8-anthraquinone-5-carboxylic acid

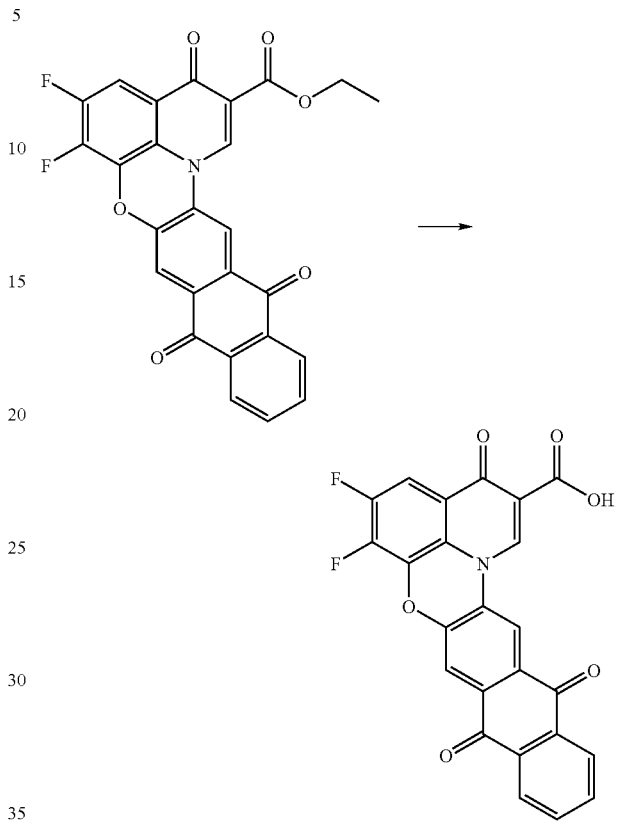

A mixture of ethyl 1,2-difluoro-4-oxo-4H-pyrido[3,2,1-kl]-8-anthraquinonenone-5-carboxylate (3.5 g, 6.8 mmol) in acetic acid:conc. HCl (1:1) (50 ml each) was heated at reflux for 2 hr. After cooling to room temperature, water (50 ml) was added and the product collected as yellow solid (94%) (M+1, 446).

Example 43

Preparation of Ethyl 1,2-Difluoro-4-oxo-4H-pyrido[3,2,1-kl]-8-phenyl-phenoxazole-5-carboxylate 2-amino(t-butoxy carbonyl)-5-amino hydroquinone

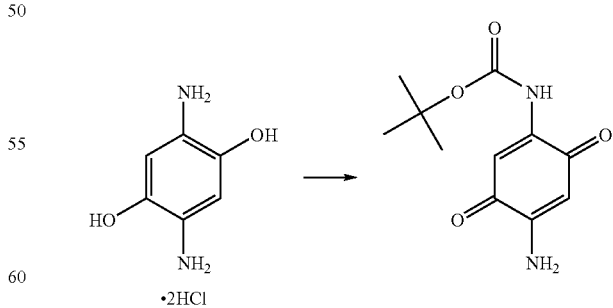

A solution of Boc anhydride (7.17 g, 33 mmol) and DIEA (17 ml, 99 mmol) in DMSO (20 ml) was added dropwise at room temperature to stirred solution of 1,4-dihydroxy-2,5-diaminobenzene (7 g, 33 mmol). After stirring for 18 hr, the product was separated between EtOAc and brine and the organic layers combined and dried over MgSO₄. After removal of solvent the residue was subjected to column chromatography on silica eluting with 25-50% EtOAc in hexane to give pure product (45%) (M+1,239).

4-hydroxy-3-amino(t-butoxy carbonyl)-phenoxazole

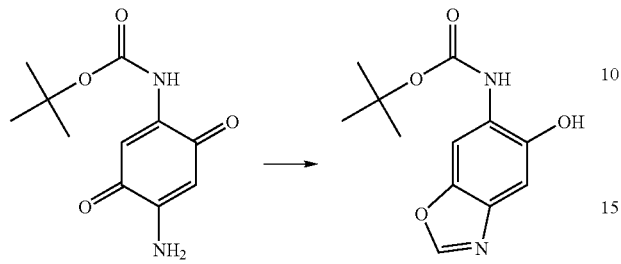

To solution of 2-amino(t-butoxy carbonyl)-5-amino hydroquinone (4.69 g, 23.3 mmol) dissolved in acetonitrile/water (1:1; 20 ml) was added Na hydrosulfite (large excess) and the mixture stirred at room temp. for 15 min. The acetonitrile was removed in vacuo and the aqueous mixture extracted with EtOAc (3×20 ml). Combined organic layers were dried over MgSO₄ and solvent removed in vacuo. The residue was taken up in neat triethyl orthoformate (100 ml), left to stir for 16 hr then heated to reflux for 10 min. The product was precipitated following cooling to room temp. by the addition of water (83%) (M+1, 251).

4-hydroxy-2-amino phenoxazole

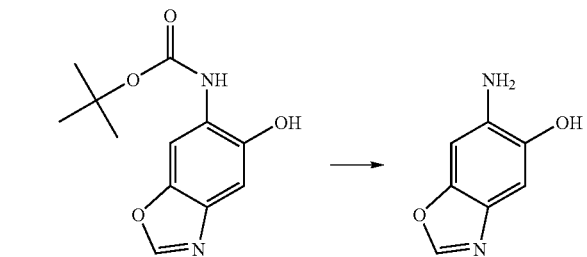

4-Hydroxy-3-amino(t-butoxy carbonyl)-phenoxazole (3 g, 12 mmol) was dissolved in neat TFA (100 ml) and allowed to stir at room temperature for 1 hour. TFA was removed in vacuo to leave the final product as a TFA salt (quant.) (M−1, 149)

Ethyl-2-(2',3',4',5'-tetrafluorobenzoyl-)-3-(N-(4-hydroxy-2-amino phenoxazole))-prop-2-enoate

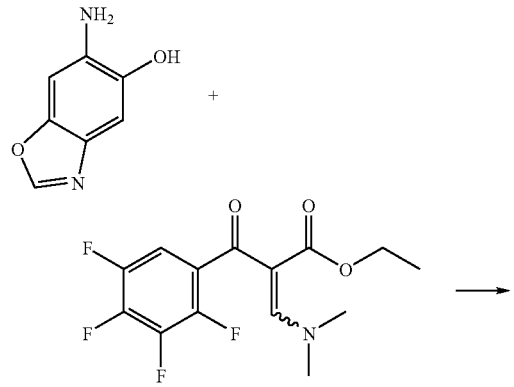

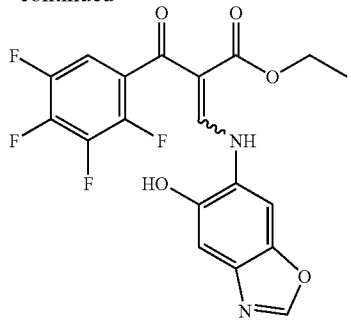

A solution of ethyl-2-(2',3',4',5'-tetrafluorobenzoyl-)-3-(dimethylamino)-prop-2-enoate (7.34 g, 23 mmol) and 2-amino-4-phenyl-phenol (3.45 g, 23 mmol) in EtOAc (20 ml) containing triethylamine (10 ml) was stirred under vacuum on the rotary evaporator for 3 hours. The EtOAc was removed in vacuo and the residue subjected to column chromatography on silica eluting with 50% EtOAc in hexane to give pure product (72%) (M+1, 425).

Ethyl 1,2-Difluoro-4-oxo-4H-pyrido[3,2,1-kl]-8-phenyl-phenoxazole-5-carboxylate

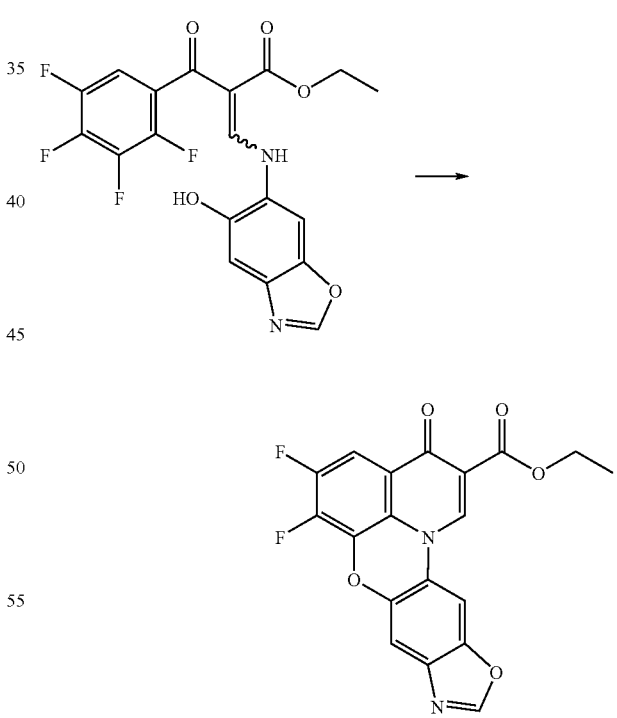

A solution of ethyl-2-(2',3',4',5'-tetrafluorobenzoyl-)-3-(N-(4-hydroxy-2-amino phenoxazole))-prop-2-enoate (3.5 g, 8.25 mmol) in DMSO (50 m) containing K₂CO₃ (large excess) was heated at 80° C. for 10 min. After cooling to room temperature, water was added to precipitate the product as a yellow sold (82%) (M+1, 385).

Example 44

Preparation of 1,2-Difluoro-4-oxo-4H-pyrido[3,2,1-kl]-8-(3'-hydroxy-4'-amino phenyl)-5-carboxylic acid

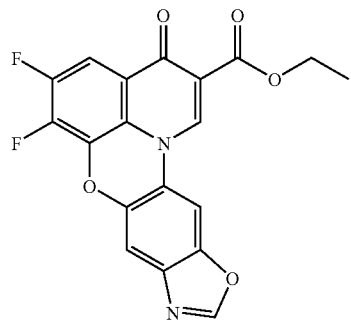

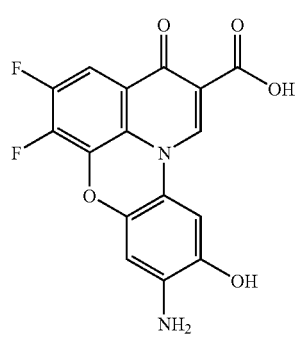

A mixture of ethyl 1,2-difluoro-4-oxo-4H-pyrido[3,2,1-kl]-8-phenyl-phenoxazole-5-carboxylate (2.3 g, 6 mmol) in acetic acid:conc. HCl (1:1; 100 ml) was heated to reflux for 30 min. After cooling to room temp., volatiles were removed in vacuo to leave the product as a brown solid (82%) (M+1, 347).

Example 45

Preparation of 1,2-Difluoro-4-oxo-4H-pyrido[3,2,1-kl]-8-(nitro-phenoxazine)-5-carboxylic acid 1,2-Difluoro-4-oxo-4H-pyrido[3,2,1-kl]-8-(3'-hydroxy-4'-amino-(N-2''-fluoro-4''-nitro phenyl)-phenyl))-5-carboxylic acid

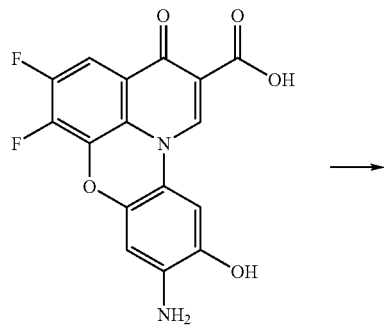

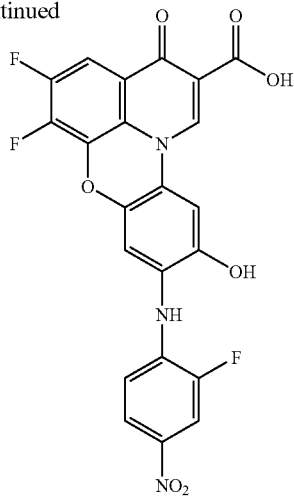

A solution of 1,2-difluoro-4-oxo-4H-pyrido[3,2,1-kl]-8-(3'-hydroxy-4'-amino phenyl)-5-carboxylic acid (0.5 g, 1.44 mmol), 3,4-difluoro-nitro benzene (0.5 ml, 4.3 mmol) and DIEA (1 ml) was heated to 90° C. in NMP (50 ml) for 30 min. After cooling to room temp. the product was precipitated by the addition of water and filtered (63%) (M+1, 486).

1,2-Difluoro-4-oxo-4H-pyrido[3,2,1-kl]-8-(nitro-phenoxazine)-5-carboxylic acid

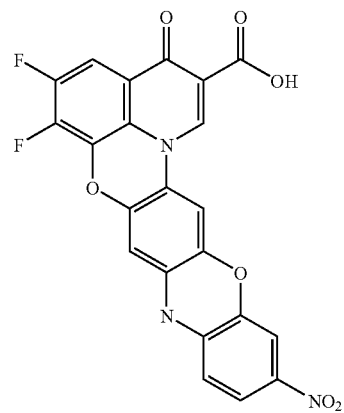

A solution of 2-difluoro-4-oxo-4H-pyrido[3,2,1-kl]-8-(3'-hydroxy-4'-amino phenyl)-5-carboxylic acid (0.3 g, 0.6 mmol) in DMSO (50 ml) containing an excess of $K_2CO_3$ was stirred and heated to 110° C. for 1 hr. After cooling to room temp. the product was precipitated by the addition of 3M HCl and filtered (71%) (M+1, 465).

Example 46

Preparation of 1,2-Difluoro-4-oxo-4H-pyrido[3,2,1-kl]-8-(amino-phenoxazine)-5-carboxylic acid

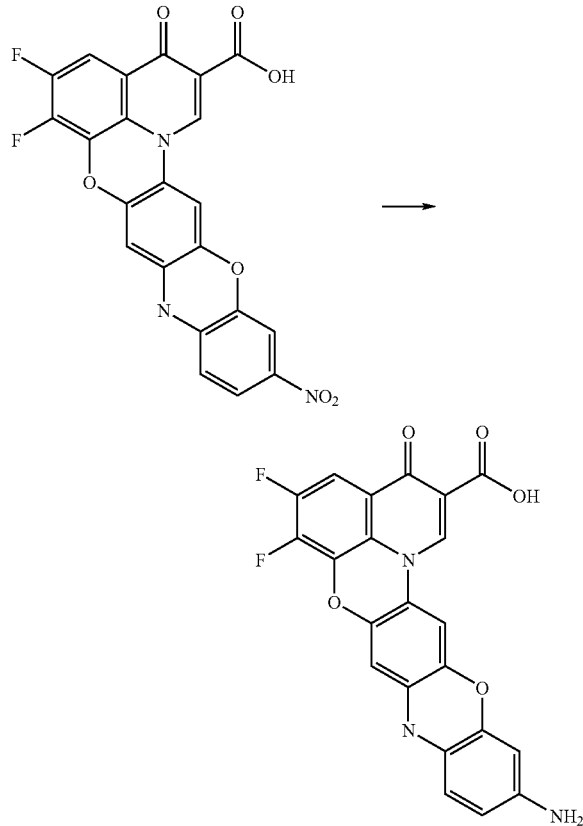

A mixture of 1,2-difluoro-4-oxo-4H-pyrido[3,2,1-kl]-8-(nitro-phenoxazine)-5-carboxylic acid (0.1 g, 0.2 mmol) and Tin (II) chloride (0.15 g, 0.6 mmol) in acetic acid:conc. HCl (1:1; 50 ml) was heated to reflux for four hr. After cooling to room temp. the product was precipitated by the addition of water and filtered (72%) (M+1,435).

Example 47

Preparation of Preparation of Amide Derivatives of Substituted Quinobenzoxazine Analogs

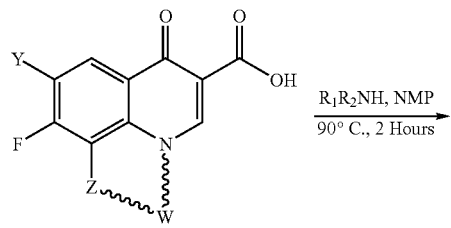

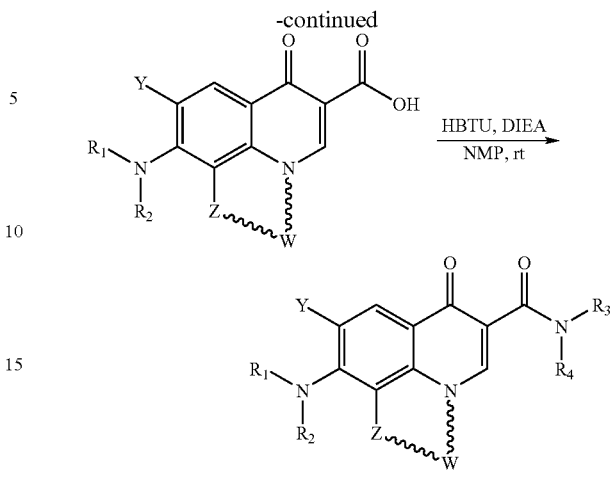

To a series of solutions of the fluoroacid (0.5 mmol) in NMP (3.6 mL) was added the amines $NHR_1R_2$ (0.5-2.0 mmol) at room temperature. The vessels were sealed and heated on a 90° C. hotplate with constant stirring for 1-2 hours until the reactions were determined to be complete by HPLC/MS analysis. The reaction mixtures were allowed to cool to room temperature and water was added (20 mL). The resulting precipitates were collected by vacuum filtration and dried under vacuum. In cases where 1.0 equivalent of amine was used, the resulting reaction mixtures were used in the next step "as is." The resulting solids or solutions were treated with HBTU (2.5 eq.) and DIEA in 3.6 mL NMP and allowed to stir for 30 minutes at room temperature under an inert atmosphere. These solutions were added to a series of amines $NHR_3R_4$ (2.5 equivalents) in a 96 well format (Whatman Uniplate, 2 mL) and allowed to react for 2 hours. Methanol was then added (50-100 µL) and the plate was filtered (Whatman Unifilter Polypropylene). The resulting liquids were directly chromatographed on reverse HPLC (Waters Xterra 19×50 mm) with mass directed collection (Micromass ZQ, Waters FCII). The fractions were analyzed for purity (MS TIC, UV) and dried by vacuum evaporation (Savant) with an average yield of 5-10 mg). Tables 1 and 2 list exemplary ester-substituted and amide-substituted quinobenzoxazines analogs, respectively.

Example 48

Antitumor Data

Two xenograft models for inoculation were harvested and diluted to a concentration of $50\times10^6$ cells/ml or $100\times10^6$ cells/ml. Four to six week old nude mice were injected with 0.1 ml of the cell suspension which contains between $5\times10^6$ and $10\times10^6$ cells. When tumors are of a suitable size compound dosing is commenced. Tumor sizes are measured throughout the treatment period with calipers and body weights also measured.

Figure 2:
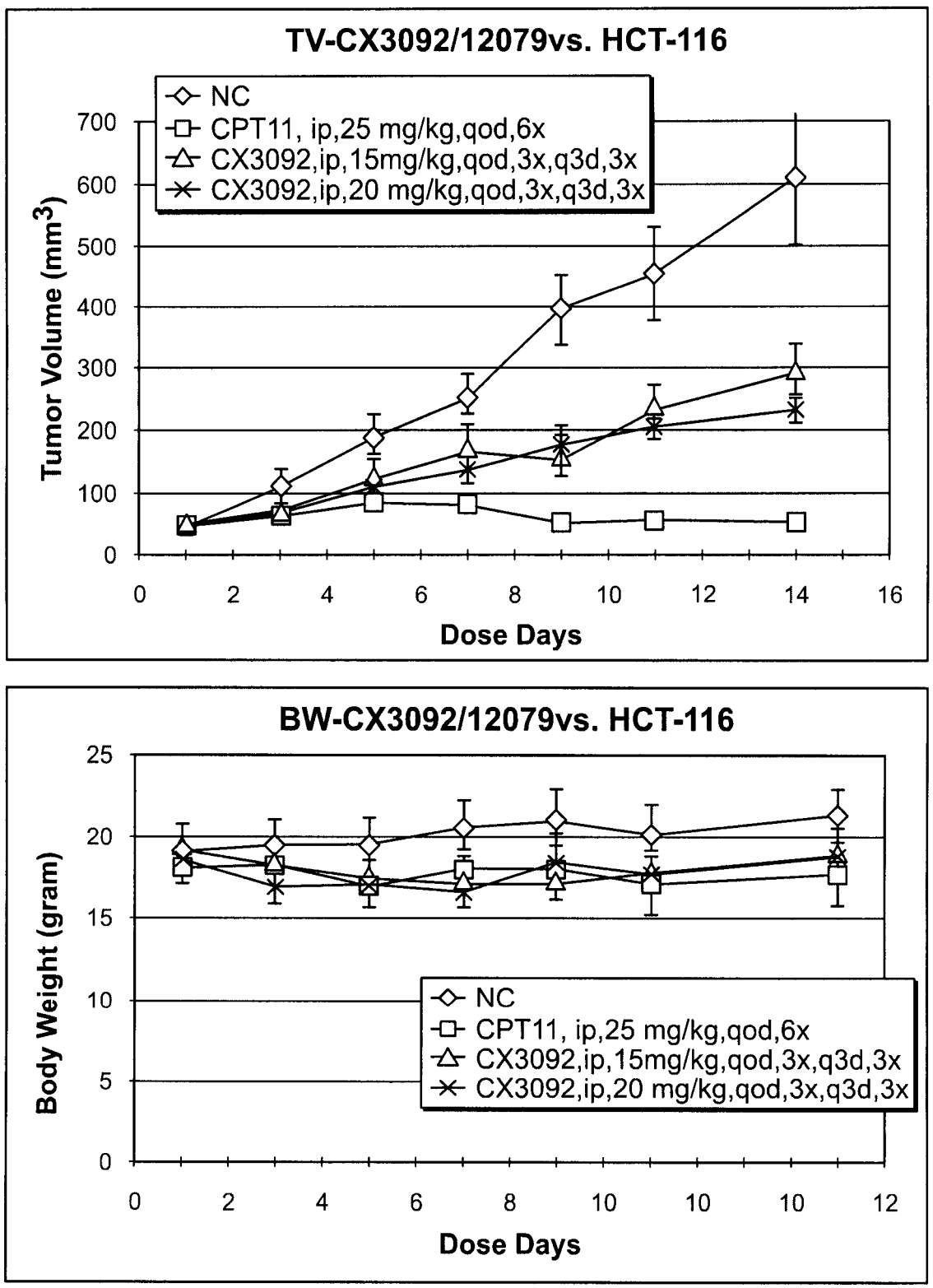
FIG. 2 shows antitumor activity of a compound having formula 1 tested in HCT 116.

Antitumor activities for compounds CX-3092 (1204) and CX-1535 (148) are shown in FIGS. 1 and 2, indicating efficacy (slow tumor weight gain) and a lack of toxicity (little body weight change). FIG. 1 shows the antitumor activity of compound 494 in Ramos, a model for fatal childhood leukemia. FIG. 2 shows the antitumor activity of compound 516 in HCT-116, a model of colorectal cancer.

Example 49

Cell Proliferation and/or Cytotoxicity Assay

Cell Culture

Human cervical epithelial cells (HeLa cells) were obtained from American Type Culture Collection (Manassas, Va.). Cells were grown in Eagle's minimum essential medium (MEM, Hyclone, Utah) supplemented with 2 mM Glutamine, 0.1 mM nonessential amino acid, 1 mM Na Pyruvate, 1.5 g/L NaHCO$_3$, 50 mg/L gentamicin, and 10% fetal bovine serum (Hyclone, USA) in a humidified atmosphere of 5% CO$_2$ at 37° C.

MTS Assay

Antiproliferative effects of anticancer drugs were tested by the CellTiter 96 AQ$_{ueous}$ assay (Promega, Wis.), which is a colorimetric assay for determining the number of viable cells. (See, e.g., Wang, L., et al., *Methods Cell Sci* (1996) 18:249-255).

Cells (4,500 cells/well) were seeded on 96 well flat bottom plates (Corning, N.Y.) in 100 µl of culture medium without any anticancer drug on day 0, and the culture medium was exchanged for that contained anticancer drugs at various concentrations on day 1. After incubation for 3 days under normal growth conditions (on day 4), the monolayers were washed once in PBS, and the medium was switched to 100 µl of PBS in each of the 96 well plate. After mixing MTS and PMS at the ratio of 20:1, 20 µl of MTS/PMS solution was added to each of the 96 well plate and incubated for 4 hours in a humidified atmosphere of 5% CO$_2$ at 37° C. The absorbance was read at 490 nm using FLUOstar Galaxy 96 well plate reader (BMG Labtechnologies, Germany). µM concentrations (MTS data) reported in Tables 1-2 are concentrations at which 50% of antiproliferative cell response is seen. Compounds whose IC$_{50}$ values were greater than 5 µM were not reported.

Example 50

Measurement of mRNA Values in Cell Assays

Real-time quantitative PCR (QPCR) method was used to detect accurately the changes of the target c-myc and the endogenous reference GAPDH gene copies in the same tube. Cells (15,000 cells/well) were seed on 96 well flat bottom plates (Corning, N.Y.) and incubated under normal growth conditions for overnight. The next day, the culture medium was exchanged for that contained anticancer drugs at various concentrations and incubate for 4 hrs in a humidified atmosphere of 5% CO$_2$ at 37° C. Total RNA (tRNA) was extracted using the RNeasy 96 Kit (QIAGEN, CA). The concentration of the tRNA was determined by the RiboGreen RNA Quantitation Reagent (Molecular Probes, Oreg.).

Reverse-transcription (RT) reaction was occurred using 50 ng of tRNA from each well in a 25 µl reaction containing 1× TaqMan RT buffer, 2.5 uM random hexamers, 5.5 mM MgCl$_2$, 0.5 mM each deoxynucleoside triphosphate (dNTP), 30 U MultiScribe Reverse Transcriptase, and 10 U RNase inhibitor. RT reactions were incubated for 10 min at 25° C., reverse-transcribed for 30 min at 48° C., inactivated for 5 min at 95° C., and placed at 4° C. All RT reagents were purchased from Applied Biosystems, CA.

Real-Time QPCR reaction was performed in a 50 µl reaction containing the 5 µl of cDNA, 1× Universal PCR Master Mix, 1×c-myc Pre-Developed Primers and Probe set, and 0.8×GAPDH Pre-Developed Primers and Probe set. Because of the relative abundance of GAPDH gene in Hela, GAPDH primers and probe concentration were adjusted to get accurate threshold cycles (C$_T$) for both genes in the same tube. The threshold cycle (C$_T$) indicates the fractional cycle number at which the amount of amplified target reaches a fixed threshold. By doing so, the GAPDH amplification was stopped before it can limit the common reactants available for amplification of the c-myc, resulted in a reduction in ΔRn value of GAPDH, but no effect on its C$_T$ value, and equal amplification efficiency for both genes. The ΔRn value represents the normalized reporter signal minus the baseline signal. ΔRn increases during PCR as amplicon copy number increases until the reaction approaches a plateau.

The c-myc probe was labeled with 6FAM™ dye-MGB and the GAPDH probe was labeled with VIC™ dye-MGB. Pre-incubation was performed for 2 min at 50° C. to activate AmpErase UNG enzyme and then for 10 min at 95° C. to activate AmpliTaq DNA Polymerase. DNA was amplified for 40 cycles of 15 sec at 95° C. and 1 min at 60° C. Human c-myc and GAPDH cDNA were amplified, detected, and quantitated in real time using the ABI Prism 7000 Sequence Detection system (Applied Biosystems, CA), which was set to detect both 6-FAM and VIC reporter dyes simultaneously.

The data was analyzed by using the ABI PRISM Sequence Detection System and Microsoft Excel. Relative quantitation was done using the standard curve and comparative C$_T$ method at the same time, and both methods gave equivalent results. The cycle at which the amplification plot crosses the C$_T$ is known to accurately reflect relative mRNA values. (See, Heid, et al., *Genome Res.* (1996) 6:986-994; Gibson, et al, *Genome Res.* (1996) 6:995-1001). QPCR reactions were set up in triplicate at each cDNA sample and the triplicate C$_T$ values were averaged. All reagents including Pre-Developed Primers and probe set were purchased from Applied Biosystems, CA. µM concentrations (STOP data) reported in Tables 1-2 are concentrations at which 50% inhibition of c-myc mRNA levels are seen. Compounds whose IC$_{50}$ values were greater than 5 µM were not reported.

It is understood that the foregoing detailed description and accompanying examples are merely illustrative, and are not to be taken as limitations upon the scope of the invention. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof. U.S. patents and publications referenced herein are incorporated by reference.

TABLE 1

| | Structure | Stop Data c-Myc μM | MTS Data Hella μM |
|---|---|---|---|
| 1 | 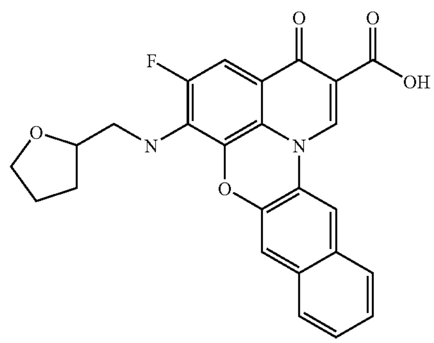 | 4 | |
| 2 | 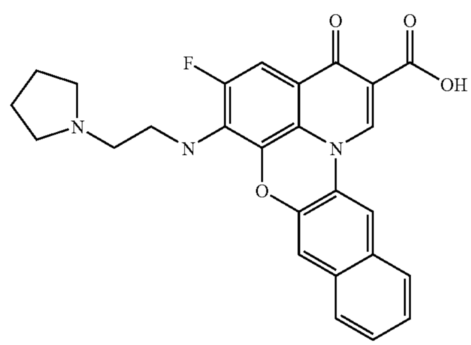 | 2.5 | |
| 3 | 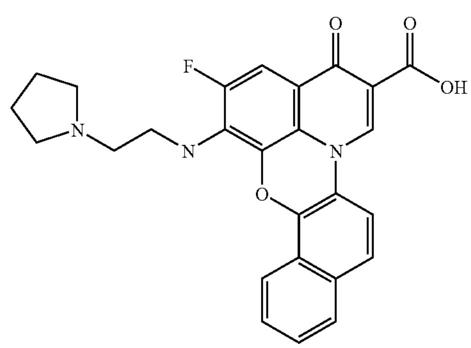 | 2.5 | |
| 4 | 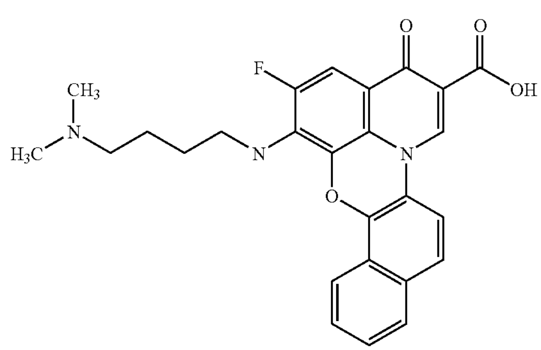 | 1.76 | |

TABLE 1-continued

| | Structure | Stop Data c-Myc μM | MTS Data Hella μM |
|---|---|---|---|
| 5 | 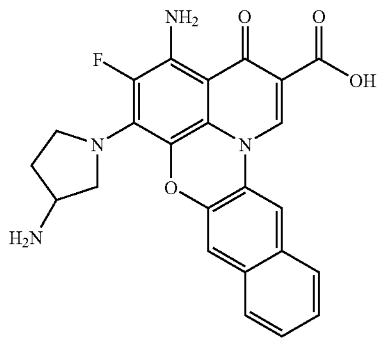 | 1.75 | 7.20 |
| 6 | 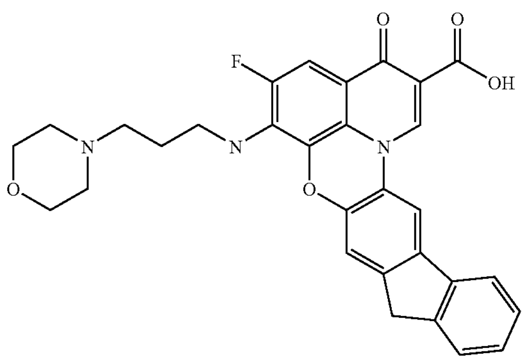 | 1.75 | |
| 7 | 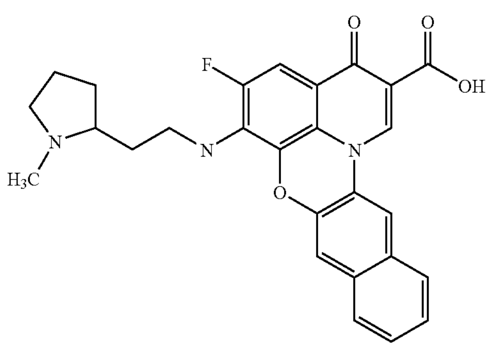 | 1.75 | |
| 8 | 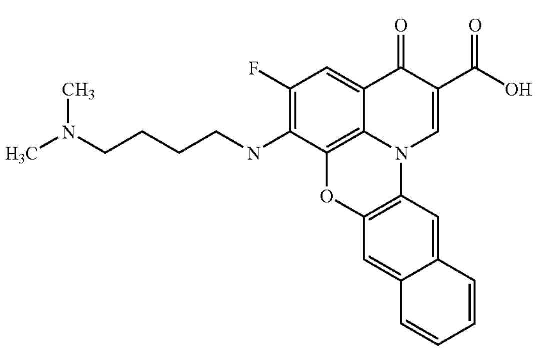 | 1.75 | |

TABLE 1-continued
| Structure | Stop Data c-Myc μM | MTS Data Hella μM |
|---|---|---|
| 9 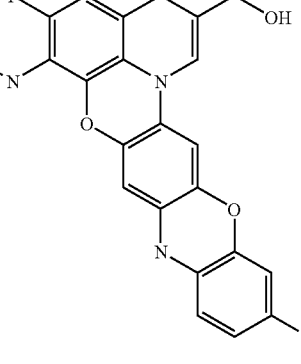 | | 1.75 |
| 10 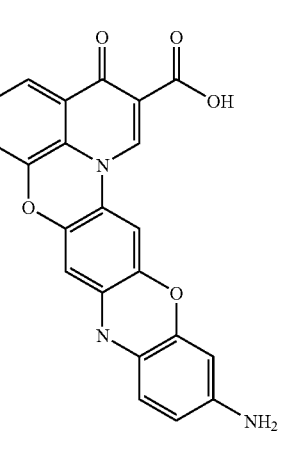 | | 1.75 |
| 11 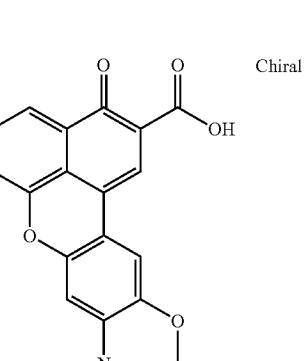 Chiral | | 1.75 |

TABLE 1-continued

| | Structure | Stop Data c-Myc μM | MTS Data Hella μM |
|---|---|---|---|
| 12 | 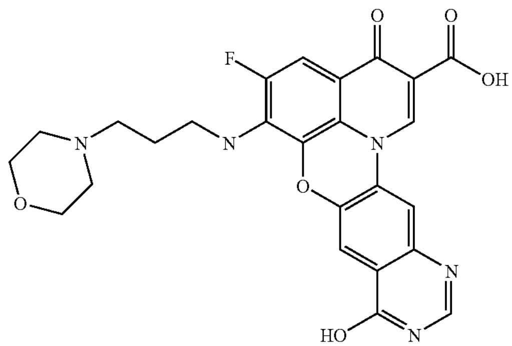 | | 1.75 |
| 13 | 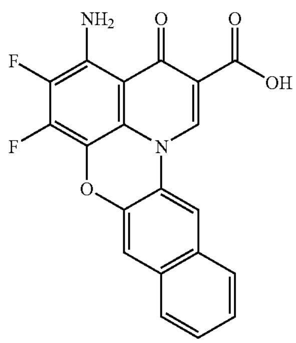 | | 1.75 |
| 14 | 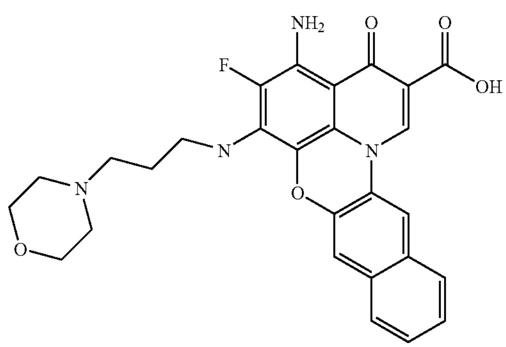 | | 1.75 |
| 15 | 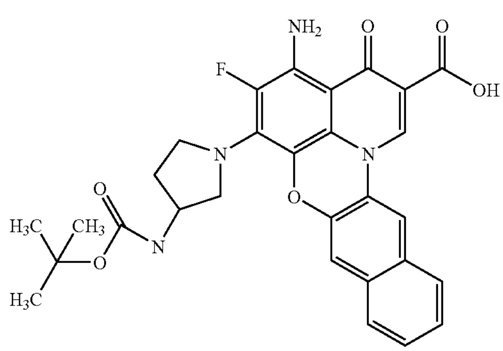 | | 1.75 |

TABLE 1-continued

| Structure | Stop Data c-Myc μM | MTS Data Hella μM |
|---|---|---|
| 16 | | 0.9 |
| 17 | | 0.75 |
| 18 | | 0.75 |

TABLE 1-continued

| | Structure | Stop Data c-Myc μM | MTS Data Hella μM |
|---|---|---|---|
| 19 | 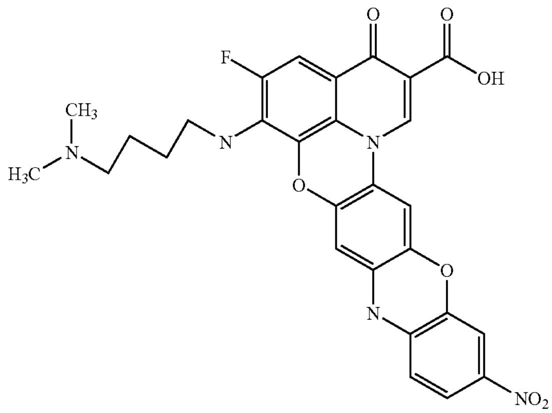 | | 0.75 |
| 20 | 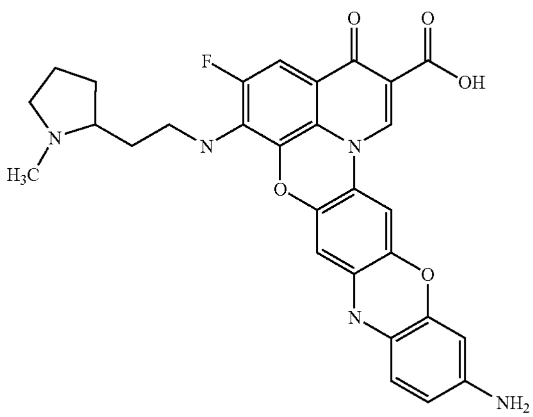 | | 0.75 |
| 21 | 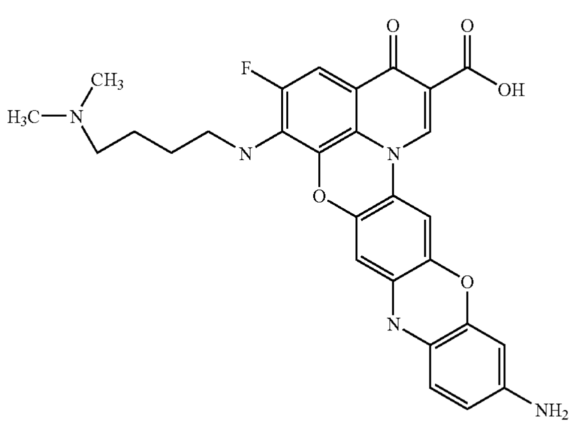 | | 0.75 |

TABLE 1-continued

| | Structure | Stop Data c-Myc μM | MTS Data Hella μM |
|---|---|---|---|
| 22 | (structure) | 0.75 | |
| 23 | (structure) | 0.75 | |
| 24 | (structure) Chiral | 0.5 | 7.00 |
| 25 | (structure) | 0.25 | 0.20 |

TABLE 2

| | Structure | Stop Data c-Myc μM | MTS Data Hella μM |
|---|---|---|---|
| 26 | Chiral | 4 | 0.73 |
| 27 | 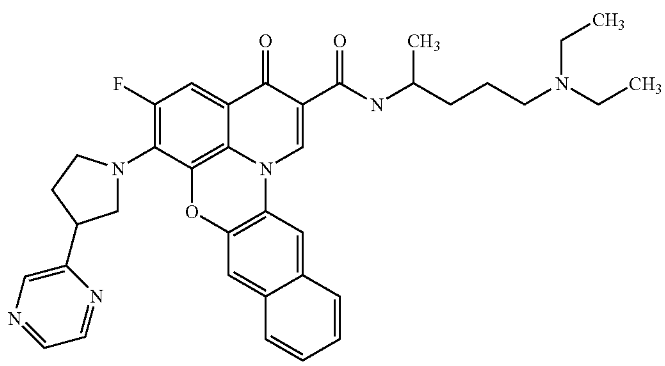 | 3 | 3.80 |
| 28 | 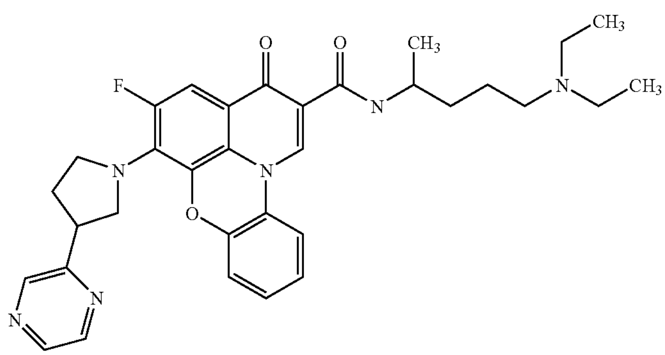 | 3 | 2.50 |
| 29 | 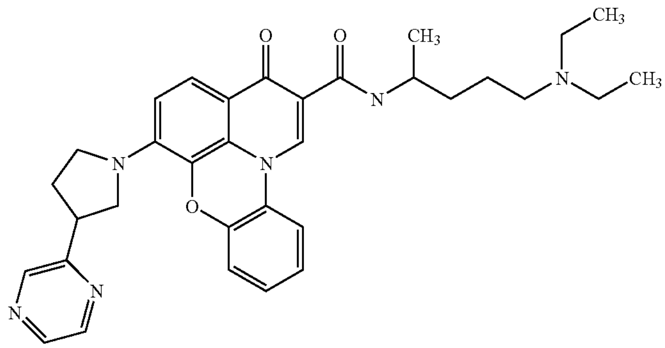 | 3 | 2.00 |

TABLE 2-continued
| | Structure | Stop Data c-Myc μM | MTS Data Hella μM |
|---|---|---|---|
| 30 | 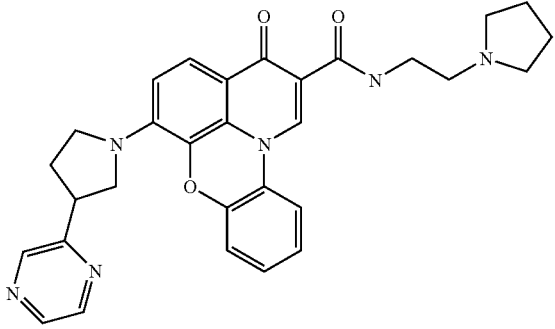 | 3 | 1.80 |
| 31 | 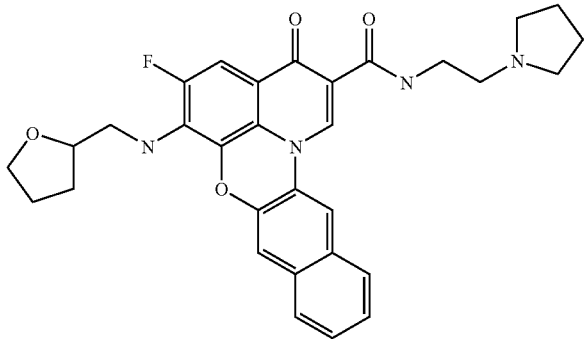 | 3 | 1.40 |
| 32 | 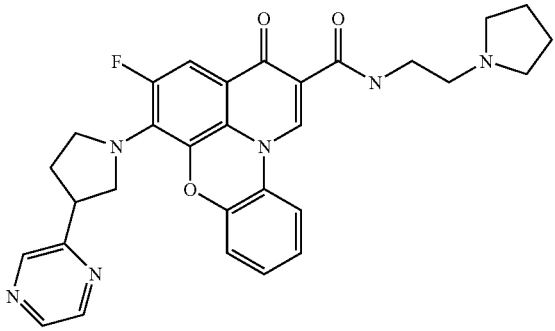 | 3 | 0.60 |
| 33 | 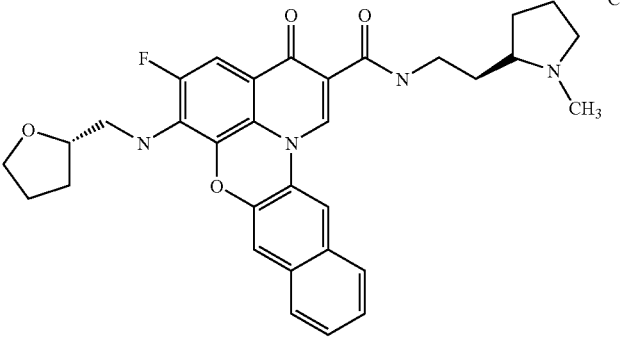 | 3 | 0.29 |

TABLE 2-continued

| | Structure | Stop Data c-Myc μM | MTS Data Hella μM |
|---|---|---|---|
| 34 | (Chiral structure) | 3 | 0.28 |
| 35 | (Chiral structure) | 3 | 0.21 |
| 36 | (Chiral structure) | 3 | 0.16 |
| 37 | (structure) | 2.5 | 2.80 |

TABLE 2-continued

| | Structure | Stop Data c-Myc μM | MTS Data Hella μM |
|---|---|---|---|
| 38 | (Chiral) | 2.5 | 0.26 |
| 39 | 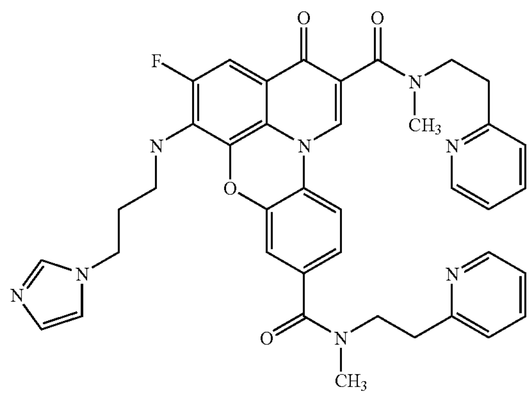 | 2.5 | |
| 40 | 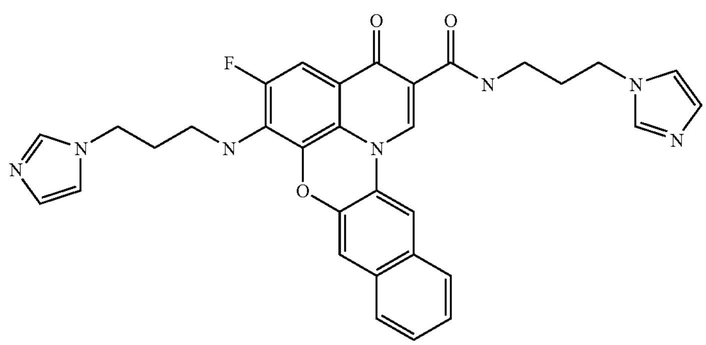 | 2.5 | |
| 41 | 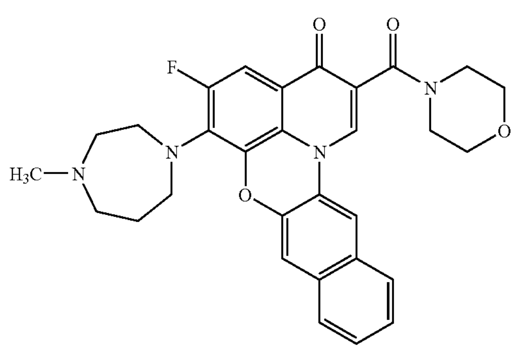 | 2.5 | |

TABLE 2-continued
| | Structure | Stop Data c-Myc μM | MTS Data Hella μM |
|---|---|---|---|
| 42 | 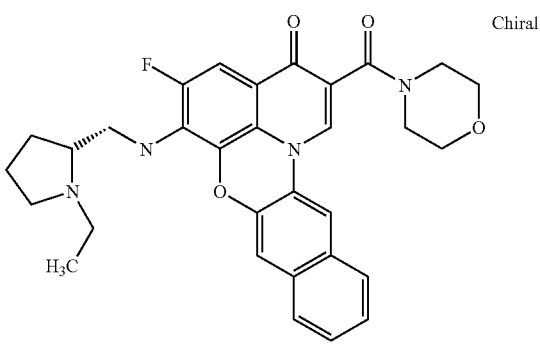 Chiral | | 2.5 |
| 43 | 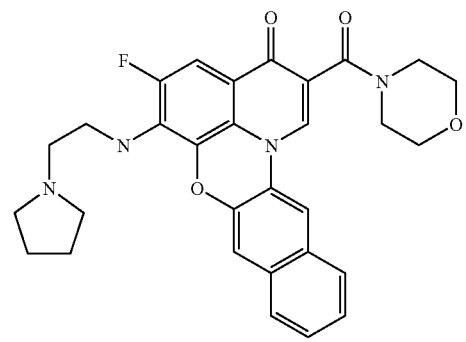 | | 2.5 |
| 44 | 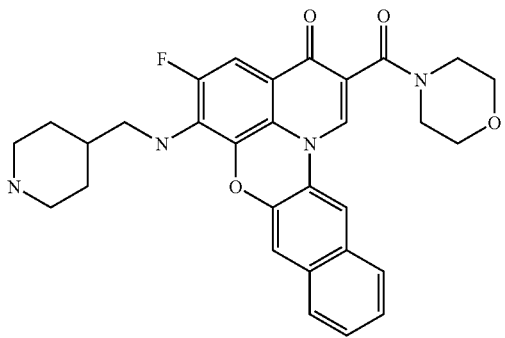 | | 2.5 |
| 45 | 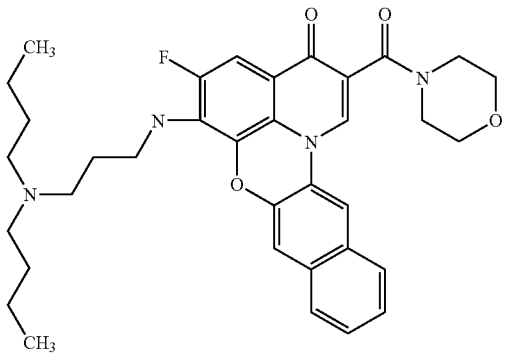 | | 2.5 |

TABLE 2-continued
| | Structure | Stop Data c-Myc μM | MTS Data Hella μM |
|---|---|---|---|
| 46 | 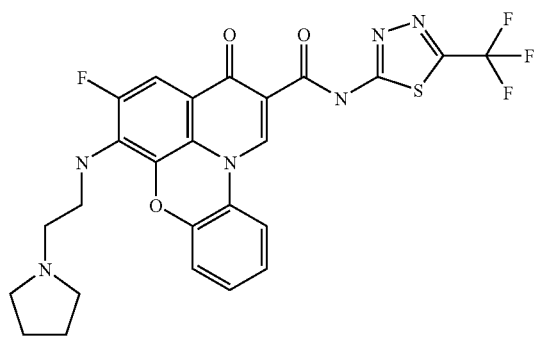 | | 2.5 |
| 47 | 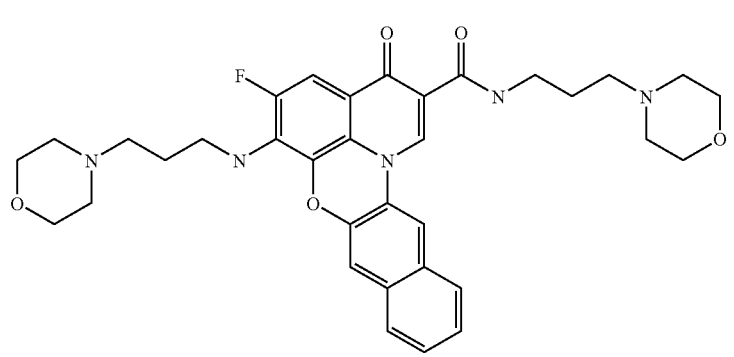 | | 2.5 |
| 48 | 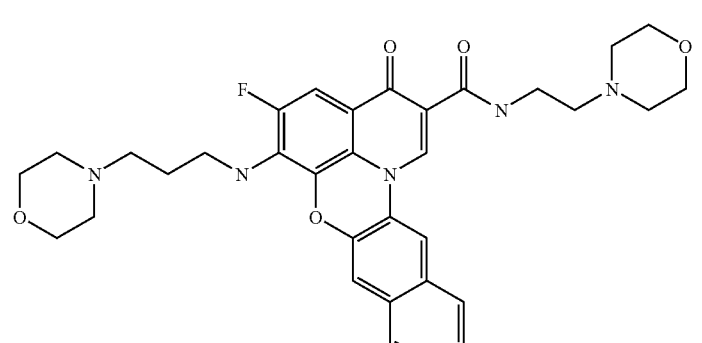 | | 2.5 |
| 49 | 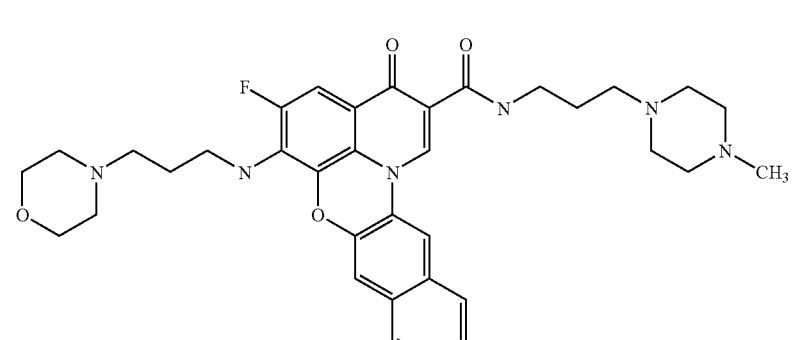 | | 2.5 |

TABLE 2-continued

| | Structure | Stop Data c-Myc μM | MTS Data Hella μM |
|---|---|---|---|
| 50 | 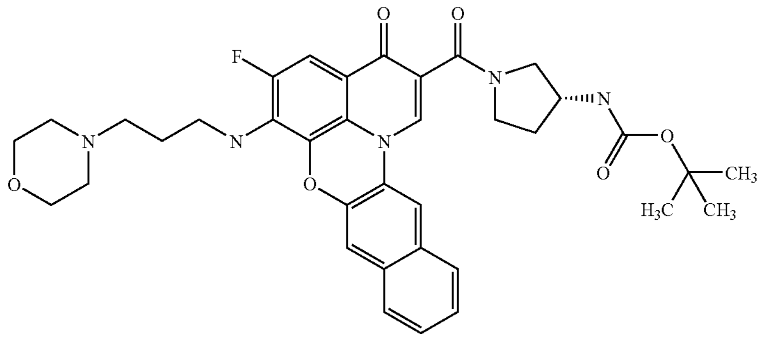 | | 2.5 |
| 51 | 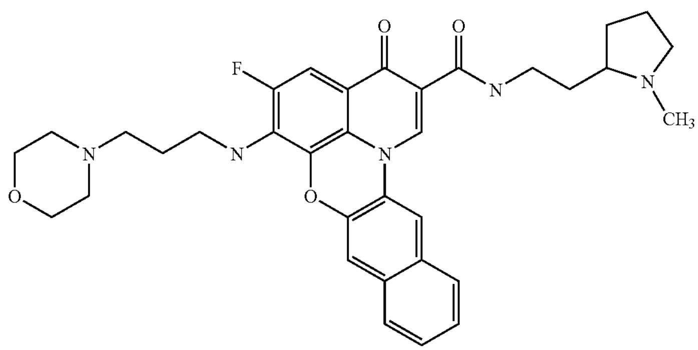 | | 2.5 |
| 52 | 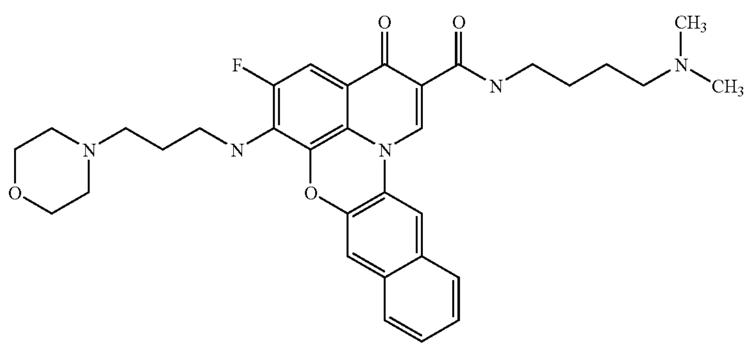 | | 2.5 |
| 53 | 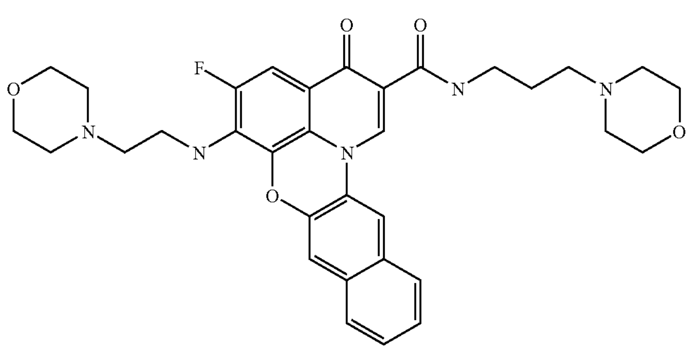 | | 2.5 |

TABLE 2-continued

| | Structure | Stop Data c-Myc μM | MTS Data Hella μM |
|---|---|---|---|
| 54 | 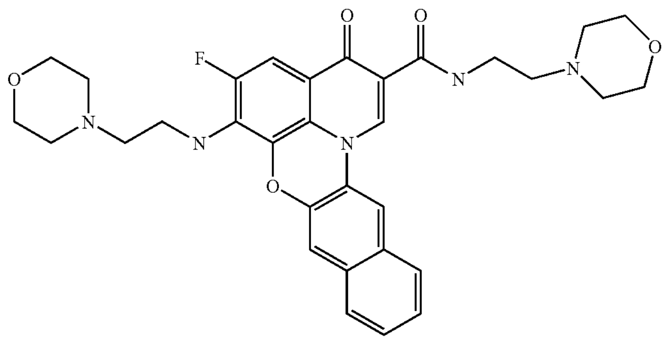 | | 2.5 |
| 55 | 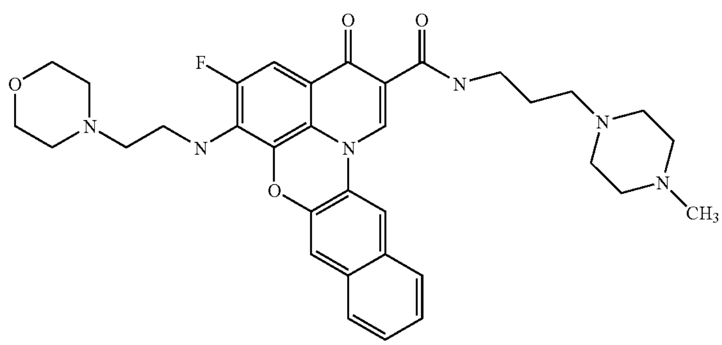 | | 2.5 |
| 56 | 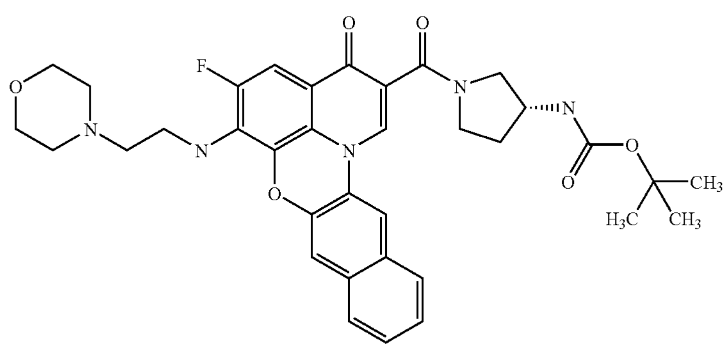 | | 2.5 |
| 57 | 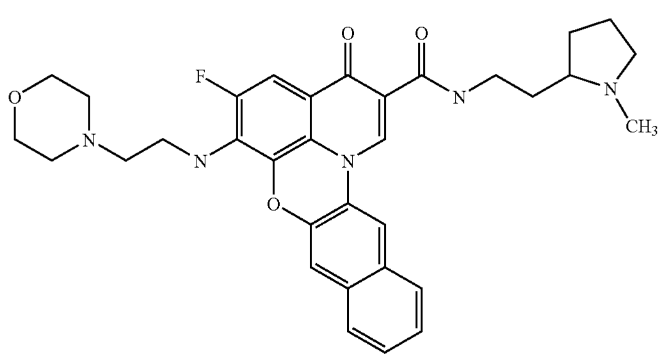 | | 2.5 |

TABLE 2-continued
| | Structure | Stop Data c-Myc μM | MTS Data Hella μM |
|---|---|---|---|
| 58 | 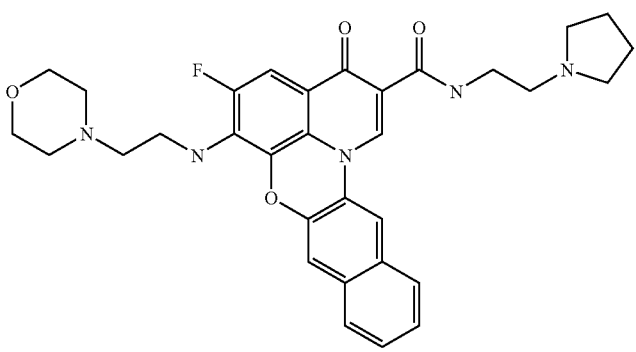 | | 2.5 |
| 59 | 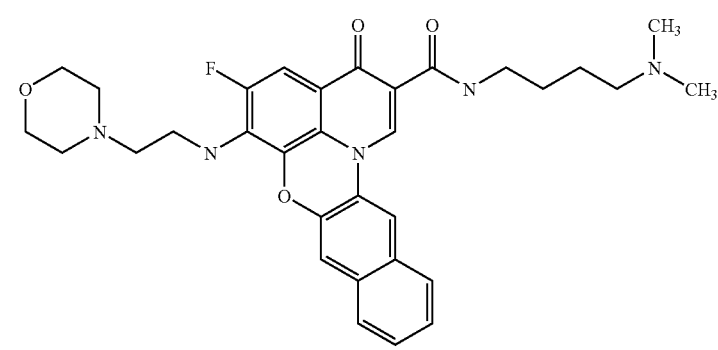 | | 2.5 |
| 60 | 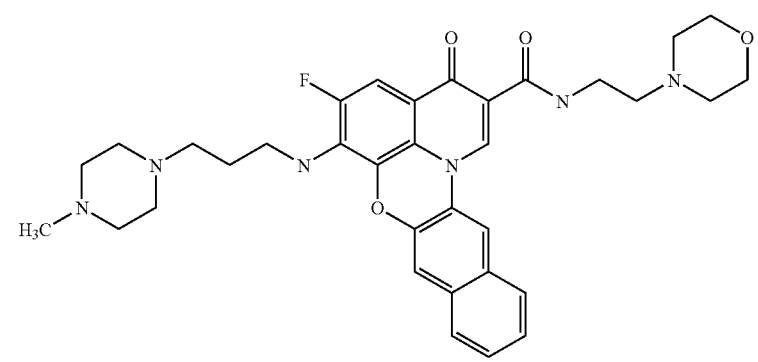 | | 2.5 |
| 61 | 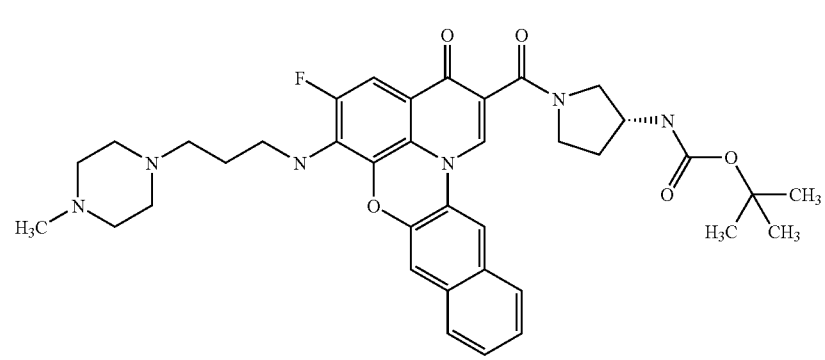 | | 2.5 |

TABLE 2-continued

| | Structure | Stop Data c-Myc µM | MTS Data Hella µM |
|---|---|---|---|
| 62 | 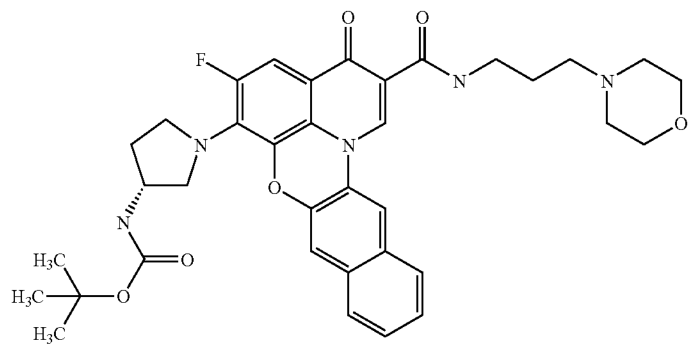 | | 2.5 |
| 63 | 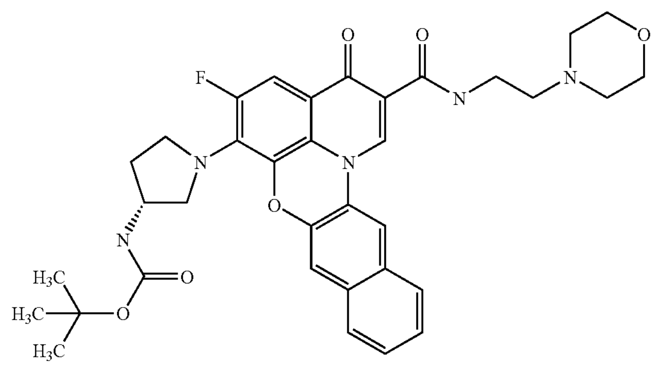 | | 2.5 |
| 64 | 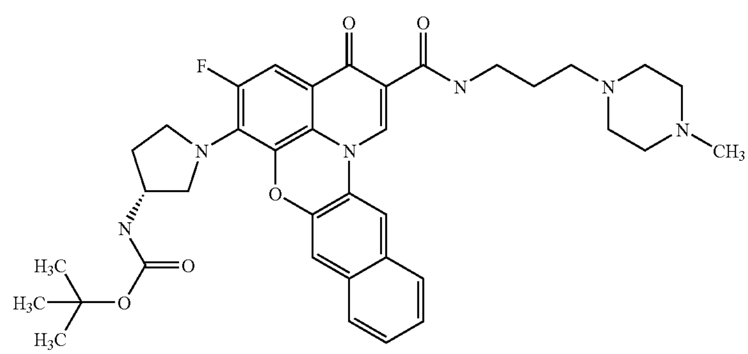 | | 2.5 |
| 65 | 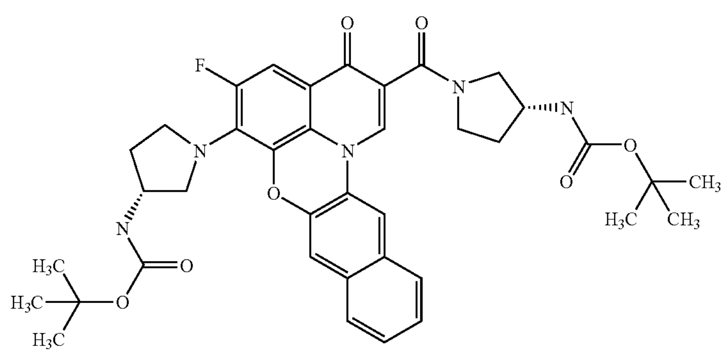 | | 2.5 |

TABLE 2-continued
| | Structure | Stop Data c-Myc μM | MTS Data Hella μM |
|---|---|---|---|
| 66 | 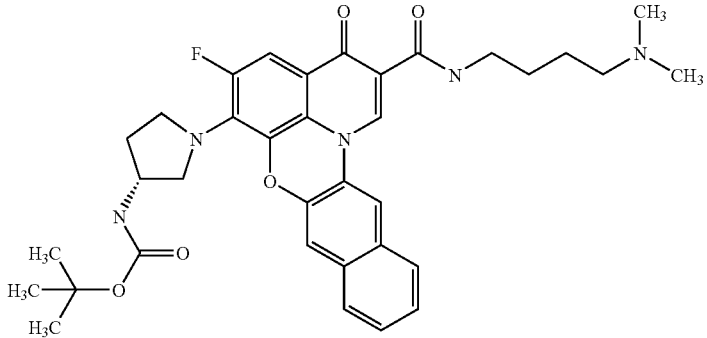 | | 2.5 |
| 67 | 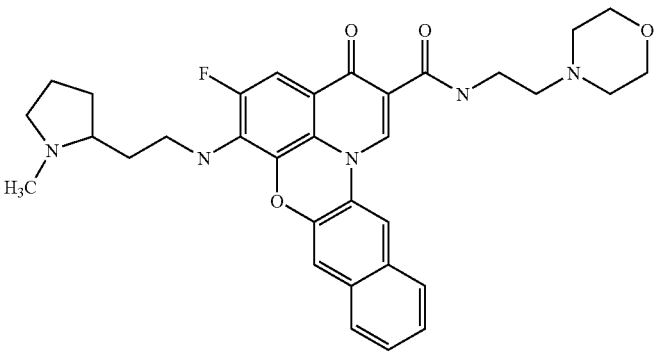 | | 2.5 |
| 68 | 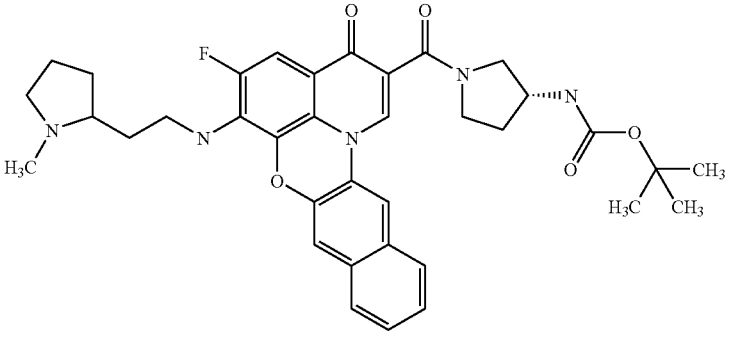 | | 2.5 |
| 69 | 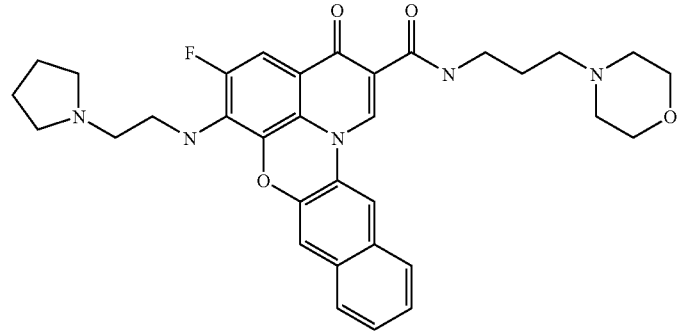 | | 2.5 |

TABLE 2-continued

| | Structure | Stop Data c-Myc μM | MTS Data Hella μM |
|---|---|---|---|
| 70 | 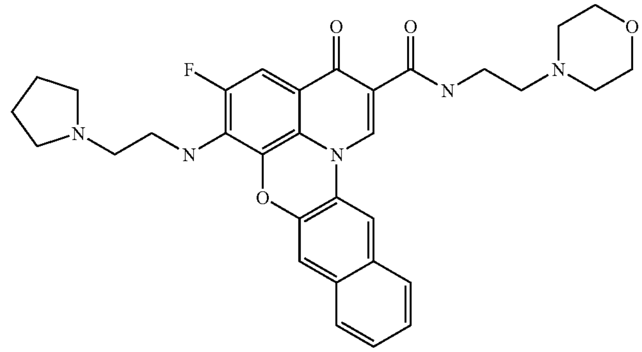 | | 2.5 |
| 71 | 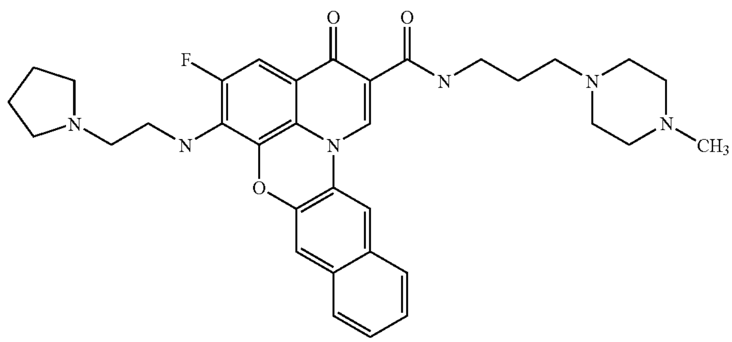 | | 2.5 |
| 72 | 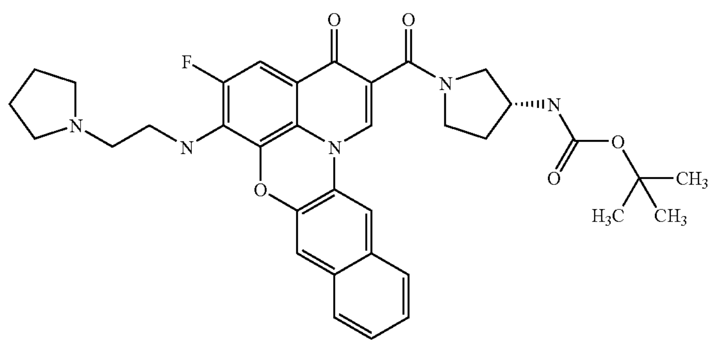 | | 2.5 |
| 73 | 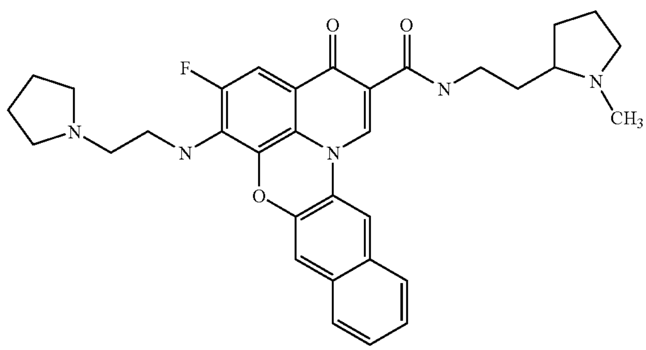 | | 2.5 |

TABLE 2-continued

| | Structure | Stop Data c-Myc μM | MTS Data Hella μM |
|---|---|---|---|
| 74 | 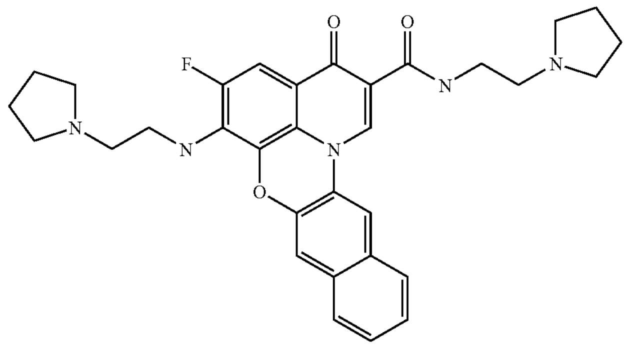 | | 2.5 |
| 75 | 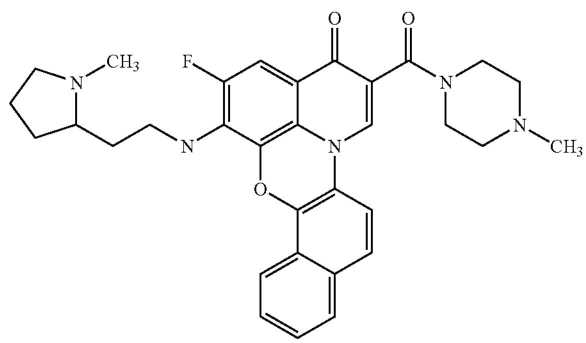 | | 2.5 |
| 76 | 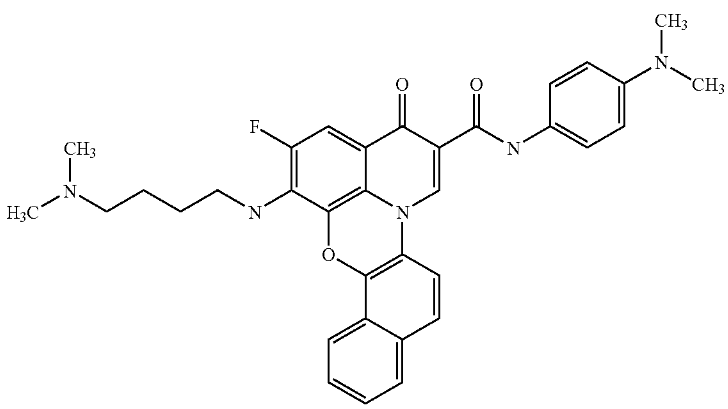 | | 2.5 |
| 77 | 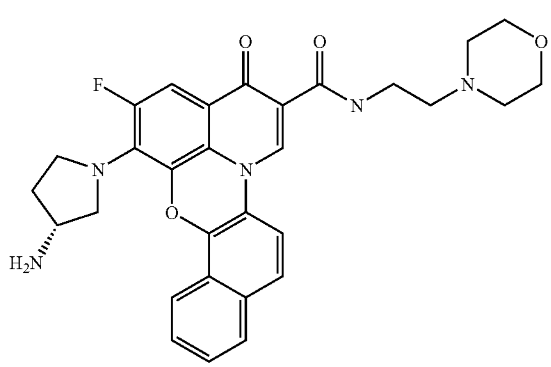 | | 2.5 |

TABLE 2-continued
| | Structure | Stop Data c-Myc μM | MTS Data Hella μM |
|---|---|---|---|
| 78 | 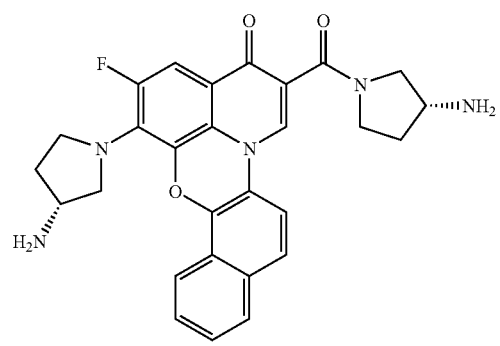 | | 2.5 |
| 79 | 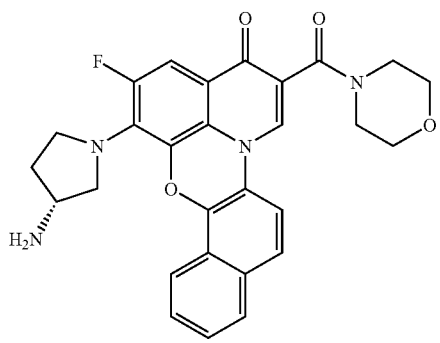 | | 2.5 |
| 80 | 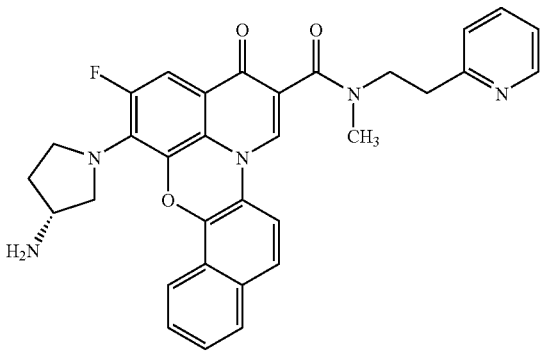 | | 2.5 |
| 81 | 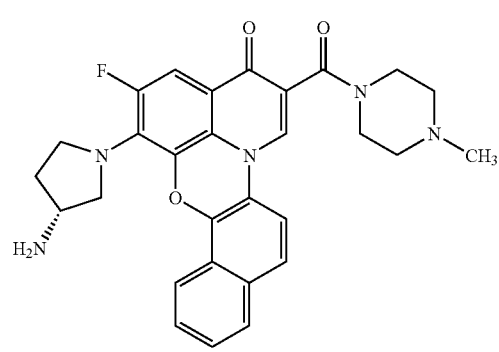 | | 2.5 |

TABLE 2-continued

| | Structure | Stop Data c-Myc μM | MTS Data Hella μM |
|---|---|---|---|
| 82 | 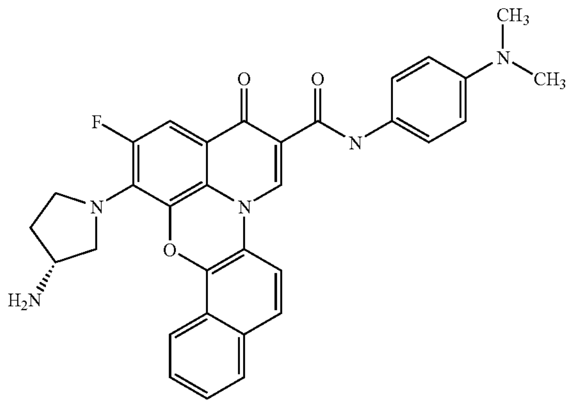 | | 2.5 |
| 83 | 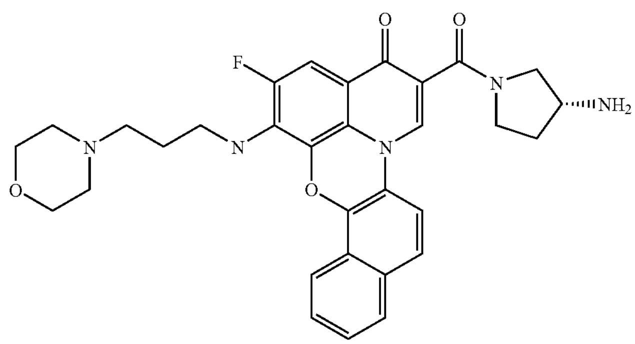 | | 2.5 |
| 84 | 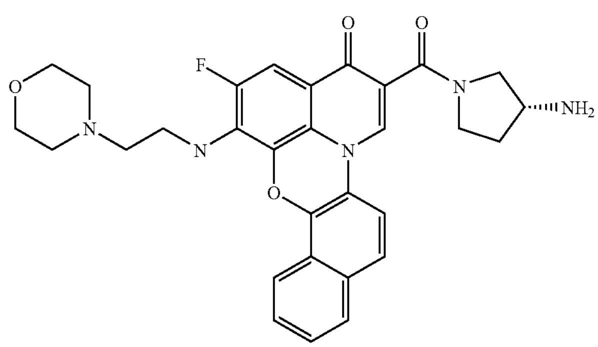 | | 2.5 |
| 85 | 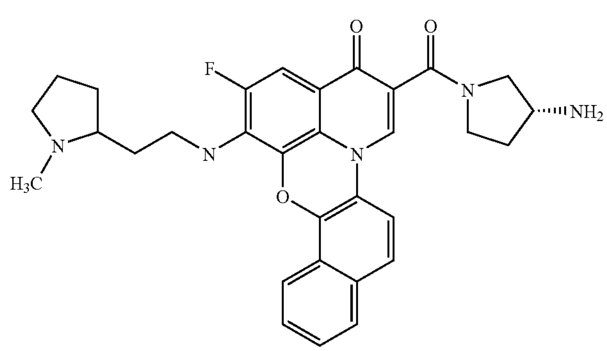 | | 2.5 |

TABLE 2-continued
| | Structure | Stop Data c-Myc μM | MTS Data Hella μM |
|---|---|---|---|
| 86 | 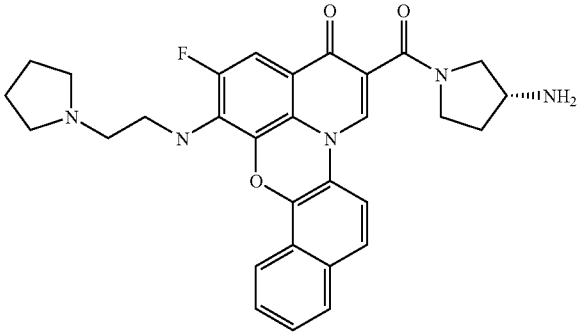 | | 2.5 |
| 87 | 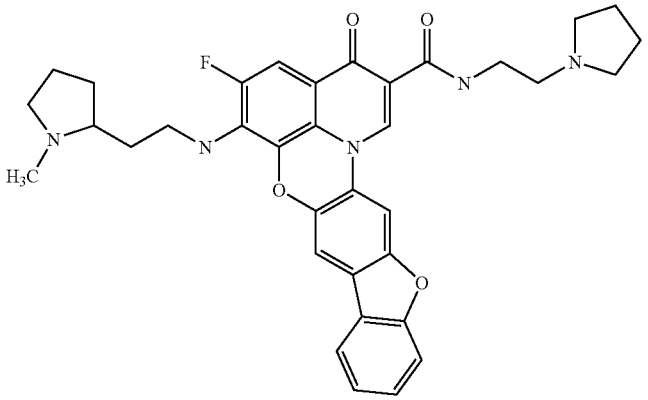 | | 2.5 |
| 88 | 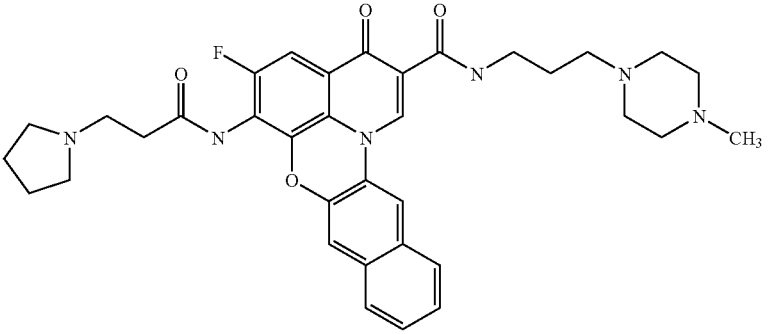 | | 2.5 |
| 89 | 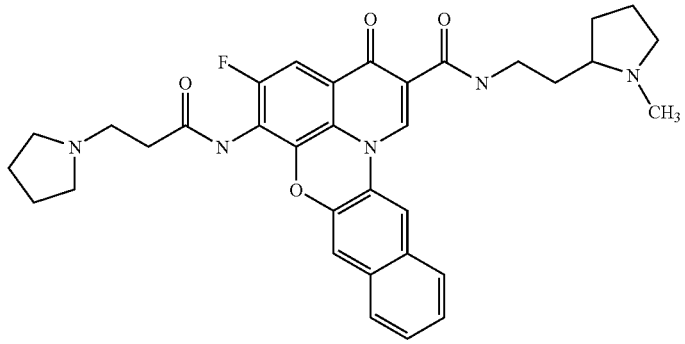 | | 2.5 |

TABLE 2-continued

| | Structure | Stop Data c-Myc μM | MTS Data Hella μM |
|---|---|---|---|
| 90 | 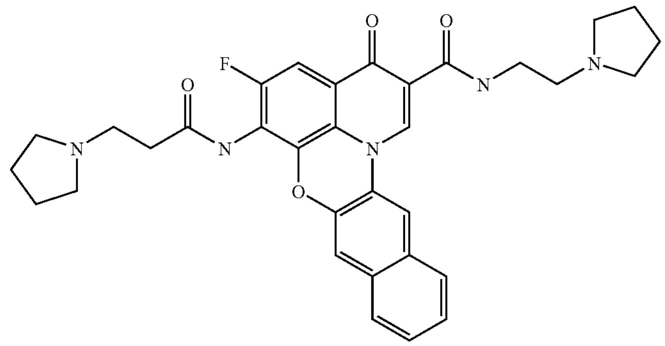 | | 2.5 |
| 91 | 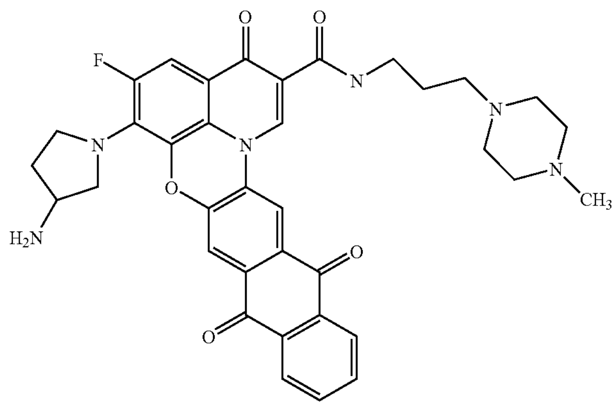 | | 2.5 |
| 92 | 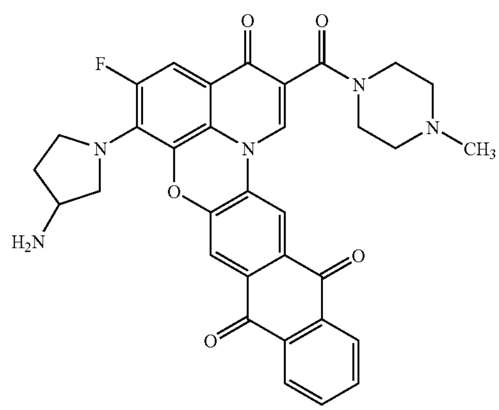 | | 2.5 |
| 93 | 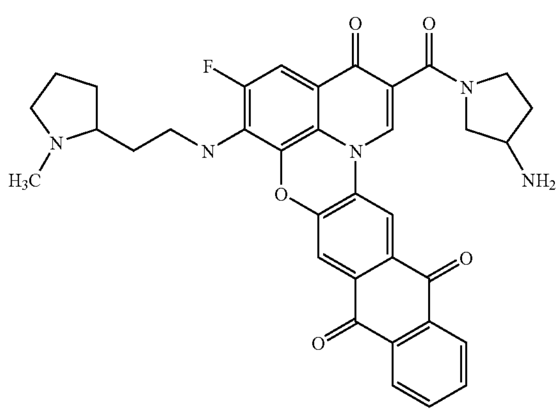 | | 2.5 |

TABLE 2-continued

| Structure | Stop Data c-Myc μM | MTS Data Hella μM |
|---|---|---|
| 94 | | 2.5 |
| 95 | | 2.5 |
| 96 | | 2.5 |

TABLE 2-continued

| | Structure | Stop Data c-Myc μM | MTS Data Hella μM |
|---|---|---|---|
| 97 | 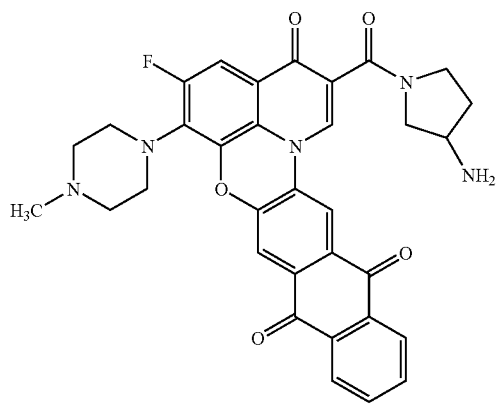 | | 2.5 |
| 98 | 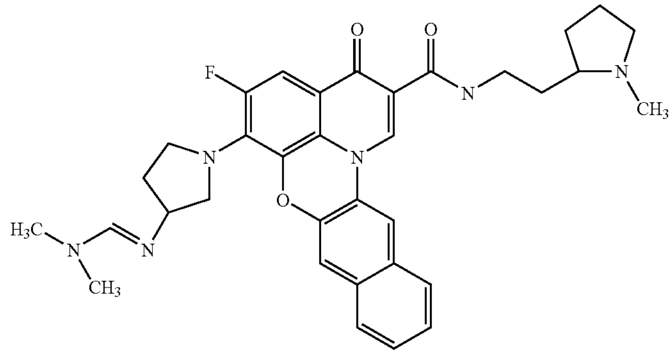 | | 2.5 |
| 99 | 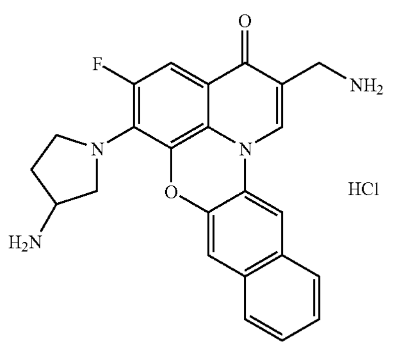 | | 2.5 |
| 100 | 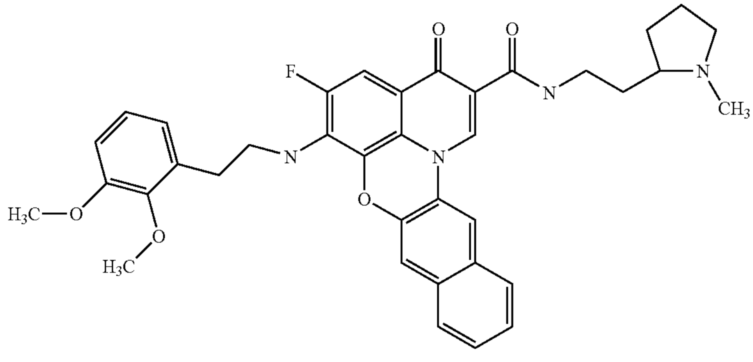 | | 2.5 |

TABLE 2-continued

| | Structure | Stop Data c-Myc μM | MTS Data Hella μM |
|---|---|---|---|
| 101 | 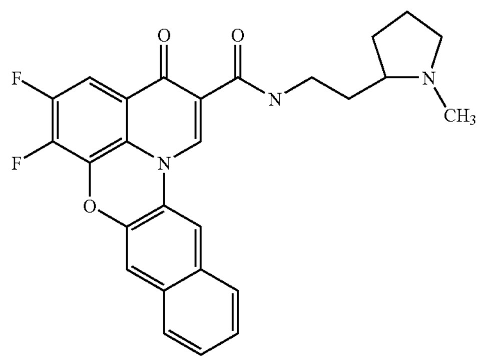 | | 2.25 |
| 102 | 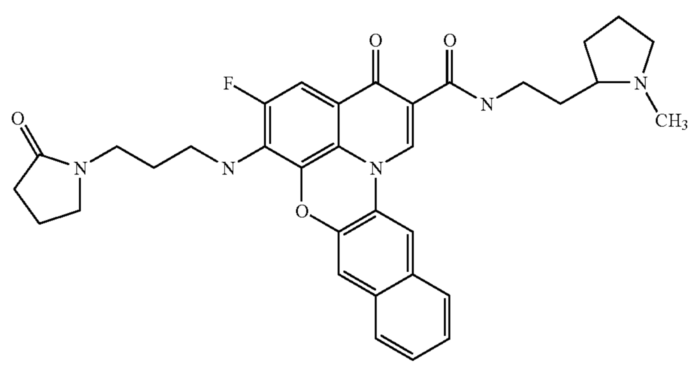 | 1.8 | 2.20 |
| 103 | 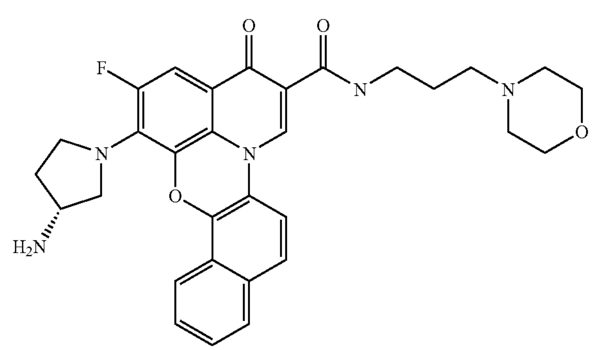 | 1.8 | |
| 104 | 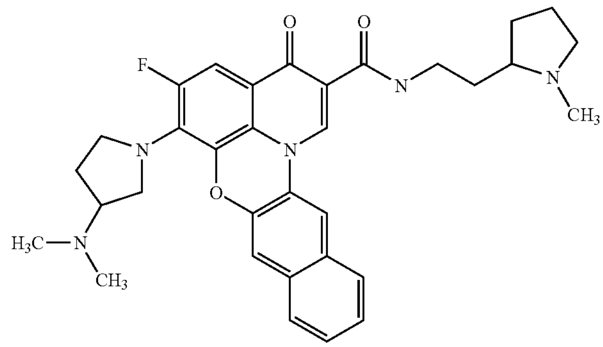 | 1.75 | 2.80 |

TABLE 2-continued

| | Structure | Stop Data c-Myc μM | MTS Data Hella μM |
|---|---|---|---|
| 105 | 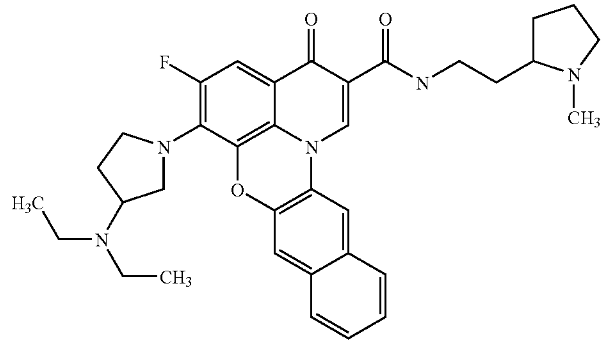 | 1.75 | 2.80 |
| 106 | Chiral | 1.75 | 2.50 |
| 107 | 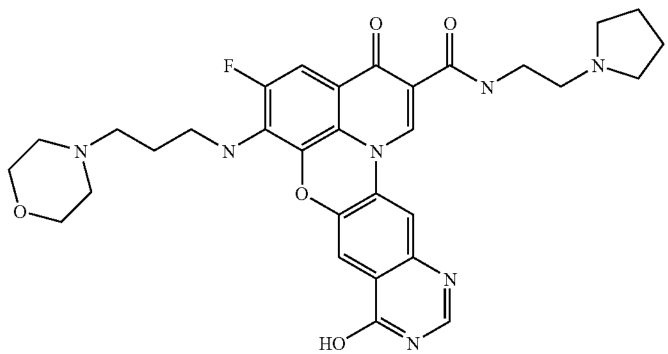 | 1.75 | 1.80 |
| 108 | Chiral | 1.75 | 0.46 |
| 109 | Chiral | 1.75 | 0.31 |

TABLE 2-continued

| | Structure | Stop Data c-Myc μM | MTS Data Hella μM |
|---|---|---|---|
| 110 | 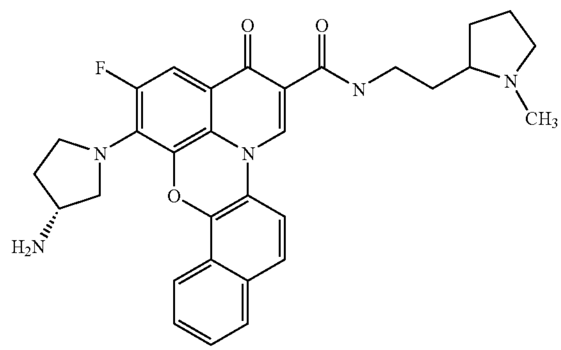 | 1.75 | 0.25 |
| 111 | 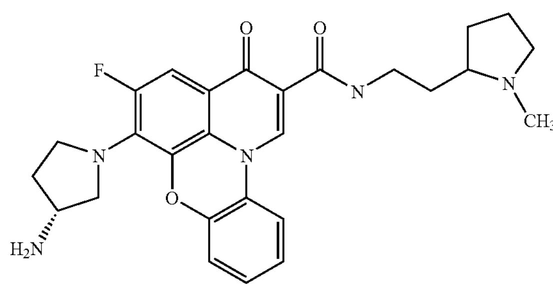 | 1.75 | 0.22 |
| 112 | 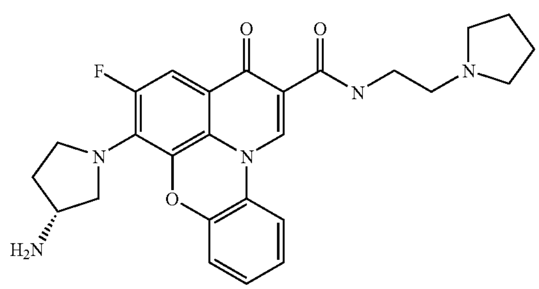 | 1.75 | 0.22 |
| 113 | 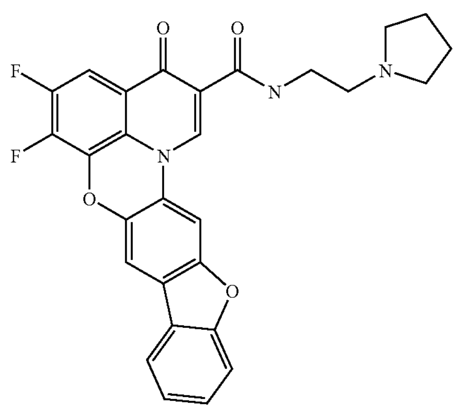 | 1.75 | |

TABLE 2-continued

| Structure | Stop Data c-Myc μM | MTS Data Hella μM |
|---|---|---|
| 114 | | 1.75 |
| 115 | | 1.75 |
| 116 (Chiral) | | 1.75 |
| 117 | | 1.75 |

TABLE 2-continued

| Structure | Stop Data c-Myc μM | MTS Data Hella μM |
|---|---|---|
| 118 | | 1.75 |
| 119 | | 1.75 |
| 120 | | 1.75 |
| 121 | | 1.75 |

TABLE 2-continued
| | Structure | Stop Data c-Myc μM | MTS Data Hella μM |
|---|---|---|---|
| 122 | 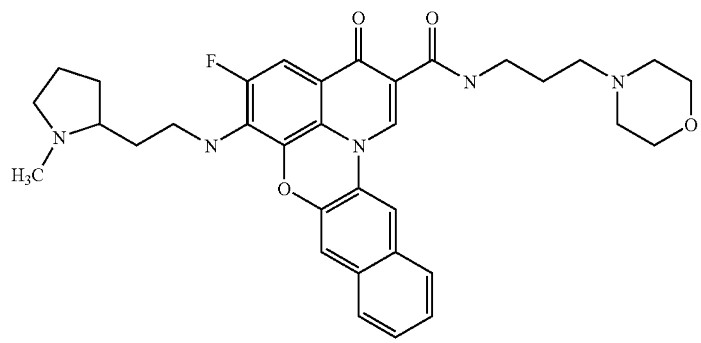 | | 1.75 |
| 123 | 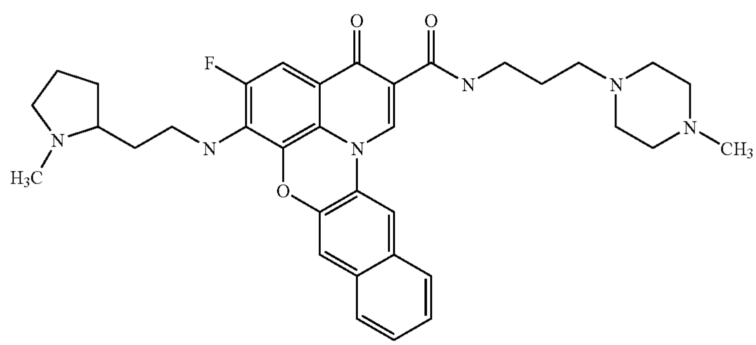 | | 1.75 |
| 124 | 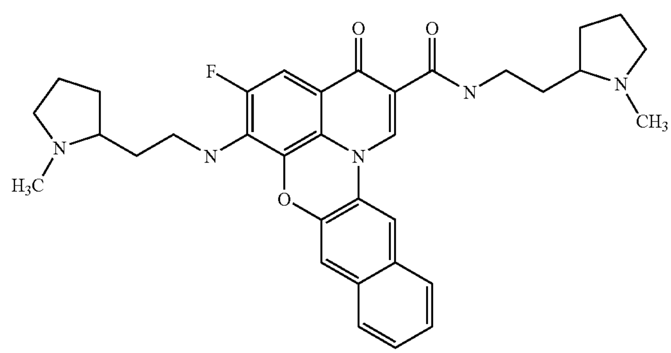 | | 1.75 |
| 125 | 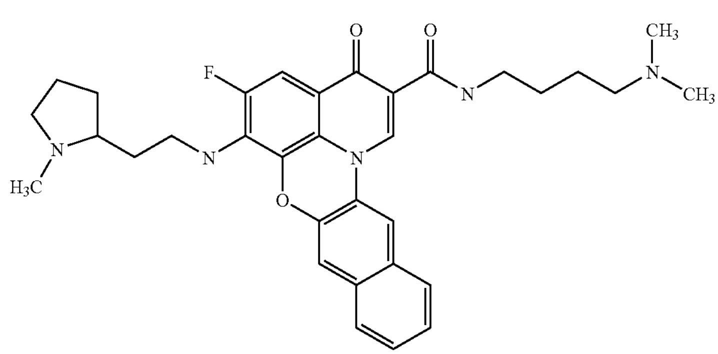 | | 1.75 |

TABLE 2-continued

| Structure | Stop Data c-Myc μM | MTS Data Hella μM |
|---|---|---|
| 126 | | 1.75 |
| 127 | | 1.75 |
| 128 | | 1.75 |
| 129 | | 1.75 |

TABLE 2-continued

| | Structure | Stop Data c-Myc μM | MTS Data Hella μM |
|---|---|---|---|
| 130 | 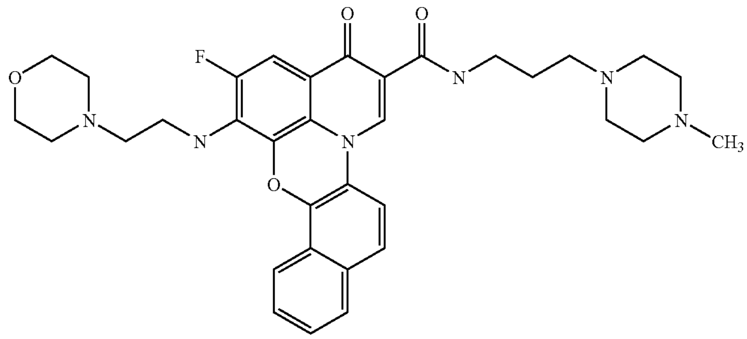 | | 1.75 |
| 131 | 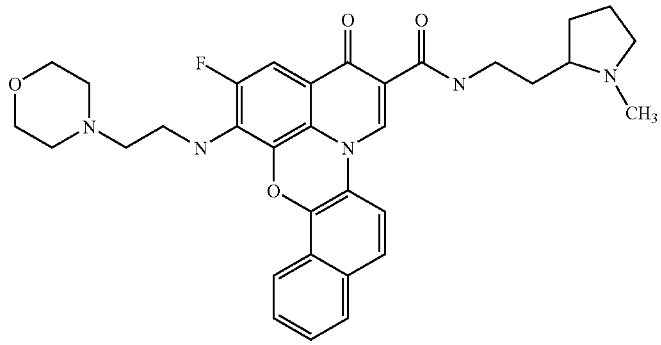 | | 1.75 |
| 132 | 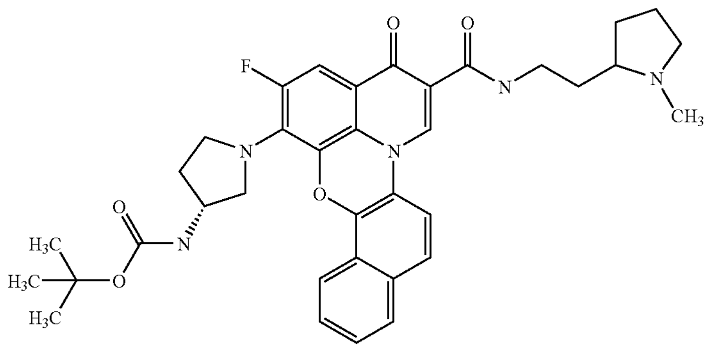 | | 1.75 |
| 133 | 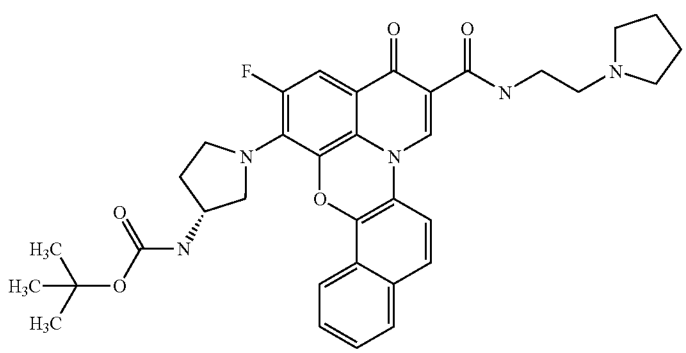 | | 1.75 |

TABLE 2-continued

| | Structure | Stop Data c-Myc µM | MTS Data Hella µM |
|---|---|---|---|
| 134 | 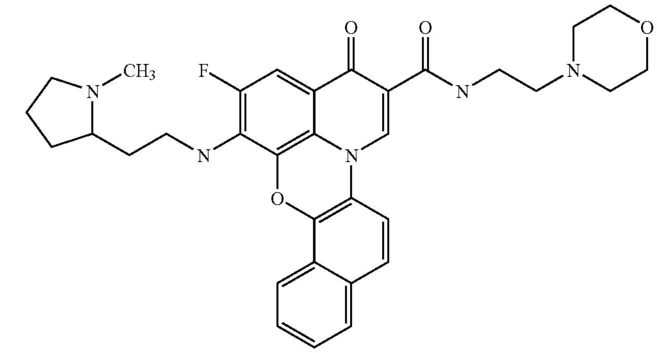 | | 1.75 |
| 135 | 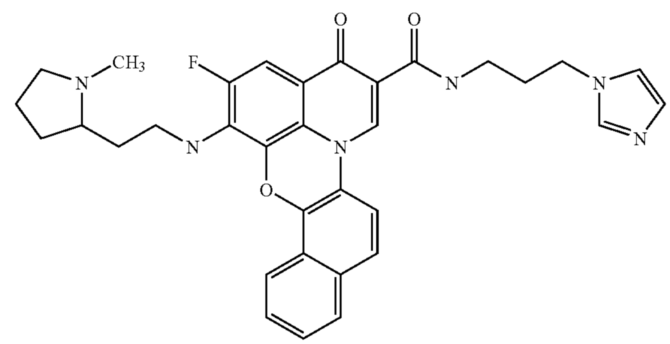 | | 1.75 |
| 136 | 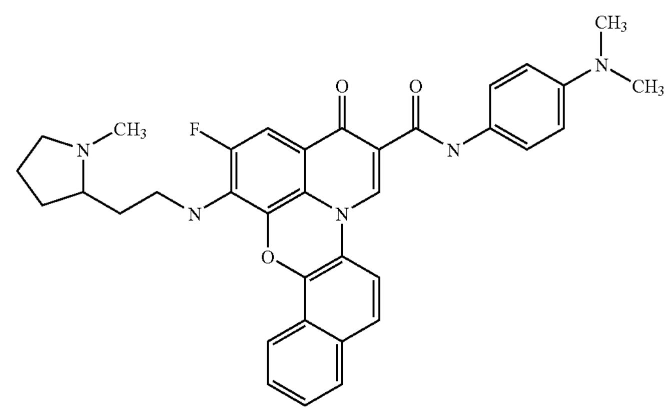 | | 1.75 |
| 137 | 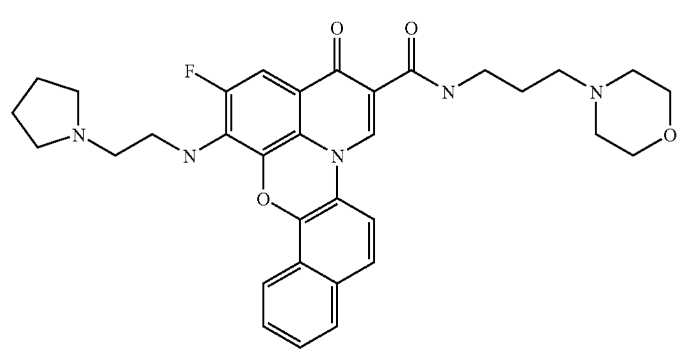 | | 1.75 |

TABLE 2-continued

| | Structure | Stop Data c-Myc μM | MTS Data Hella μM |
|---|---|---|---|
| 138 | 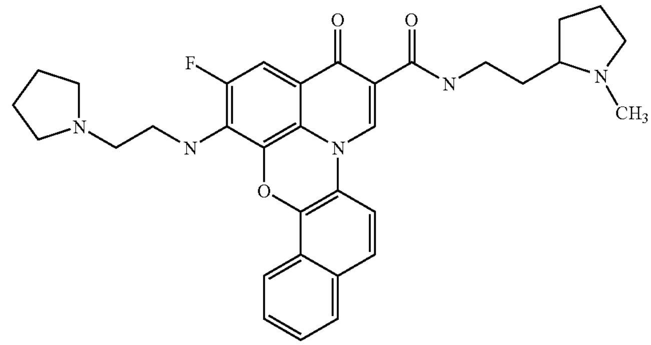 | | 1.75 |
| 139 | 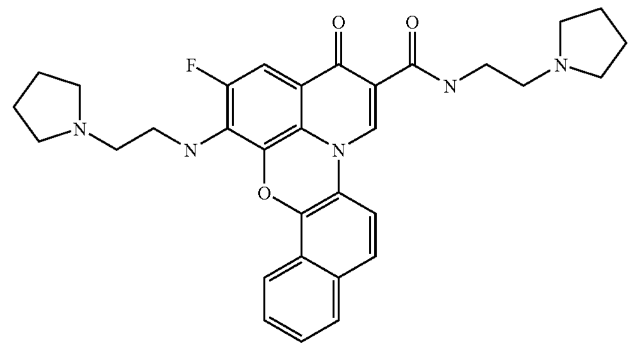 | | 1.75 |
| 140 | 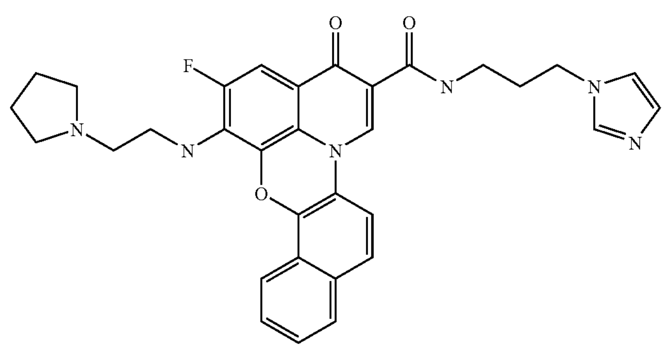 | | 1.75 |
| 141 | 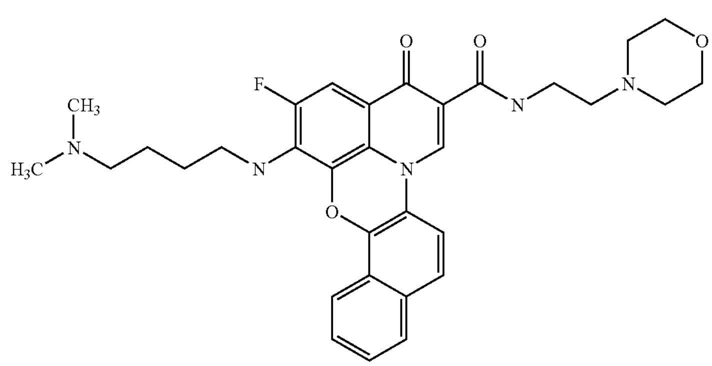 | | 1.75 |

TABLE 2-continued

| | Structure | Stop Data c-Myc μM | MTS Data Hella μM |
|---|---|---|---|
| 142 | 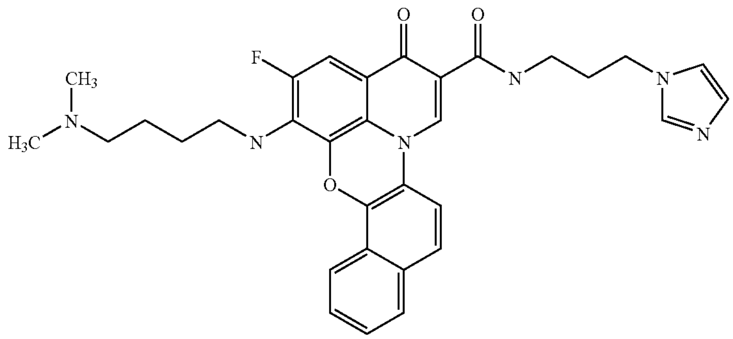 | | 1.75 |
| 143 | 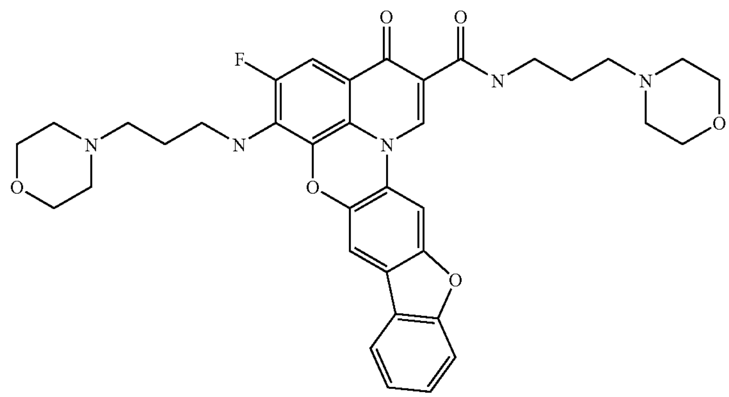 | | 1.75 |
| 144 | 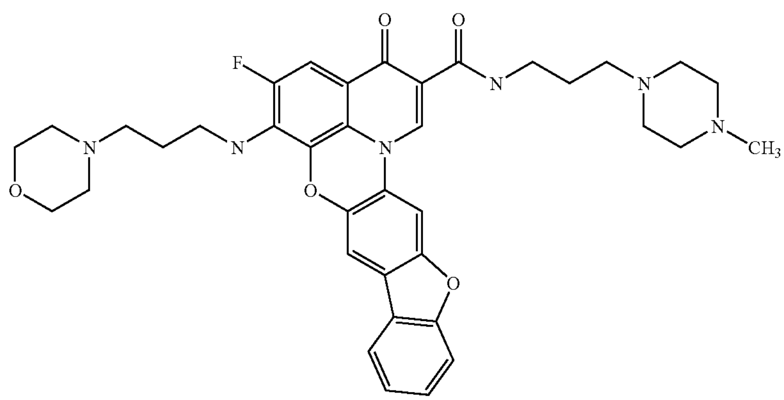 | | 1.75 |
| 145 | 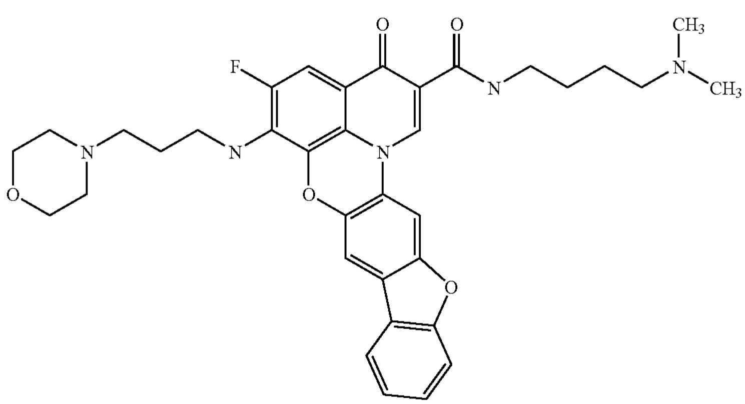 | | 1.75 |

TABLE 2-continued

| Structure | Stop Data c-Myc μM | MTS Data Hella μM |
|---|---|---|
| 146 | | 1.75 |
| 147 | | 1.75 |
| 148 | | 1.75 |

TABLE 2-continued

| | Stop Data c-Myc μM | MTS Data Hella μM |
|---|---|---|
| Structure | | |
| 149 | | 1.75 |
| 150 | | 1.75 |
| 151 | | 1.75 |

TABLE 2-continued
| Structure | Stop Data c-Myc μM | MTS Data Hella μM |
|---|---|---|
| 152 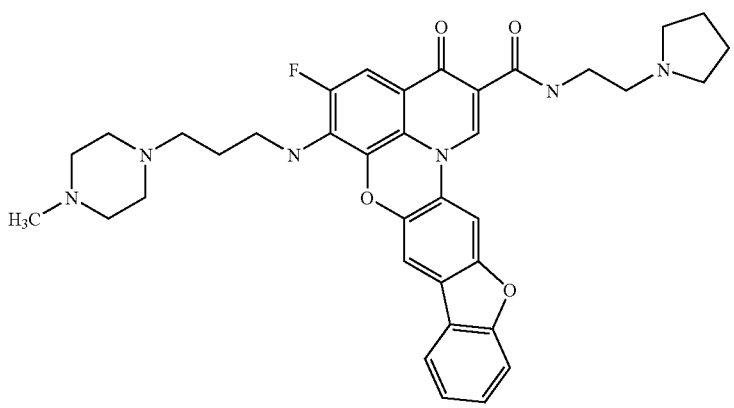 | | 1.75 |
| 153 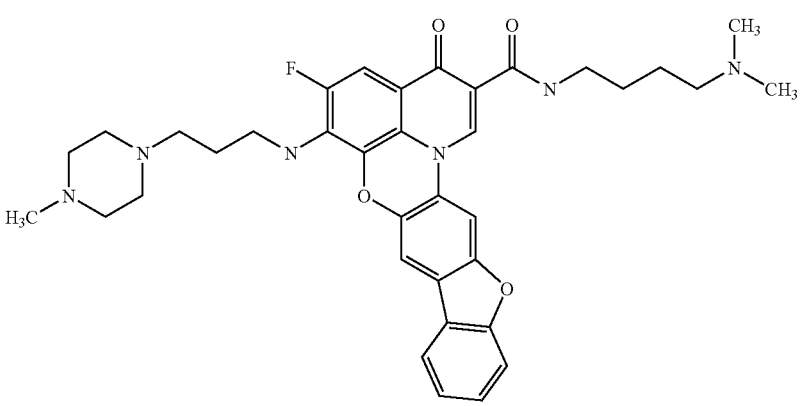 | | 1.75 |
| 154 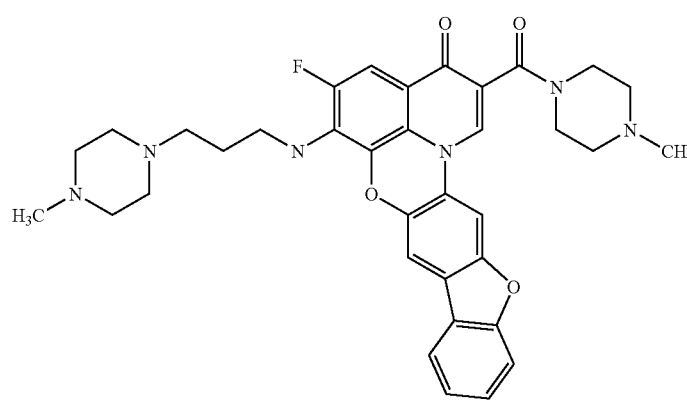 | | 1.75 |

TABLE 2-continued

| Structure | Stop Data c-Myc μM | MTS Data Hella μM |
|---|---|---|
| 155 | | 1.75 |
| 156 | | 1.75 |
| 157 | | 1.75 |
| 158 | | 1.75 |

TABLE 2-continued

| | Structure | Stop Data c-Myc μM | MTS Data Hella μM |
|---|---|---|---|
| 159 | 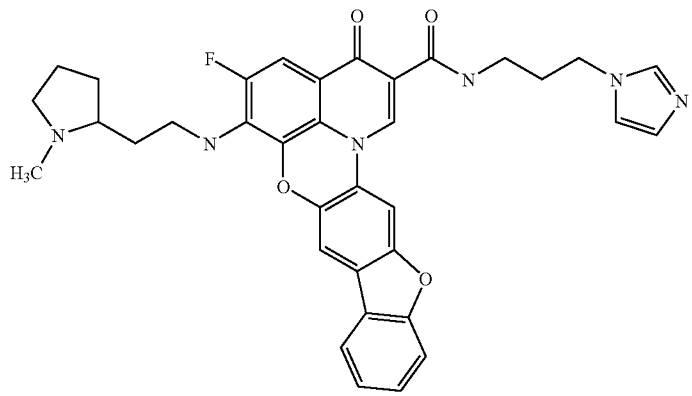 | | 1.75 |
| 160 | 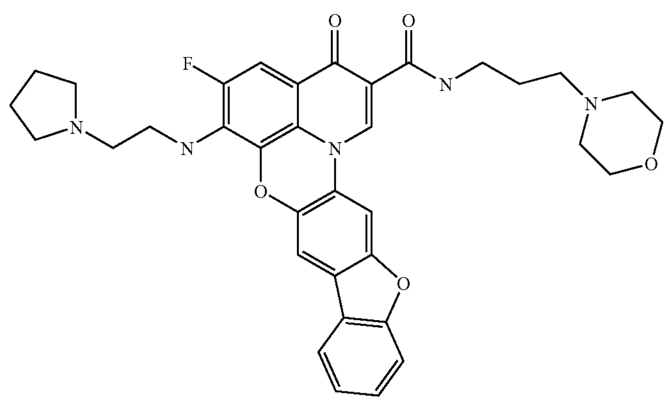 | | 1.75 |
| 161 | 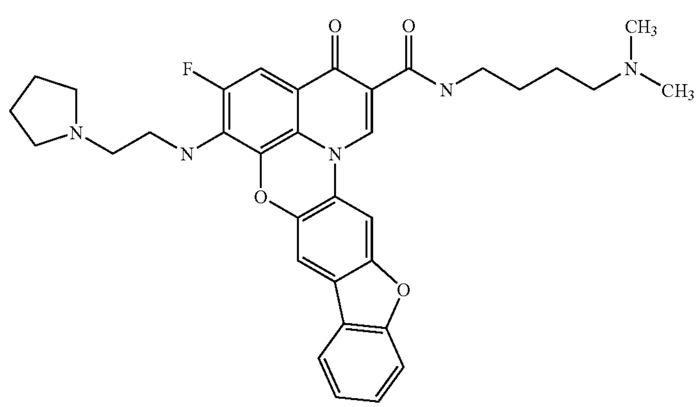 | | 1.75 |

TABLE 2-continued

| | Structure | Stop Data c-Myc μM | MTS Data Hella μM |
|---|---|---|---|
| 162 | 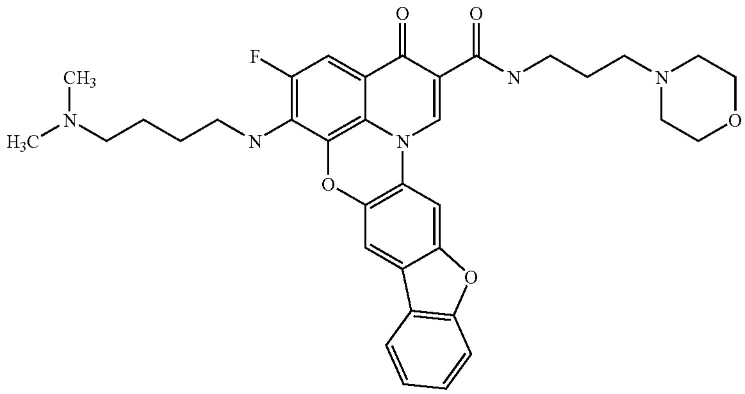 | | 1.75 |
| 163 | 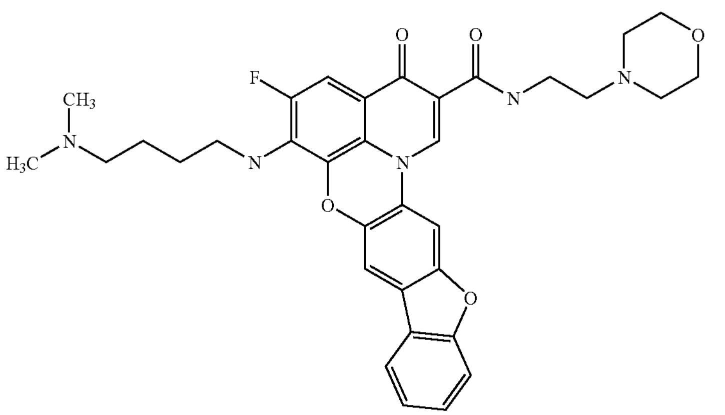 | | 1.75 |
| 164 | 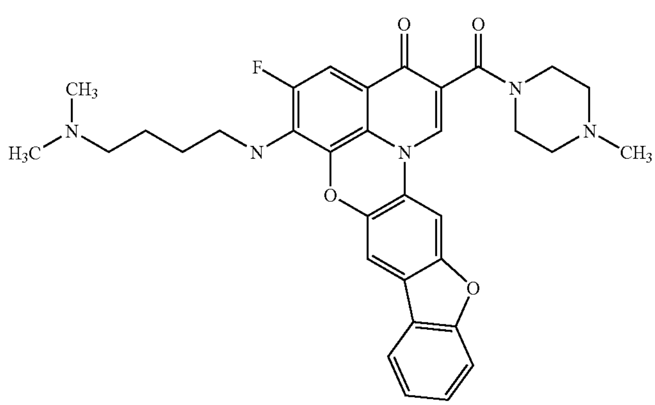 | | 1.75 |

TABLE 2-continued

| Structure | Stop Data c-Myc μM | MTS Data Hella μM |
|---|---|---|
| 165 | | 1.75 |
| 166 | | 1.75 |
| 167 | | 1.75 |

TABLE 2-continued

| Structure | Stop Data c-Myc μM | MTS Data Hella μM |
|---|---|---|
| 168 | | 1.75 |
| 169 | | 1.75 |
| 170 | | 1.75 |

TABLE 2-continued

| | Structure | | Stop Data c-Myc μM | MTS Data Hella μM |
|---|---|---|---|---|
| 171 | 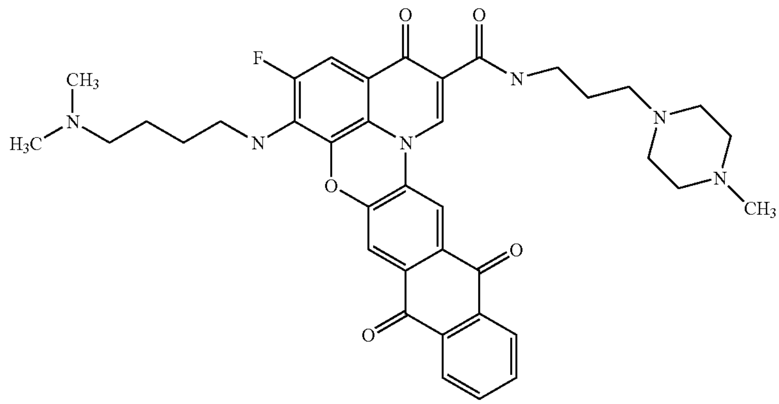 | | | 1.75 |
| 172 | 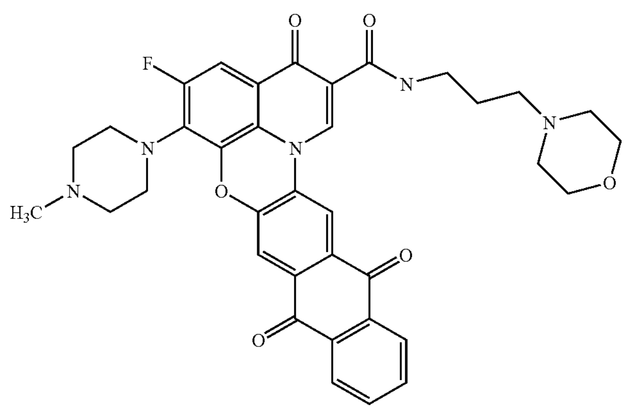 | | | 1.75 |
| 173 | 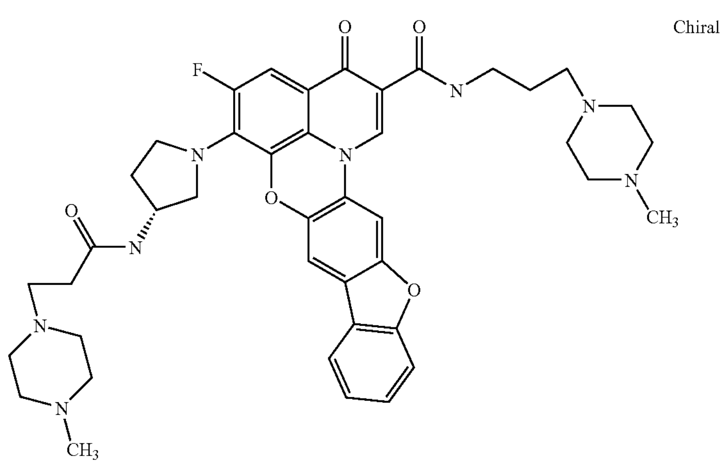 | Chiral | | 1.75 |

TABLE 2-continued

| Structure | Stop Data c-Myc μM | MTS Data Hella μM |
|---|---|---|
| 174 | Chiral | 1.75 |
| 175 | Chiral | 1.75 |
| 176 | Chiral | 1.75 |

TABLE 2-continued

| | Structure | Stop Data c-Myc μM | MTS Data Hela μM |
|---|---|---|---|
| 177 | Chiral | | 1.75 |
| 178 | 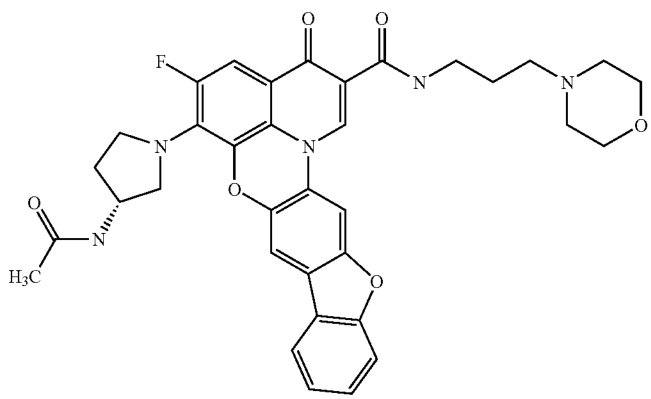 | | 1.75 |
| 179 | 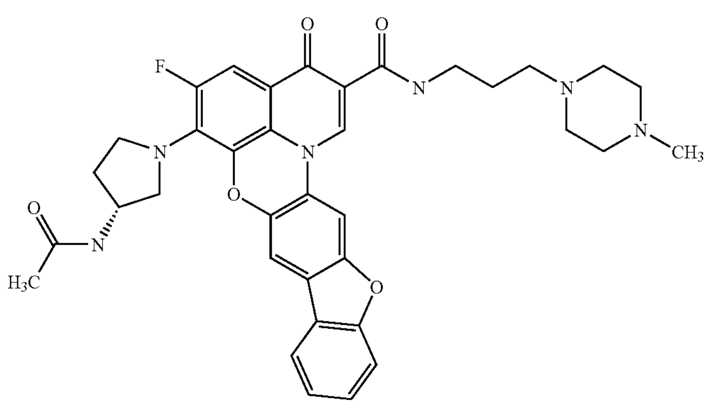 | | 1.75 |

TABLE 2-continued
| Structure | Stop Data c-Myc µM | MTS Data Hella µM |
|---|---|---|
| 180 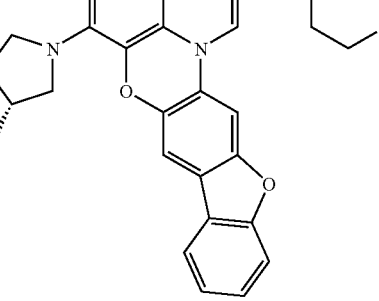 Chiral | | 1.75 |
| 181 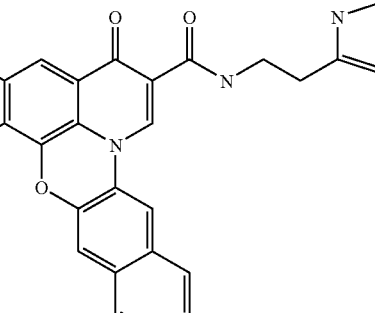 | | 1.75 |
| 182 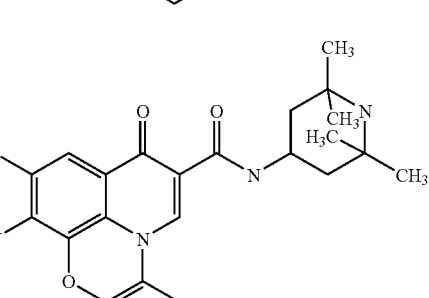 | | 1.75 |
| 183 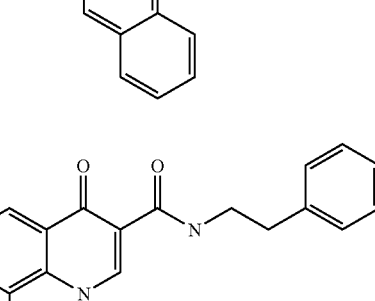 | | 1.75 |

TABLE 2-continued

| | Structure | Stop Data c-Myc μM | MTS Data Hella μM |
|---|---|---|---|
| 184 | 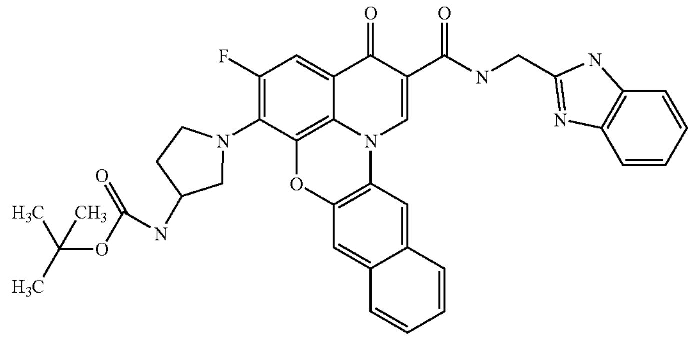 | | 1.75 |
| 185 | 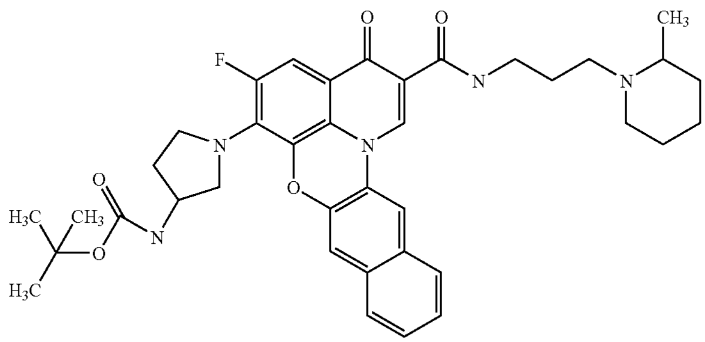 | | 1.75 |
| 186 | 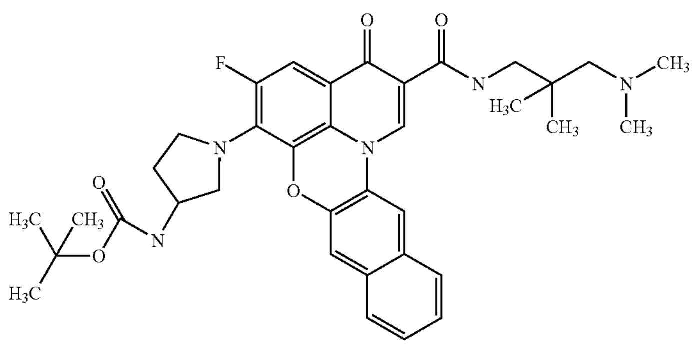 | | 1.75 |
| 187 | 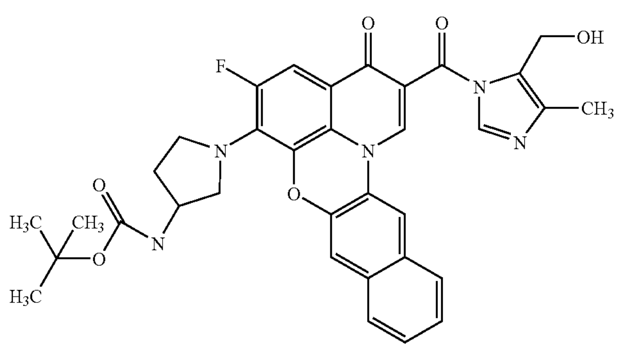 | | 1.75 |

TABLE 2-continued

| | Structure | Stop Data c-Myc μM | MTS Data Hella μM |
|---|---|---|---|
| 188 | 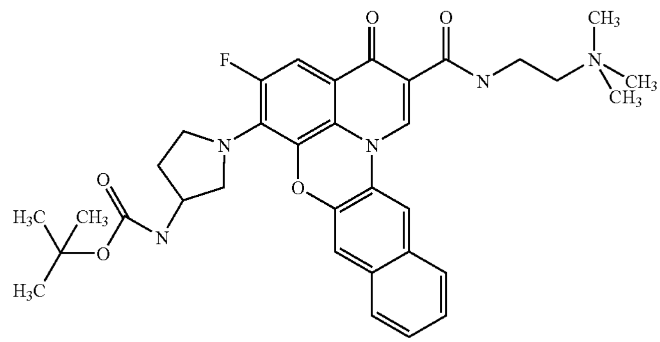 | | 1.75 |
| 189 | 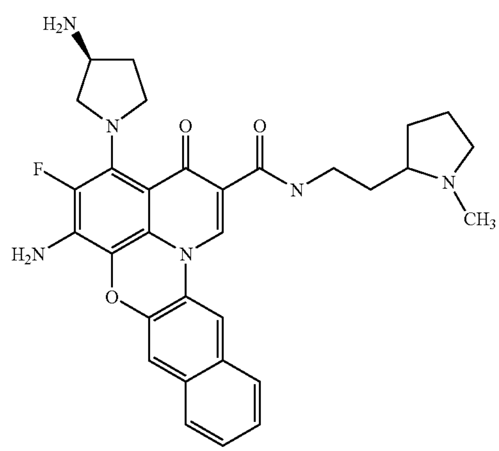 | | 1.75 |
| 190 | 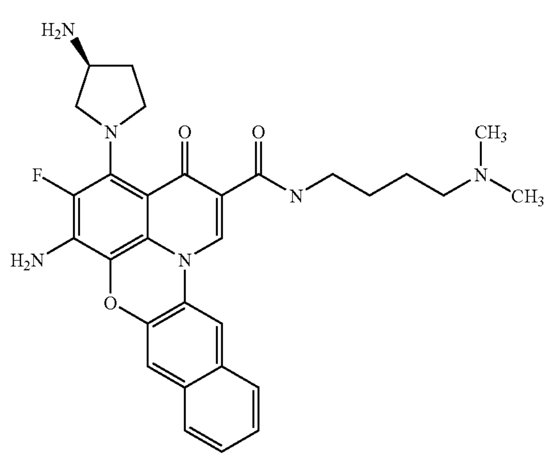 | | 1.75 |

TABLE 2-continued

| | Structure | Stop Data c-Myc μM | MTS Data Hella μM |
|---|---|---|---|
| 191 | 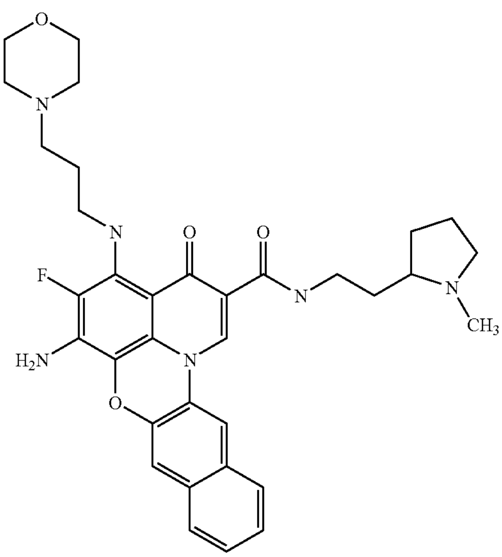 | | 1.75 |
| 192 | 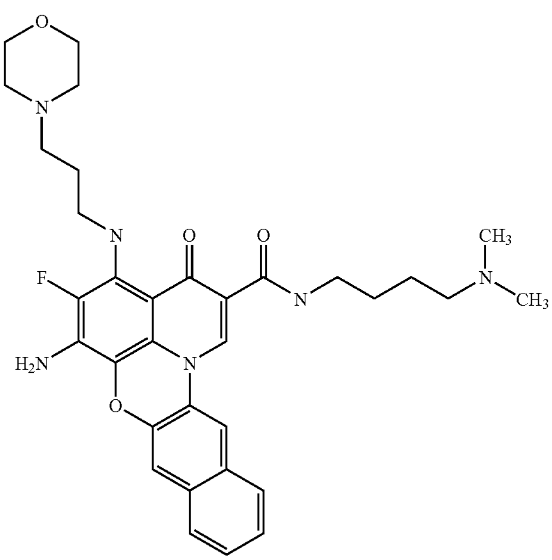 | | 1.75 |
| 193 | 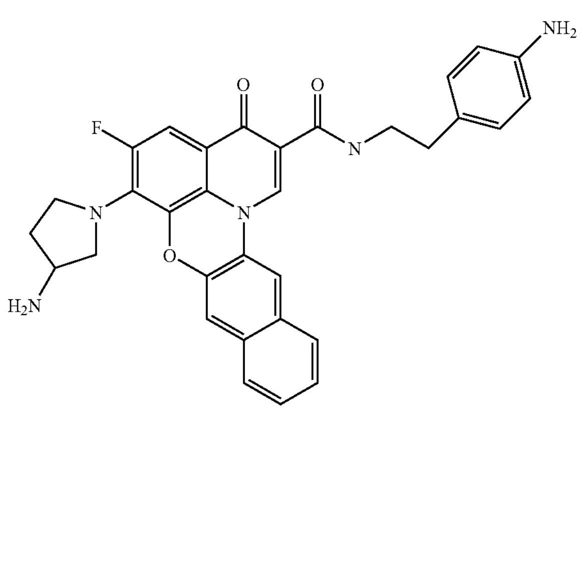 | | 1.75 |

TABLE 2-continued

| | Structure | Stop Data c-Myc μM | MTS Data Hella μM |
|---|---|---|---|
| 194 | 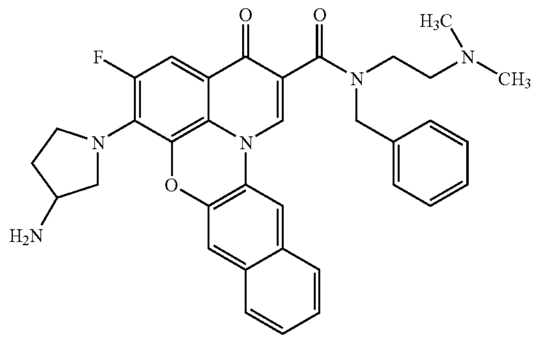 | | 1.75 |
| 195 | 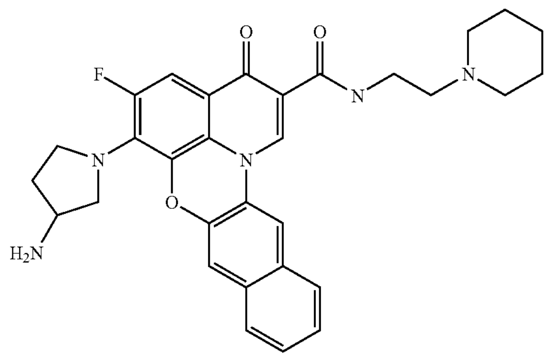 | | 1.75 |
| 196 | 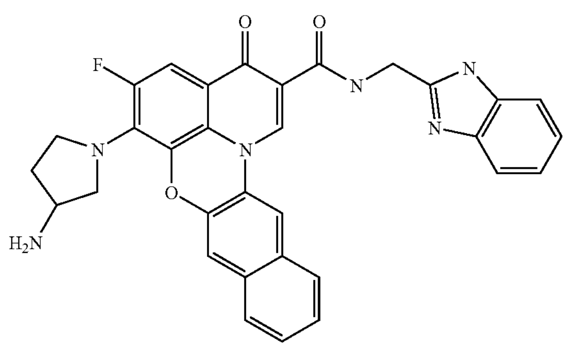 | | 1.75 |
| 197 | 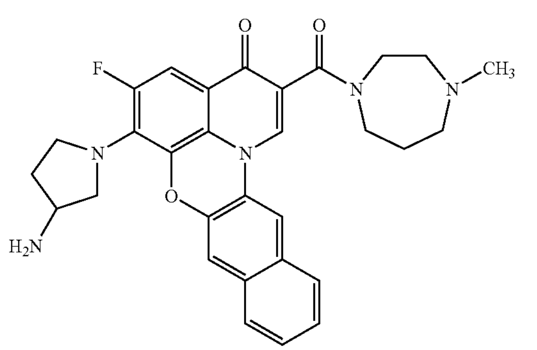 | | 1.75 |

TABLE 2-continued
| | Structure | Stop Data c-Myc μM | MTS Data Hella μM |
|---|---|---|---|
| 198 | 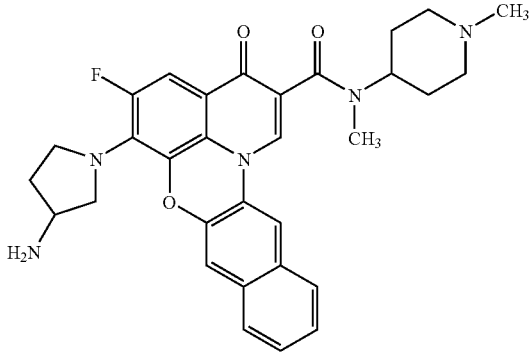 | | 1.75 |
| 199 | 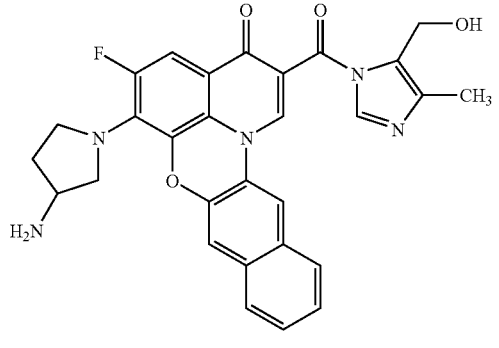 | | 1.75 |
| 200 | 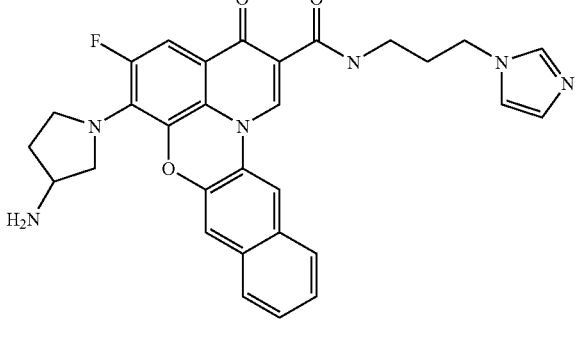 | | 1.75 |
| 201 | 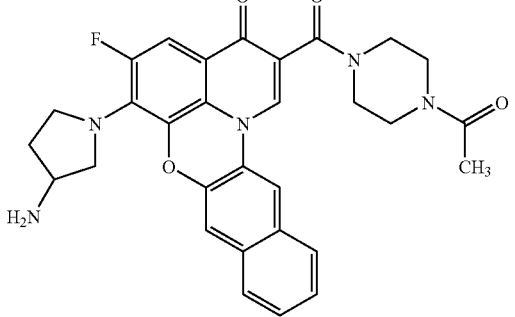 | | 1.75 |

TABLE 2-continued

| | Structure | | Stop Data c-Myc μM | MTS Data Hella μM |
|---|---|---|---|---|
| 202 | 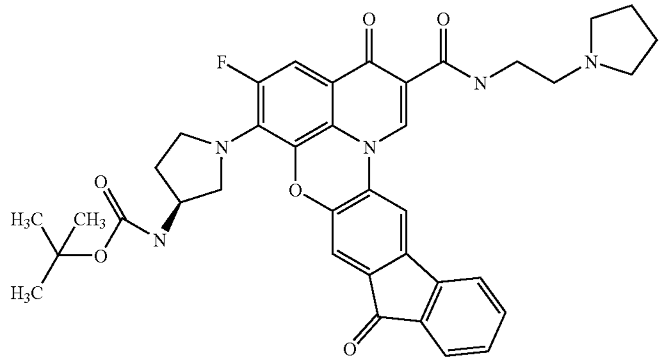 | Chiral | | 1.75 |
| 203 | 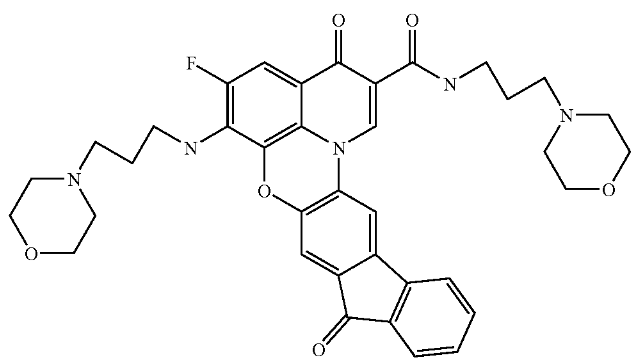 | | | 1.75 |
| 204 | 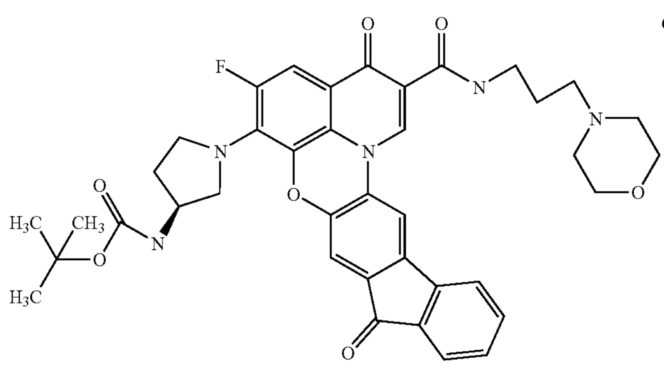 | Chiral | | 1.75 |
| 205 | 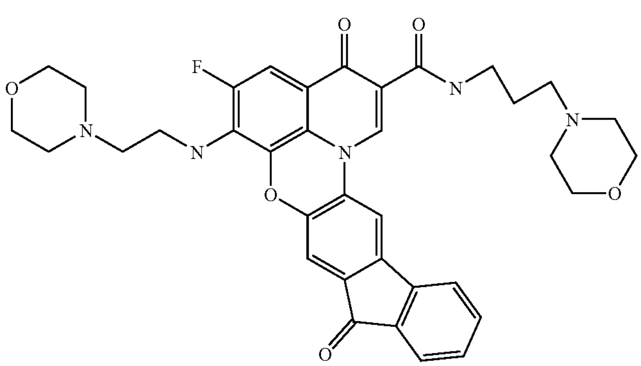 | | | 1.75 |

TABLE 2-continued

| | Structure | | Stop Data c-Myc µM | MTS Data Hella µM |
|---|---|---|---|---|
| 206 | 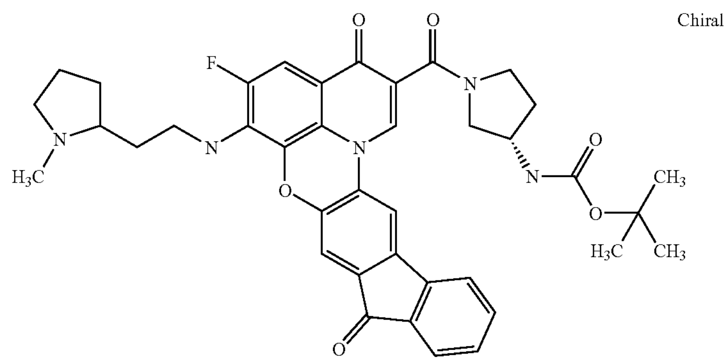 | Chiral | | 1.75 |
| 207 | 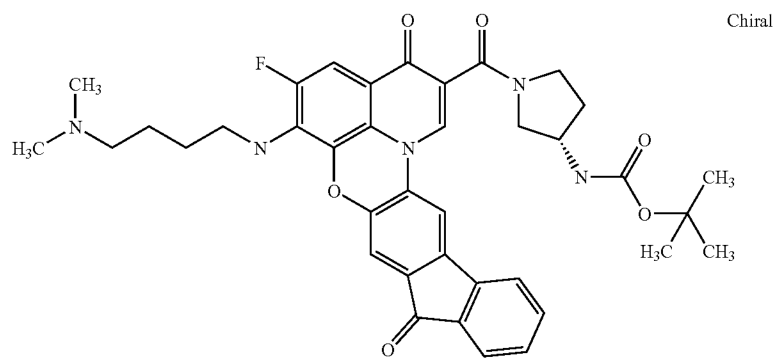 | Chiral | | 1.75 |
| 208 | 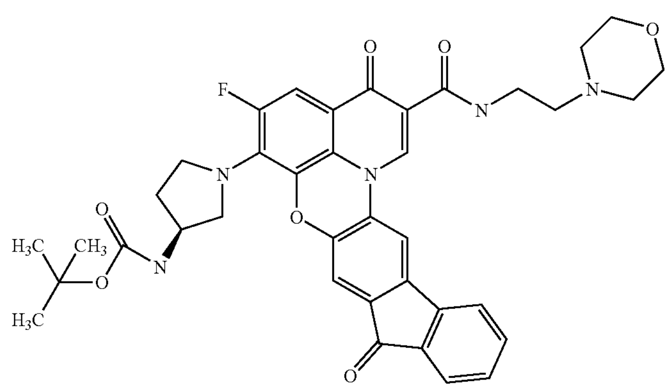 | Chiral | | 1.75 |
| 209 | 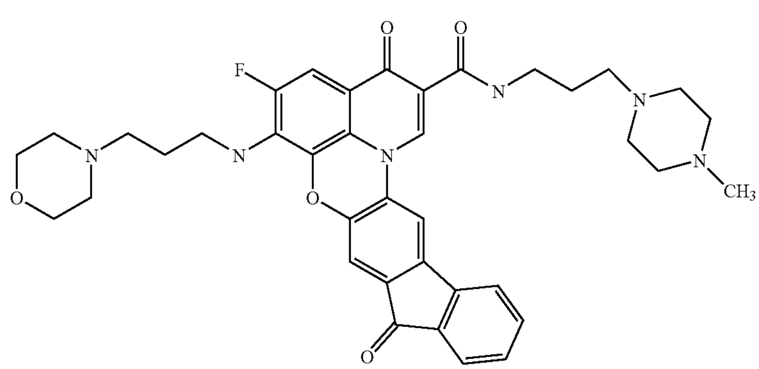 | | | 1.75 |

TABLE 2-continued

| | Structure | Stop Data c-Myc μM | MTS Data Hella μM |
|---|---|---|---|
| 210 | 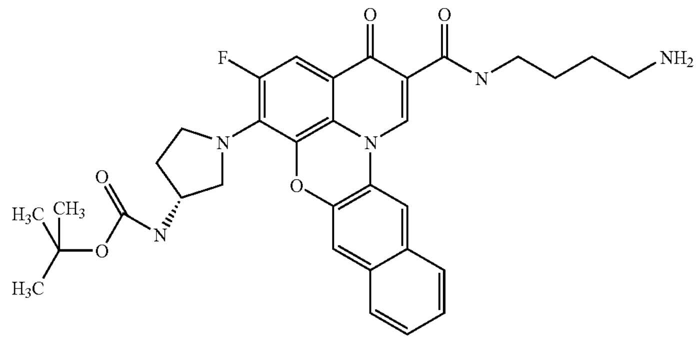 | Chiral | 1.75 |
| 211 | 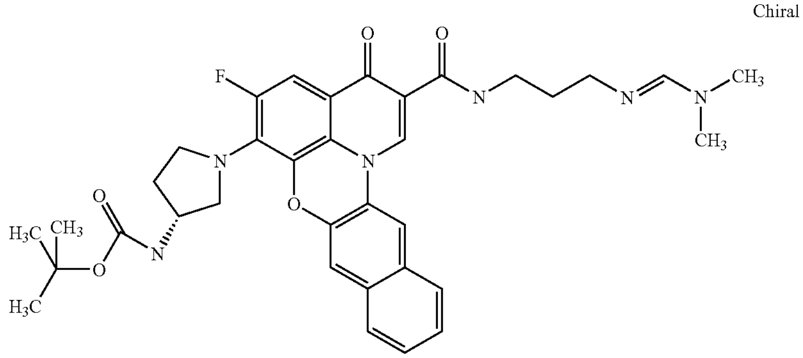 | Chiral | 1.75 |
| 212 | 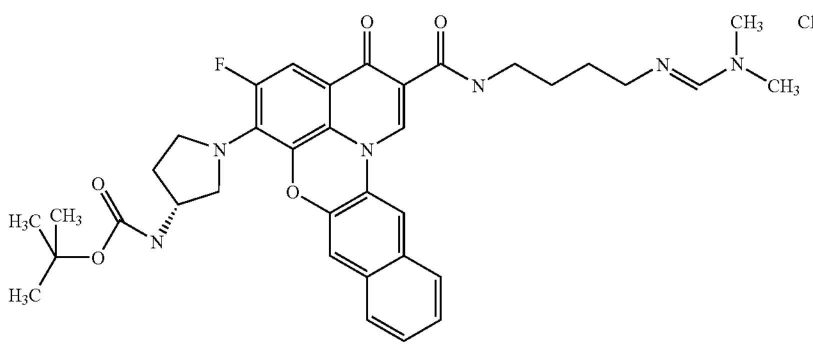 | Chiral | 1.75 |
| 213 | 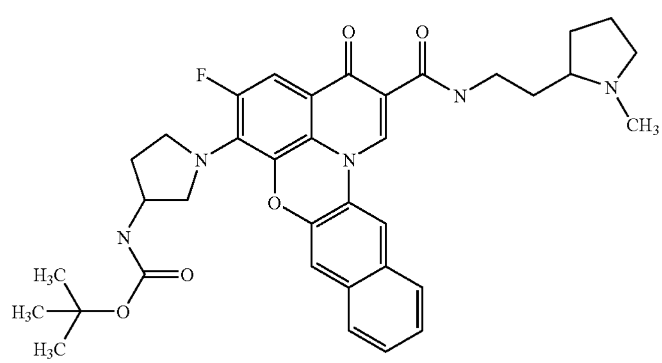 | | 1.75 |

TABLE 2-continued

| | Structure | Stop Data c-Myc μM | MTS Data Hella μM |
|---|---|---|---|
| 214 | Chiral | | 1.75 |
| 215 | Chiral | | 1.75 |
| 216 | Chiral | | 1.75 |
| 217 | Chiral | | 1.75 |

TABLE 2-continued
| | Structure | Stop Data c-Myc μM | MTS Data Hella μM |
|---|---|---|---|
| 218 | 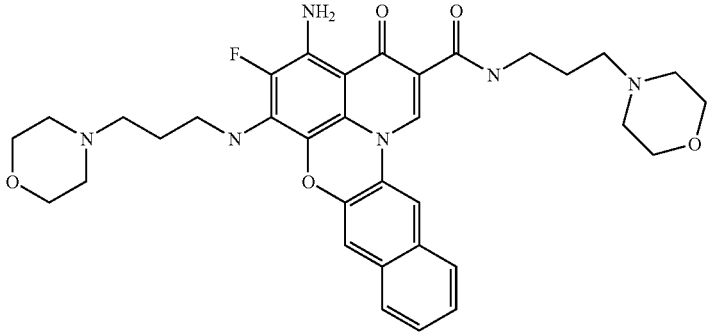 | | 1.75 |
| 219 | 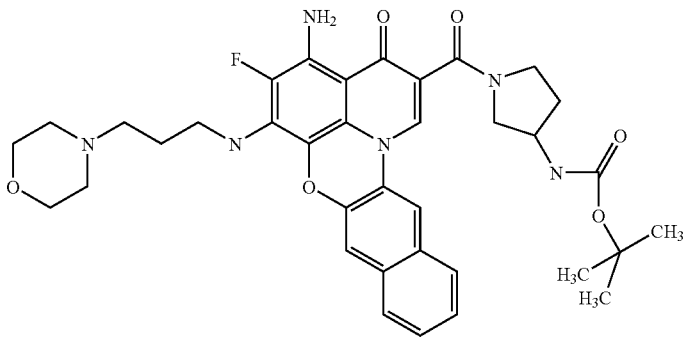 | | 1.75 |
| 220 | 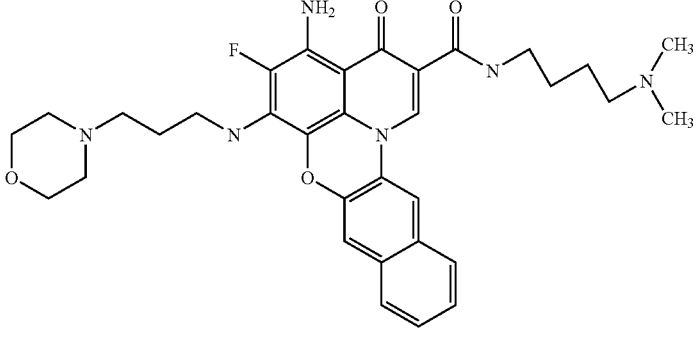 | | 1.75 |
| 221 | 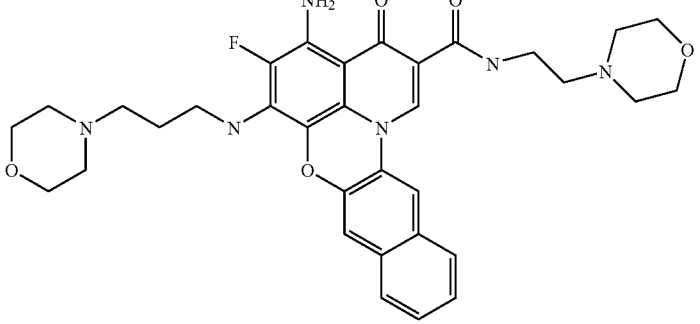 | | 1.75 |

TABLE 2-continued

| | Structure | Stop Data c-Myc μM | MTS Data Hella μM |
|---|---|---|---|
| 222 | 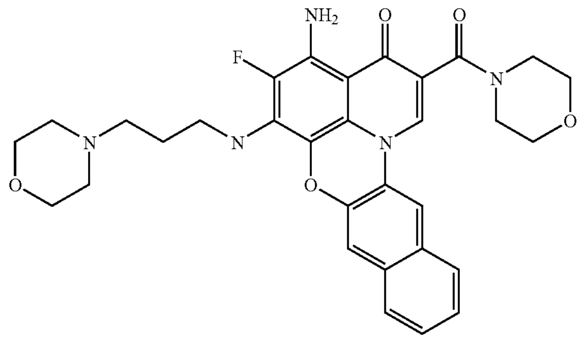 | | 1.75 |
| 223 | 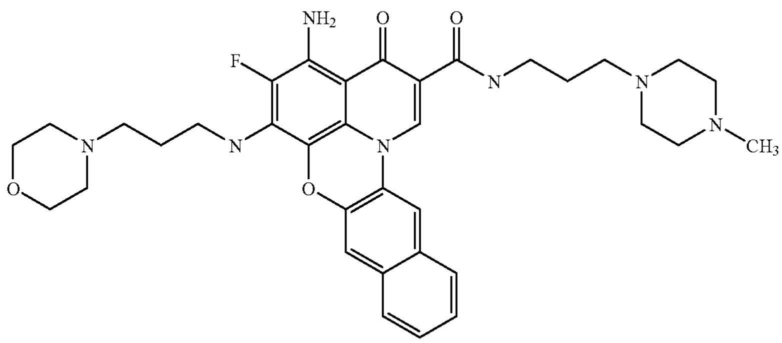 | | 1.75 |
| 224 | 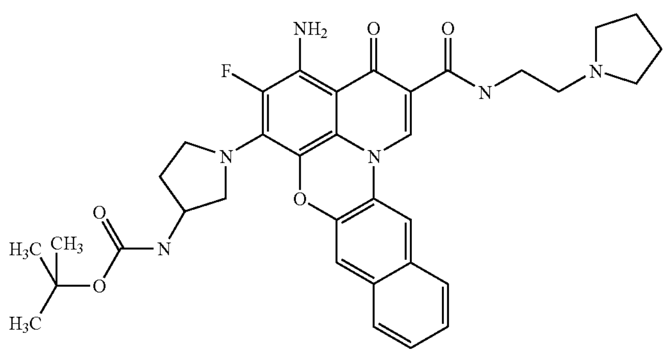 | | 1.75 |
| 225 | 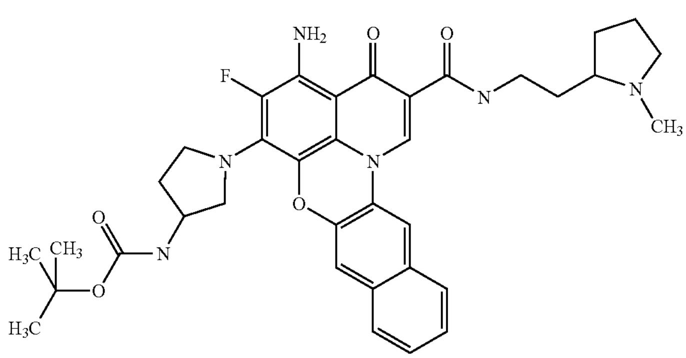 | | 1.75 |

TABLE 2-continued

| | Structure | Stop Data c-Myc μM | MTS Data Hella μM |
|---|---|---|---|
| 226 | 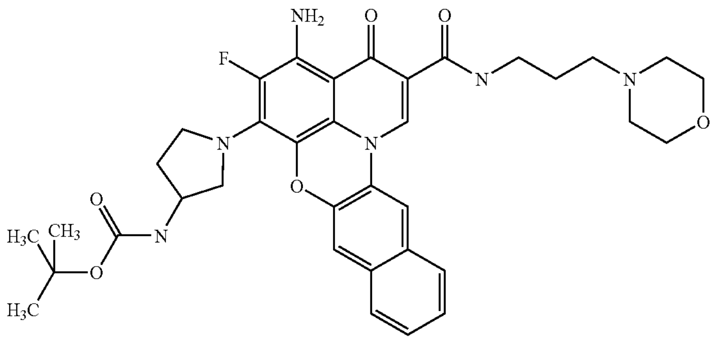 | | 1.75 |
| 227 | 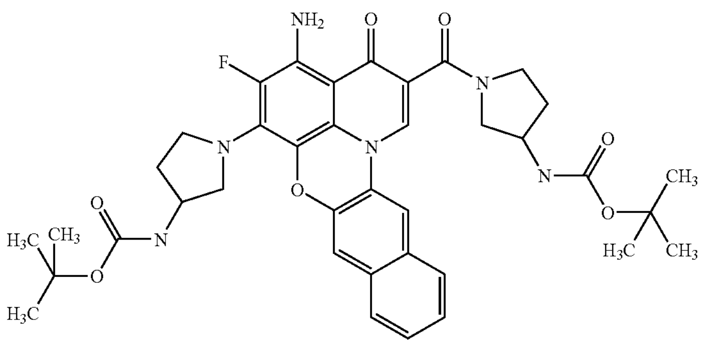 | | 1.75 |
| 228 | 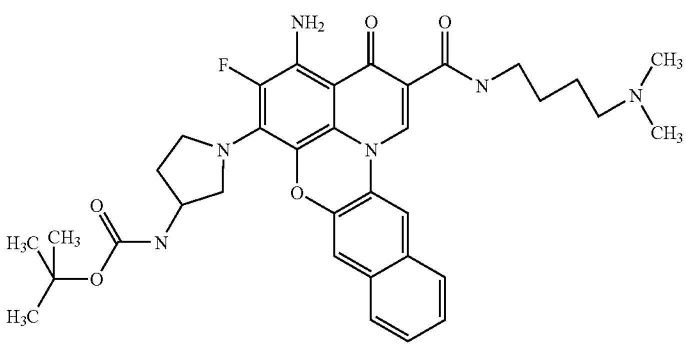 | | 1.75 |
| 229 | 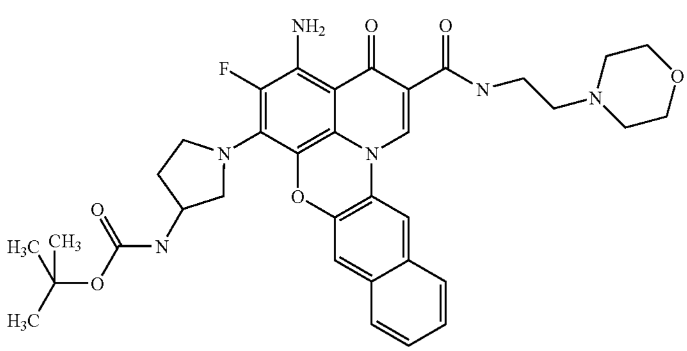 | | 1.75 |

TABLE 2-continued

| | Structure | Stop Data c-Myc μM | MTS Data Hella μM |
|---|---|---|---|
| 230 | 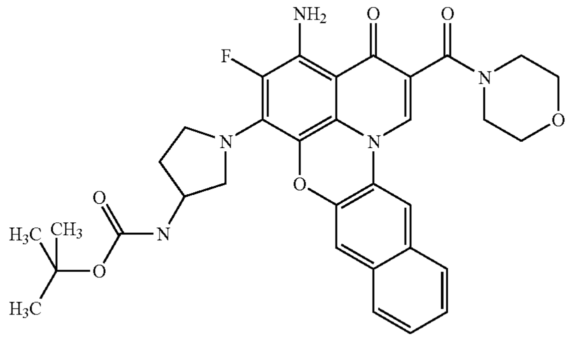 | | 1.75 |
| 231 | 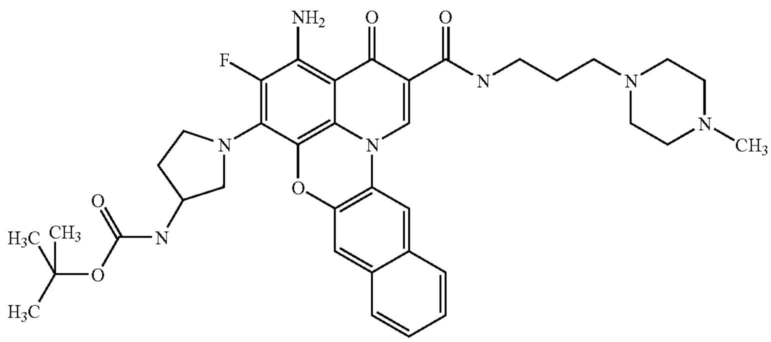 | | 1.75 |
| 232 | 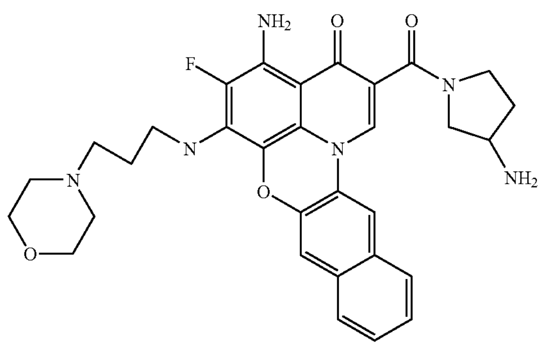 | | 1.75 |
| 233 | 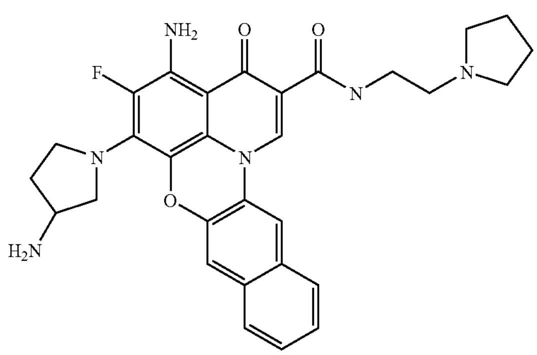 | | 1.75 |

TABLE 2-continued

| | Structure | Stop Data c-Myc μM | MTS Data Hella μM |
|---|---|---|---|
| 234 | 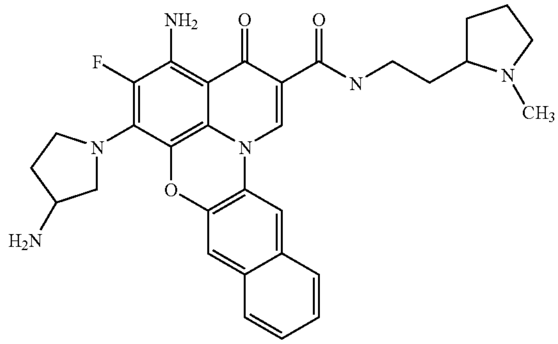 | | 1.75 |
| 235 | 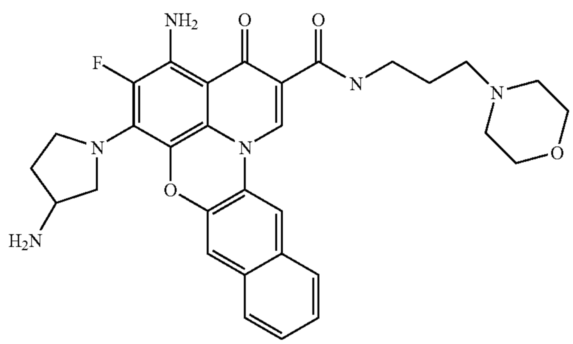 | | 1.75 |
| 236 | 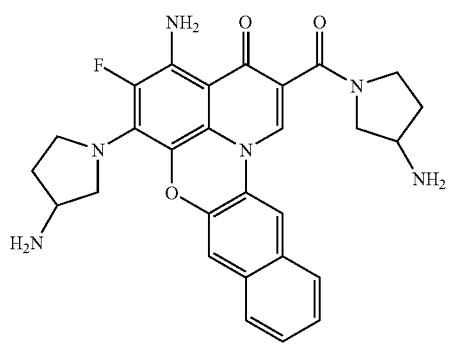 | | 1.75 |
| 237 | 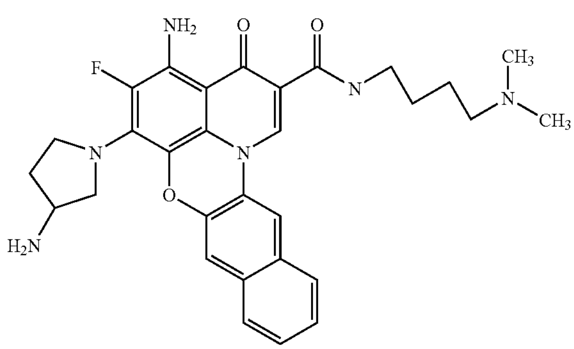 | | 1.75 |

TABLE 2-continued

| | Structure | Stop Data c-Myc μM | MTS Data Hella μM |
|---|---|---|---|
| 238 | 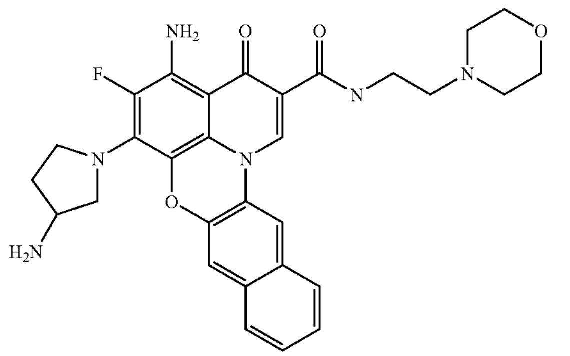 | | 1.75 |
| 239 | 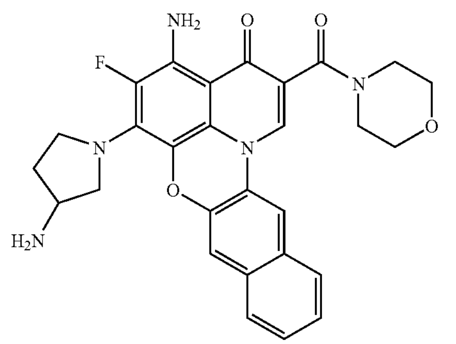 | | 1.75 |
| 240 | 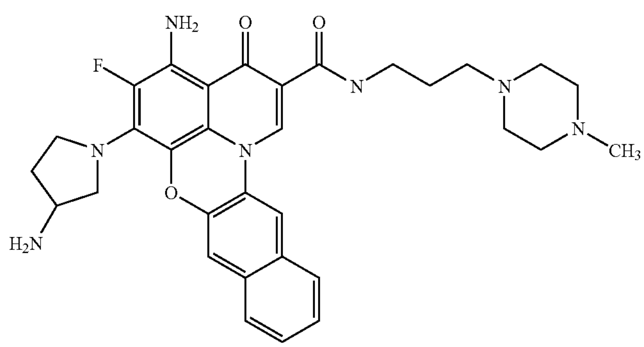 | | 1.75 |
| 241 | 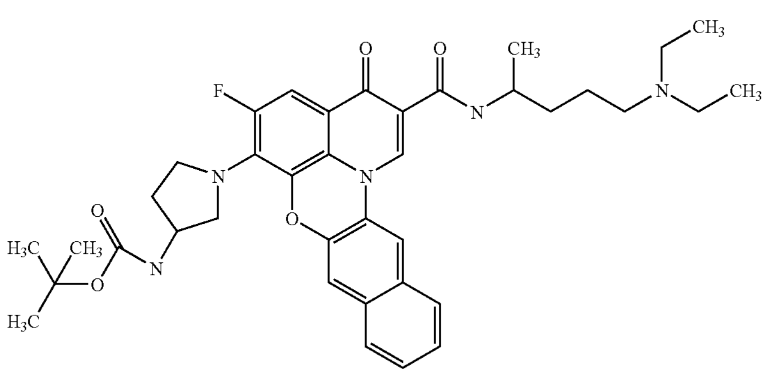 | | 1.75 |

TABLE 2-continued

| Structure | Stop Data c-Myc μM | MTS Data Hella μM |
|---|---|---|
| 242 | | 1.75 |
| 243 | | 1.75 |
| 244 | | 1.75 |
| 245 | | 1.75 |

TABLE 2-continued
| | Structure | Stop Data c-Myc µM | MTS Data Hella µM |
|---|---|---|---|
| 246 | 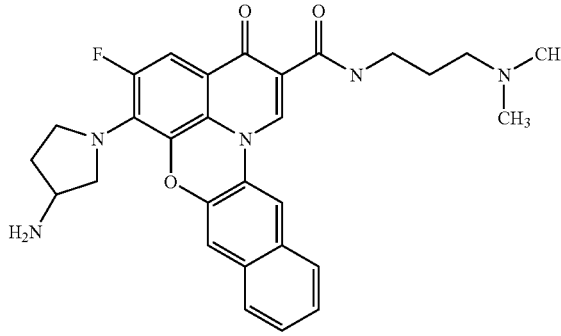 | | 1.75 |
| 247 | 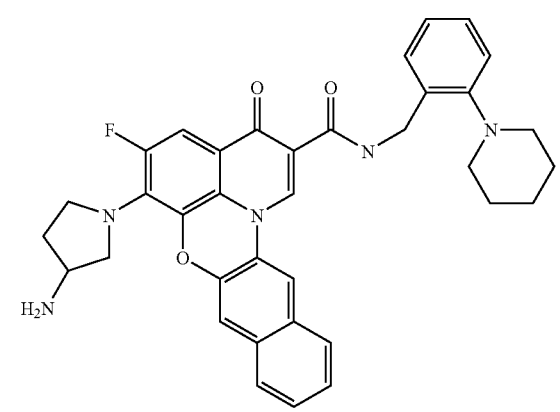 | | 1.75 |
| 248 | 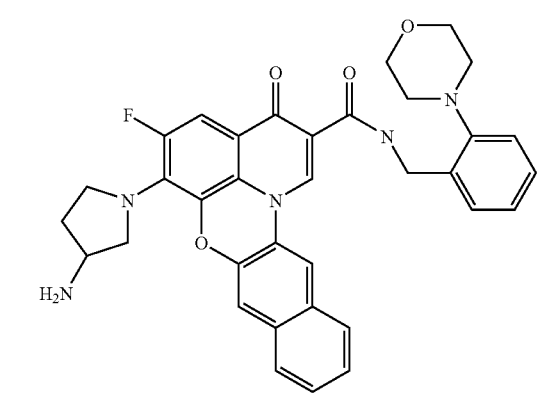 | | 1.75 |
| 249 | 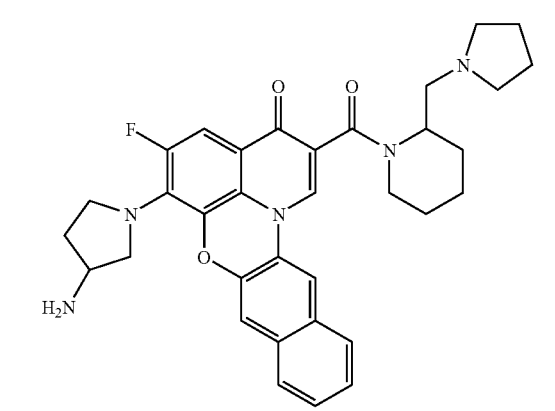 | | 1.75 |

TABLE 2-continued

| Structure | Stop Data c-Myc μM | MTS Data Hella μM |
|---|---|---|
| 250 | | 1.75 |
| 251 | | 1.75 |
| 252 | | 1.75 |
| 253 | | 1.75 |

TABLE 2-continued

| | Structure | Stop Data c-Myc μM | MTS Data Hella μM |
|---|---|---|---|
| 254 | 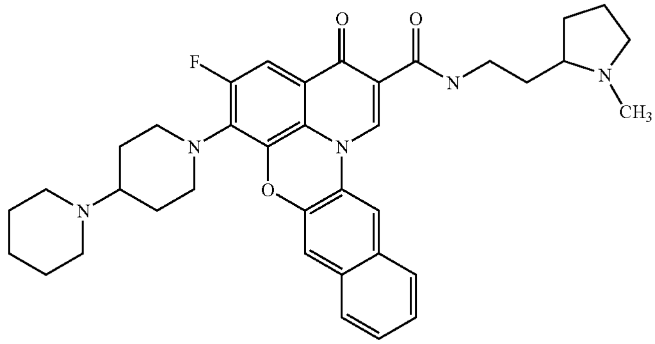 | | 1.75 |
| 255 | 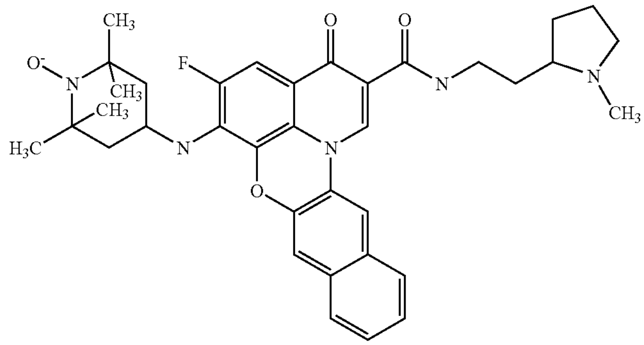 | | 1.75 |
| 256 | 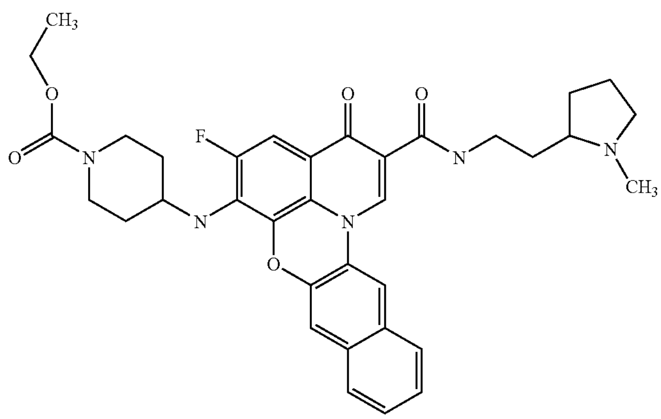 | | 1.75 |
| 257 | 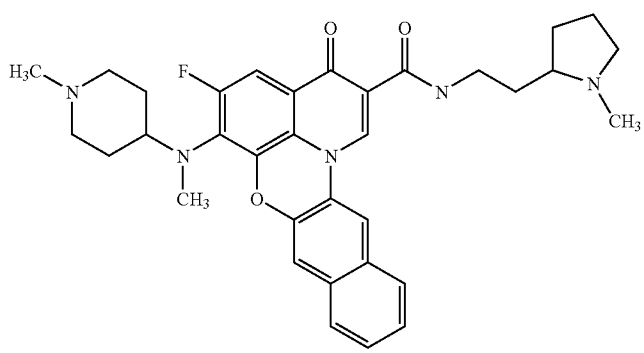 | | 1.75 |

TABLE 2-continued
| | Structure | Stop Data c-Myc μM | MTS Data Hella μM |
|---|---|---|---|
| 258 | 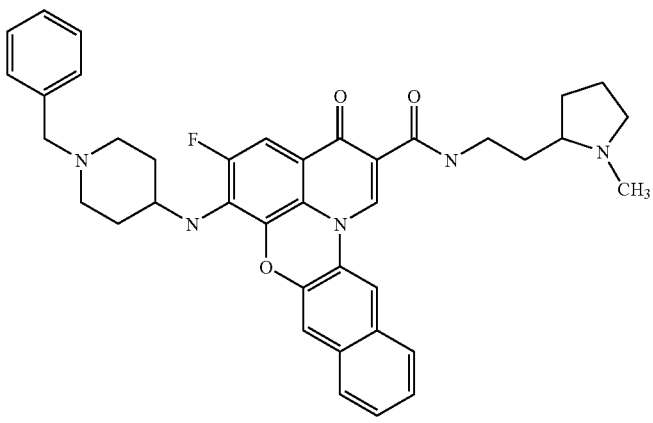 | | 1.75 |
| 259 | 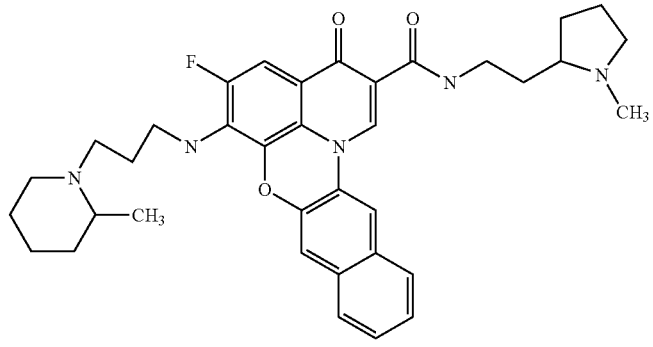 | | 1.75 |
| 260 | 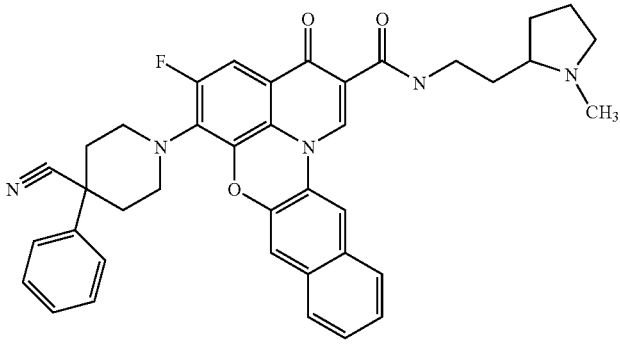 | | 1.75 |
| 261 | 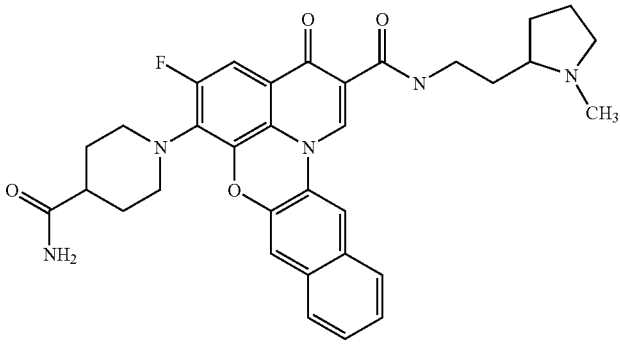 | | 1.75 |

TABLE 2-continued

| Structure | Stop Data c-Myc μM | MTS Data Hella μM |
|---|---|---|
| 262 | | 1.75 |
| 263 | | 1.75 |
| 264 | | 1.75 |
| 265 | | 1.75 |

TABLE 2-continued

| | Structure | Stop Data c-Myc μM | MTS Data Hella μM |
|---|---|---|---|
| 266 | 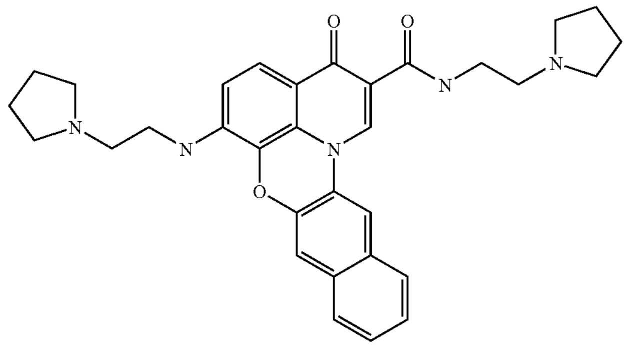 | | 1.75 |
| 267 | 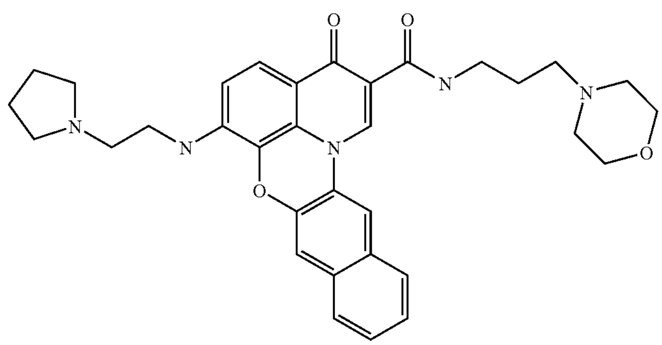 | | 1.75 |
| 268 | 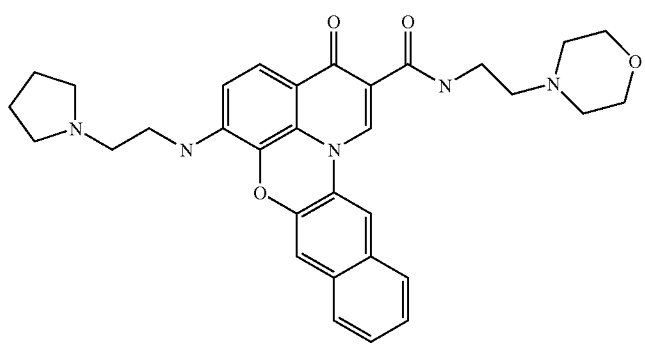 | | 1.75 |
| 269 | 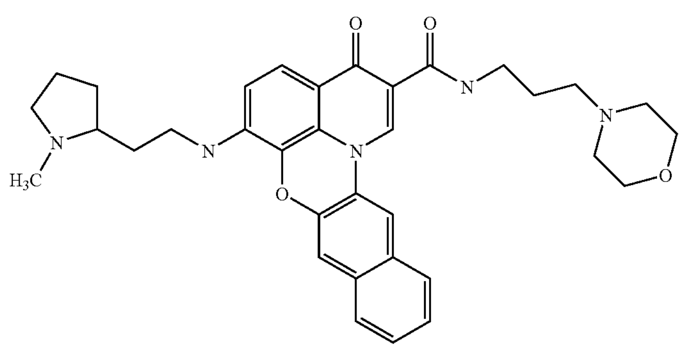 | | 1.75 |

TABLE 2-continued

| Structure | Stop Data c-Myc μM | MTS Data Hella μM |
|---|---|---|
| 270 | | 1.75 |
| 271 | | 1.75 |
| 272 | | 1.75 |
| 273 | | 1.75 |

TABLE 2-continued

| Structure | Stop Data c-Myc μM | MTS Data Hella μM |
|---|---|---|
| 274 | | 1.75 |
| 275 | | 1.75 |
| 276 | | 1.75 |
| 277 | | 1.75 |

TABLE 2-continued
| | Structure | Stop Data c-Myc μM | MTS Data Hella μM |
|---|---|---|---|
| 278 | 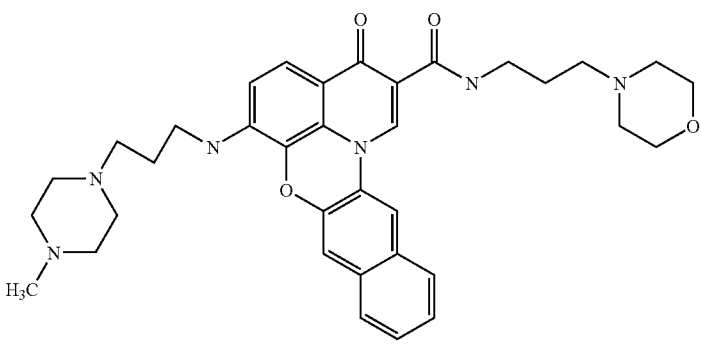 | | 1.75 |
| 279 | 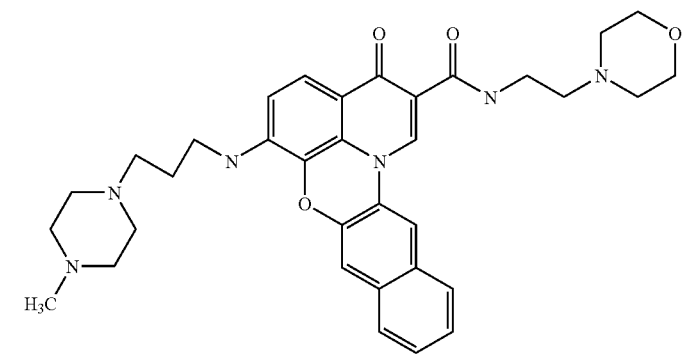 | | 1.75 |
| 280 | 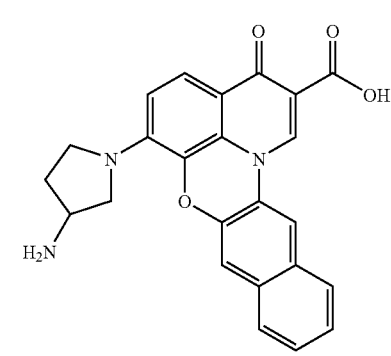 | | 1.75 |
| 281 | 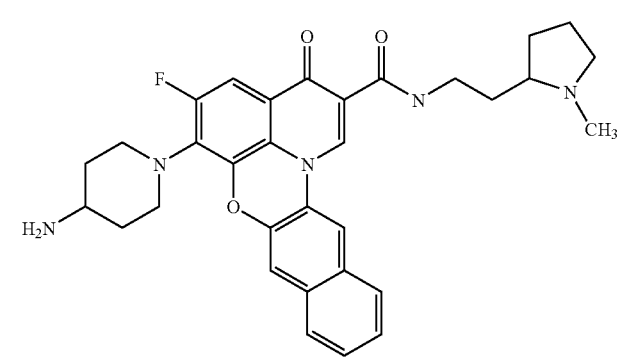 | | 1.75 |

TABLE 2-continued

| Structure | Stop Data c-Myc μM | MTS Data Hella μM |
|---|---|---|
| 282 | | 1.75 |
| 283 | | 1.75 |
| 284 | | 1.75 |
| 285 | | 1.75 |

TABLE 2-continued

| | Structure | Stop Data c-Myc μM | MTS Data Hella μM |
|---|---|---|---|
| 286 | 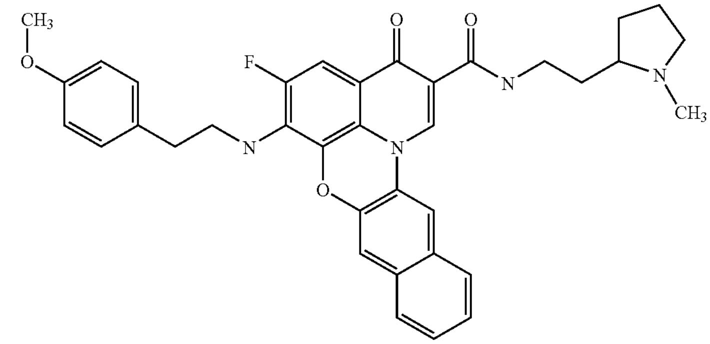 | | 1.75 |
| 287 | 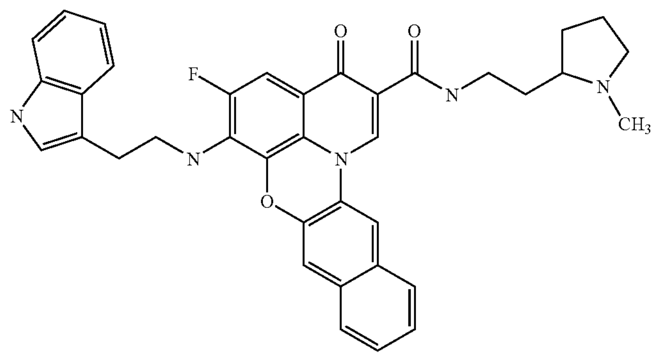 | | 1.75 |
| 288 | 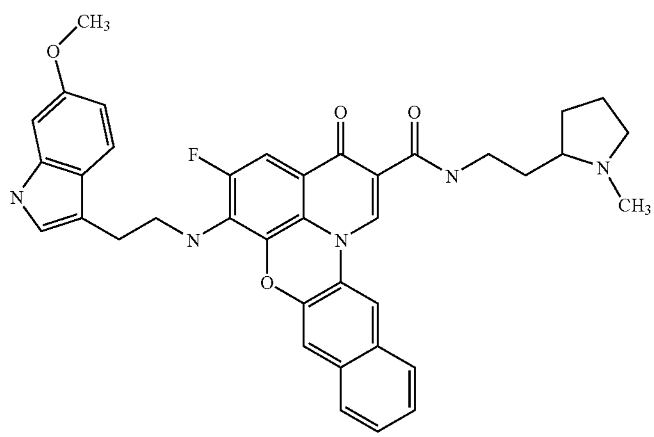 | | 1.75 |
| 289 | 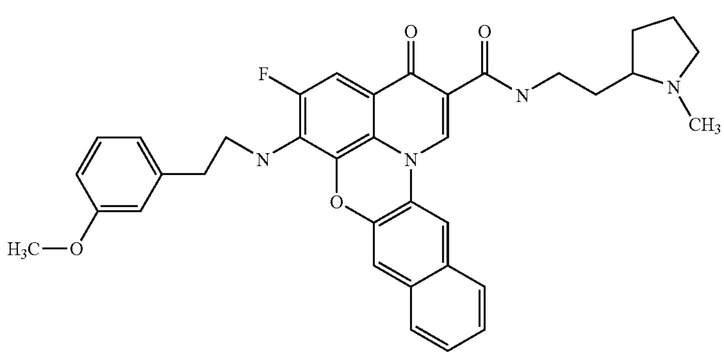 | | 1.75 |

TABLE 2-continued

| | Structure | Stop Data c-Myc µM | MTS Data Hella µM |
|---|---|---|---|
| 290 | 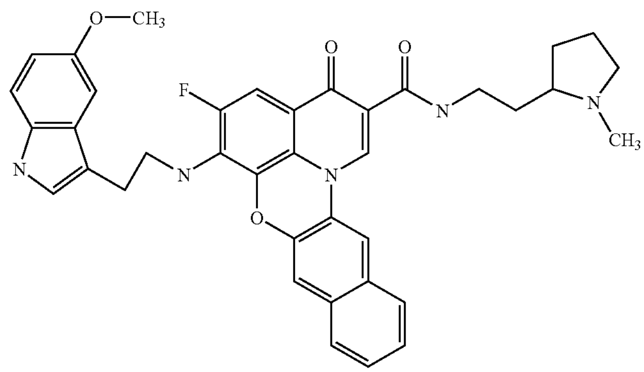 | | 1.75 |
| 291 | 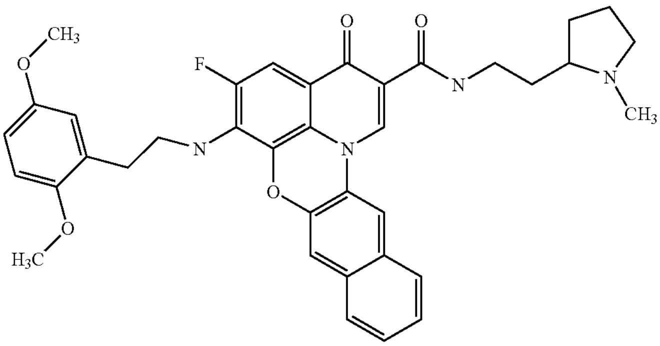 | | 1.75 |
| 292 | 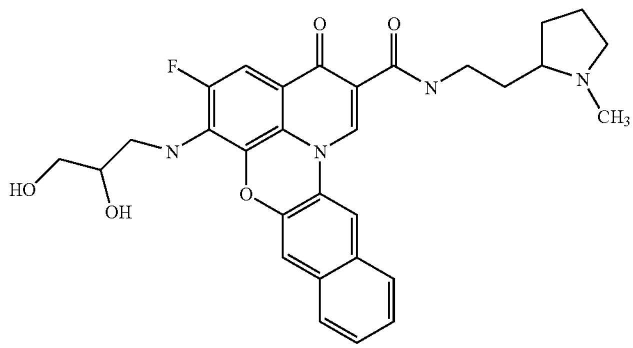 | | 1.75 |
| 293 | 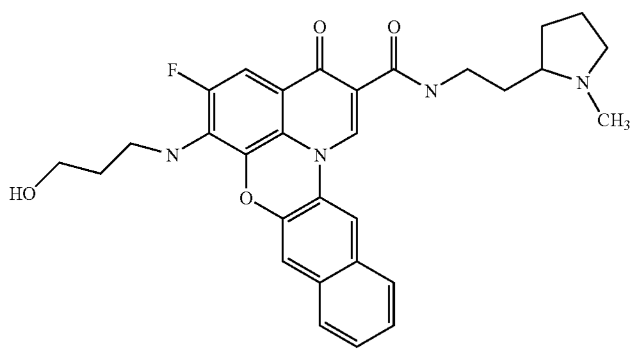 | | 1.75 |

TABLE 2-continued
| | Structure | Stop Data c-Myc μM | MTS Data Hella μM |
|---|---|---|---|
| 294 | 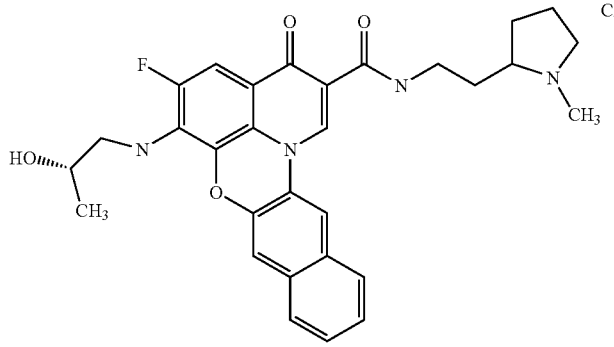 Chiral | | 1.75 |
| 295 | 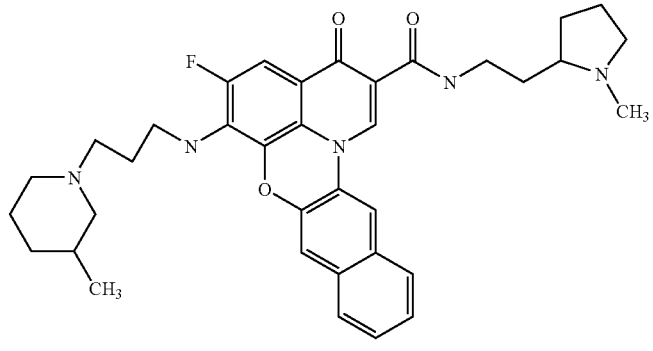 | | 1.75 |
| 296 | 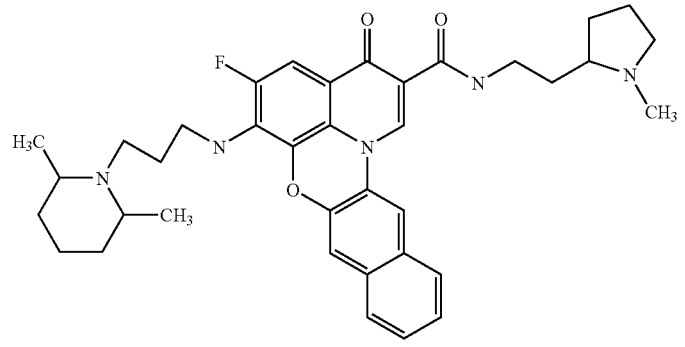 | | 1.75 |
| 297 | 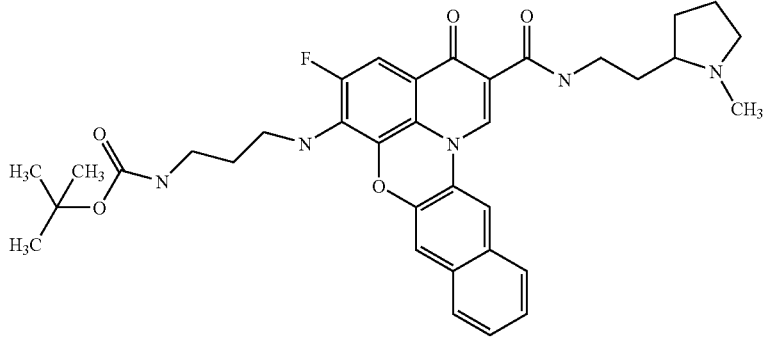 | | 1.75 |

TABLE 2-continued

| | Structure | Stop Data c-Myc μM | MTS Data Hella μM |
|---|---|---|---|
| 298 | 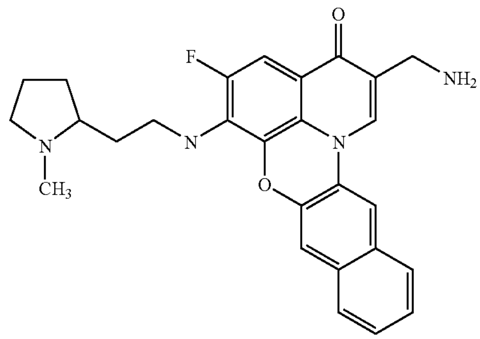 | | 1.75 |
| 299 | 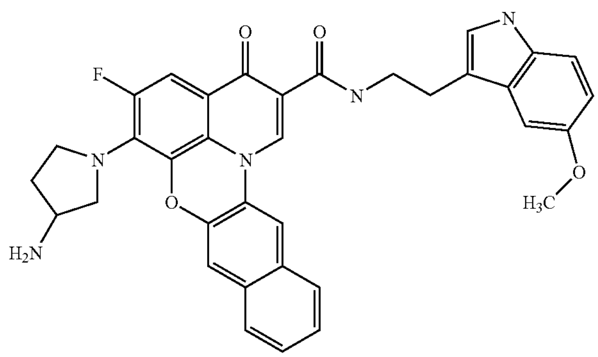 | | 1.75 |
| 300 | 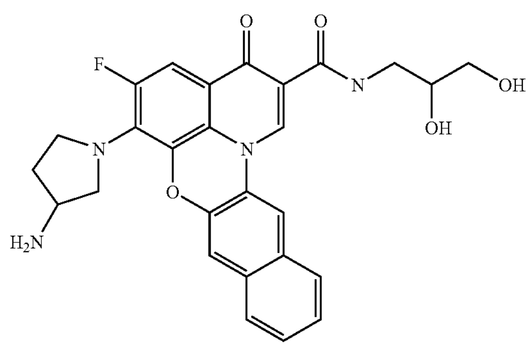 | | 1.75 |
| 301 | 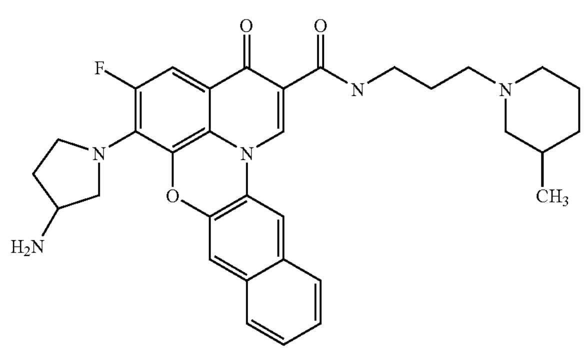 | | 1.75 |

TABLE 2-continued

| | Structure | Stop Data c-Myc μM | MTS Data Hella μM |
|---|---|---|---|
| 302 | 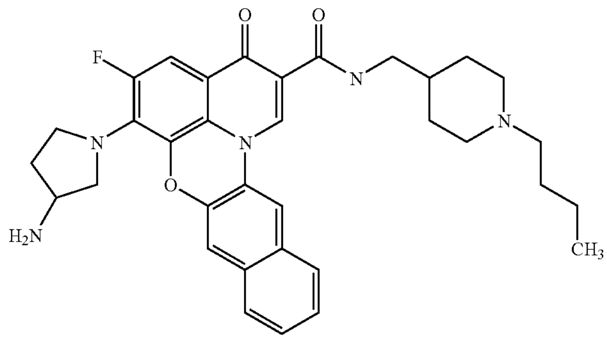 | | 1.75 |
| 303 | 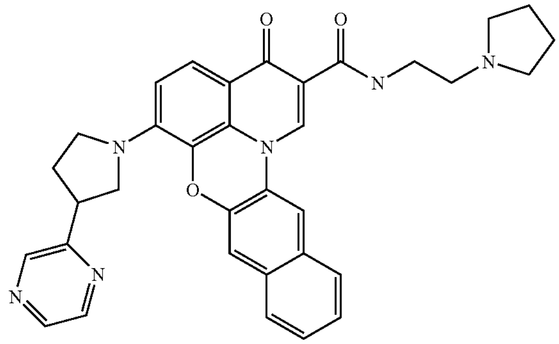 | 1.5 | 2.10 |
| 304 | 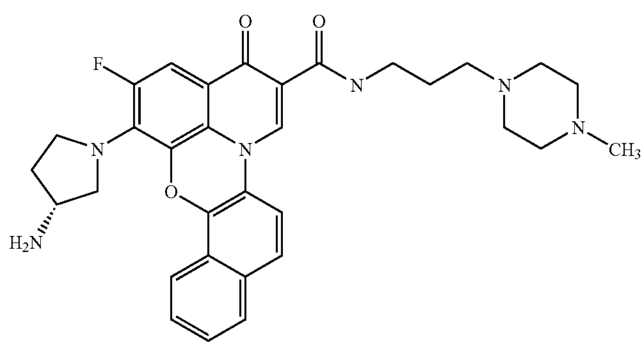 | | 1.13 |
| 305 | 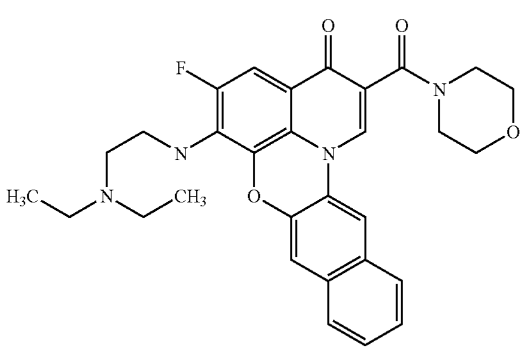 | | 1.05 |

TABLE 2-continued
| | Structure | Stop Data c-Myc μM | MTS Data Hella μM |
|---|---|---|---|
| 306 | 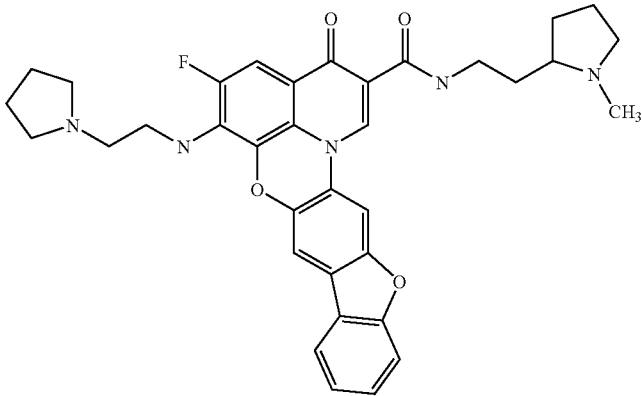 | 1 | 3.20 |
| 307 | 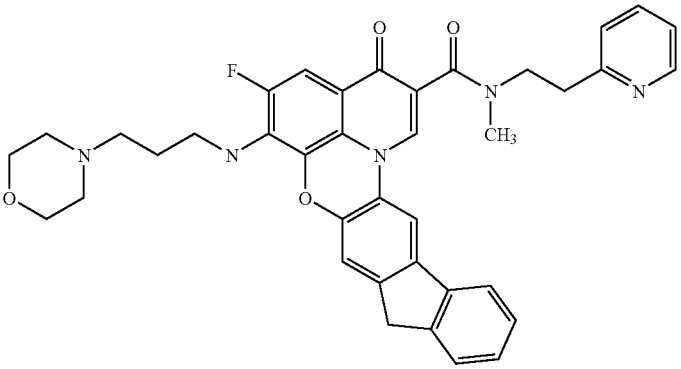 | 1 | 3.10 |
| 308 | 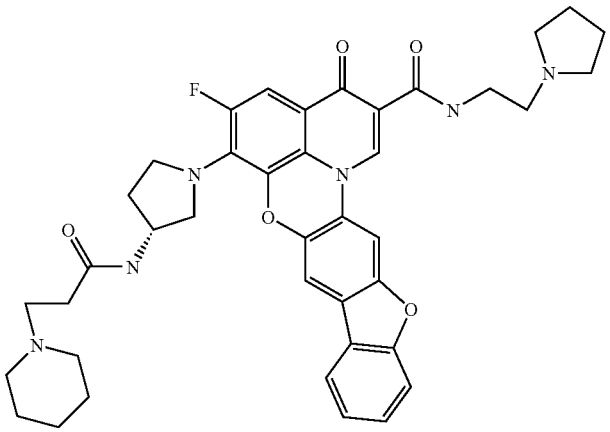 Chiral | 1 | 3.10 |

TABLE 2-continued
| | Structure | Stop Data c-Myc μM | MTS Data Hella μM |
|---|---|---|---|
| 309 | 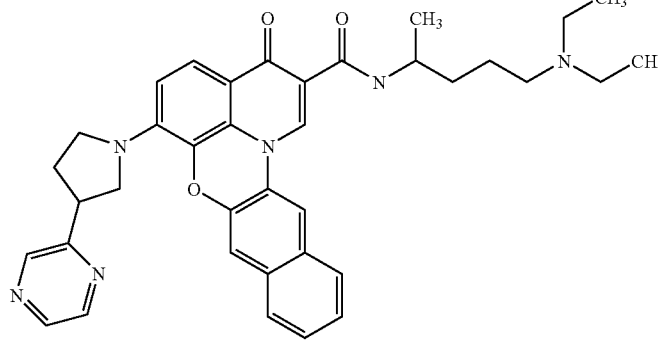 | 1 | 3.00 |
| 310 | 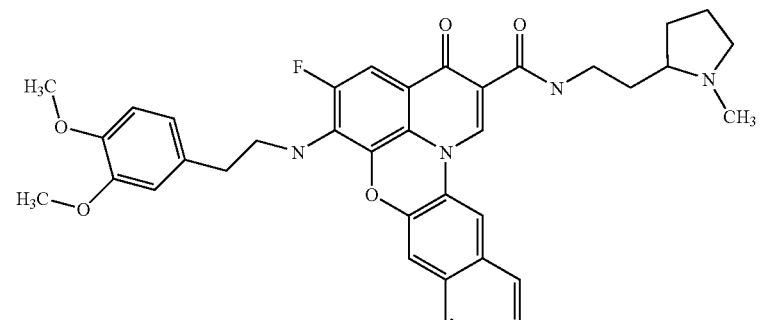 | 1 | 2.30 |
| 311 | Chiral 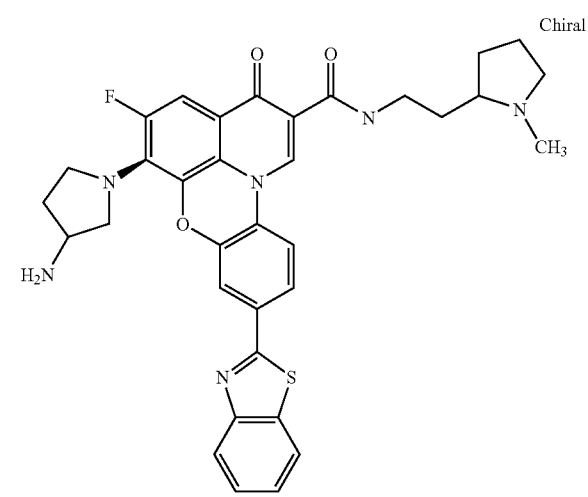 | 1 | 2.10 |
| 312 | 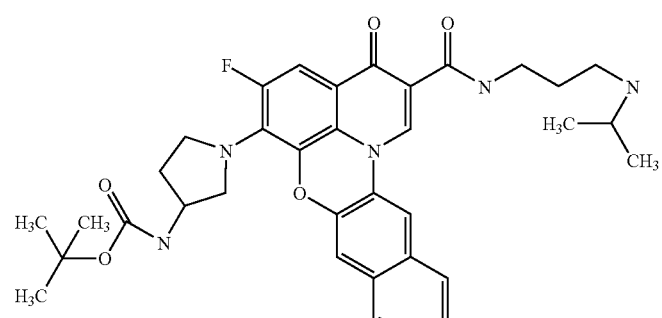 | 1 | 1.90 |

TABLE 2-continued

| | Structure | Stop Data c-Myc μM | MTS Data Hella μM |
|---|---|---|---|
| 313 | 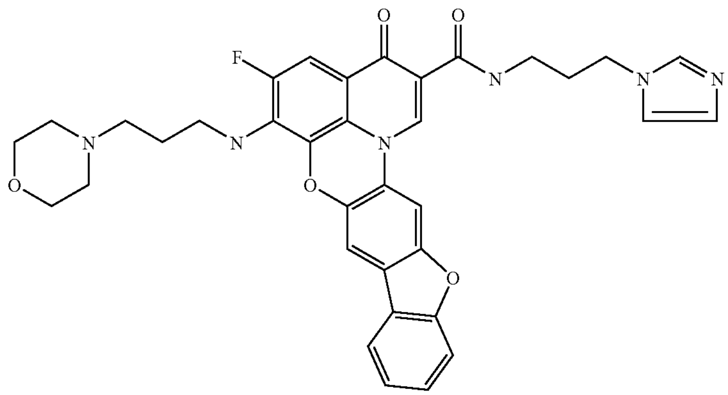 | | 1 |
| 314 | 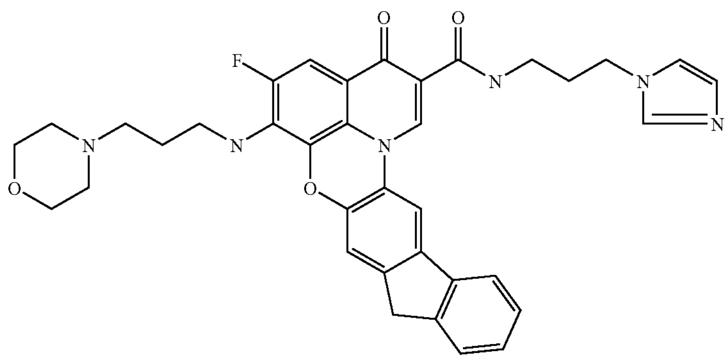 | | 1 |
| 315 | 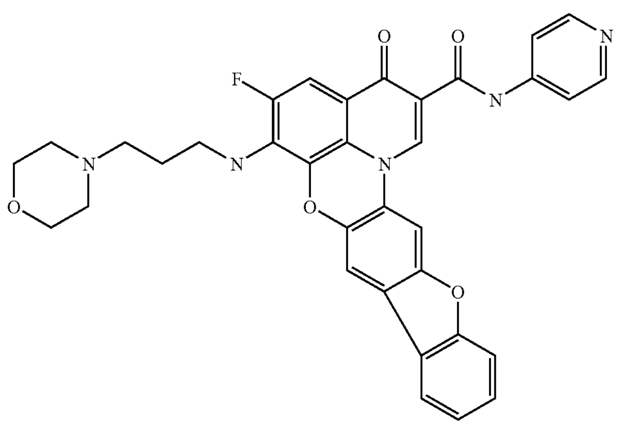 | | 1 |
| 316 | 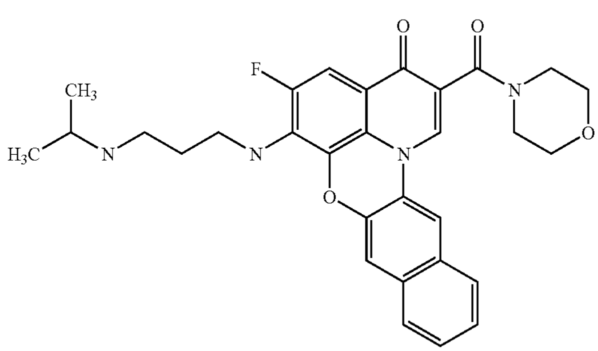 | | 1 |

TABLE 2-continued

| | Structure | Stop Data c-Myc μM | MTS Data Hella μM |
|---|---|---|---|
| 317 | 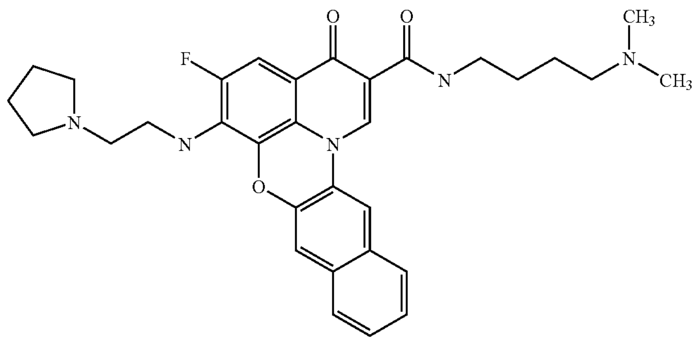 | | 1 |
| 318 | 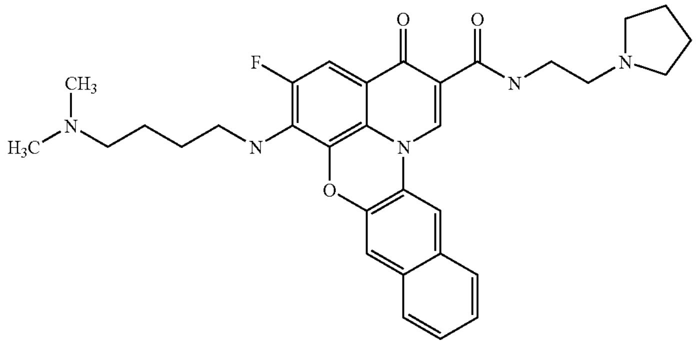 | | 1 |
| 319 | 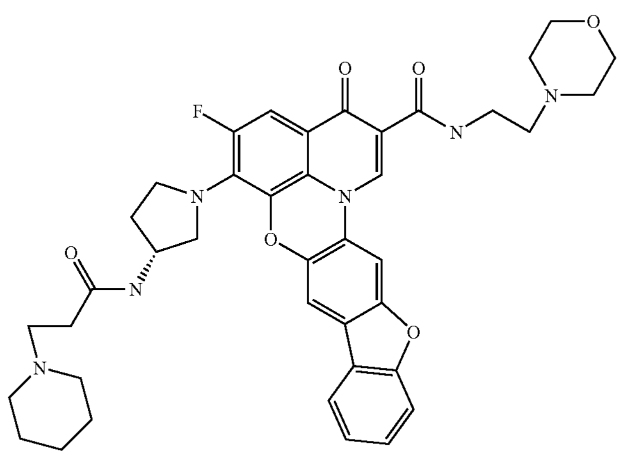 | | 1 |
| 320 | 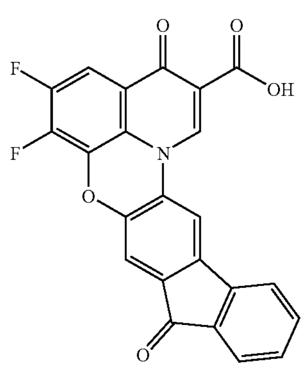 | | 1 |

TABLE 2-continued

| | Structure | Stop Data c-Myc μM | MTS Data Hella μM |
|---|---|---|---|
| 321 | 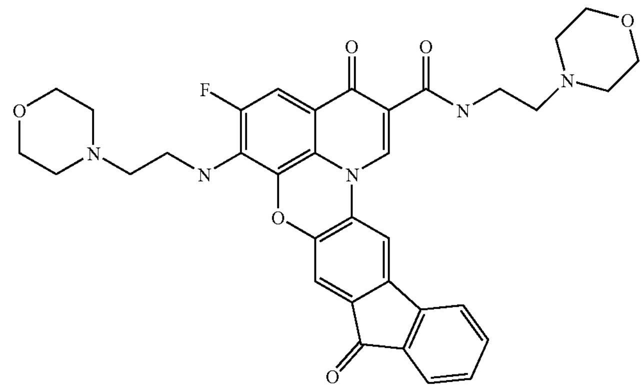 | | 1 |
| 322 | (Chiral) | | 1 |
| 323 | 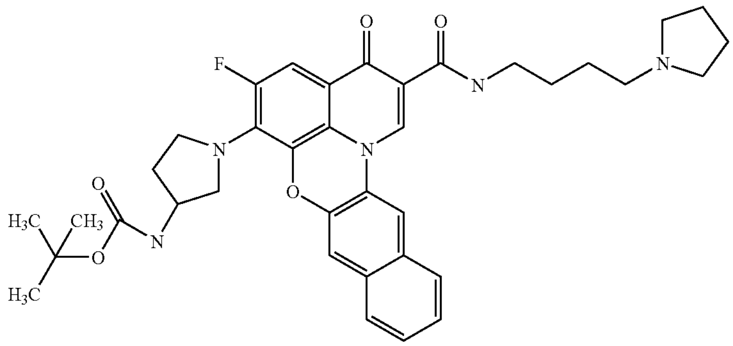 | | 1 |
| 324 | 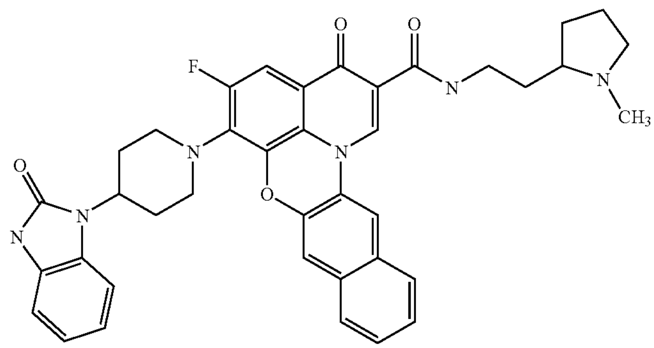 | | 1 |

TABLE 2-continued

| | Structure | Stop Data c-Myc μM | MTS Data Hella μM |
|---|---|---|---|
| 325 | 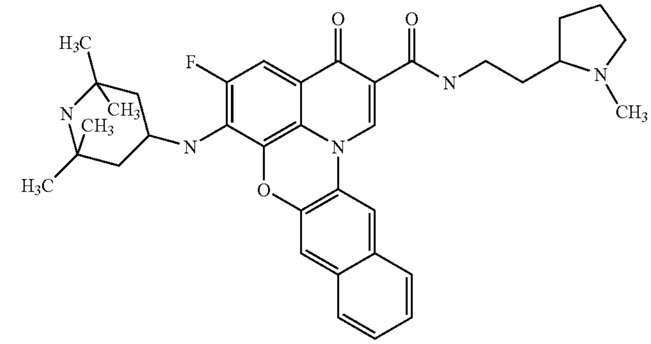 | | 1 |
| 326 | 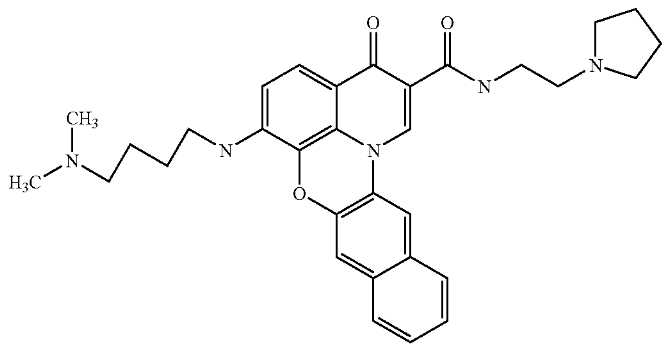 | | 1 |
| 327 | 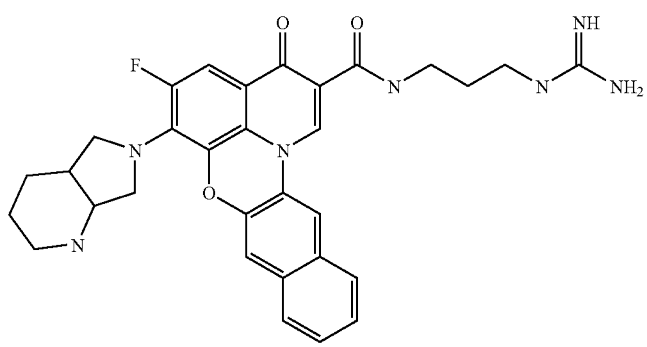 | | 1 |
| 328 | 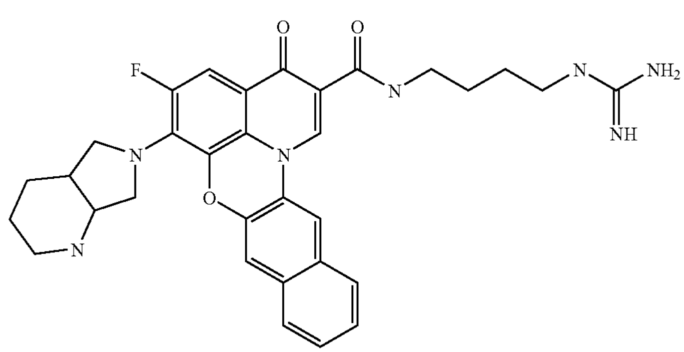 | | 1 |

TABLE 2-continued
| | Structure | Stop Data c-Myc μM | MTS Data Hella μM |
|---|---|---|---|
| 329 | 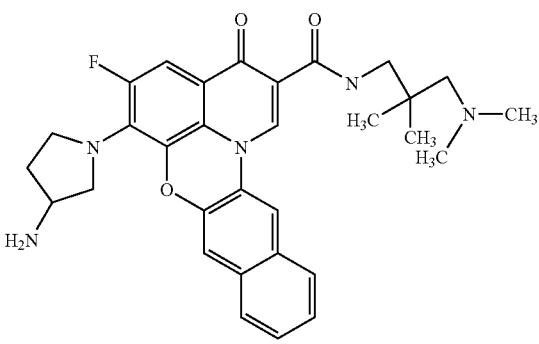 | | 1 |
| 330 | 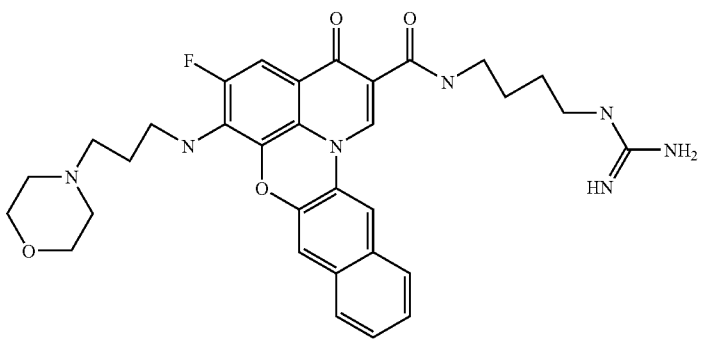 | | 1 |
| 331 | 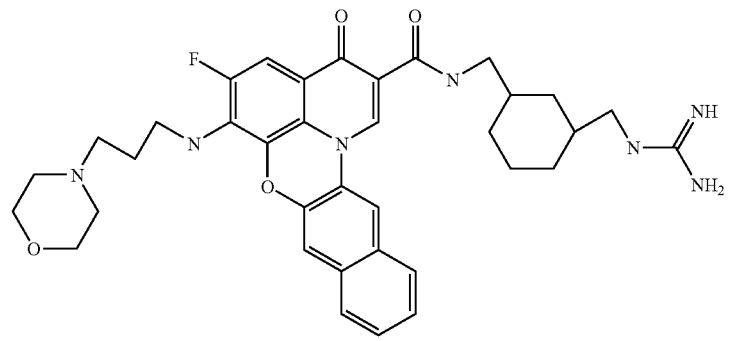 | | 1 |
| 332 | 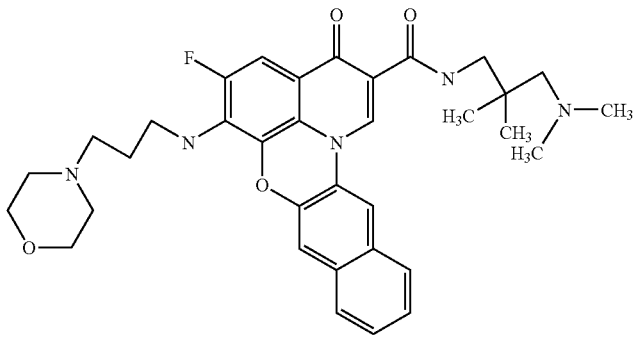 | | 1 |

TABLE 2-continued

| Structure | Stop Data c-Myc μM | MTS Data Hella μM |
|---|---|---|
| 333 | | 1 |
| 334 | | 1 |
| 335 | | 1 |
| 336 | | 1 |

TABLE 2-continued

| | Structure | Stop Data c-Myc μM | MTS Data Hella μM |
|---|---|---|---|
| 337 | 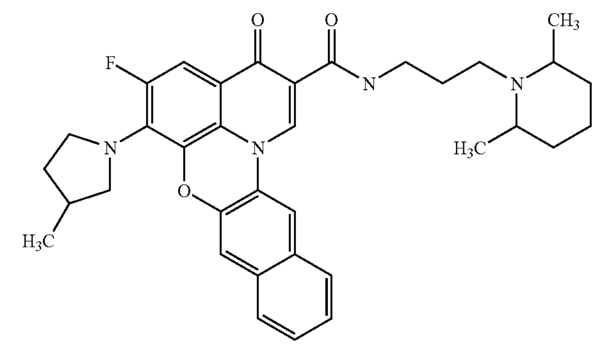 | 1 | |
| 338 | 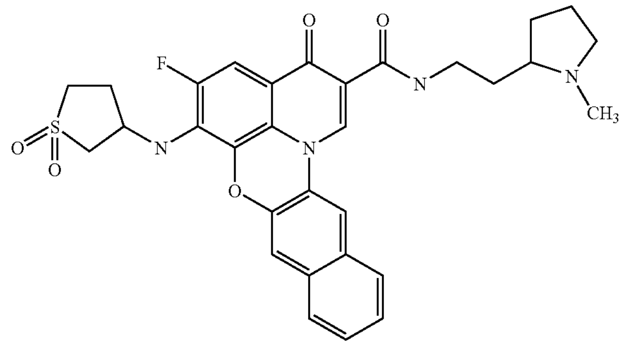 | 1 | |
| 339 | Chiral | 0.94 | |
| 340 | 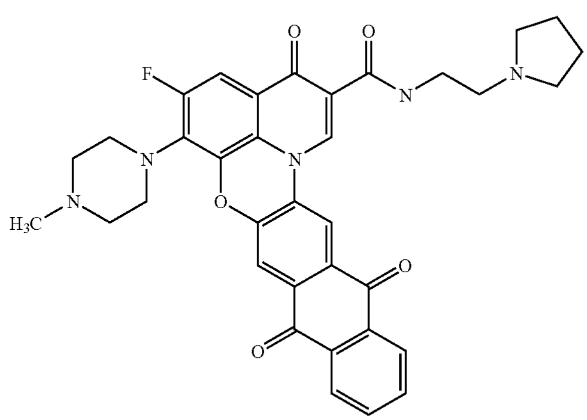 | 0.9 | 8.50 |

TABLE 2-continued
| Structure | Stop Data c-Myc μM | MTS Data Hella μM |
|---|---|---|
| 341 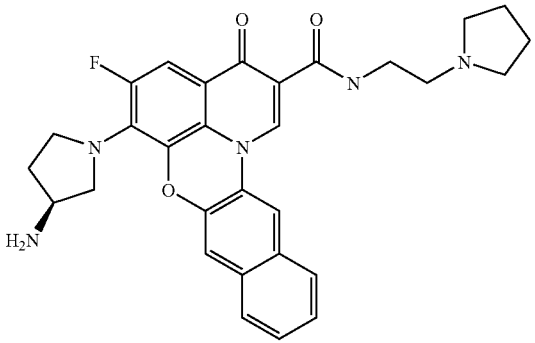 Chiral | 0.9 | 0.28 |
| 342 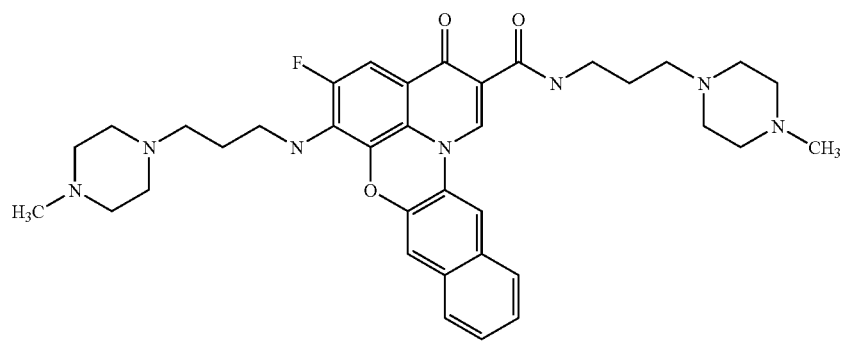 | 0.9 | |
| 343 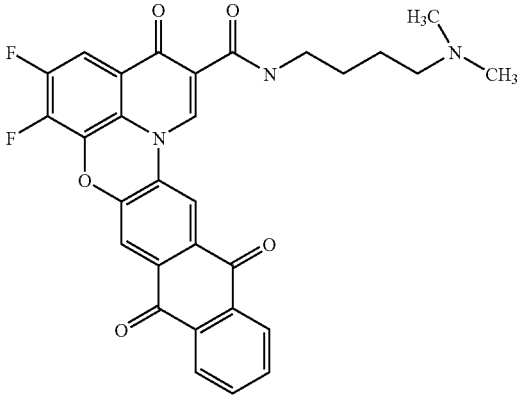 | 0.9 | |
| 344 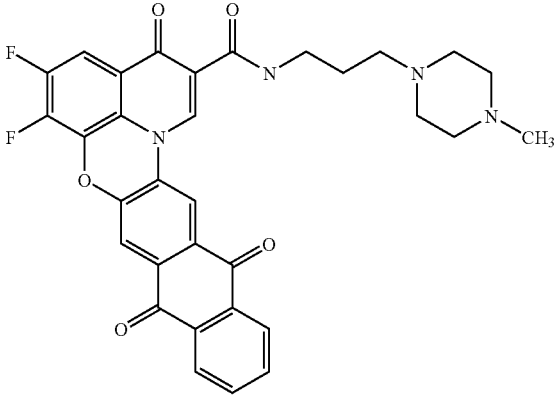 | 0.9 | |

TABLE 2-continued

| | Structure | Stop Data c-Myc μM | MTS Data Hella μM |
|---|---|---|---|
| 345 | 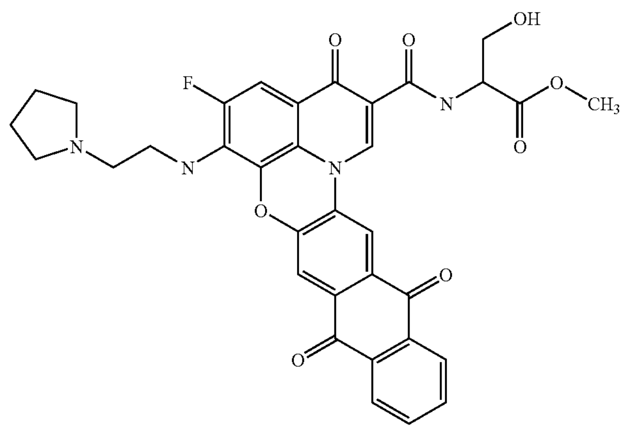 | | 0.9 |
| 346 | 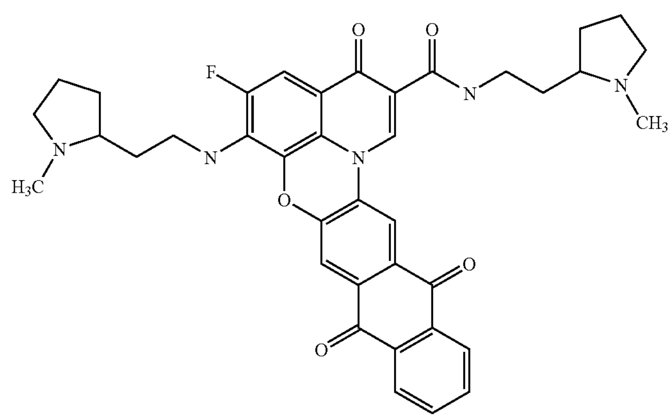 | | 0.9 |
| 347 | 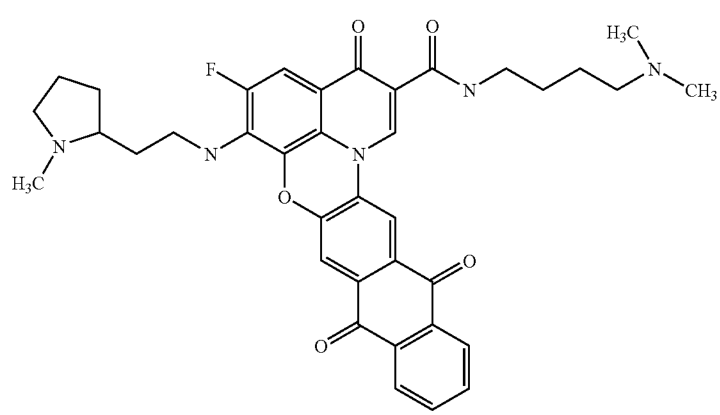 | | 0.9 |

TABLE 2-continued

| | Structure | Stop Data c-Myc μM | MTS Data Hella μM |
|---|---|---|---|
| 348 | 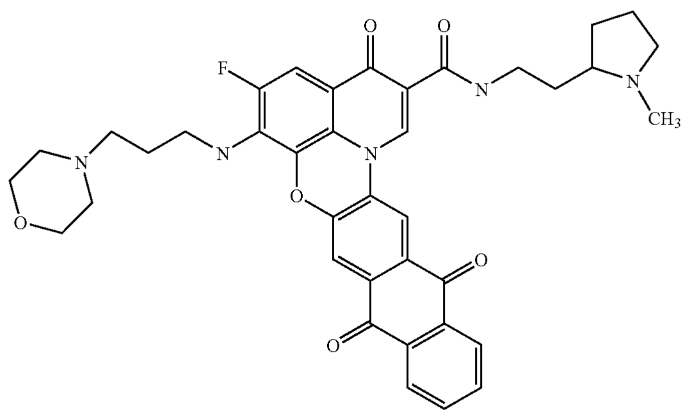 | | 0.9 |
| 349 | 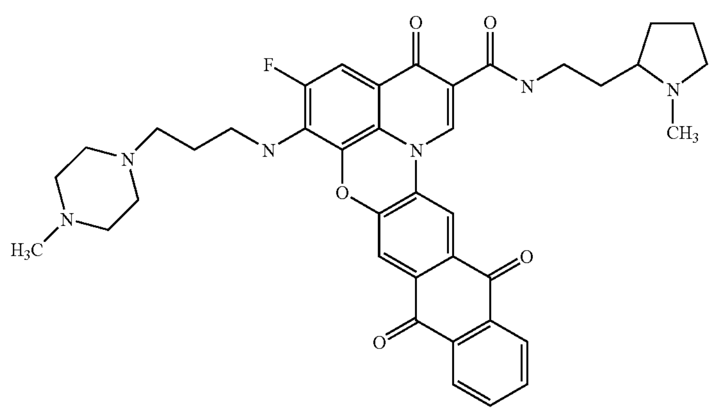 | | 0.9 |
| 350 | 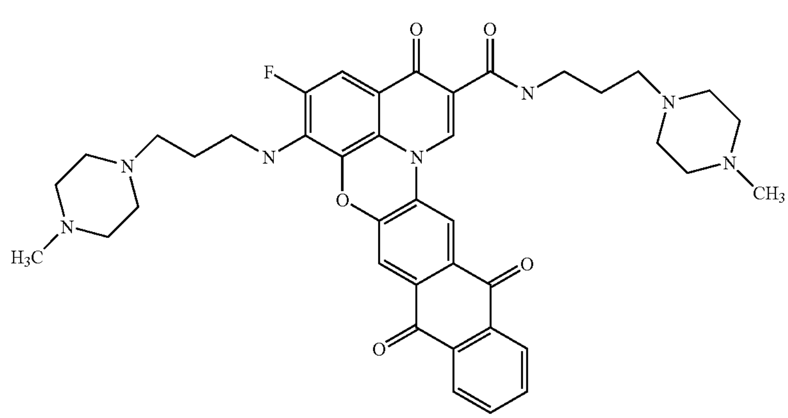 | | 0.9 |

TABLE 2-continued

| | Structure | Stop Data c-Myc μM | MTS Data Hella μM |
|---|---|---|---|
| 351 | 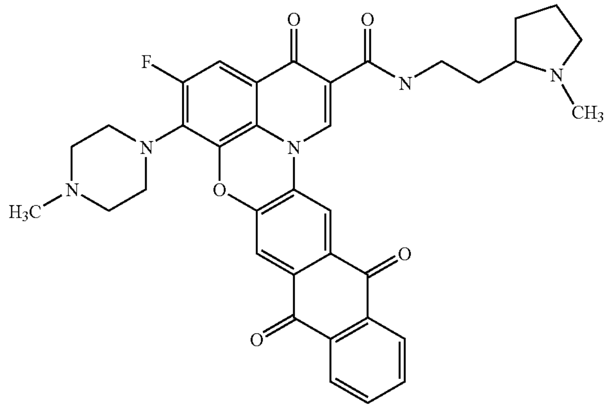 | | 0.9 |
| 352 | 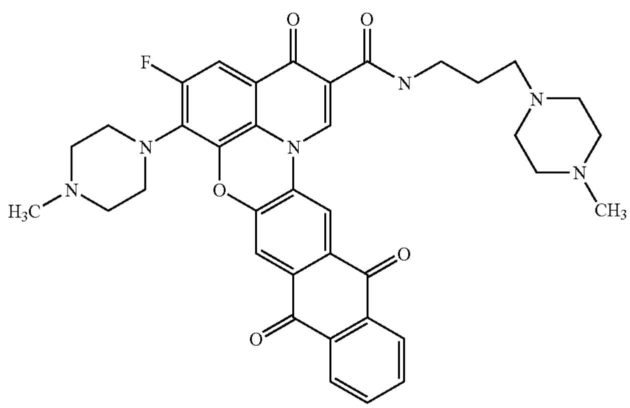 | | 0.9 |
| 353 | 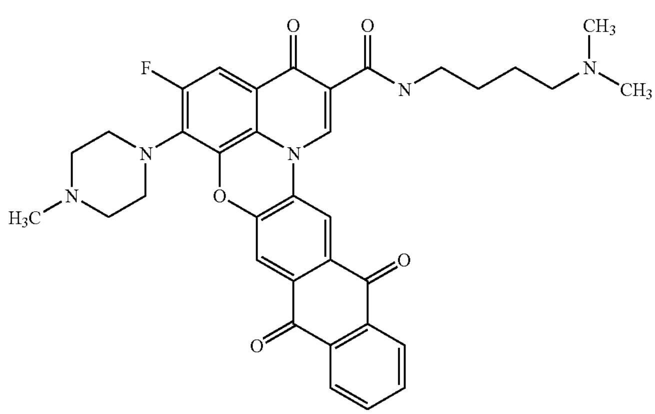 | | 0.9 |

TABLE 2-continued

| | Structure | Stop Data c-Myc μM | MTS Data Hella μM |
|---|---|---|---|
| 354 | 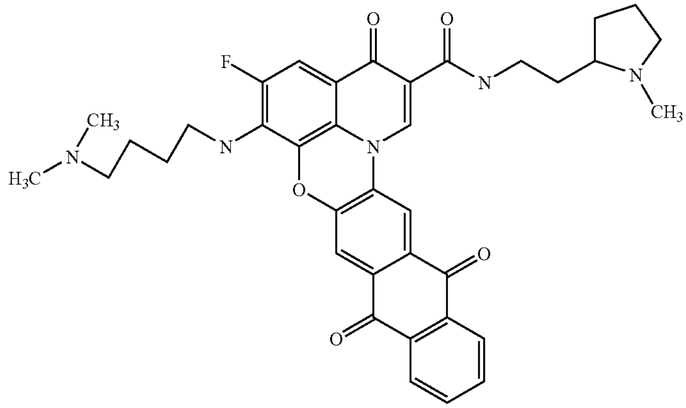 | | 0.9 |
| 355 | Chiral | | 0.89 |
| 356 | Chiral | | 0.85 |

TABLE 2-continued

| | Structure | Stop Data c-Myc μM | MTS Data Hella μM |
|---|---|---|---|
| 357 | Chiral | 0.75 | 8.60 |
| 358 | Chiral | 0.75 | 5.70 |
| 359 | 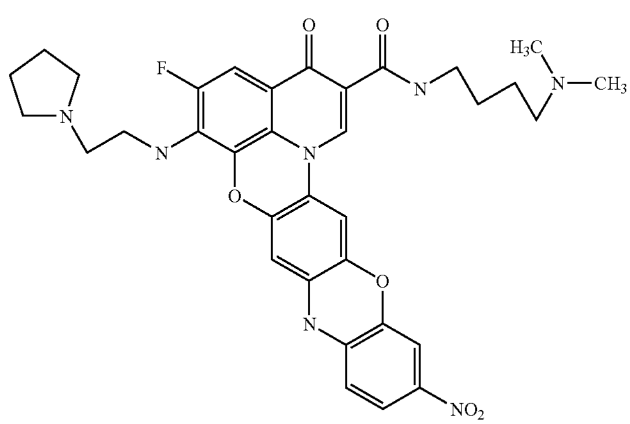 | 0.75 | 4.80 |

TABLE 2-continued

| Structure | Stop Data c-Myc μM | MTS Data Hella μM |
|---|---|---|
| 360 (Chiral) | 0.75 | 4.50 |
| 361 | 0.75 | 4.20 |
| 362 | 0.75 | 4.00 |

TABLE 2-continued

| | Structure | Stop Data c-Myc μM | MTS Data Hella μM |
|---|---|---|---|
| 363 | 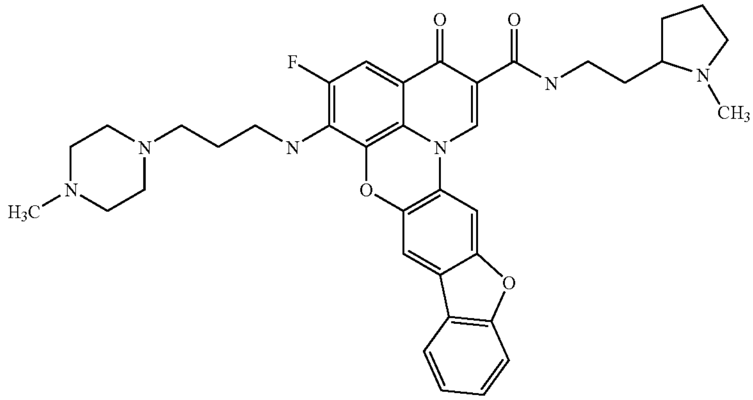 | 0.75 | 3.80 |
| 364 | 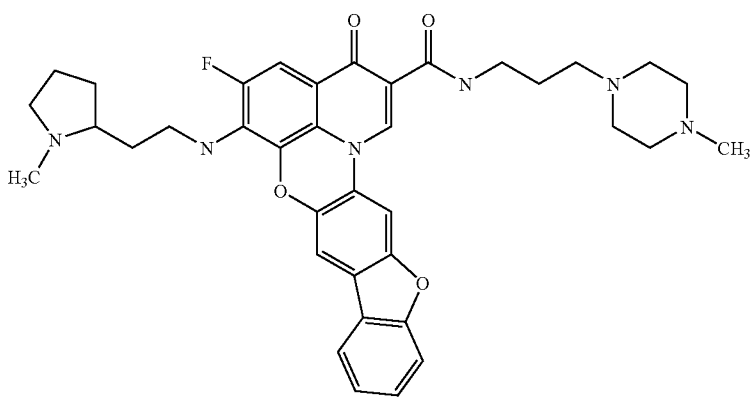 | 0.75 | 3.80 |
| 365 | 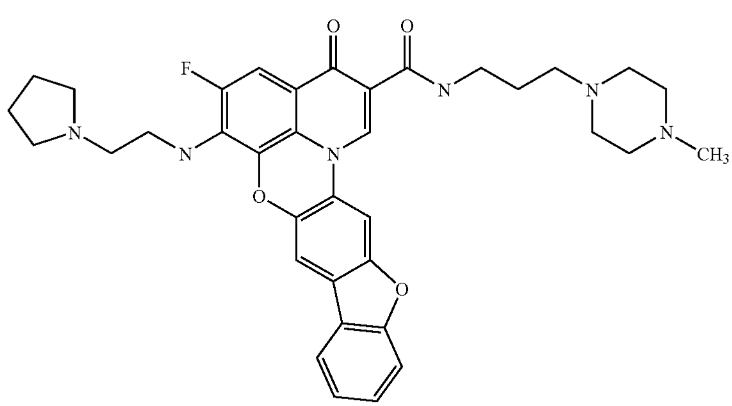 | 0.75 | 3.80 |

TABLE 2-continued

| | Structure | Stop Data c-Myc μM | MTS Data Hella μM |
|---|---|---|---|
| 366 | 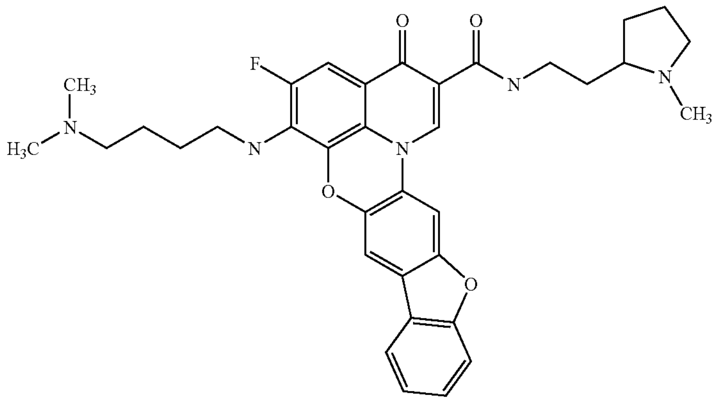 | 0.75 | 3.70 |
| 367 | 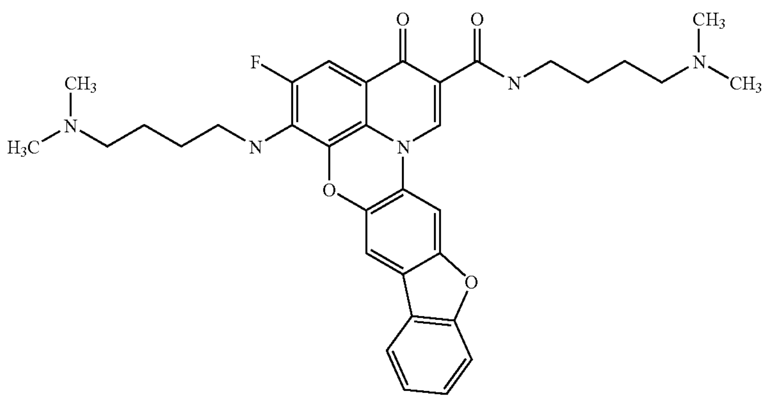 | 0.75 | 3.70 |
| 368 | 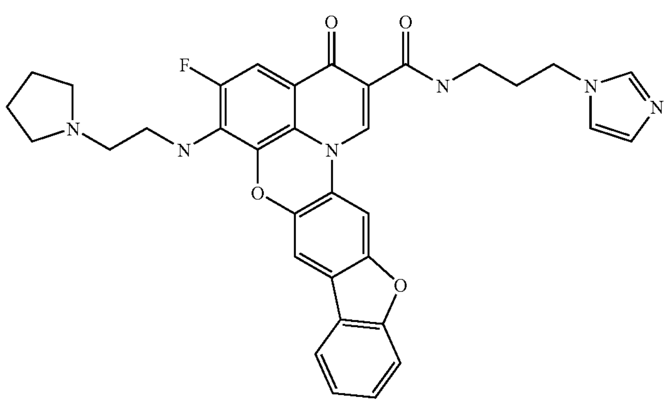 | 0.75 | 3.60 |

TABLE 2-continued

| | Structure | Stop Data c-Myc μM | MTS Data Hella μM |
|---|---|---|---|
| 369 | 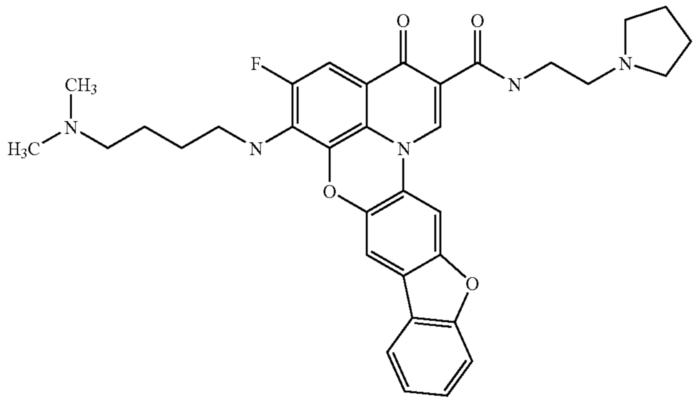 | 0.75 | 3.50 |
| 370 | 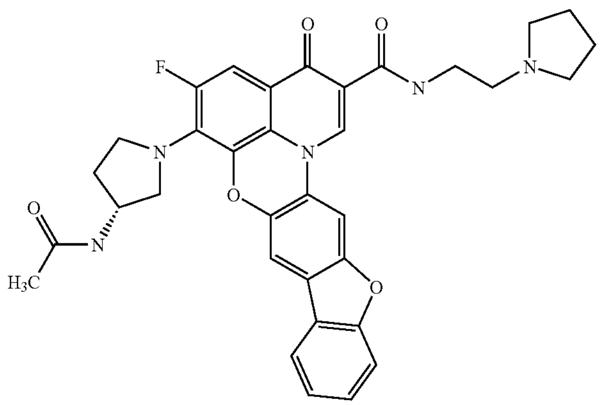 | 0.75 | 3.50 |
| 371 | Chiral | 0.75 | 3.50 |
| 372 | 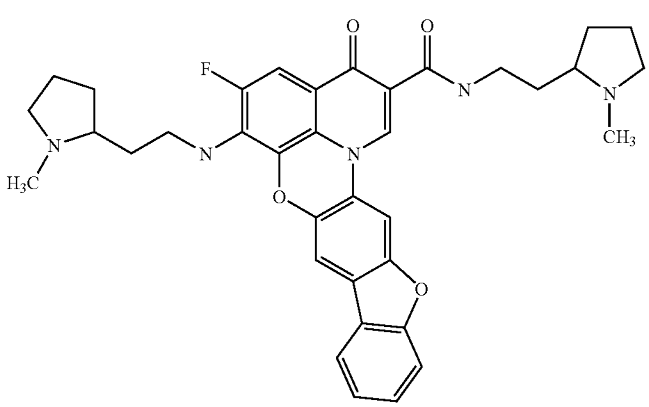 | 0.75 | 3.40 |

TABLE 2-continued

| | Structure | Stop Data c-Myc μM | MTS Data Hella μM |
|---|---|---|---|
| 373 | 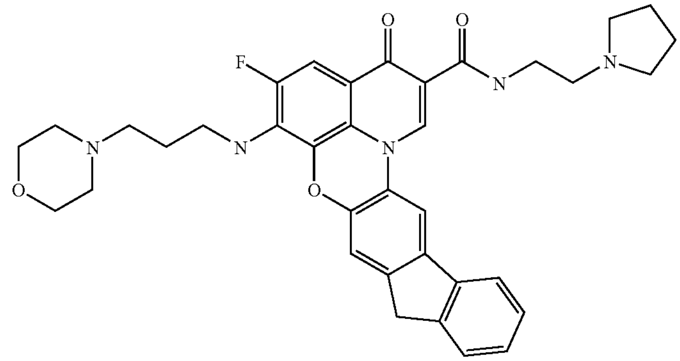 | 0.75 | 3.30 |
| 374 | 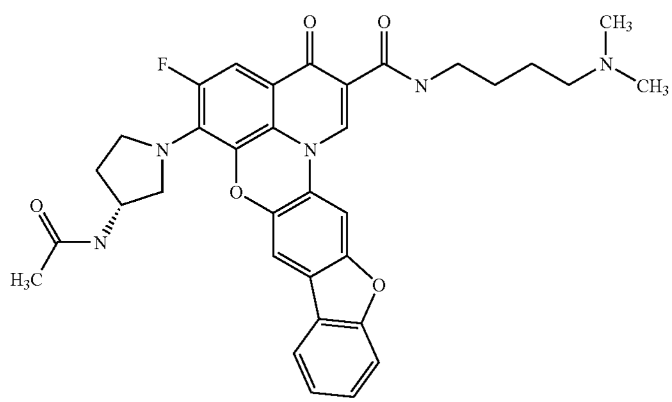 | 0.75 | 3.30 |
| 375 | 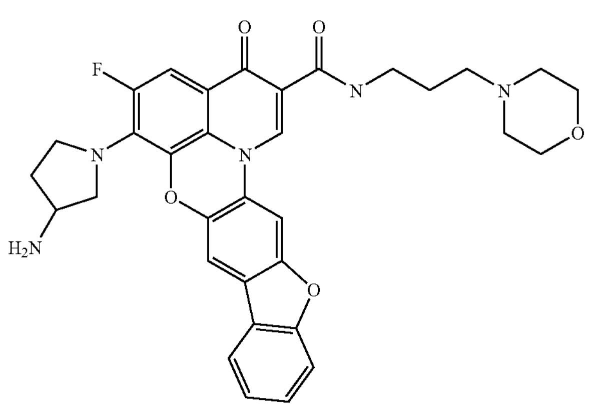 | 0.75 | 2.70 |

TABLE 2-continued
| | Structure | Stop Data c-Myc µM | MTS Data Hella µM |
|---|---|---|---|
| 376 | 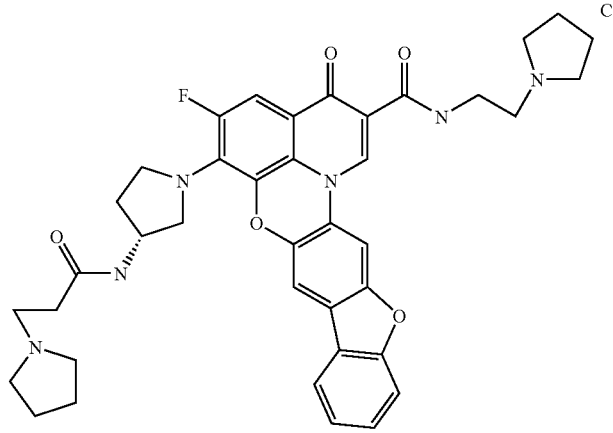 Chiral | 0.75 | 2.40 |
| 377 | 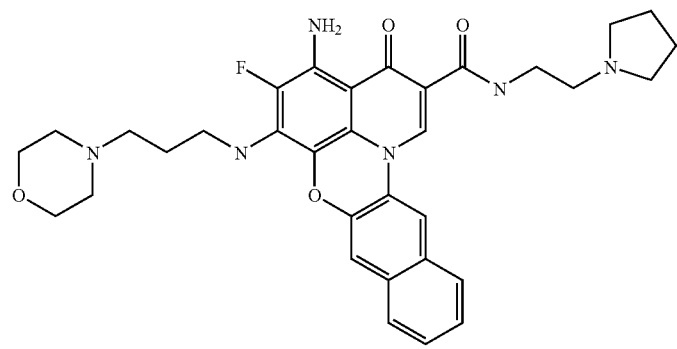 | 0.75 | 2.20 |
| 378 | 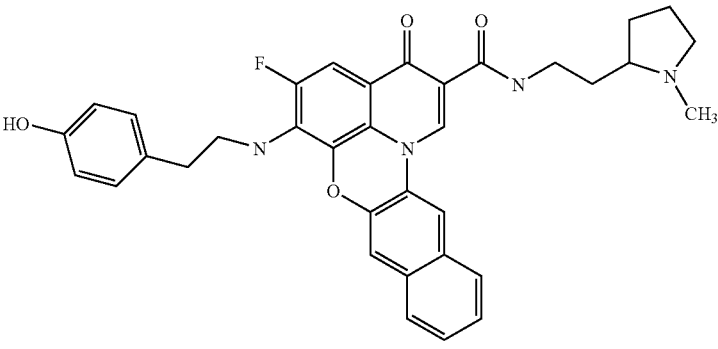 | 0.75 | 2.10 |
| 379 | 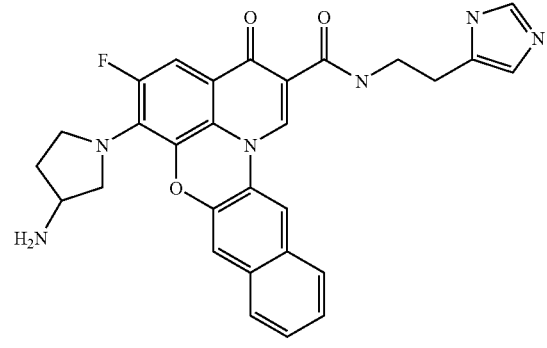 | 0.75 | 1.90 |

TABLE 2-continued

| | Structure | Stop Data c-Myc μM | MTS Data Hella μM |
|---|---|---|---|
| 380 | 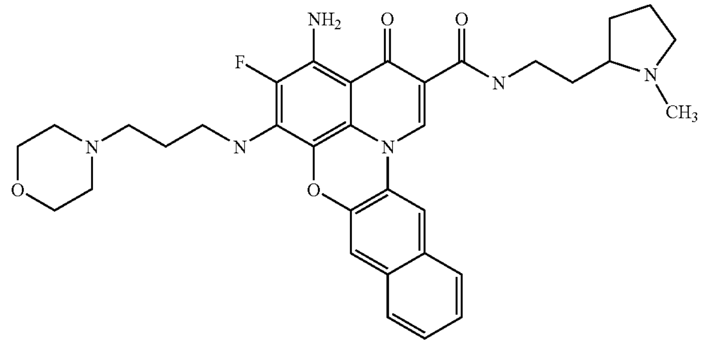 | 0.75 | 1.80 |
| 381 | 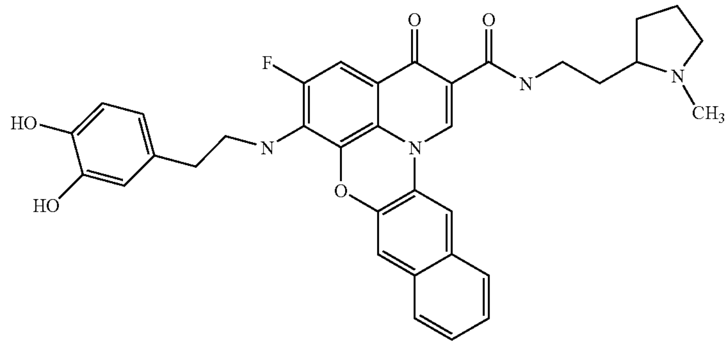 | 0.75 | 1.80 |
| 382 | 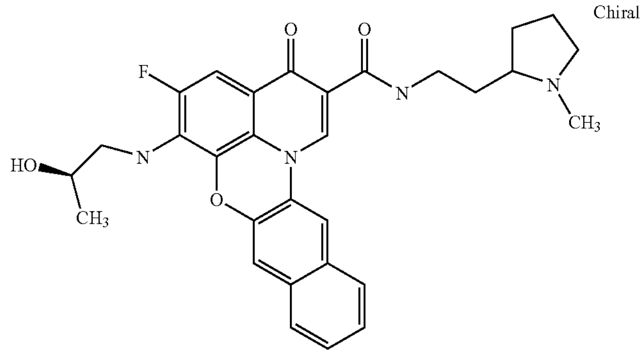 | 0.75 | 1.80 |
| 383 | 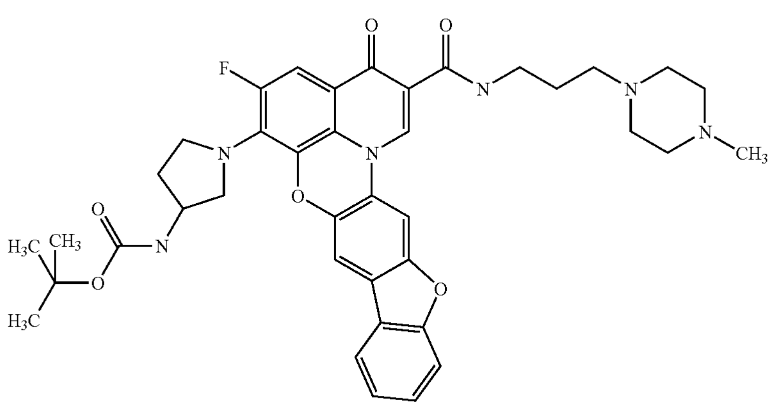 | 0.75 | 0.37 |

TABLE 2-continued

| | Structure | Stop Data c-Myc μM | MTS Data Hella μM |
|---|---|---|---|
| 384 | 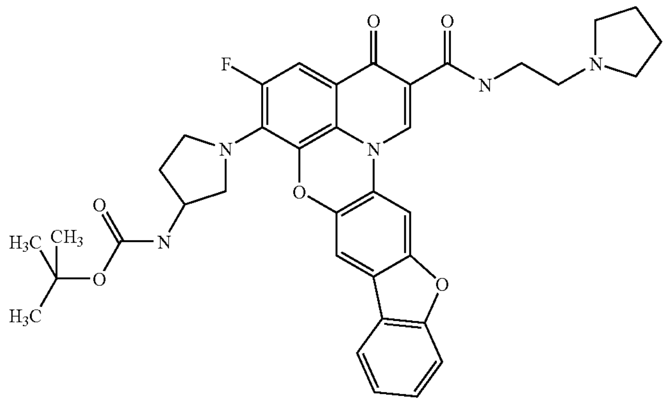 | 0.75 | 0.37 |
| 385 | 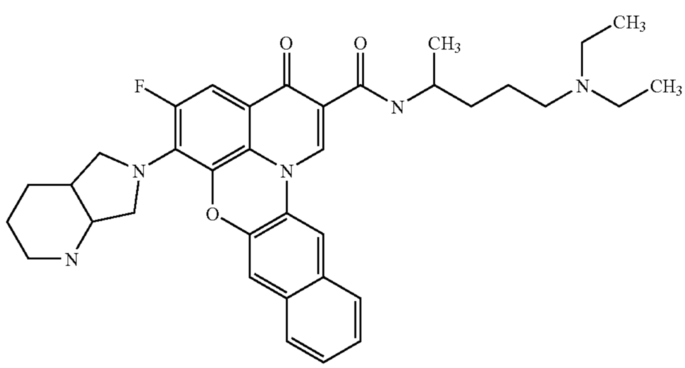 | 0.75 | 0.36 |
| 386 | 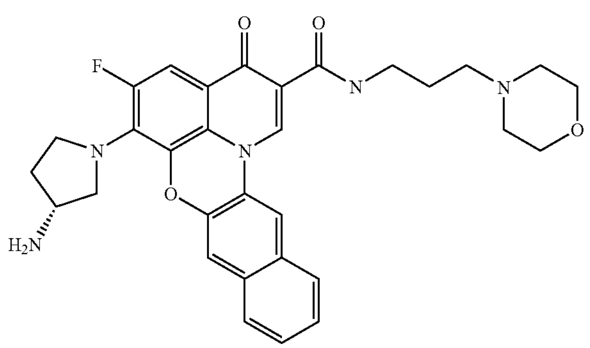 | 0.75 | 0.34 |
| 387 | 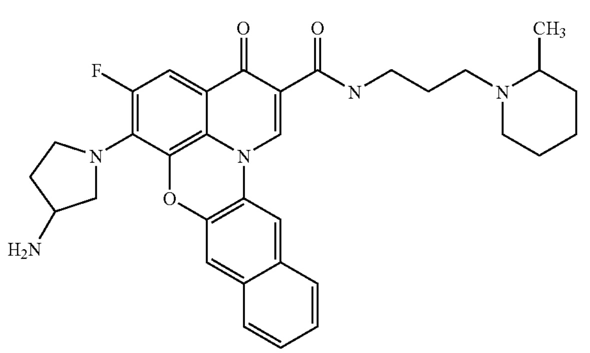 | 0.75 | 0.33 |

TABLE 2-continued

| | Structure | Stop Data c-Myc μM | MTS Data Hella μM |
|---|---|---|---|
| 388 | 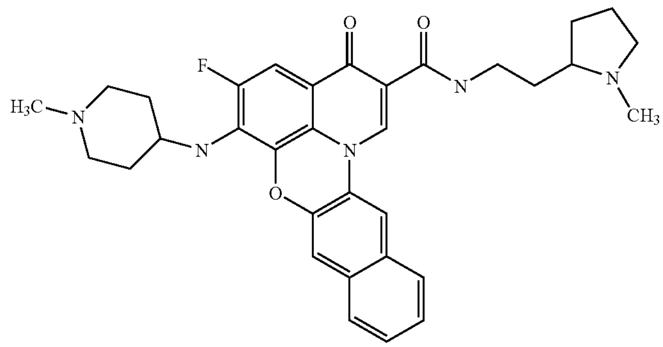 | 0.75 | 0.31 |
| 389 | 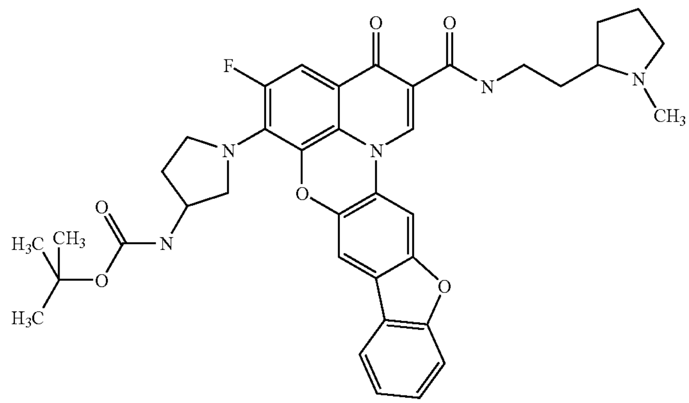 | 0.75 | 0.29 |
| 390 | 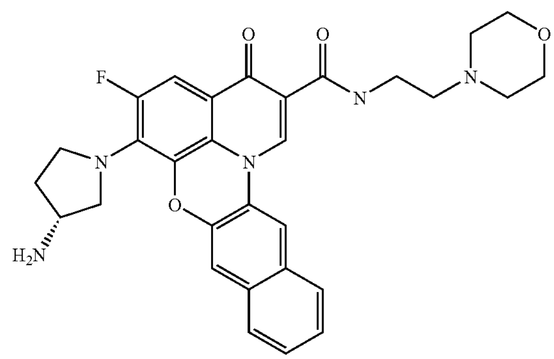 | 0.75 | 0.24 |
| 391 | 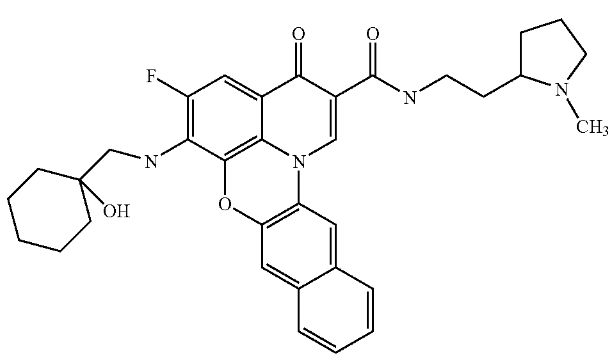 | 0.75 | 0.24 |

TABLE 2-continued

| | Structure | Stop Data c-Myc µM | MTS Data Hella µM |
|---|---|---|---|
| 392 | 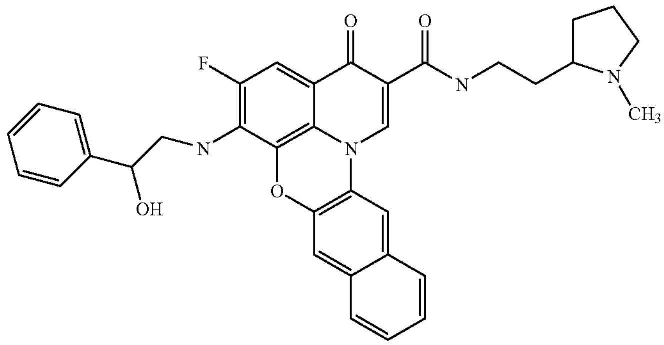 | 0.75 | 0.19 |
| 393 | 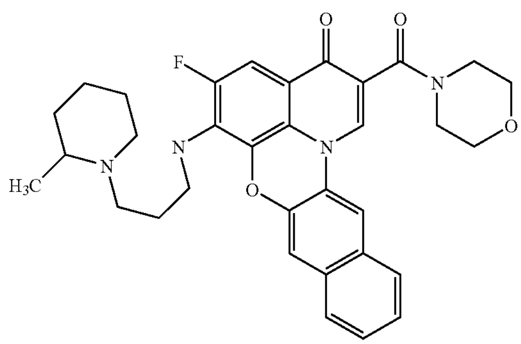 | 0.75 | |
| 394 | 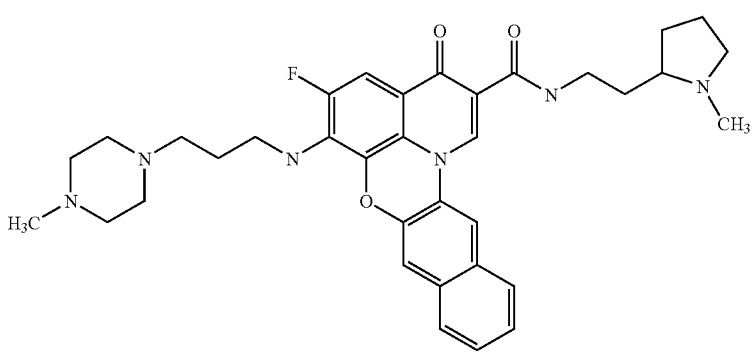 | 0.75 | |
| 395 | 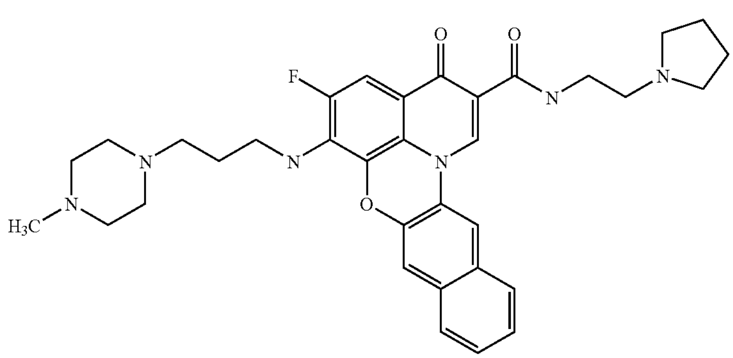 | 0.75 | |

TABLE 2-continued
| | Structure | Stop Data c-Myc μM | MTS Data Hella μM |
|---|---|---|---|
| 396 | 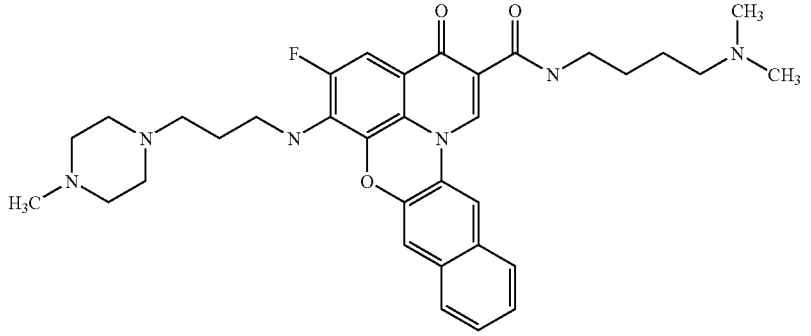 | | 0.75 |
| 397 | 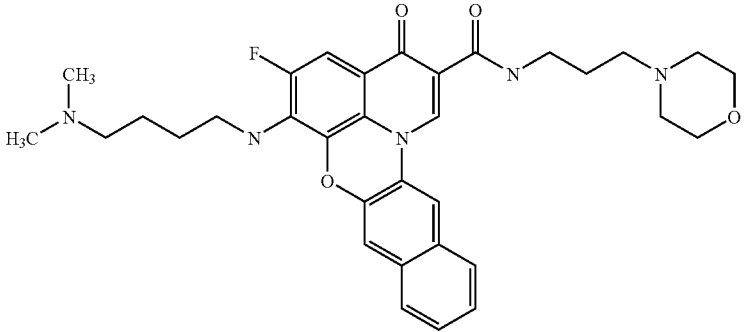 | | 0.75 |
| 398 | 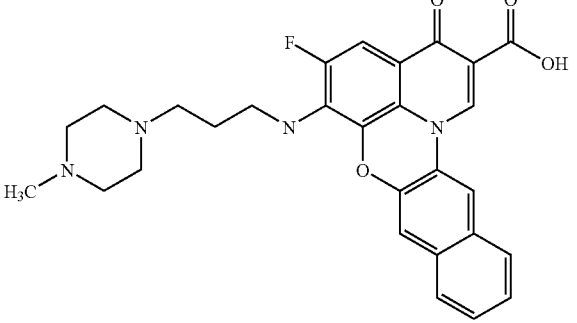 | | 0.75 |
| 399 | 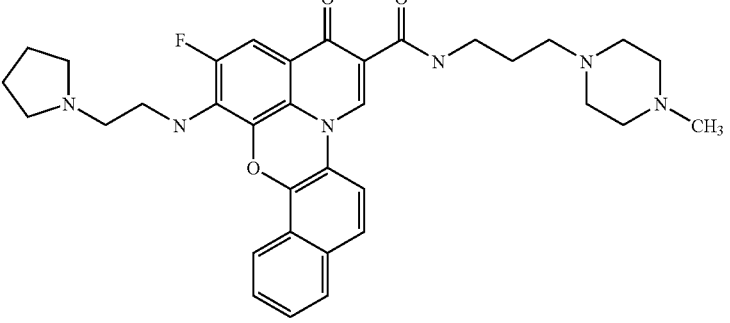 | | 0.75 |

TABLE 2-continued

| | Structure | Stop Data c-Myc μM | MTS Data Hella μM |
|---|---|---|---|
| 400 | 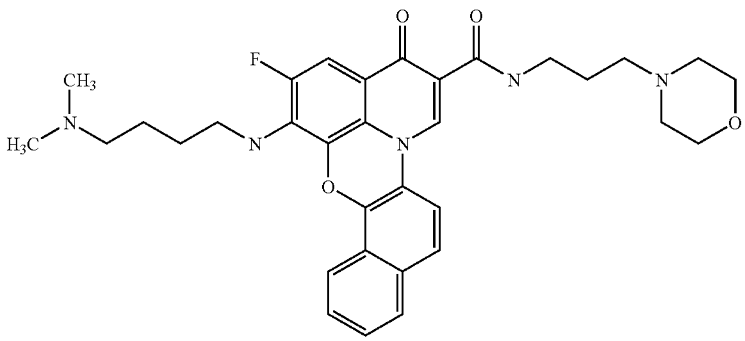 | | 0.75 |
| 401 | 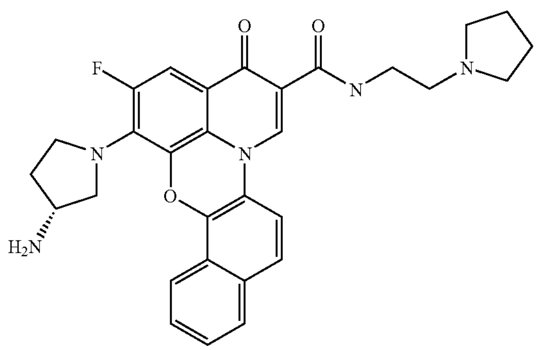 | | 0.75 |
| 402 | Chiral | | 0.75 |

TABLE 2-continued
| | Structure | | Stop Data c-Myc μM | MTS Data Hella μM |
|---|---|---|---|---|
| 403 | 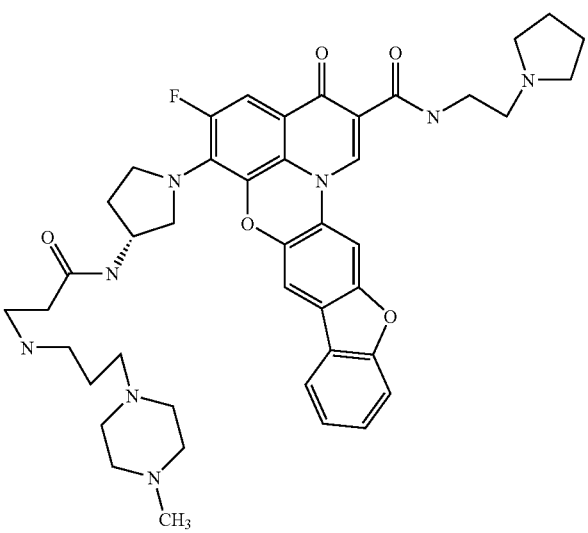 | Chiral | | 0.75 |
| 404 | 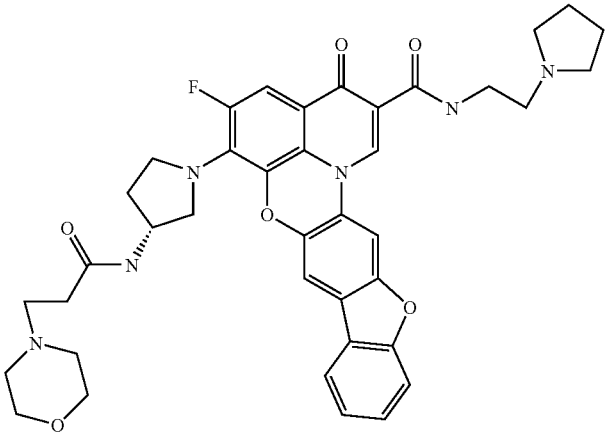 | Chiral | | 0.75 |
| 405 | 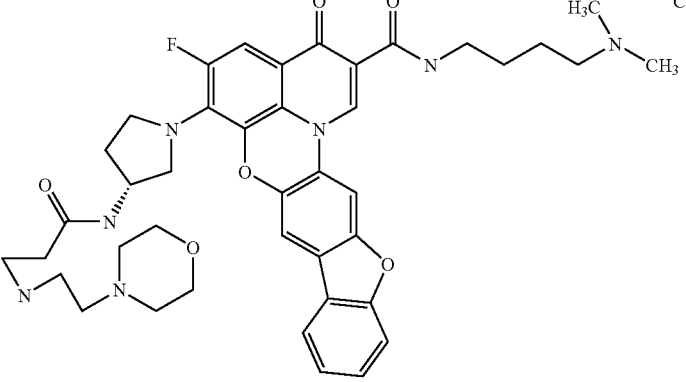 | Chiral | | 0.75 |

TABLE 2-continued

| | Structure | Stop Data c-Myc μM | MTS Data Hella μM |
|---|---|---|---|
| 406 | 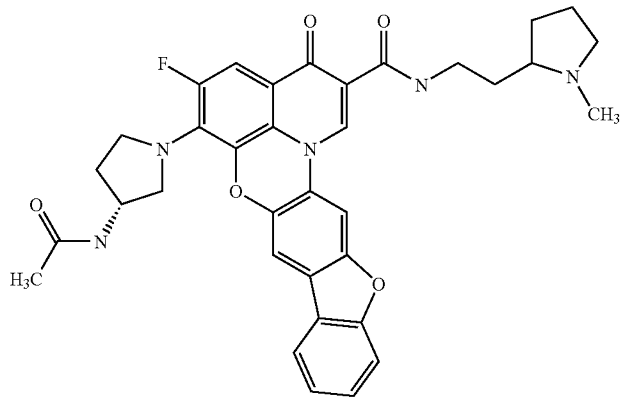 | | 0.75 |
| 407 | 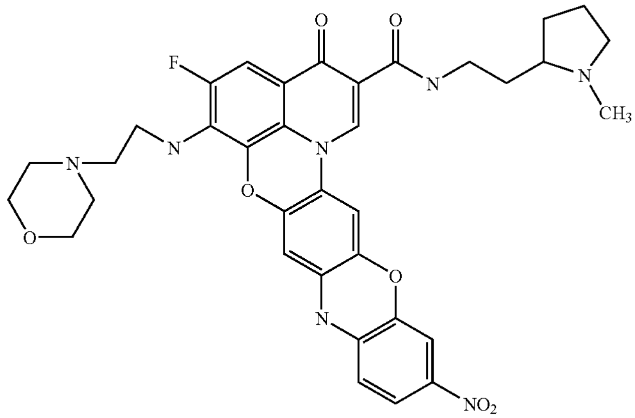 | | 0.75 |
| 408 | 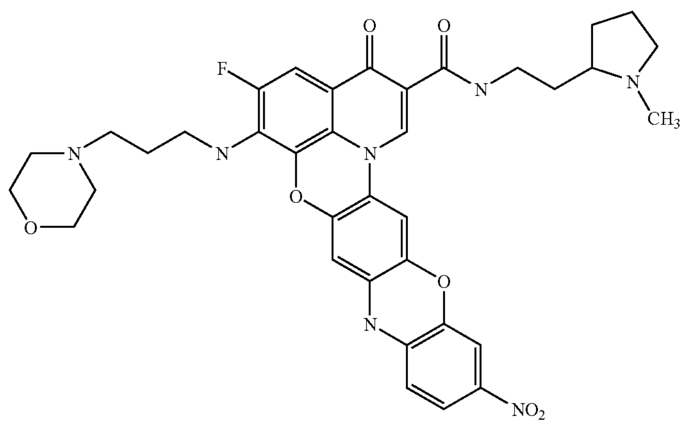 | | 0.75 |

TABLE 2-continued

| | Structure | Stop Data c-Myc μM | MTS Data Hella μM |
|---|---|---|---|
| 409 | 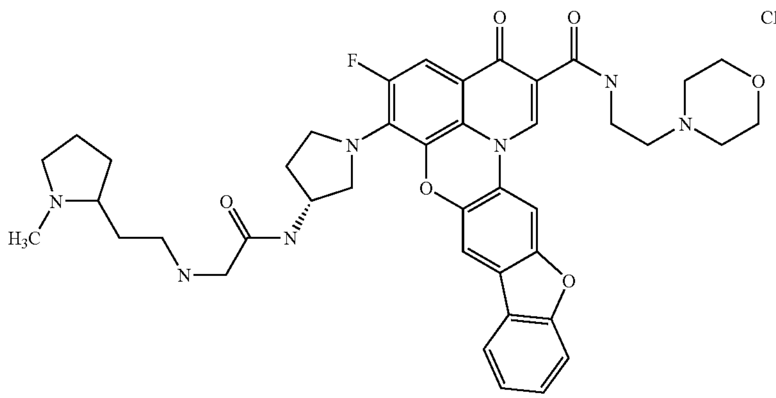 | Chiral | 0.75 |
| 410 | 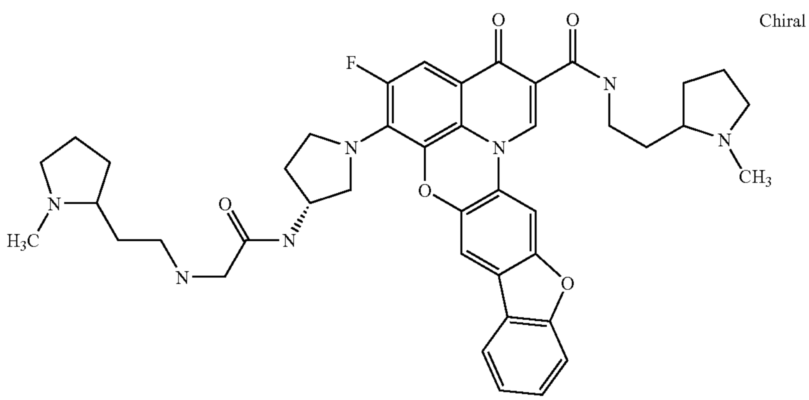 | Chiral | 0.75 |
| 411 | 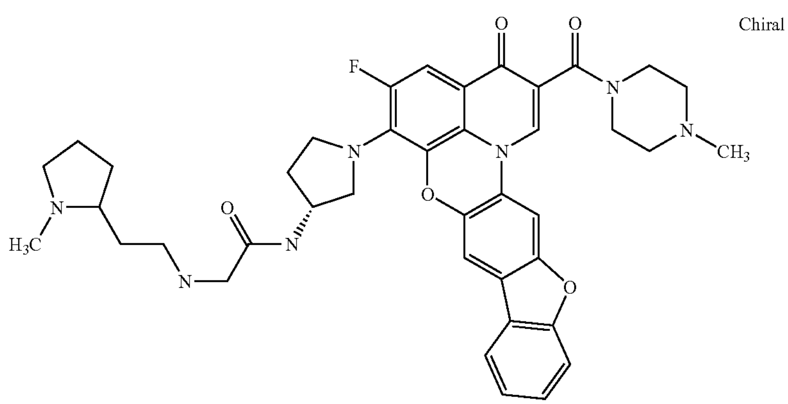 | Chiral | 0.75 |

TABLE 2-continued

| | Structure | Stop Data c-Myc μM | MTS Data Hella μM |
|---|---|---|---|
| 412 | Chiral | | 0.75 |
| 413 | Chiral | | 0.75 |
| 414 | Chiral | | 0.75 |

TABLE 2-continued

| | Structure | Stop Data c-Myc μM | MTS Data Hella μM |
|---|---|---|---|
| 415 | 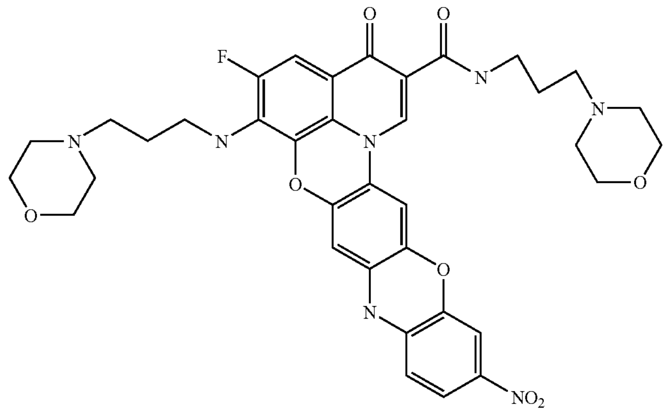 | | 0.75 |
| 416 | 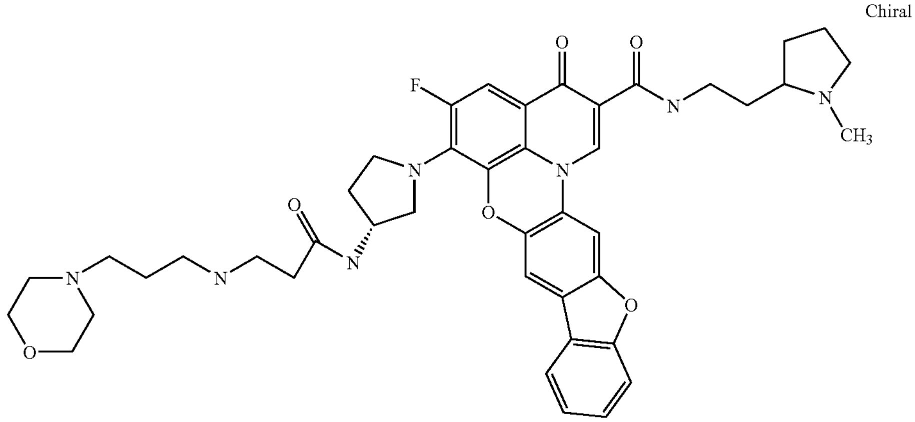 | Chiral | 0.75 |
| 417 | 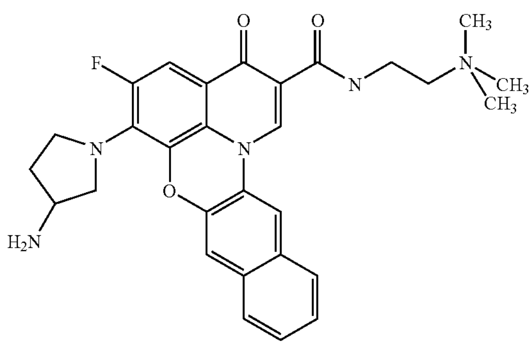 | | 0.75 |
| 418 | 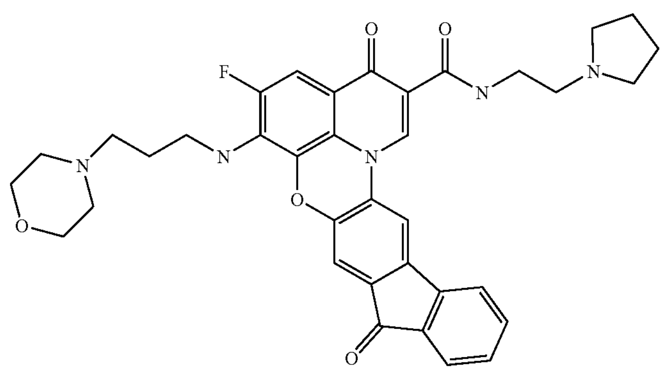 | | 0.75 |

TABLE 2-continued

| | Structure | Stop Data c-Myc μM | MTS Data Hella μM |
|---|---|---|---|
| 419 | 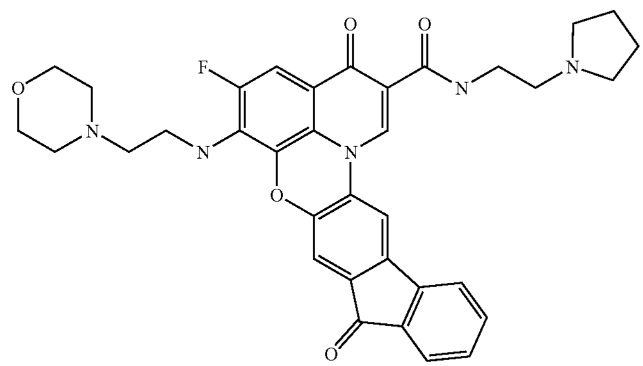 | | 0.75 |
| 420 | 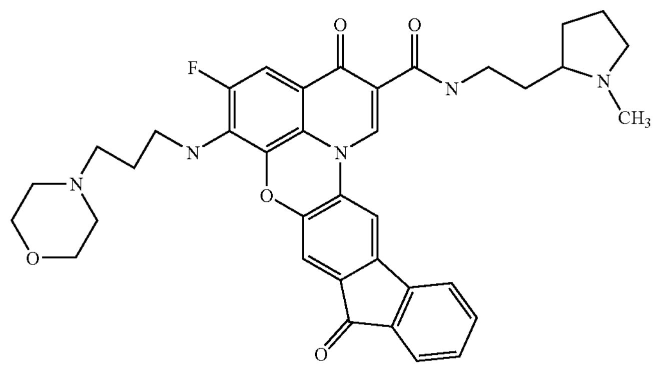 | | 0.75 |
| 421 | Chiral | | 0.75 |
| 422 | 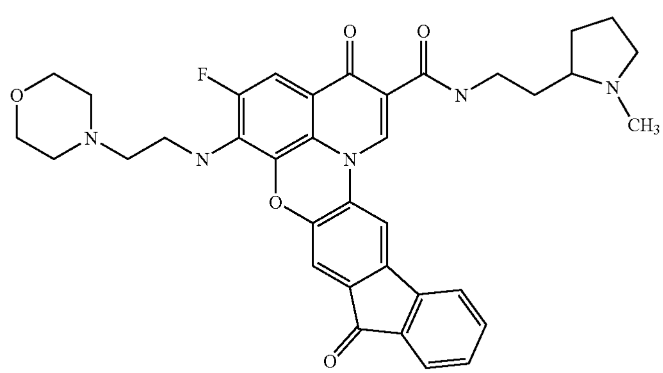 | | 0.75 |

TABLE 2-continued

| Structure | Stop Data c-Myc μM | MTS Data Hella μM |
|---|---|---|
| 423 | | 0.75 |
| 424 | | 0.75 |
| 425 | | 0.75 |
| 426 | | 0.75 |

TABLE 2-continued

| | Structure | Stop Data c-Myc μM | MTS Data Hella μM |
|---|---|---|---|
| 427 | Chiral | | 0.75 |
| 428 | Chiral | | 0.75 |
| 429 | Chiral | | 0.75 |
| 430 | 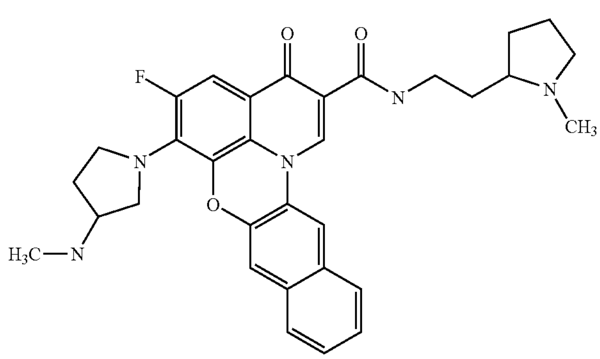 | | 0.75 |

TABLE 2-continued

| | Structure | Stop Data c-Myc μM | MTS Data Hella μM |
|---|---|---|---|
| 431 | 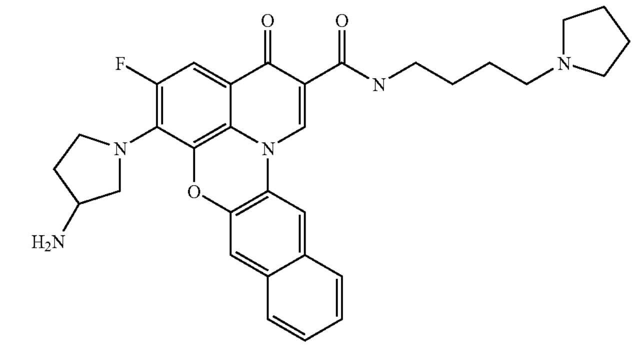 | | 0.75 |
| 432 | 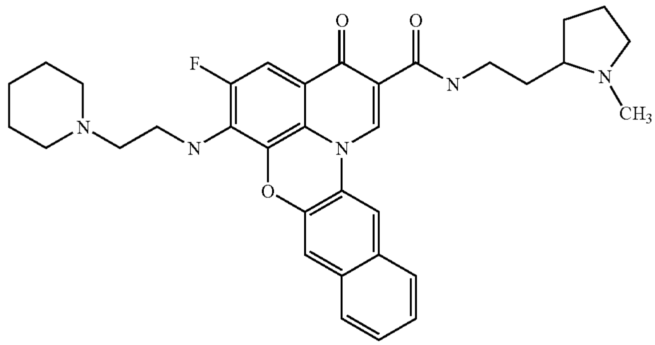 | | 0.75 |
| 433 | 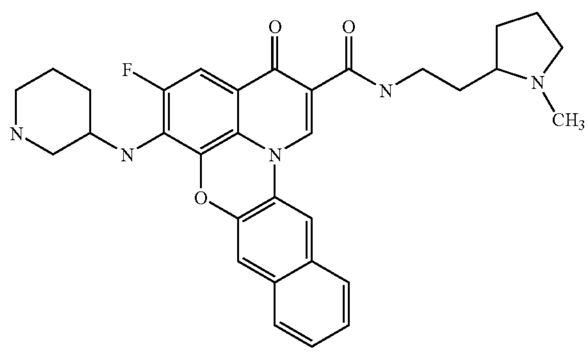 | | 0.75 |
| 434 | 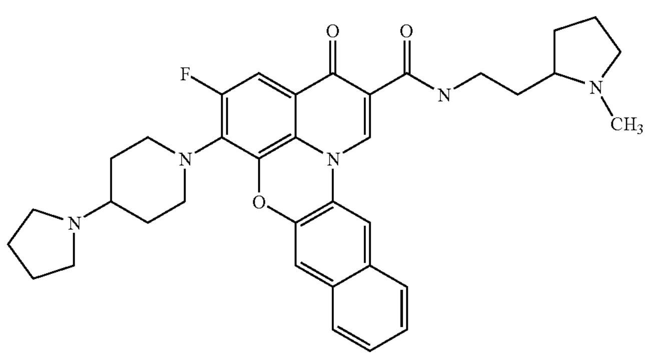 | | 0.75 |

TABLE 2-continued

| | Structure | Stop Data c-Myc μM | MTS Data Hella μM |
|---|---|---|---|
| 435 | 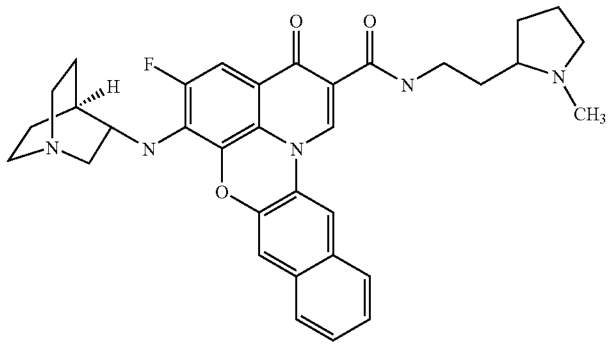 | | 0.75 |
| 436 | 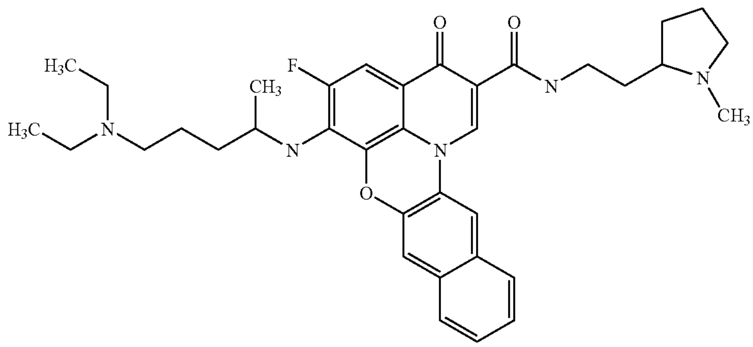 | | 0.75 |
| 437 | 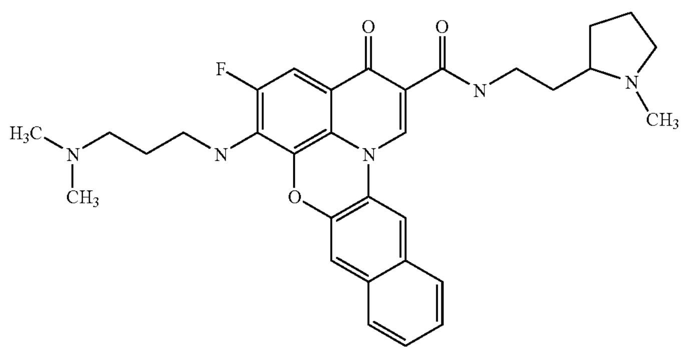 | | 0.75 |
| 438 | 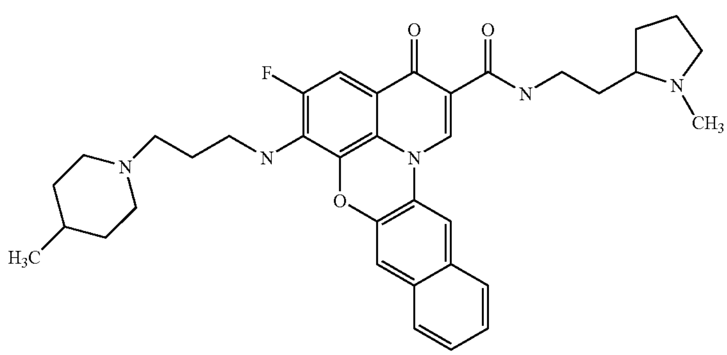 | | 0.75 |

TABLE 2-continued

| | Structure | Stop Data c-Myc μM | MTS Data Hella μM |
|---|---|---|---|
| 439 | 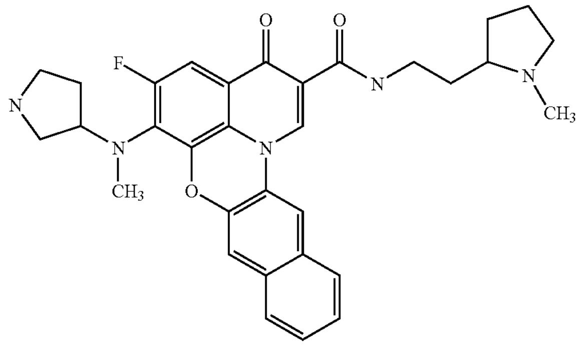 | | 0.75 |
| 440 | 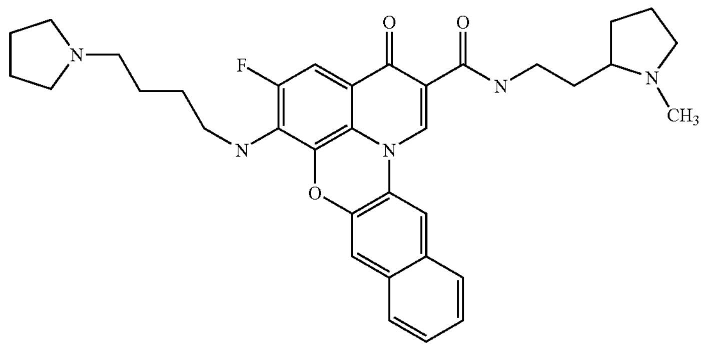 | | 0.75 |
| 441 | 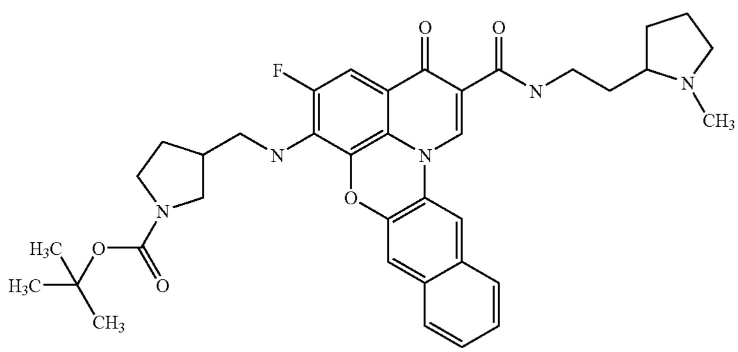 | | 0.75 |
| 442 | 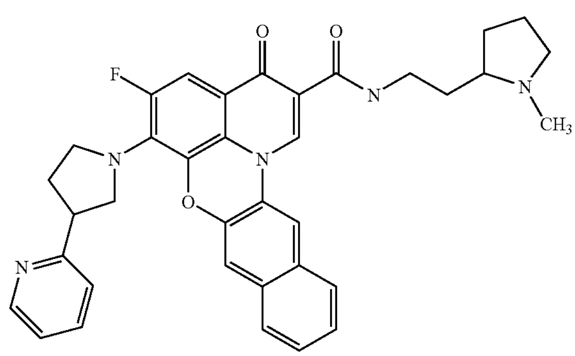 | | 0.75 |

TABLE 2-continued

| | Structure | Stop Data c-Myc μM | MTS Data Hella μM |
|---|---|---|---|
| 443 | 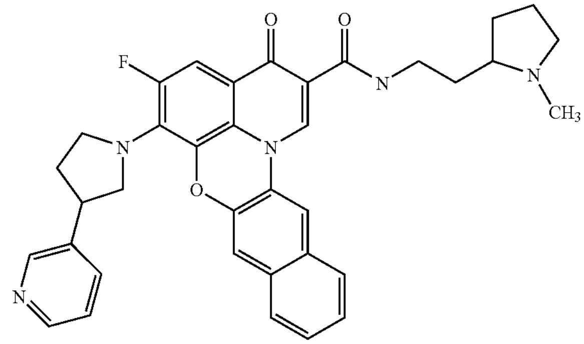 | | 0.75 |
| 444 | Chiral | | 0.75 |
| 445 | Chiral | | 0.75 |
| 446 | 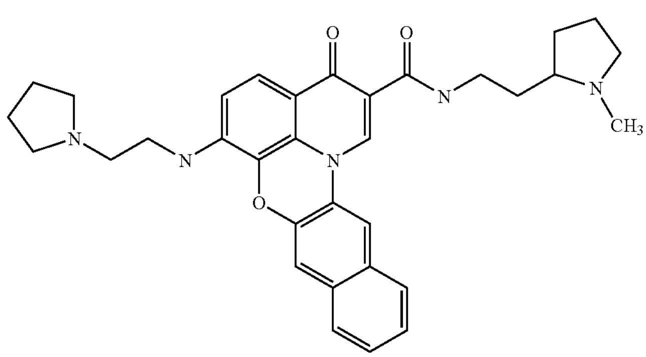 | | 0.75 |

TABLE 2-continued

| | Structure | Stop Data c-Myc μM | MTS Data Hella μM |
|---|---|---|---|
| 447 | 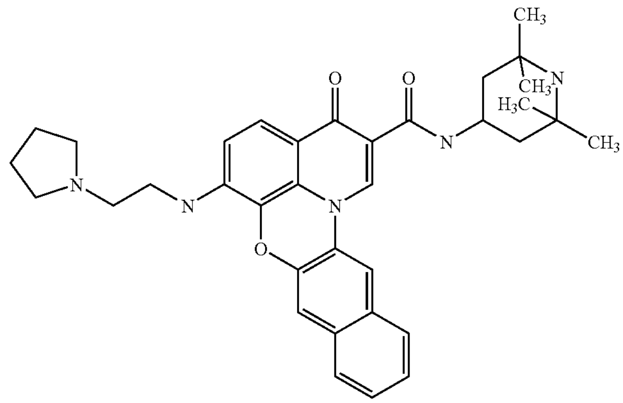 | | 0.75 |
| 448 | 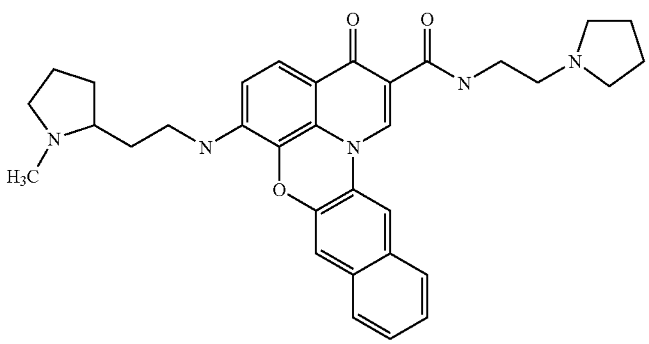 | | 0.75 |
| 449 | 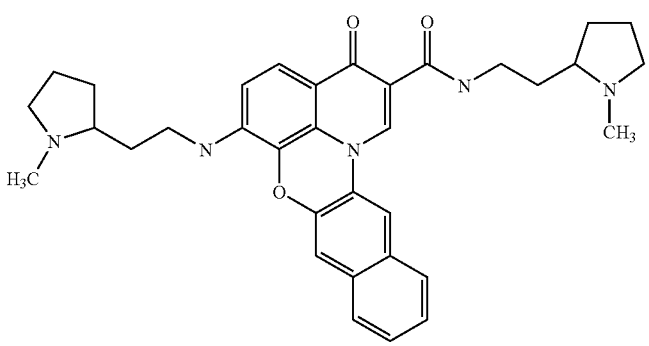 | | 0.75 |
| 450 | 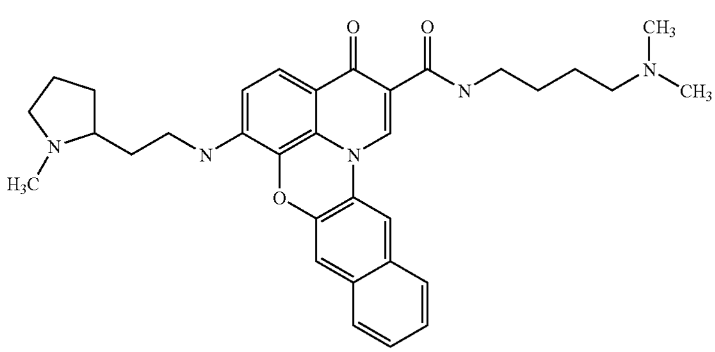 | | 0.75 |

TABLE 2-continued

| | Structure | Stop Data c-Myc μM | MTS Data Hella μM |
|---|---|---|---|
| 451 | 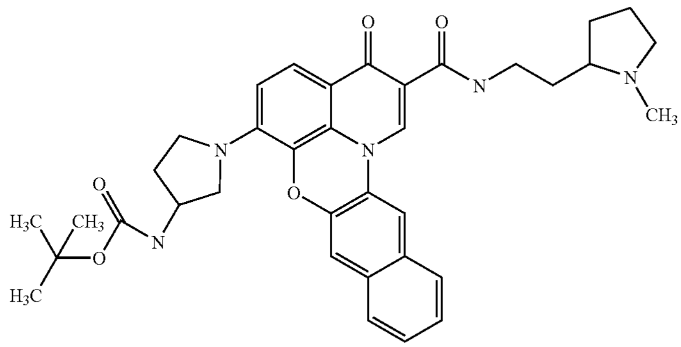 | | 0.75 |
| 452 | 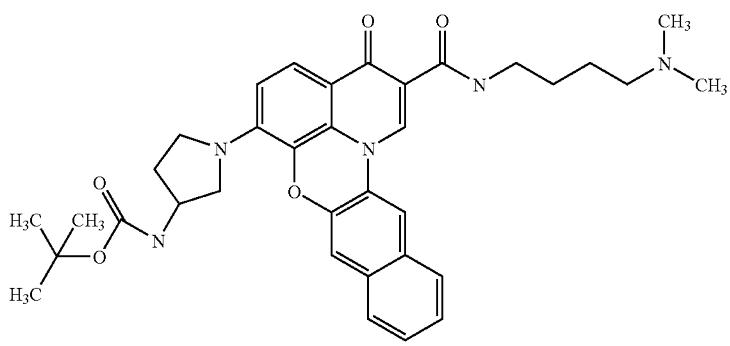 | | 0.75 |
| 453 | 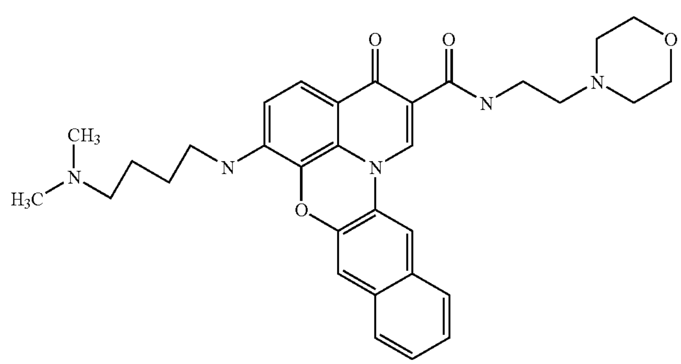 | | 0.75 |
| 454 | 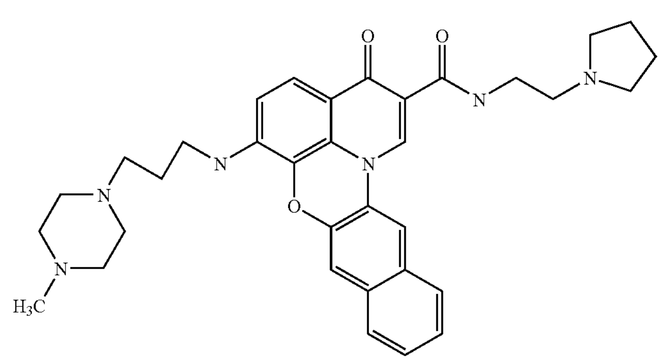 | | 0.75 |

TABLE 2-continued
| | Structure | Stop Data c-Myc μM | MTS Data Hella μM |
|---|---|---|---|
| 455 | 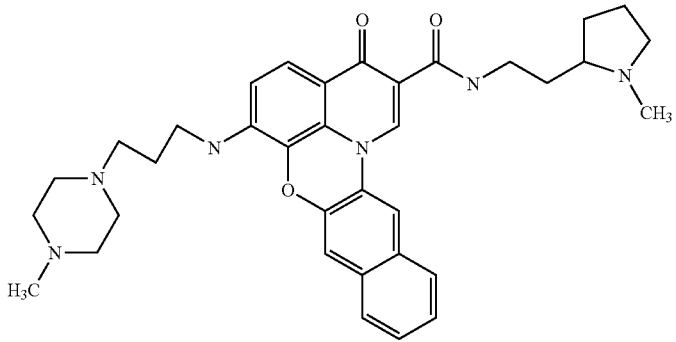 | | 0.75 |
| 456 | 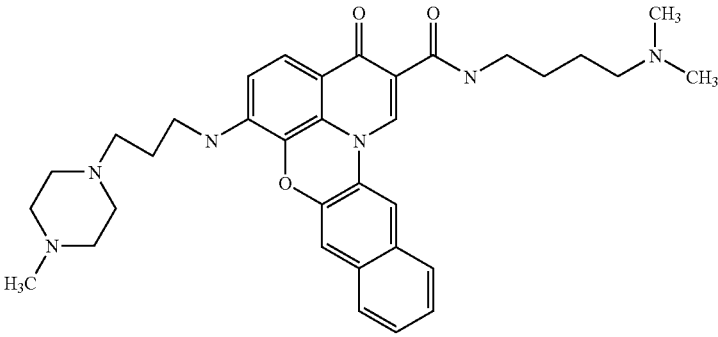 | | 0.75 |
| 457 | 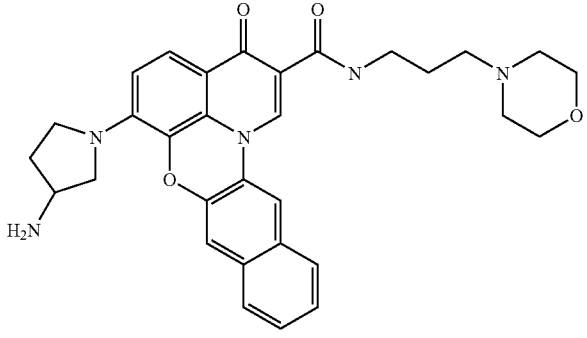 | | 0.75 |
| 458 | 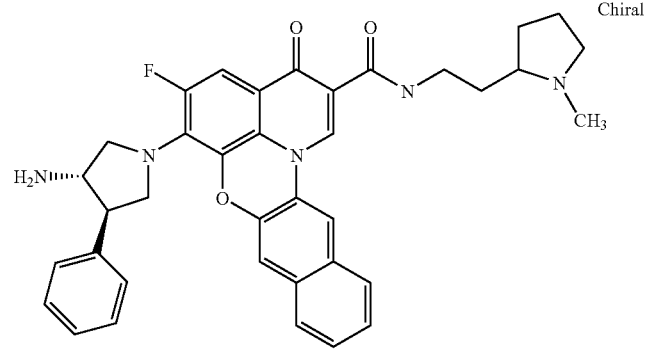 Chiral | | 0.75 |

TABLE 2-continued

| | Structure | Stop Data c-Myc μM | MTS Data Hella μM |
|---|---|---|---|
| 459 | 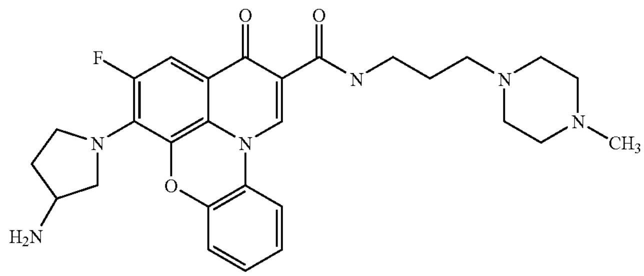 | | 0.75 |
| 460 | 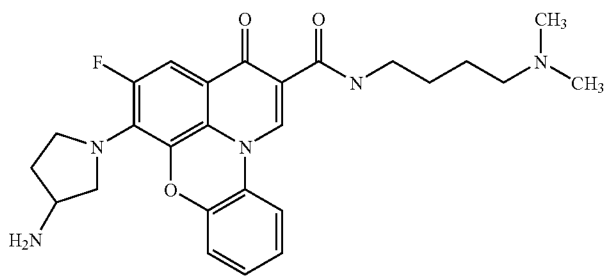 | | 0.75 |
| 461 | 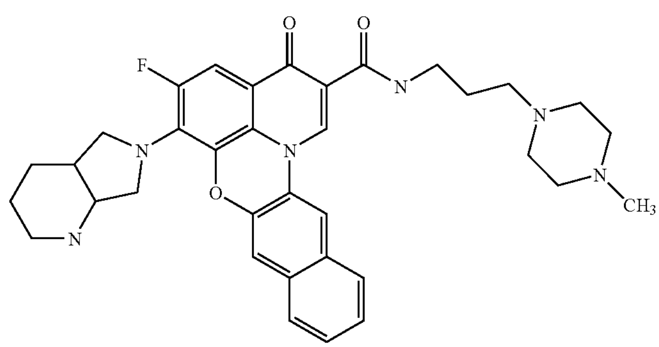 | | 0.75 |
| 462 | 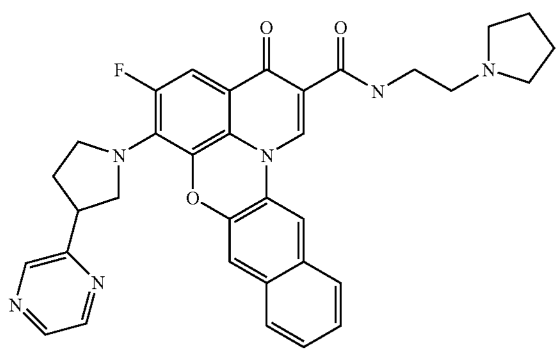 | | 0.75 |

TABLE 2-continued

| | Structure | Stop Data c-Myc μM | MTS Data Hella μM |
|---|---|---|---|
| 463 | 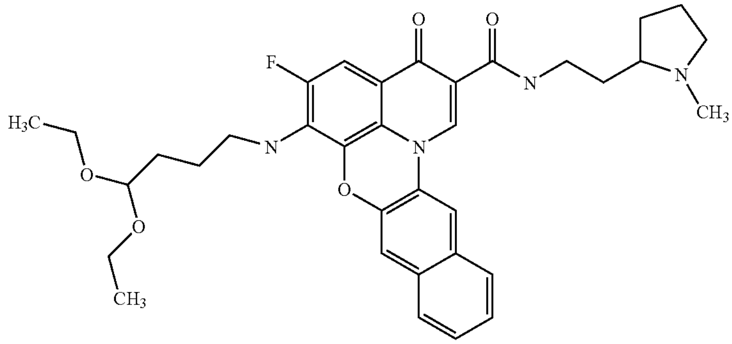 | | 0.75 |
| 464 | 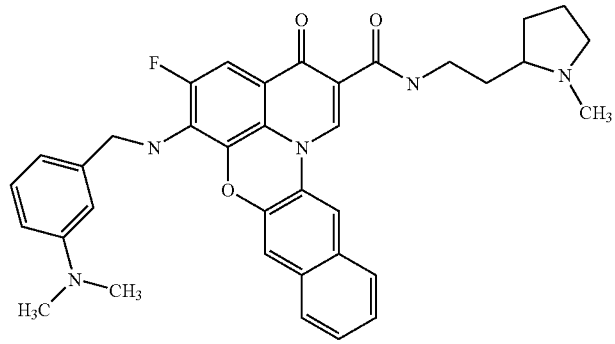 | | 0.75 |
| 465 | 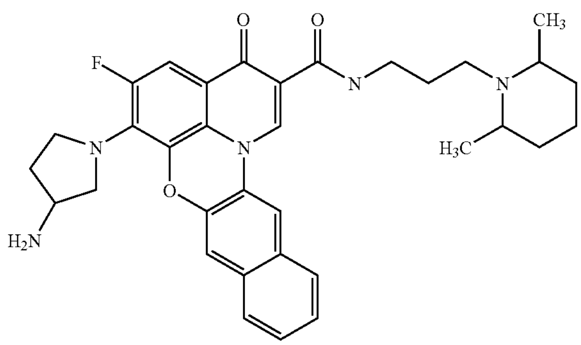 | | 0.75 |
| 466 | 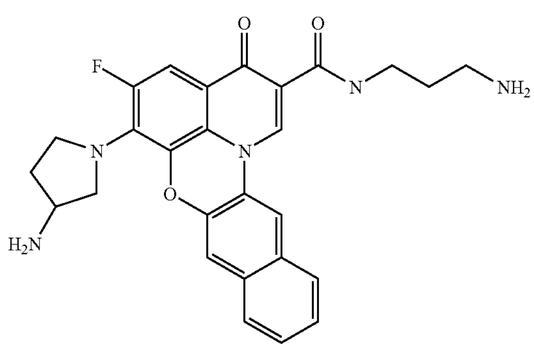 | | 0.75 |

TABLE 2-continued
| | Structure | Stop Data c-Myc μM | MTS Data Hella μM |
|---|---|---|---|
| 467 | 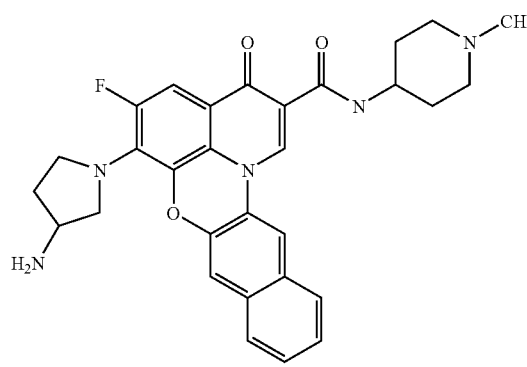 | | 0.75 |
| 468 | 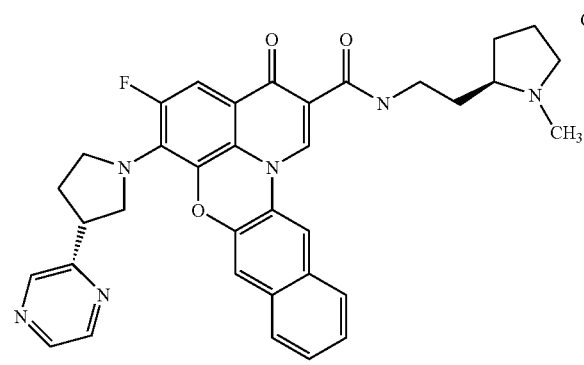 Chiral | | 0.74 |
| 469 | 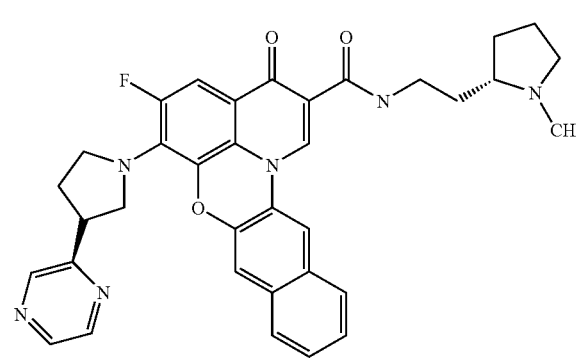 Chiral | | 0.73 |
| 470 | 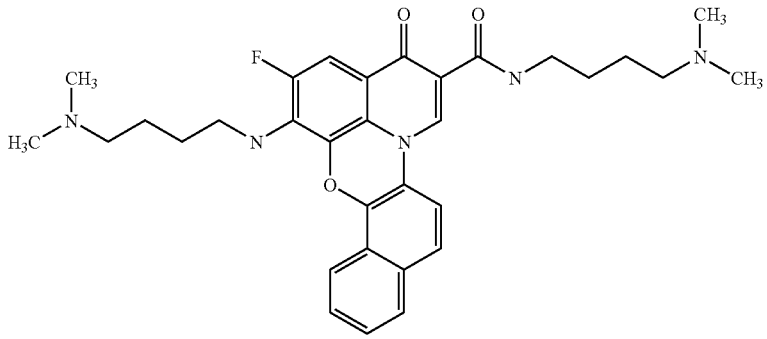 | | 0.64 |

TABLE 2-continued

| | Structure | Stop Data c-Myc μM | MTS Data Hella μM |
|---|---|---|---|
| 471 | 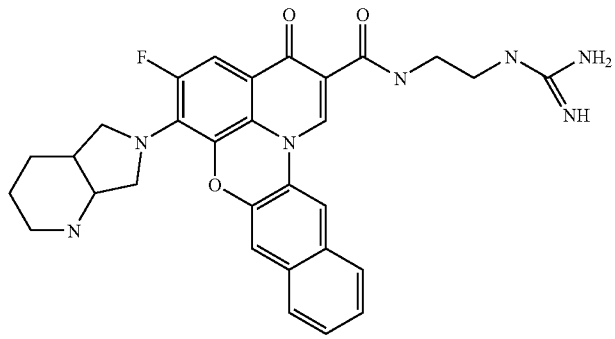 | 0.64 | |
| 472 | 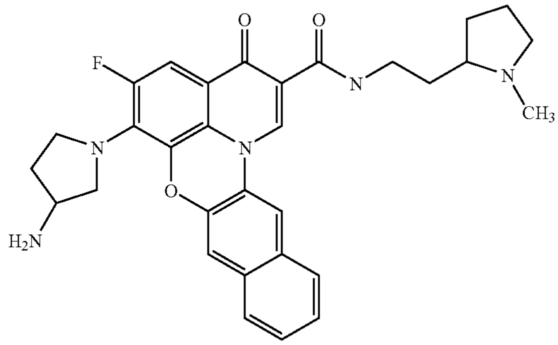 | 0.62 | 3.30 |
| 473 | 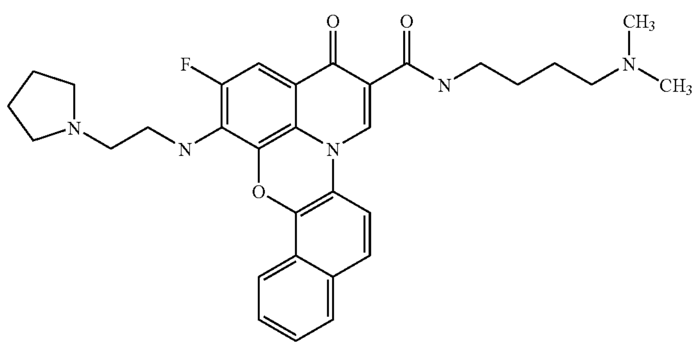 | 0.62 | |
| 474 | Chiral | 0.58 | 0.37 |

TABLE 2-continued
| | Structure | Stop Data c-Myc μM | MTS Data Hella μM |
|---|---|---|---|
| 475 | 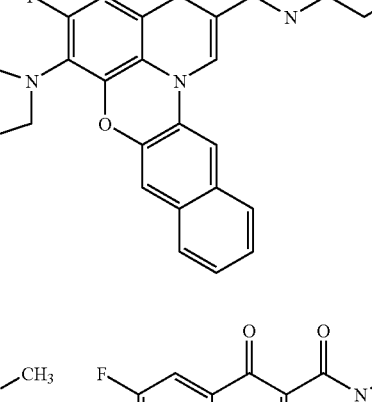 | 0.58 | 0.24 |
| 476 | 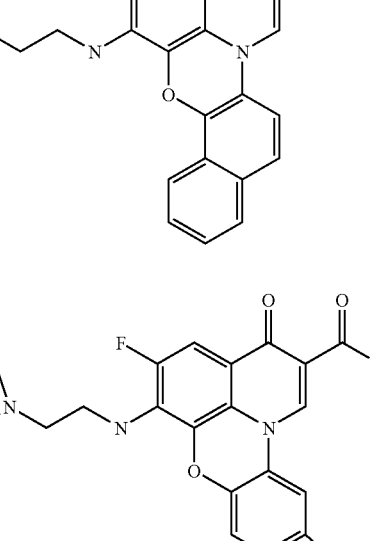 | 0.58 | |
| 477 | 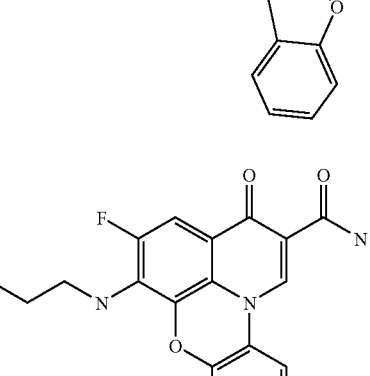 | 0.55 | 2.10 |
| 478 | 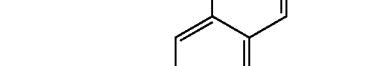 | 0.53 | |

TABLE 2-continued

| | Structure | Stop Data c-Myc μM | MTS Data Hella μM |
|---|---|---|---|
| 479 | 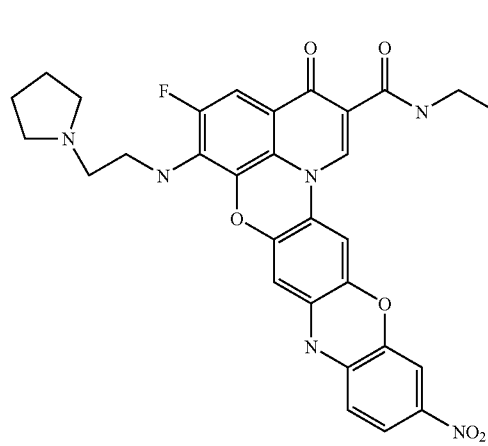 | 0.5 | 7.40 |
| 480 | (Chiral) | 0.5 | 3.70 |
| 481 | 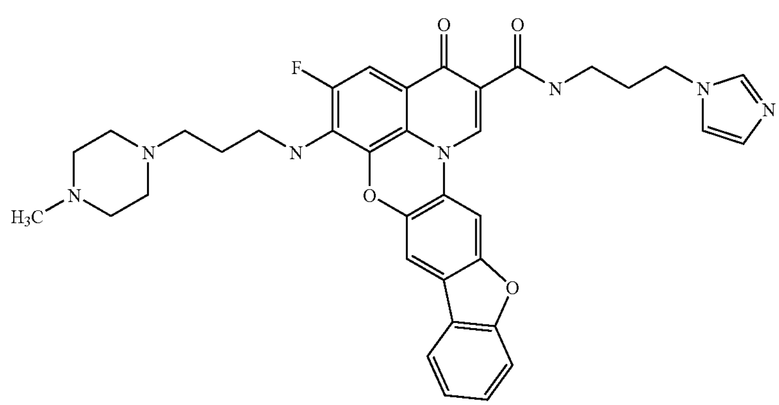 | 0.5 | 3.60 |

TABLE 2-continued

| | Structure | Stop Data c-Myc μM | MTS Data Hella μM |
|---|---|---|---|
| 482 | 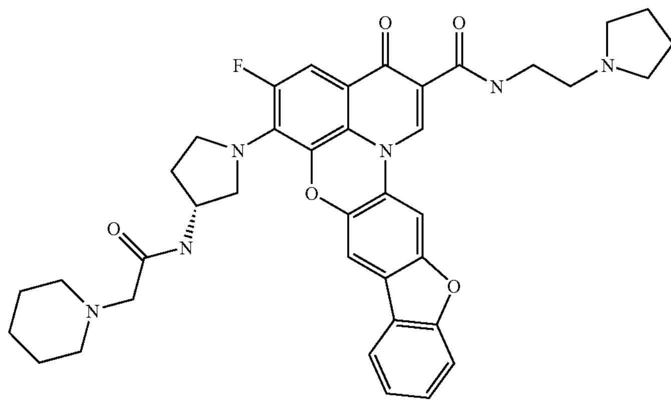 | 0.5 | 3.40 |
| 483 | 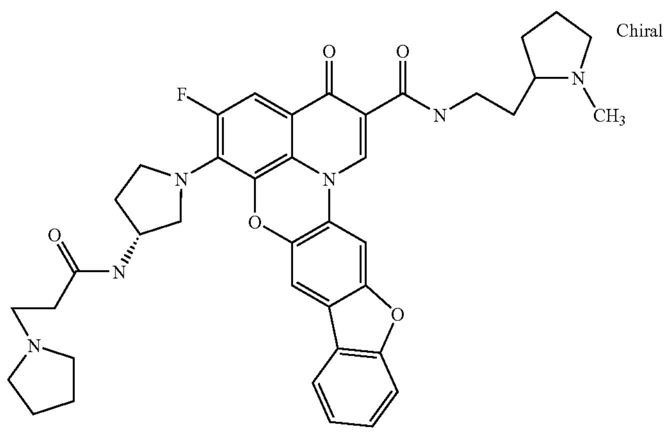 | 0.5 | 3.20 |
| 484 | 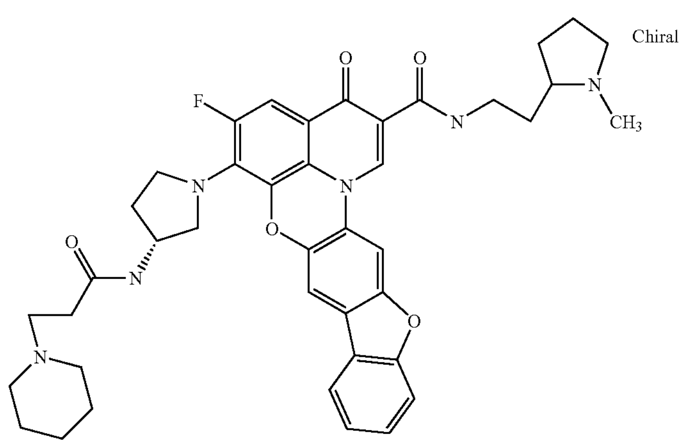 | 0.5 | 3.10 |

TABLE 2-continued

| | Structure | Stop Data c-Myc μM | MTS Data Hella μM |
|---|---|---|---|
| 485 | Chiral | 0.5 | 0.50 |
| 486 | Chiral | 0.5 | 0.39 |
| 487 | 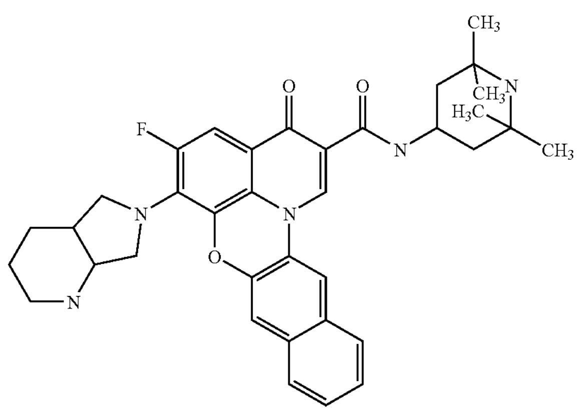 | 0.5 | 0.18 |
| 488 | 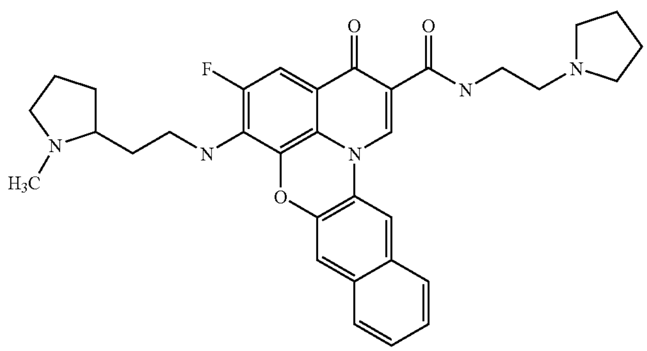 | 0.5 | |

TABLE 2-continued

| | Structure | Stop Data c-Myc μM | MTS Data Hella μM |
|---|---|---|---|
| 489 | 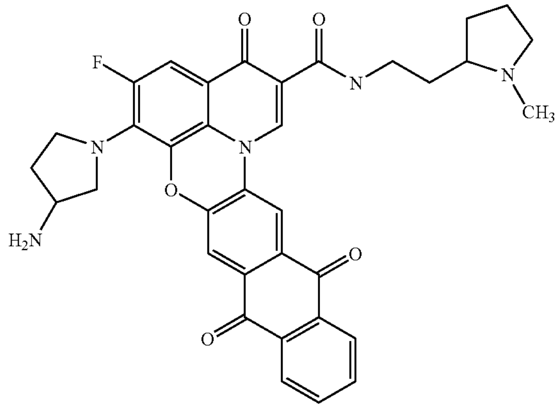 | 0.5 | |
| 490 | 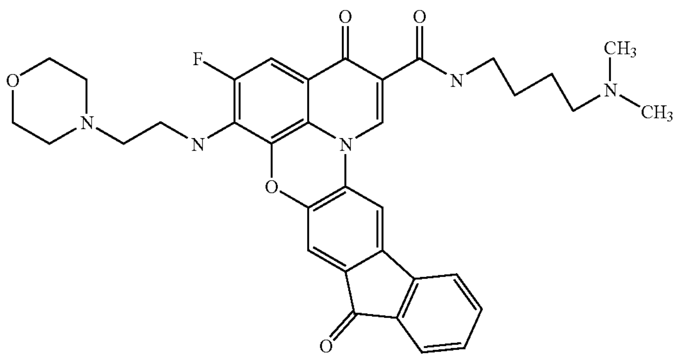 | 0.5 | |
| 491 | 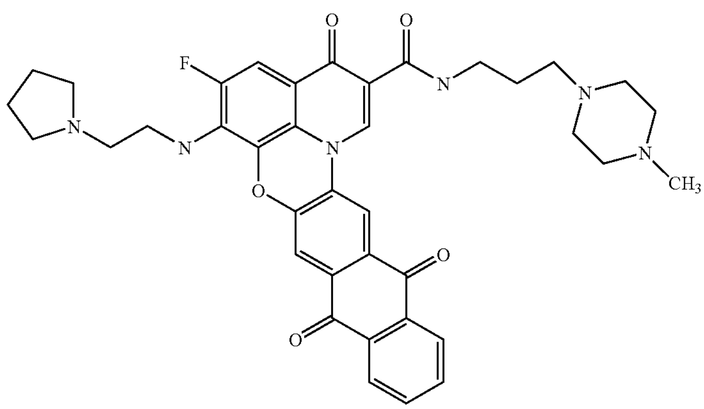 | 0.45 | |
| 492 | 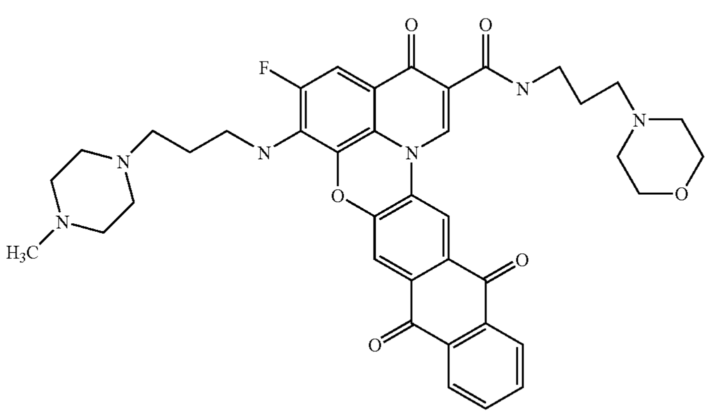 | 0.45 | |

TABLE 2-continued
| | Structure | Stop Data c-Myc μM | MTS Data Hella μM |
|---|---|---|---|
| 493 | 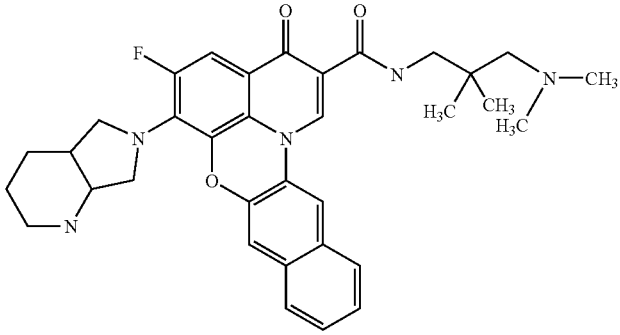 | 0.44 | 0.40 |
| 494 | 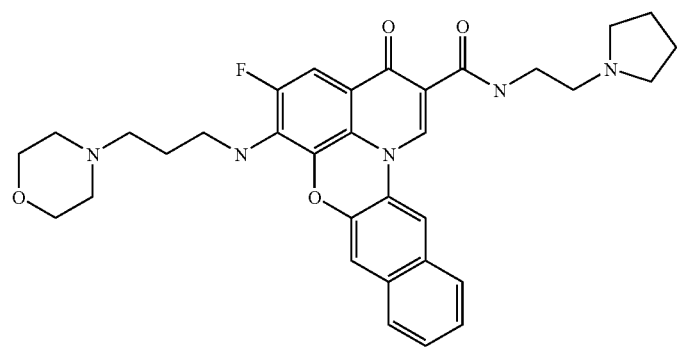 | 0.44 | 0.19 |
| 495 | 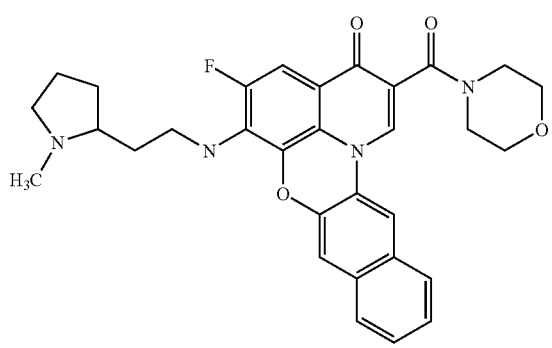 | 0.42 | |
| 496 | 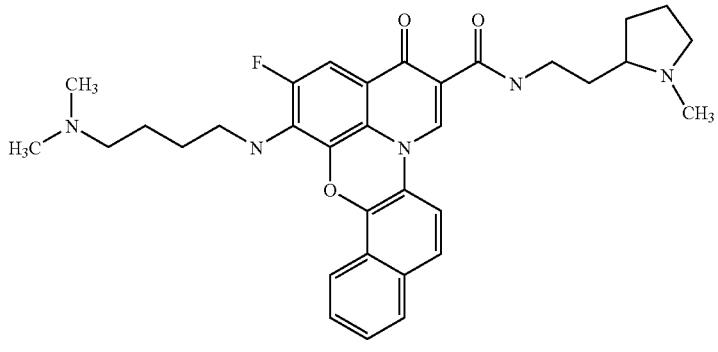 | 0.41 | 4.00 |

TABLE 2-continued

| | Structure | Stop Data c-Myc μM | MTS Data Hella μM |
|---|---|---|---|
| 497 | 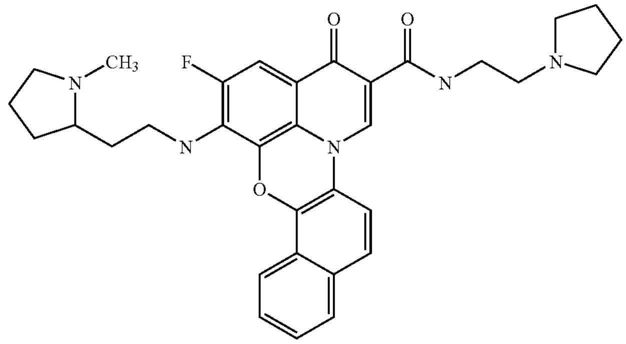 | 0.41 | 2.10 |
| 498 | 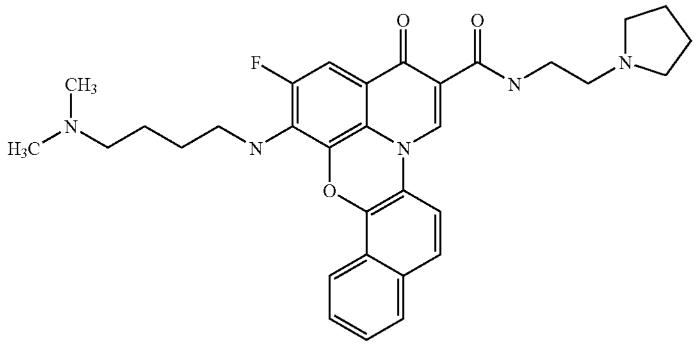 | 0.41 | |
| 499 | 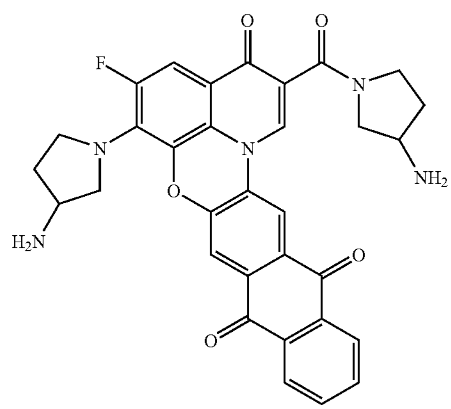 | 0.4 | |
| 500 | 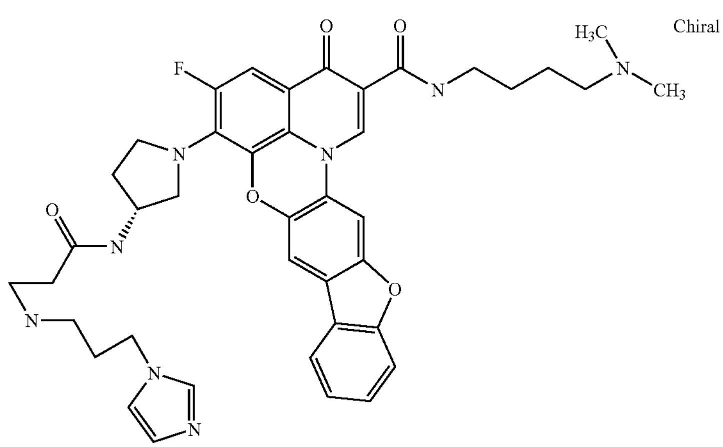 | 0.375 | 5.60 |

TABLE 2-continued

| | Structure | Stop Data c-Myc μM | MTS Data Hella μM |
|---|---|---|---|
| 501 | 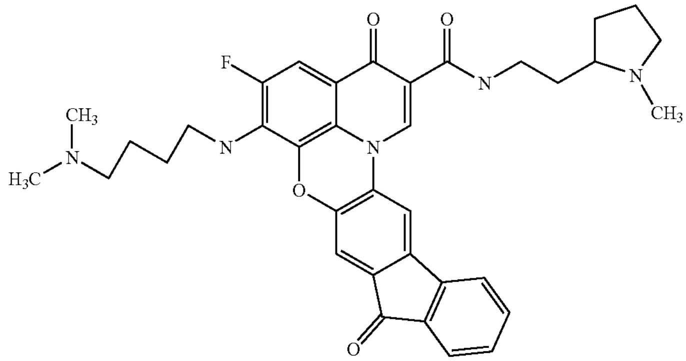 | 0.375 | 4.20 |
| 502 | 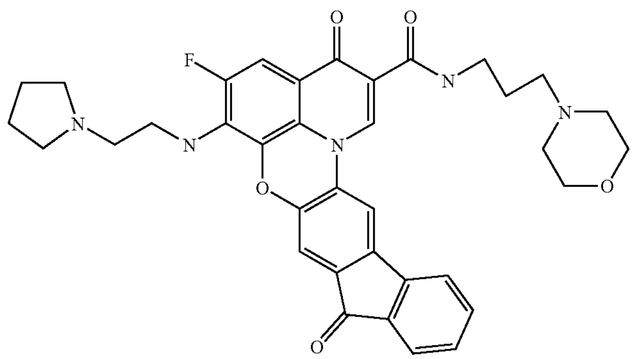 | 0.375 | 4.00 |
| 503 | (Chiral) | 0.375 | 4.00 |
| 504 | (Chiral) | 0.375 | 3.40 |

TABLE 2-continued

| | Structure | Stop Data c-Myc μM | MTS Data Hella μM |
|---|---|---|---|
| 505 | Chiral | 0.375 | 3.40 |
| 506 | Chiral | 0.375 | 3.40 |
| 507 | Chiral | 0.375 | 3.30 |

TABLE 2-continued

| | Structure | Stop Data c-Myc μM | MTS Data Hella μM |
|---|---|---|---|
| 508 | Chiral | 0.375 | 3.20 |
| 509 | 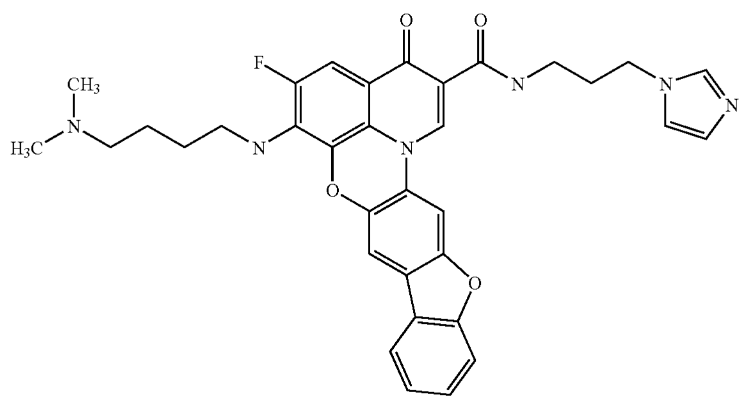 | 0.375 | 3.10 |
| 510 | Chiral | 0.375 | 3.10 |
| 511 | Chiral | 0.375 | 3.10 |

TABLE 2-continued

| | Structure | Stop Data c-Myc μM | MTS Data Hella μM |
|---|---|---|---|
| 512 | 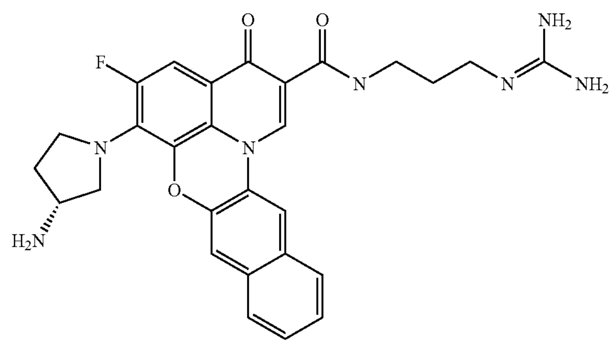 | 0.375 | 3.10 |
| 513 | 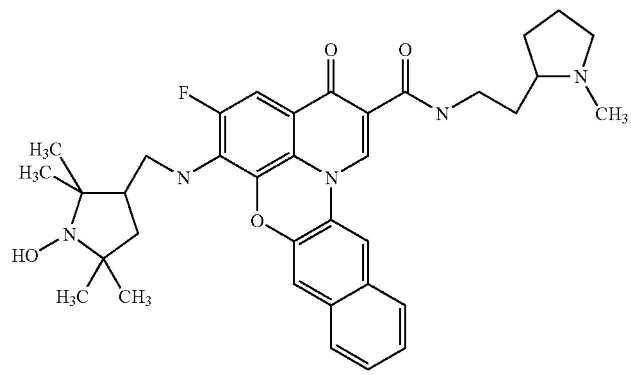 | 0.375 | 3.10 |
| 514 | 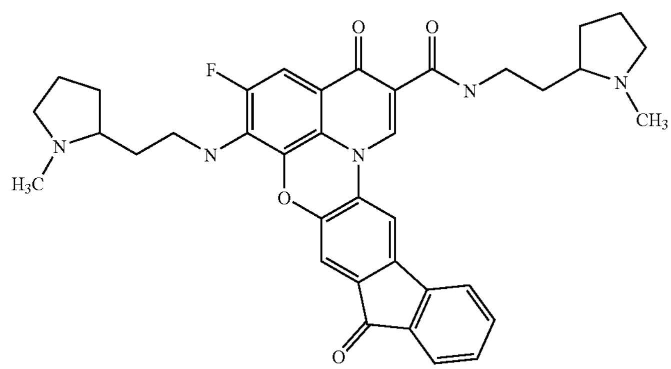 | 0.375 | 2.90 |
| 515 | 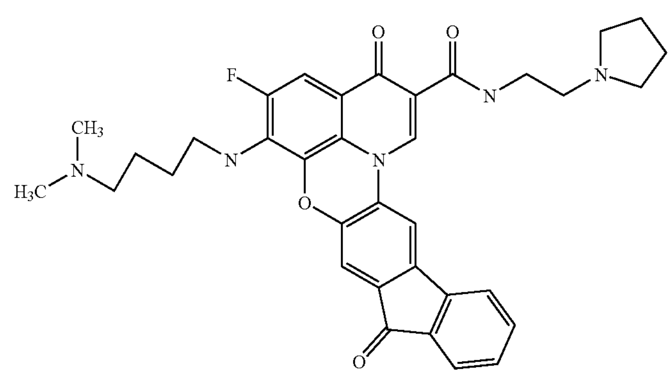 | 0.375 | 2.50 |

TABLE 2-continued

| | Structure | Stop Data c-Myc μM | MTS Data Hella μM |
|---|---|---|---|
| 516 | 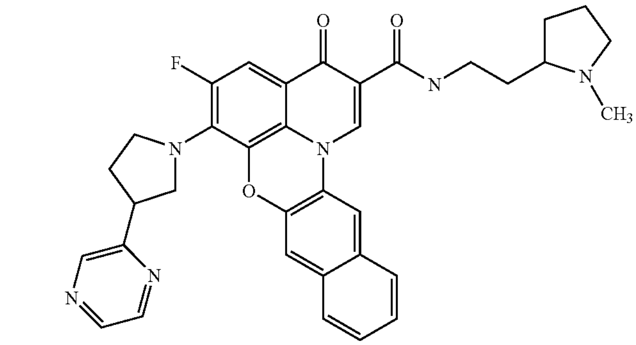 | 0.375 | 2.30 |
| 517 | 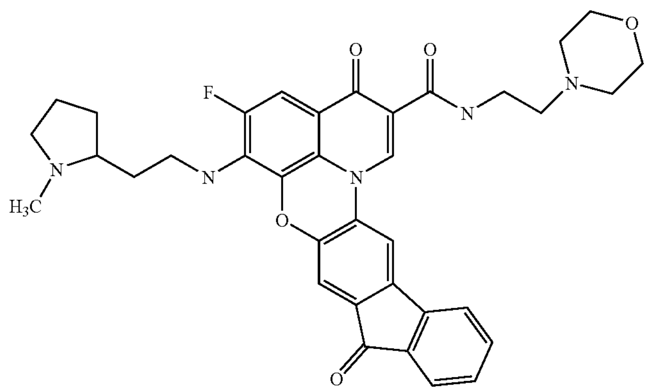 | 0.375 | 2.20 |
| 518 | 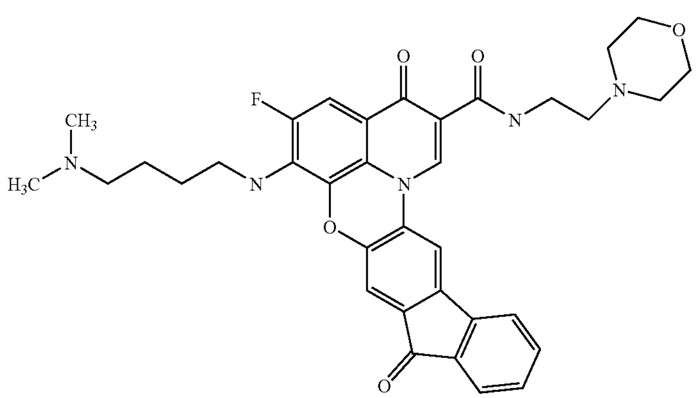 | 0.375 | 2.20 |
| 519 | 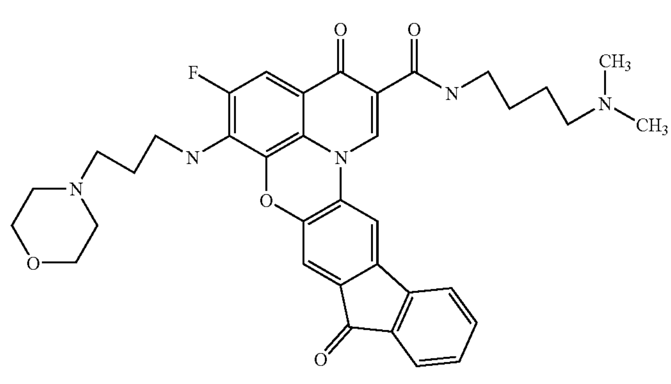 | 0.375 | 2.10 |

TABLE 2-continued
| | Structure | Stop Data c-Myc μM | MTS Data Hella μM |
|---|---|---|---|
| 520 | Chiral 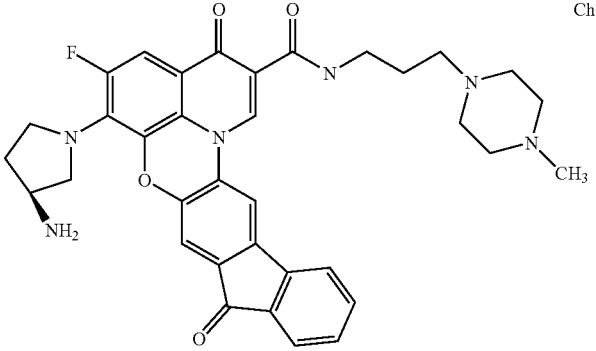 | 0.375 | 1.90 |
| 521 | 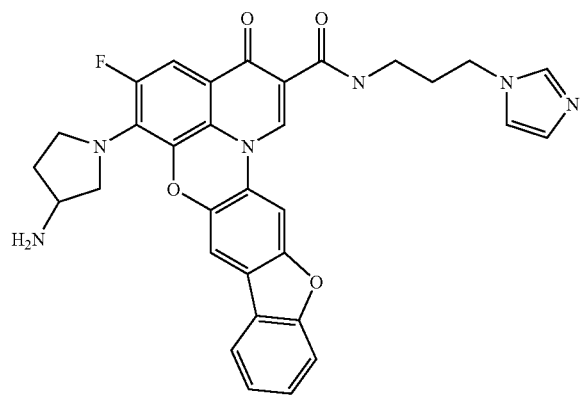 | 0.375 | 1.70 |
| 522 | 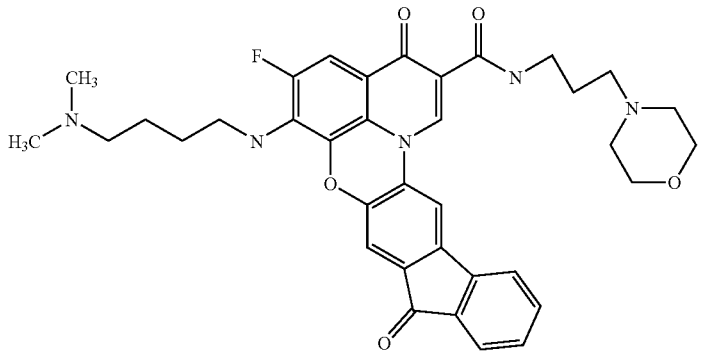 | 0.375 | 1.70 |
| 523 | 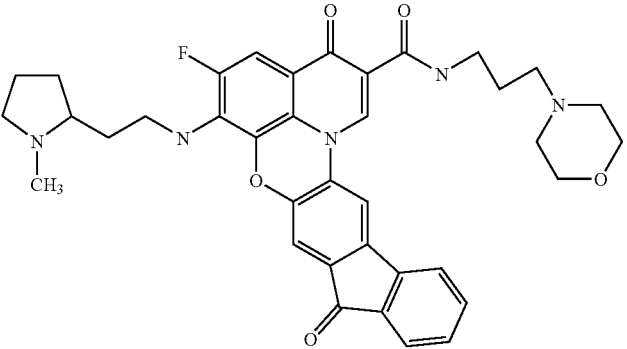 | 0.375 | 1.60 |

TABLE 2-continued
| | Structure | Stop Data c-Myc μM | MTS Data Hella μM |
|---|---|---|---|
| 524 | 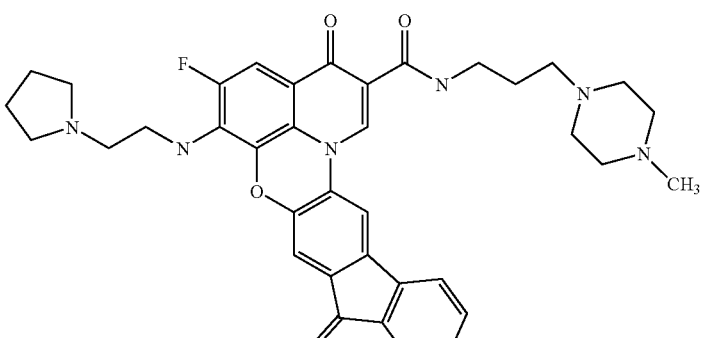 | 0.375 | 1.50 |
| 525 | 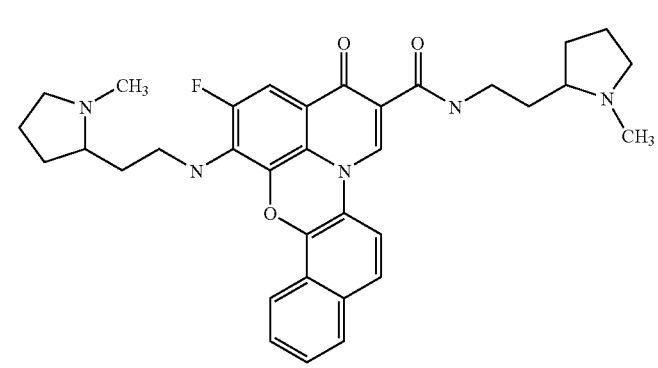 | 0.375 | 1.,2 |
| 526 | 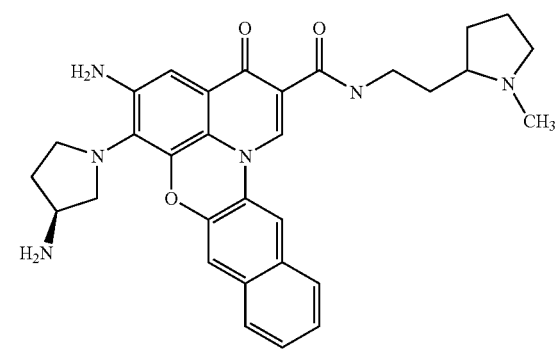 | 0.375 | 0.90 |
| 527 | 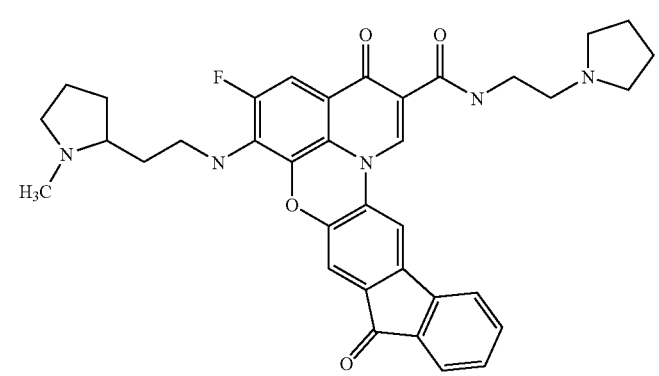 | 0.375 | 0.79 |

TABLE 2-continued
| | Structure | Stop Data c-Myc μM | MTS Data Hella μM |
|---|---|---|---|
| 528 | 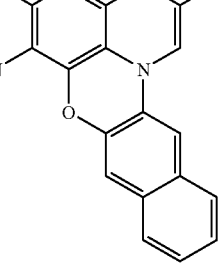 Chiral | 0.375 | 0.75 |
| 529 | 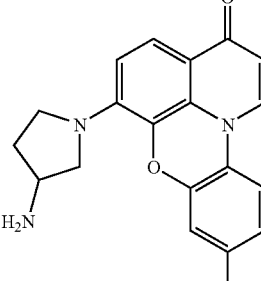 | 0.375 | 0.75 |
| 530 | 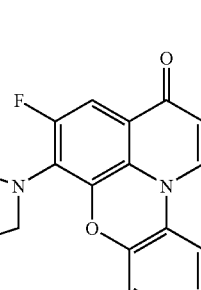 | 0.375 | 0.72 |
| 531 | 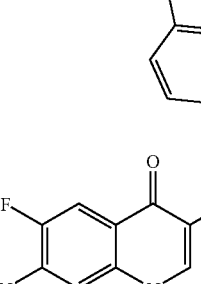 | 0.375 | 0.48 |

TABLE 2-continued

| | Structure | Stop Data c-Myc μM | MTS Data Hella μM |
|---|---|---|---|
| 532 | 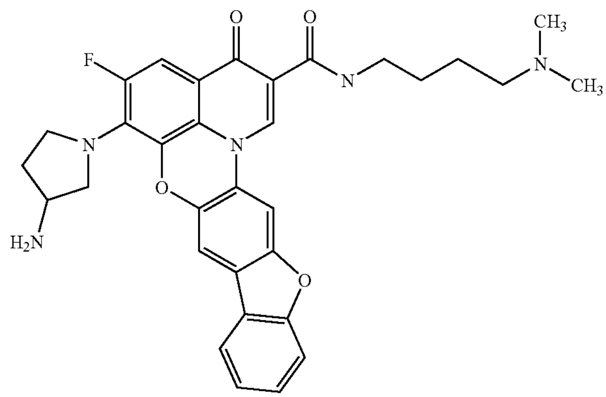 | 0.375 | 0.44 |
| 533 | Chiral | 0.375 | 0.40 |
| 534 | 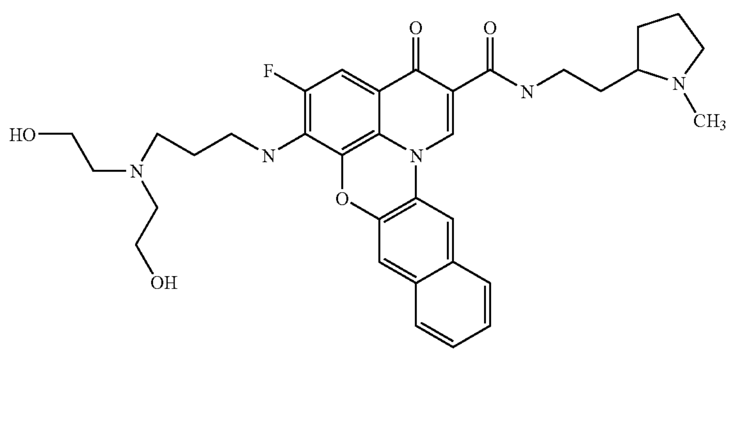 | 0.375 | 0.40 |

TABLE 2-continued

| | Structure | Stop Data c-Myc μM | MTS Data Hella μM |
|---|---|---|---|
| 535 | 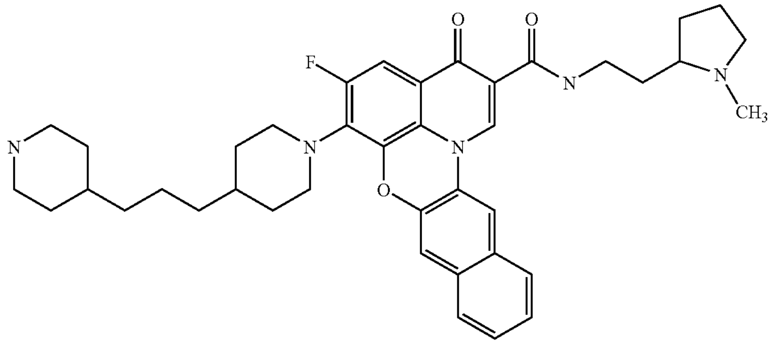 | 0.375 | 0.31 |
| 536 | 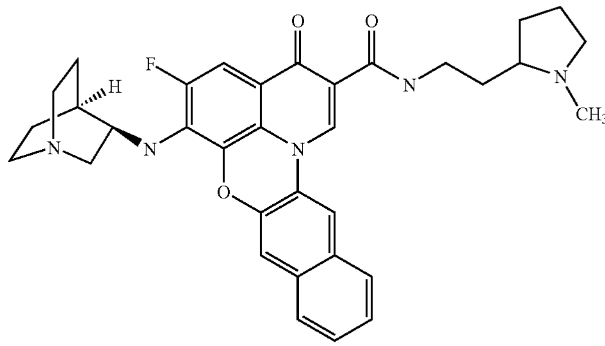 | 0.375 | 0.31 |
| 537 | 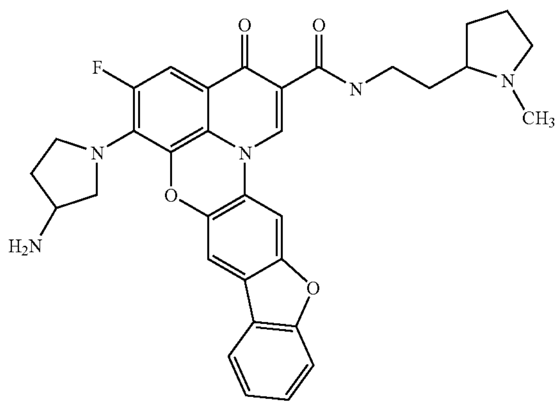 | 0.375 | 0.29 |
| 538 | 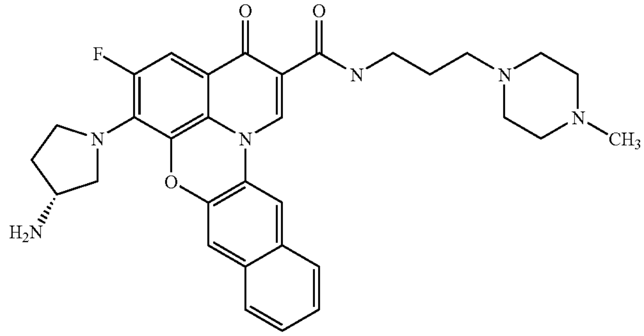 | 0.375 | 0.28 |

TABLE 2-continued

| | Structure | Stop Data c-Myc μM | MTS Data Hella μM |
|---|---|---|---|
| 539 | 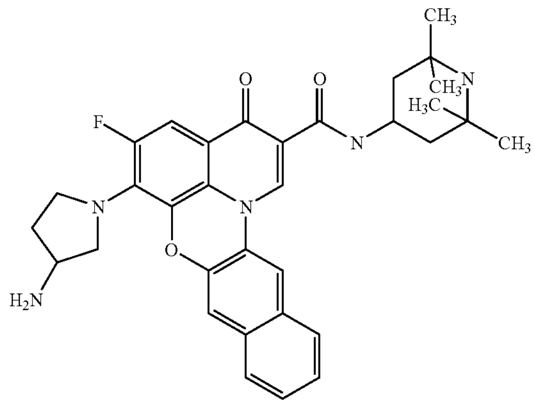 | 0.375 | 0.28 |
| 540 | 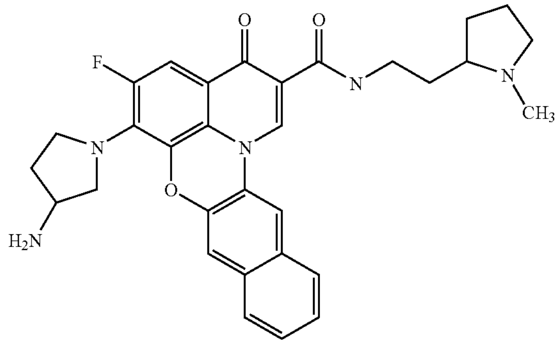 | 0.375 | 0.27 |
| 541 | 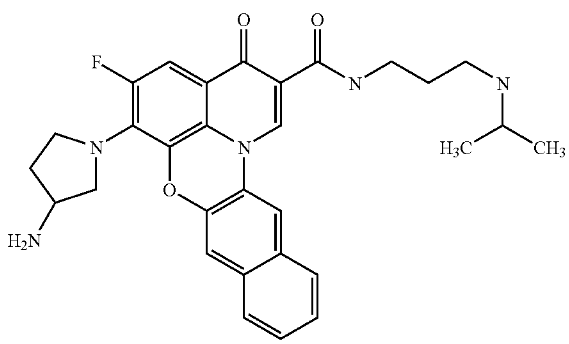 | 0.375 | 0.27 |
| 542 | 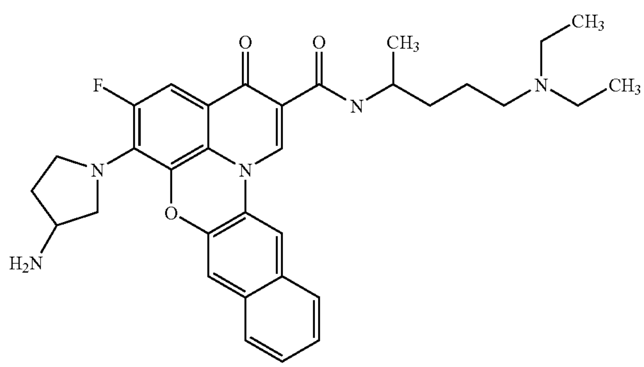 | 0.375 | 0.23 |

TABLE 2-continued

| | Structure | Stop Data c-Myc μM | MTS Data Hella μM |
|---|---|---|---|
| 543 | 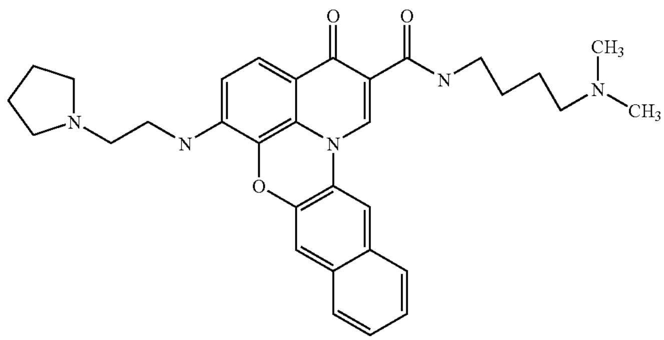 | 0.375 | 0.20 |
| 544 | 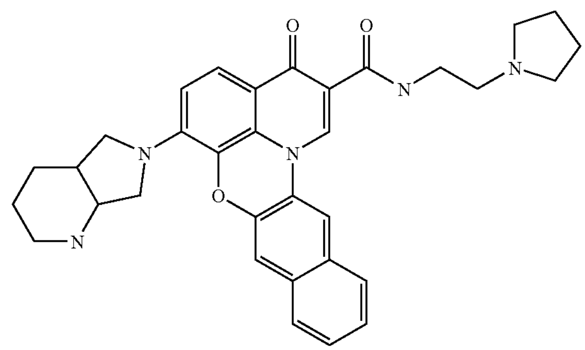 | 0.375 | 0.20 |
| 545 | 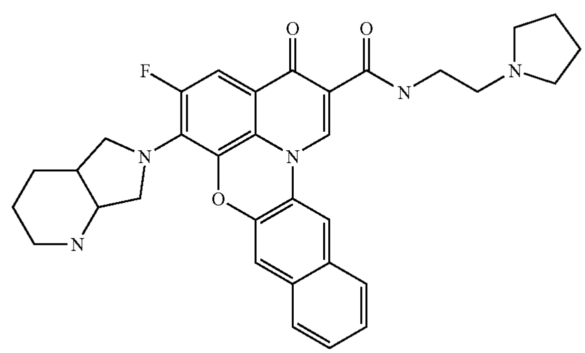 | 0.375 | 0.15 |
| 546 | 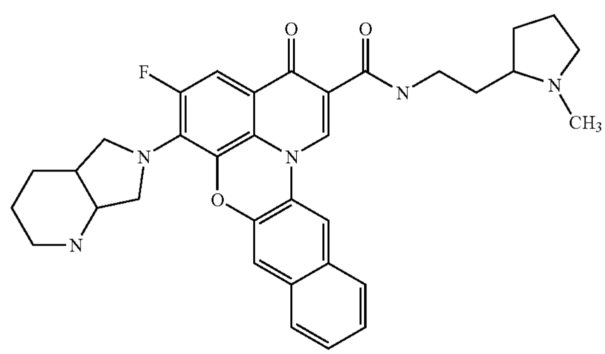 | 0.375 | 0.10 |

TABLE 2-continued

| | Structure | Stop Data c-Myc μM | MTS Data Hella μM |
|---|---|---|---|
| 547 | 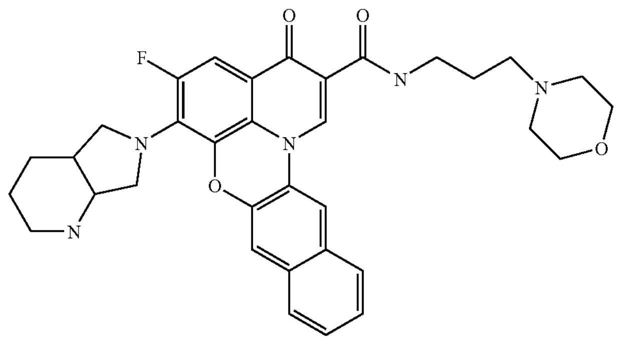 | 0.375 | 0.10 |
| 548 | 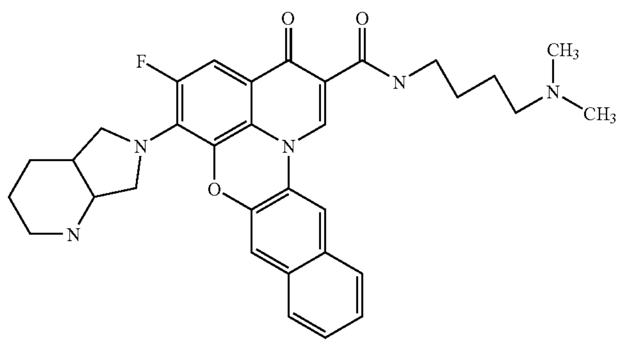 | 0.375 | 0.10 |
| 549 | 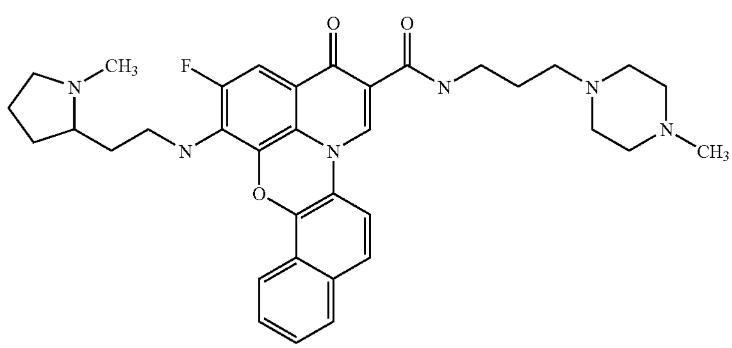 | 0.375 | |
| 550 | 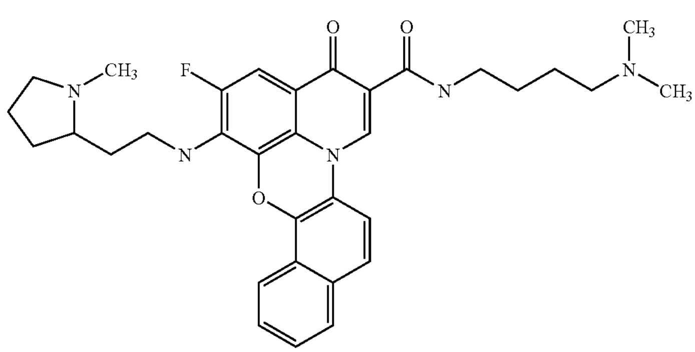 | 0.375 | |

TABLE 2-continued

| Structure | Stop Data c-Myc μM | MTS Data Hella μM |
|---|---|---|
| 551 | | 0.375 |
| 552 | | 0.375 |
| 553 | | 0.375 |

TABLE 2-continued

| Structure | Stop Data c-Myc μM | MTS Data Hella μM |
|---|---|---|
| 554 | | 0.375 |
| 555 | | 0.375 |
| 556 | | 0.375 |

TABLE 2-continued

| | Structure | Stop Data c-Myc μM | MTS Data Hella μM |
|---|---|---|---|
| 557 | 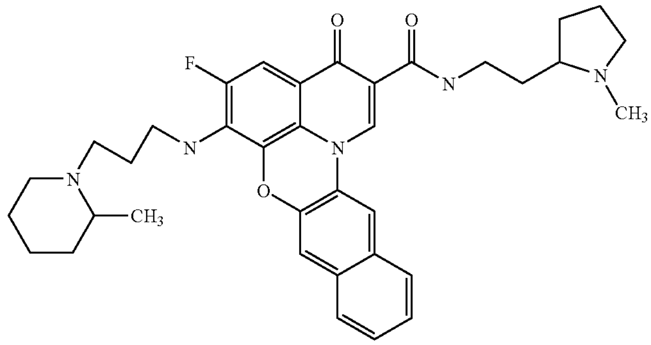 | | 0.375 |
| 558 | 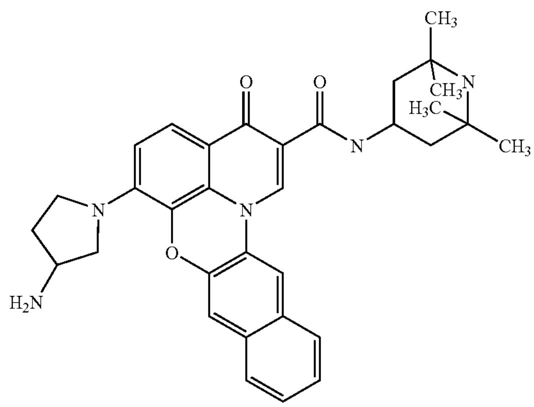 | | 0.375 |
| 559 | 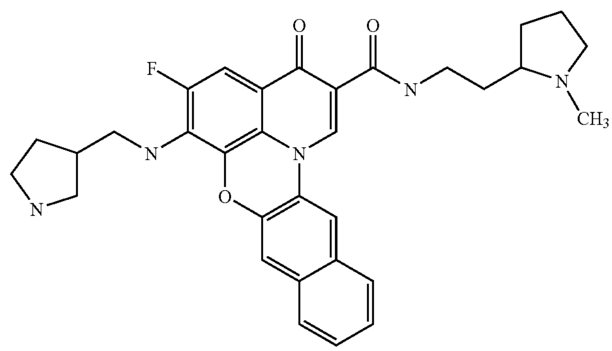 | | 0.375 |
| 560 | 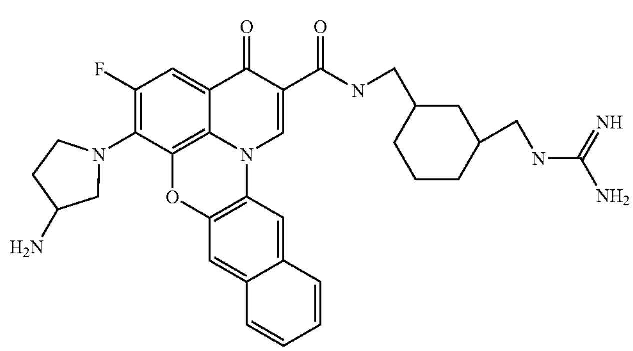 | | 0.37 |

TABLE 2-continued

| | Structure | Stop Data c-Myc μM | MTS Data Hella μM |
|---|---|---|---|
| 561 | 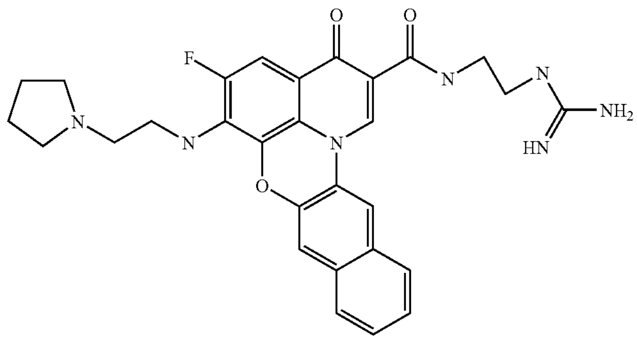 | 0.34 | |
| 562 | 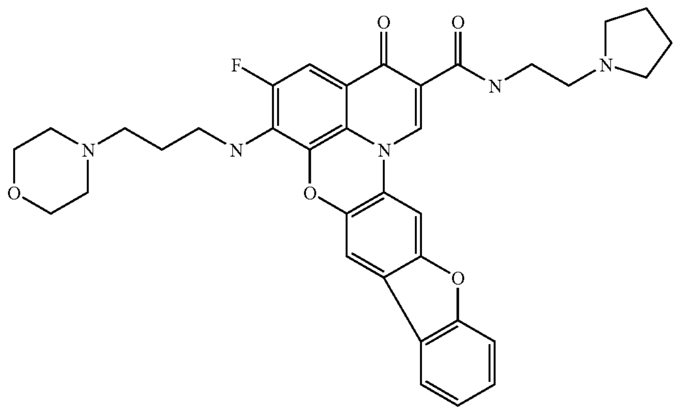 | 0.32 | 0.85 |
| 563 | 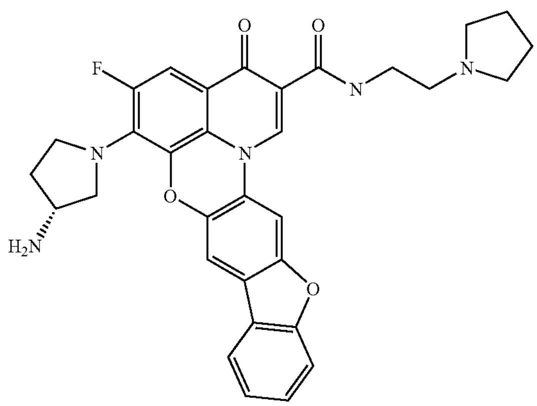 | 0.25 | 0.31 |
| 564 | (Chiral) | 0.25 | 0.29 |

TABLE 2-continued

| | Structure | Stop Data c-Myc μM | MTS Data Hella μM |
|---|---|---|---|
| 565 | 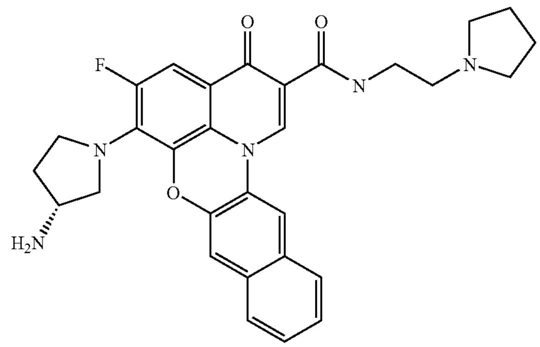 | 0.25 | 0.20 |
| 566 | 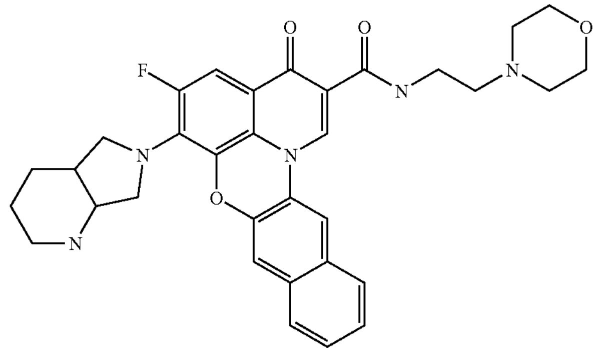 | 0.25 | 0.03 |
| 567 | 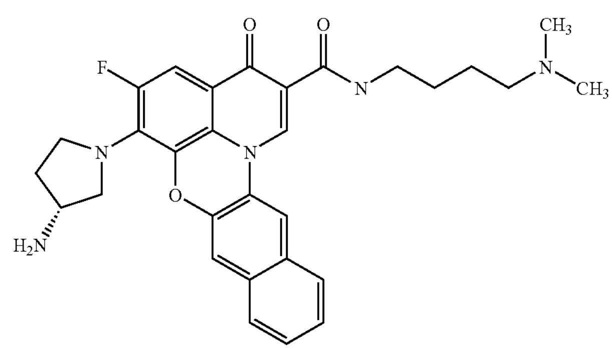 | 0.25 | |
| 568 | 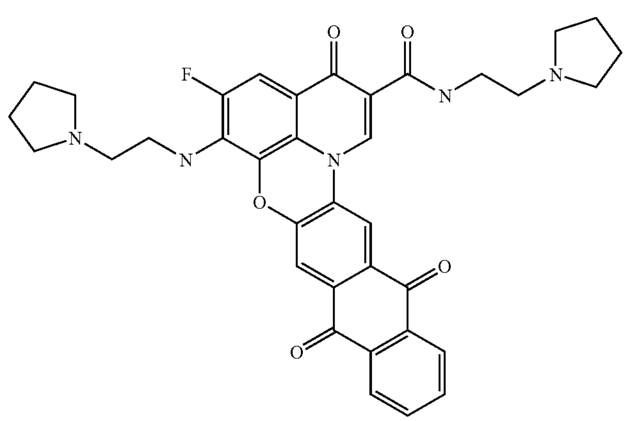 | 0.22 | 4.10 |

TABLE 2-continued
| | Structure | Stop Data c-Myc μM | MTS Data Hella μM |
|---|---|---|---|
| 569 | 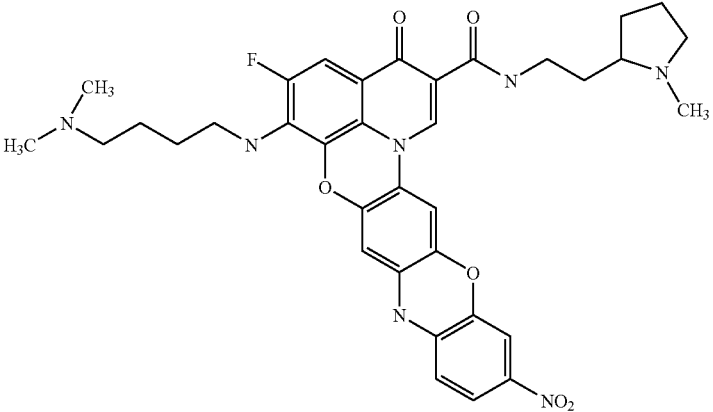 | 0.18 | 7.80 |
| 570 | 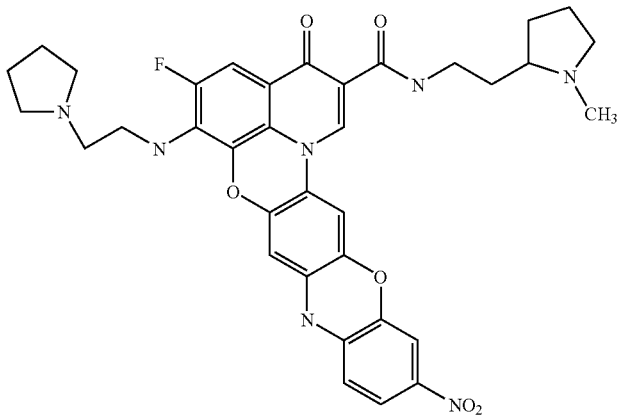 | 0.18 | 6.80 |
| 571 | 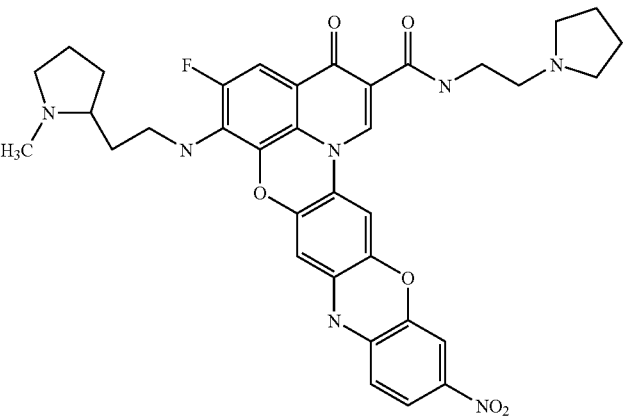 | 0.18 | 4.80 |

TABLE 2-continued

| Structure | Stop Data c-Myc μM | MTS Data Hella μM |
|---|---|---|
| 572 | 0.18 | 4.80 |
| 573 (Chiral) | 0.18 | 4.50 |
| 574 | 0.18 | 4.00 |

TABLE 2-continued

| | Structure | Stop Data c-Myc μM | MTS Data Hella μM |
|---|---|---|---|
| 575 | 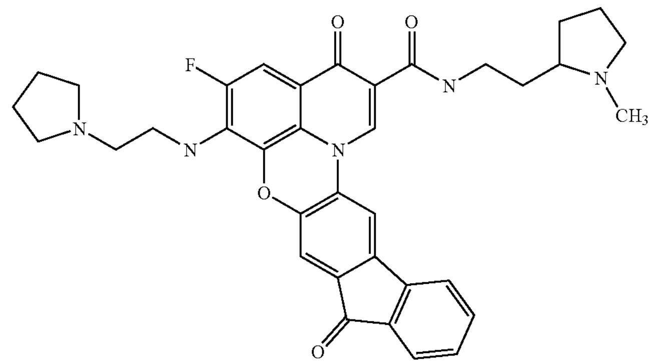 | 0.18 | 2.10 |
| 576 | 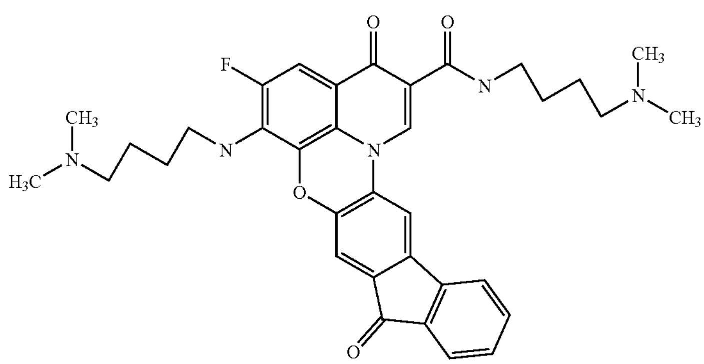 | 0.18 | 2.10 |
| 577 | 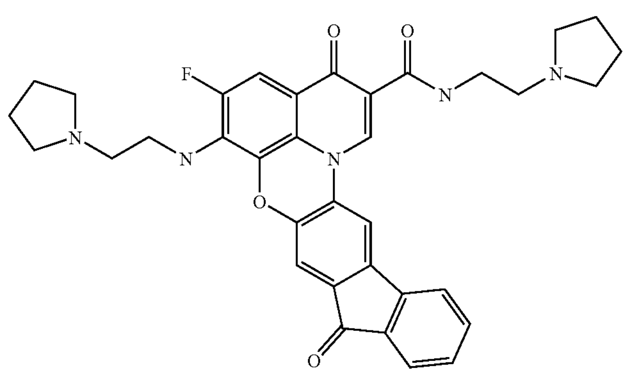 | 0.18 | 1.10 |
| 578 | 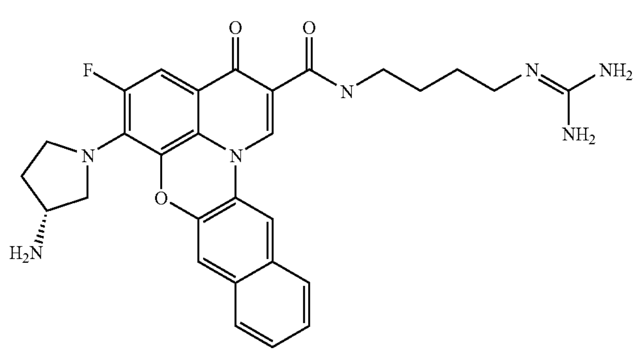 | 0.18 | 0.58 |

TABLE 2-continued
| | Structure | Stop Data c-Myc μM | MTS Data Hella μM |
|---|---|---|---|
| 579 | 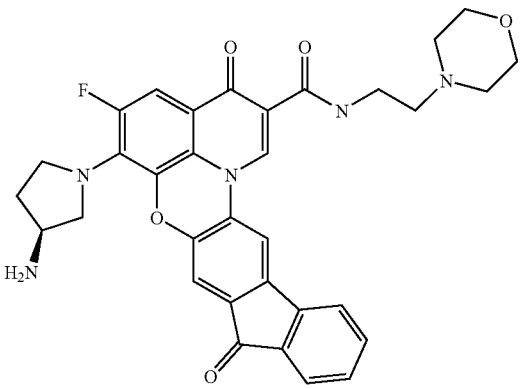 Chiral | 0.18 | 0.49 |
| 580 | 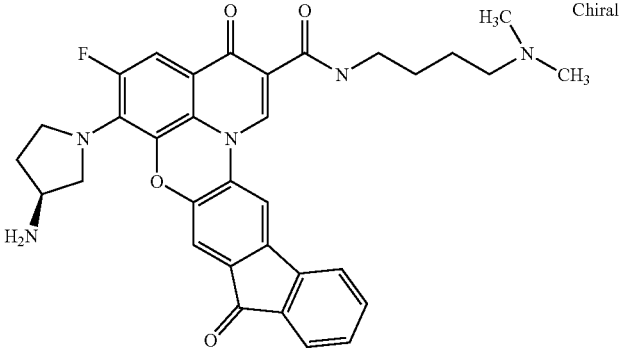 Chiral | 0.18 | 0.30 |
| 581 | 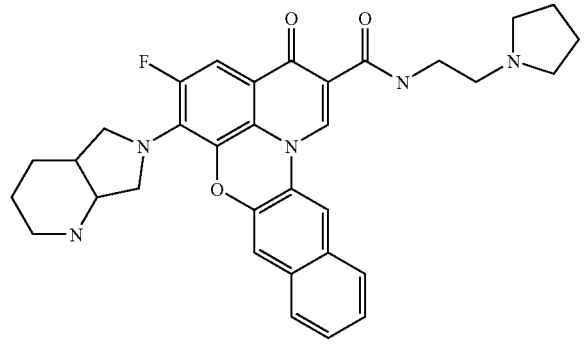 | 0.18 | 0.30 |
| 582 | 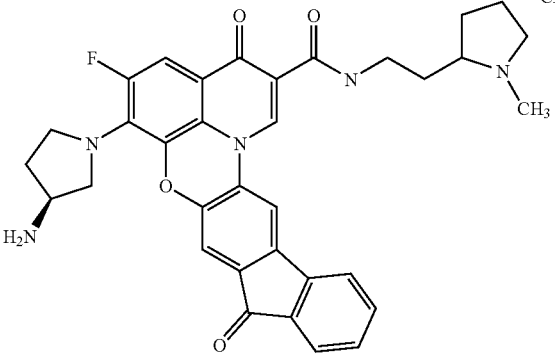 Chiral | 0.18 | 0.28 |

TABLE 2-continued

| | Structure | Stop Data c-Myc μM | MTS Data Hella μM |
|---|---|---|---|
| 583 | Chiral | 0.18 | 0.25 |
| 584 | 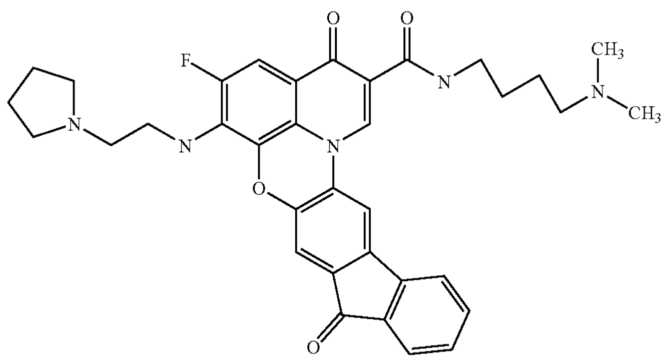 | 0.18 | 0.19 |
| 585 | 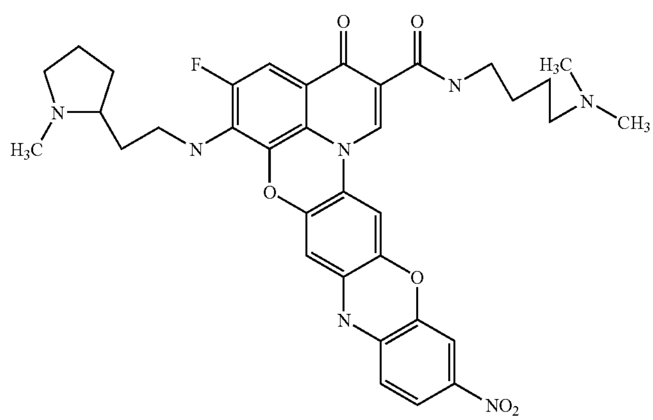 | 0.18 | |
| 586 | 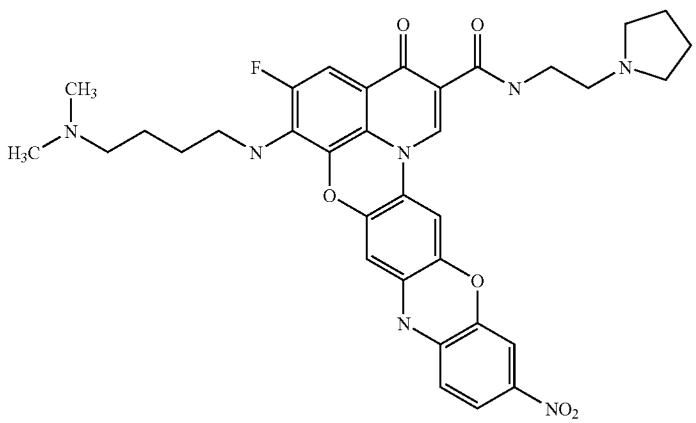 | 0.18 | |

TABLE 2-continued

| | Structure | Stop Data c-Myc μM | MTS Data Hella μM |
|---|---|---|---|
| 587 | 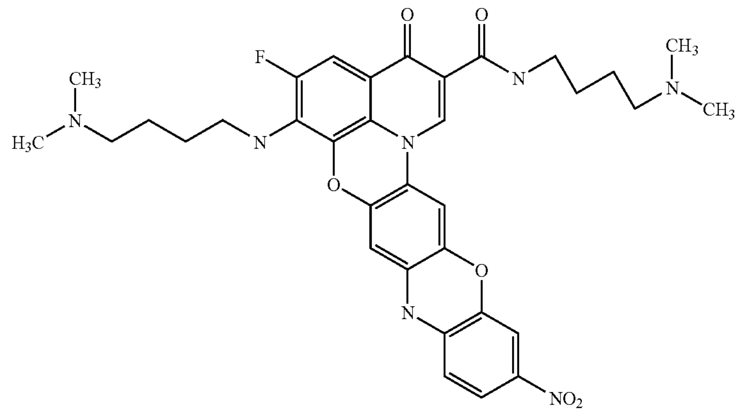 | | 0.18 |
| 588 | 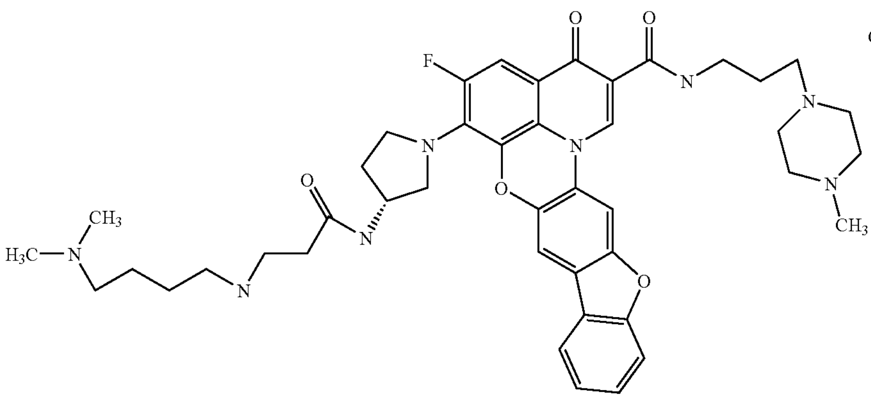 | Chiral | 0.18 |
| 589 | 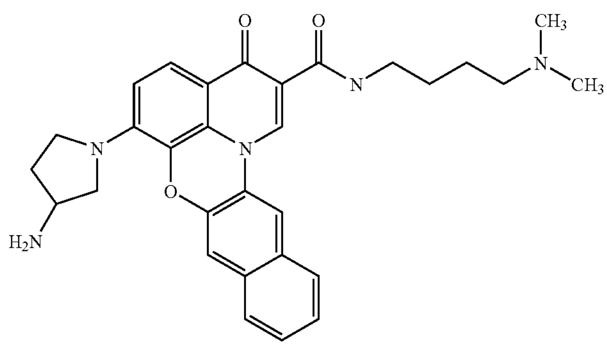 | | 0.18 |
| 590 | 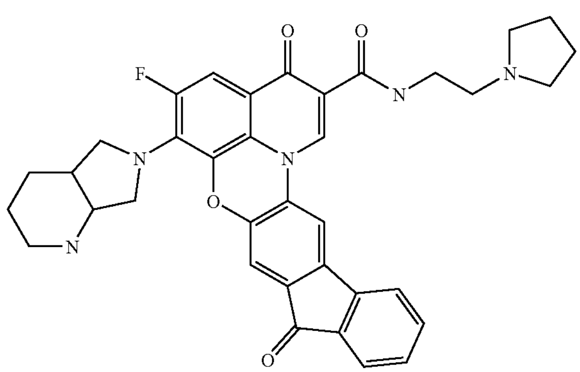 | | 0.18 |

TABLE 2-continued

| Structure | Stop Data c-Myc μM | MTS Data Hella μM |
|---|---|---|
| 591 | 0.13 | 3.30 |
| 592 | 0.1 | 3.80 |
| 1467 | 0.25 | 0.35 |
| 1468 | 0.375 | 0.35 |

TABLE 2-continued
| | Structure | Stop Data c-Myc μM | MTS Data Hella μM |
|---|---|---|---|
| 1469 | 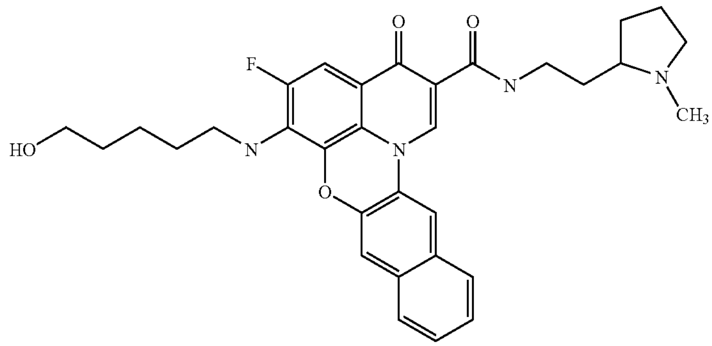 | | 1.75 |
| 1470 | 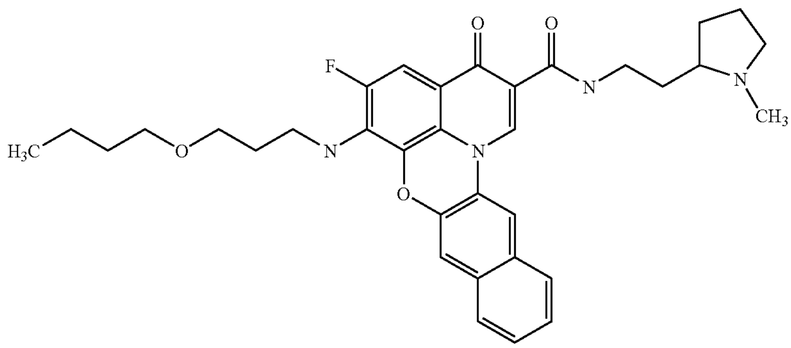 | | 1.75 |
| 1471 | 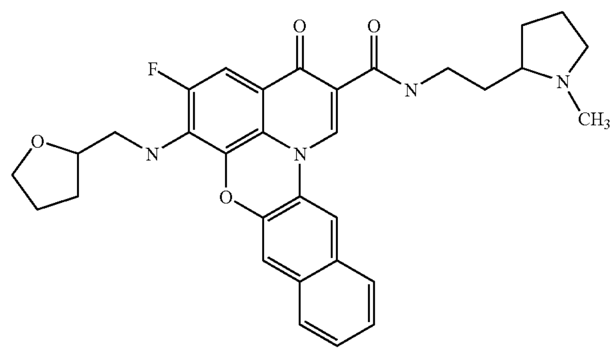 | | 5 |
TABLE 3
593
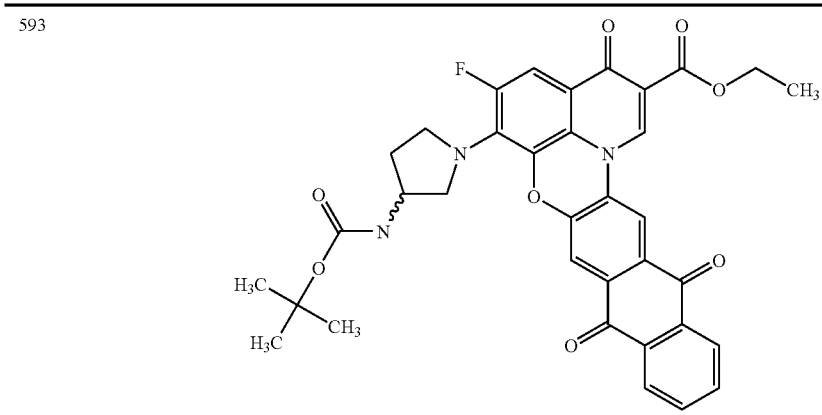

TABLE 3-continued
594 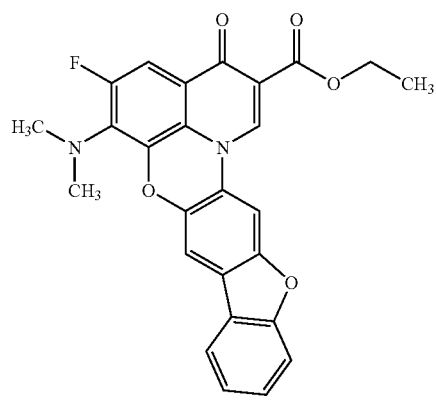
595 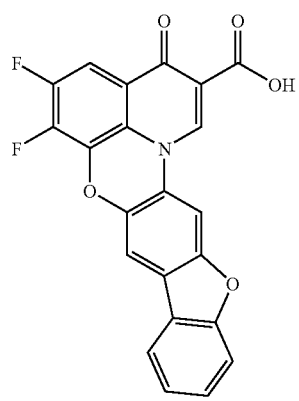
596 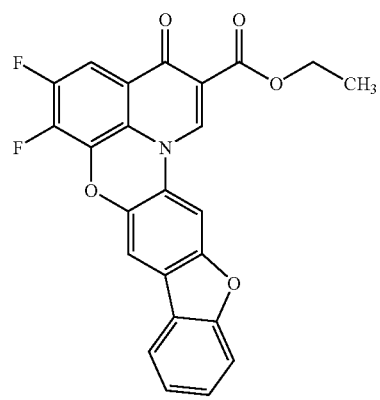
597 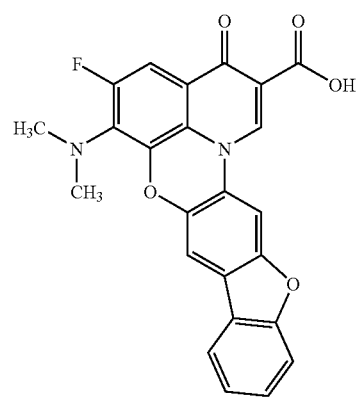

TABLE 3-continued
598
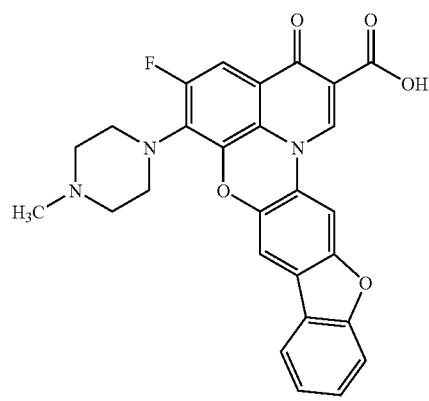
599
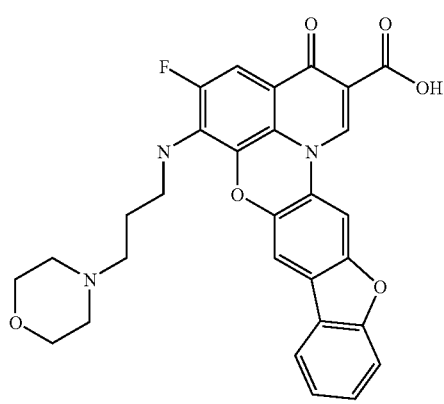
600
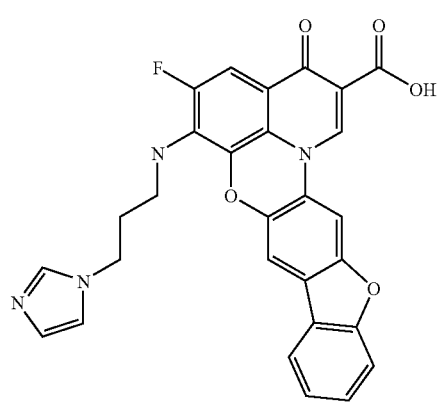
601
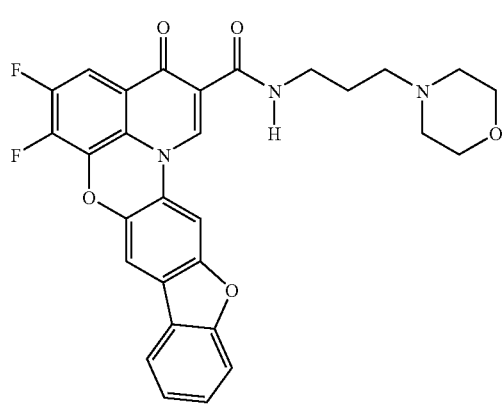

TABLE 3-continued
602
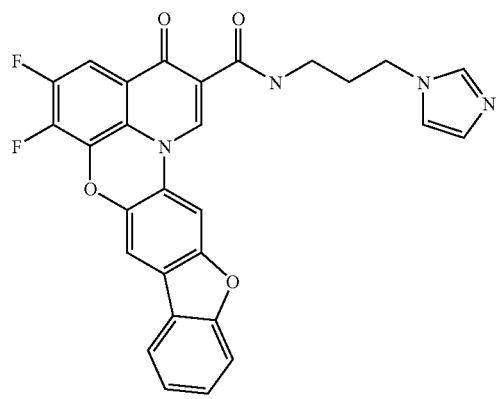
603
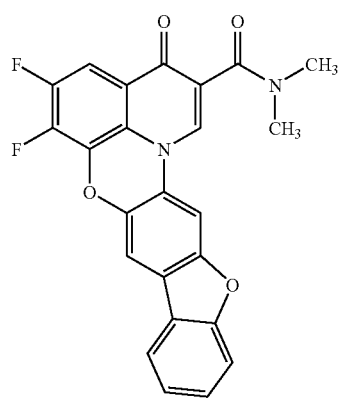
604
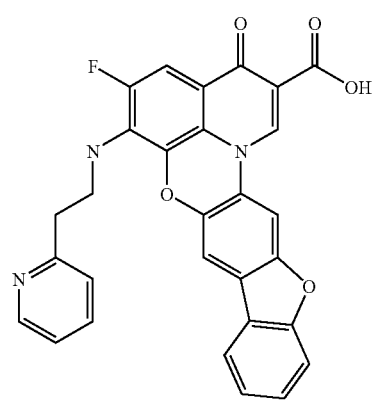
605
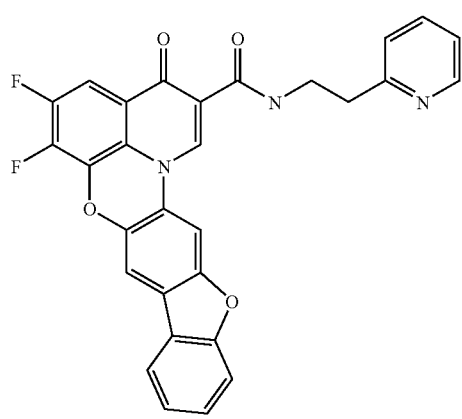

TABLE 3-continued
606
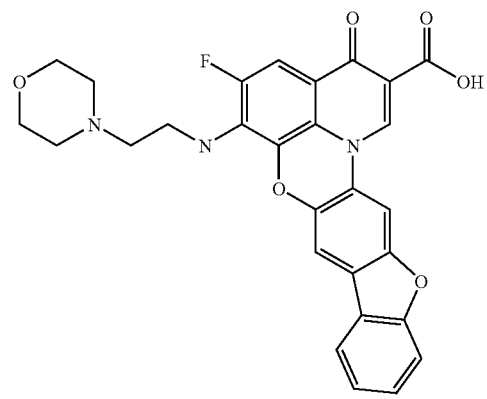
607
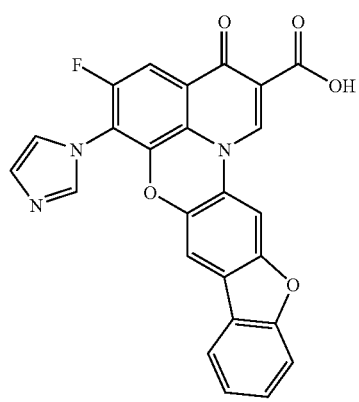
608
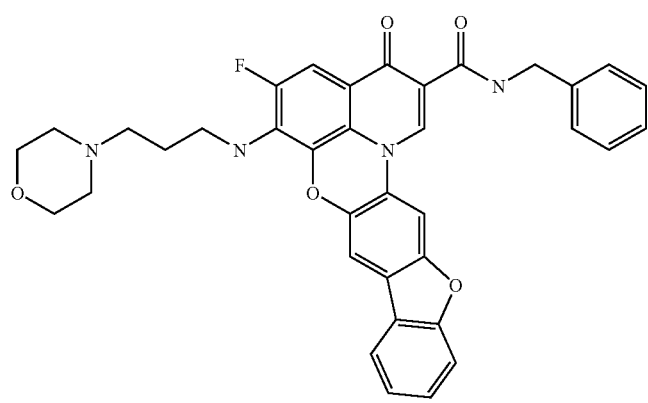
609
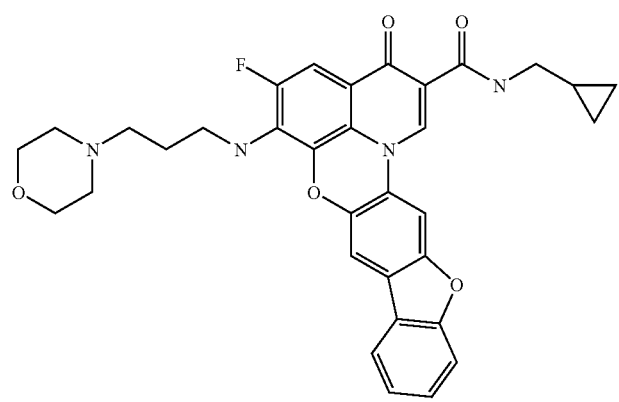

TABLE 3-continued
610
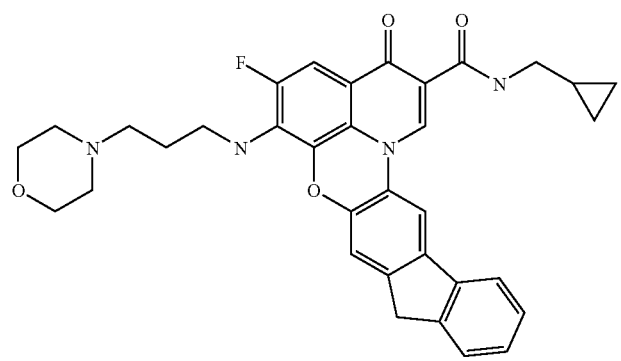
611
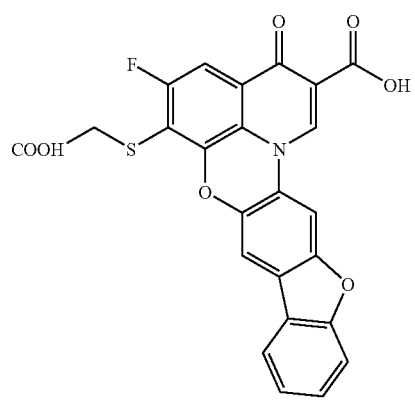
612
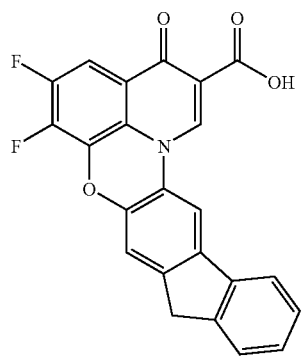
613
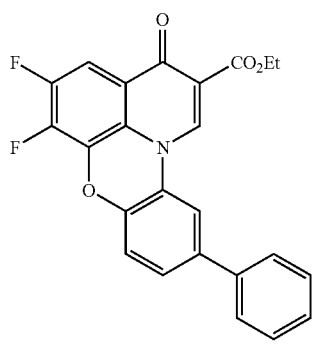

TABLE 3-continued
614
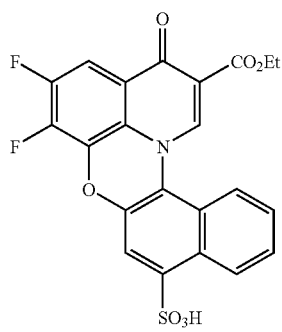
615
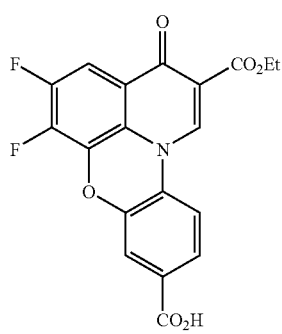
616
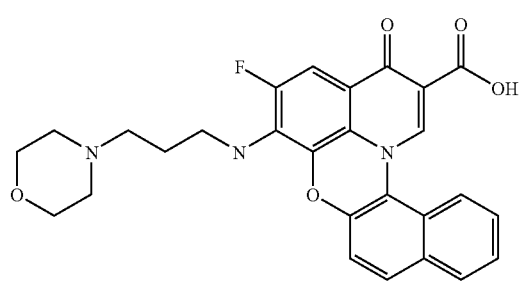
617
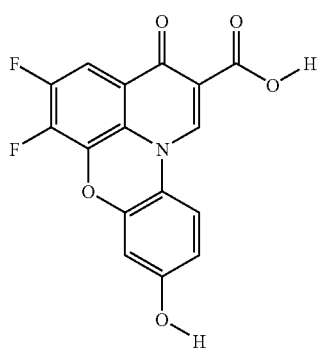
618
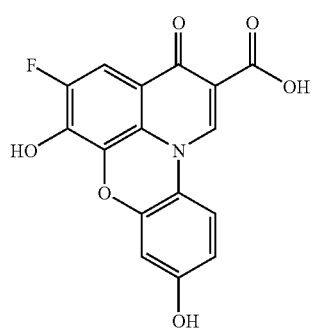

TABLE 3-continued
619
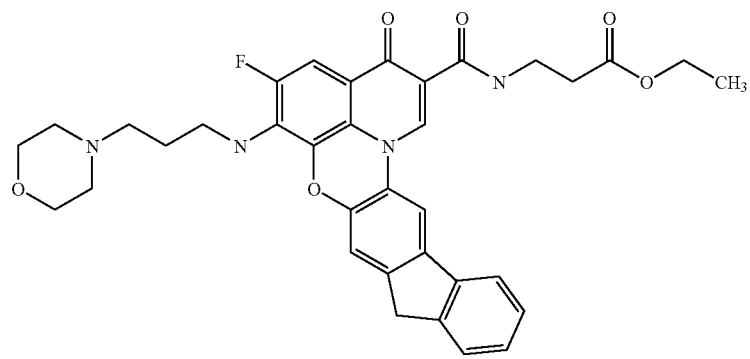
620
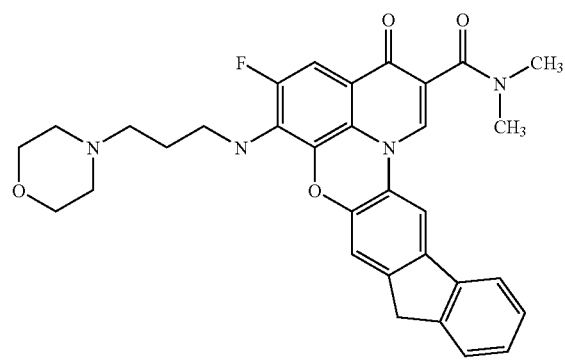
621
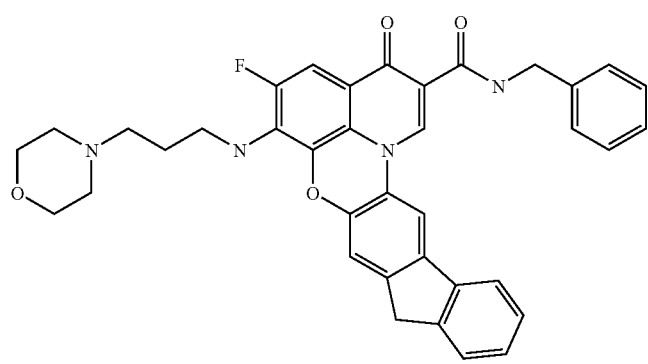
622
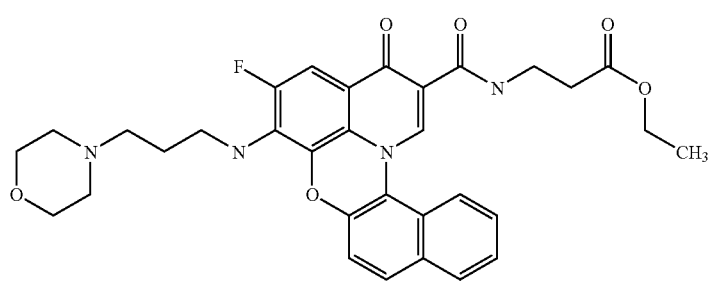

TABLE 3-continued
| 623 | 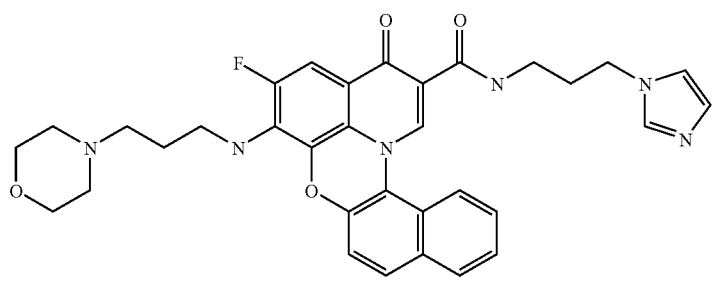 |
| --- | --- |
| 624 | 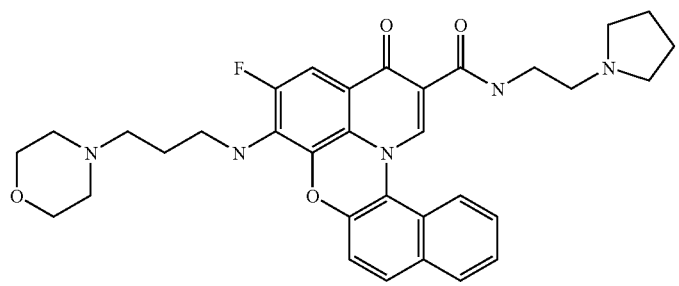 |
| 625 | 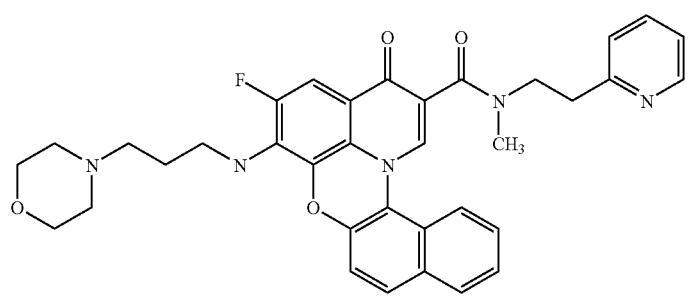 |
| 626 | 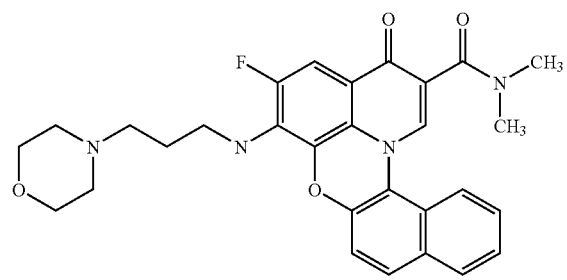 |
| 627 | 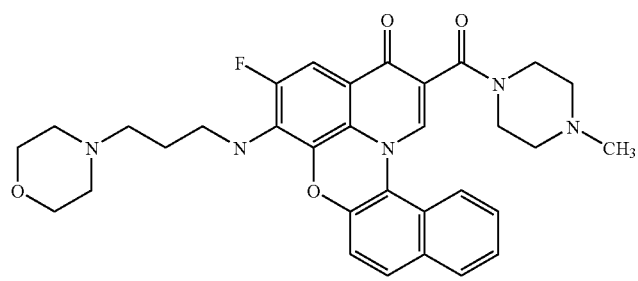 |

TABLE 3-continued
628 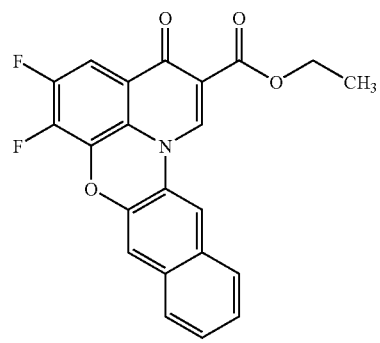
629 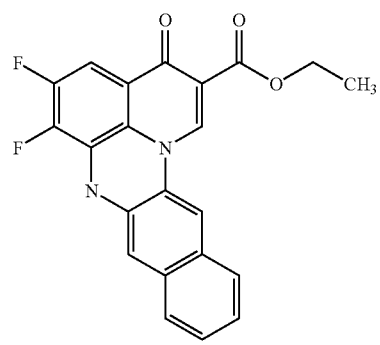
630 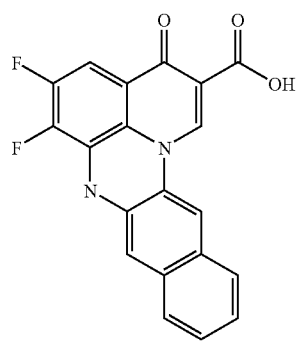
631 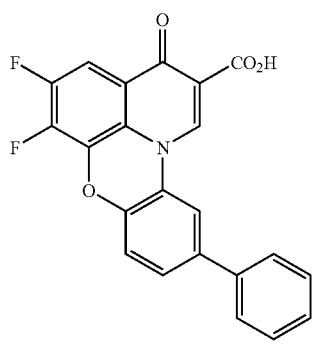

TABLE 3-continued
632
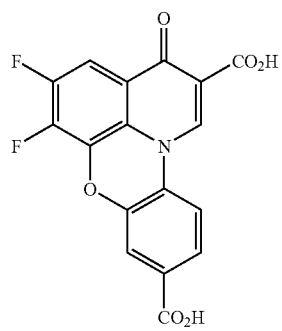
633
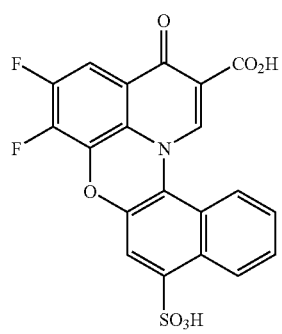
634
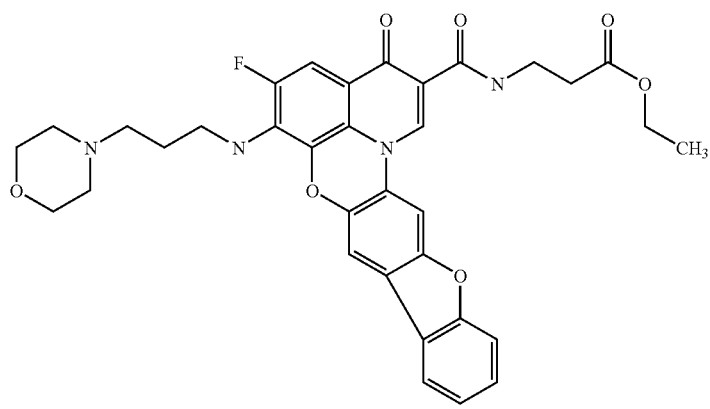
635
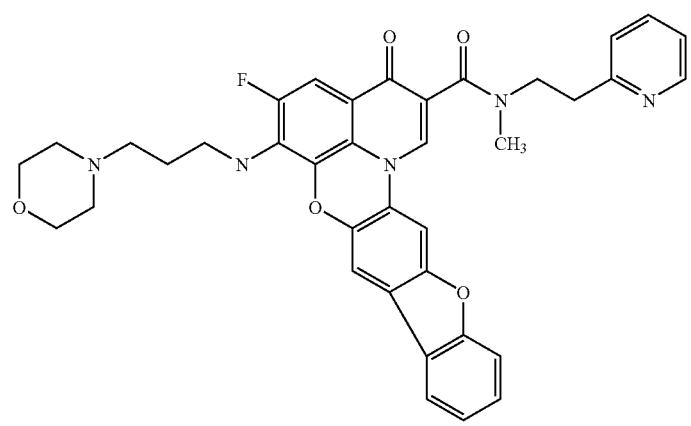

TABLE 3-continued
| 636 | 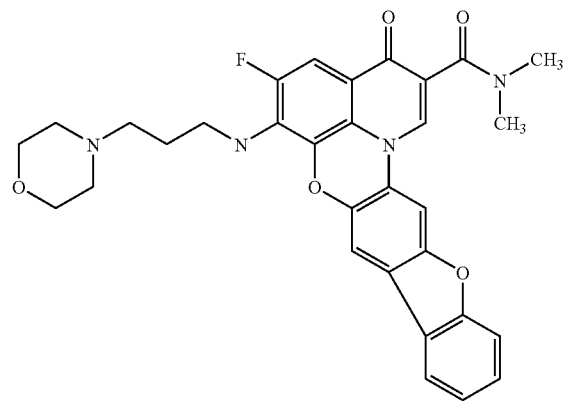 |
| --- | --- |
| 637 | 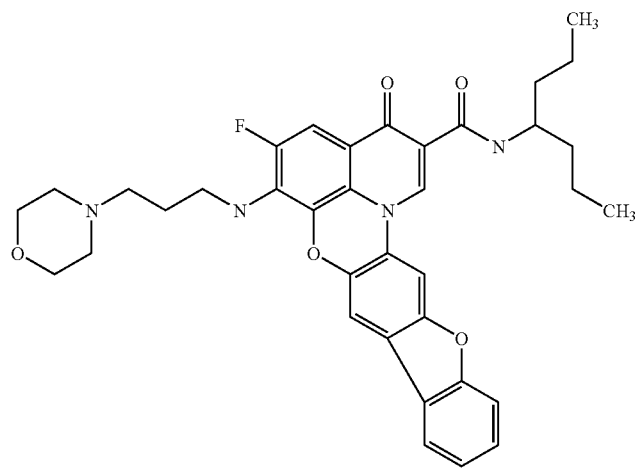 |
| 638 | 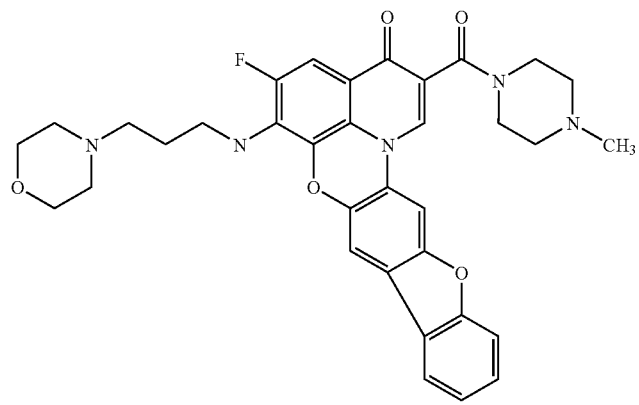 |

TABLE 3-continued
639
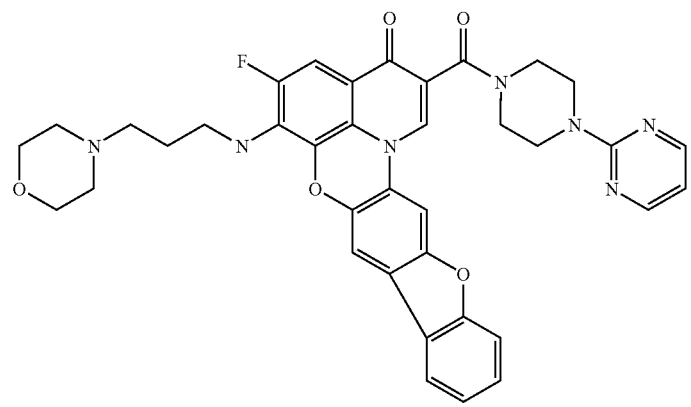
640
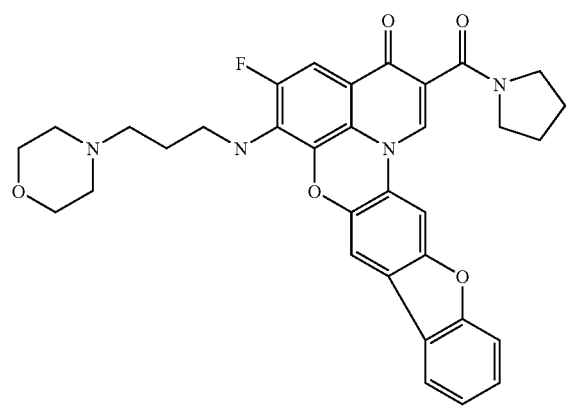
641
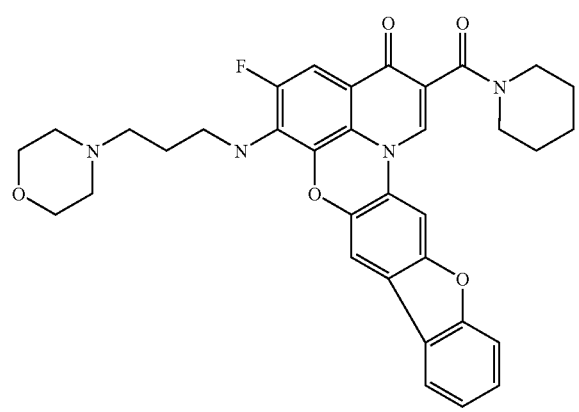
642
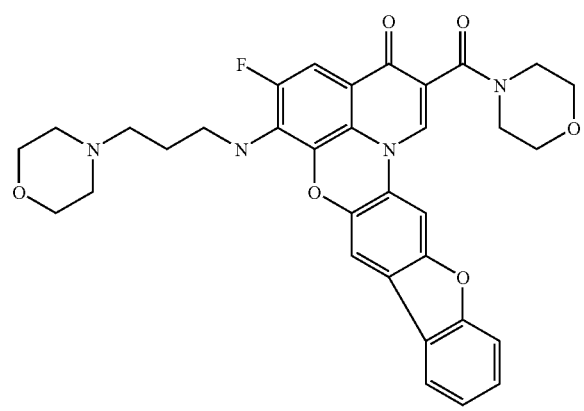

TABLE 3-continued
643
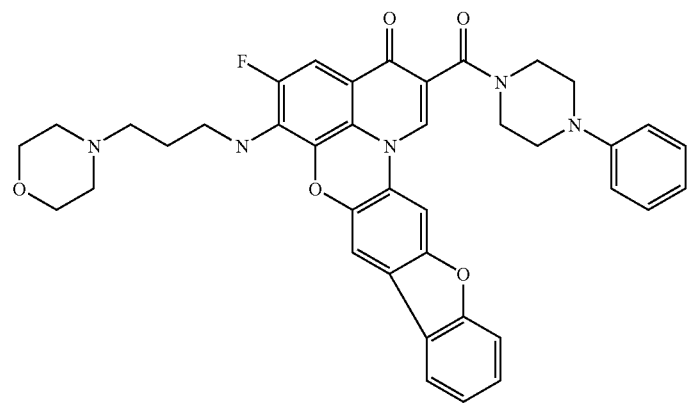
644
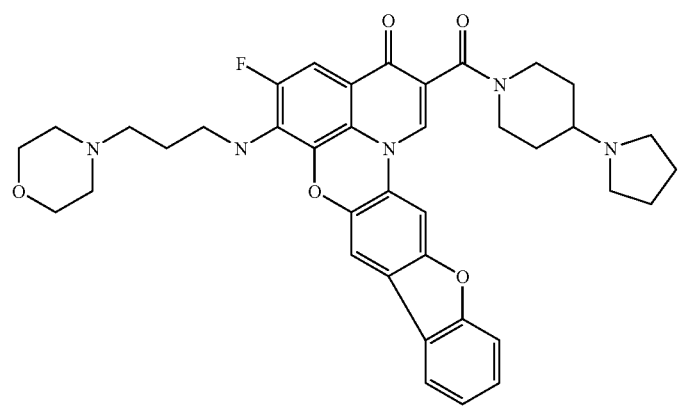
645
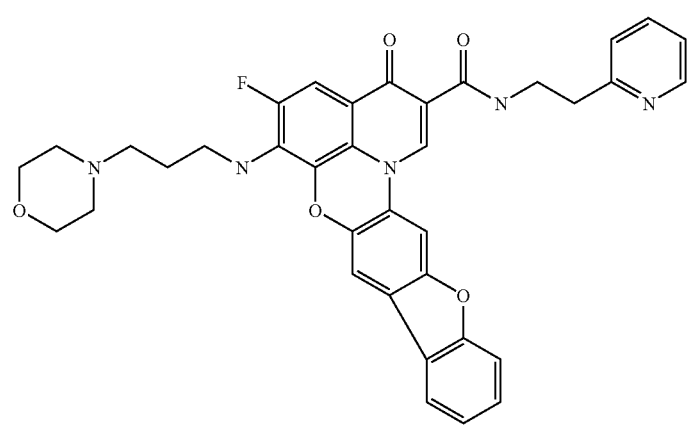
646
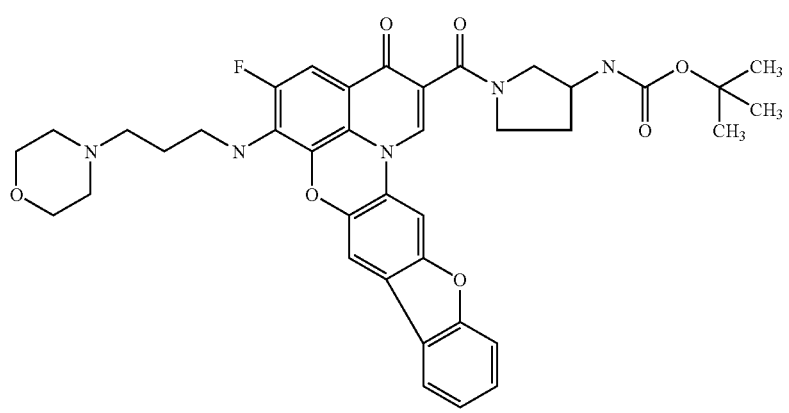

TABLE 3-continued
647 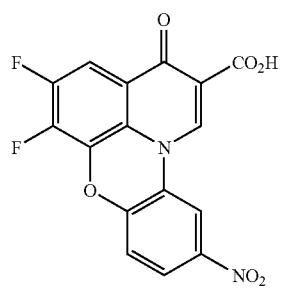
648 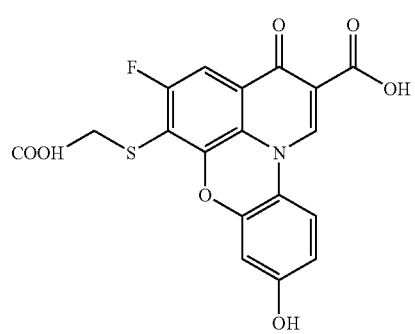
649 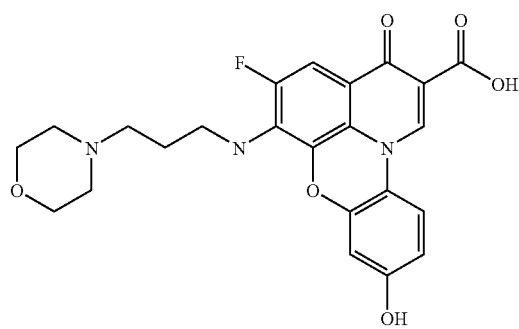
650 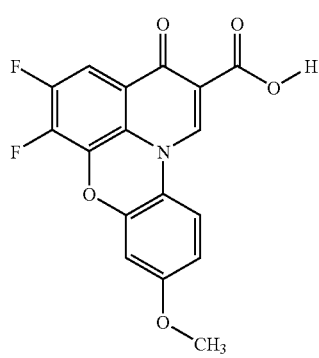
651 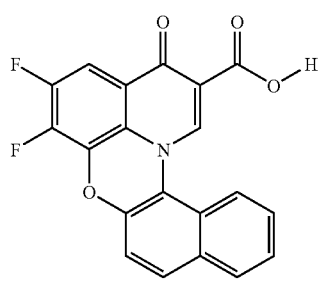

TABLE 3-continued
652
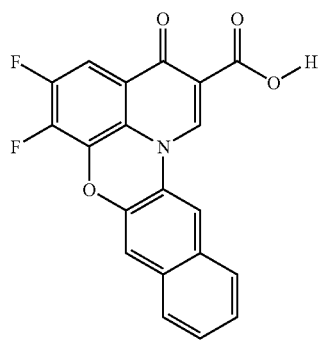
653
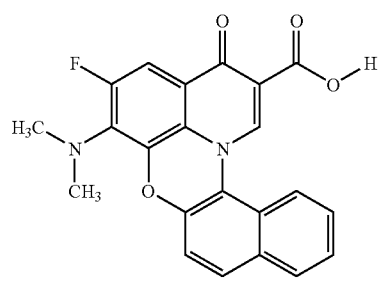
654
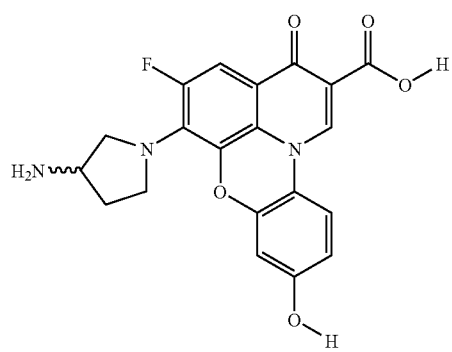
655
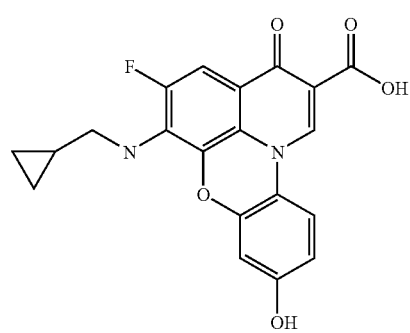
656
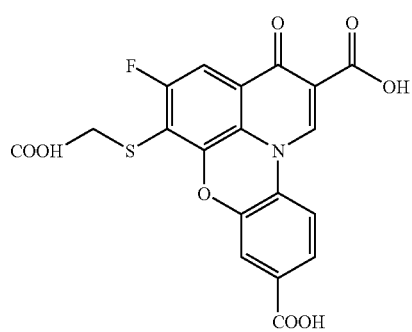

TABLE 3-continued
657 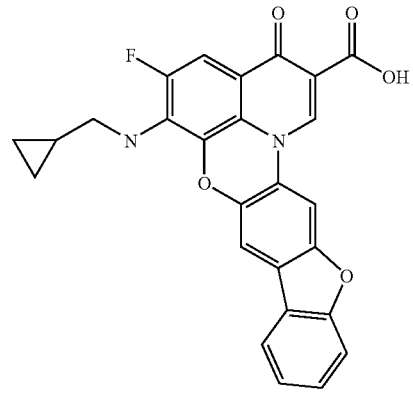
658 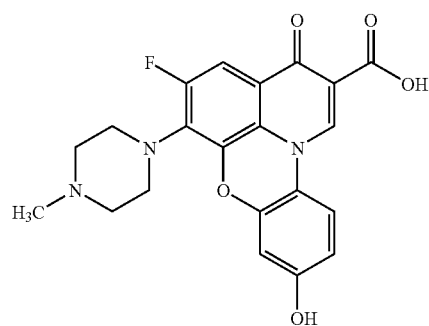
659 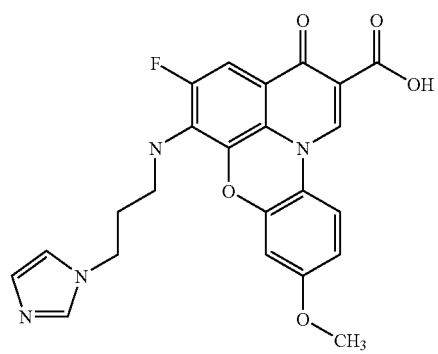
660 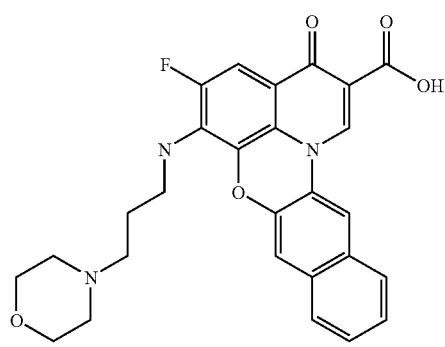

TABLE 3-continued
661
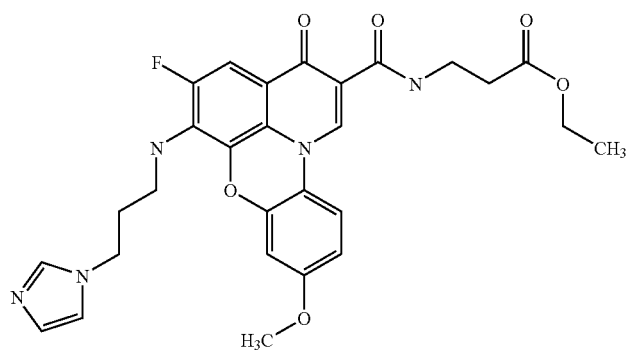
662
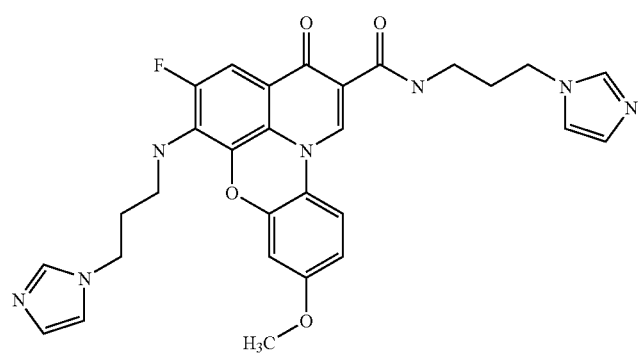
663
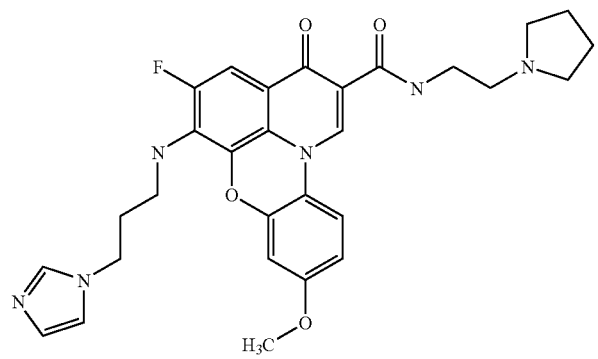
664
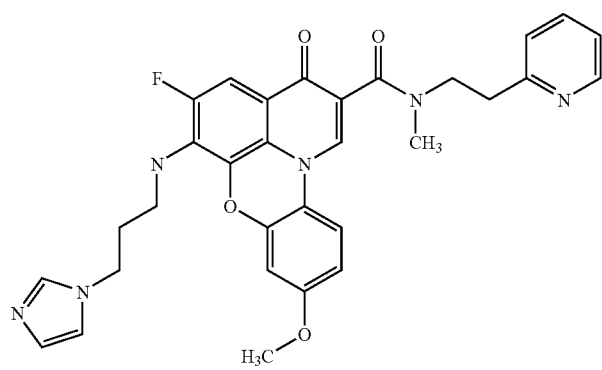

TABLE 3-continued
665
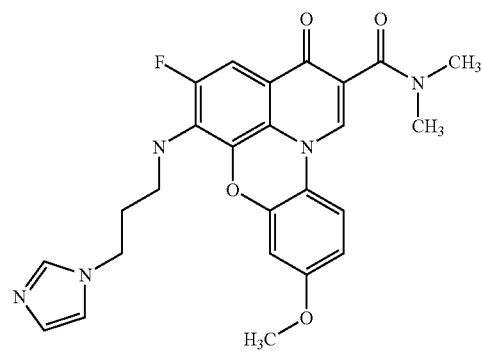
666
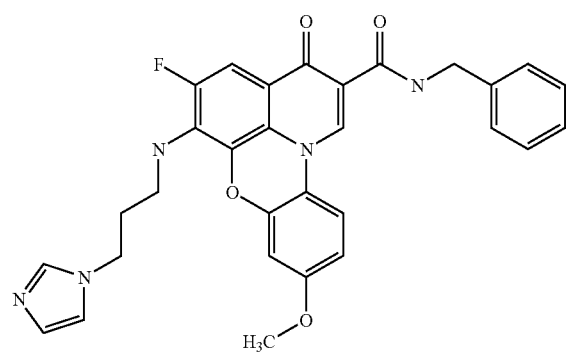
667
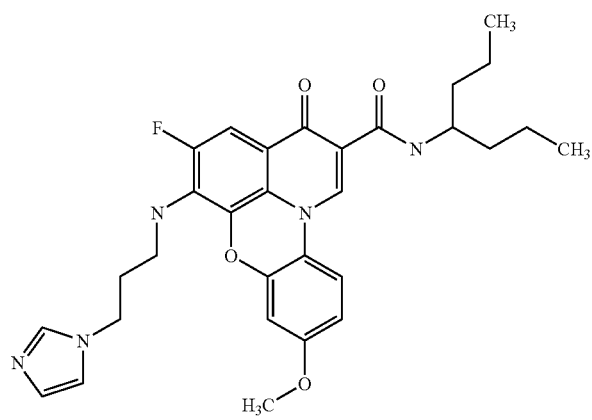
668
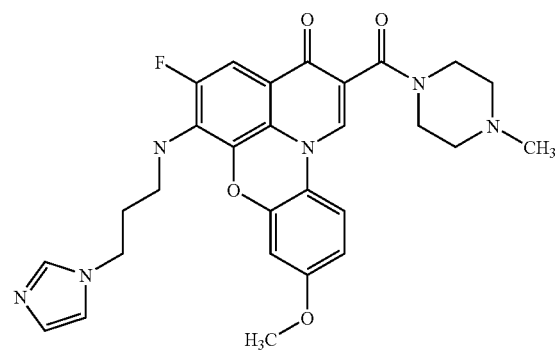

TABLE 3-continued
669 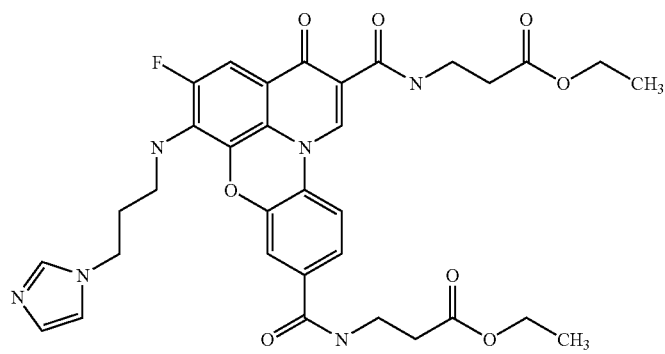
670 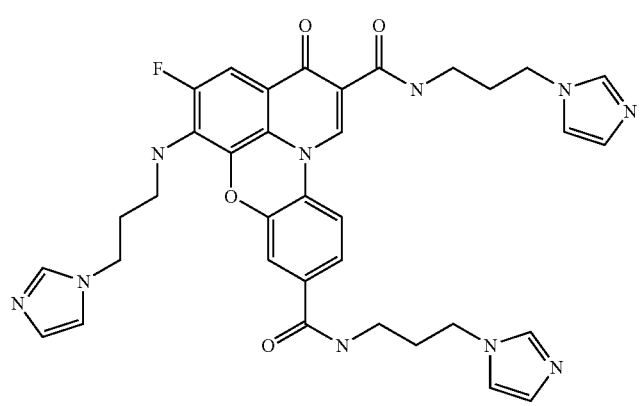
671 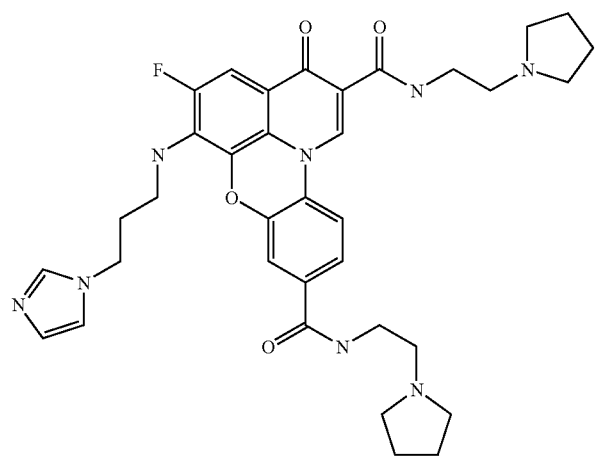
672 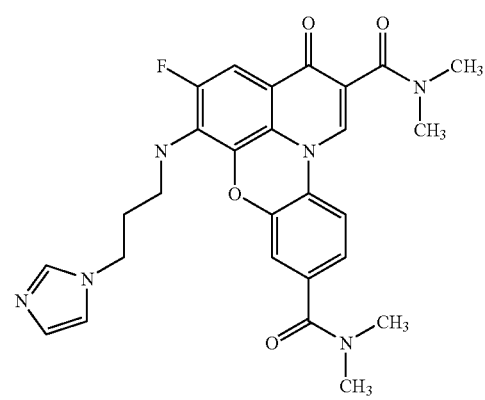

TABLE 3-continued
| 673 | 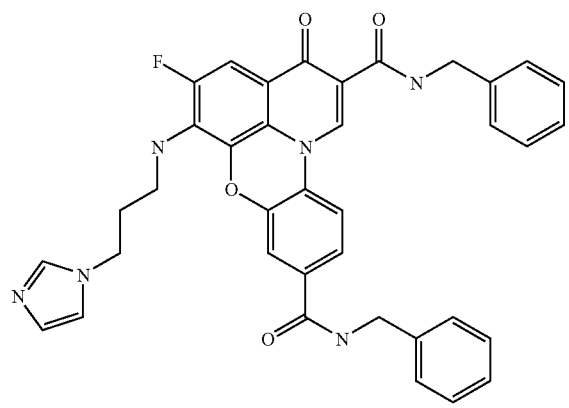 |
| 674 | 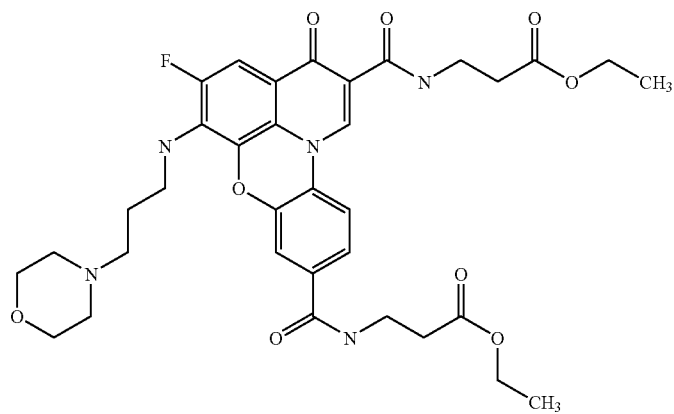 |
| 675 | 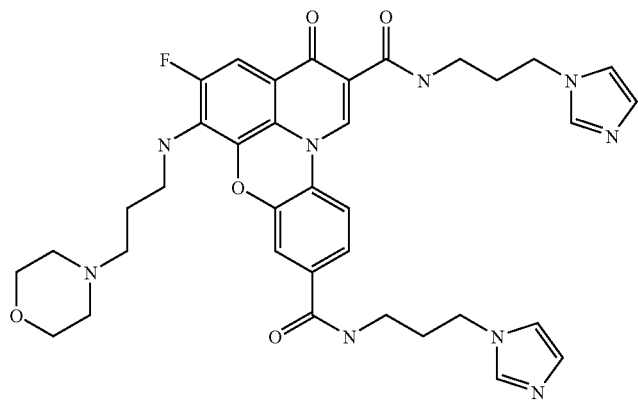 |
| 676 | 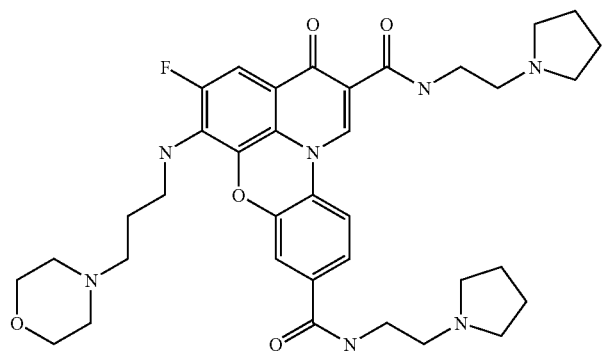 |

TABLE 3-continued
677 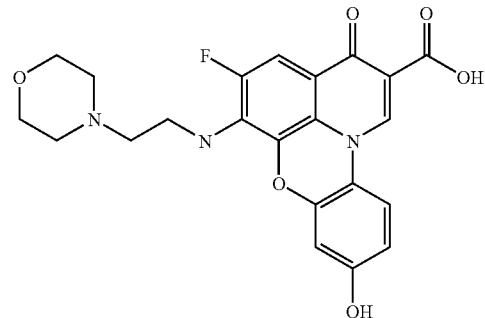
678 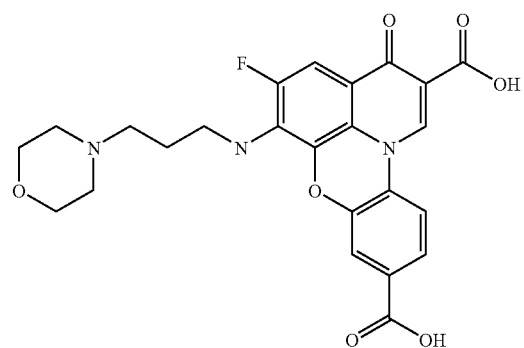
679 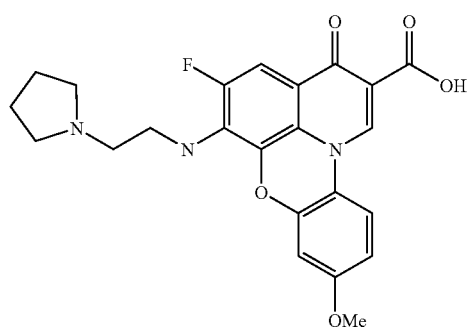
680 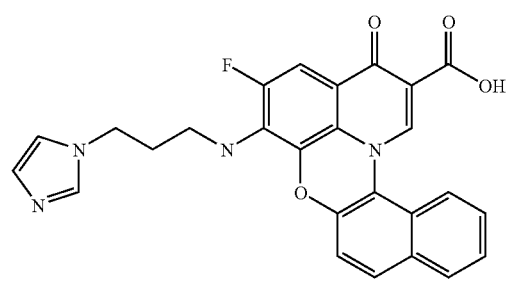
681 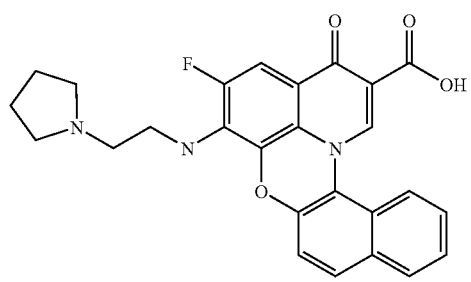

TABLE 3-continued
682
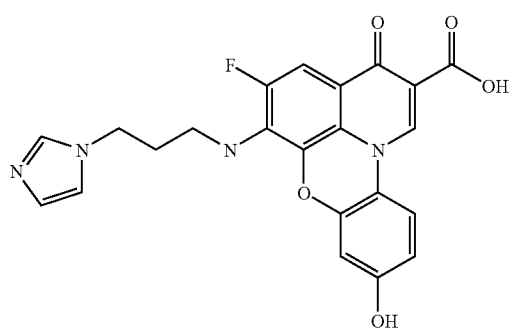
683
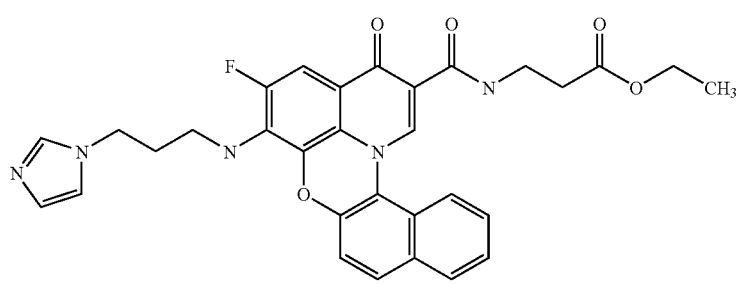
684
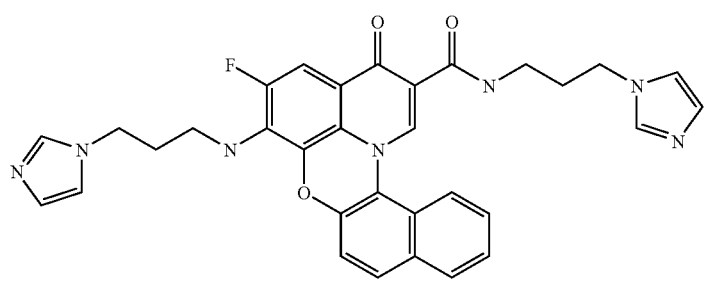
685
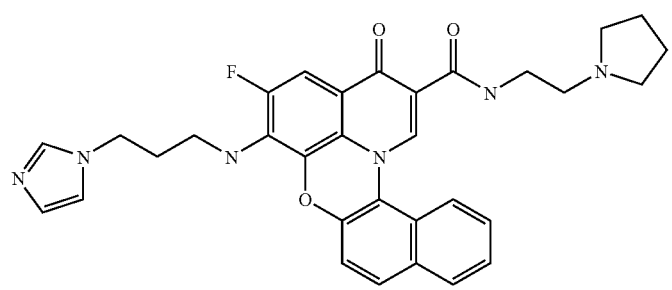
686
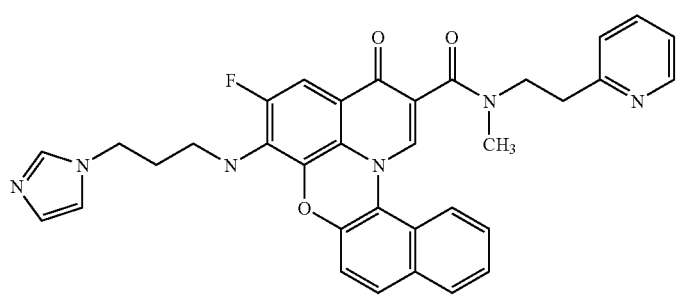

TABLE 3-continued
| 687 | 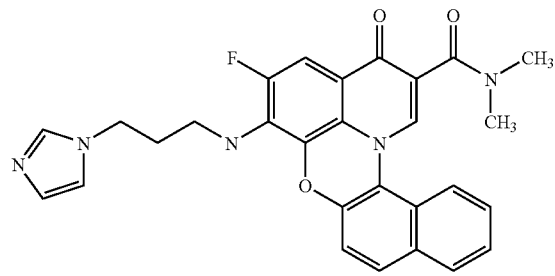 |
| --- | --- |
| 688 | 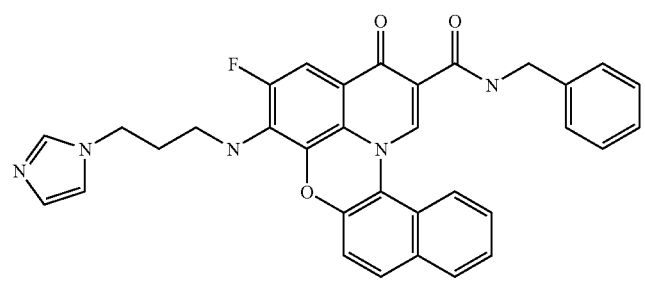 |
| 689 | 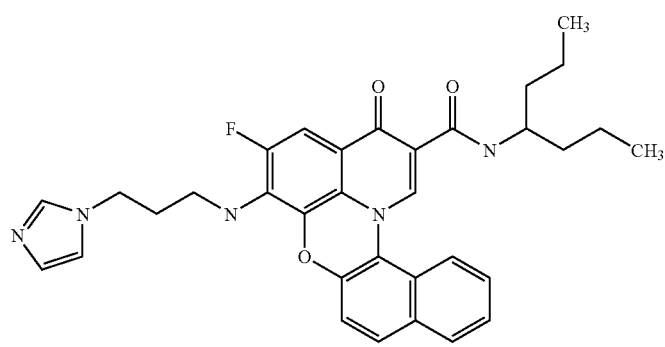 |
| 690 | 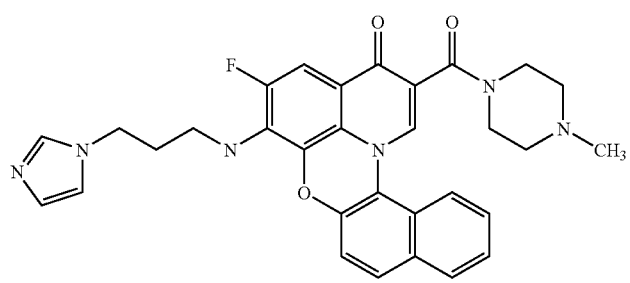 |
| 691 | 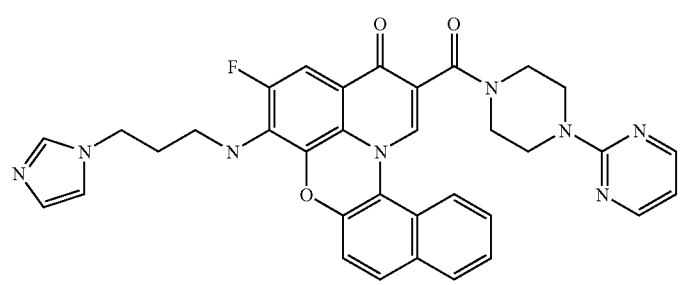 |

TABLE 3-continued
692
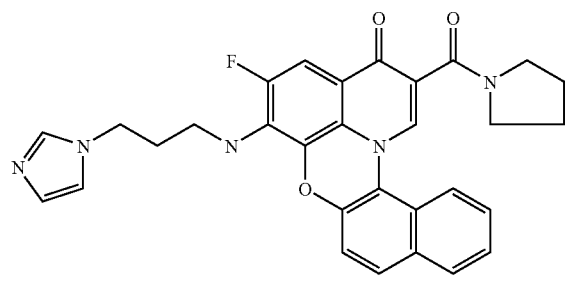
693
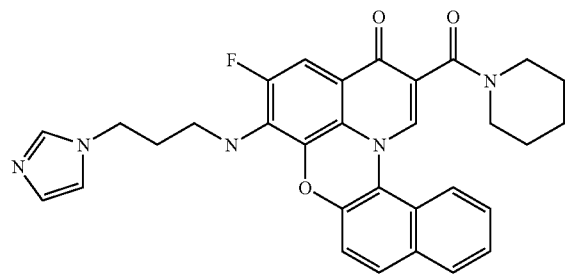
694
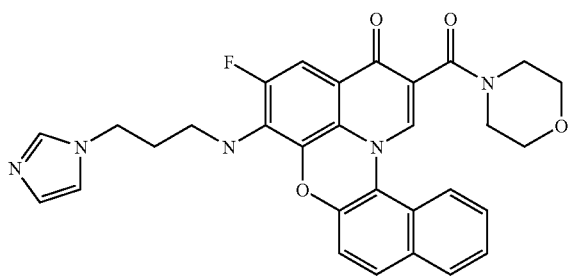
695
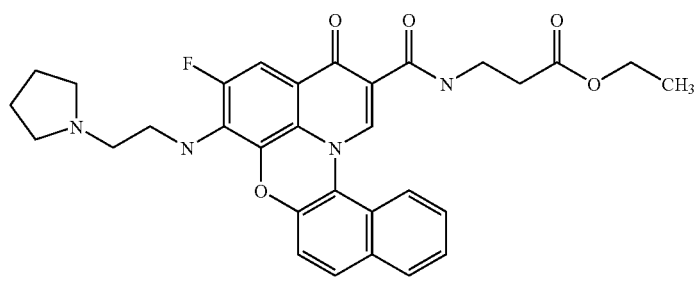
696
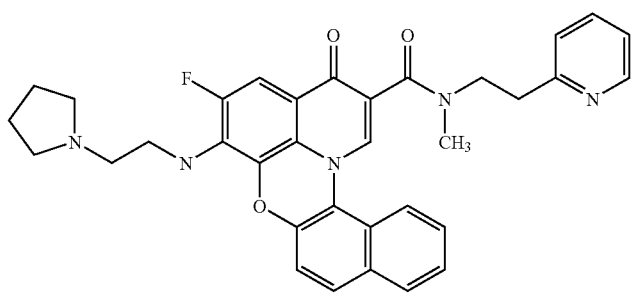

TABLE 3-continued
697 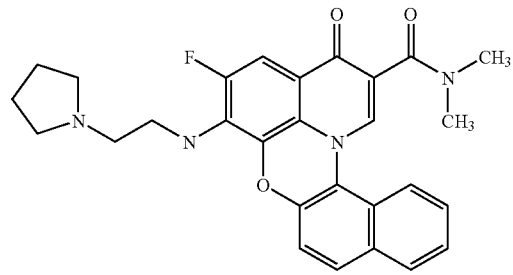
698 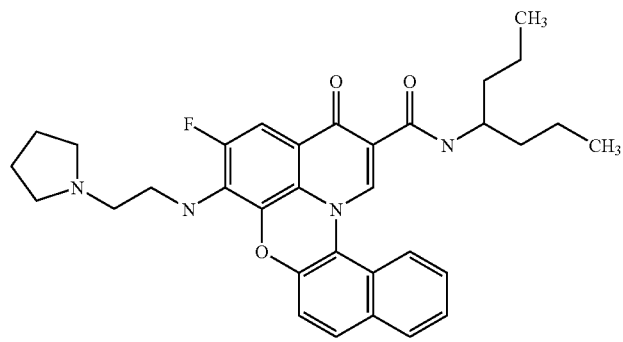
699 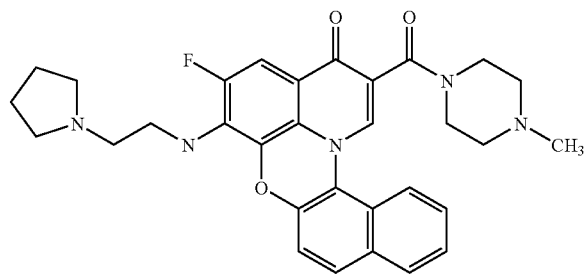
700 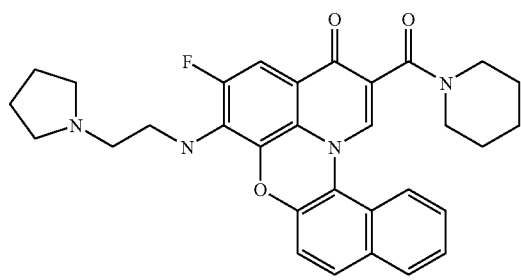
701 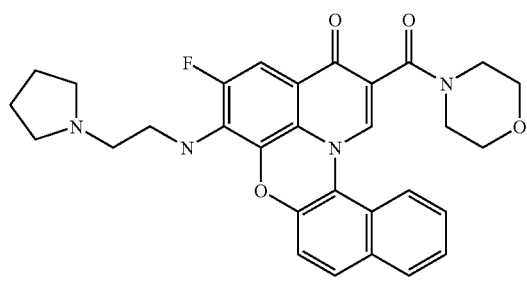

TABLE 3-continued
702 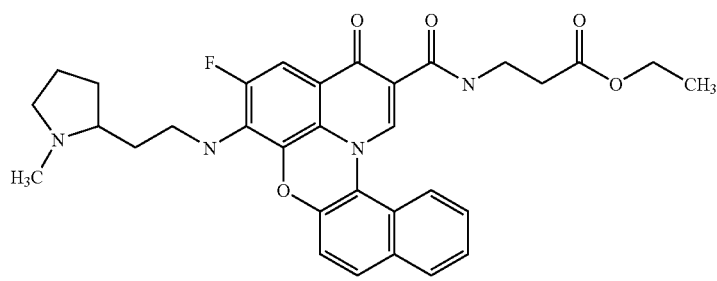
703 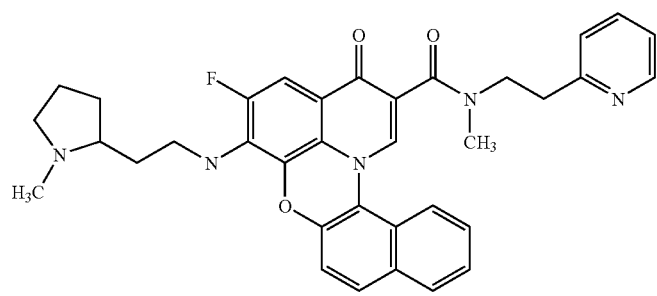
704 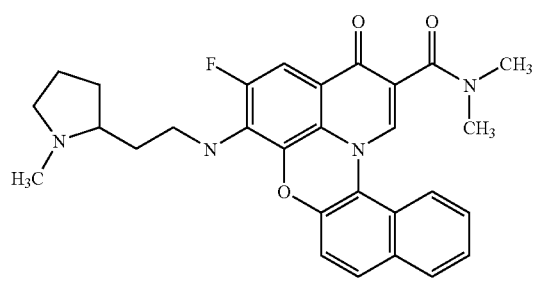
705 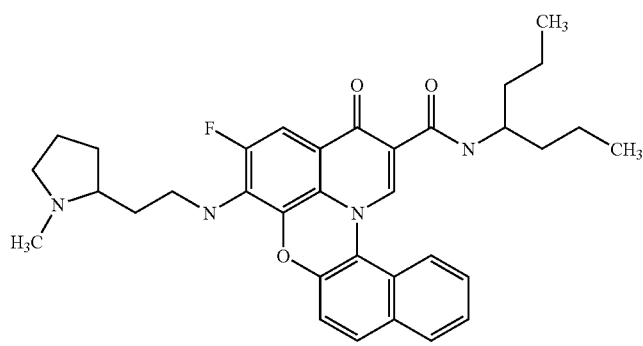
706 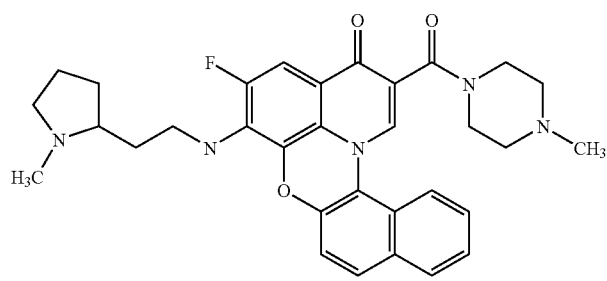

TABLE 3-continued
707 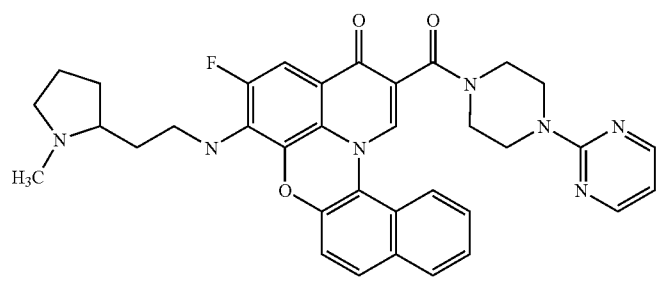
708 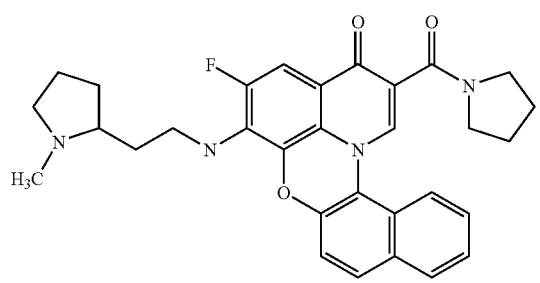
709 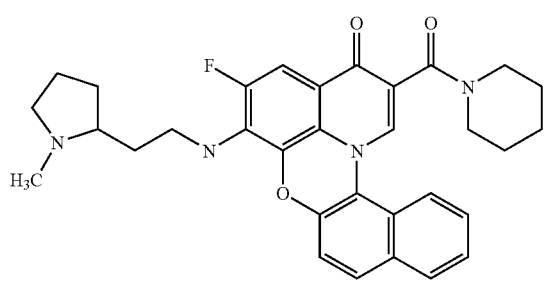
710 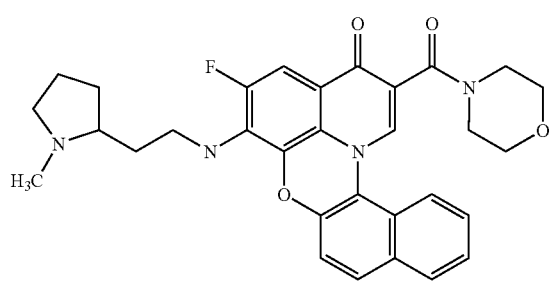
711 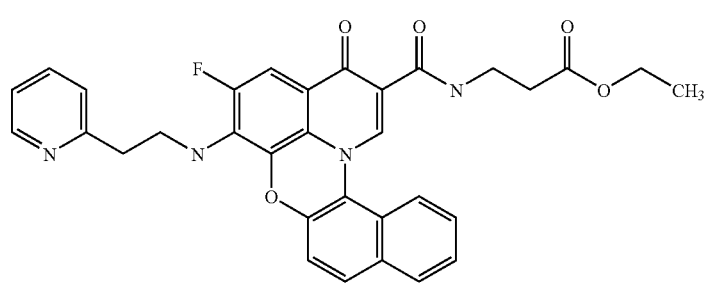

TABLE 3-continued
712 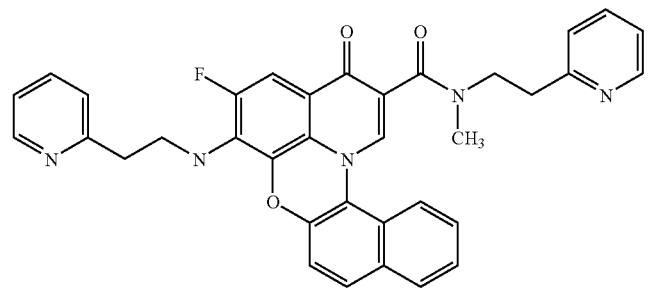
713 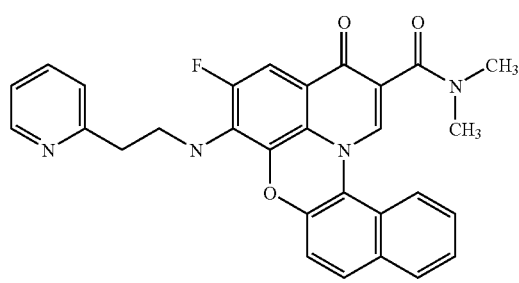
714 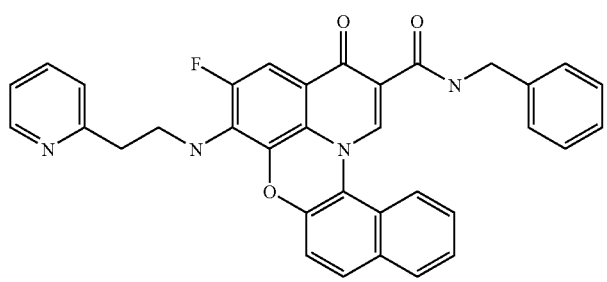
715 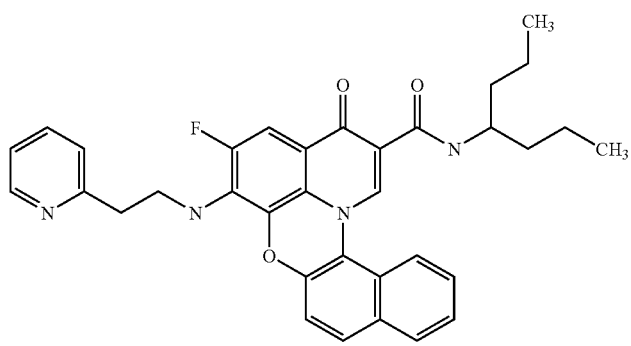
716 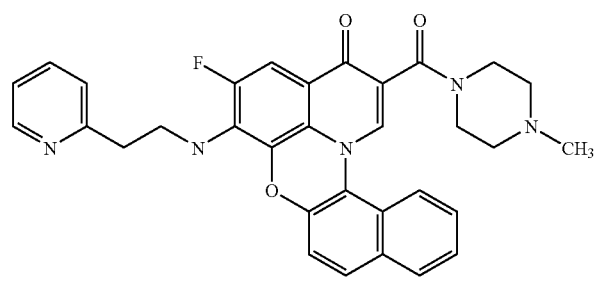

TABLE 3-continued
717
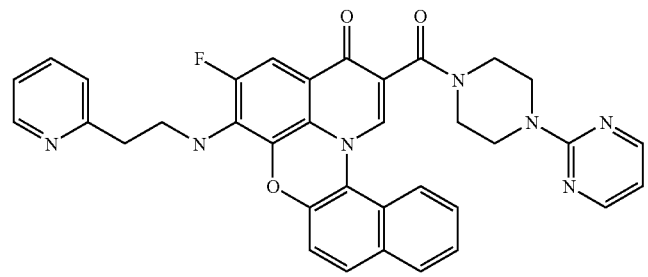
718
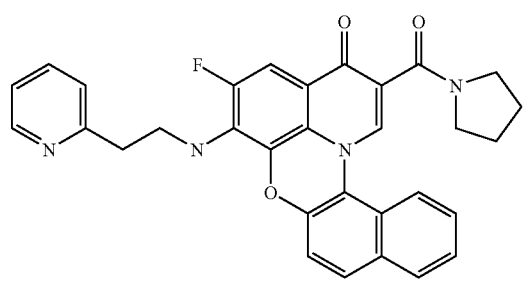
719
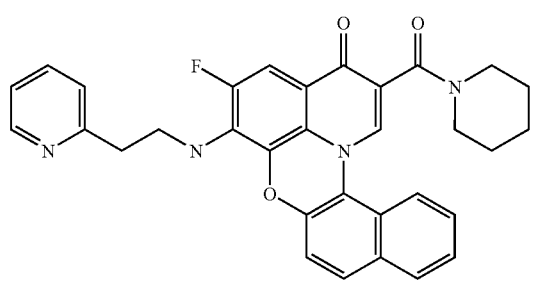
720
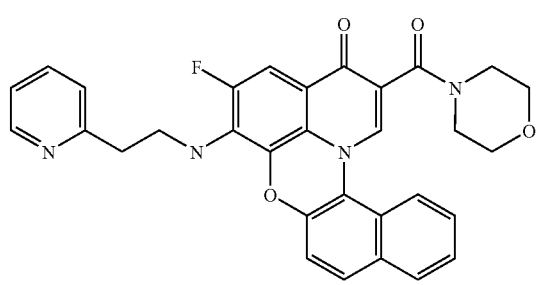
721
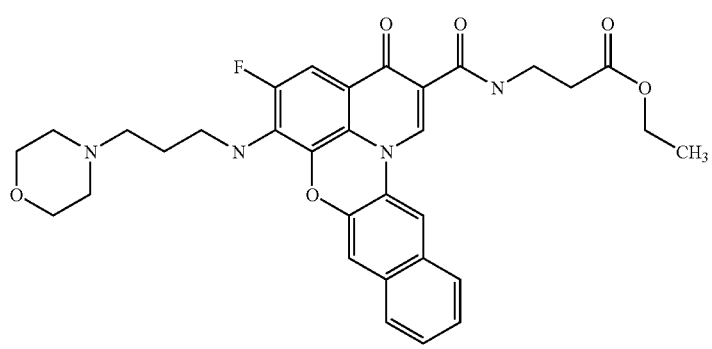

TABLE 3-continued
722
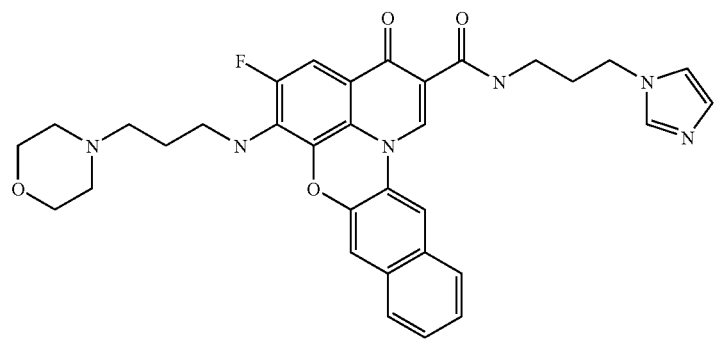
723
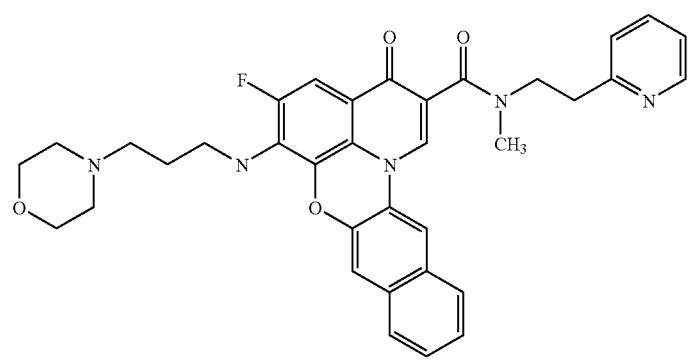
724
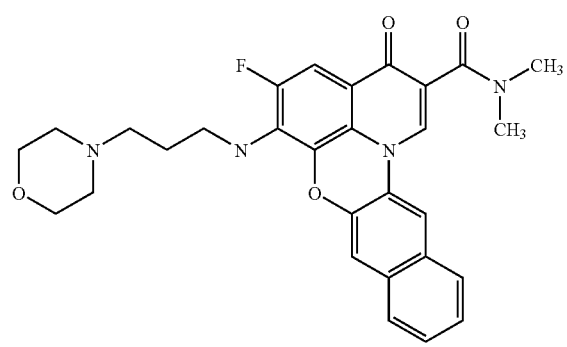
725
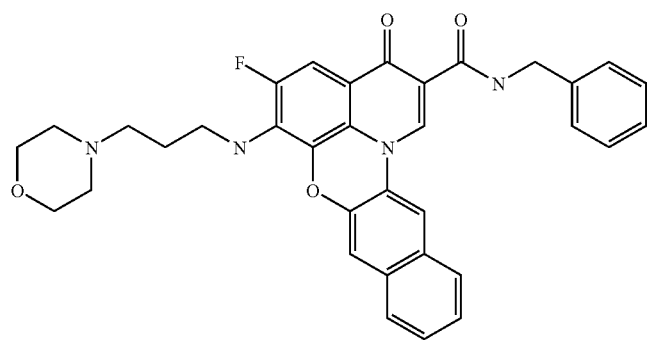

TABLE 3-continued
726
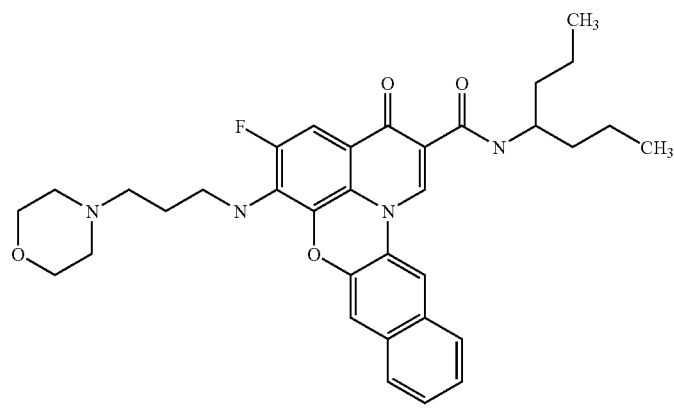
727
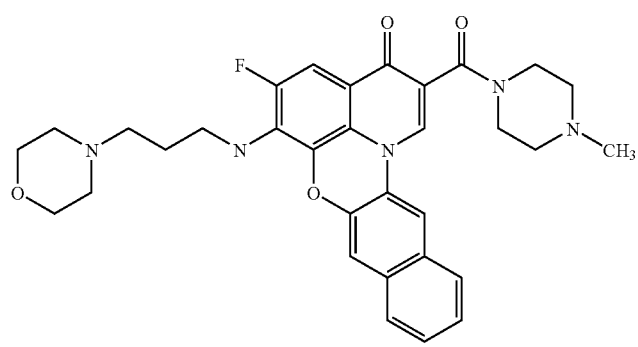
728
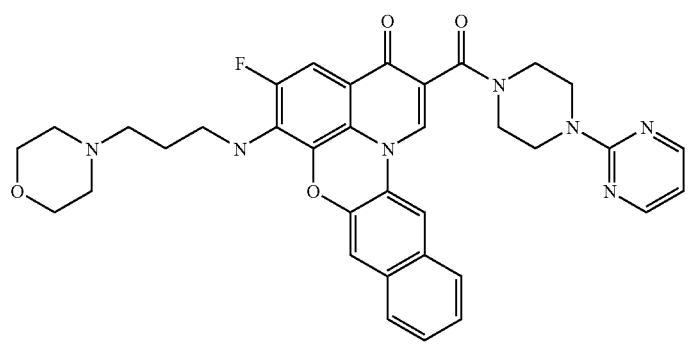
729
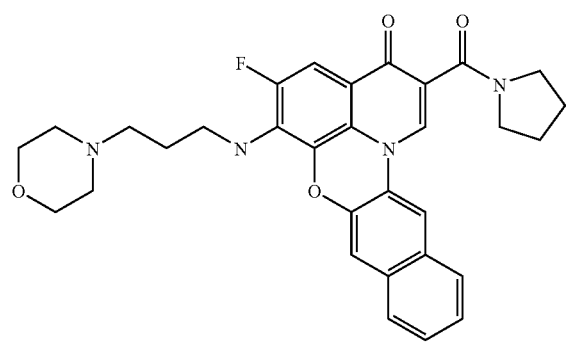

TABLE 3-continued
730
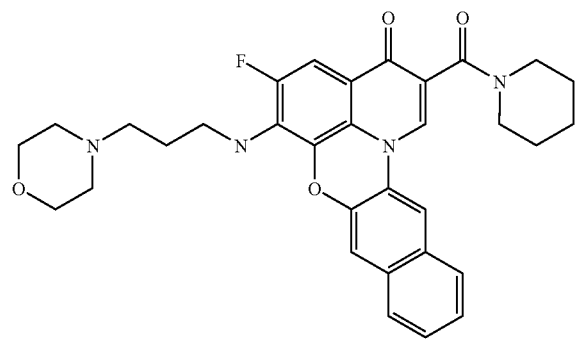
731
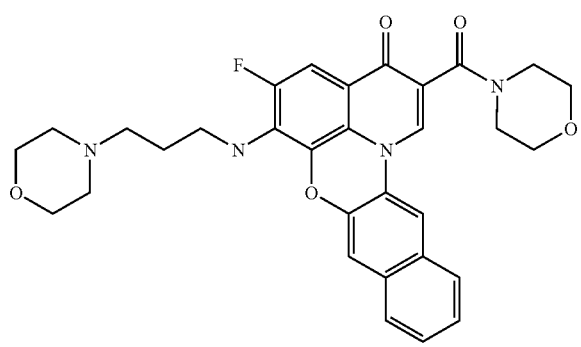
732
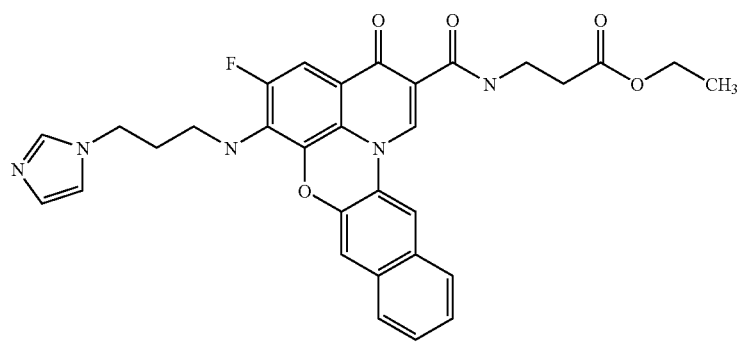
733
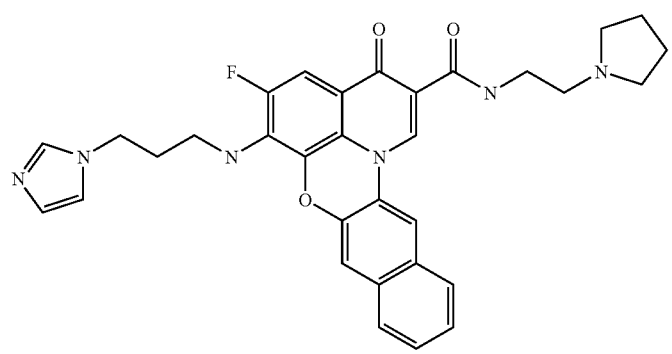

TABLE 3-continued
734 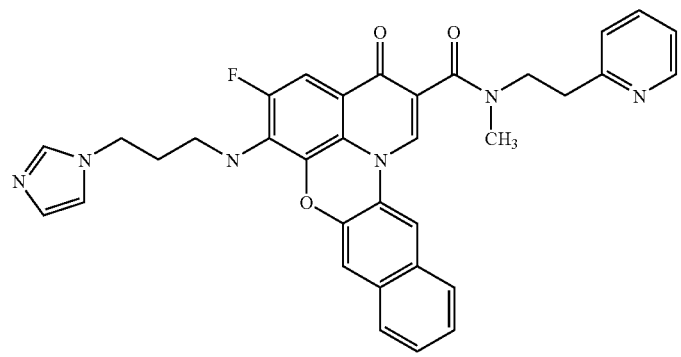
735 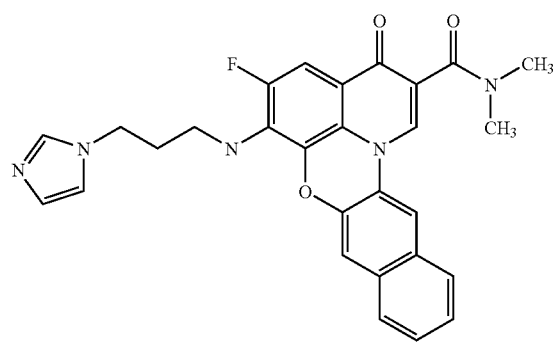
736 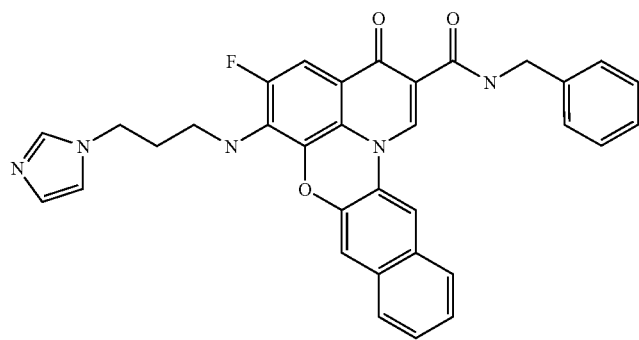
737 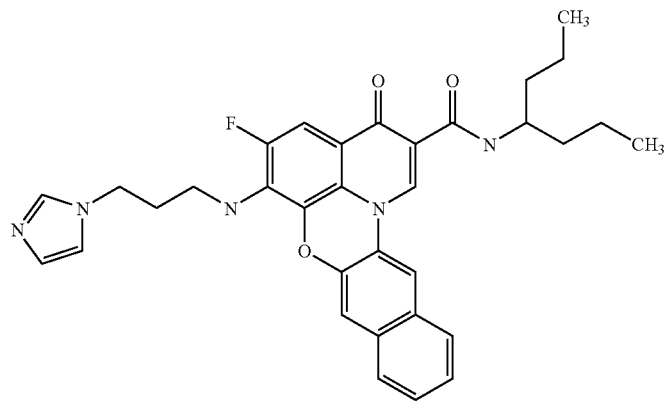

TABLE 3-continued
738
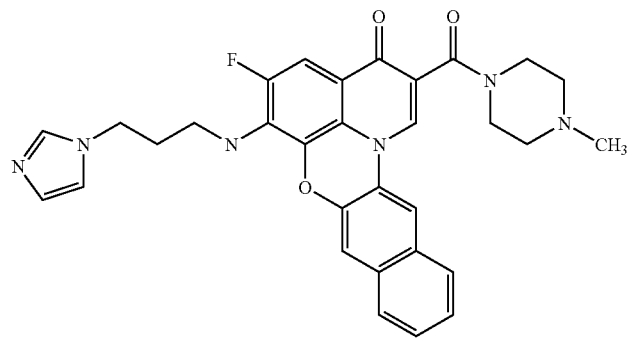
739
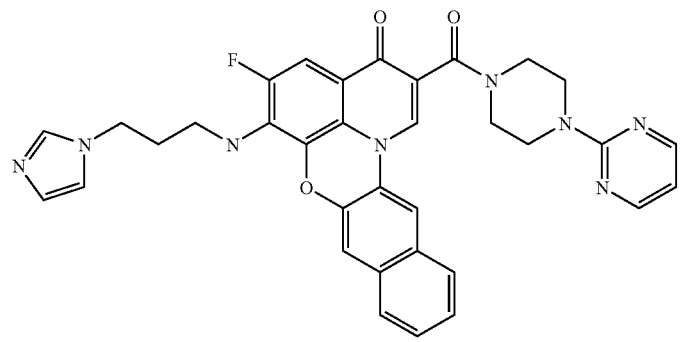
740
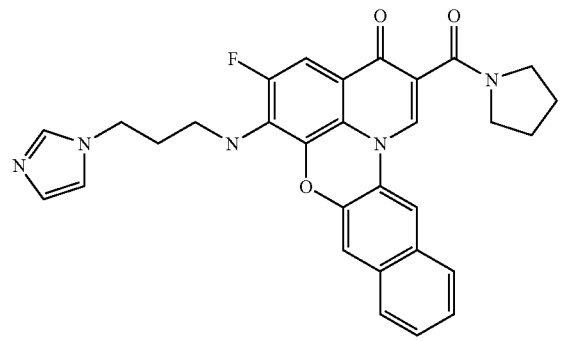
741
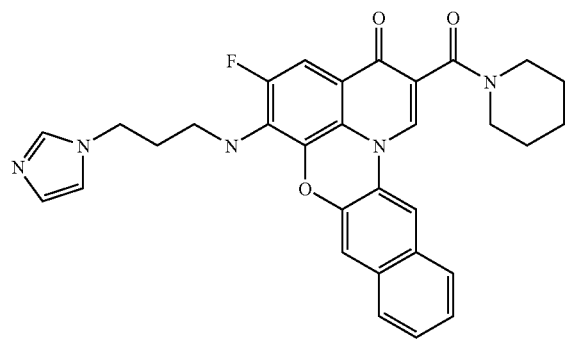

TABLE 3-continued
742
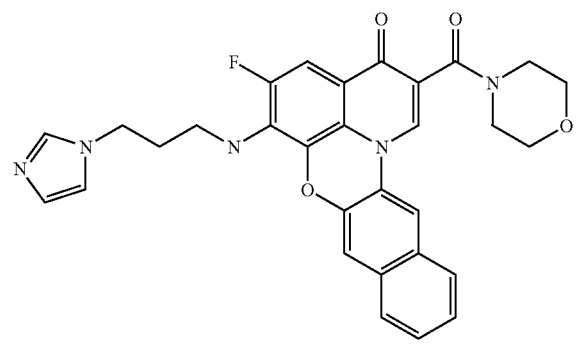
743
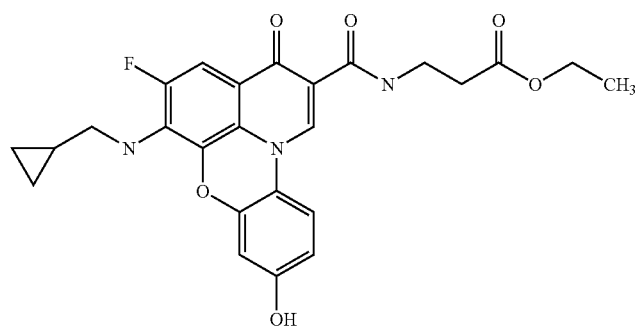
744
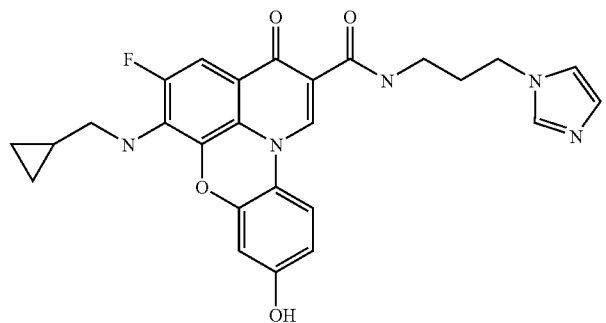
745
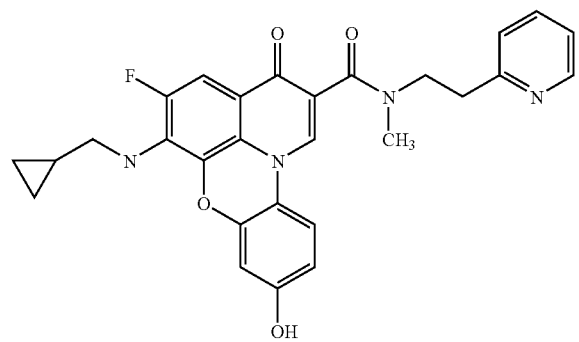

TABLE 3-continued
| 746 | 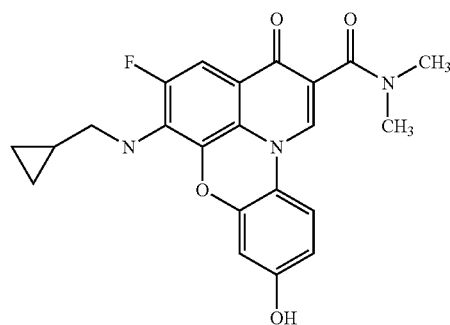 |
| 747 | 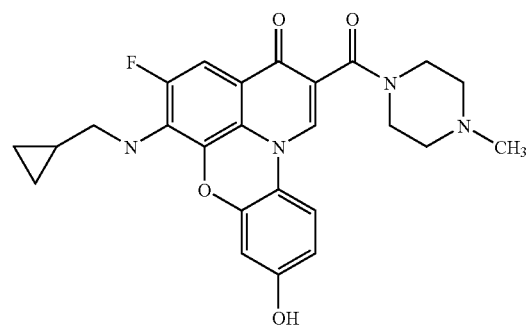 |
| 748 | 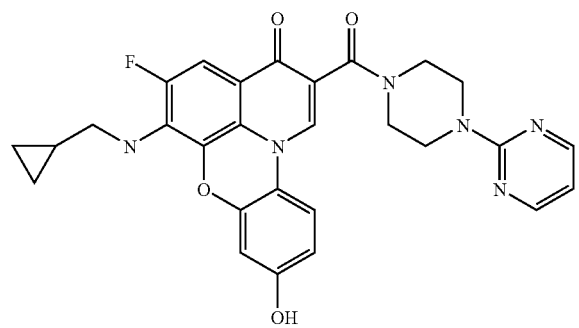 |
| 749 | 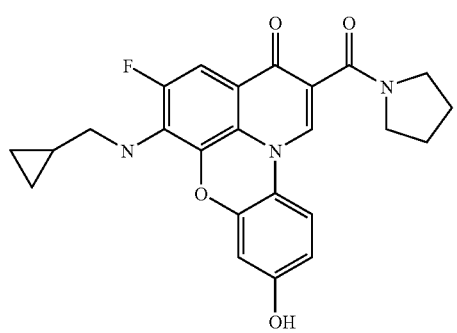 |

TABLE 3-continued
| 750 | 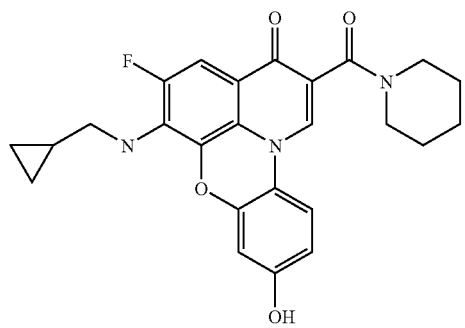 |
| 751 | 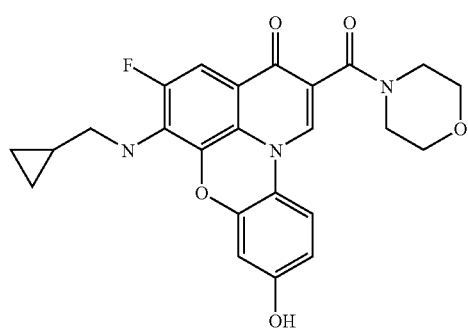 |
| 752 | 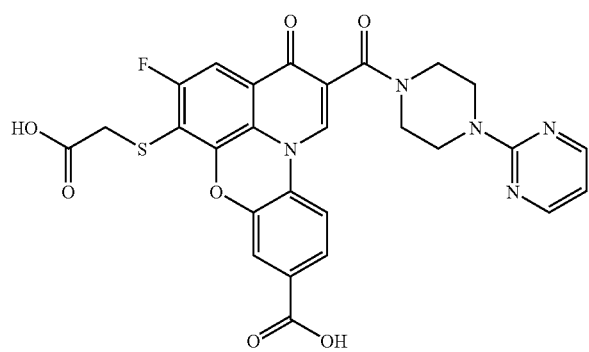 |
| 753 | 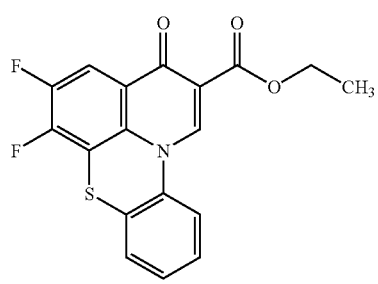 |
| 754 | 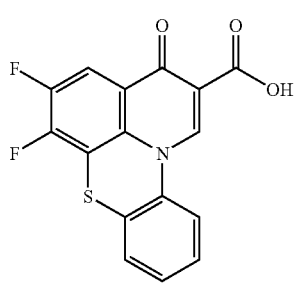 |

TABLE 3-continued
| 755 | 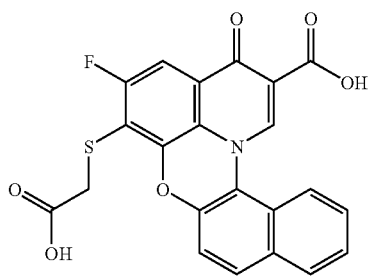 |
| --- | --- |
| 756 | 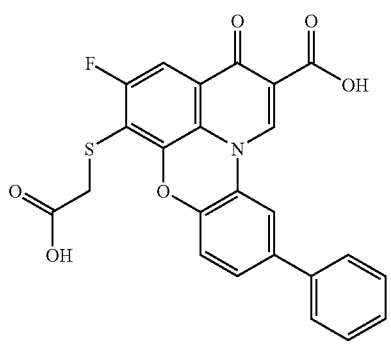 |
| 757 | 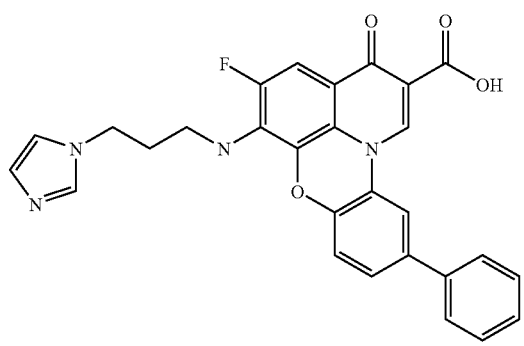 |
| 758 | 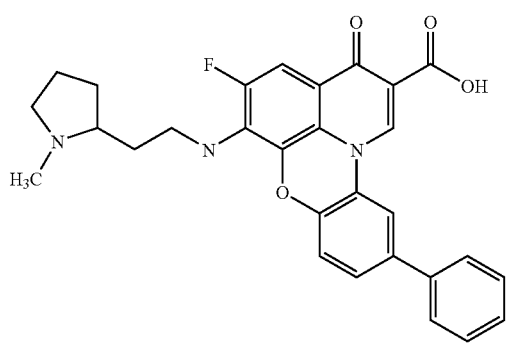 |
| 759 | 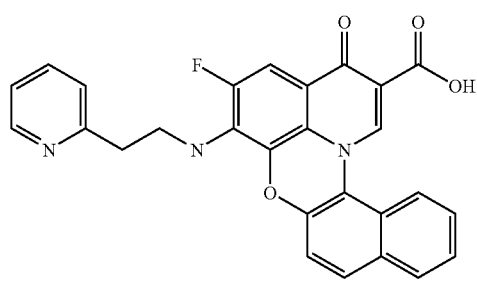 |

TABLE 3-continued
760 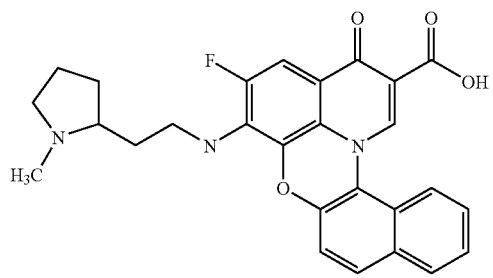
761 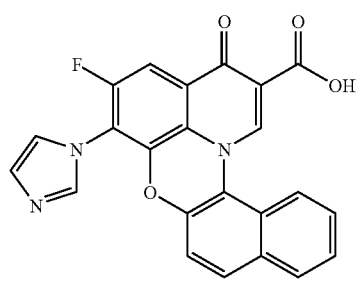
762 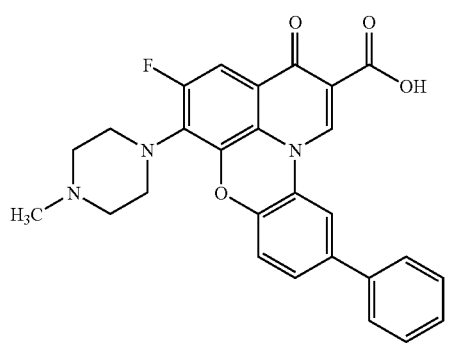
763 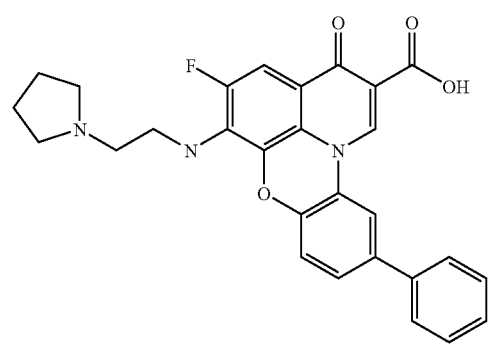
764 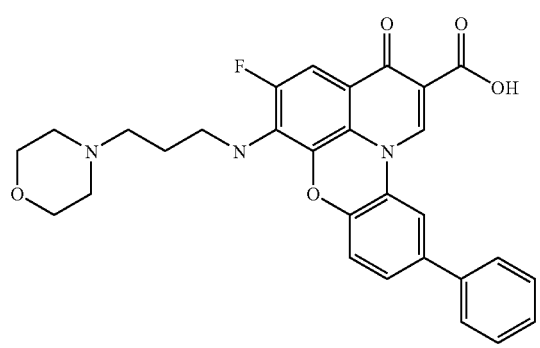

TABLE 3-continued
765
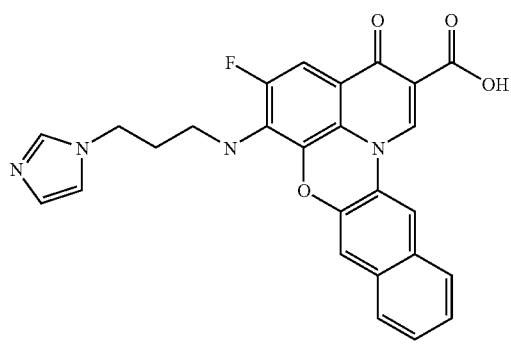
766
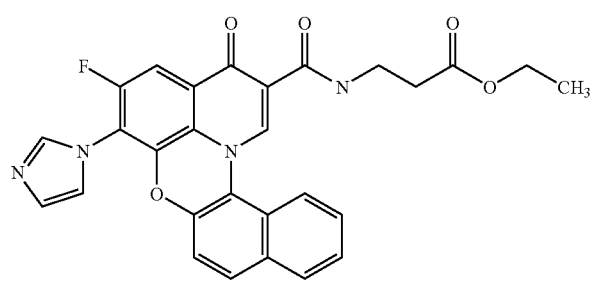
767
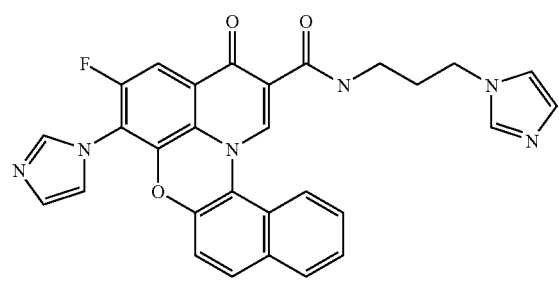
768
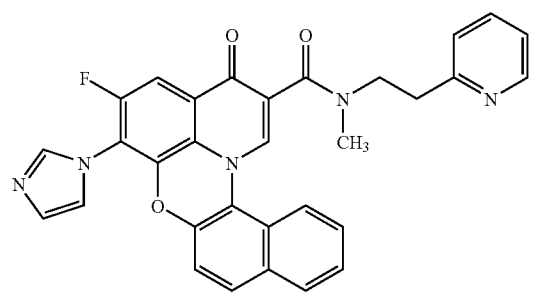
769
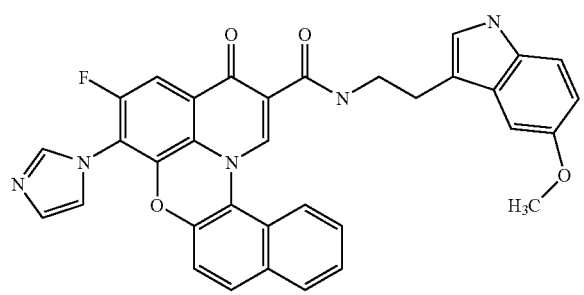

TABLE 3-continued
| 770 | 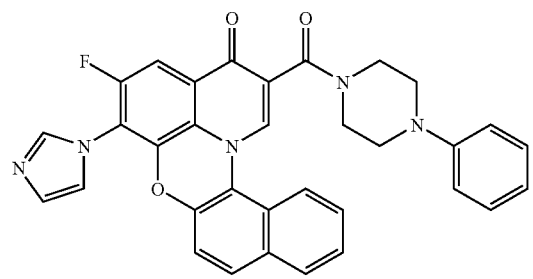 |
| --- | --- |
| 771 | 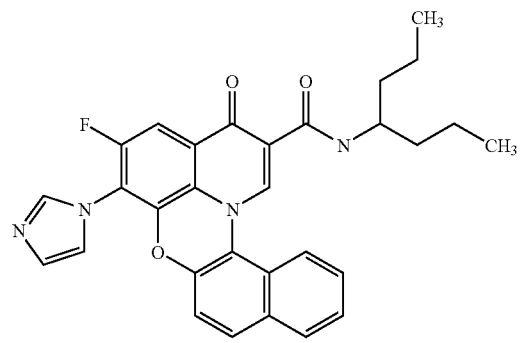 |
| 772 | 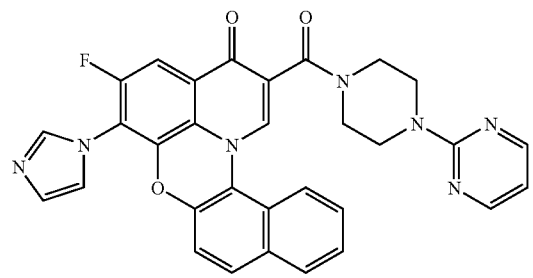 |
| 773 | 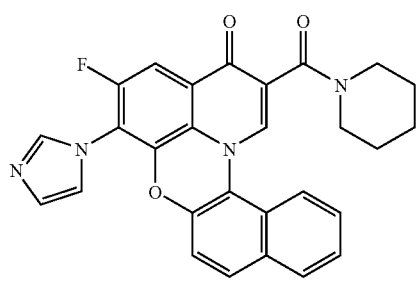 |
| 774 | 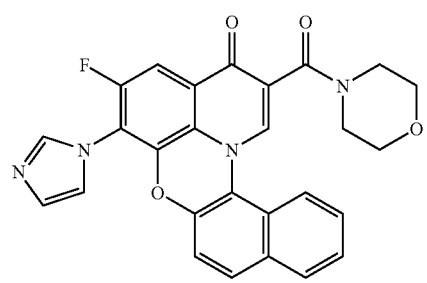 |

TABLE 3-continued
775
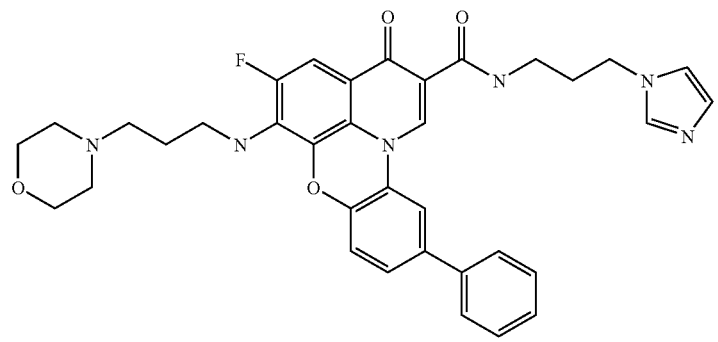
776
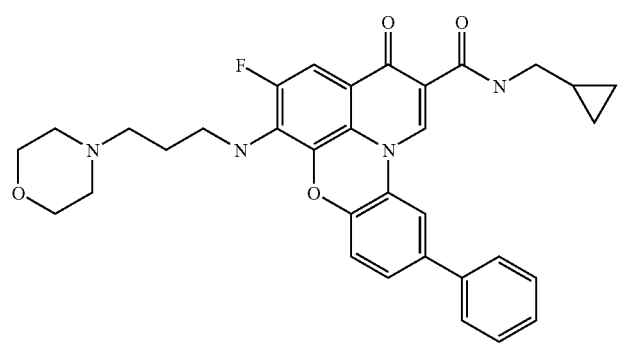
777
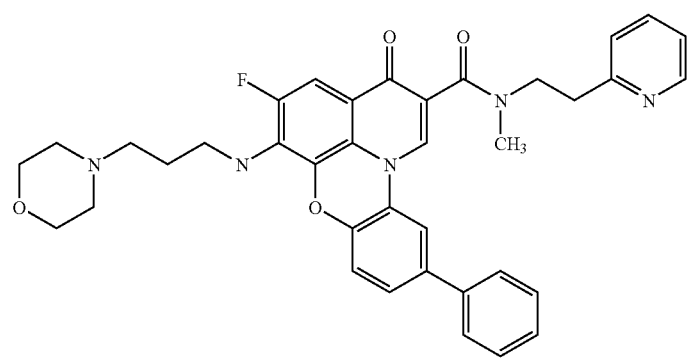
778
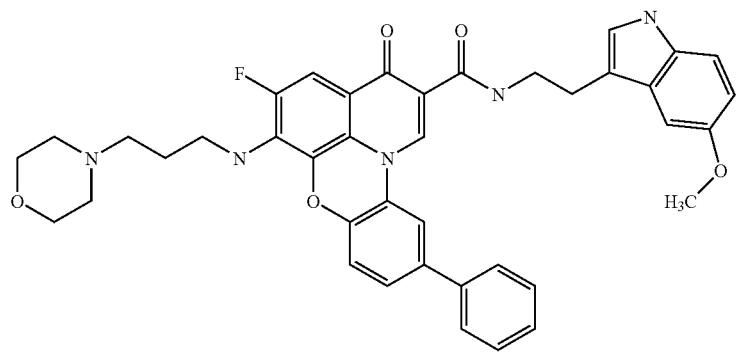

TABLE 3-continued
779
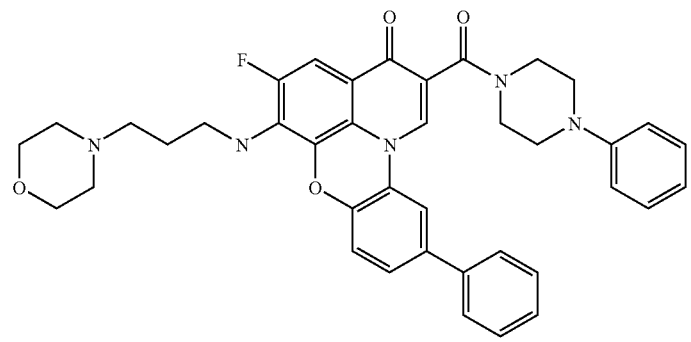
780
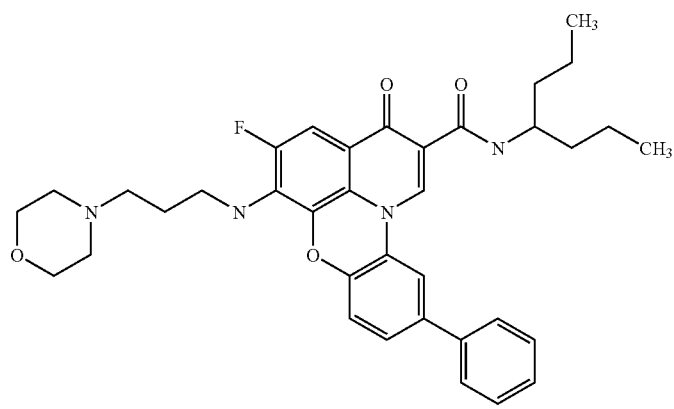
781
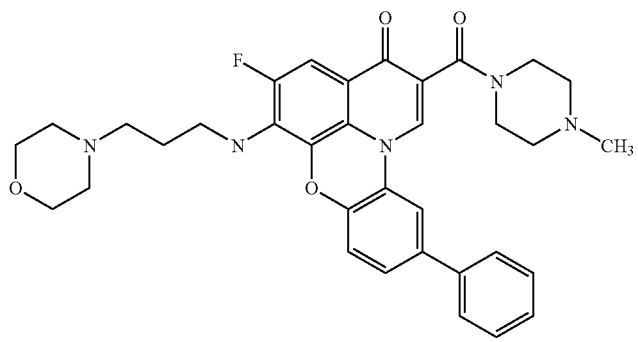
782
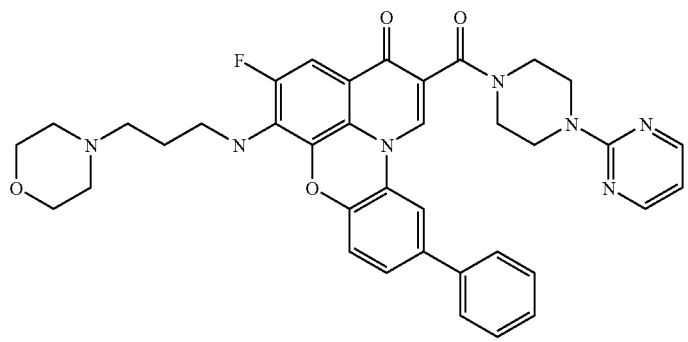

TABLE 3-continued
783
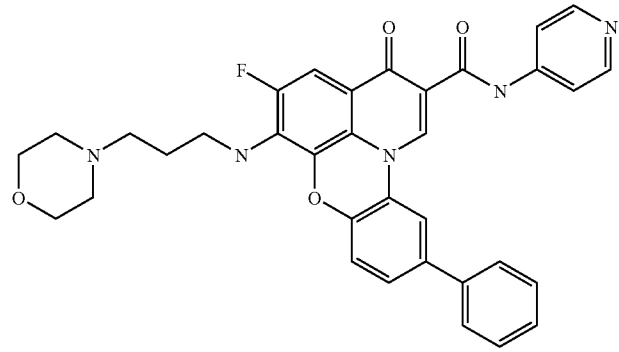
784
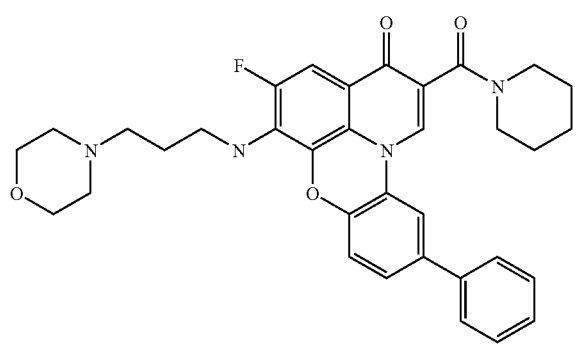
785
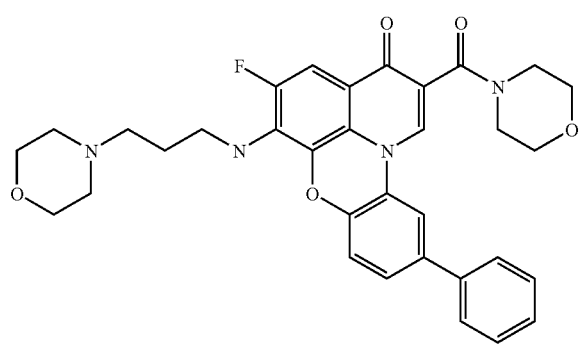
786
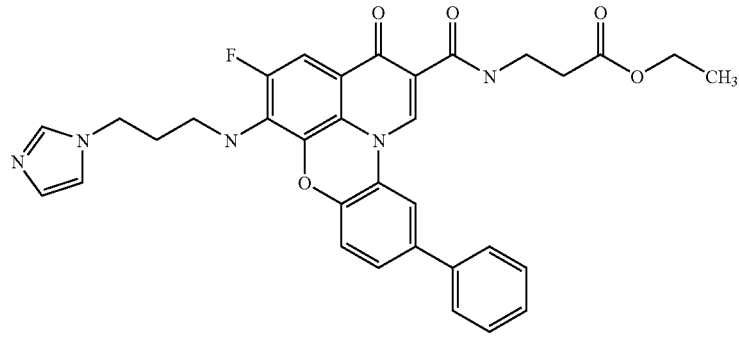

TABLE 3-continued
787
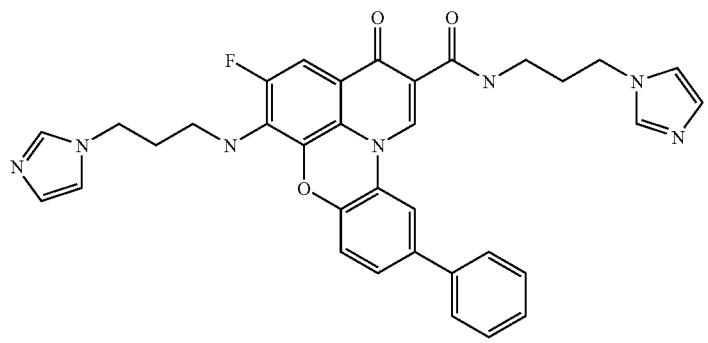
788
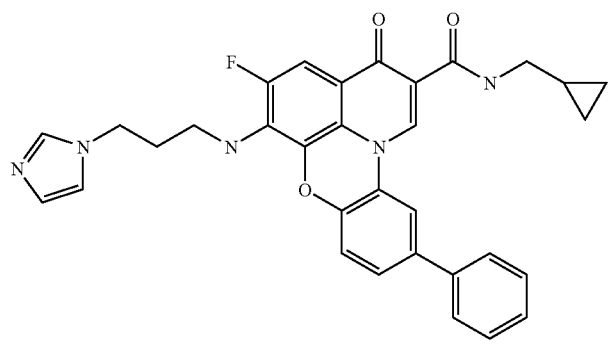
789
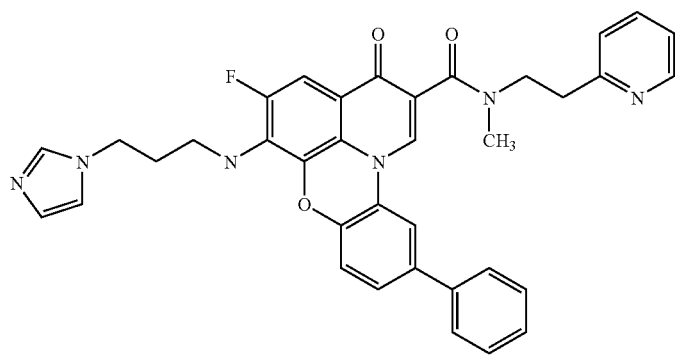
790
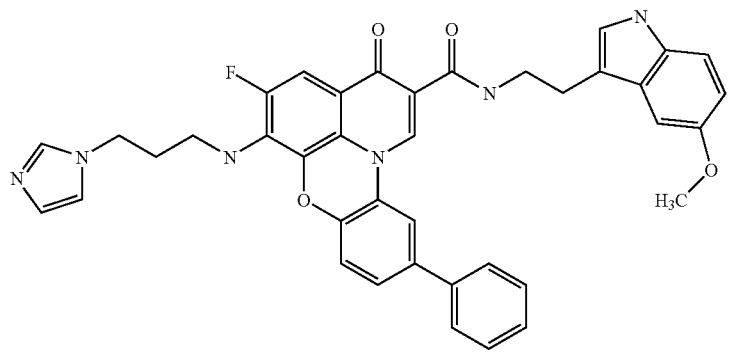

TABLE 3-continued
791 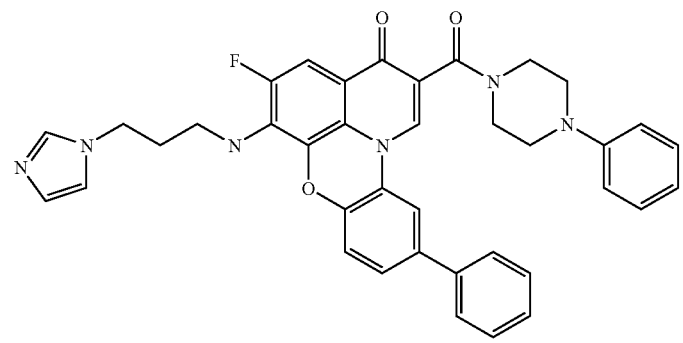
792 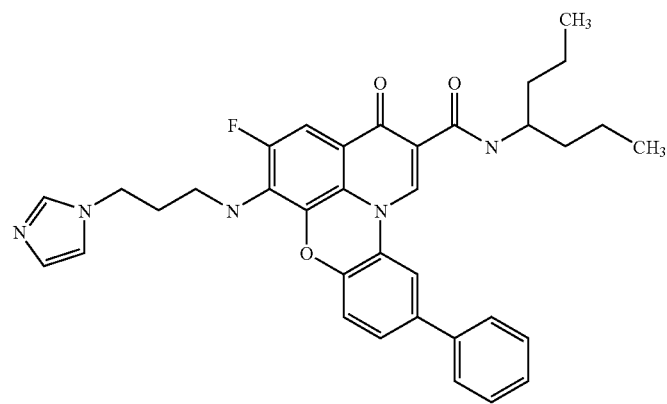
793 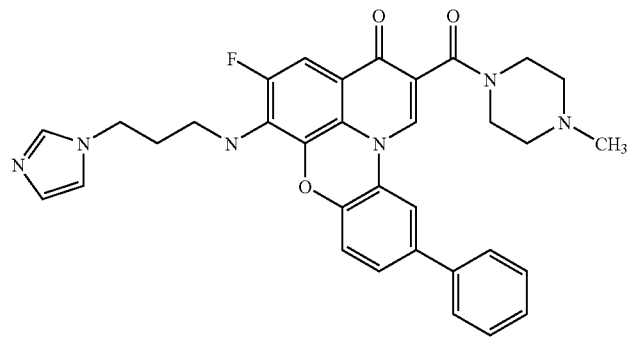
794 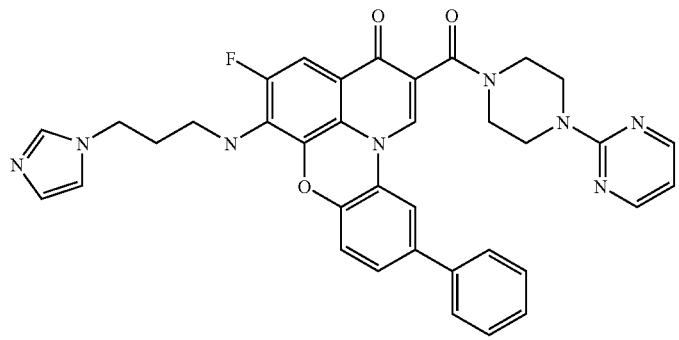

TABLE 3-continued
795 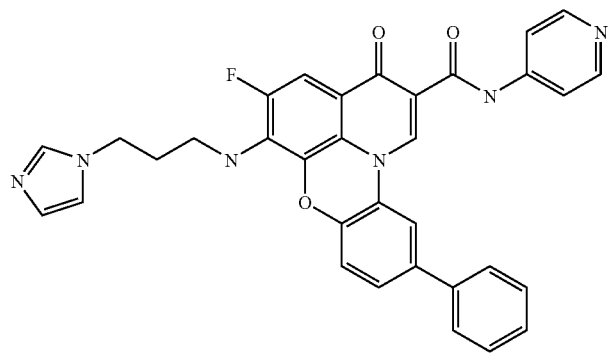
796 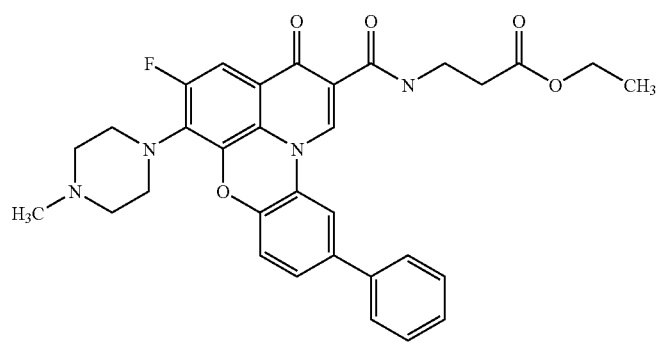
797 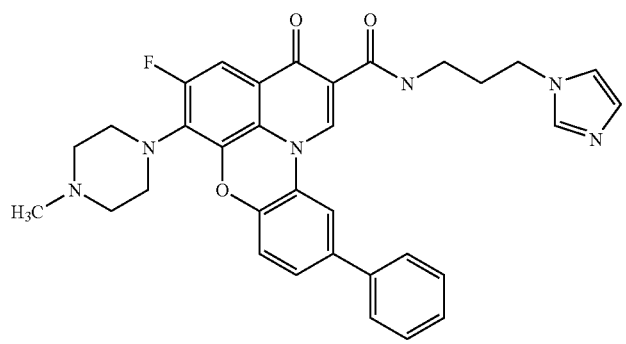
798 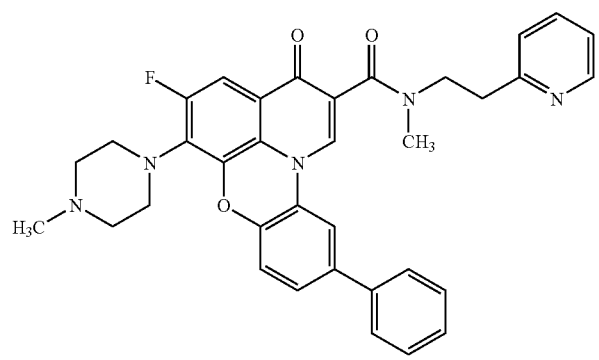

TABLE 3-continued
799
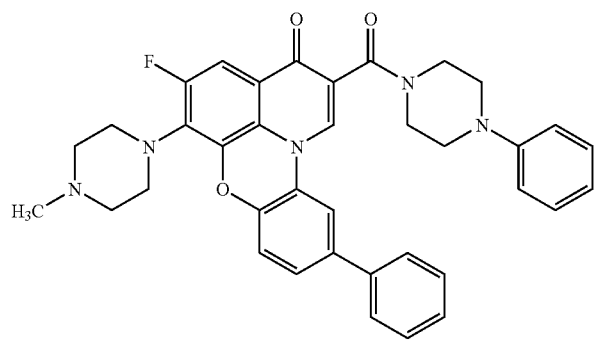
800
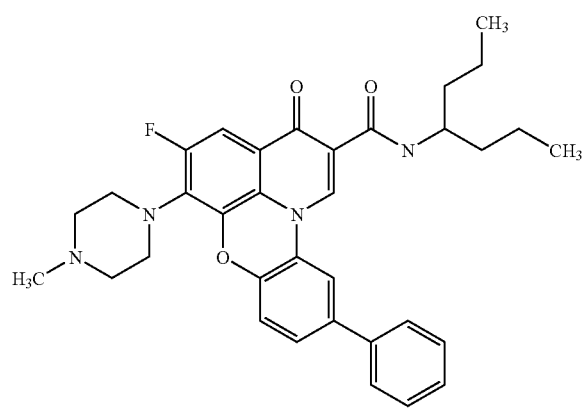
801
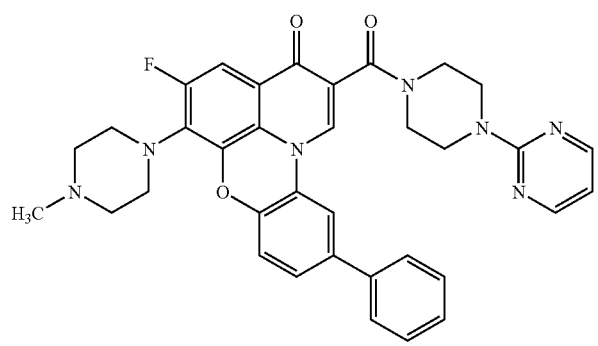
802
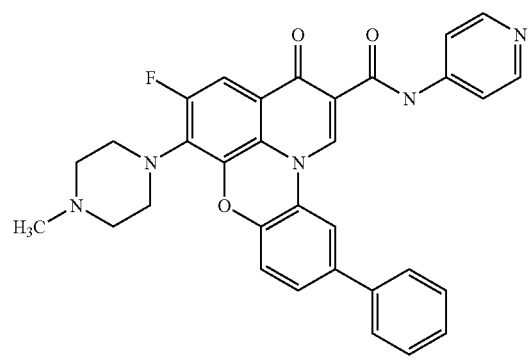

TABLE 3-continued
803
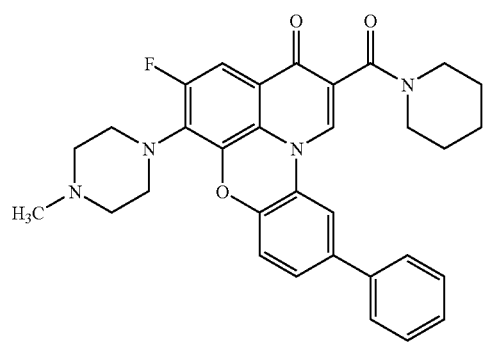
804
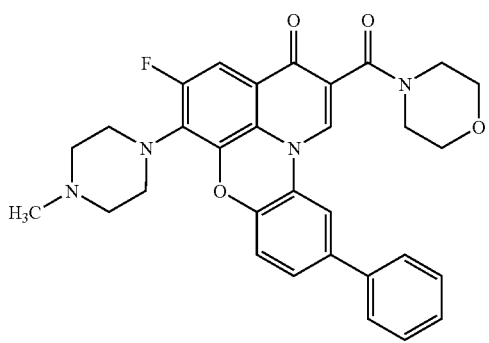
805
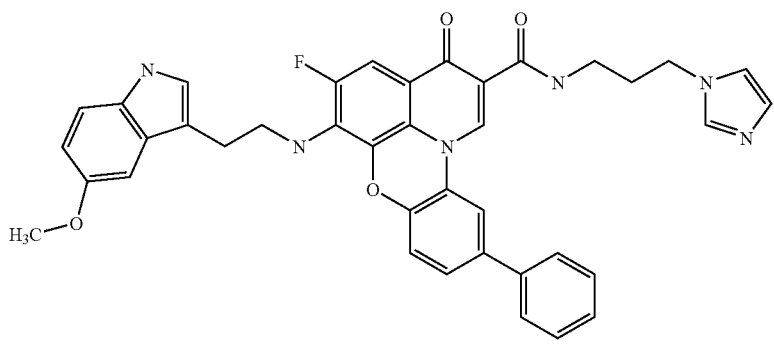
806
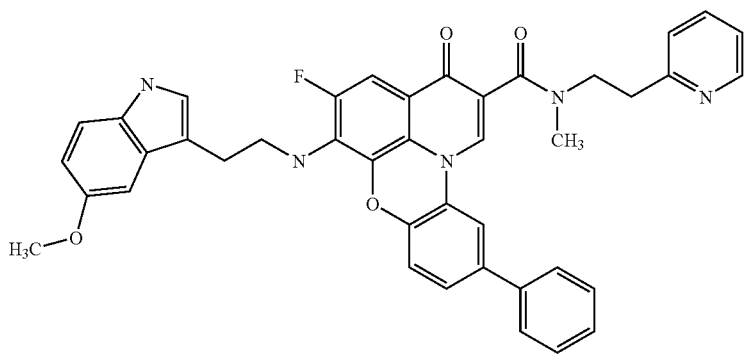

TABLE 3-continued
807
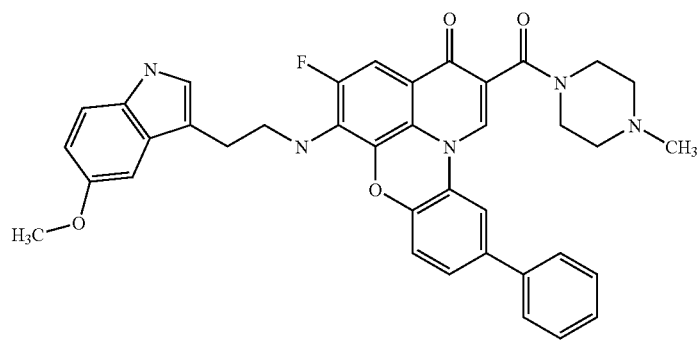
808
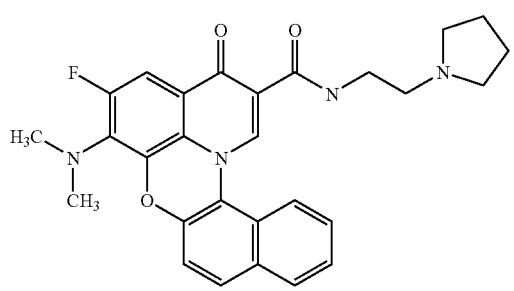
809
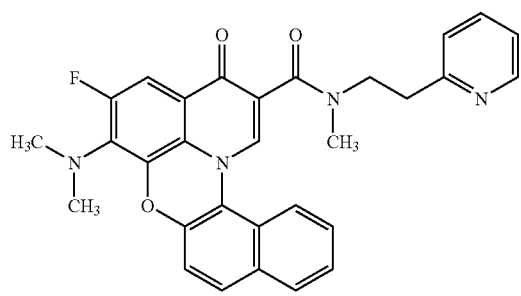
810
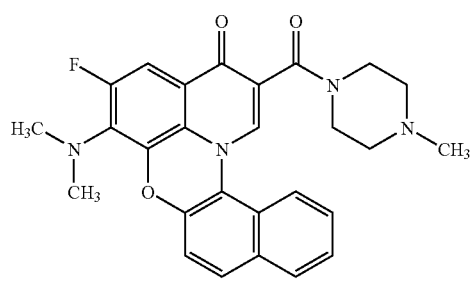
811
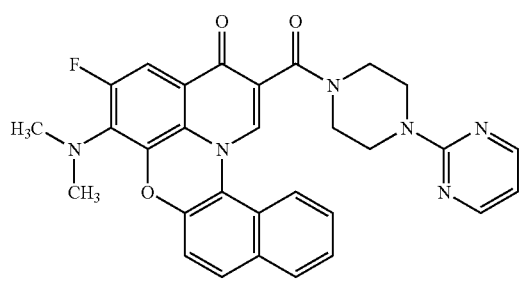

TABLE 3-continued
| 812 | 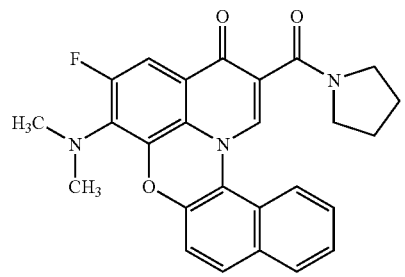 |
| 813 | 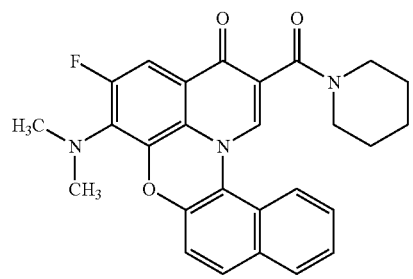 |
| 814 | 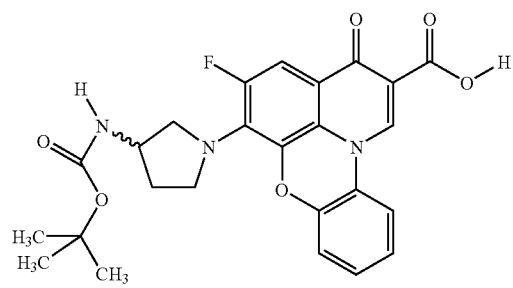 |
| 815 | 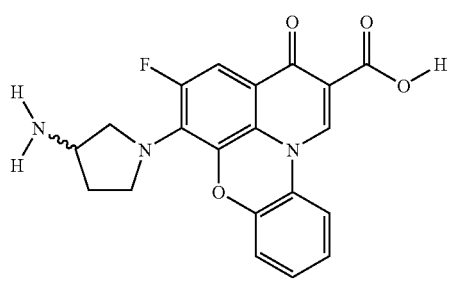 |
| 816 | 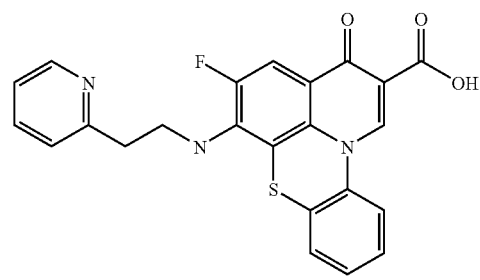 |

TABLE 3-continued
817
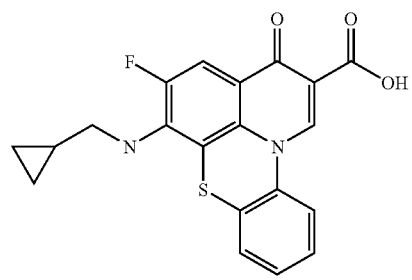
818
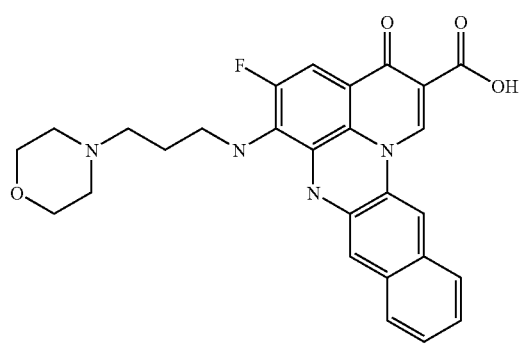
819
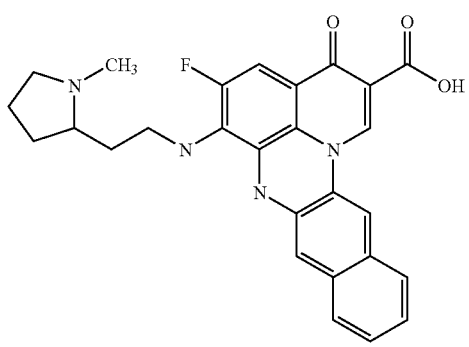
820
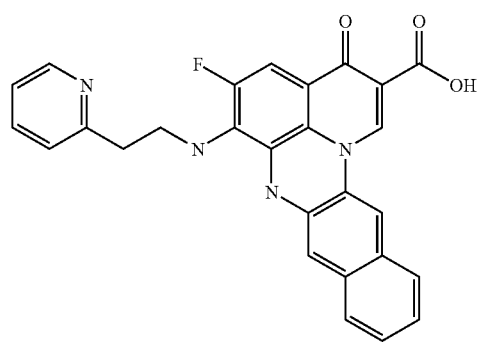
821
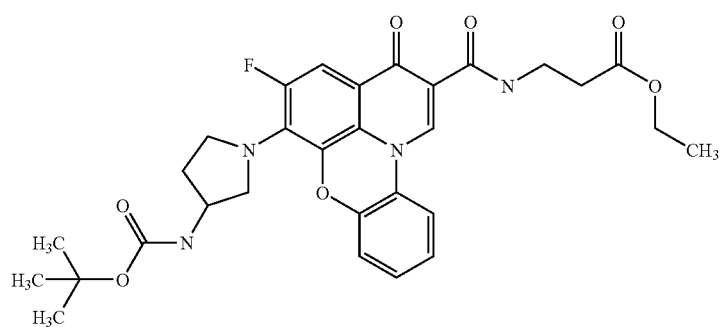

TABLE 3-continued
822
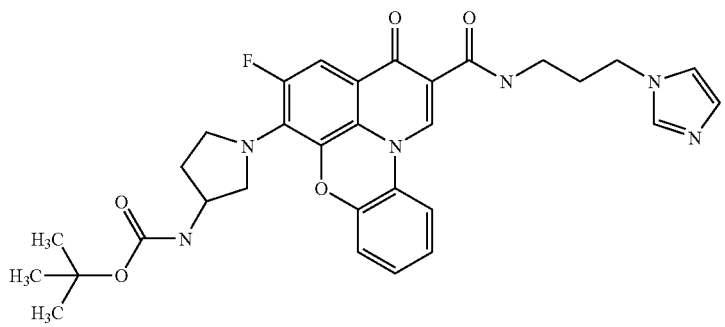
823
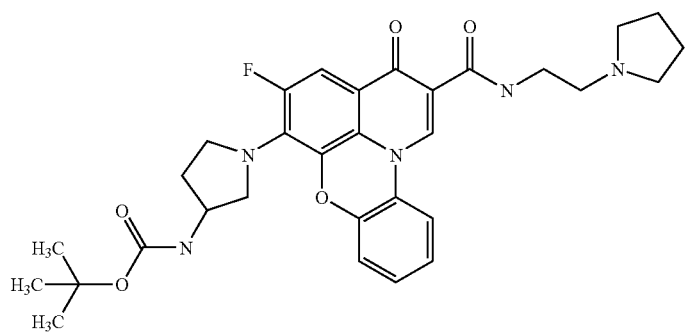
824
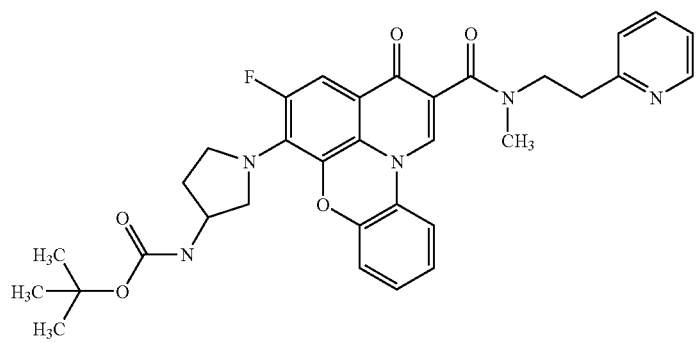
825
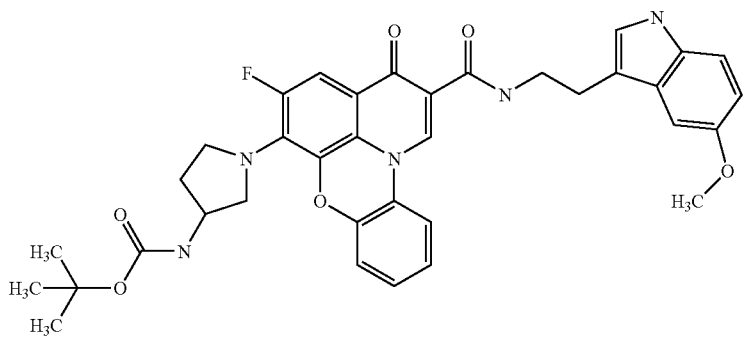

TABLE 3-continued
| 826 | 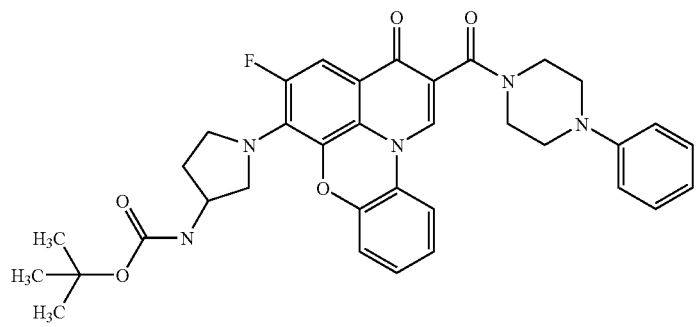 |
| 827 | 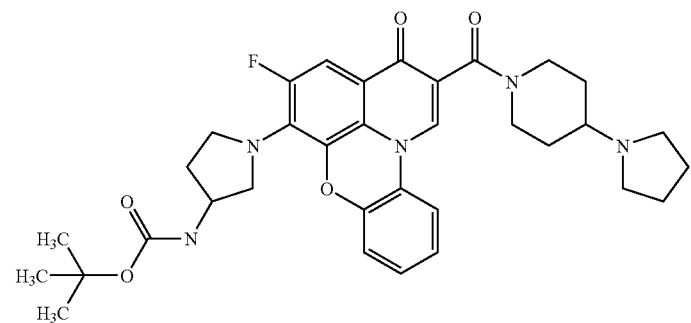 |
| 828 | 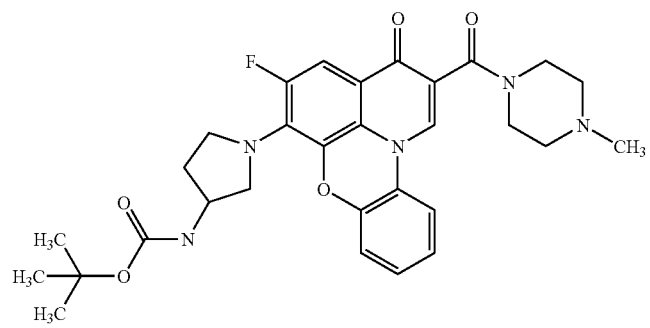 |
| 829 | 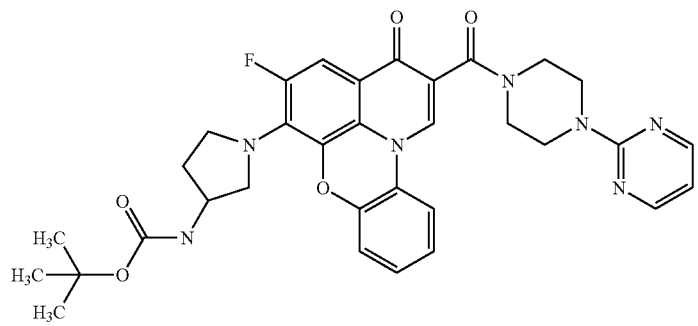 |
| 830 | 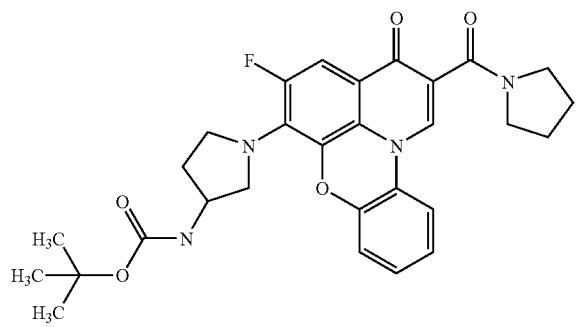 |

TABLE 3-continued
| 831 | 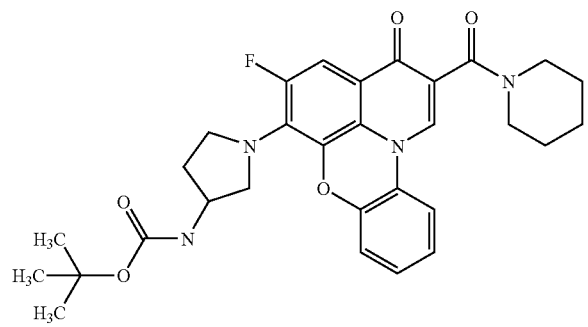 |
| 832 | 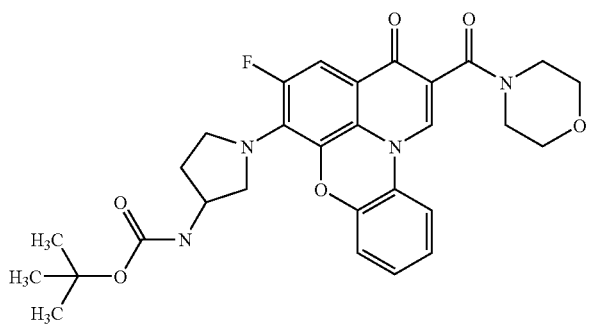 |
| 833 | 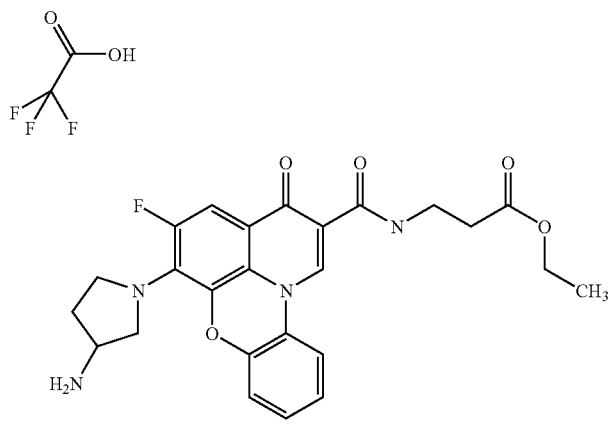 |
| 834 | 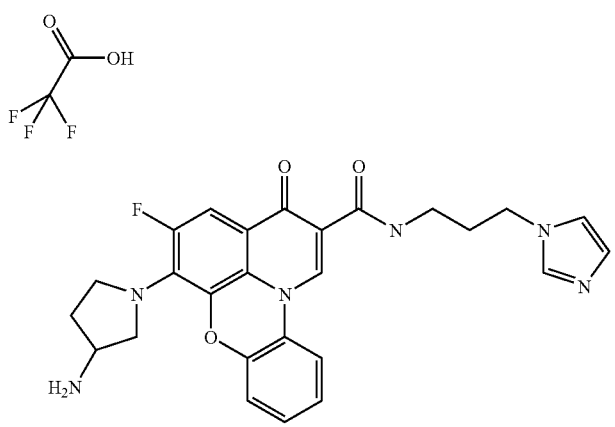 |

TABLE 3-continued
| 835 | 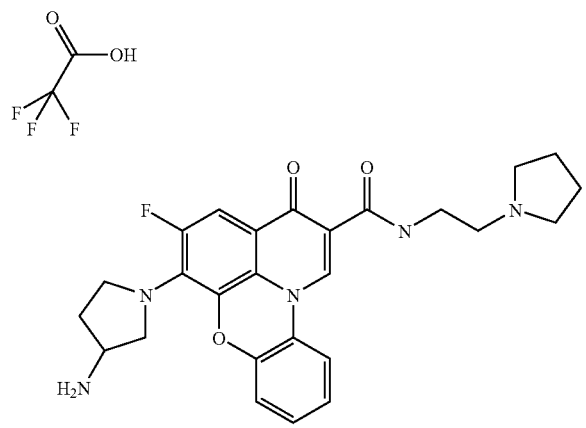 |
| --- | --- |
| 836 | 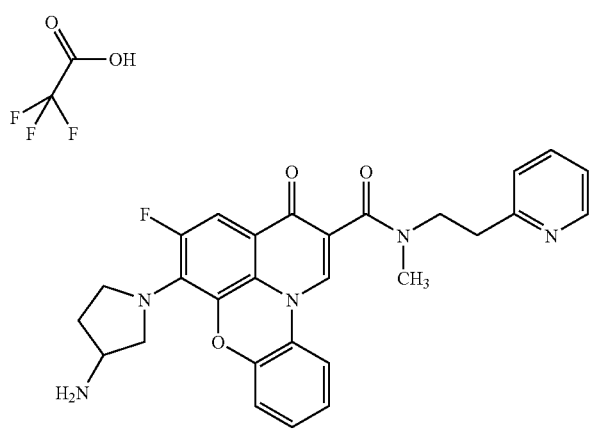 |
| 837 | 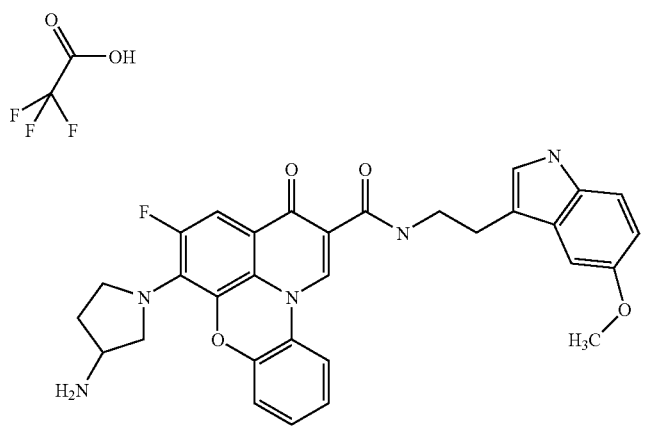 |

TABLE 3-continued
| 838 | 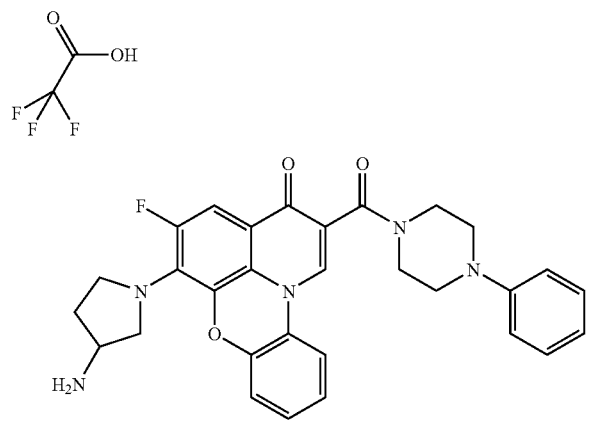 |
|---|---|
| 839 | 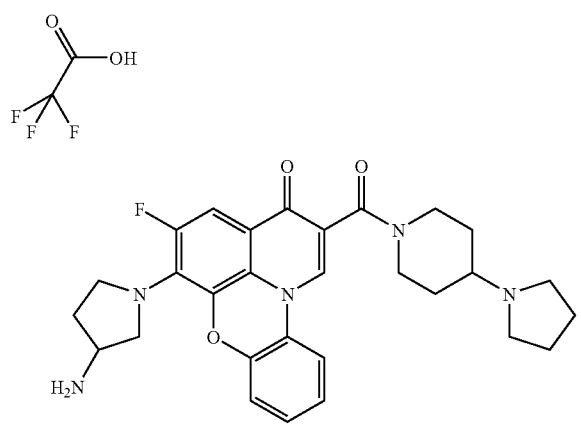 |
| 840 | 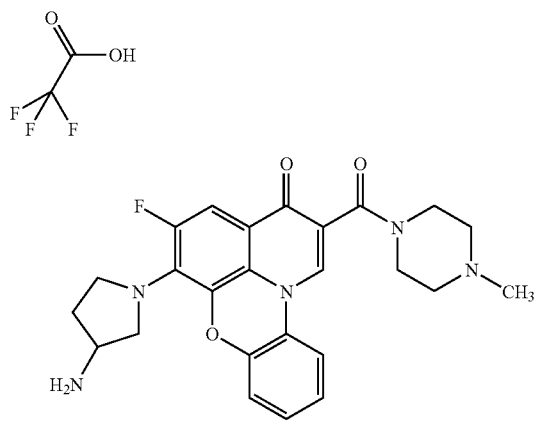 |

TABLE 3-continued
841
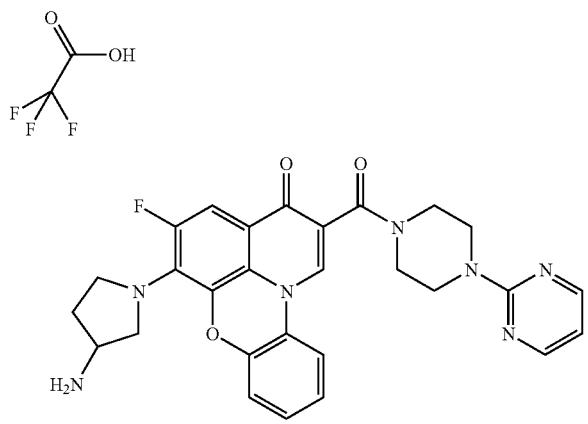
842
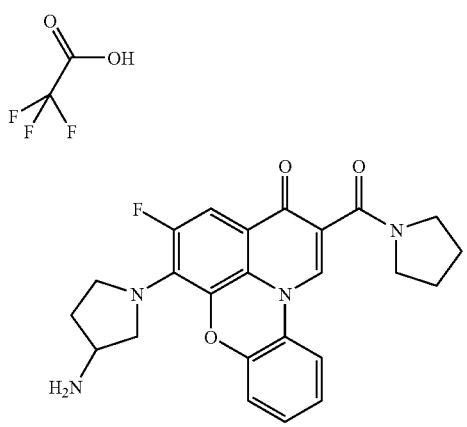
843
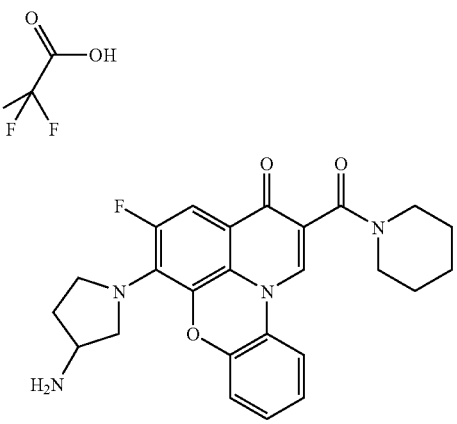

TABLE 3-continued
844 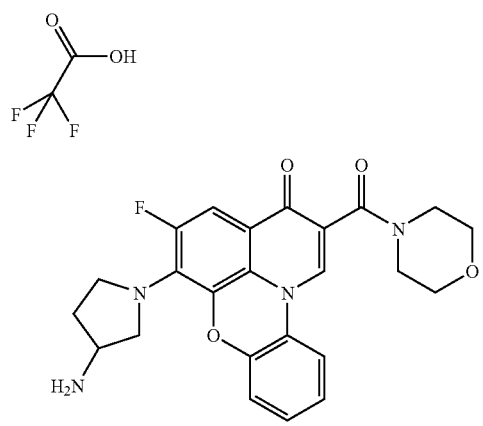
845 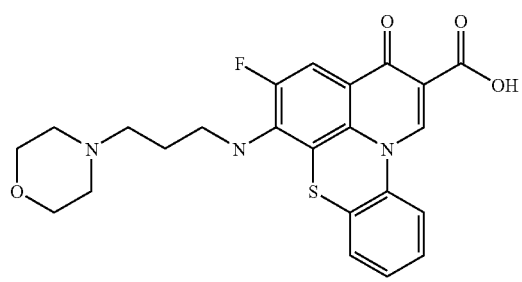
846 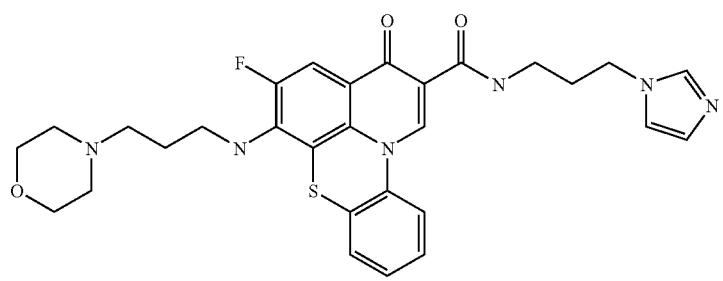
847 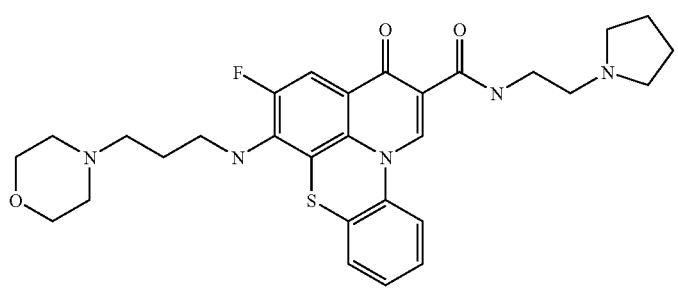
848 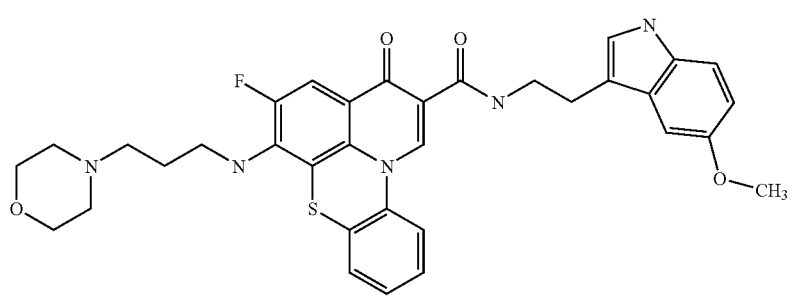

TABLE 3-continued
849
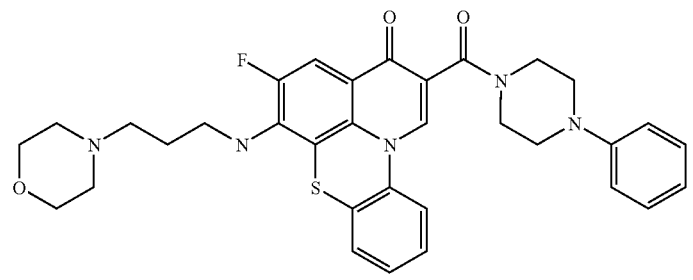
850
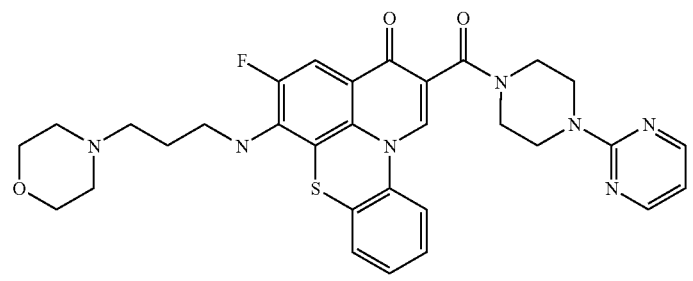
851
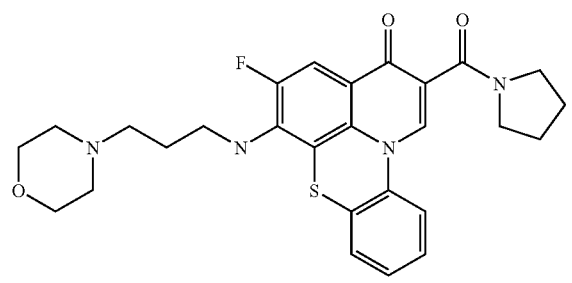
852
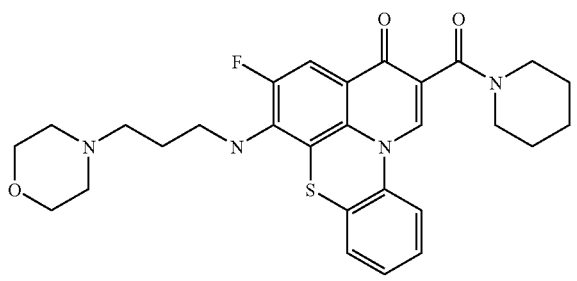
853
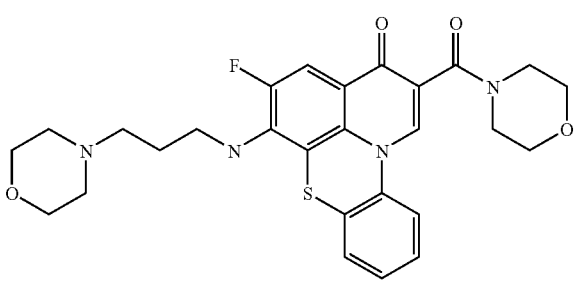

TABLE 3-continued
| | |
|---|---|
| 854 | 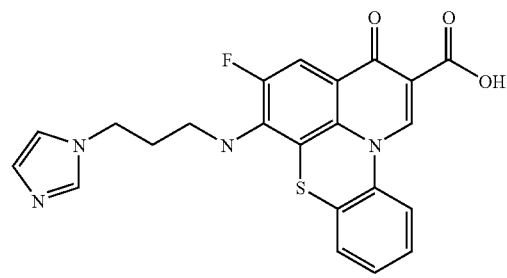 |
| 855 | 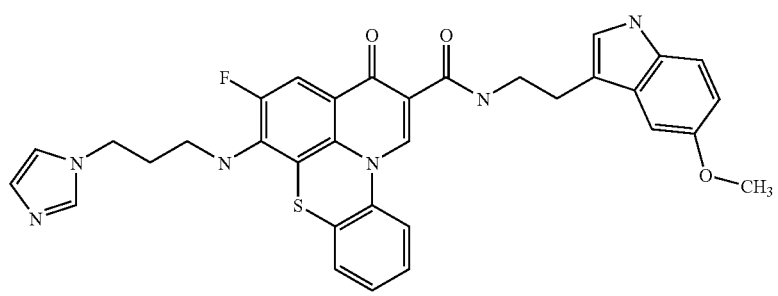 |
| 856 | 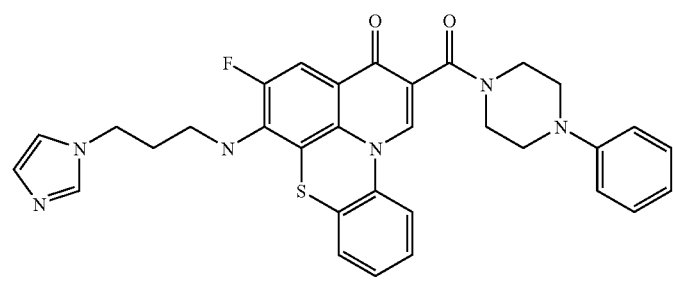 |
| 857 | 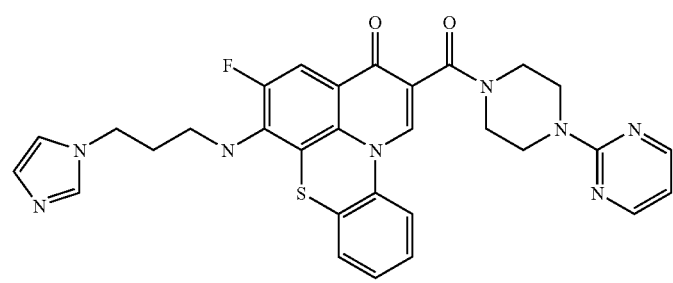 |
| 858 | 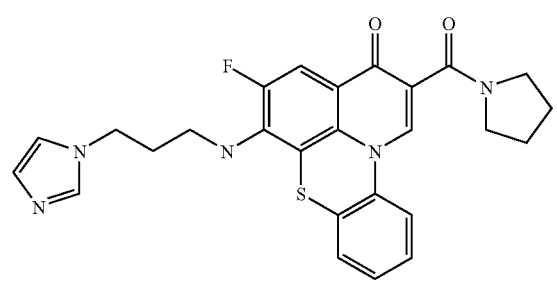 |

TABLE 3-continued
859
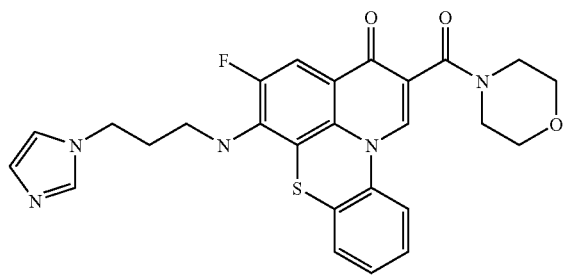
860
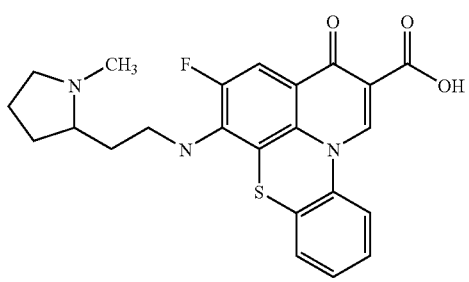
861
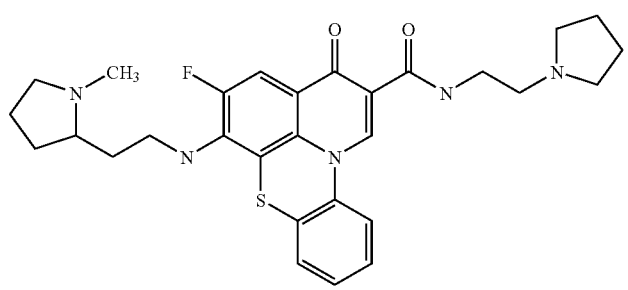
862
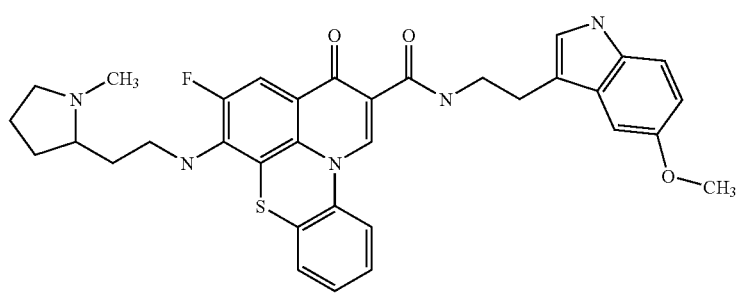
863
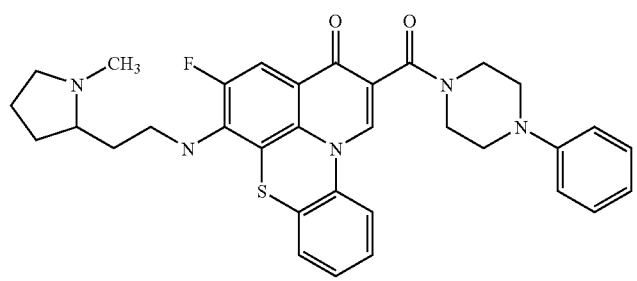

TABLE 3-continued
| 864 | 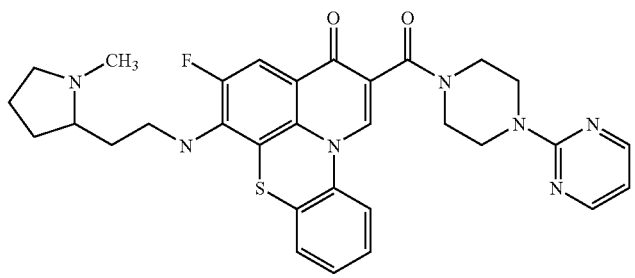 |
| --- | --- |
| 865 | 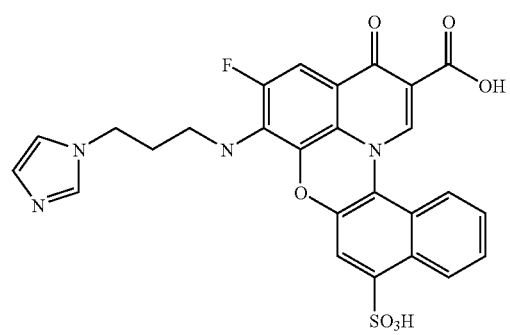 |
| 866 | 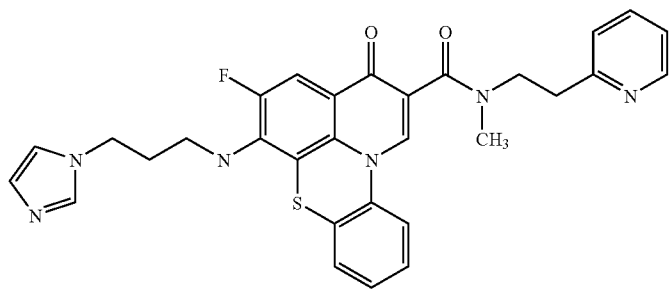 |
| 867 | 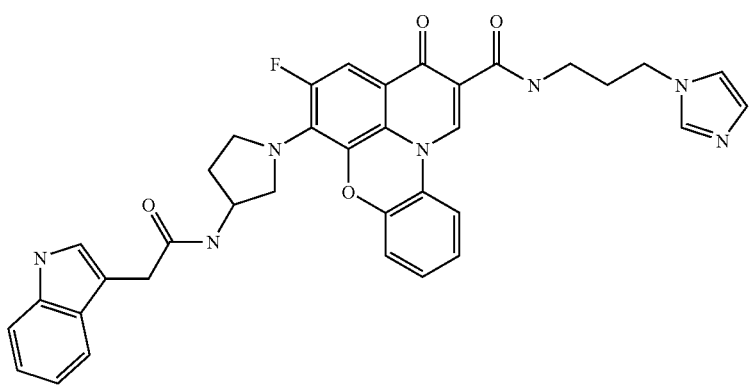 |

TABLE 3-continued
868
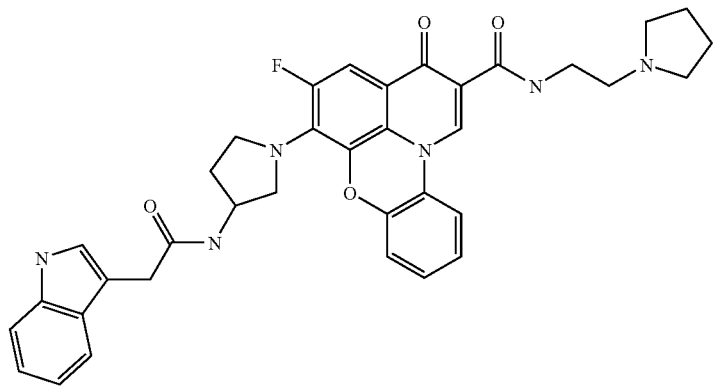
869
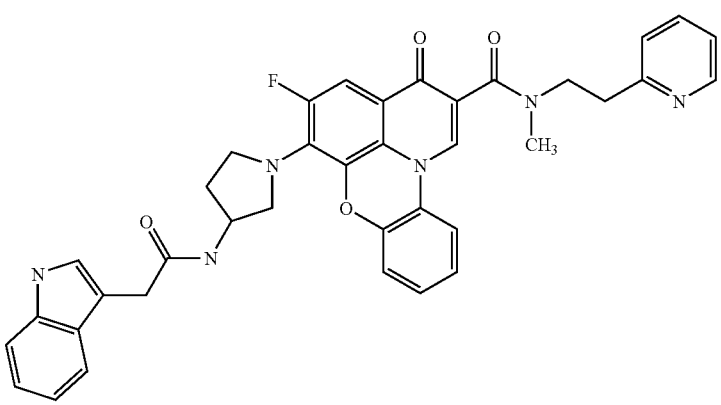
870
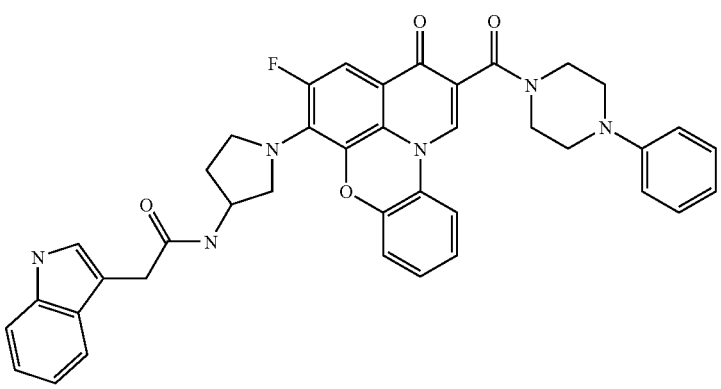
871
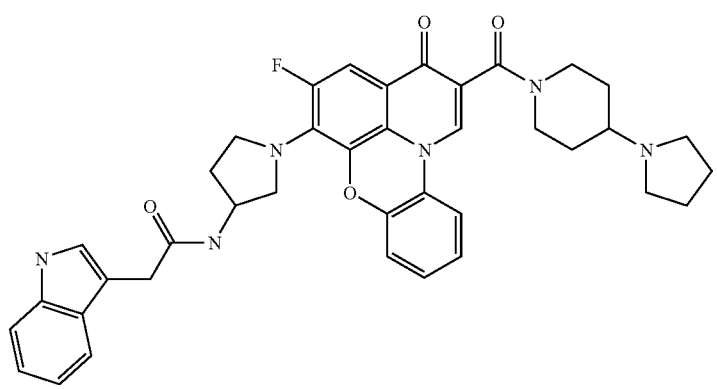

TABLE 3-continued
872
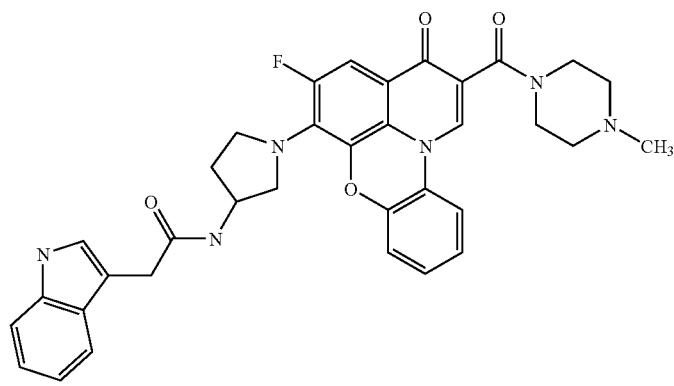
873
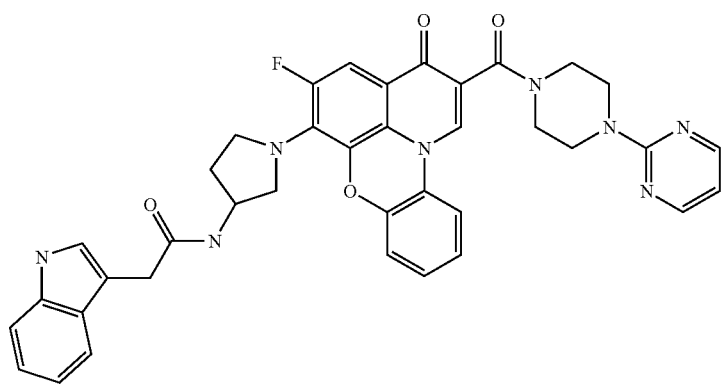
874
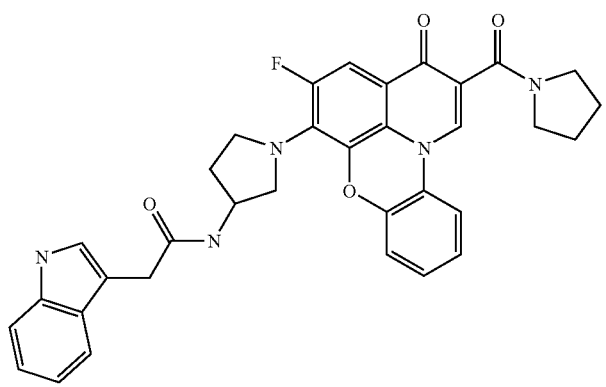
875
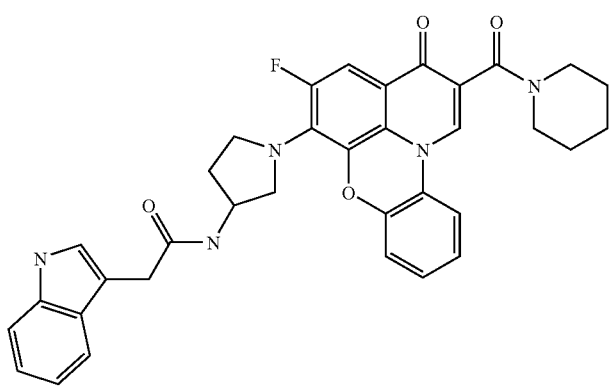

TABLE 3-continued
876
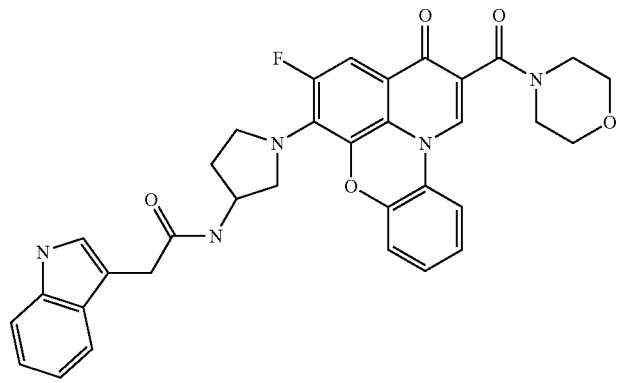
877
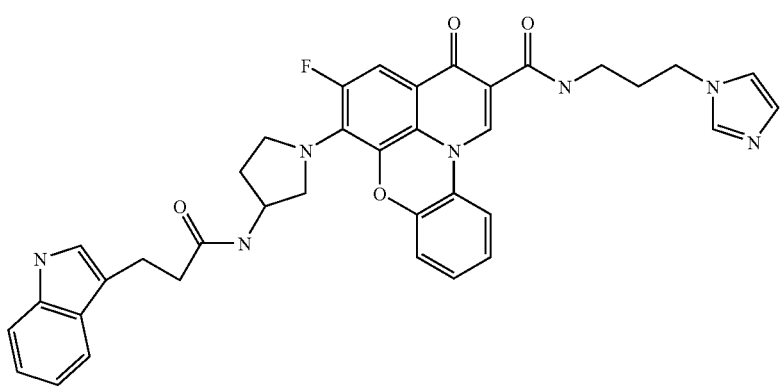
878
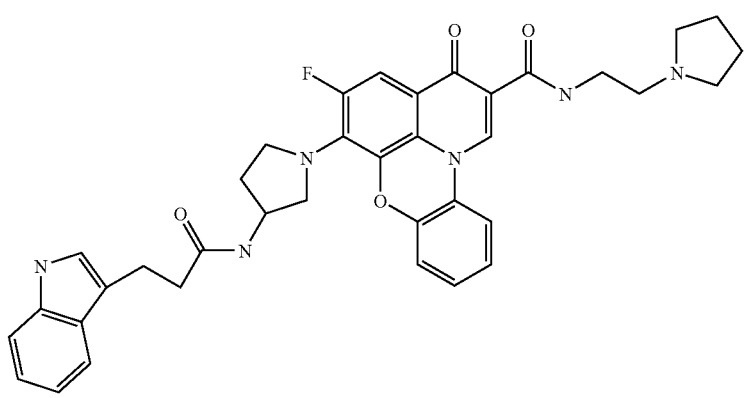
879
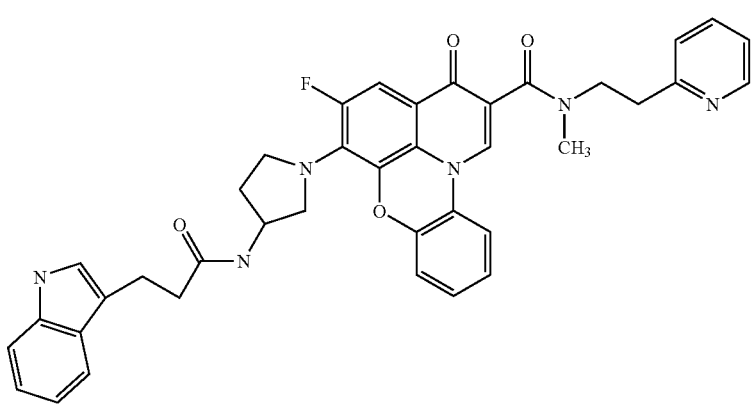

TABLE 3-continued
880
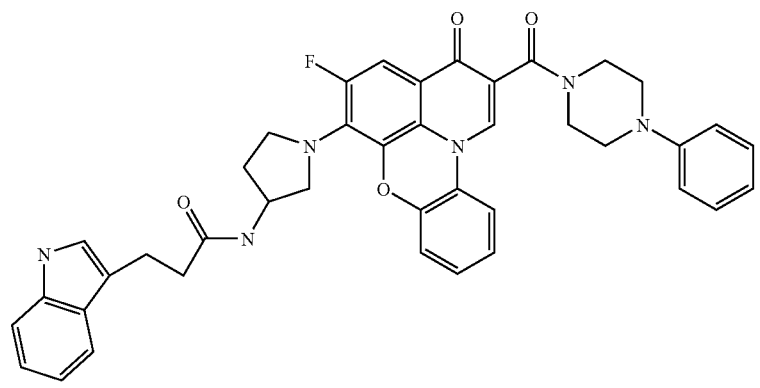
881
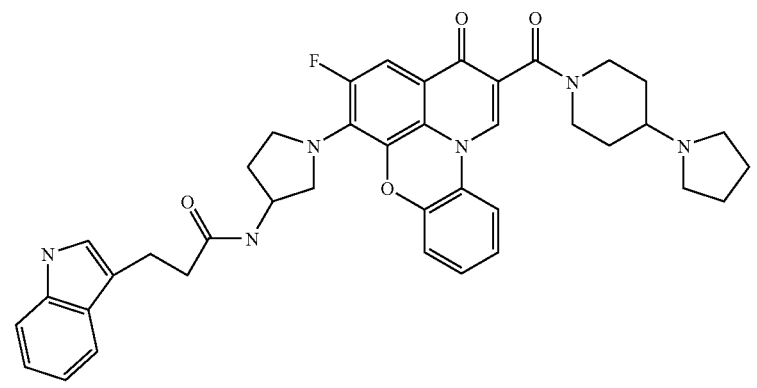
882
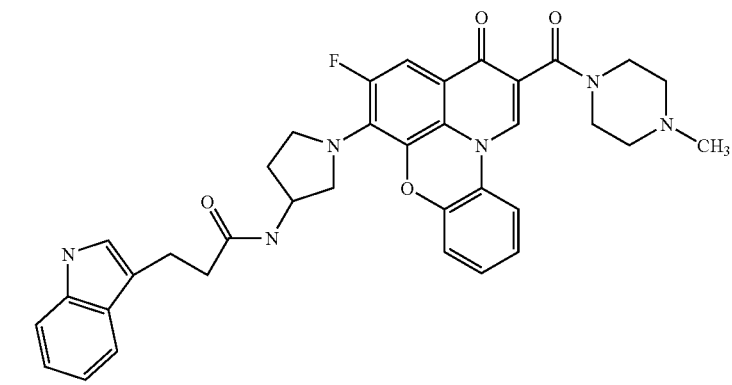
883
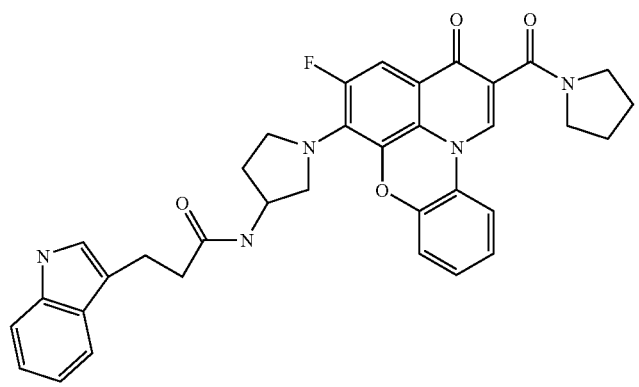

TABLE 3-continued
884
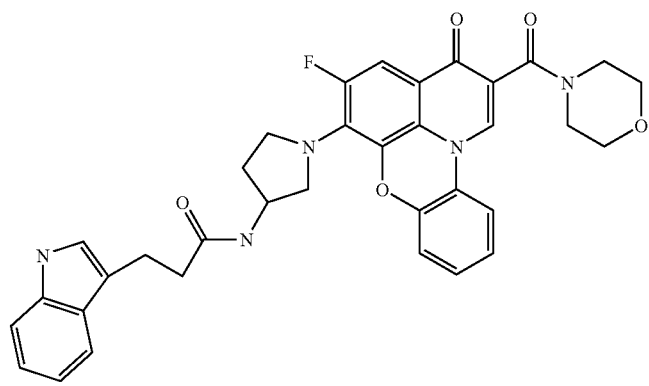
885
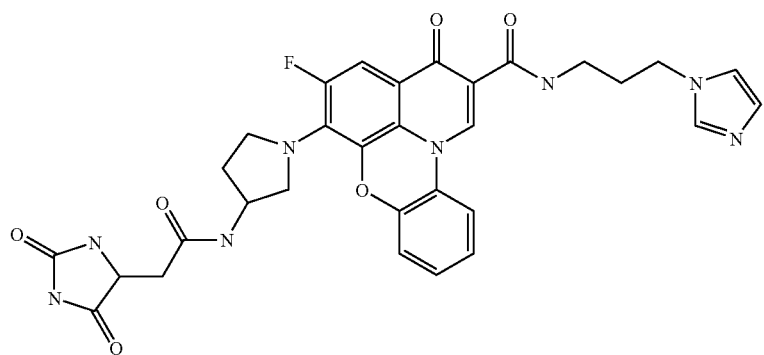
886
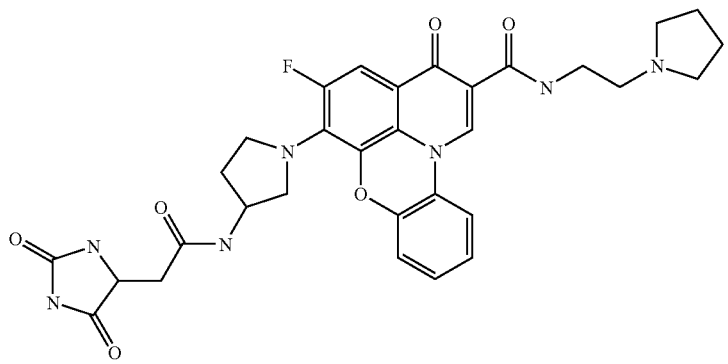
887
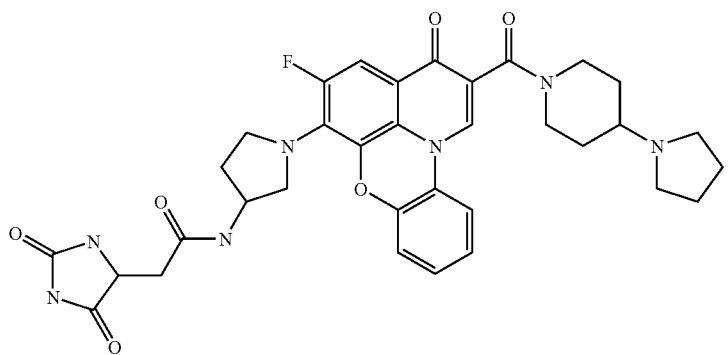

TABLE 3-continued
888
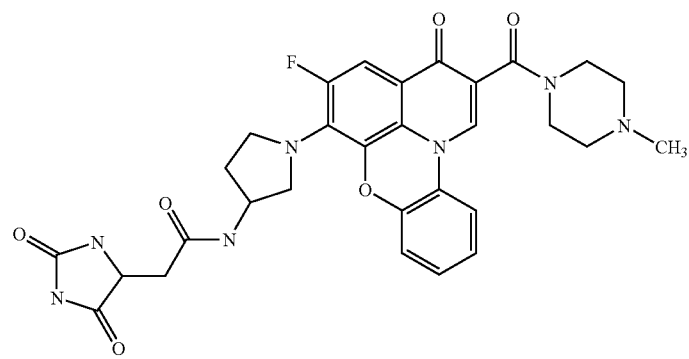
889
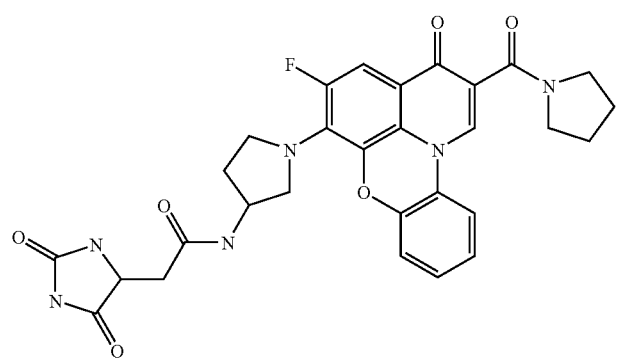
890
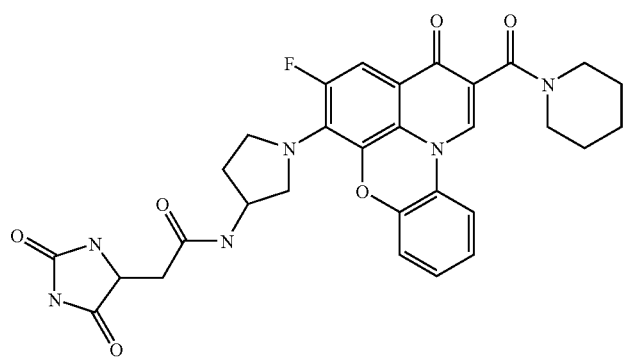
891
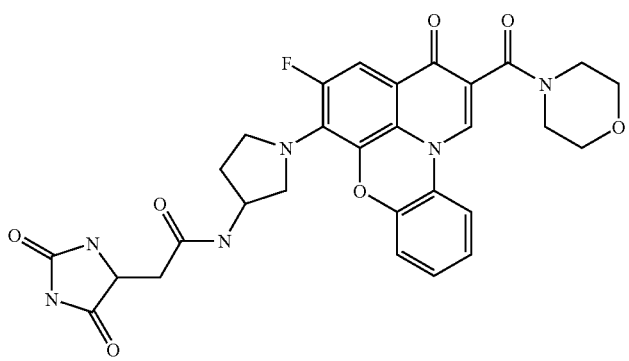

TABLE 3-continued
892
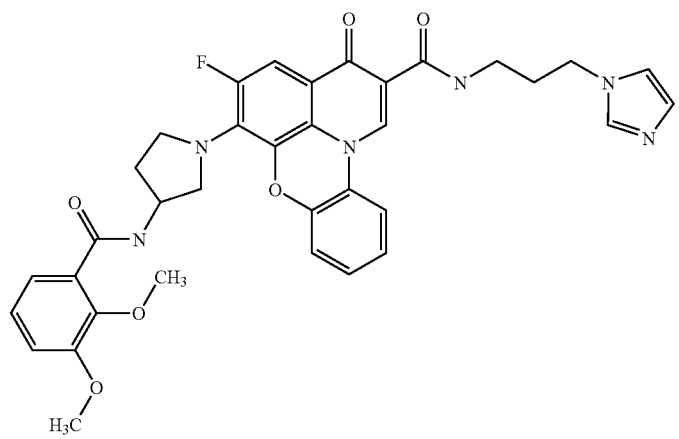
893
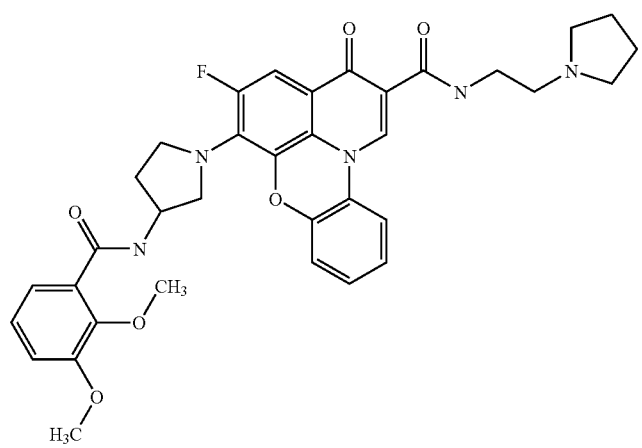
894
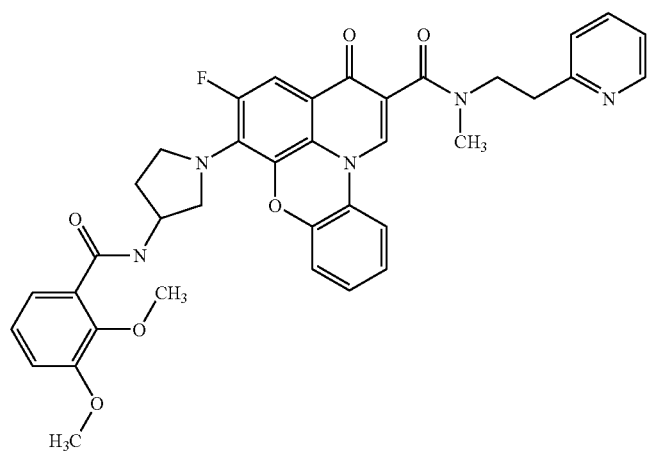

TABLE 3-continued
895
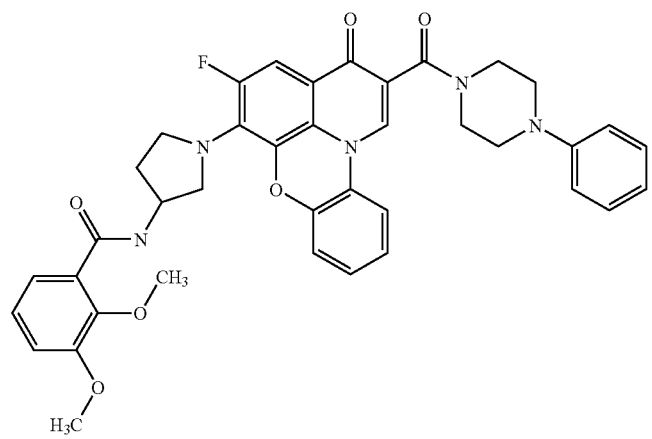
896
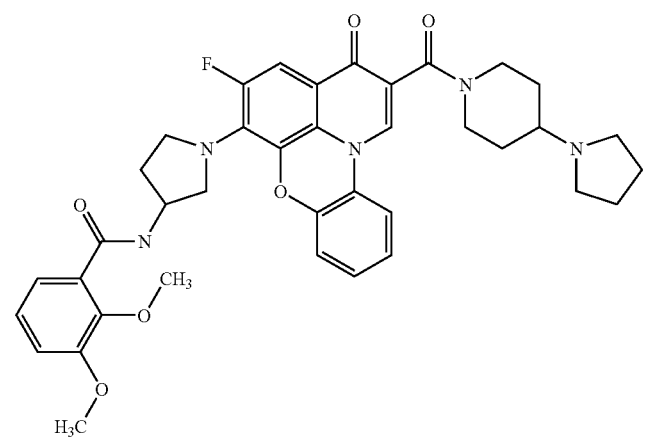
897
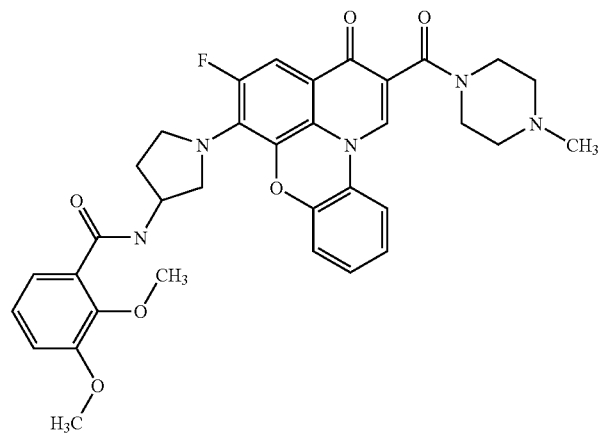

TABLE 3-continued
898 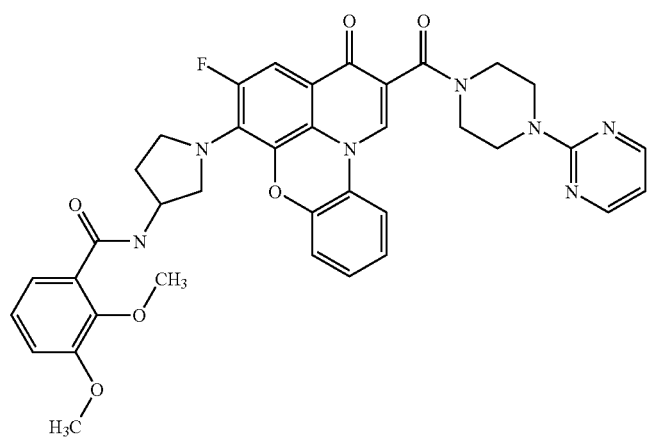
899 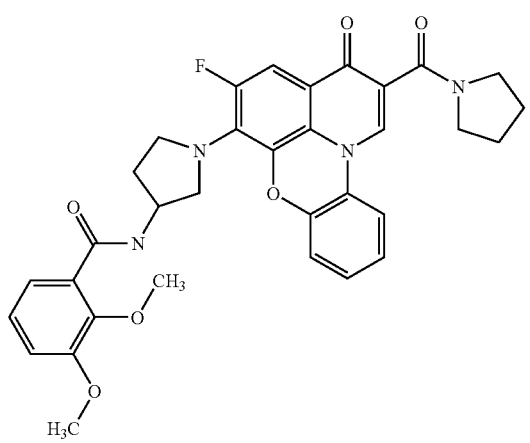
900 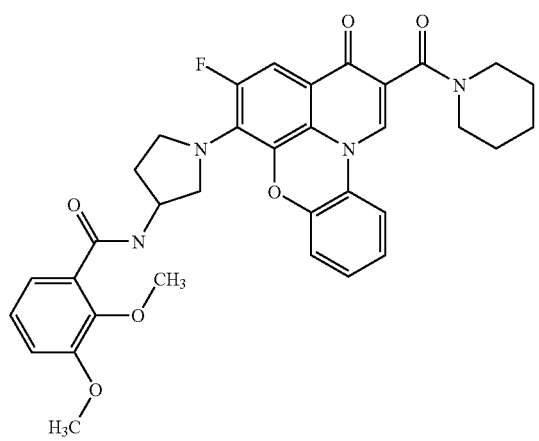

TABLE 3-continued
901
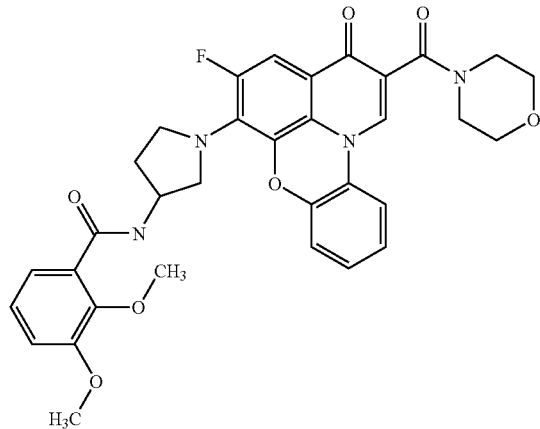
902
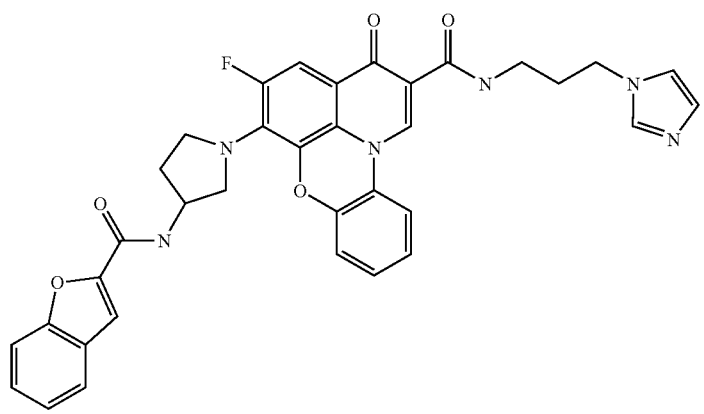
903
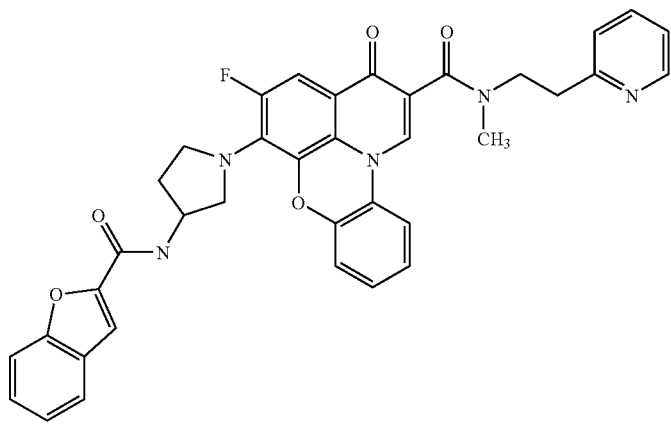

TABLE 3-continued
904
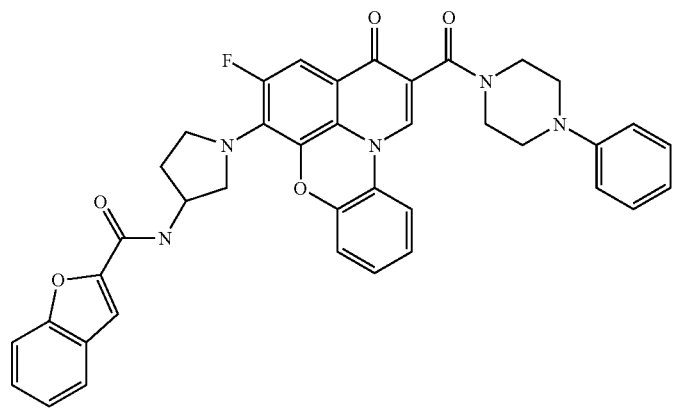
905
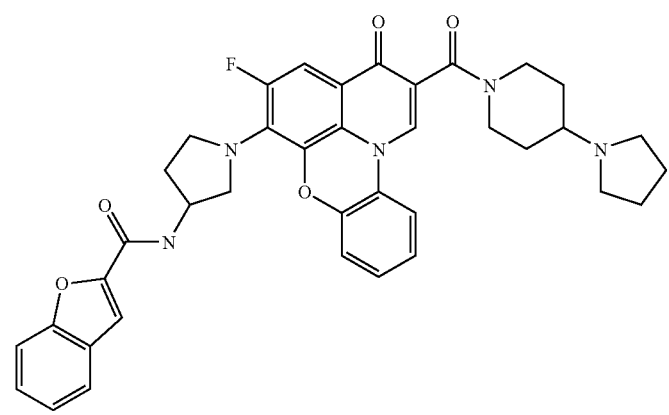
906
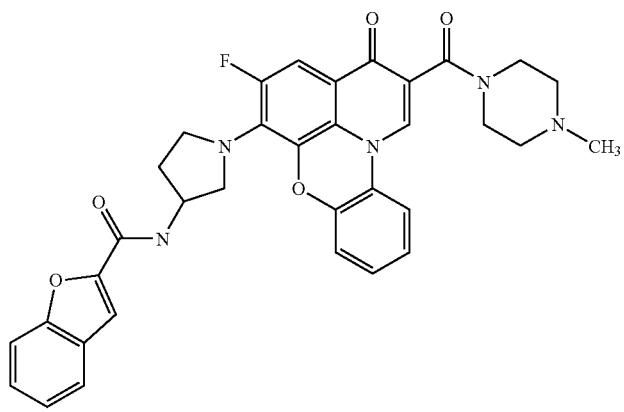
907
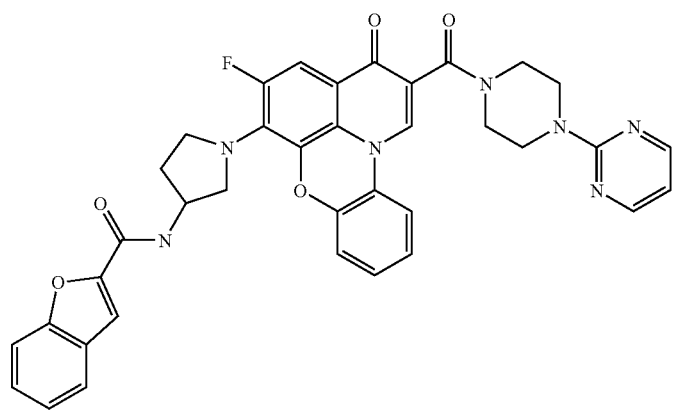

TABLE 3-continued
908
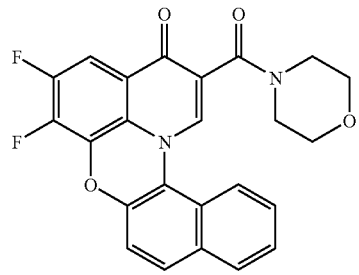
909
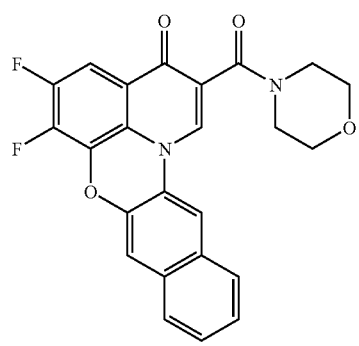
910
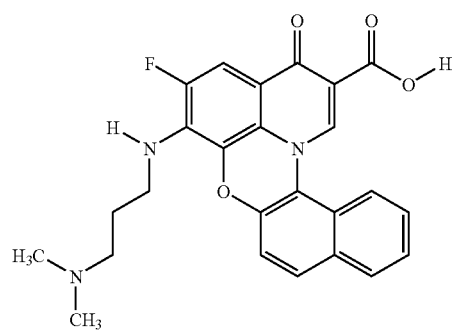
911
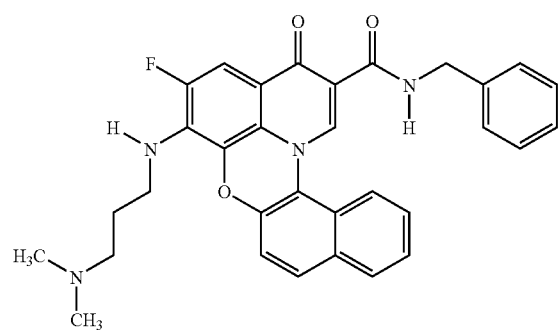

TABLE 3-continued
912
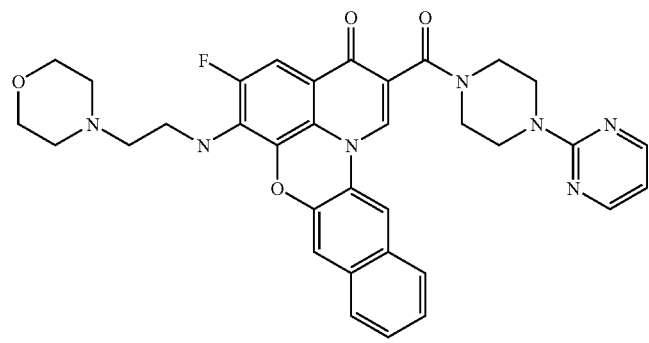
913
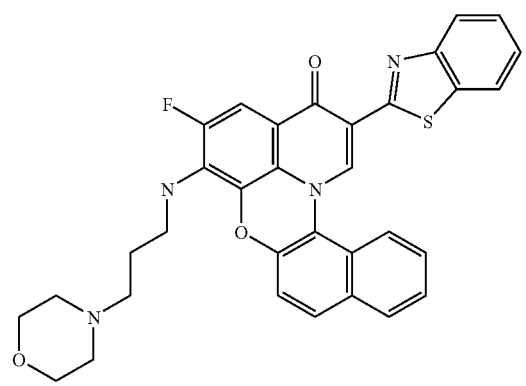
914
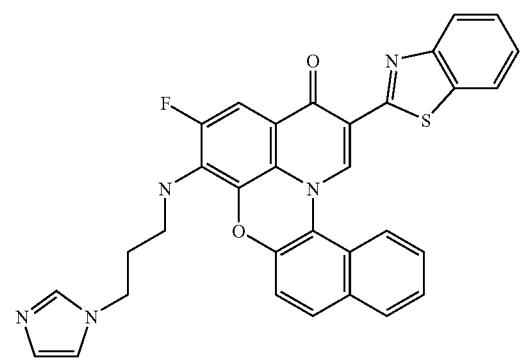
915
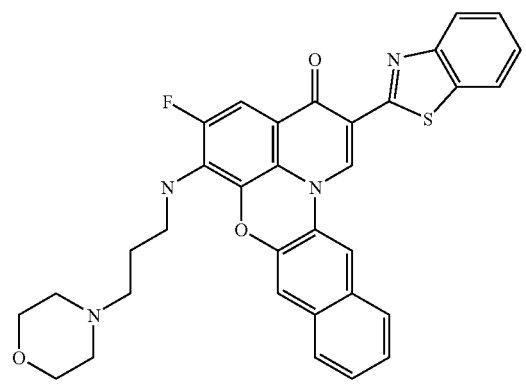

TABLE 3-continued
916
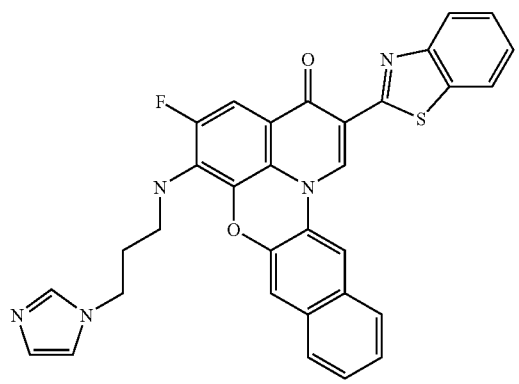
917
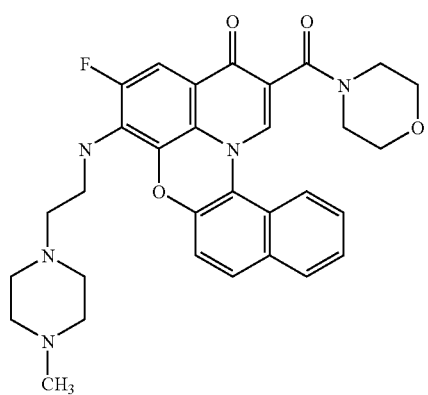
918
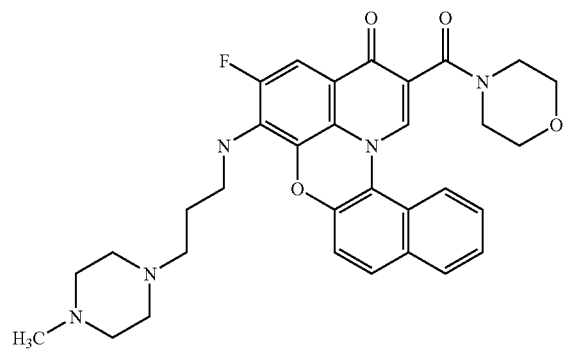
919
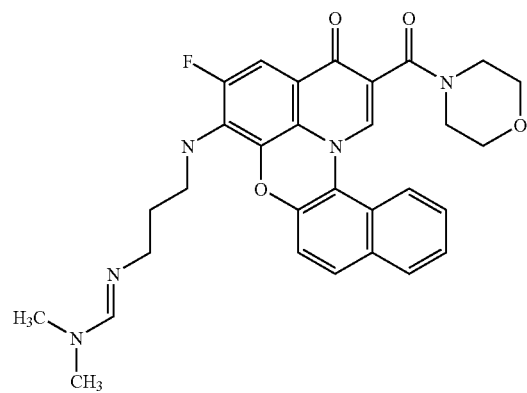

TABLE 3-continued
920 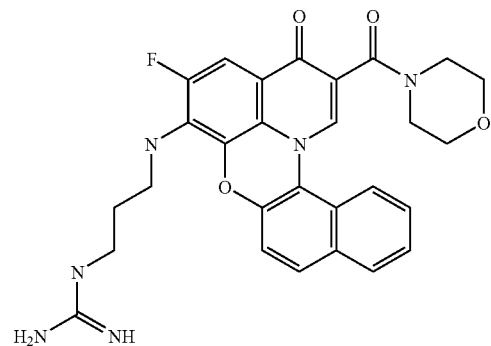
921 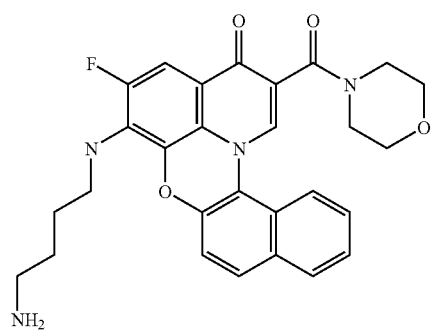
922 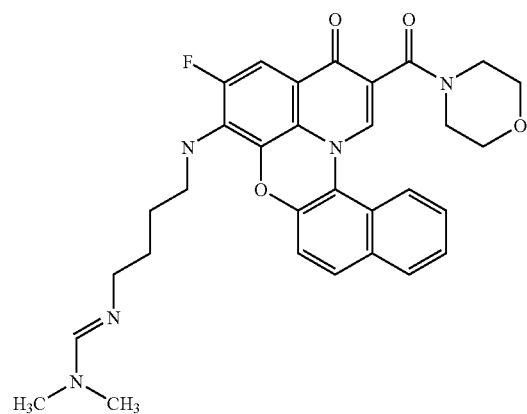
923 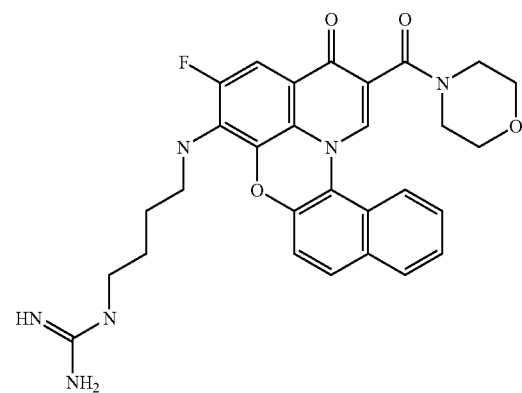

TABLE 3-continued
| 924 | 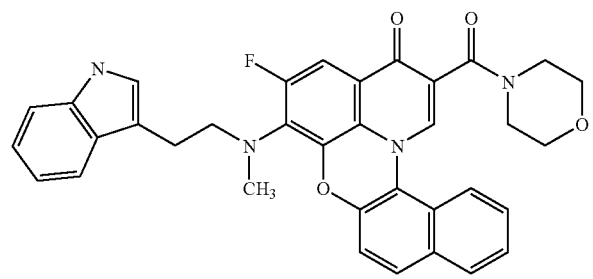 |
| 925 | 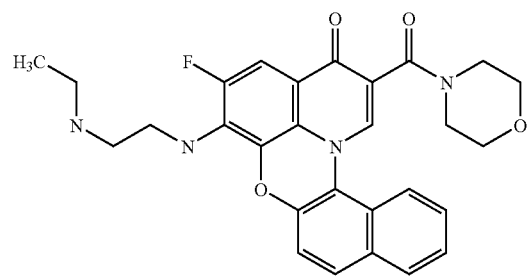 |
| 926 | 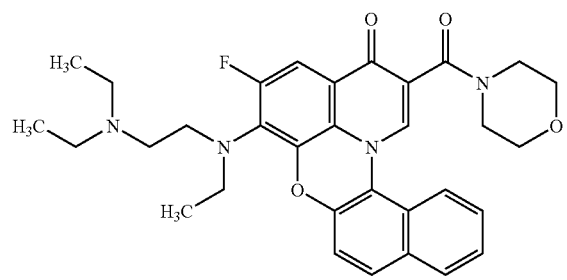 |
| 927 | 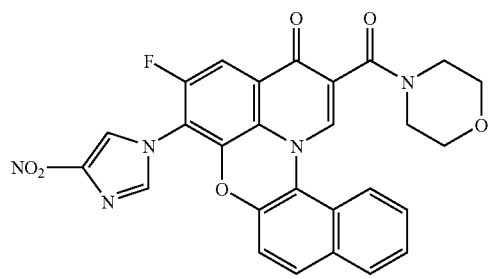 |
| 928 | 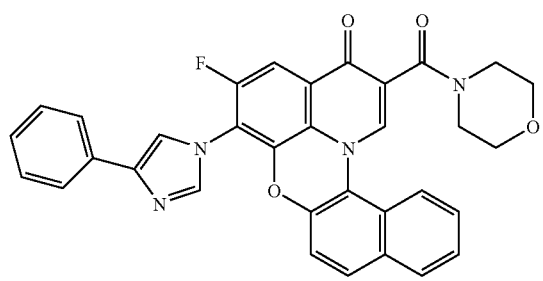 |

TABLE 3-continued
929
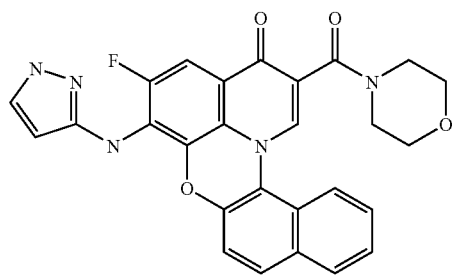
930
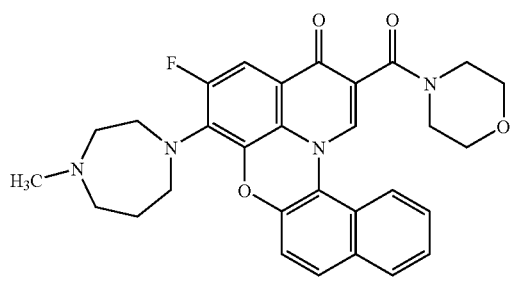
931
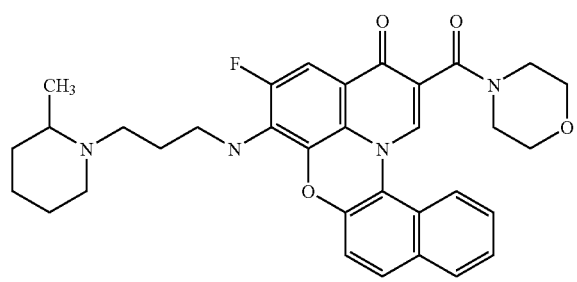
932
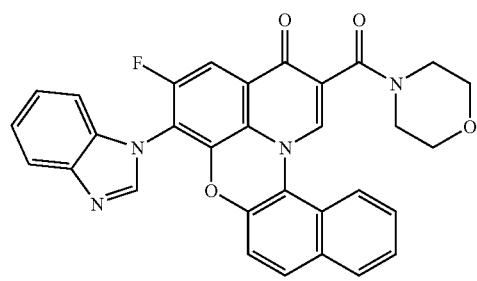
933
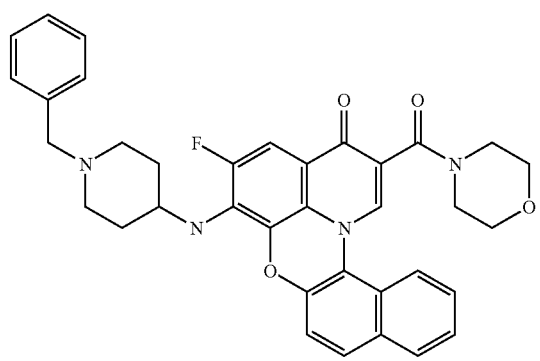

TABLE 3-continued
934 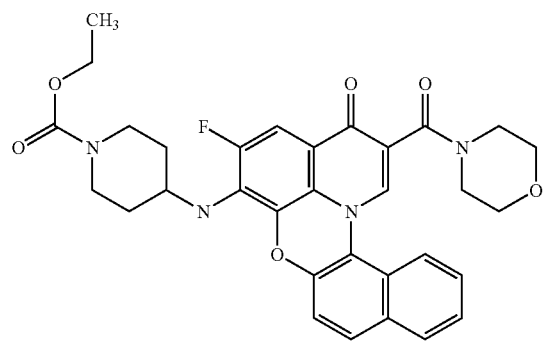
935 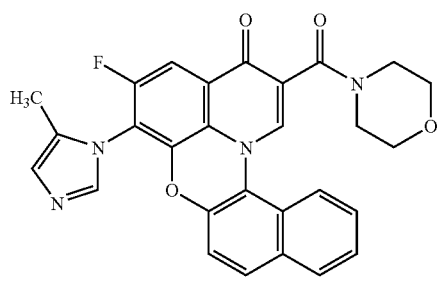
936 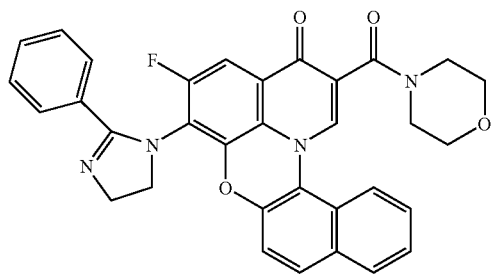
937 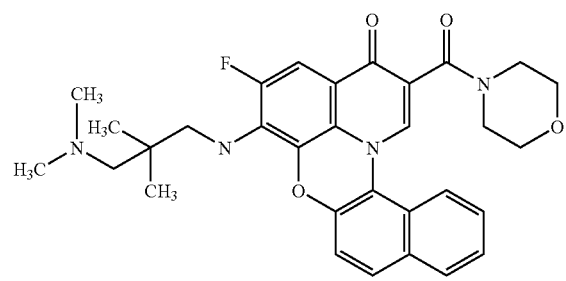
938 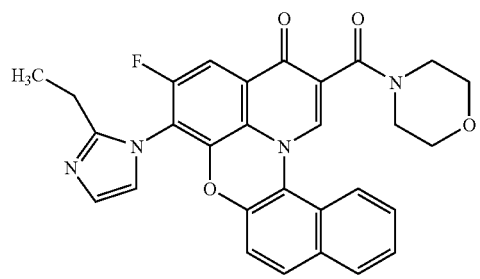

TABLE 3-continued
| | |
|---|---|
| 939 | 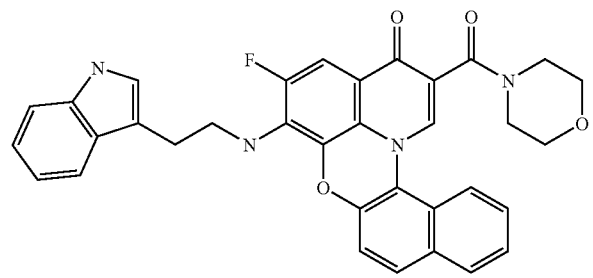 |
| 940 | 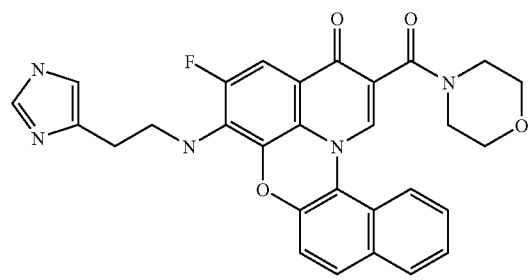 |
| 941 | 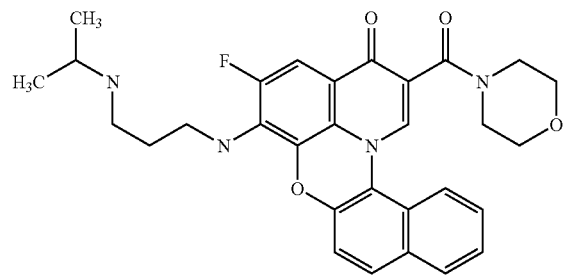 |
| 942 | 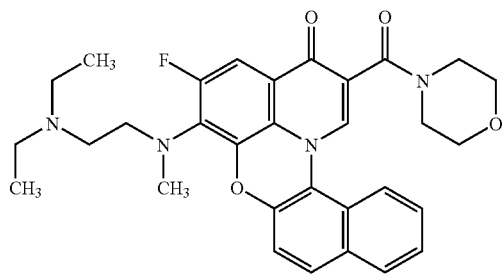 |
| 943 | 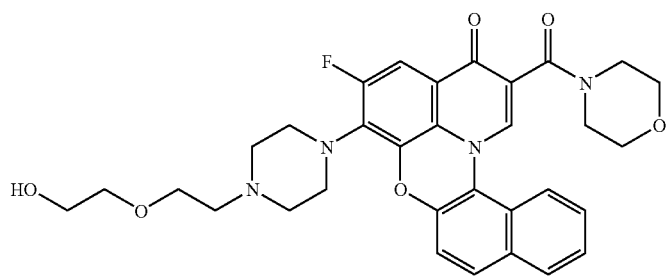 |

TABLE 3-continued
944 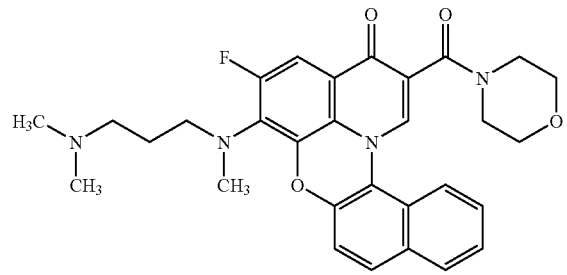
945 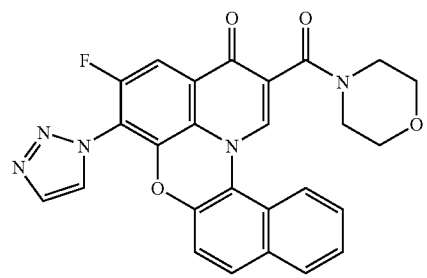
946 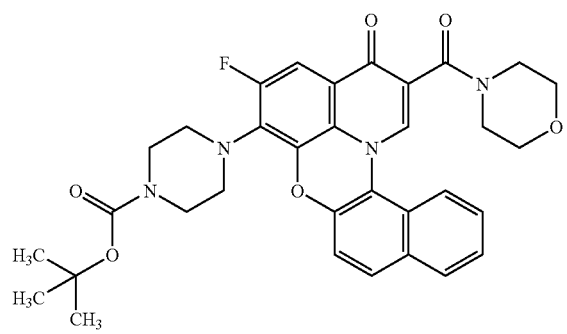
947 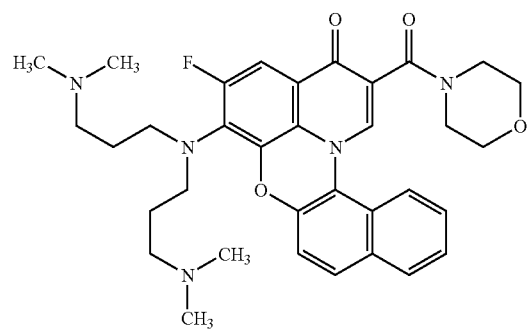
948 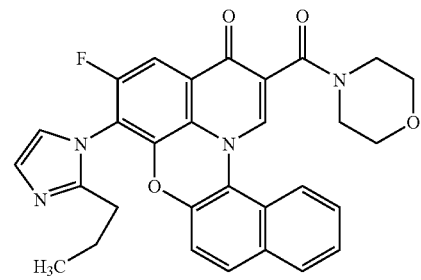

TABLE 3-continued
949 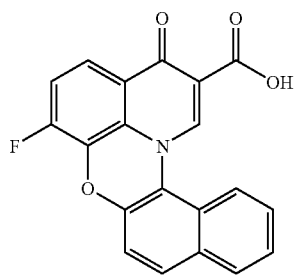
950 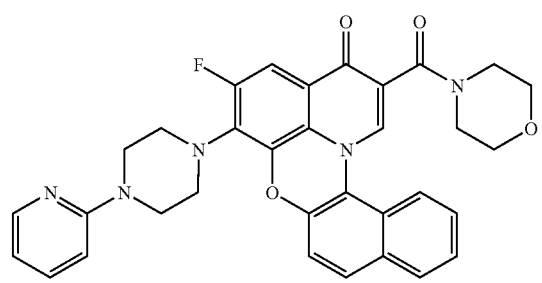
951 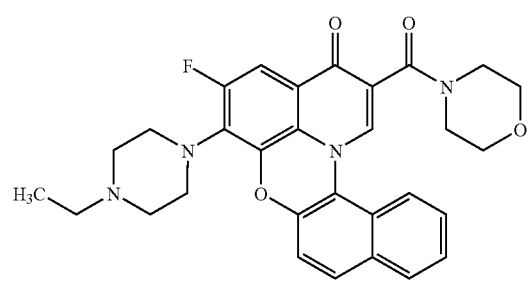
952 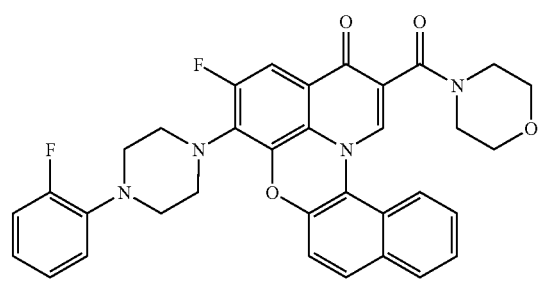
953 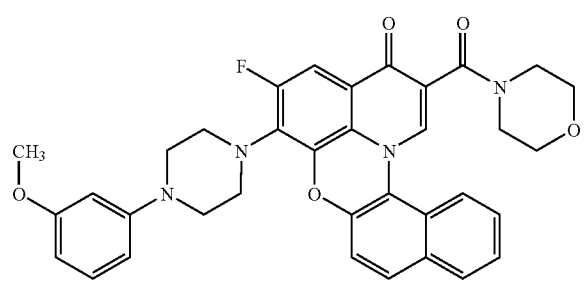

TABLE 3-continued
| 954 | 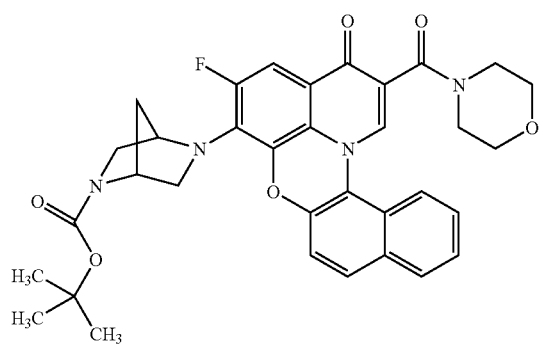 |
| 955 | 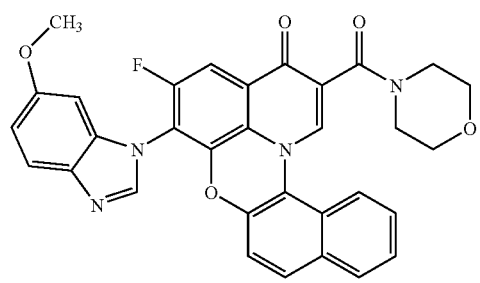 |
| 956 | 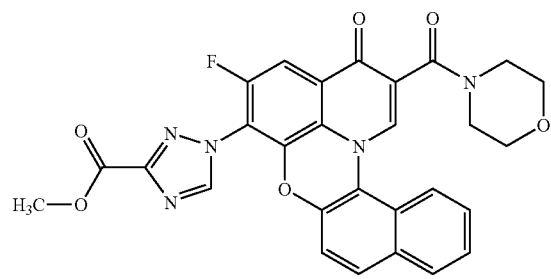 |
| 957 | 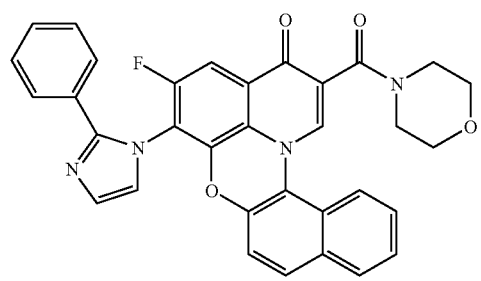 |
| 958 | 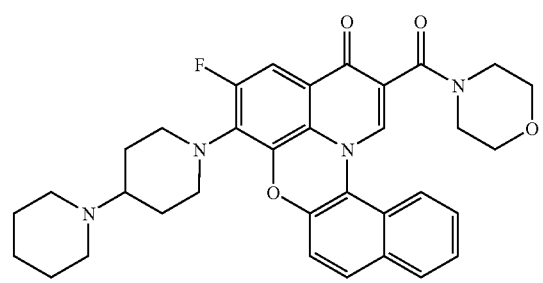 |

TABLE 3-continued
| 959 | 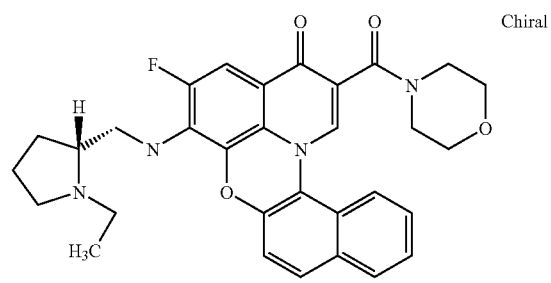 Chiral |
| 960 | 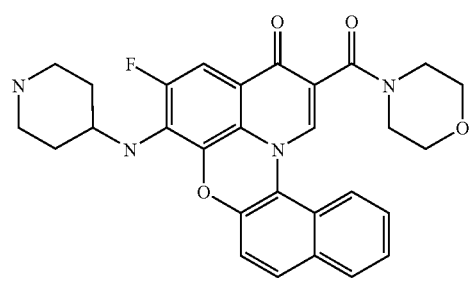 |
| 961 | 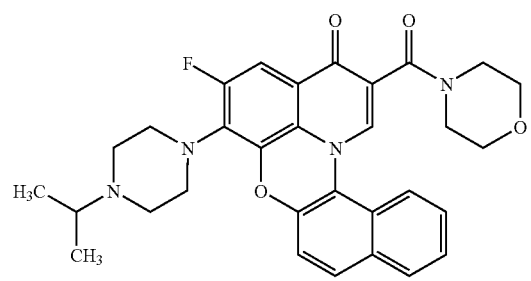 |
| 962 | 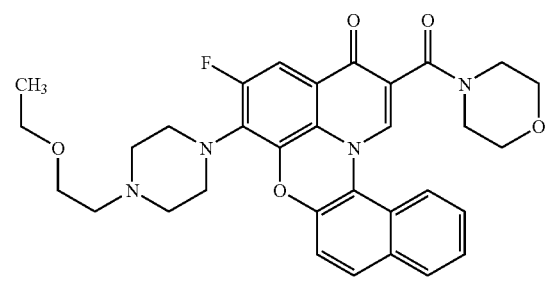 |
| 963 | 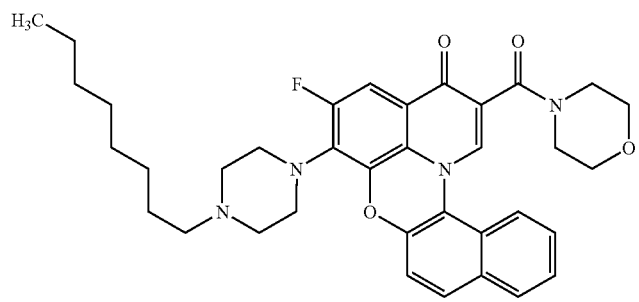 |

TABLE 3-continued
964
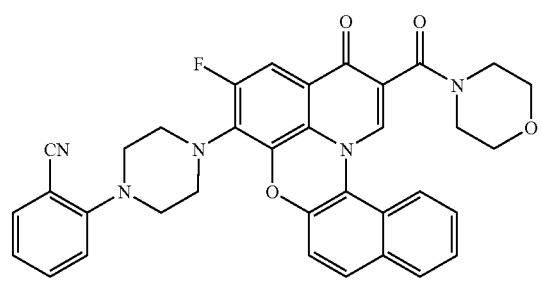
965
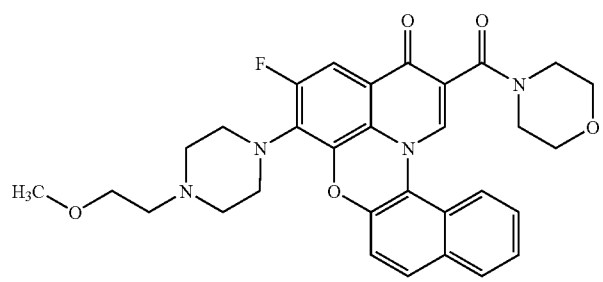
966
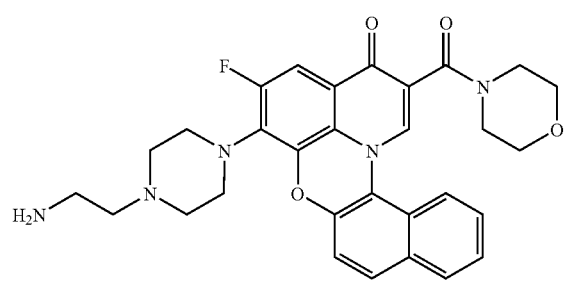
967
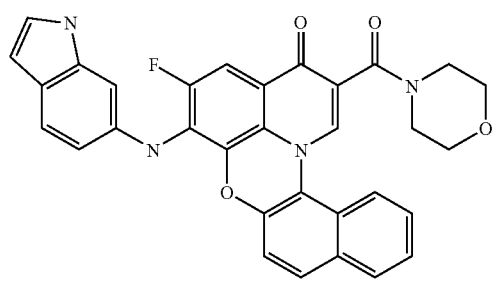
968
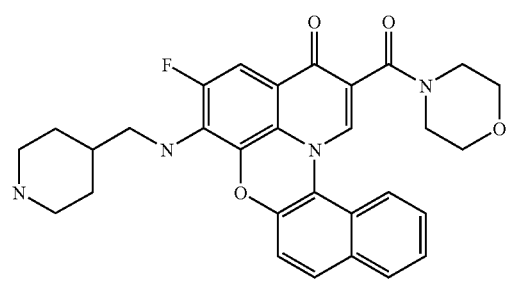

TABLE 3-continued
969
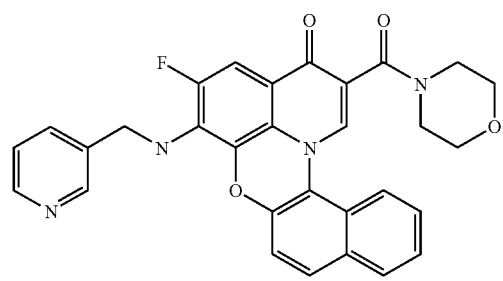
970
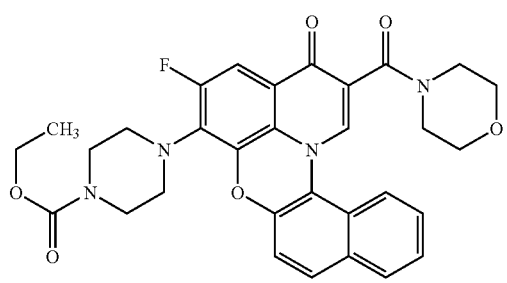
971
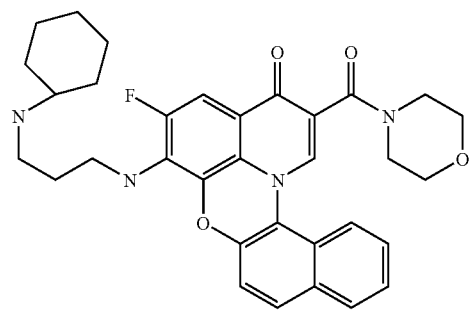
972
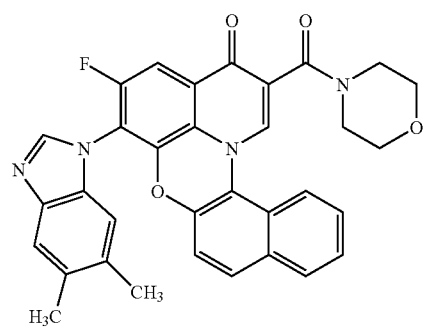
973
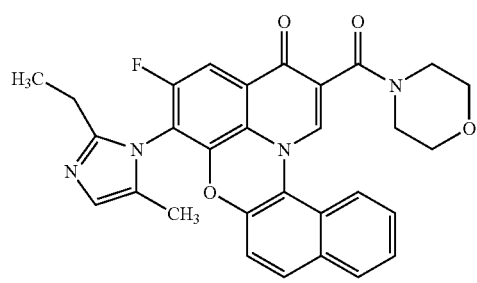

TABLE 3-continued
974
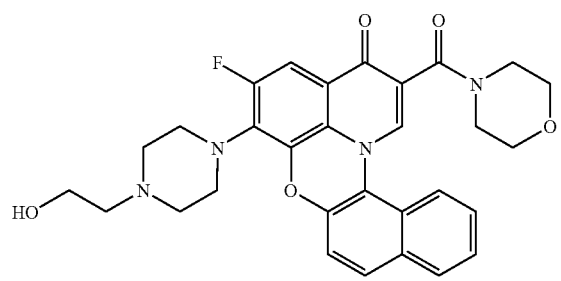
975
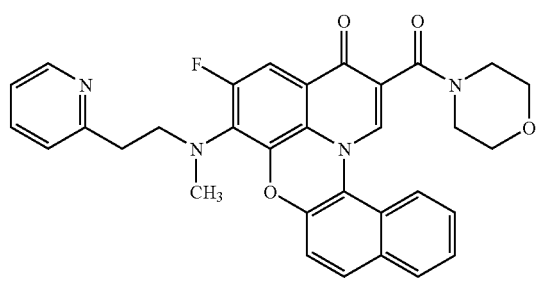
976
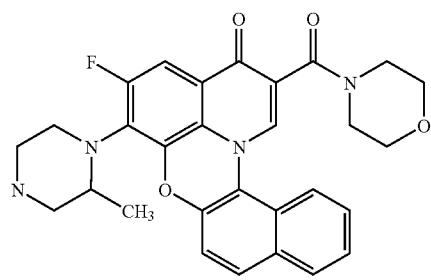
977
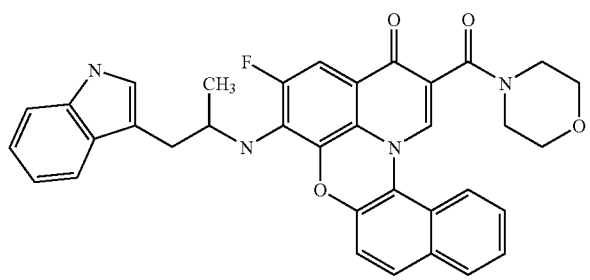
978
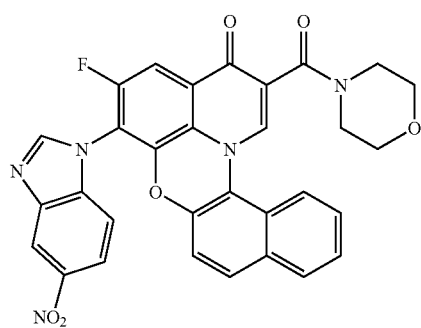

TABLE 3-continued
| 979 | 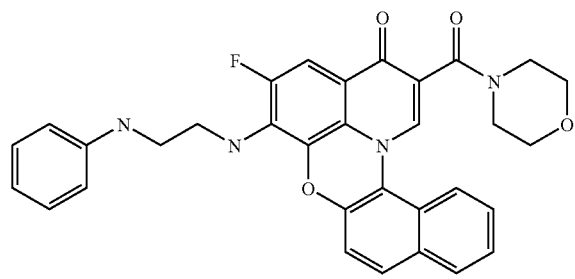 |
| --- | --- |
| 980 | 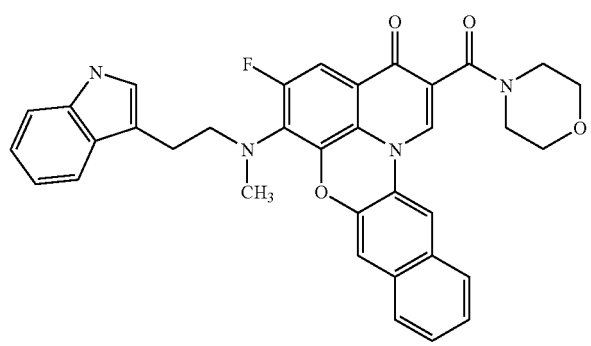 |
| 981 | 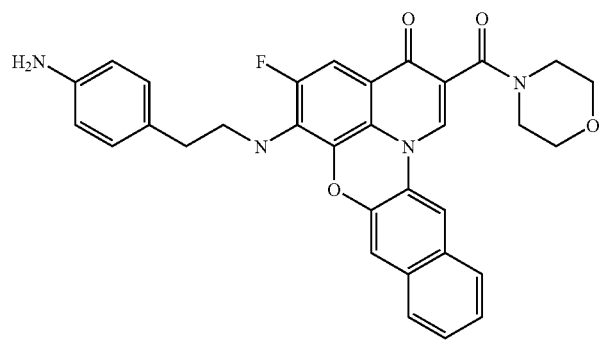 |
| 982 | 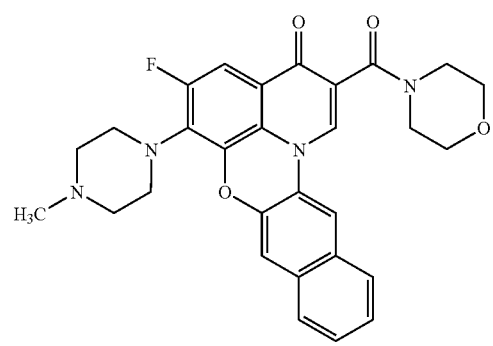 |

TABLE 3-continued
983 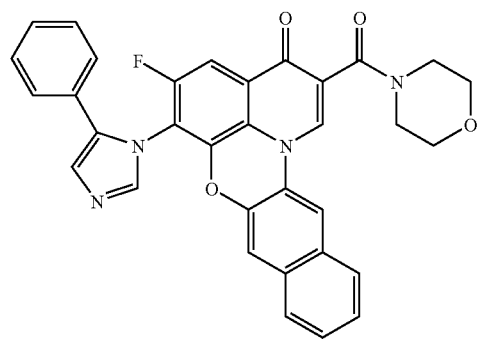
984 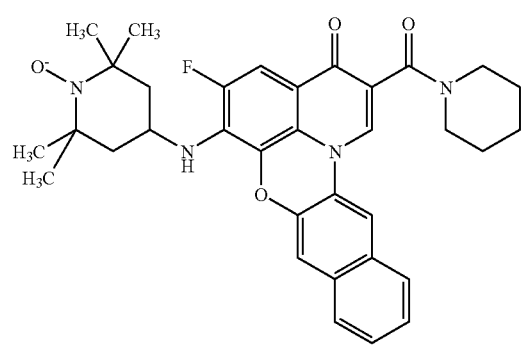
985 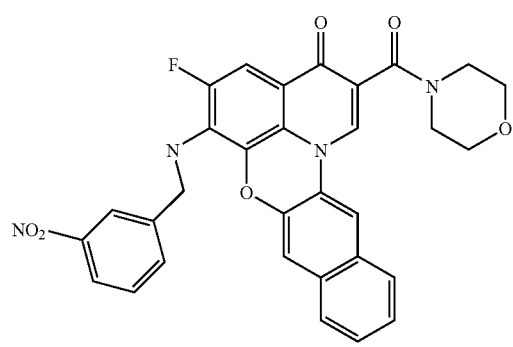
986 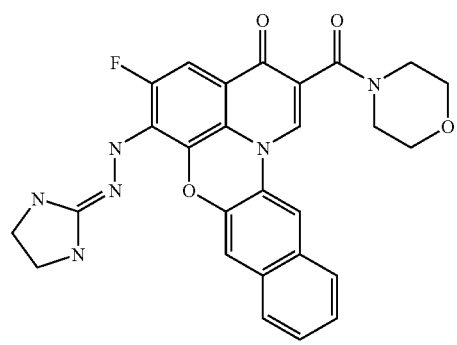

TABLE 3-continued
| 987 | 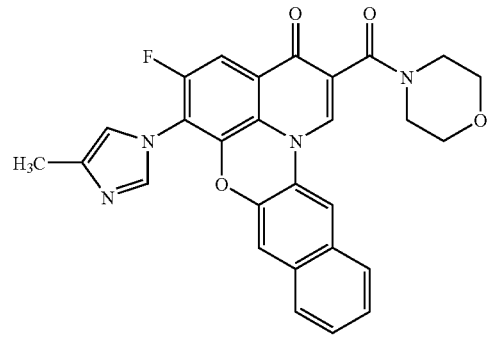 |
| --- | --- |
| 988 | 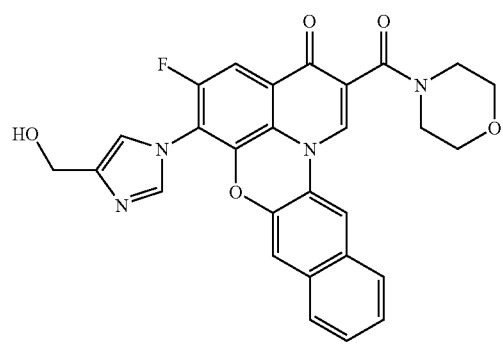 |
| 989 | 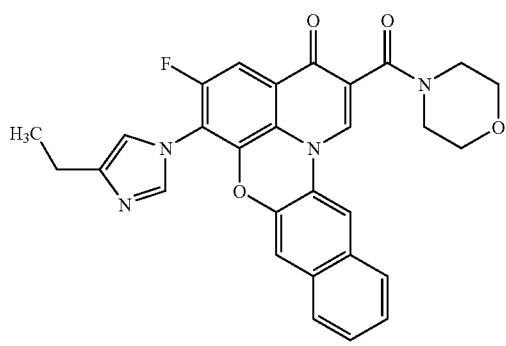 |
| 990 | 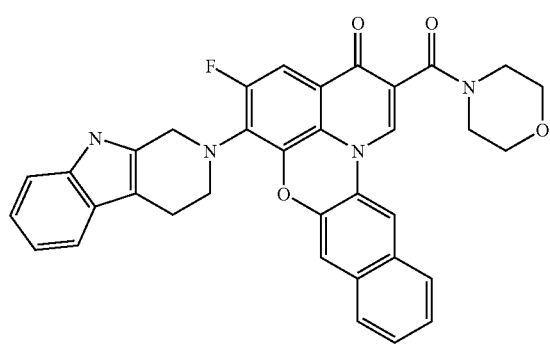 |

TABLE 3-continued
991 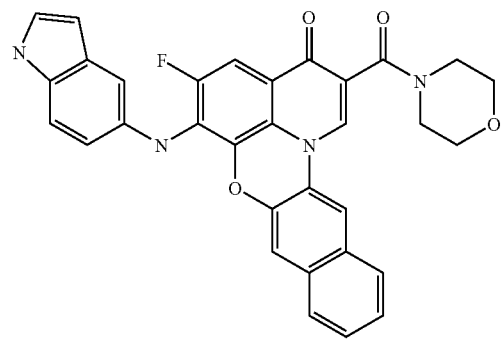
992 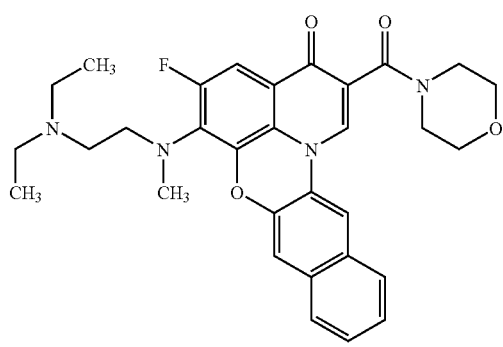
993 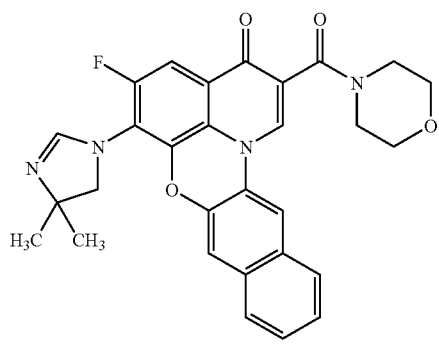
994 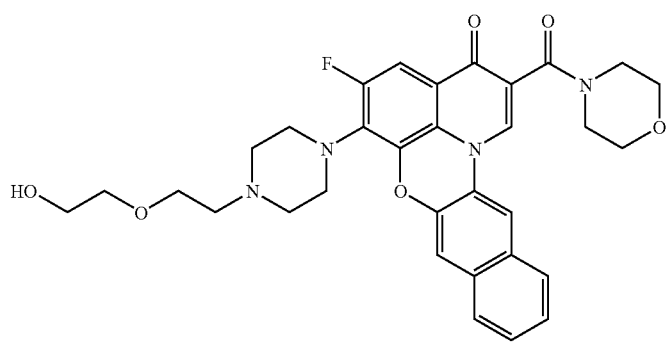

TABLE 3-continued
995 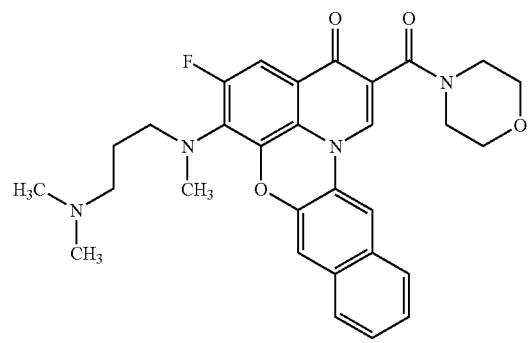
996 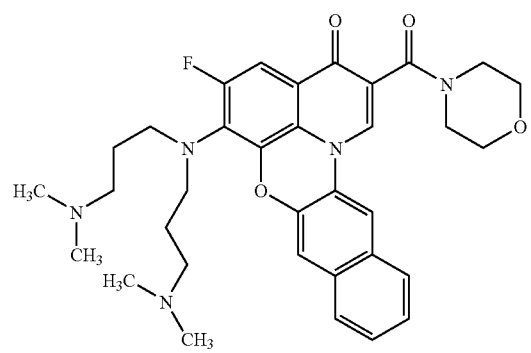
997 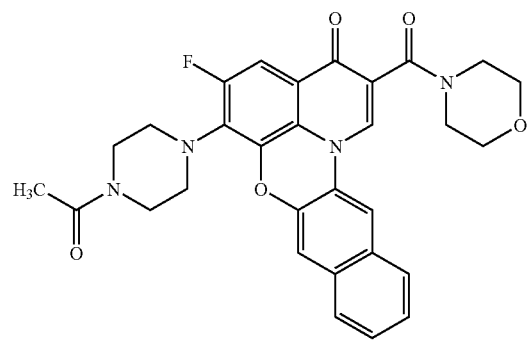
998 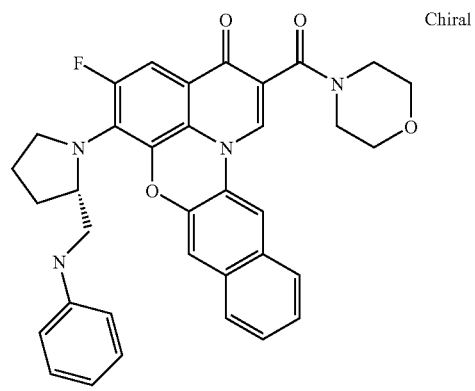

TABLE 3-continued
999
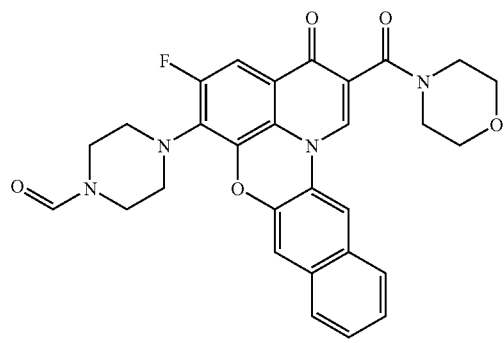
1000
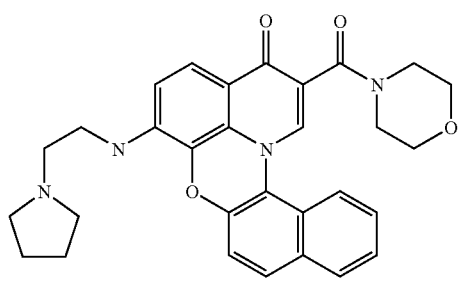
1001
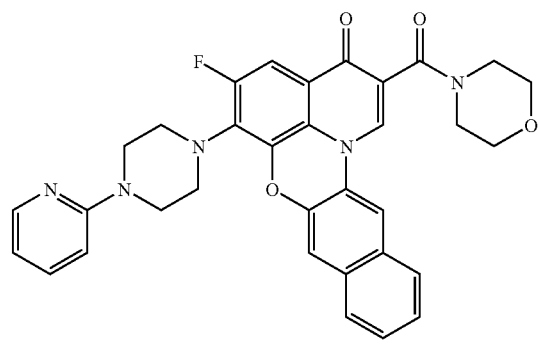
1002
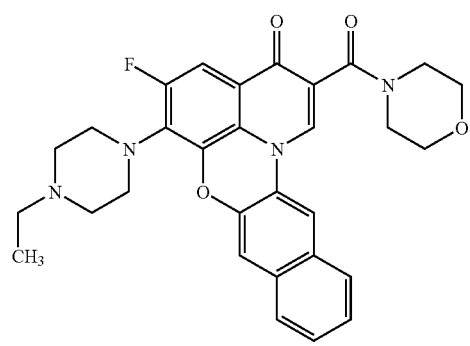

TABLE 3-continued
1003 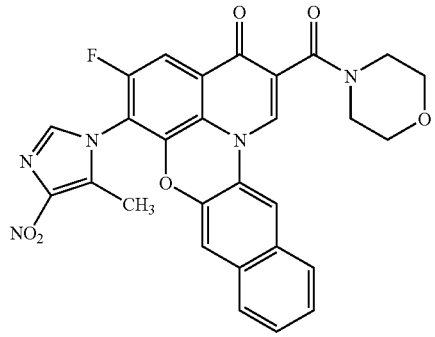
1004 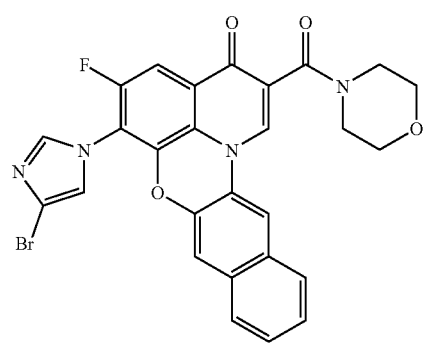
1005 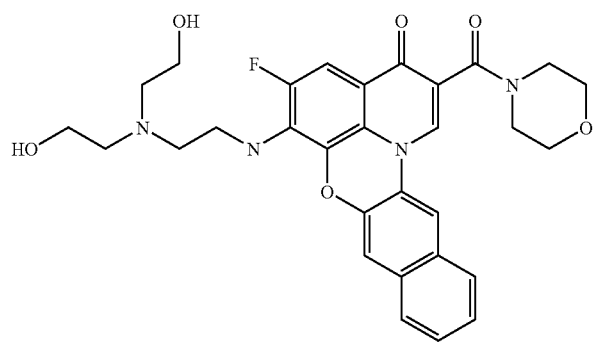
1006 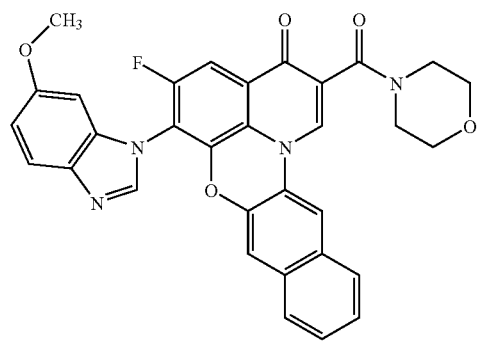

TABLE 3-continued
1007 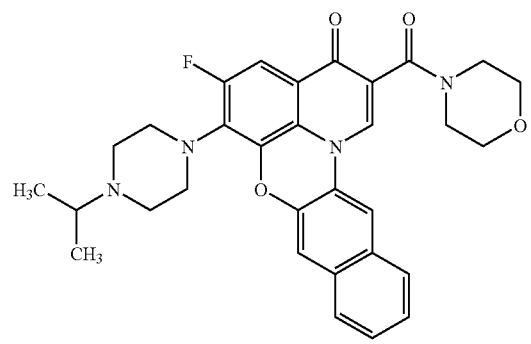
1008 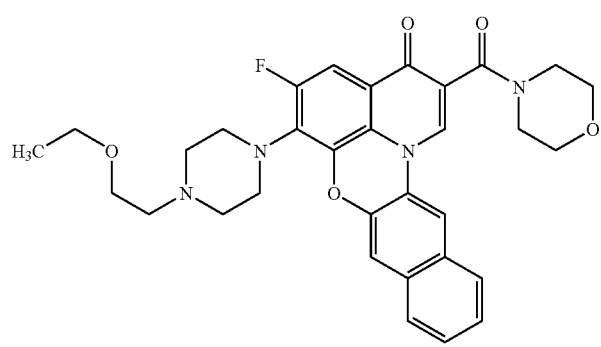
1009 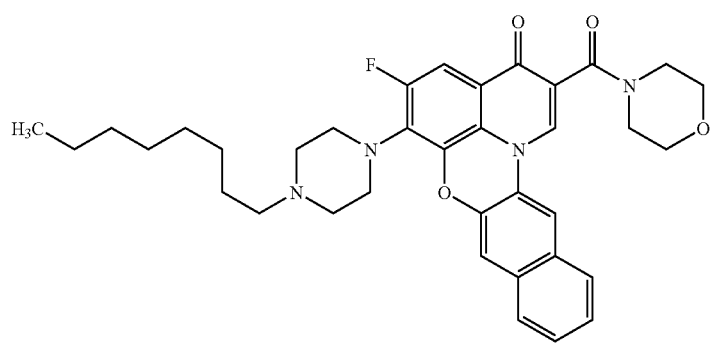
1010 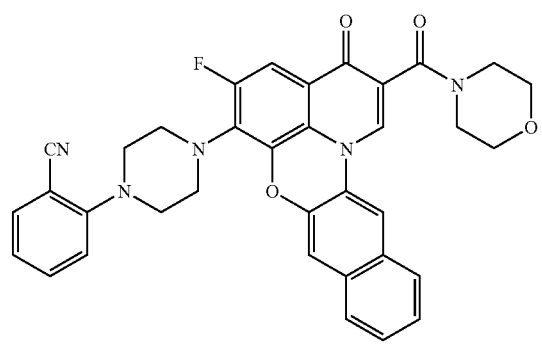

TABLE 3-continued
1011 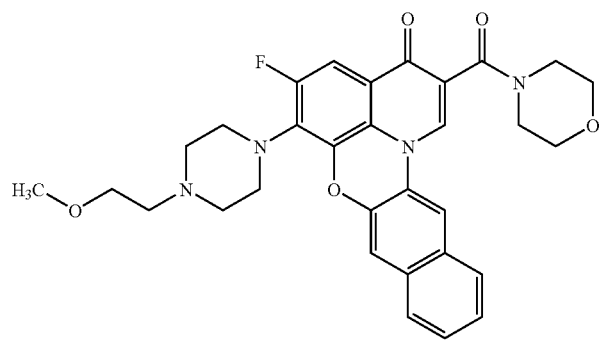
1012 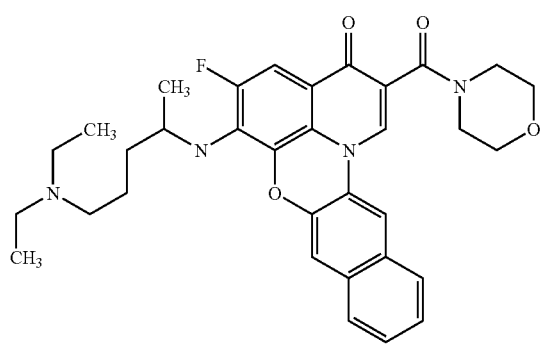
1013 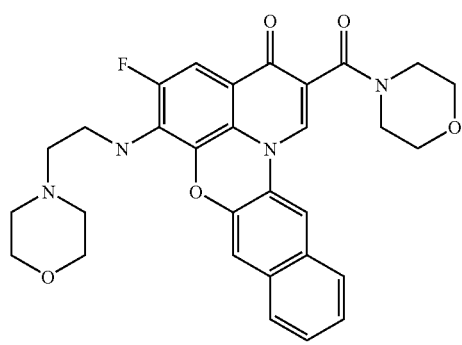
1014 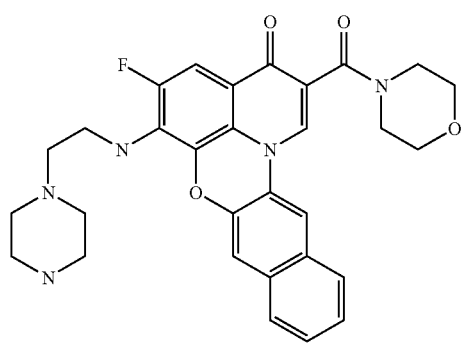

TABLE 3-continued
1015
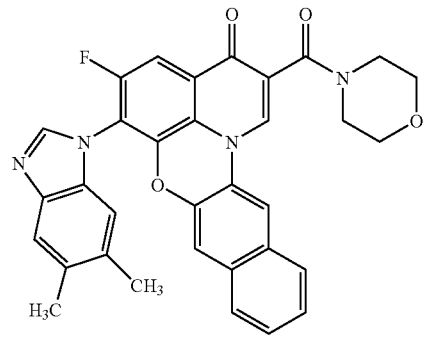
1016
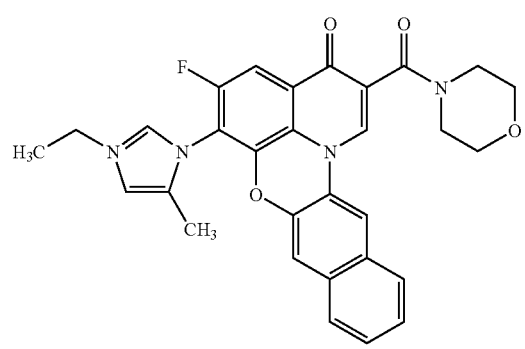
1017
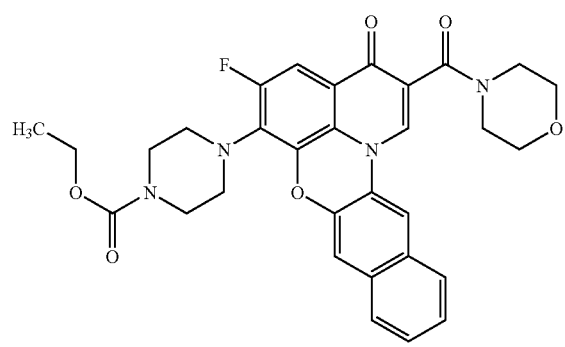
1018
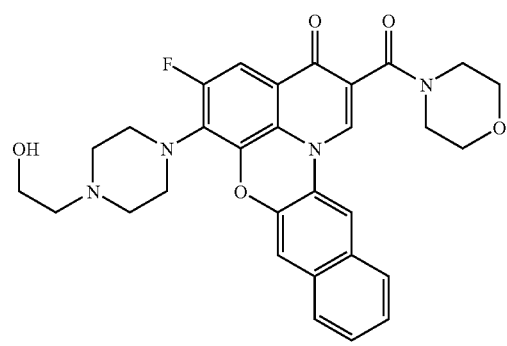

TABLE 3-continued
1019
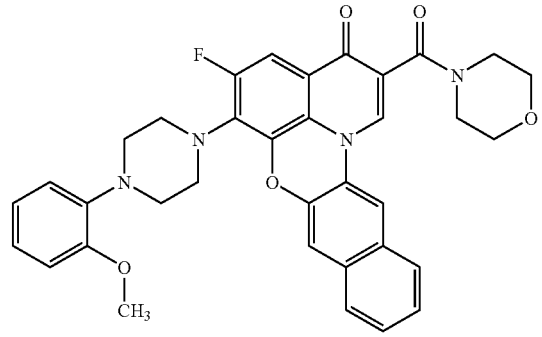
1020
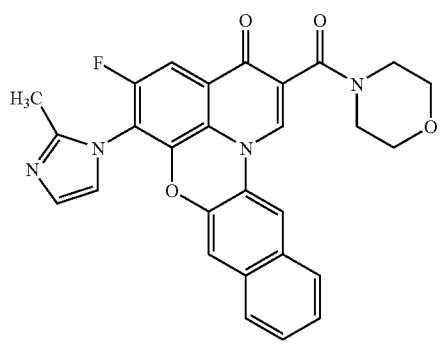
1021
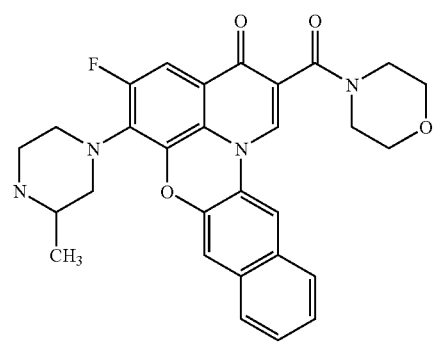
1022
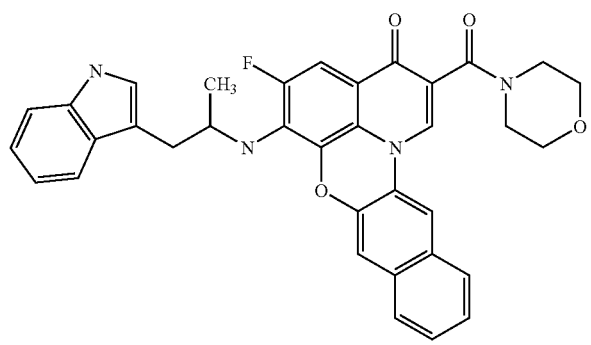

TABLE 3-continued
1023 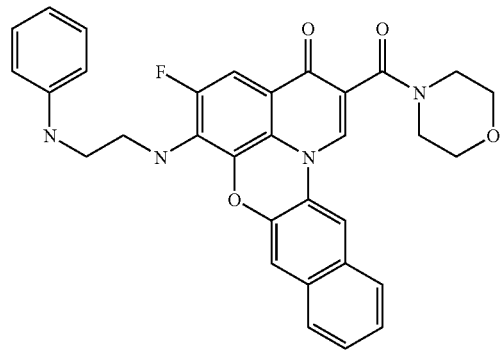
1024 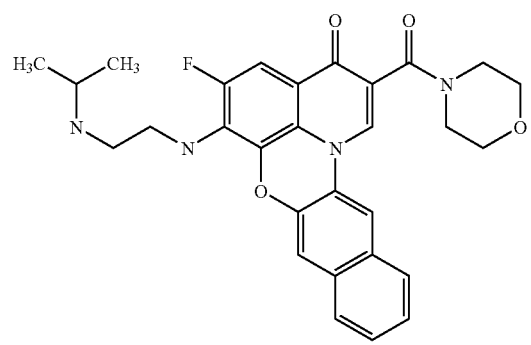
1025 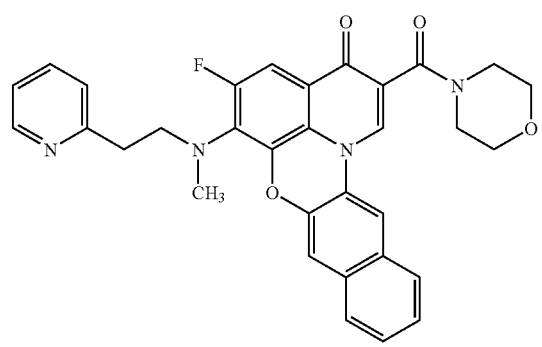
1026 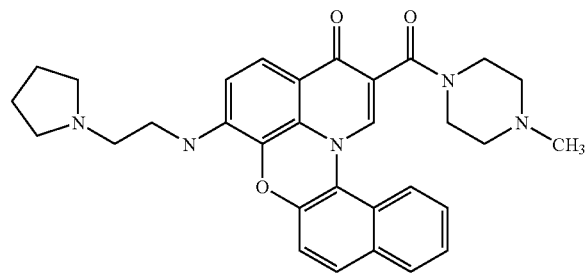
1027 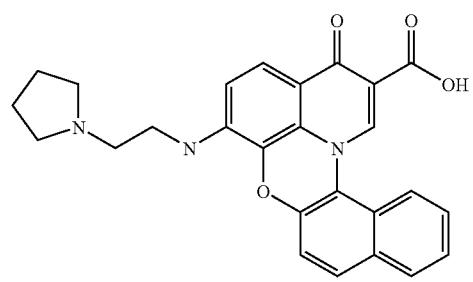

TABLE 3-continued
1028 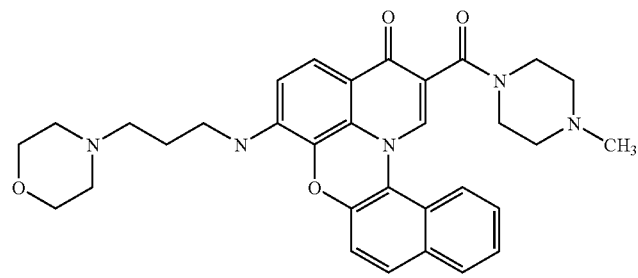
1029 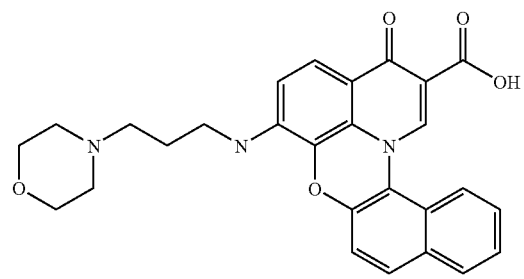
1030 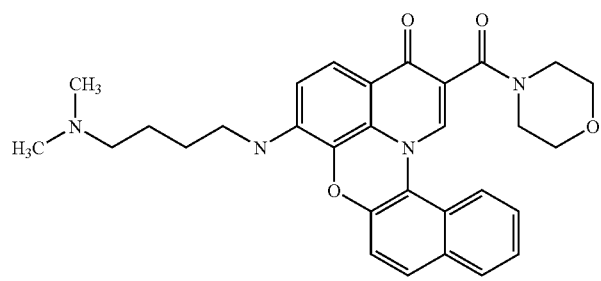
1031 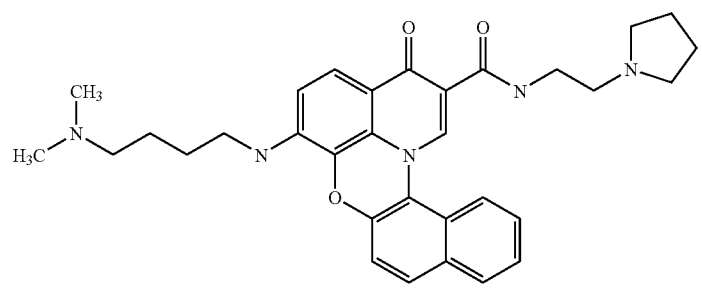
1032 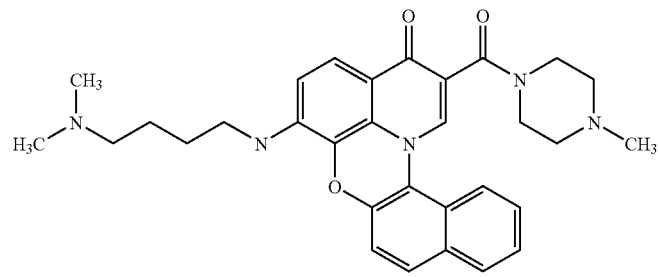

TABLE 3-continued
1033 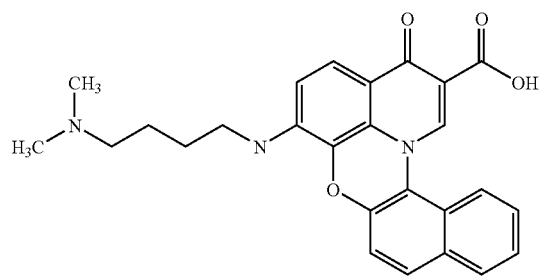
1034 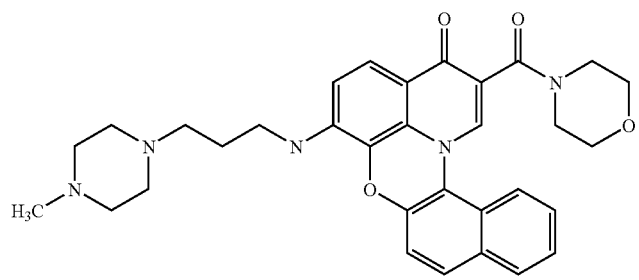
1035 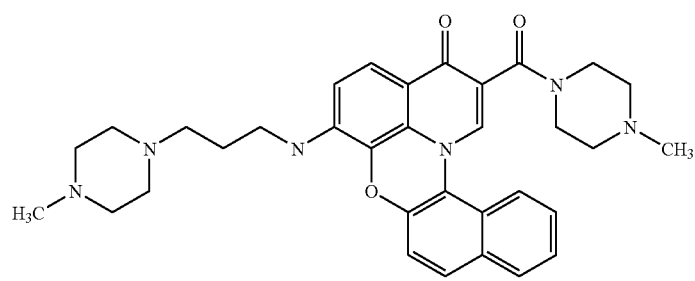
1036 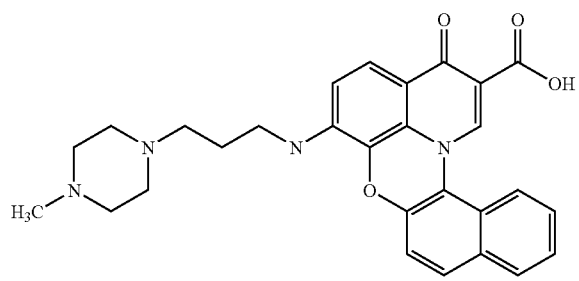
1037 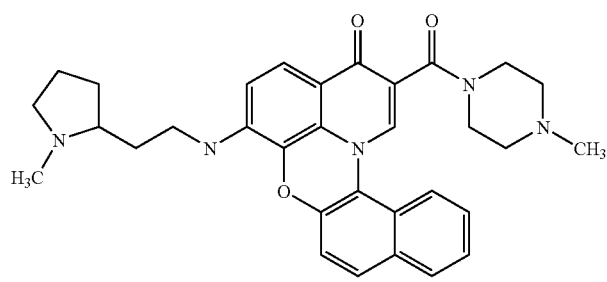

TABLE 3-continued
1038 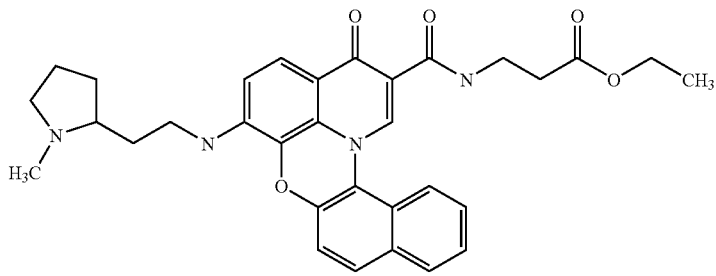
1039 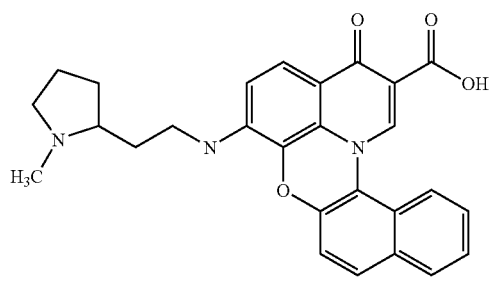
1040 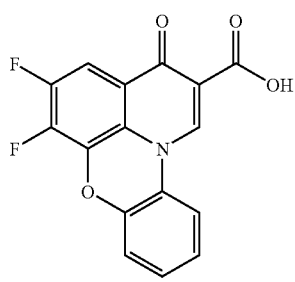
1041 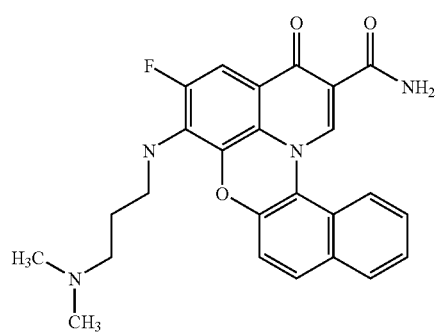
1042 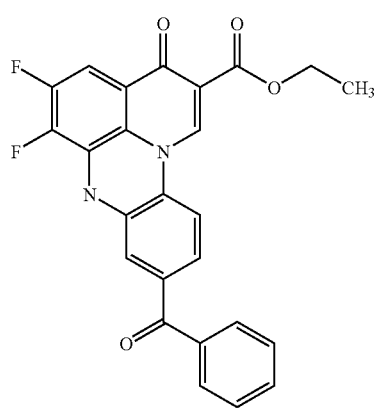

TABLE 3-continued
1043
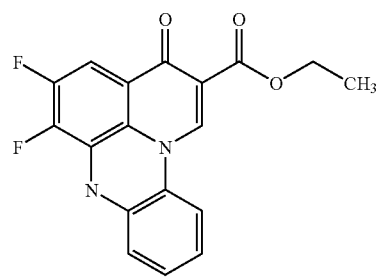
1044
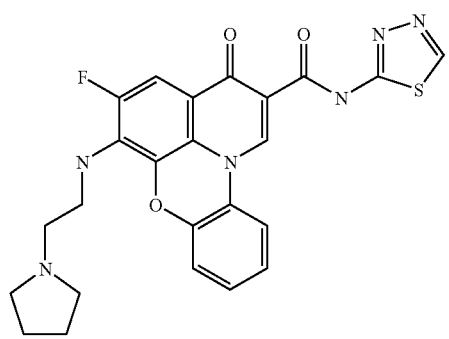
1045
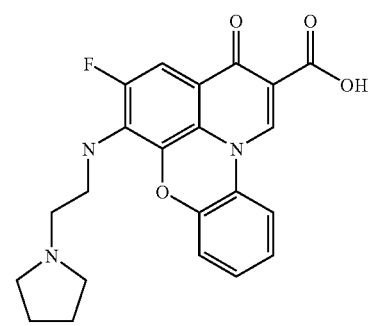
1046
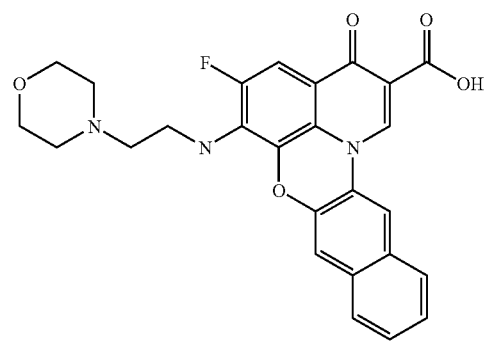
1047
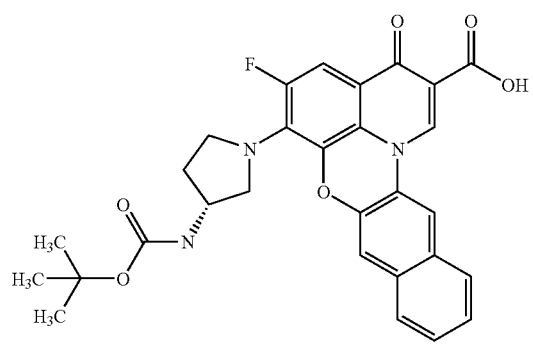

TABLE 3-continued
1048 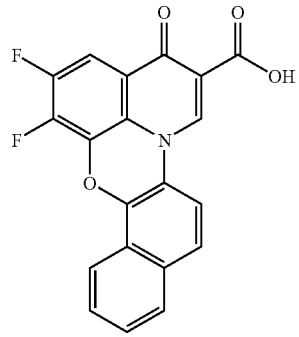
1049 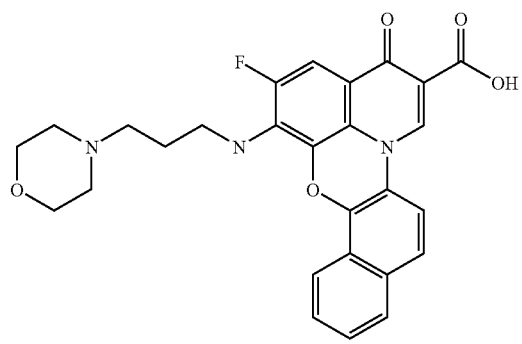
1050 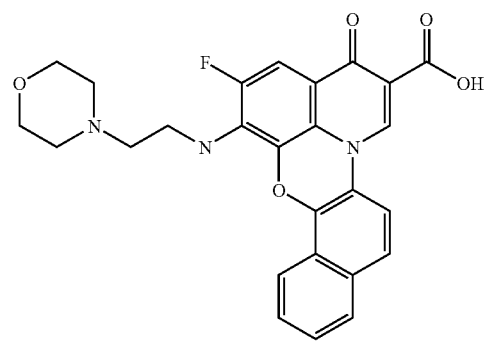
1051 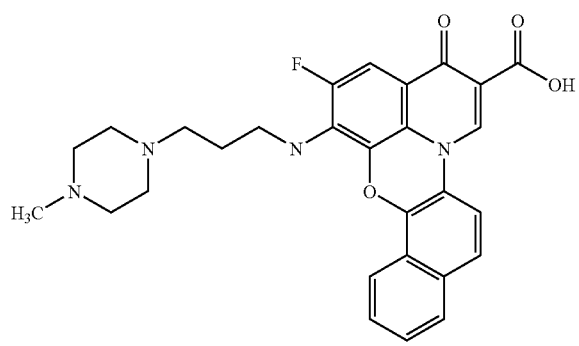

TABLE 3-continued
1052
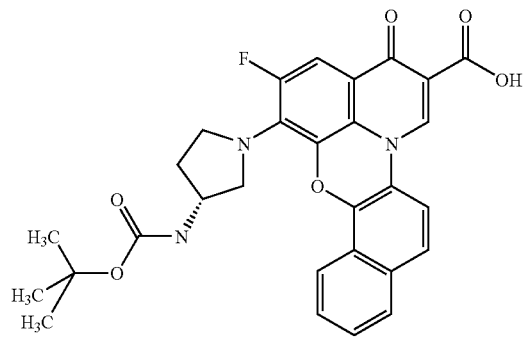
1053
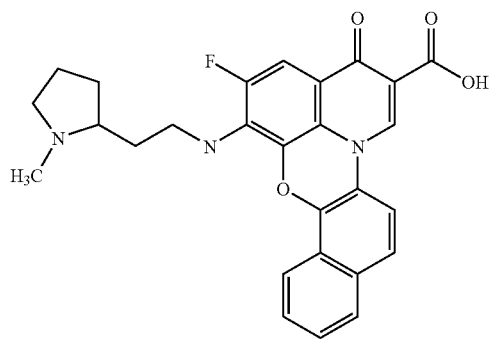
1054
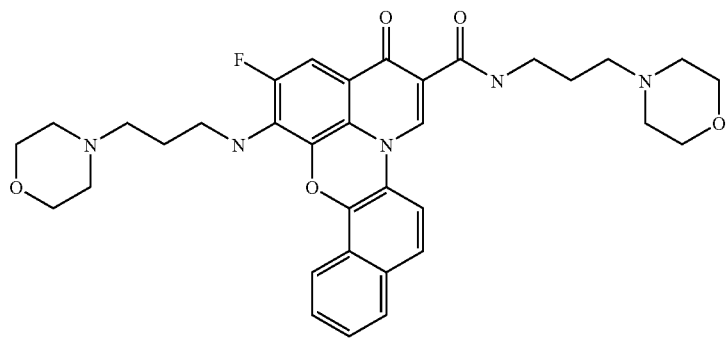
1055
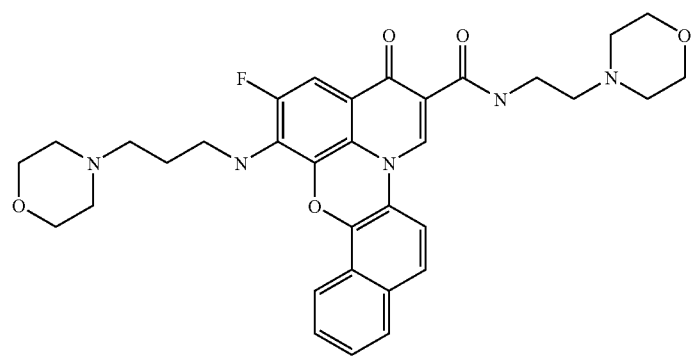

TABLE 3-continued
| 1056 | 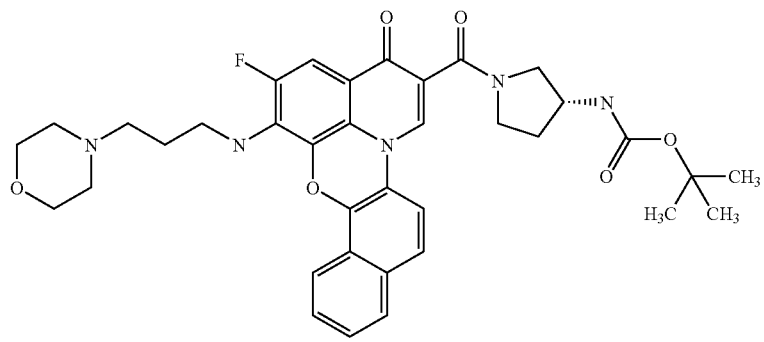 |
| --- | --- |
| 1057 | 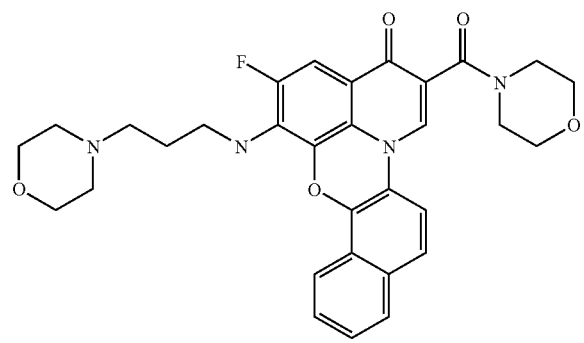 |
| 1058 | 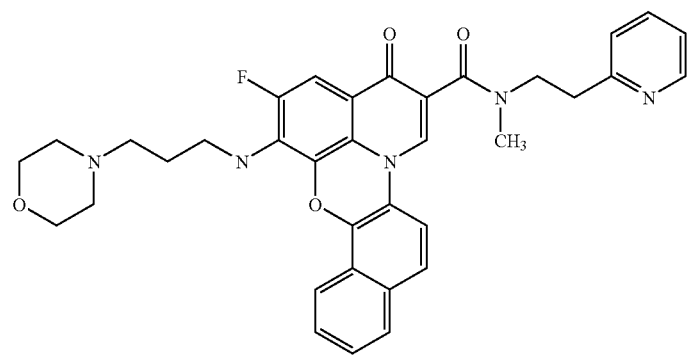 |
| 1059 | 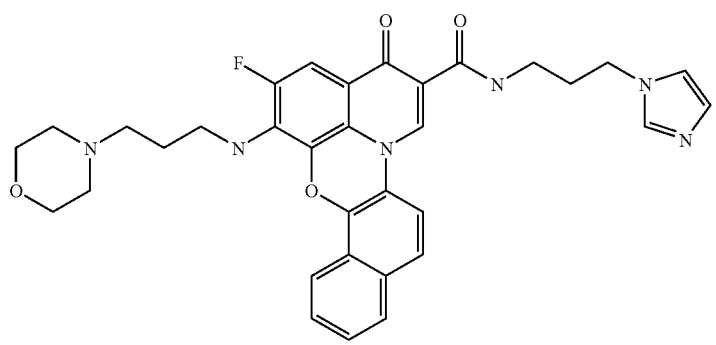 |

TABLE 3-continued
1060
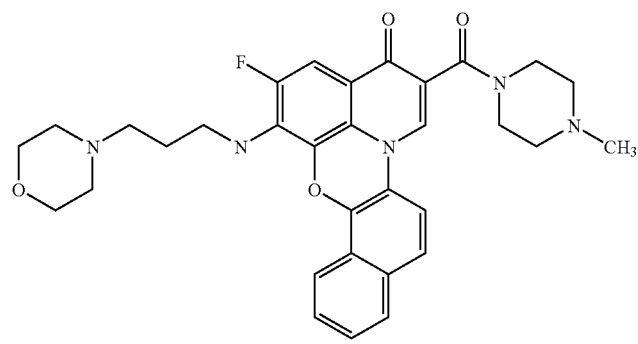
1061
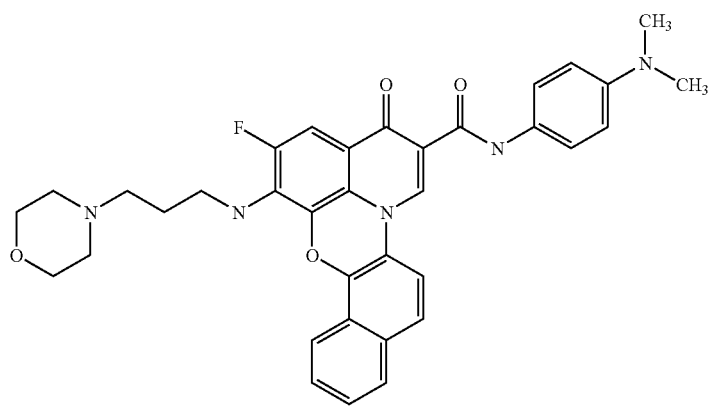
1062
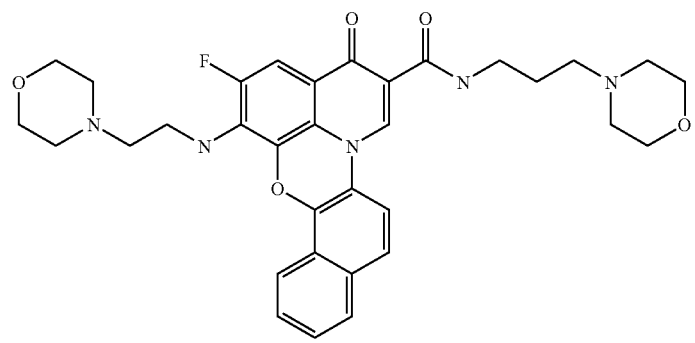
1063
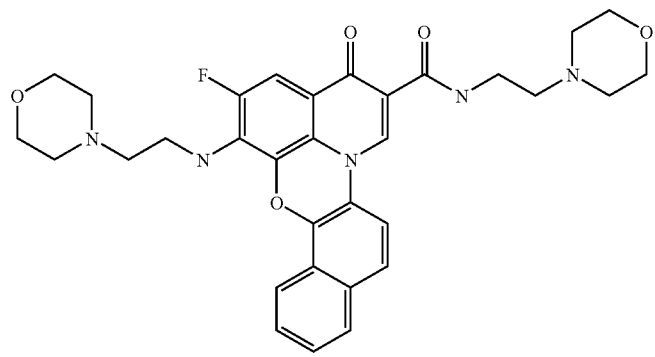

TABLE 3-continued
1064
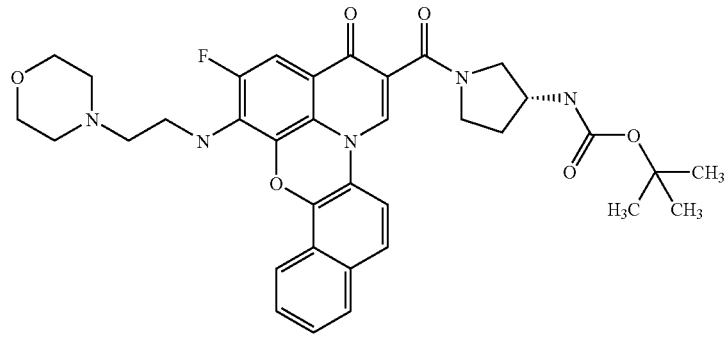
1065
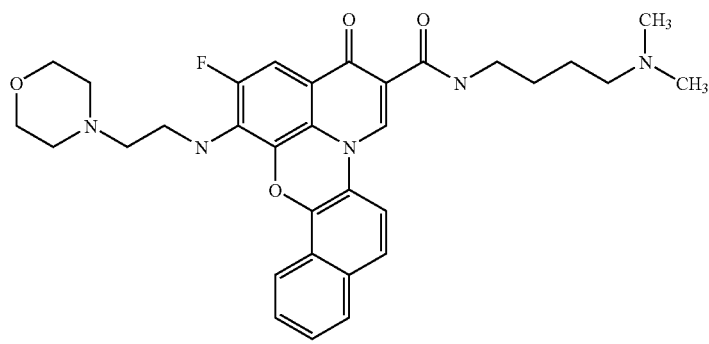
1066
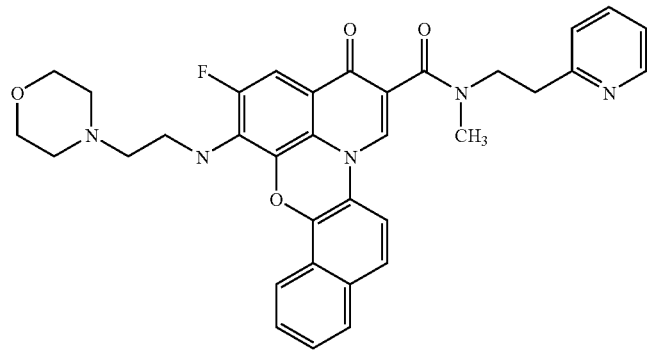
1067
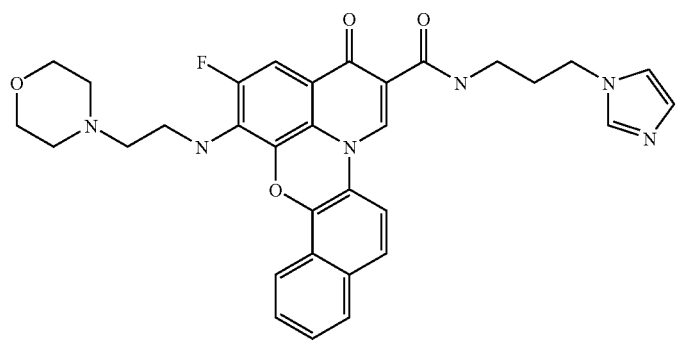

TABLE 3-continued
1068
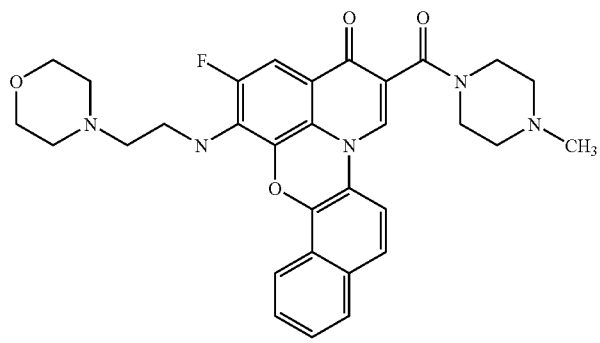
1069
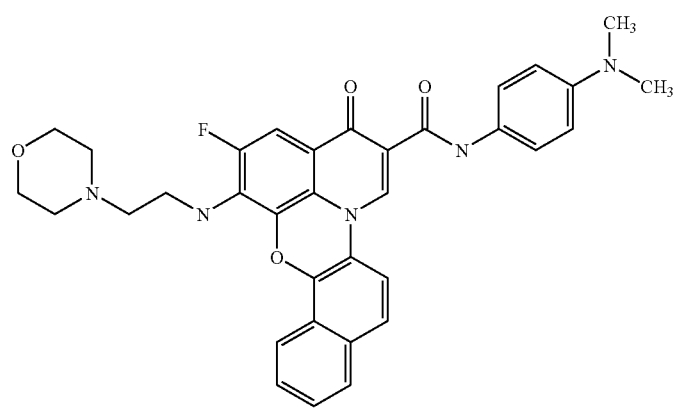
1070
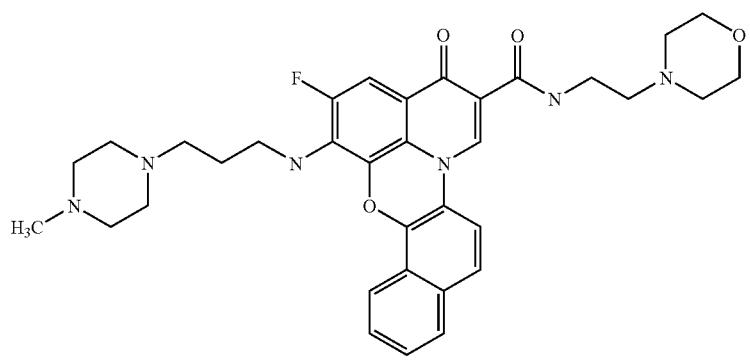
1071
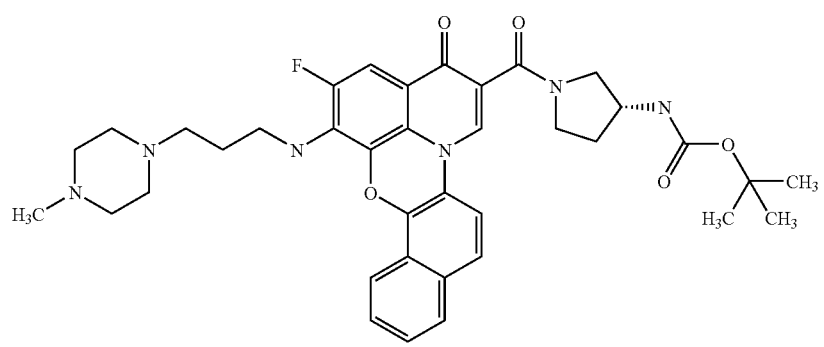

TABLE 3-continued
1072
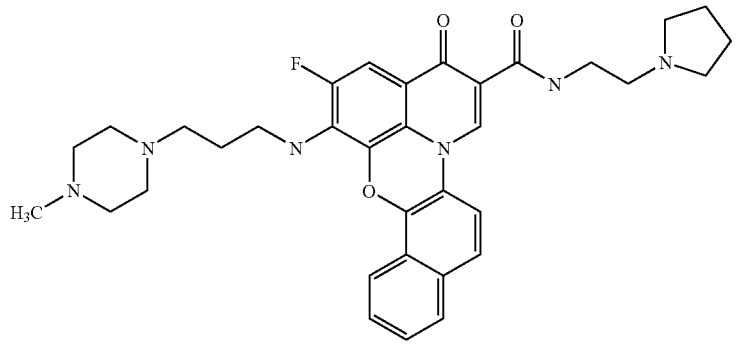
1073
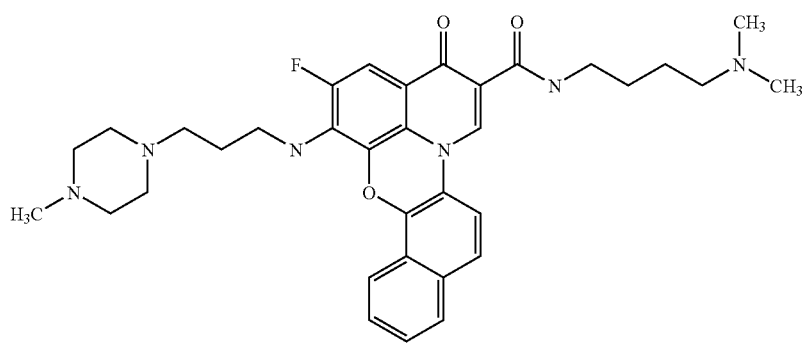
1074
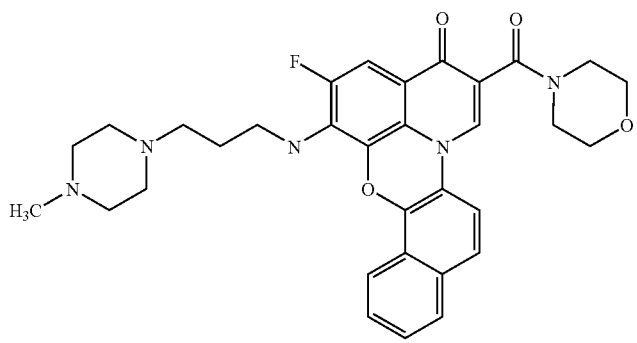
1075
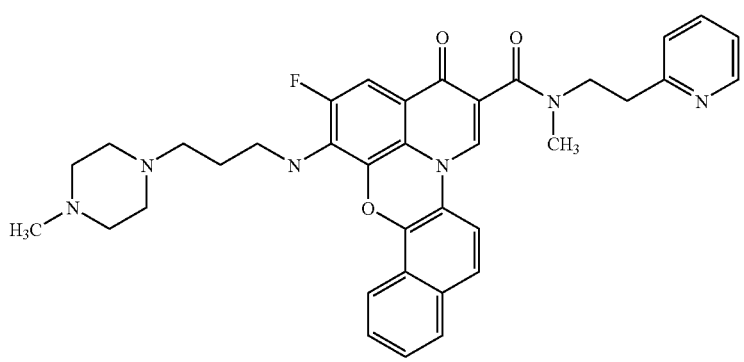

TABLE 3-continued
1076
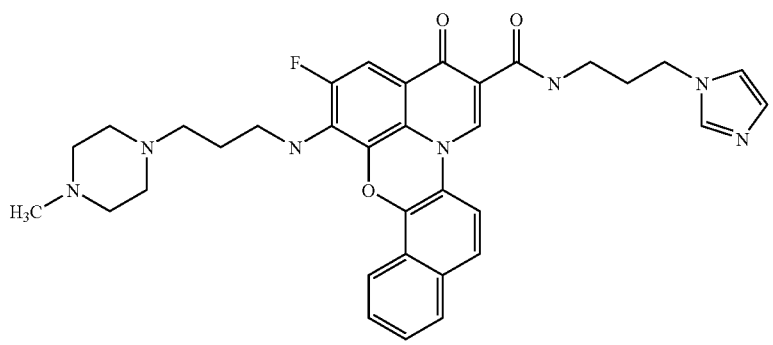
1077
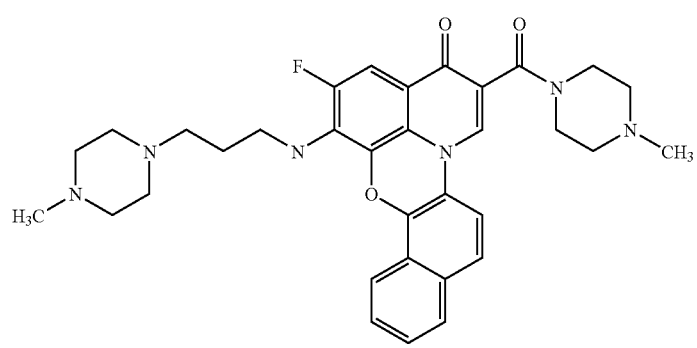
1078
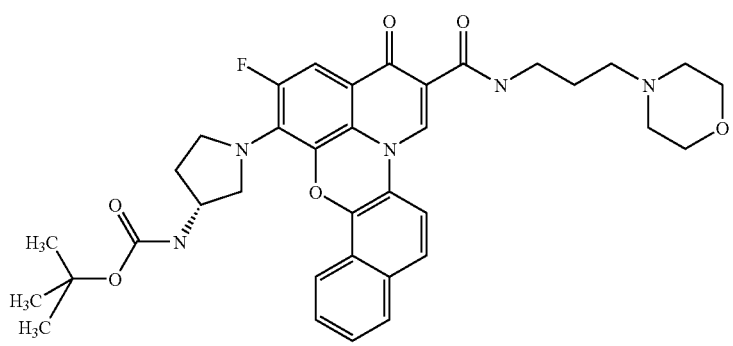
1079
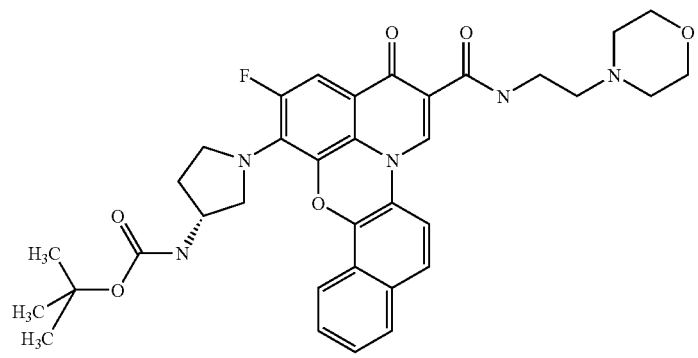

TABLE 3-continued
1080
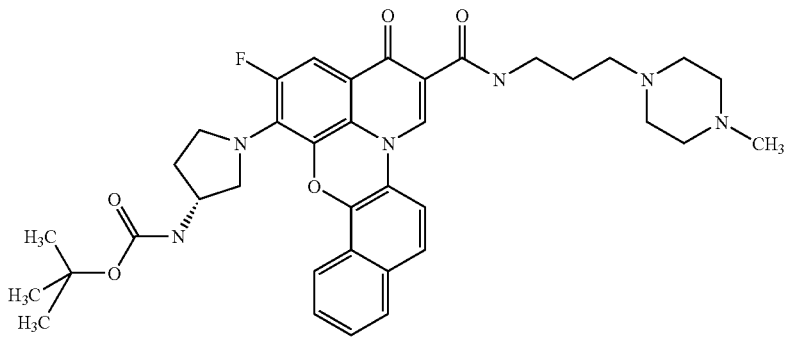
1081
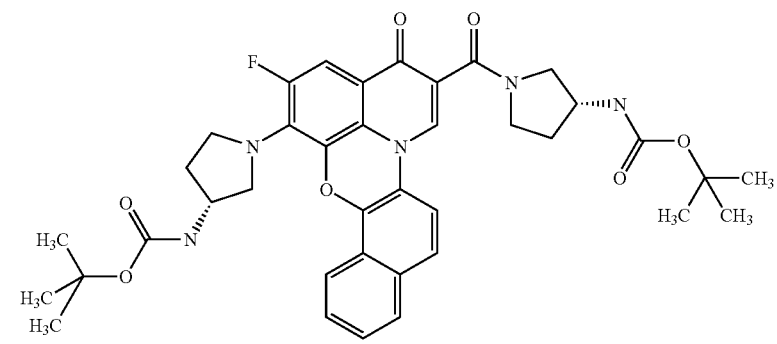
1082
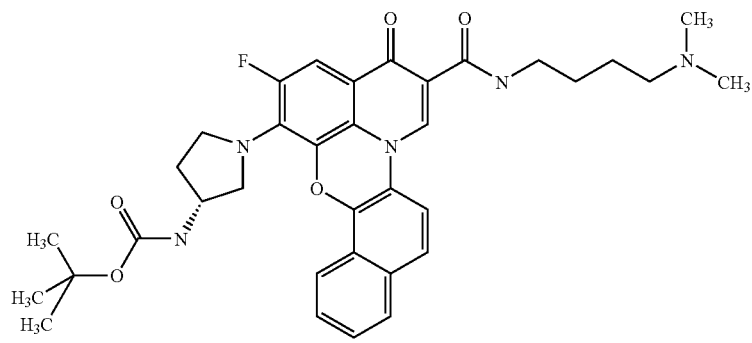
1083
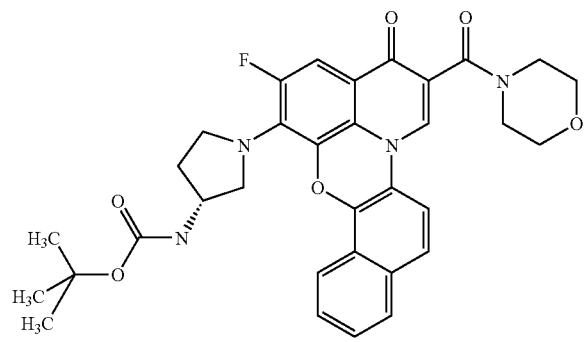

TABLE 3-continued
1084
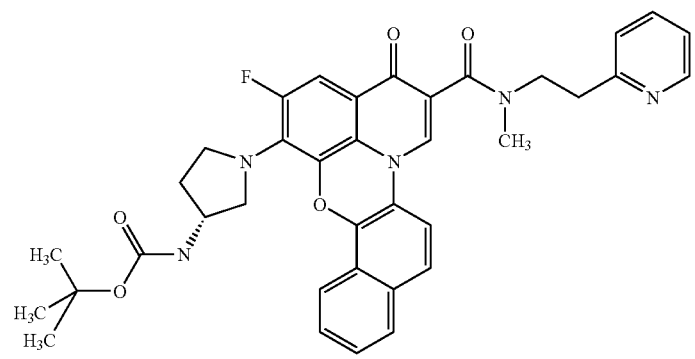
1085
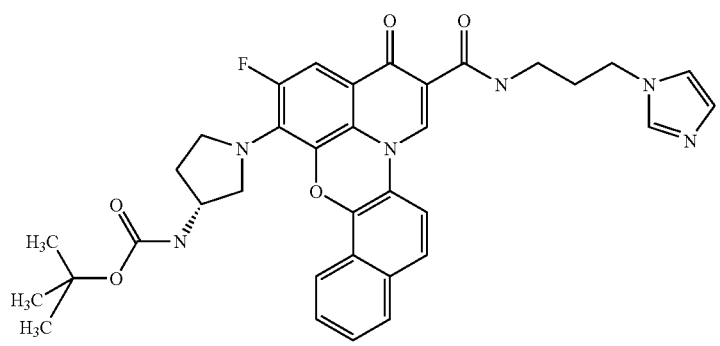
1086
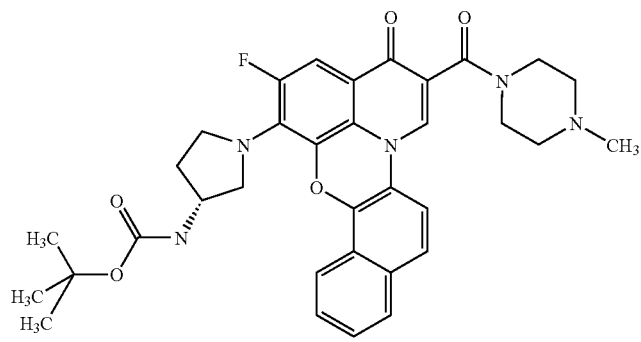
1087
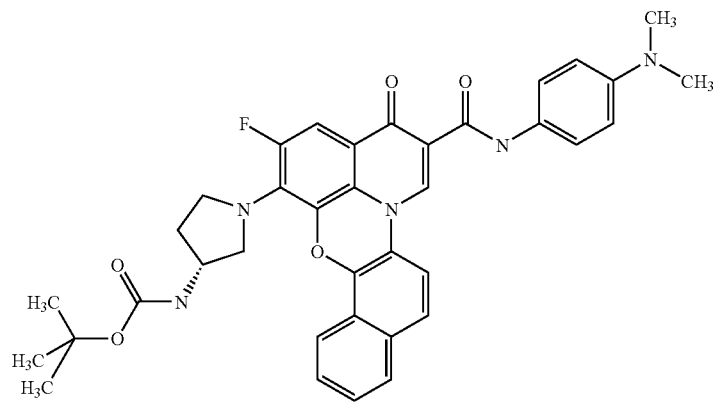

TABLE 3-continued
1088
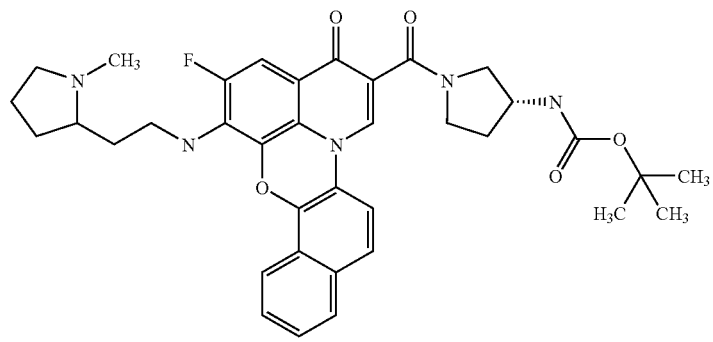
1089
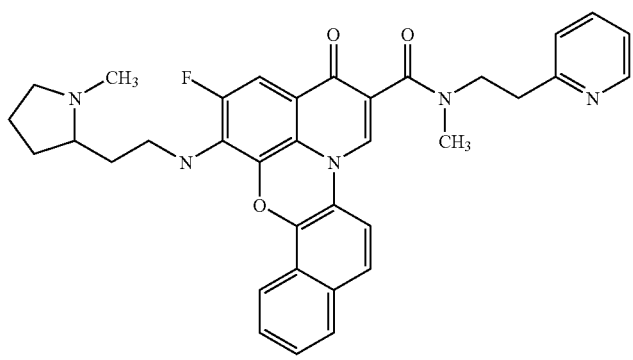
1090
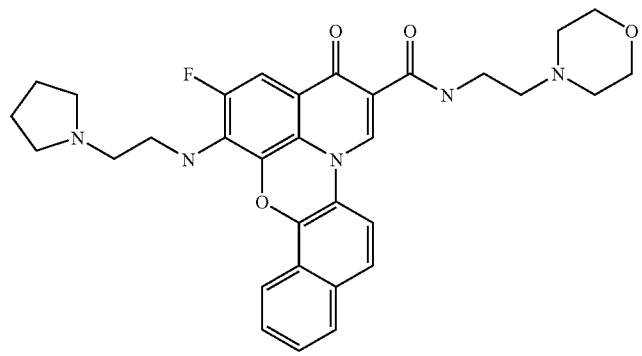
1091
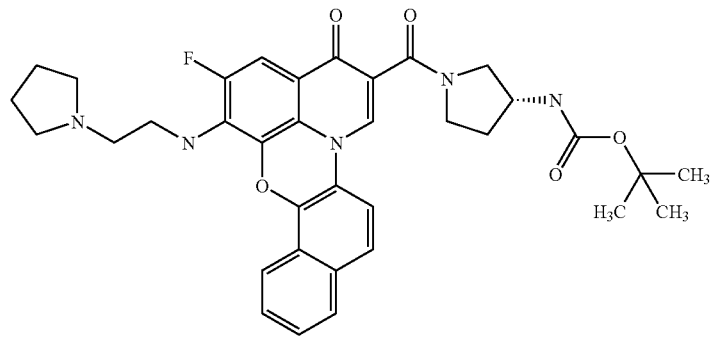

TABLE 3-continued
1092
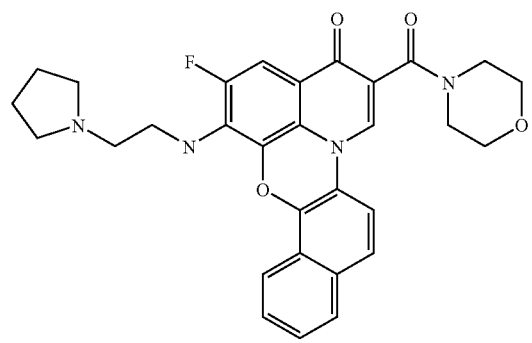
1093
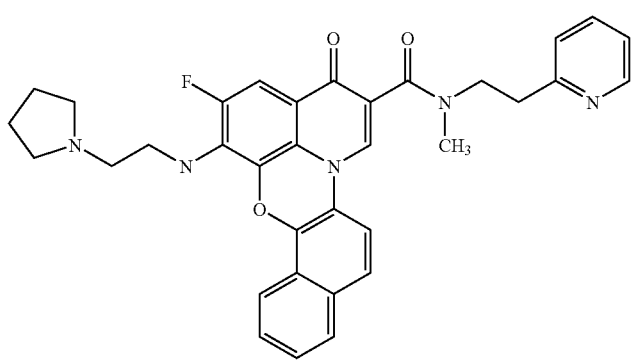
1094
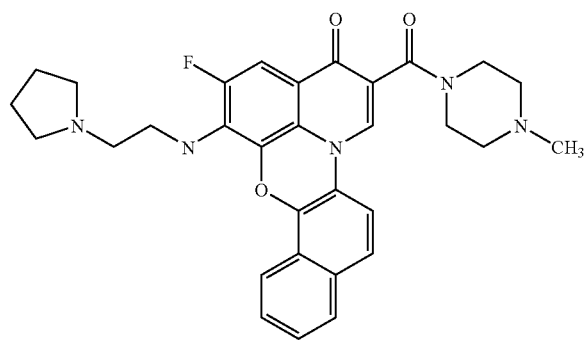
1095
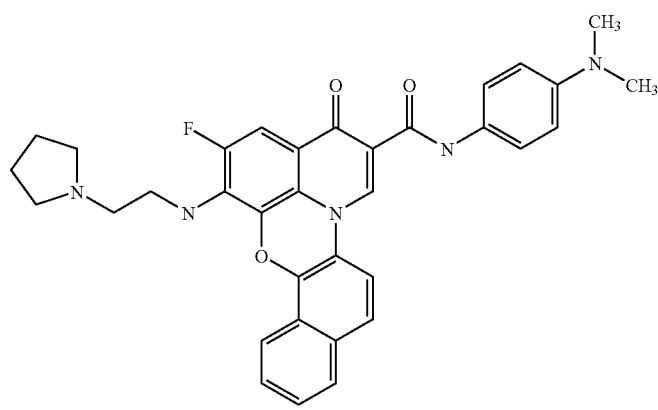

TABLE 3-continued
1096
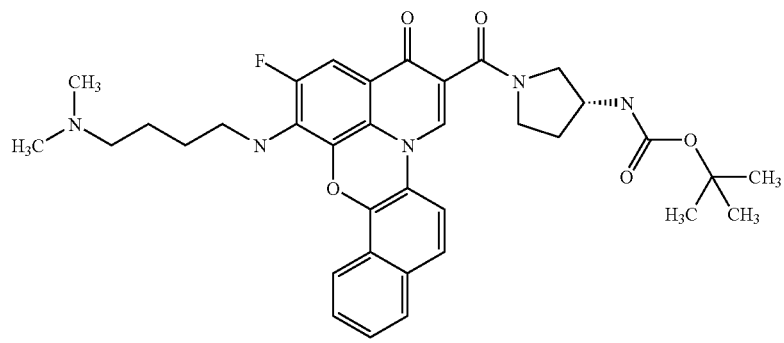
1097
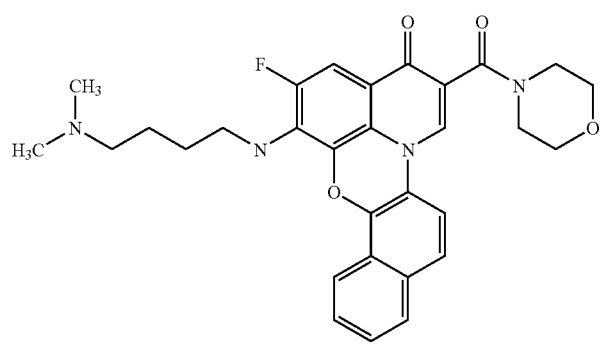
1098
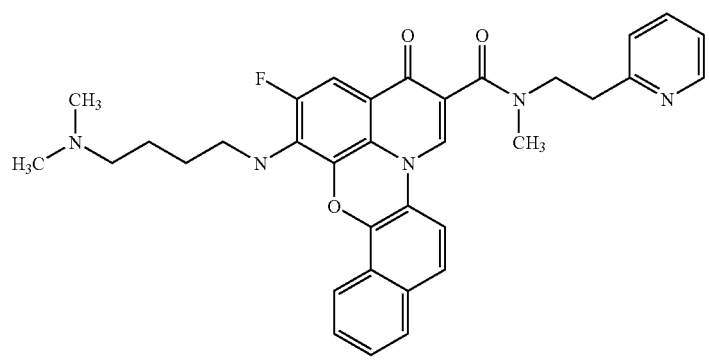
1099
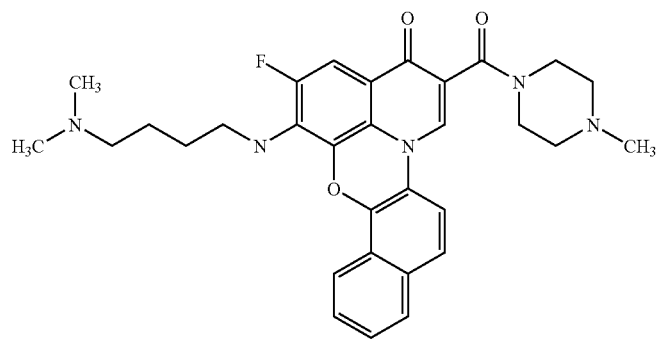

TABLE 3-continued
1100 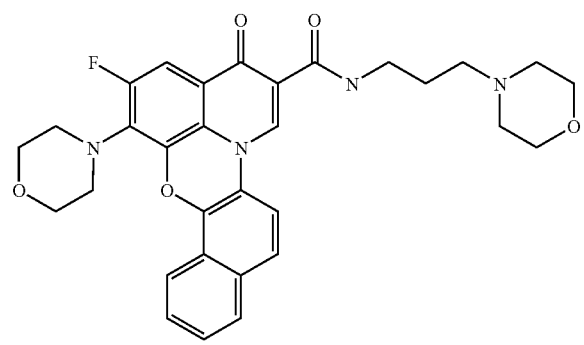
1101 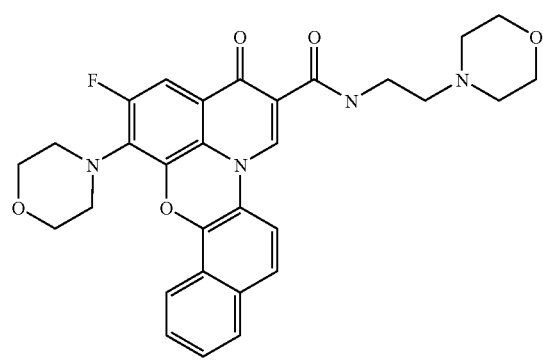
1102 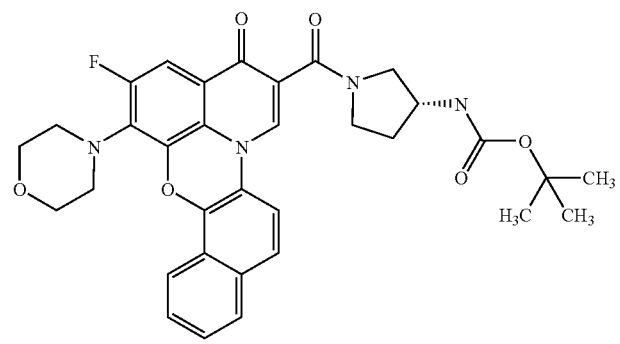
1103 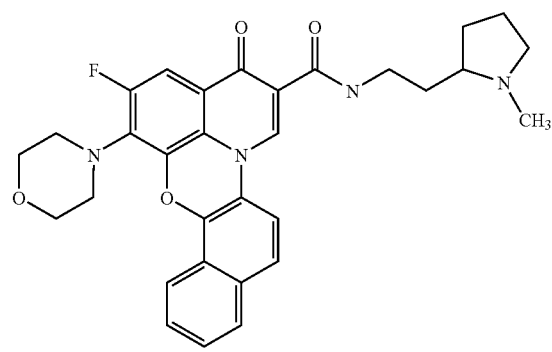

TABLE 3-continued
1104 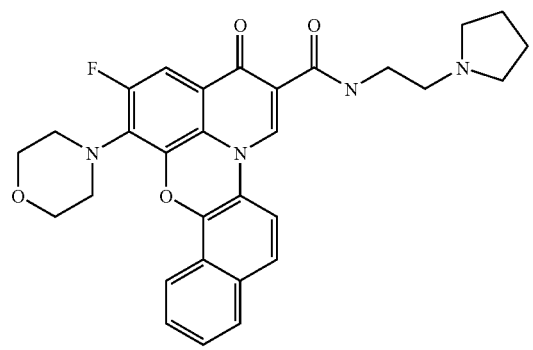
1105 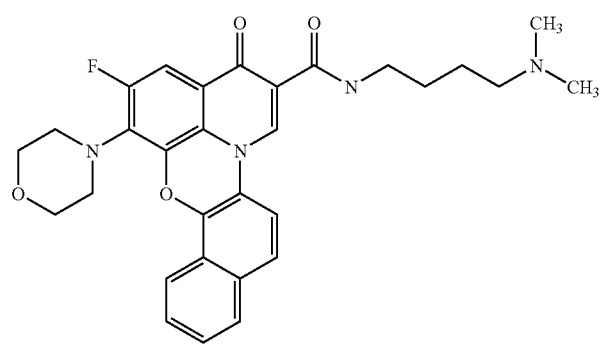
1106 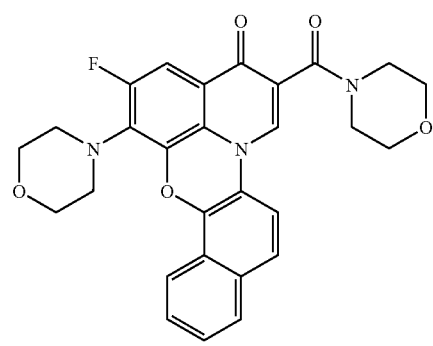
1107 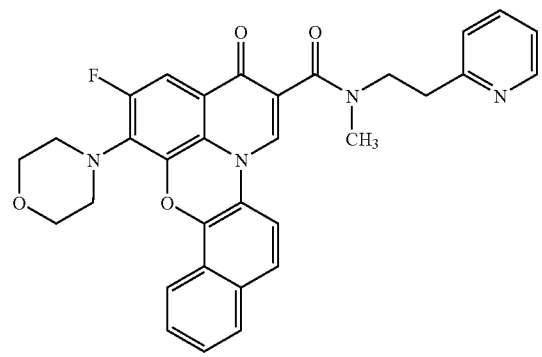

TABLE 3-continued
1108 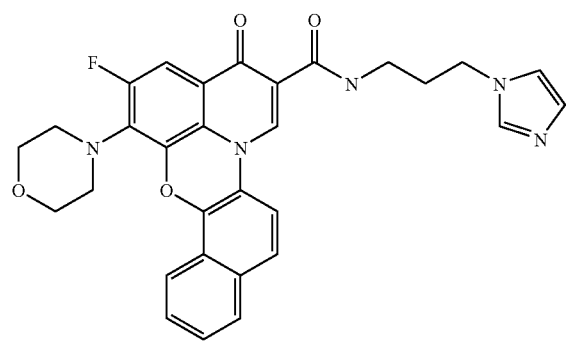
1109 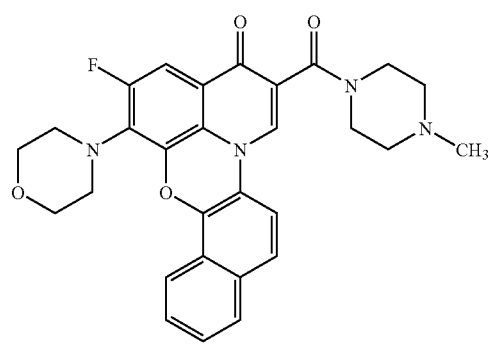
1110 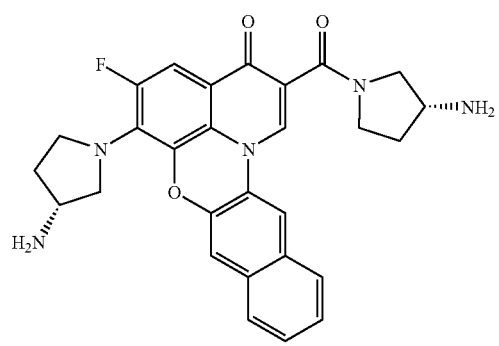
1111 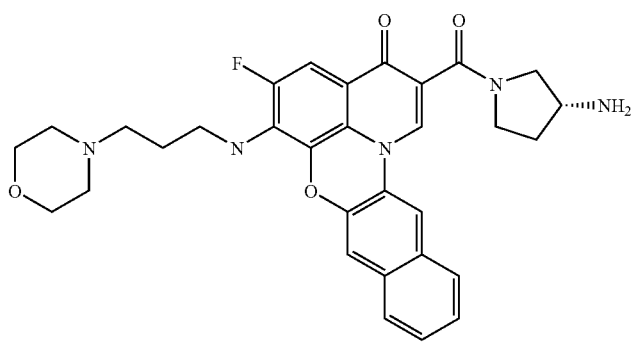

TABLE 3-continued
1112 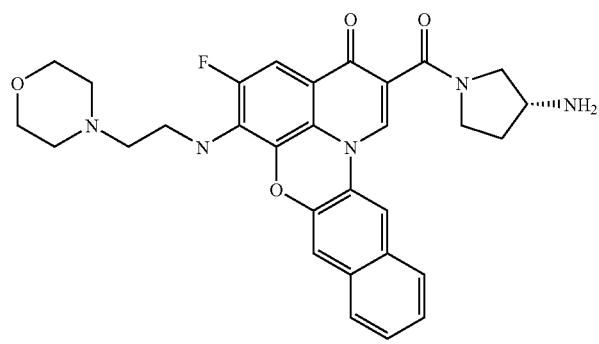
1113 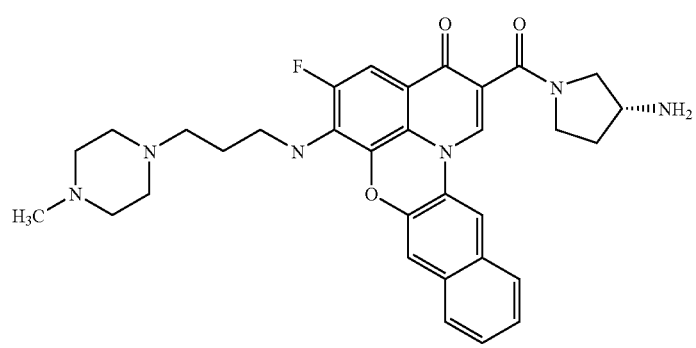
1114 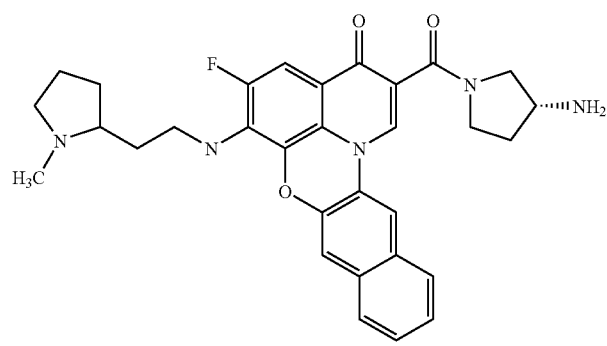
1115 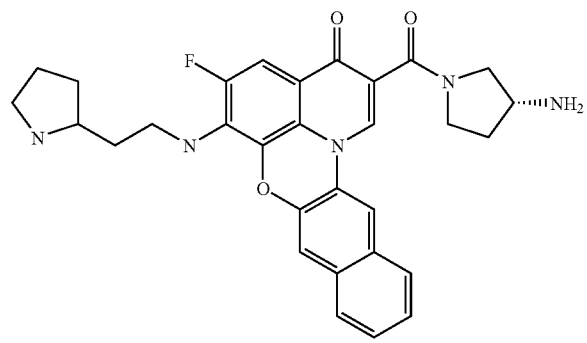

TABLE 3-continued
1116 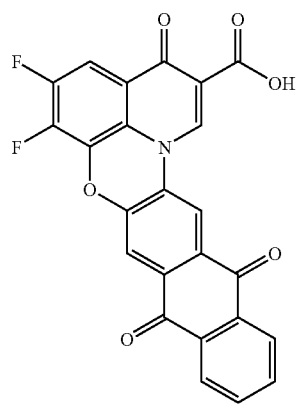
1117 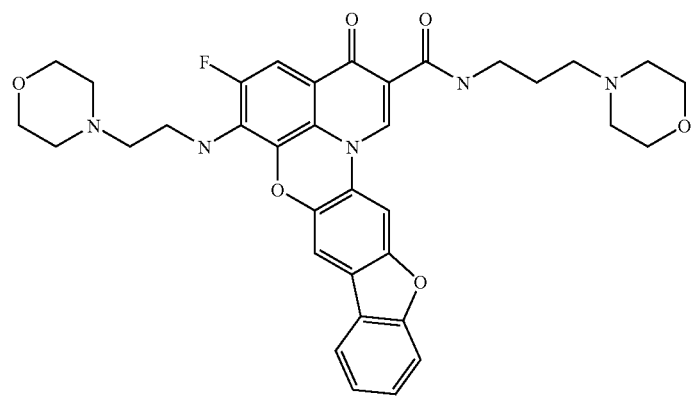
1118 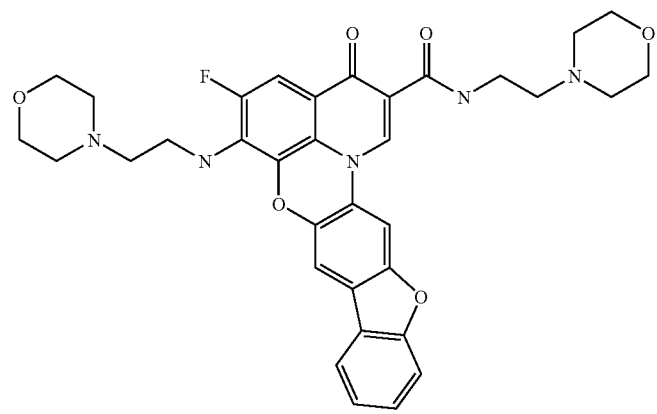
1119 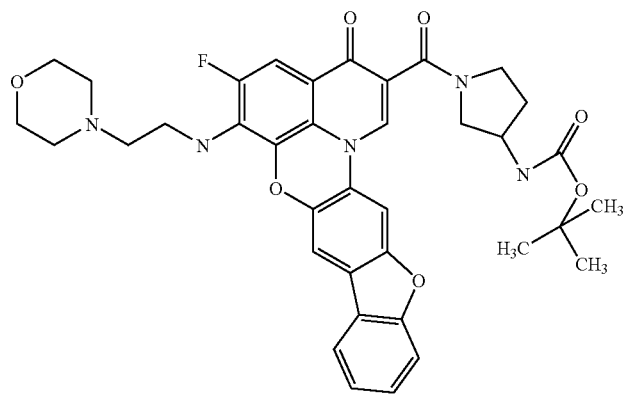

TABLE 3-continued
1120
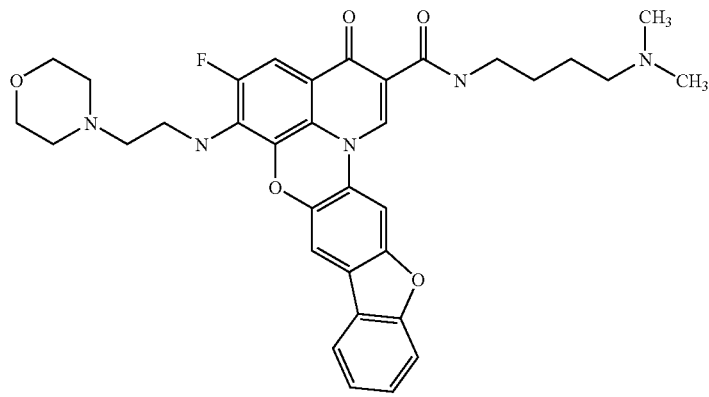
1121
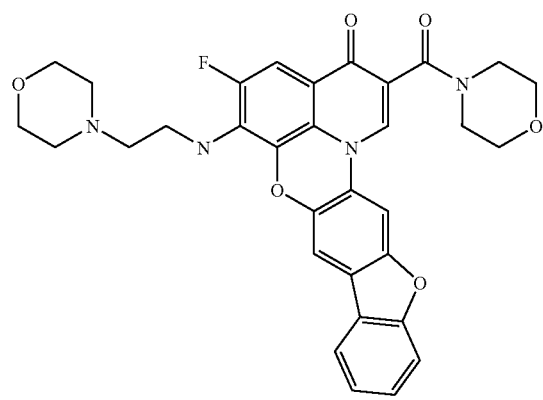
1122
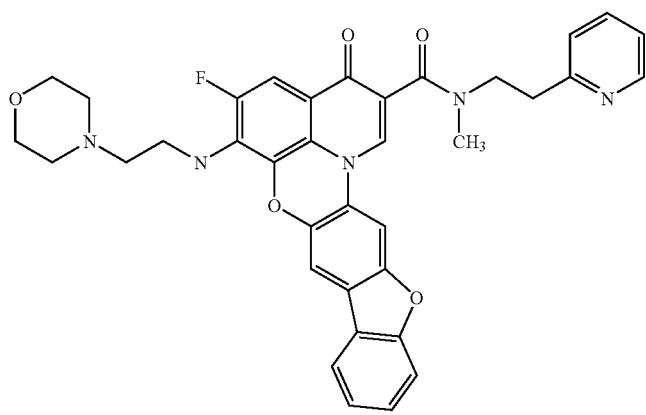
1123
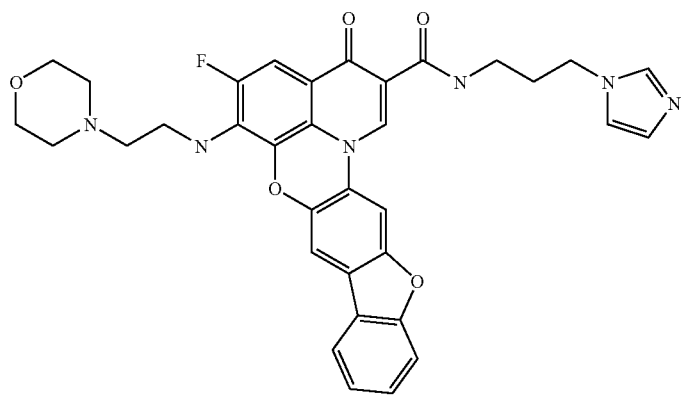

TABLE 3-continued
| 1124 | 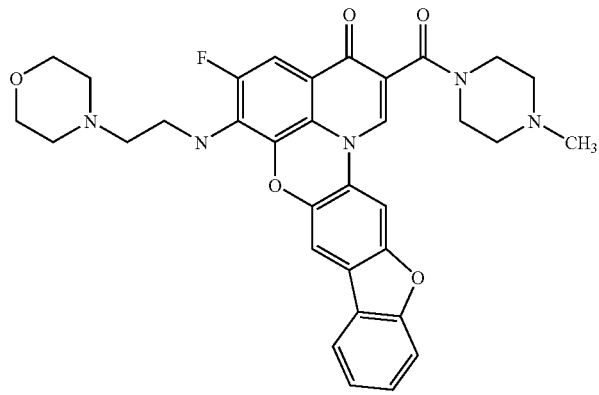 |
| --- | --- |
| 1125 | 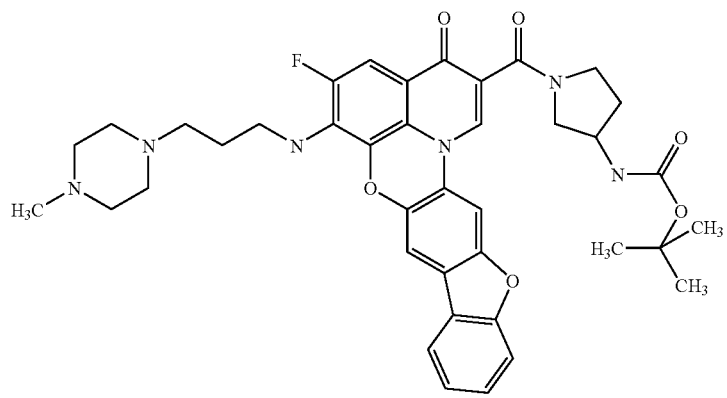 |
| 1126 | 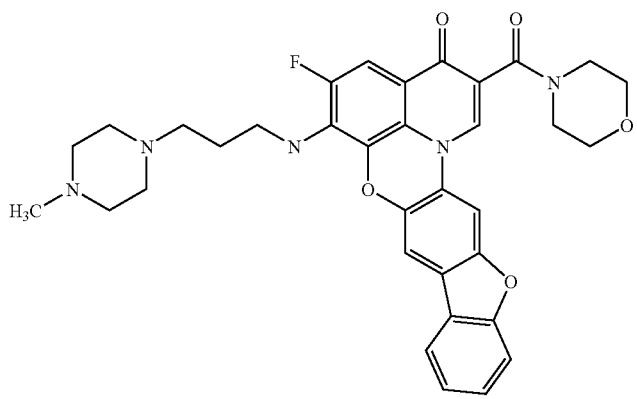 |
| 1127 | 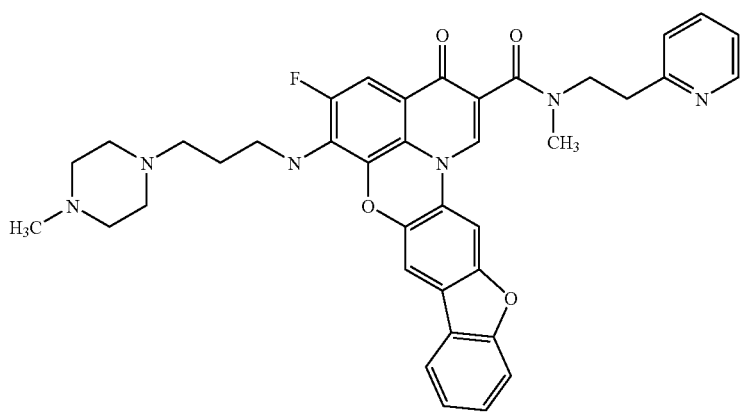 |

TABLE 3-continued
1128
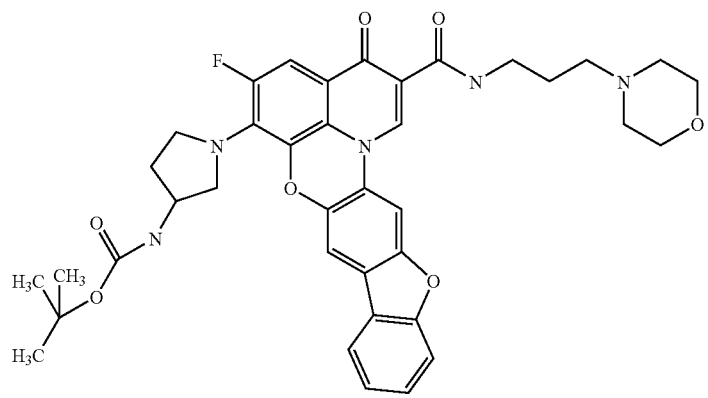
1129
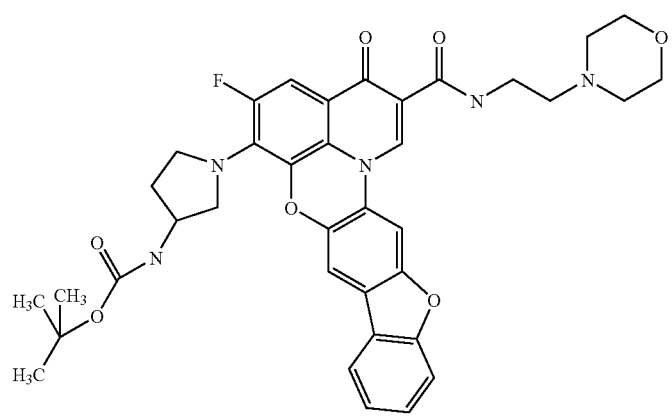
1130
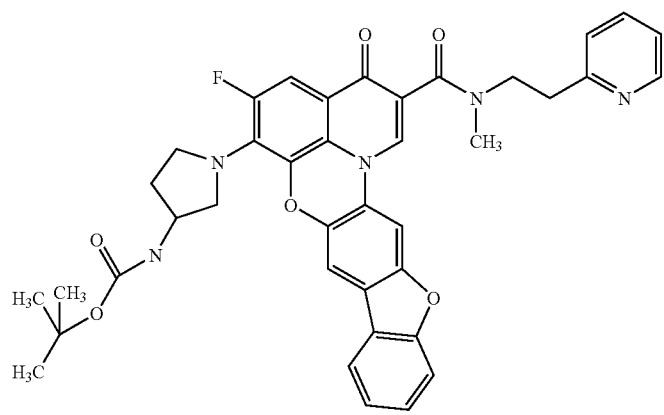
1131
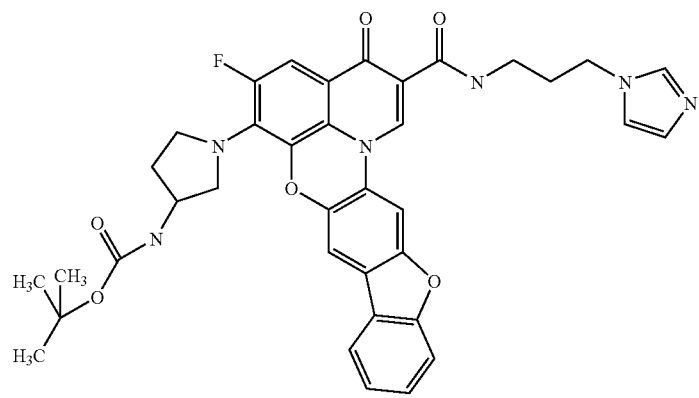

TABLE 3-continued
| 1132 | 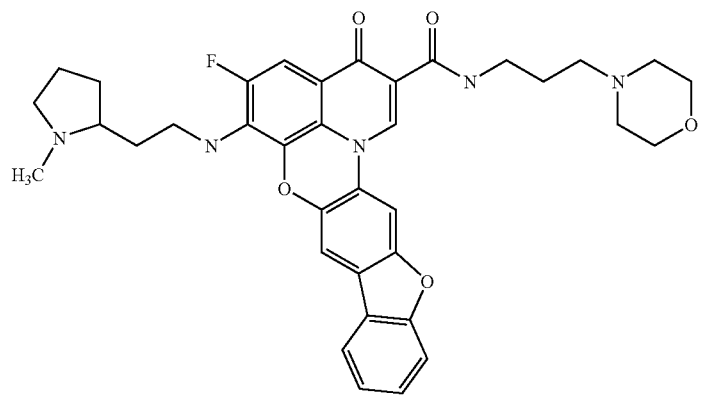 |
| --- | --- |
| 1133 | 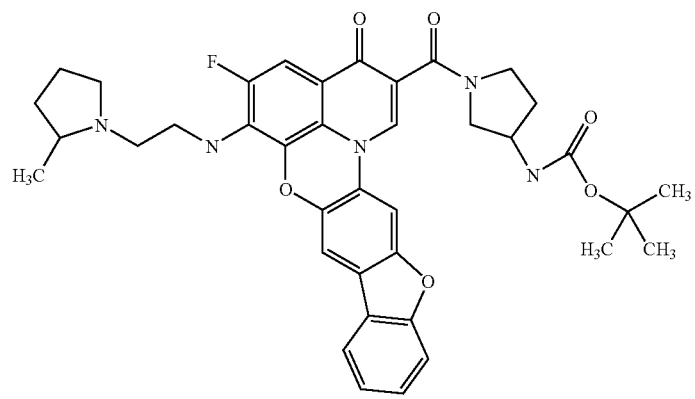 |
| 1134 | 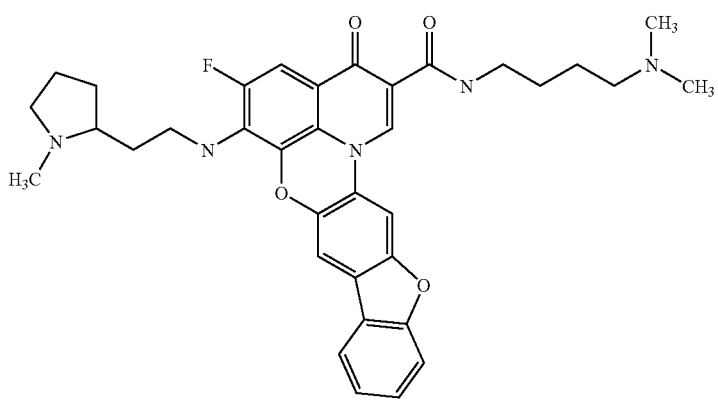 |
| 1135 | 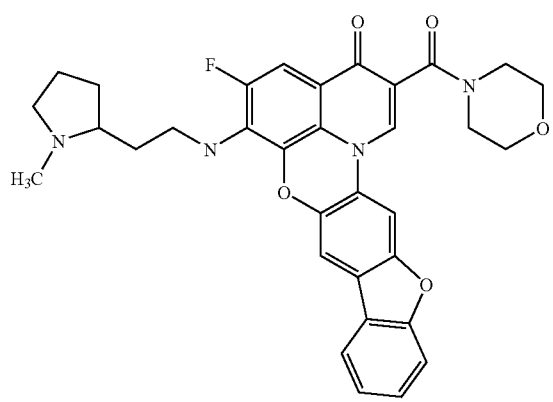 |

TABLE 3-continued
1136
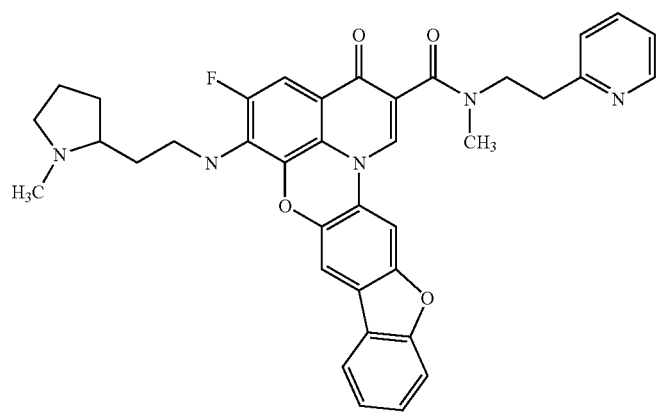
1137
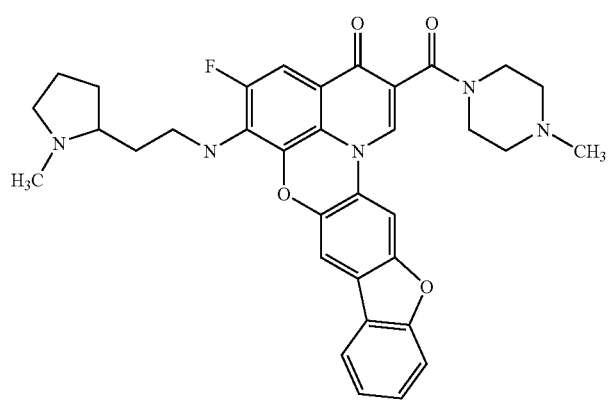
1138
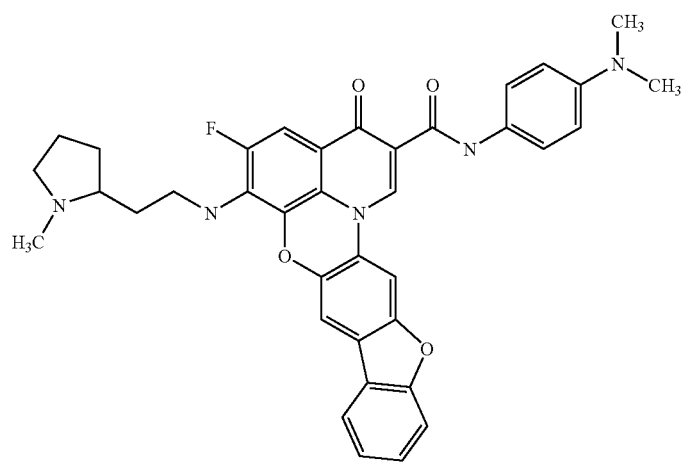

TABLE 3-continued
1139 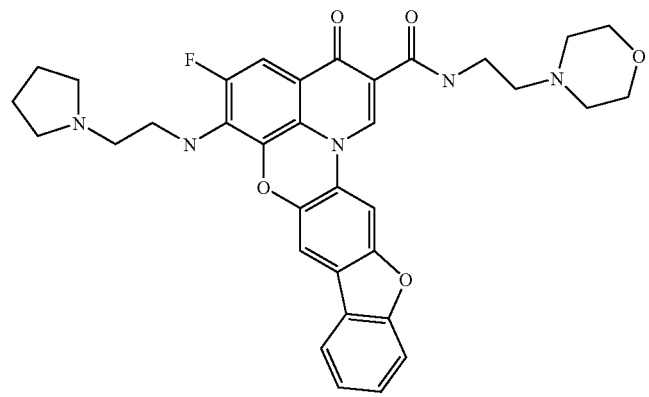
1140 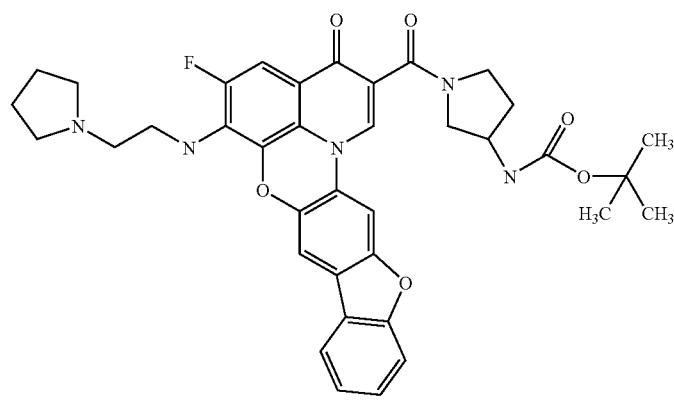
1141 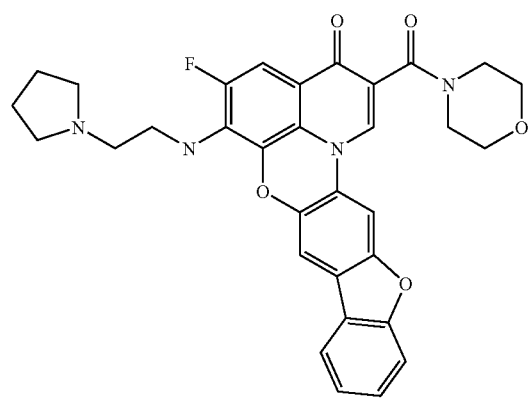
1142 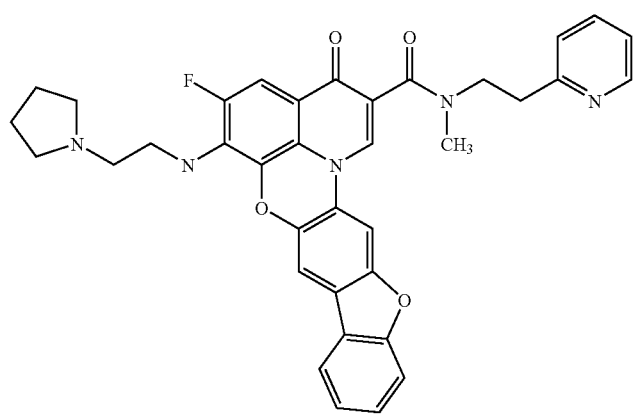

TABLE 3-continued
| 1143 | 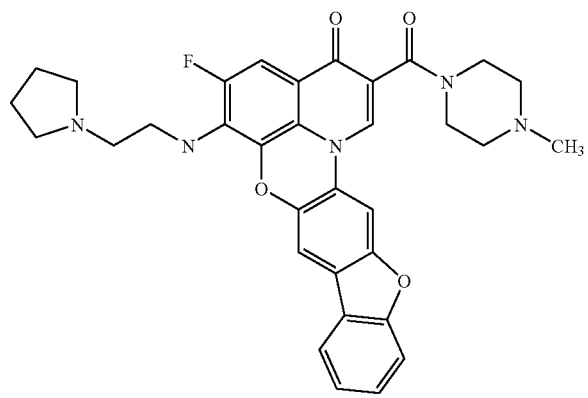 |
| --- | --- |
| 1144 | 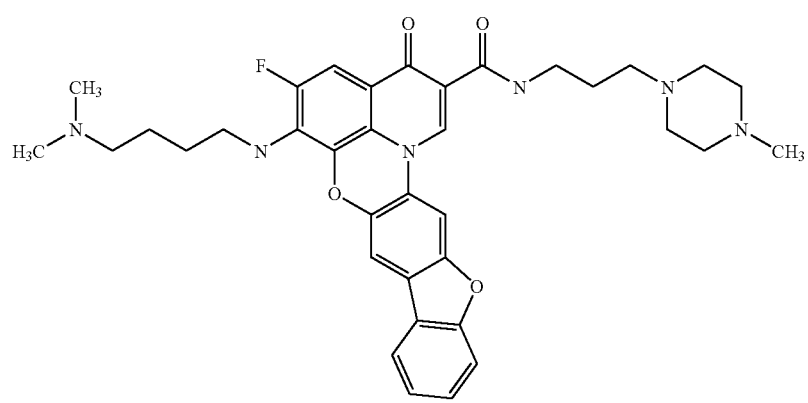 |
| 1145 | 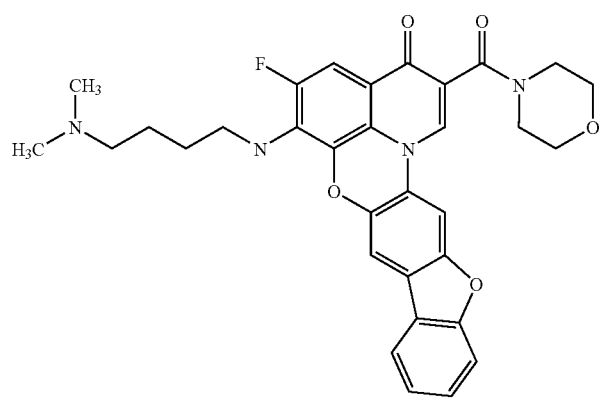 |
| 1146 | 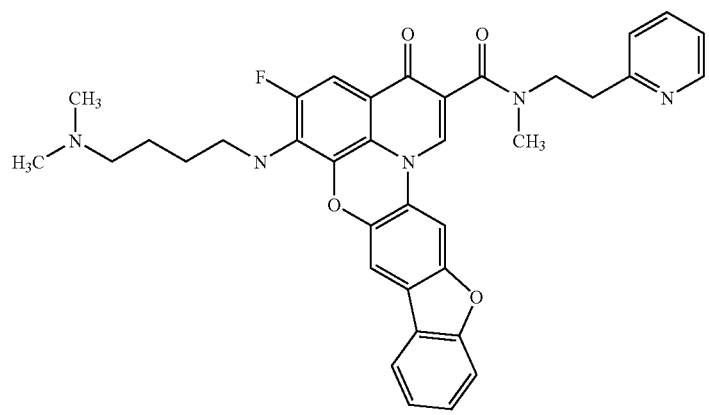 |

TABLE 3-continued
1147 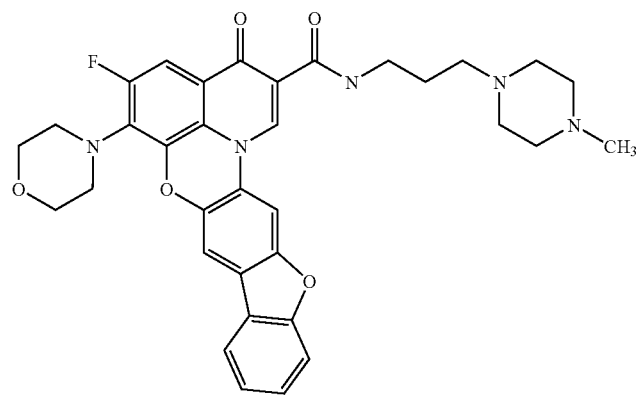
1148 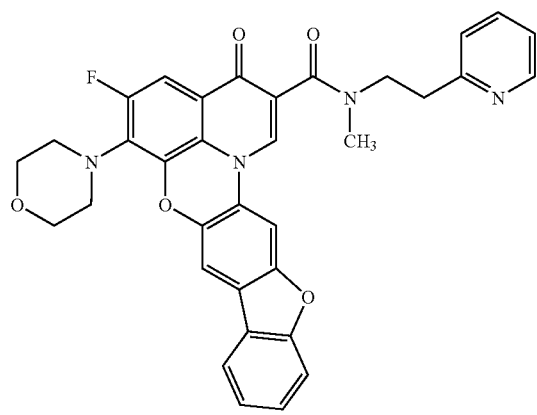
1149 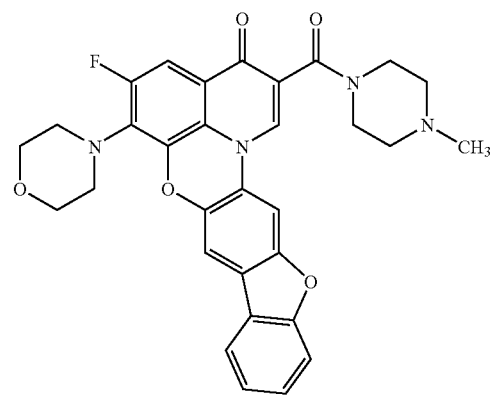
1150 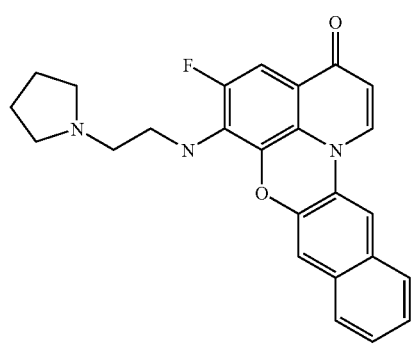

TABLE 3-continued
1151
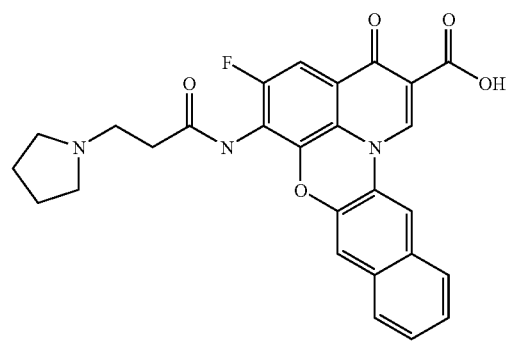
1152
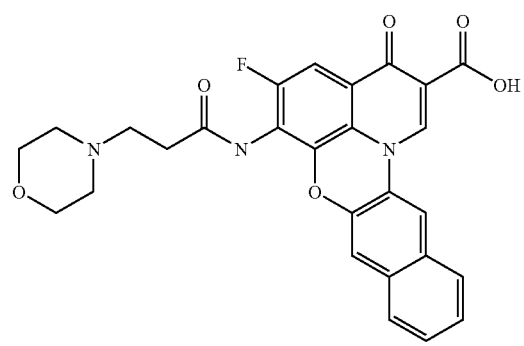
1153
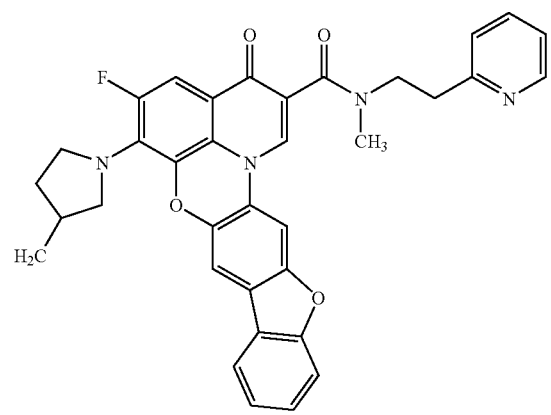
1154
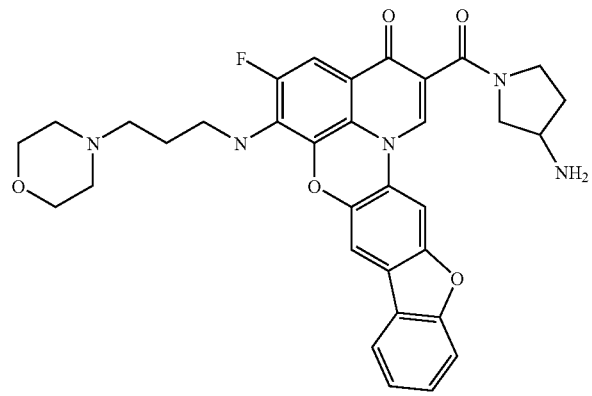

TABLE 3-continued
| 1155 | 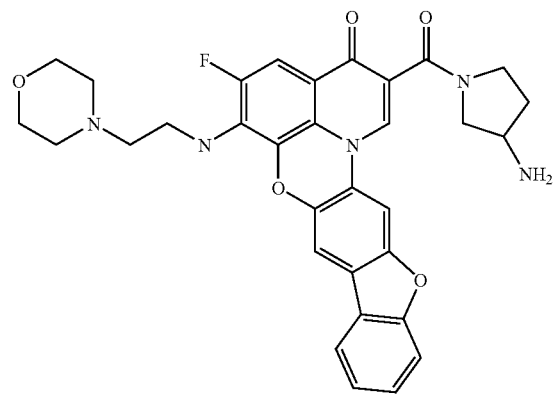 |
| 1156 | 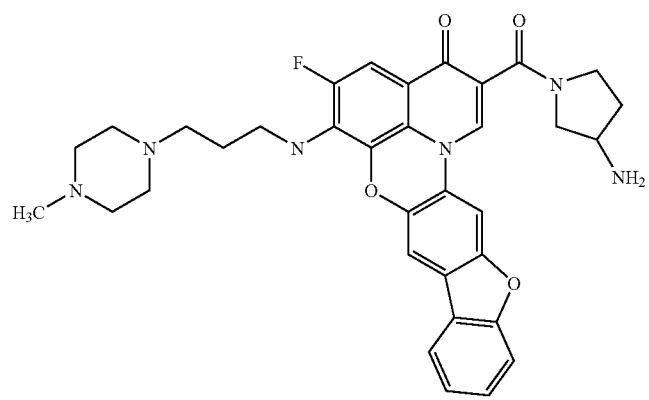 |
| 1157 | 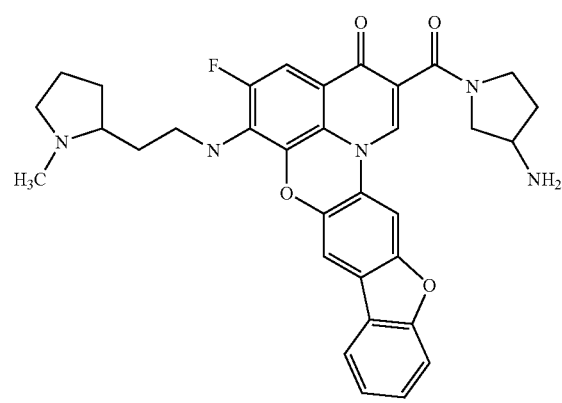 |
| 1158 | 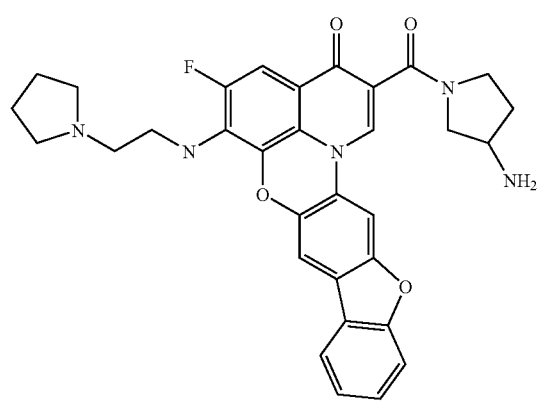 |

TABLE 3-continued
1159 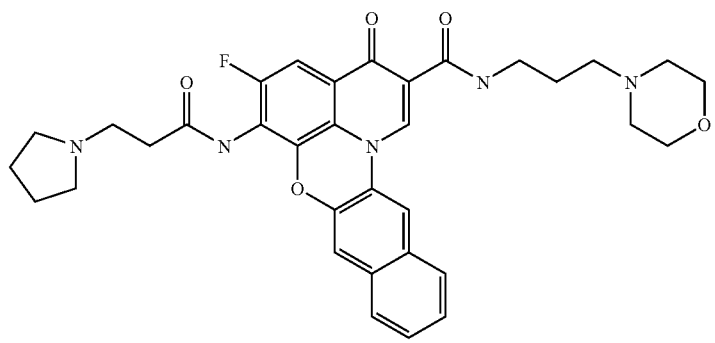
1160 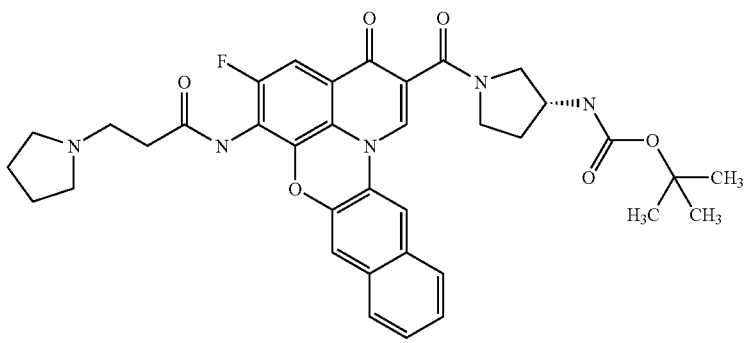
1161 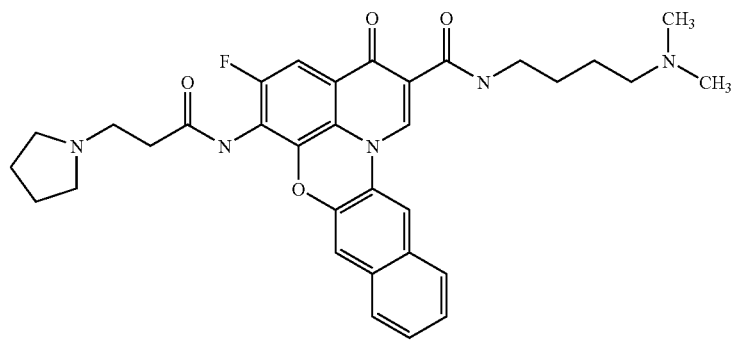
1162 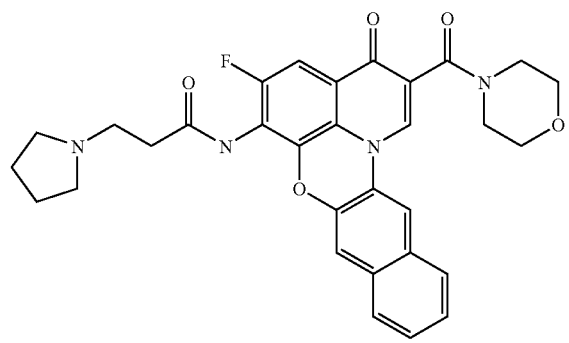

TABLE 3-continued
1163 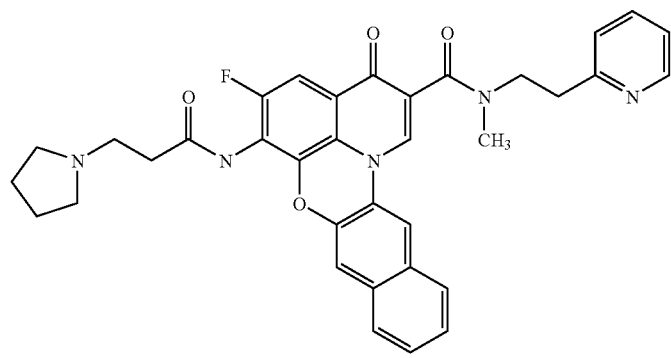
1164 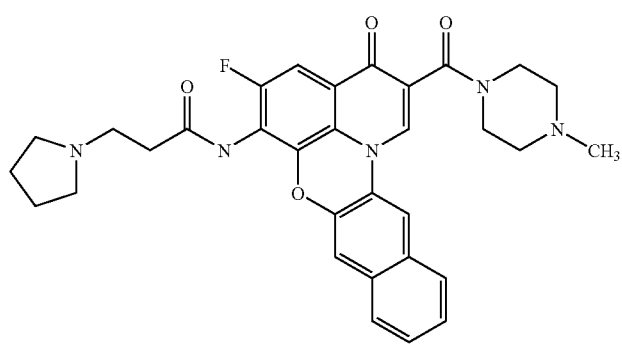
1165 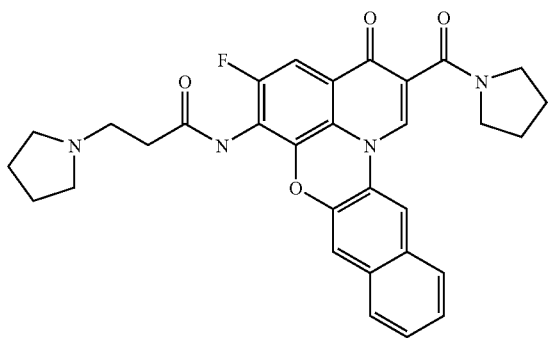
1166 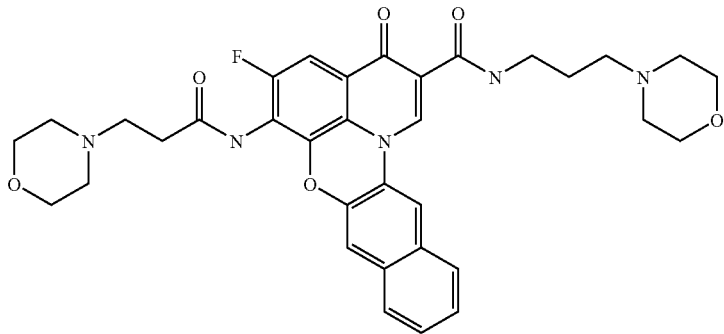

TABLE 3-continued
1167
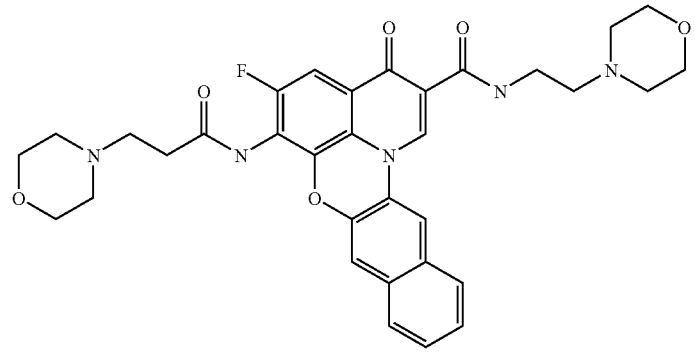
1168
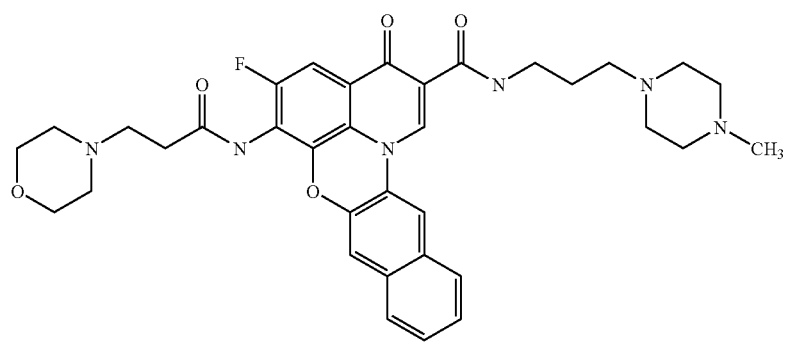
1169
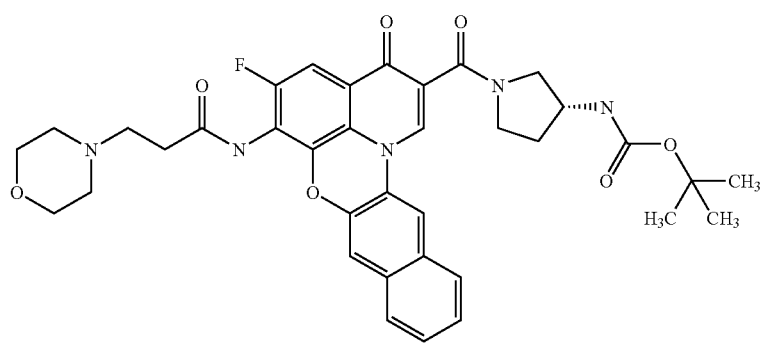
1170
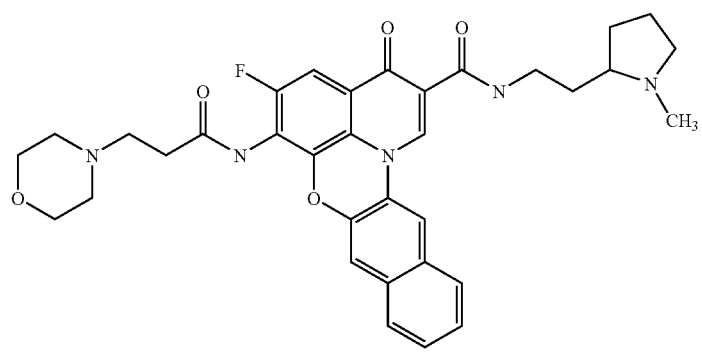

TABLE 3-continued
1171 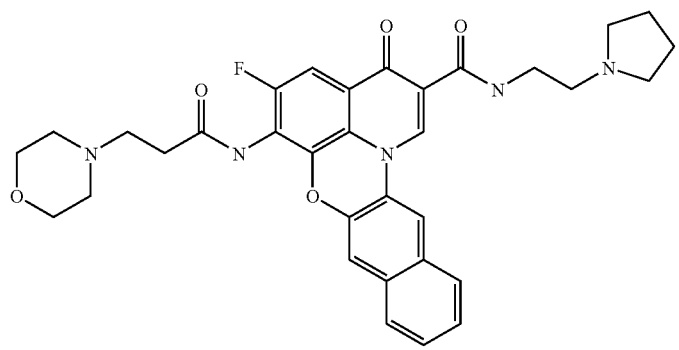
1172 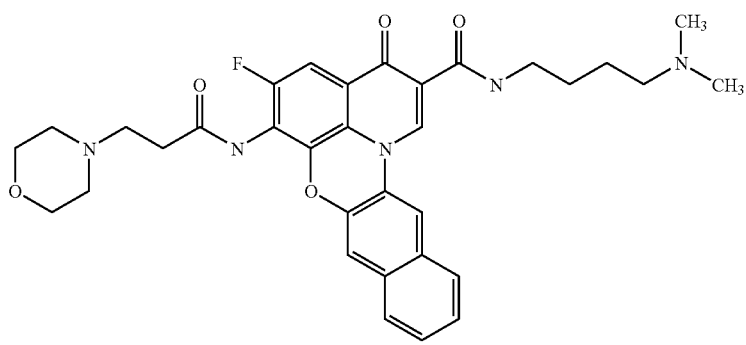
1173 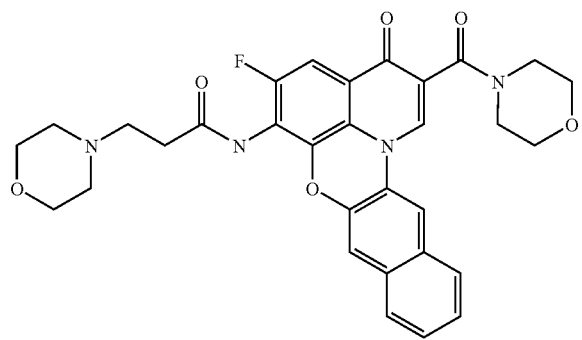
1174 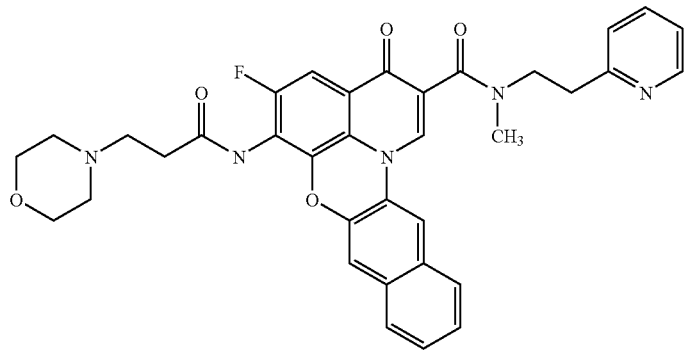

TABLE 3-continued
1175 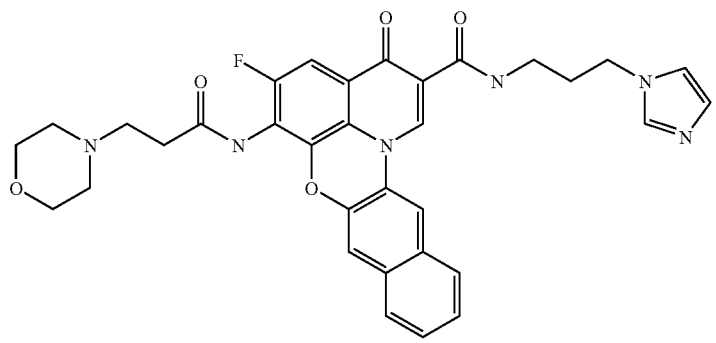
1176 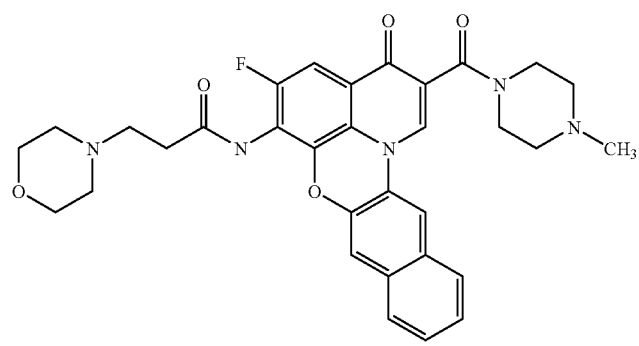
1177 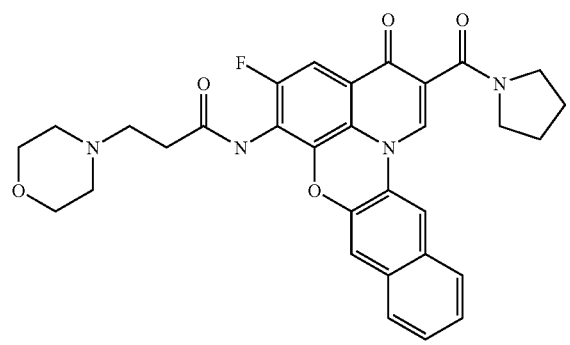
1178 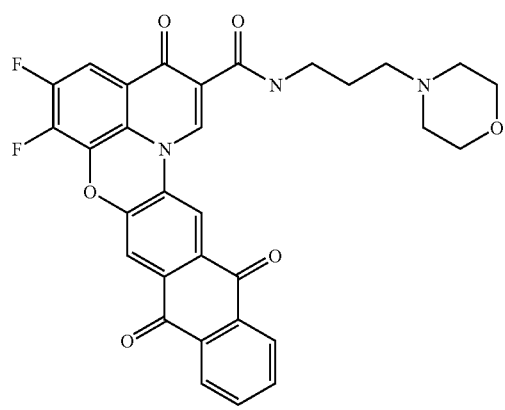

TABLE 3-continued
1179 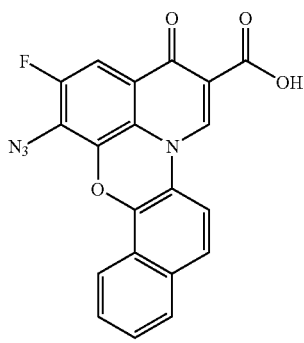
1180 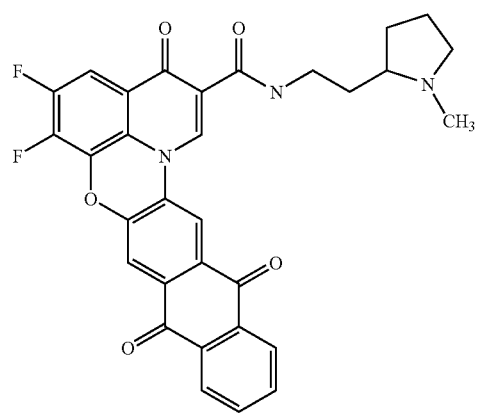
1181 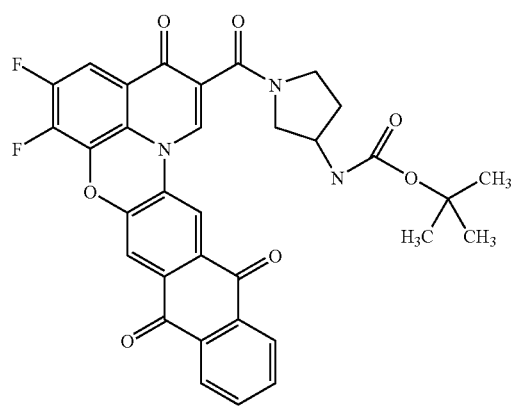
1182 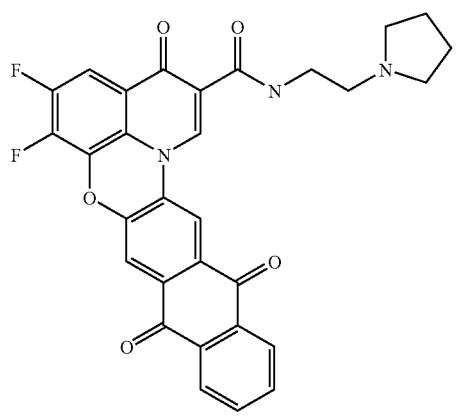

TABLE 3-continued
| 1183 | 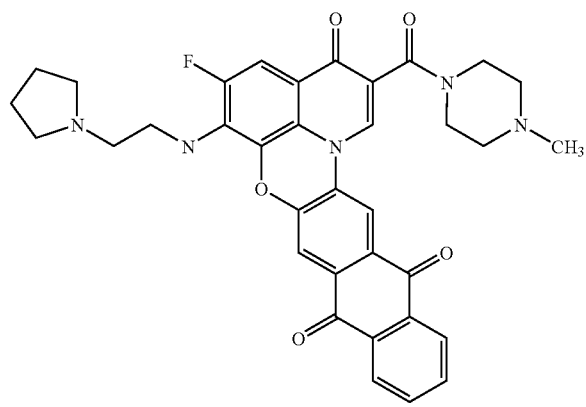 |
| 1184 | 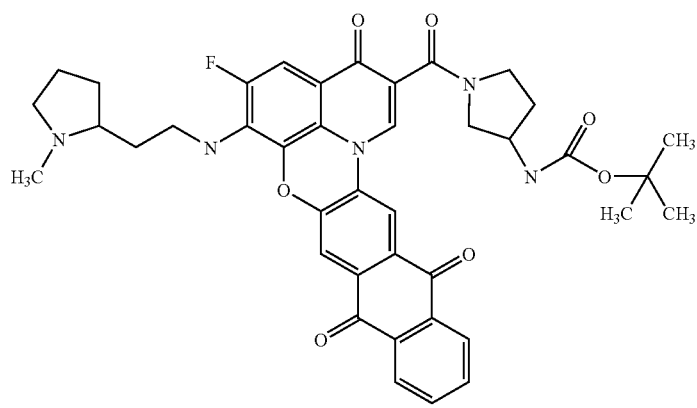 |
| 1185 | 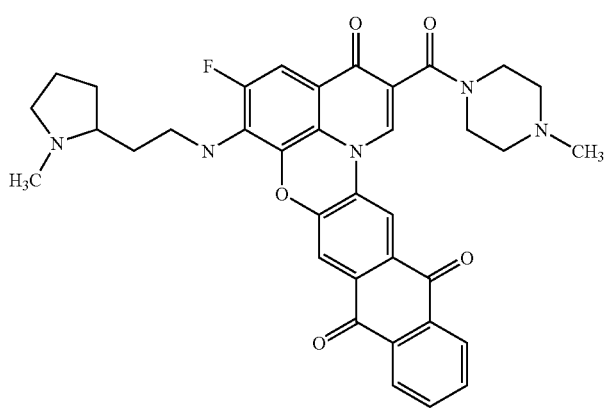 |
| 1186 | 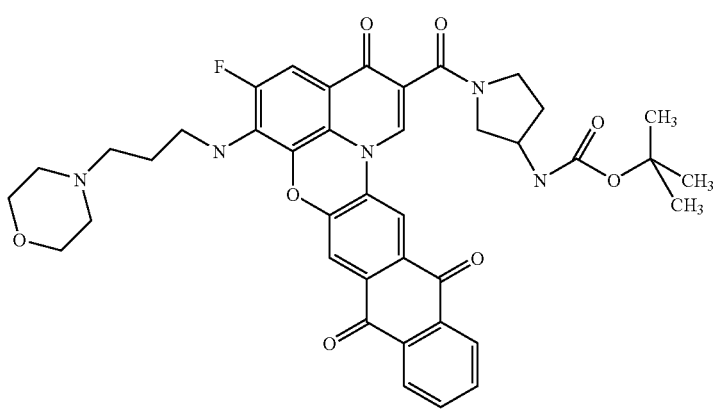 |

TABLE 3-continued
1187
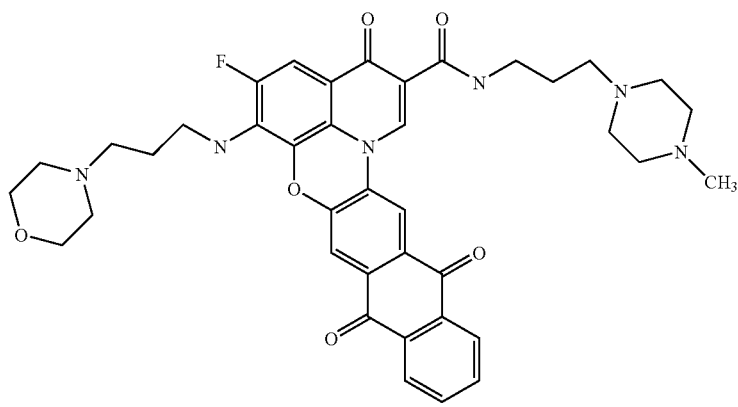
1188
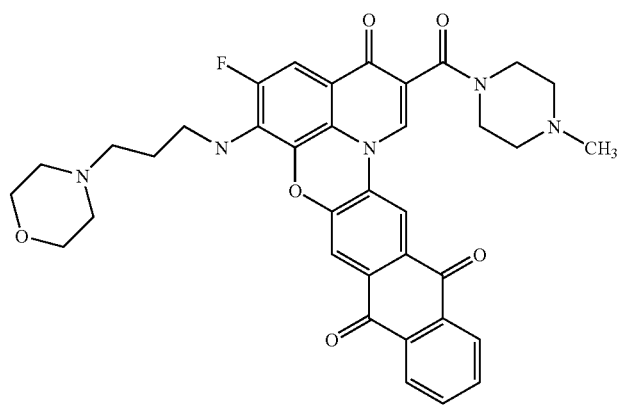
1189
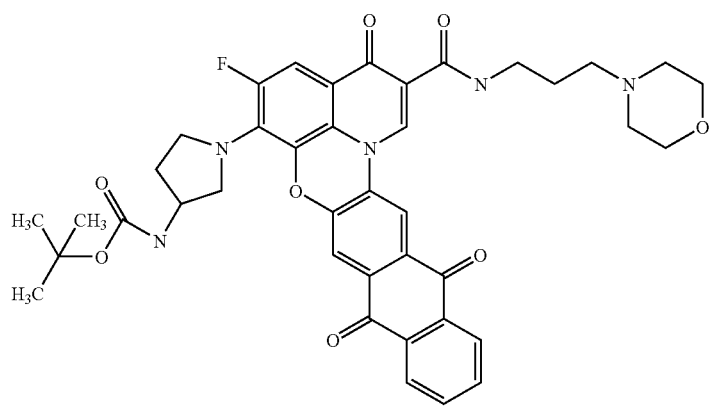
1190
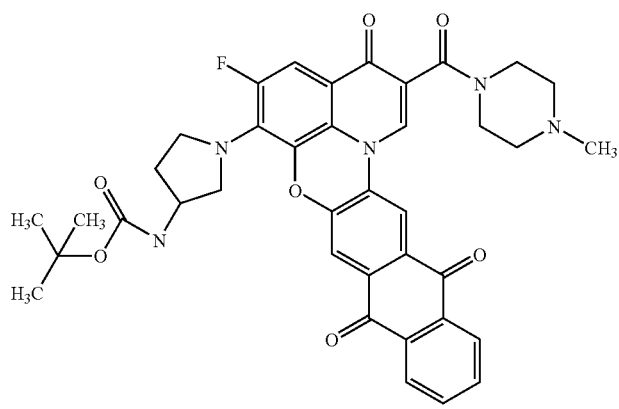

TABLE 3-continued
1191 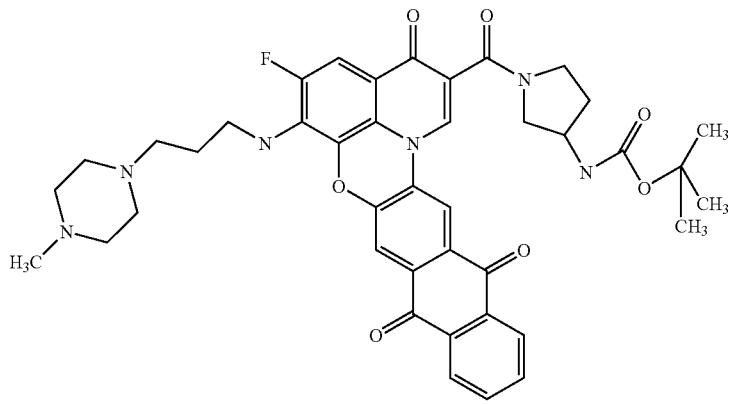
1192 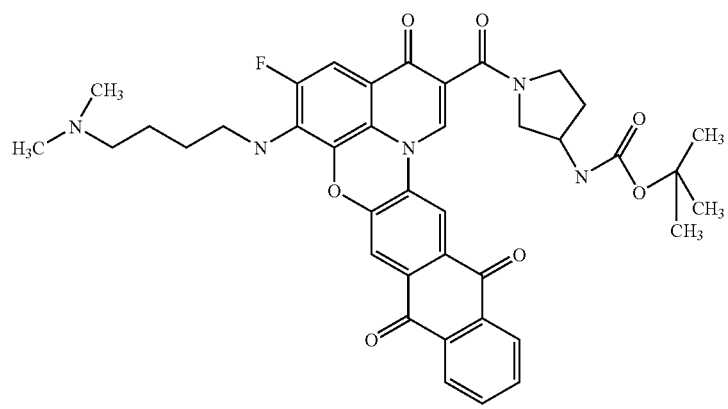
1193 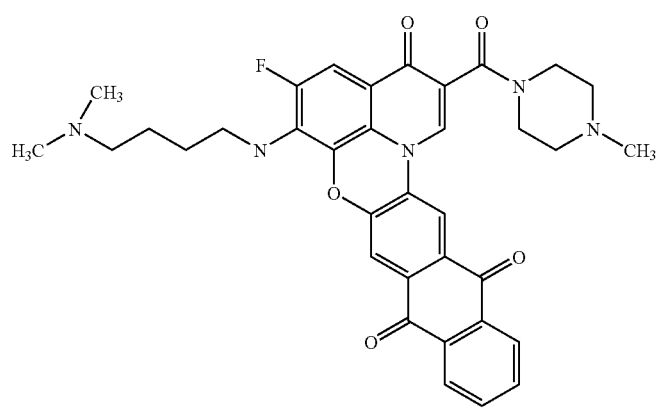
1194 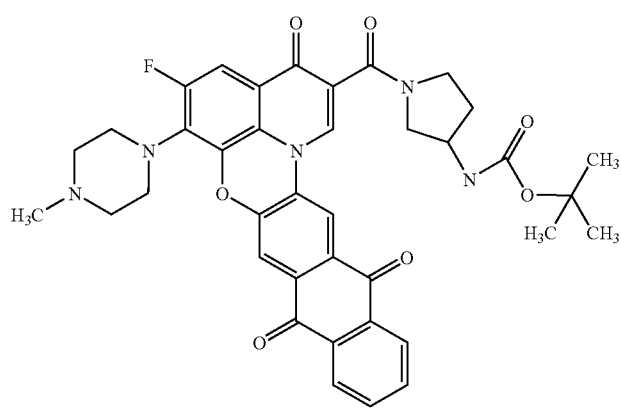

TABLE 3-continued
1195
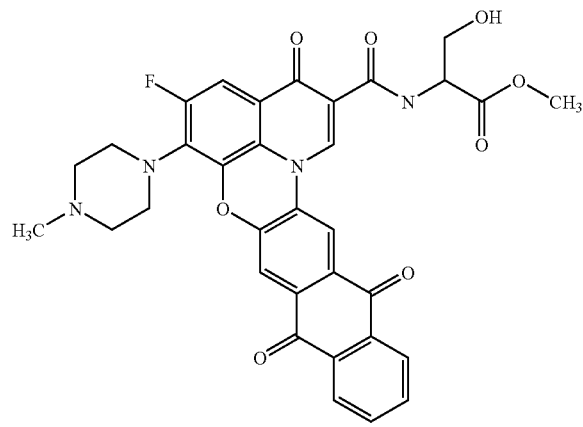
1196
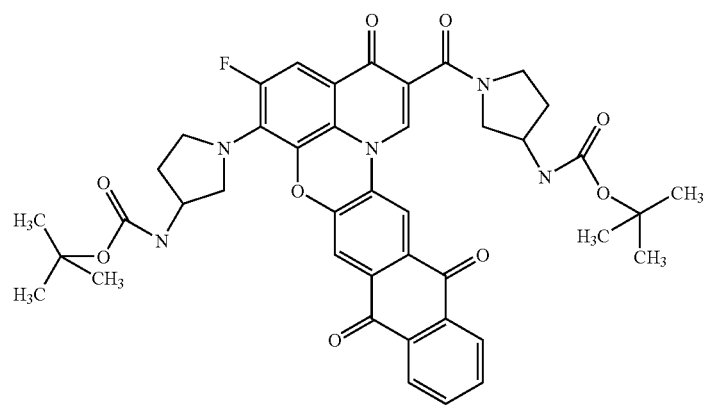
1197
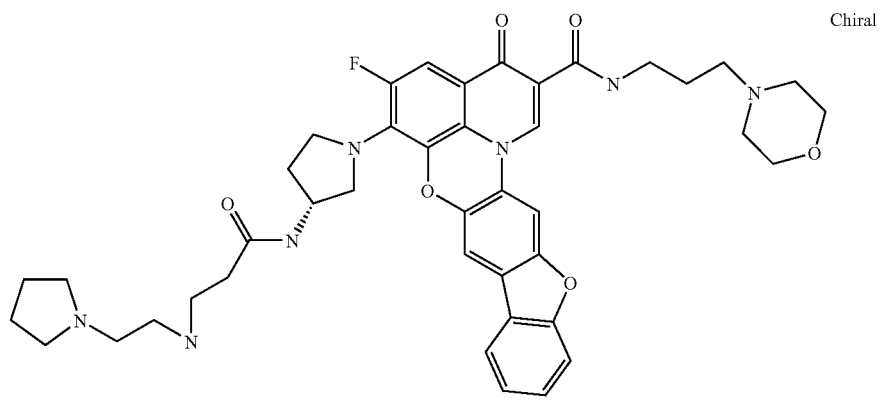
Chiral

TABLE 3-continued
| 1198 | 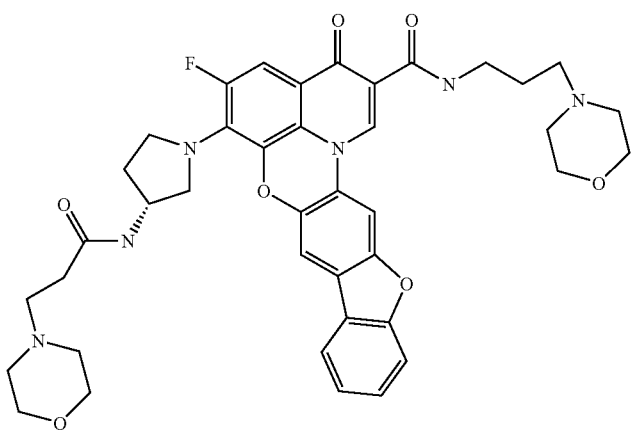 | Chiral |
| 1199 | 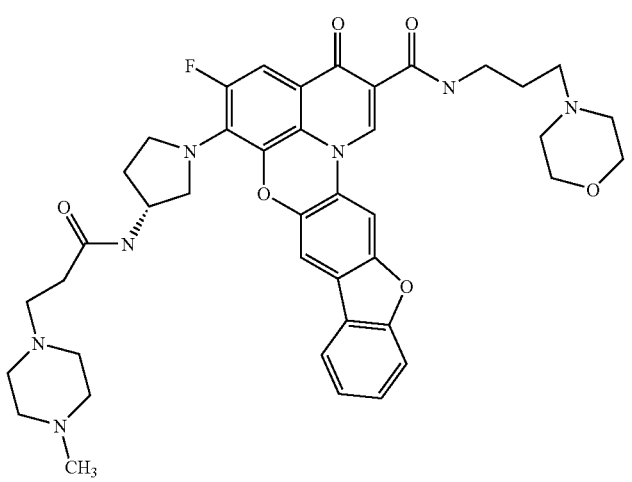 | Chiral |
| 1200 | 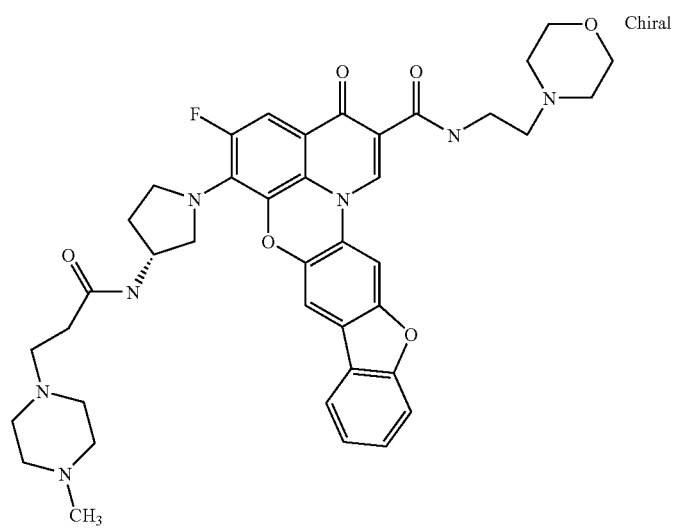 | Chiral |

TABLE 3-continued
1201 Chiral
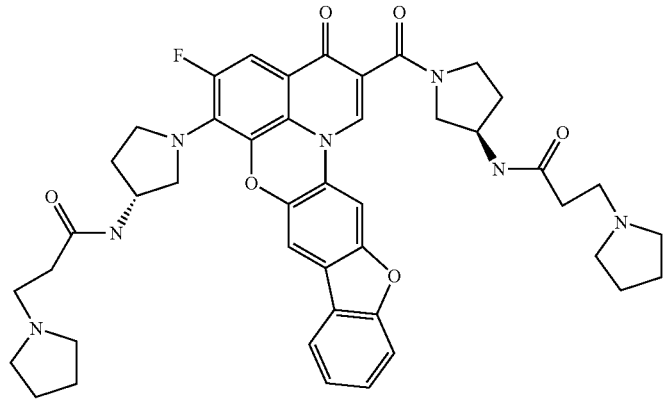
1202 Chiral
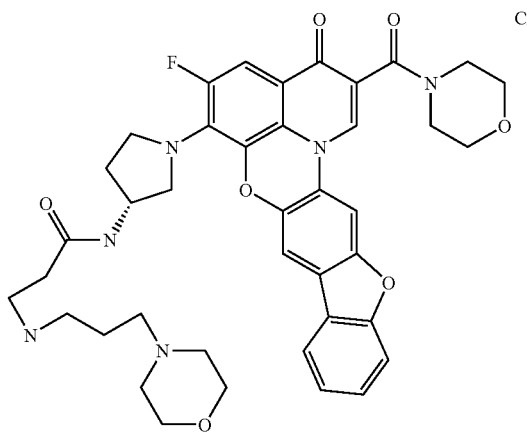
1203 Chiral
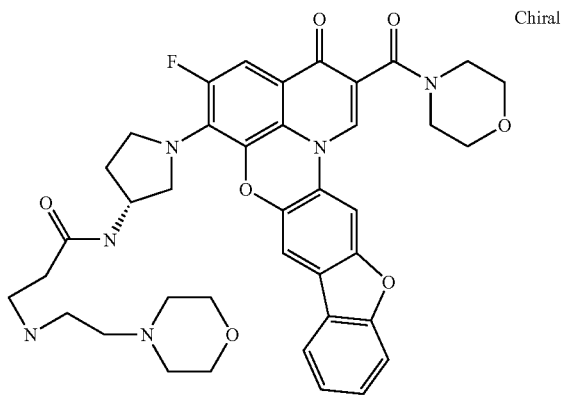

TABLE 3-continued
1204 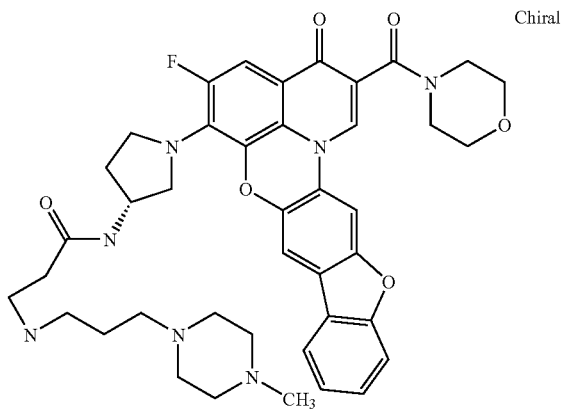 Chiral
1205 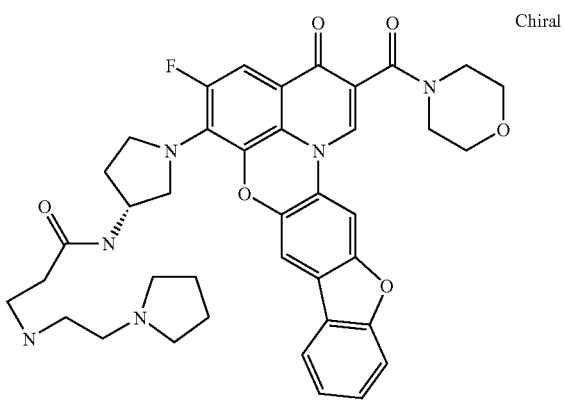 Chiral
1206 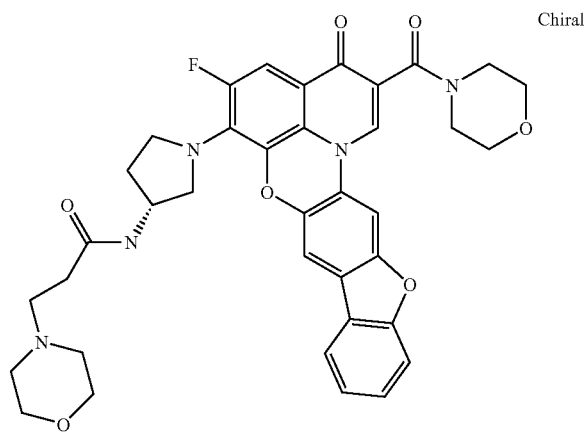 Chiral TABLE 3-continued
1207 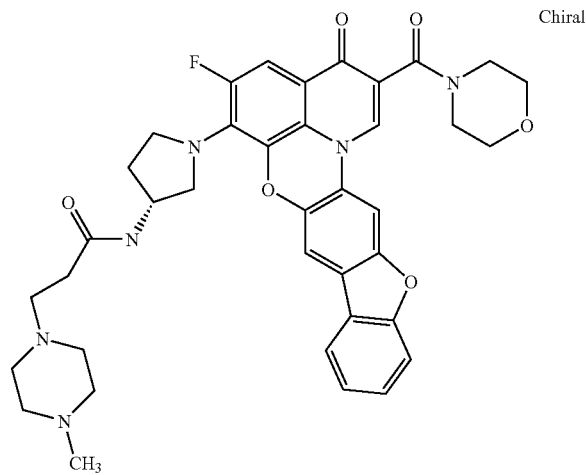
1208 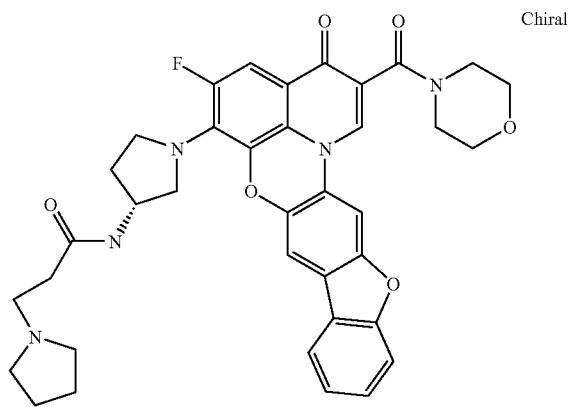
1209 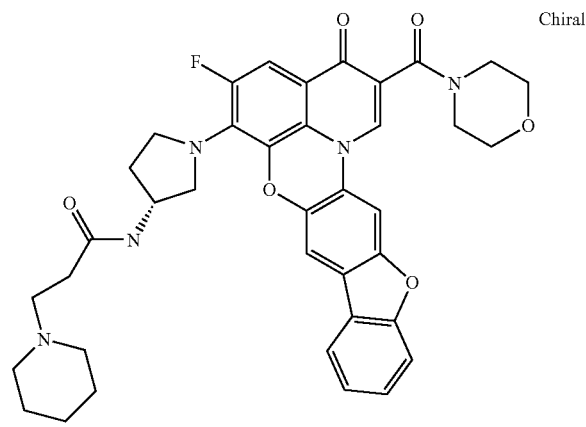

TABLE 3-continued
1210 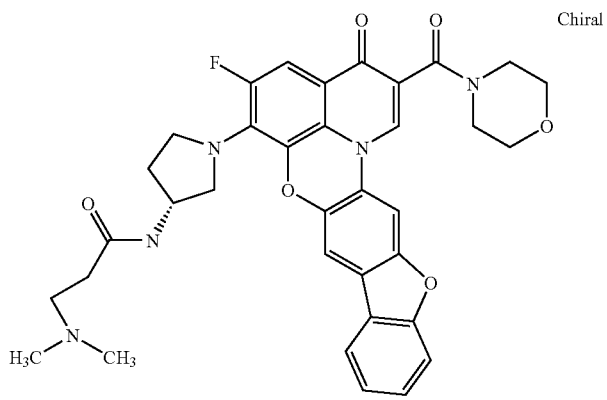 Chiral
1211 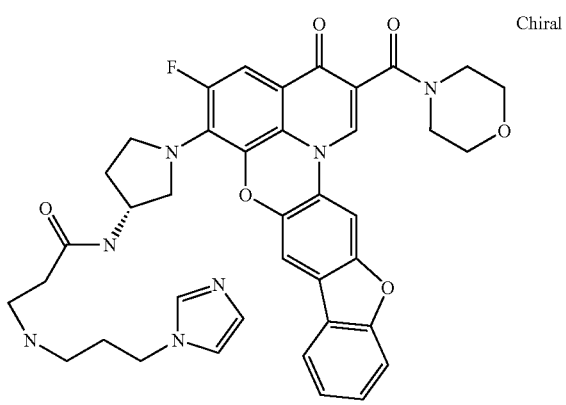 Chiral
1212 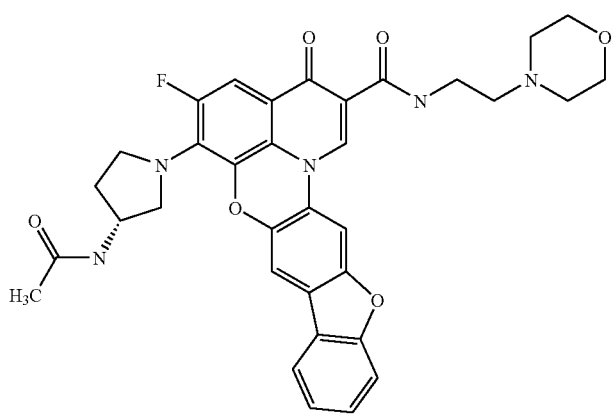
1213 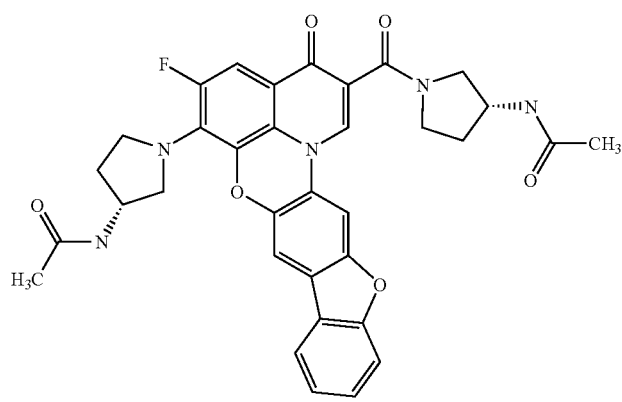

TABLE 3-continued
1214
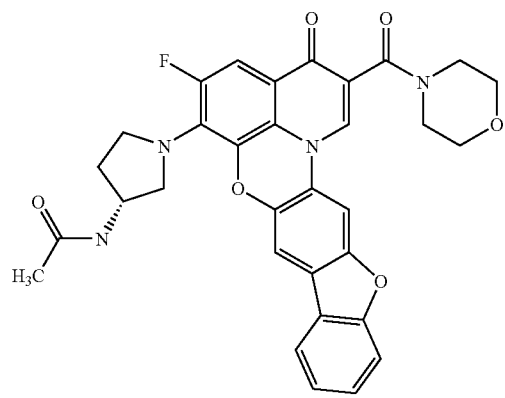
1215
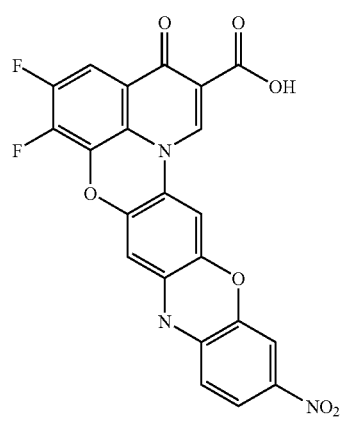
1216
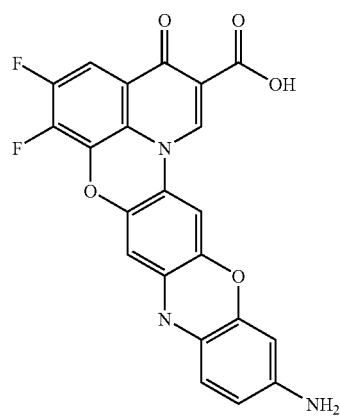

TABLE 3-continued
1217 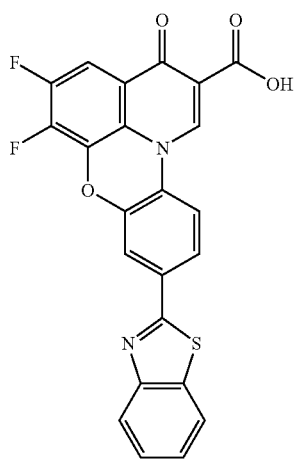
1218 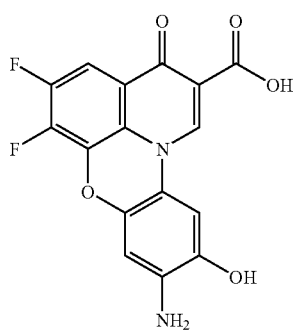
1219 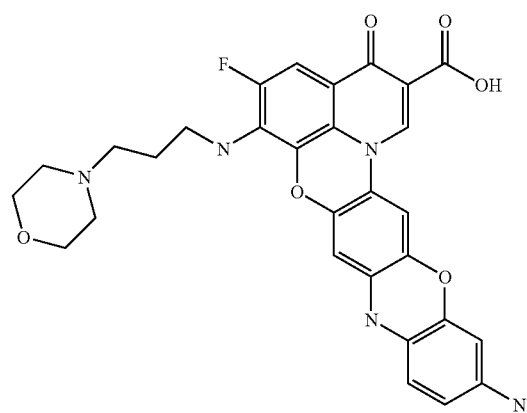
1220 Chiral 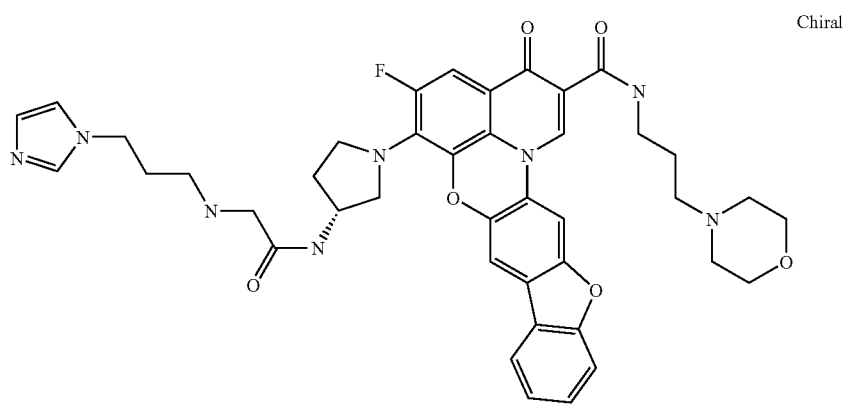

TABLE 3-continued
1221 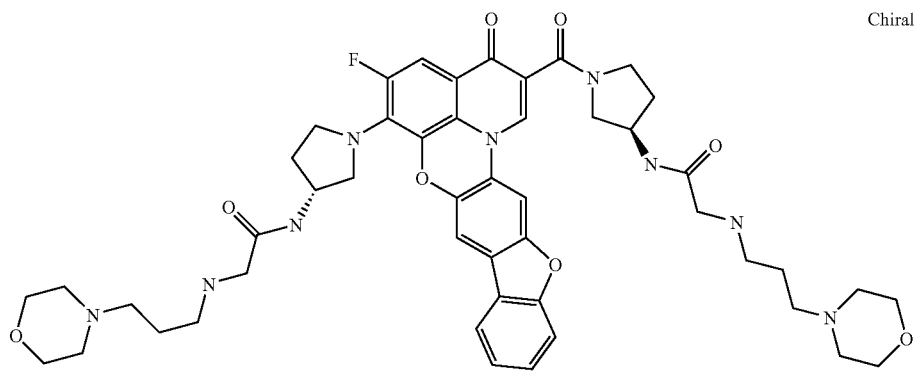 Chiral
1222 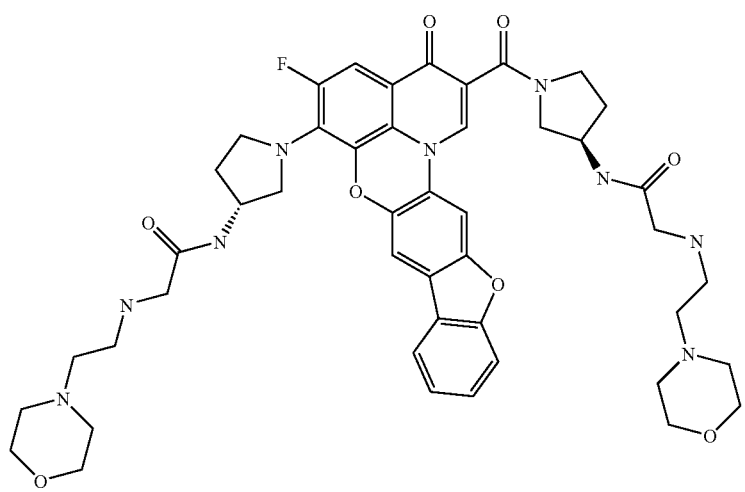 Chiral
1223 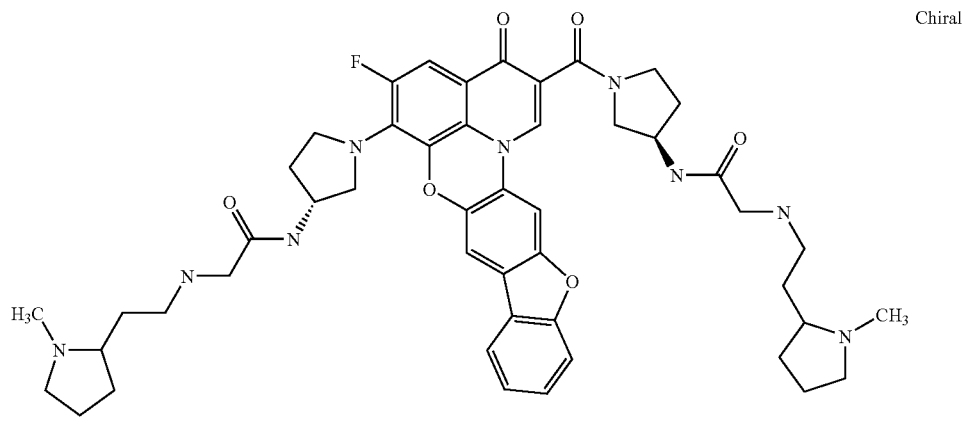 Chiral TABLE 3-continued
1224 Chiral
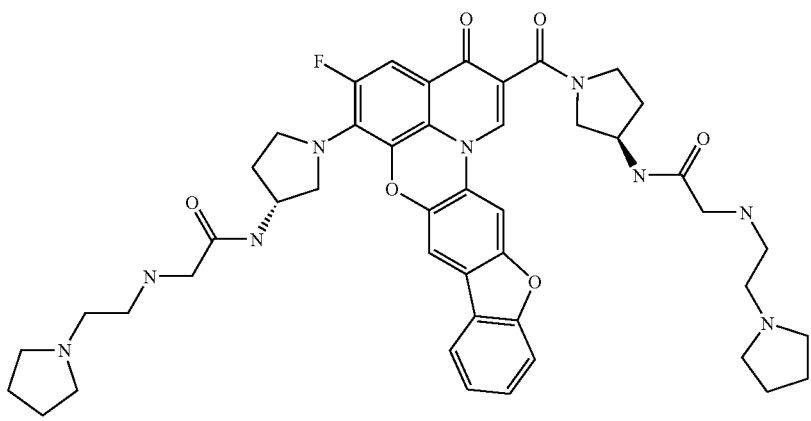
1225 Chiral
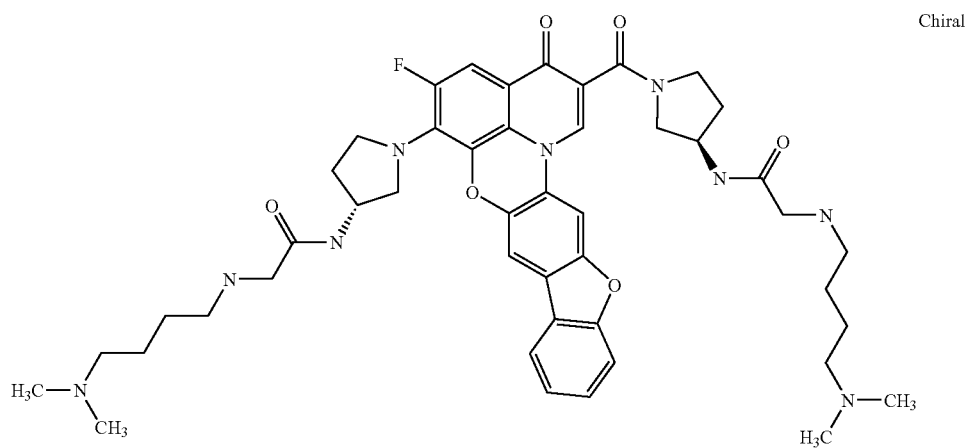
1226 Chiral
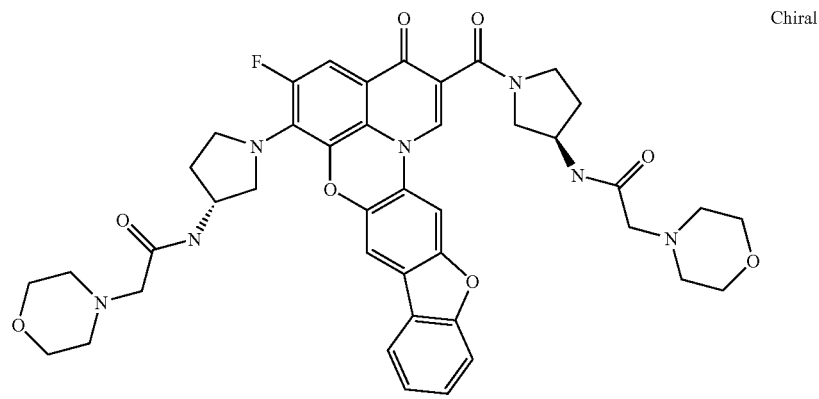

TABLE 3-continued
1227 Chiral
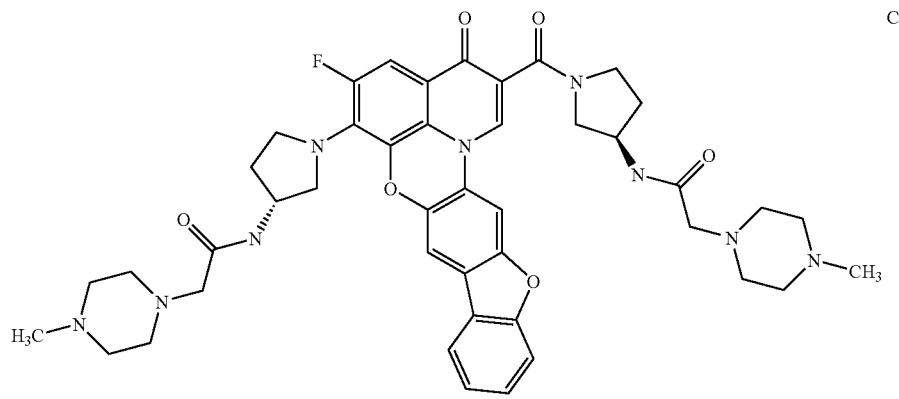
1228 Chiral
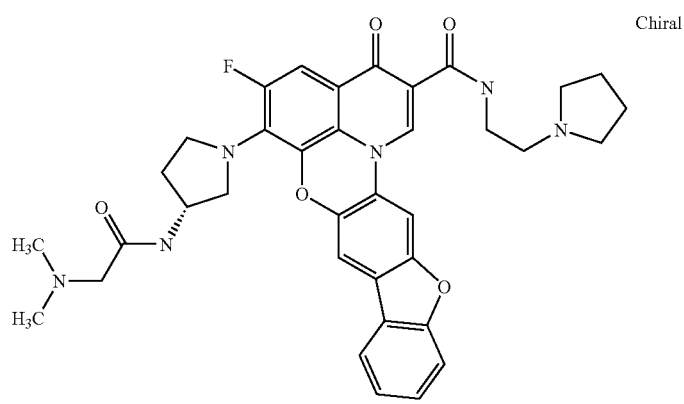
1229 Chiral
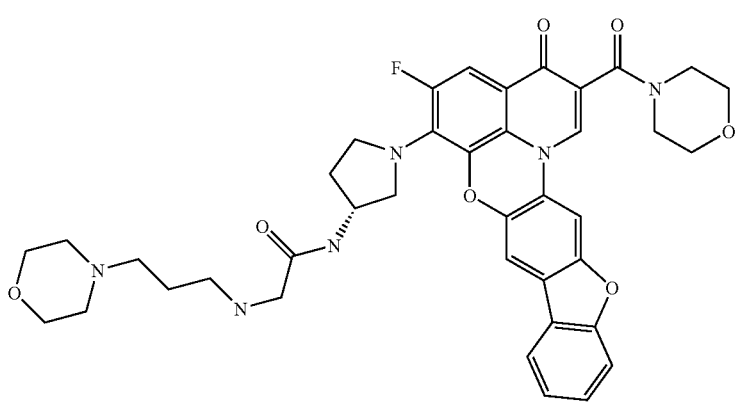
1230 Chiral
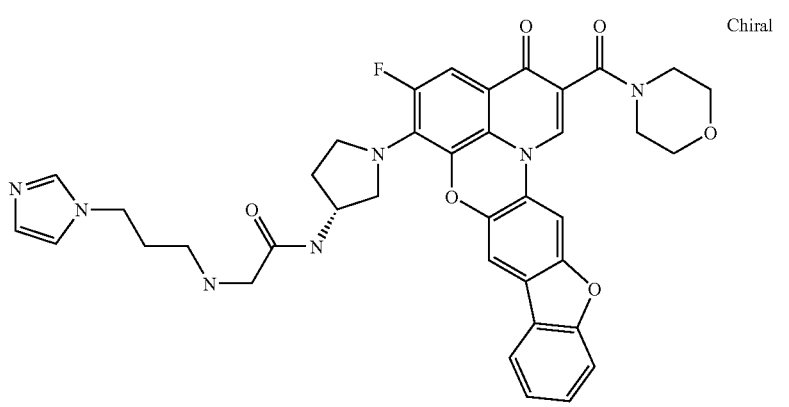

TABLE 3-continued
1231
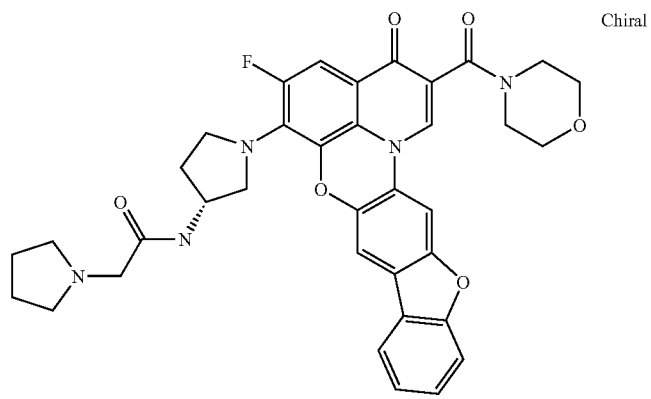
1232
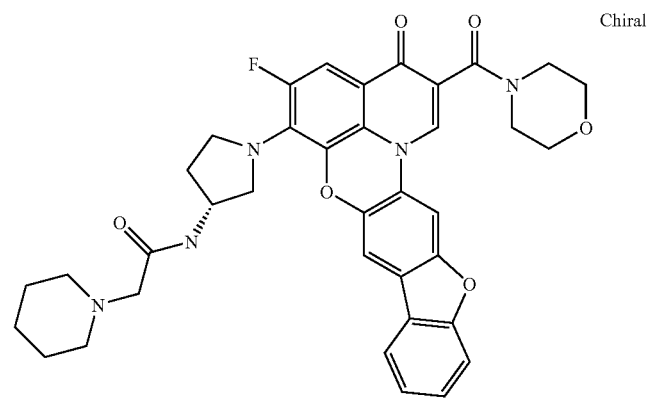
1233
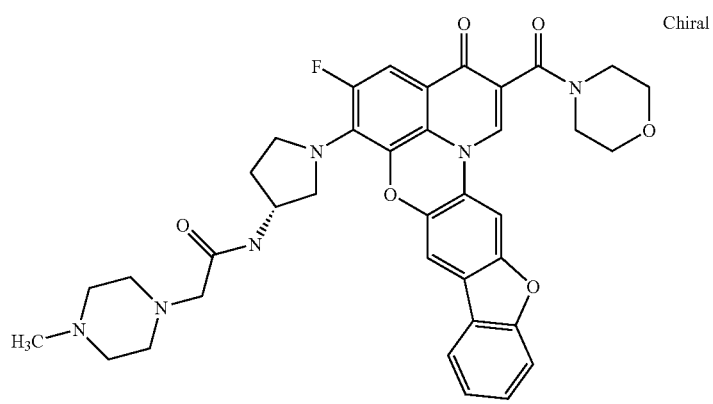
1234
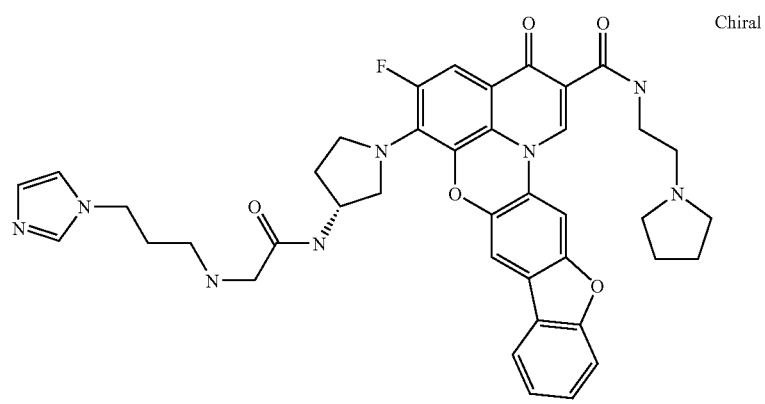

TABLE 3-continued
1235 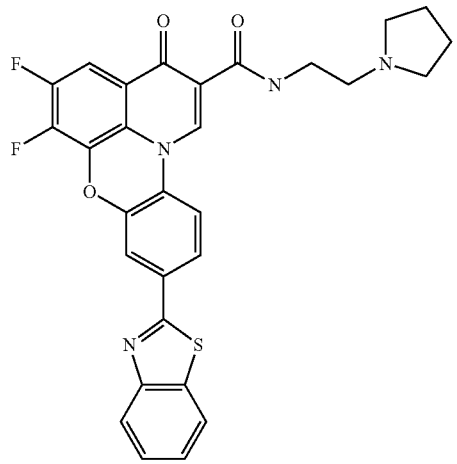
1236 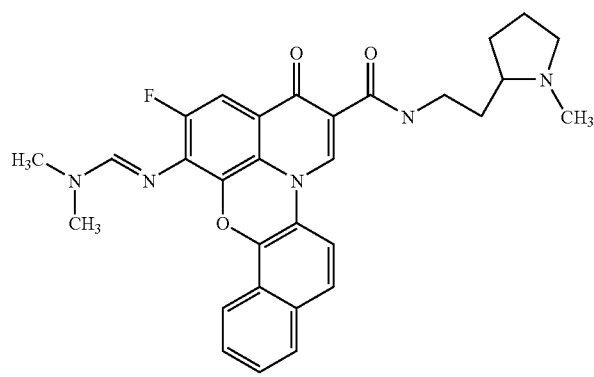
1237 Chiral 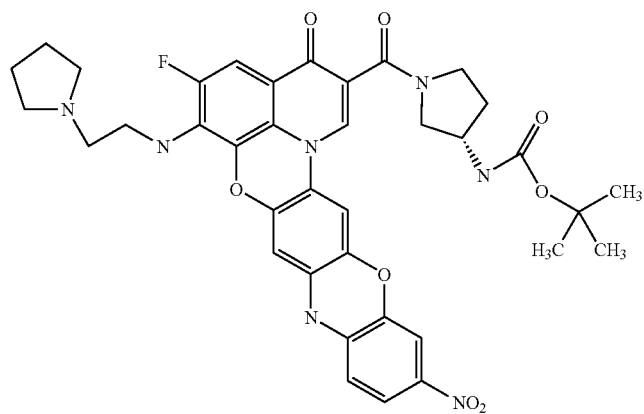

TABLE 3-continued
1238 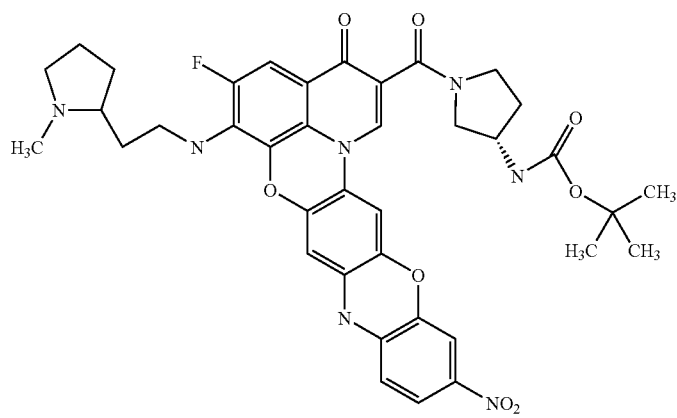
1239 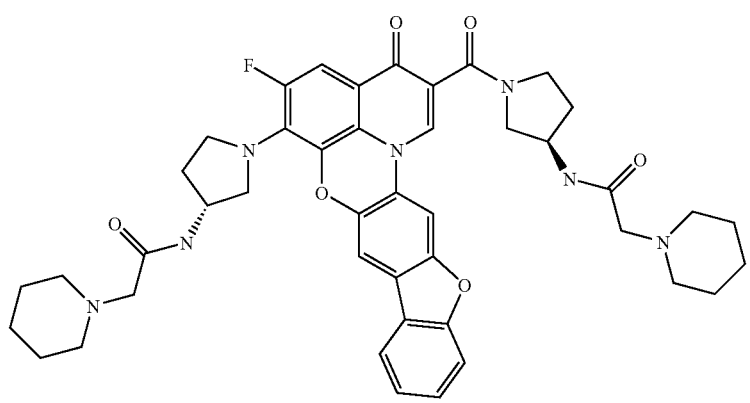
1240 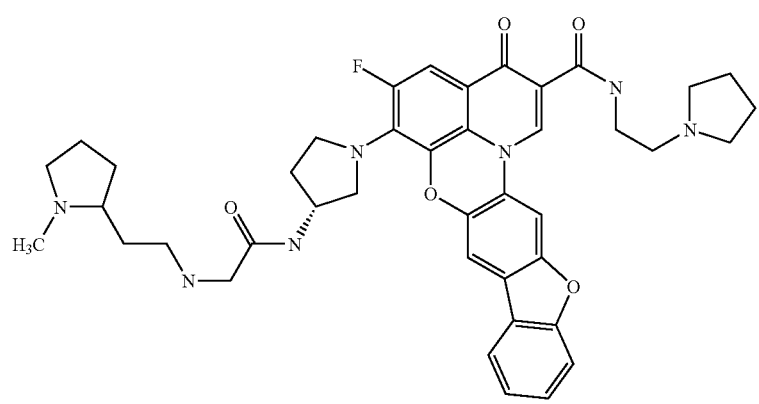
1241 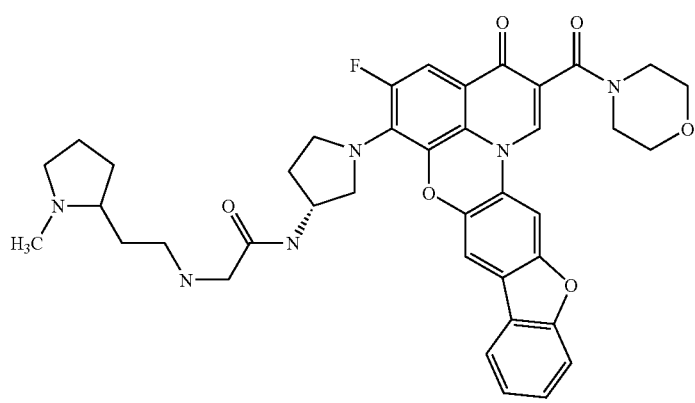

TABLE 3-continued
1242 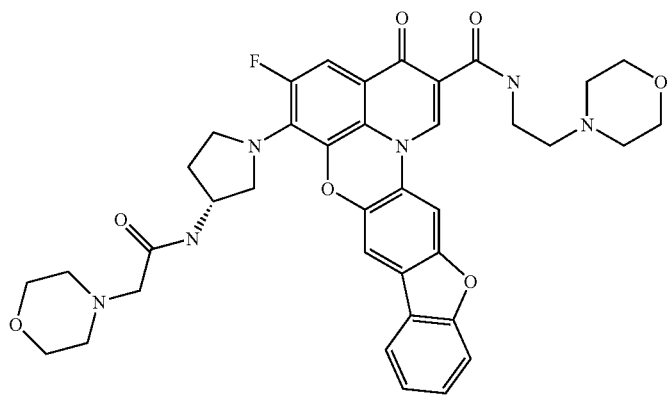 Chiral
1243 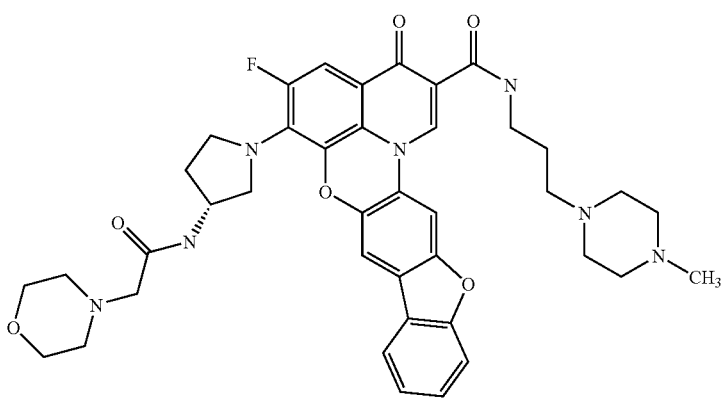 Chiral
1244 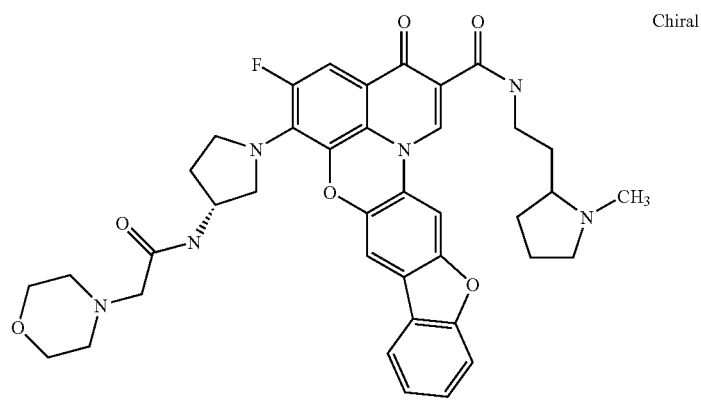 Chiral
1245 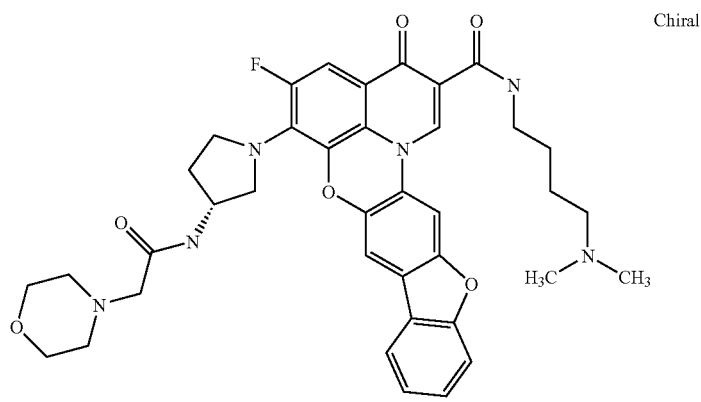 Chiral TABLE 3-continued
1246 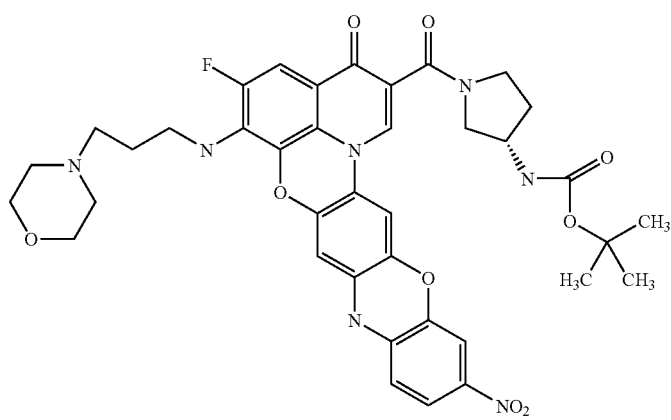
1247 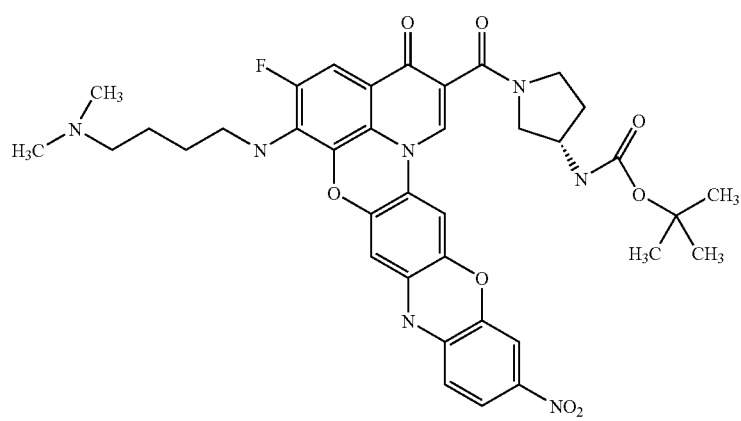
1248 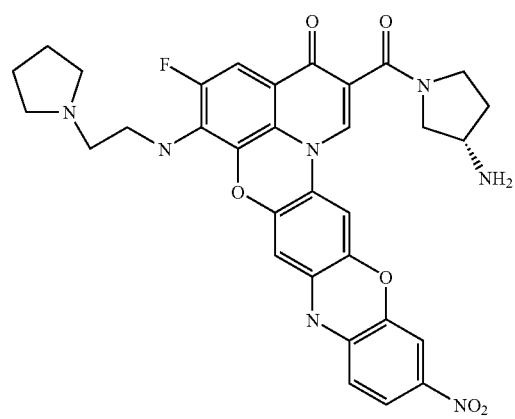

TABLE 3-continued
| 1249 | 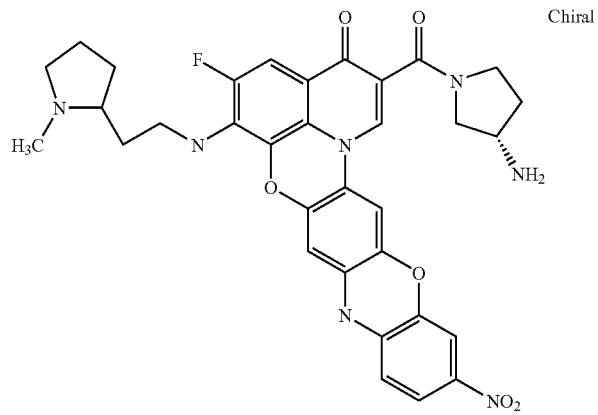 | Chiral |
| --- | --- | --- |
| 1250 | 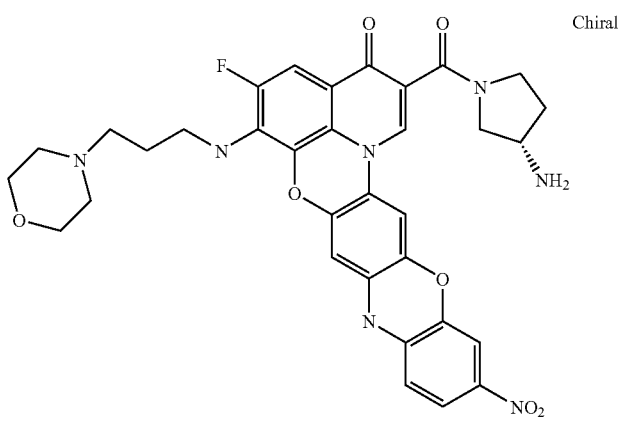 | Chiral |
| 1251 | 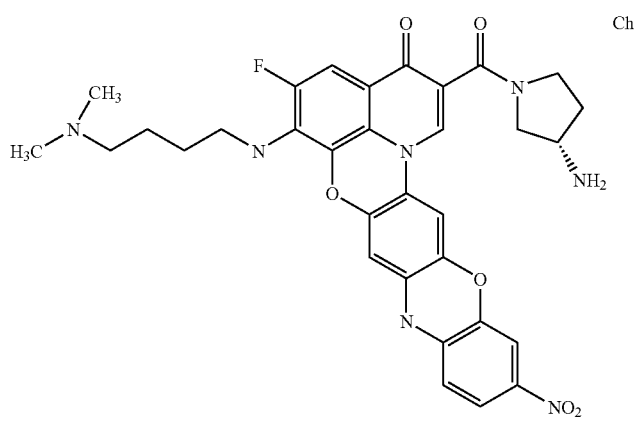 | Chiral |
| 1252 | 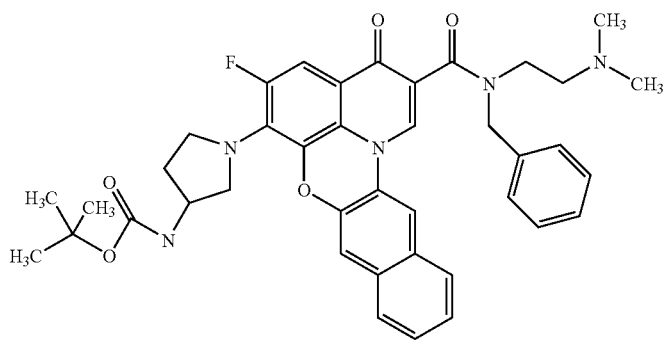 | |

TABLE 3-continued
1253
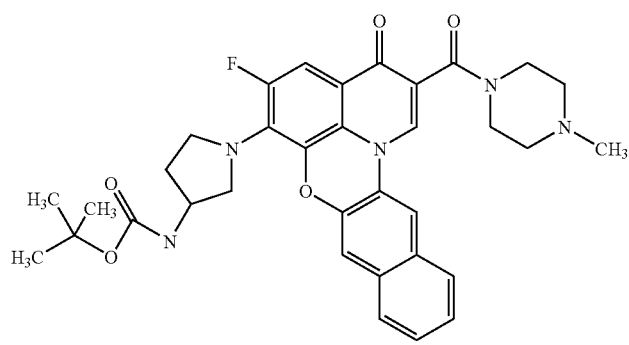
1254
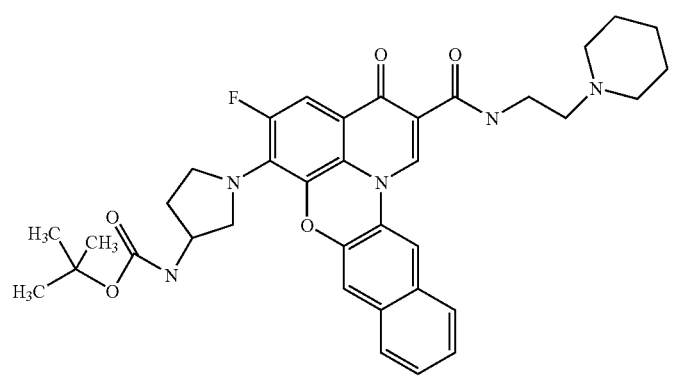
1255
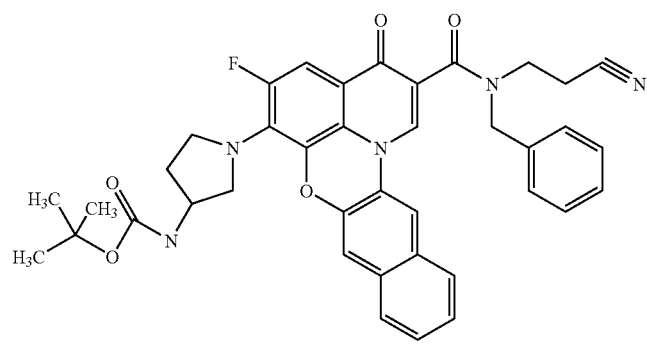
1256
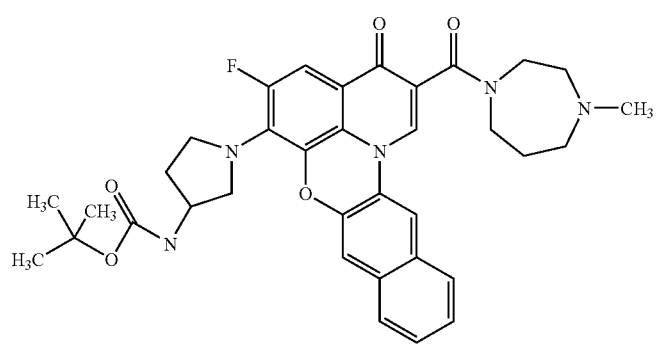

TABLE 3-continued
1257
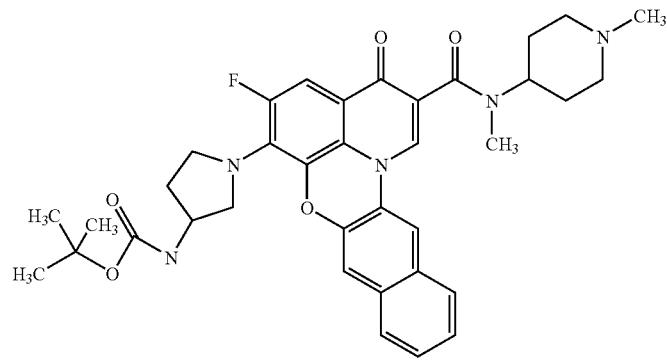
1258
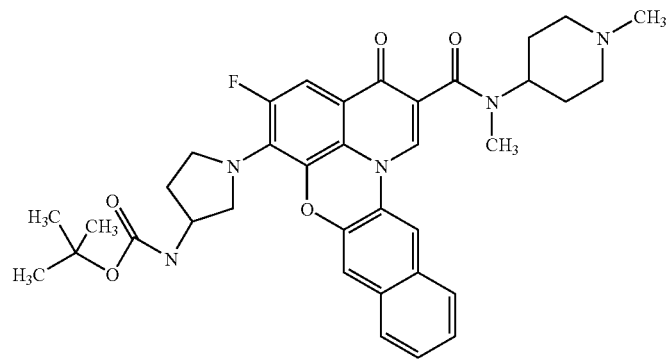
1259
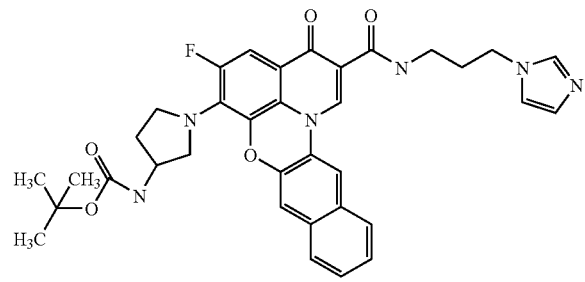
1260
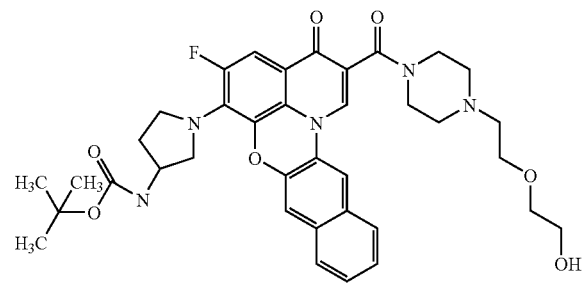
1261
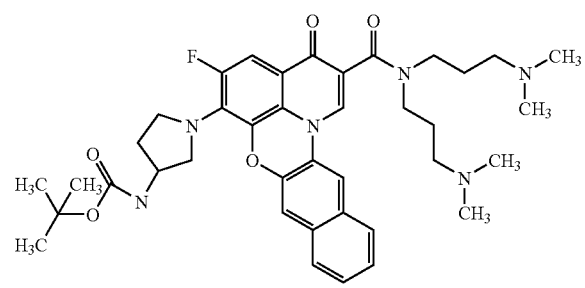

TABLE 3-continued
1262
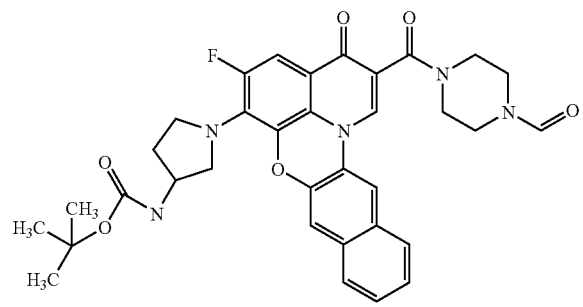
1263
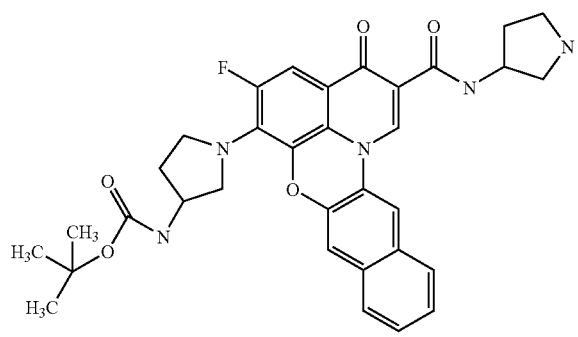
1264
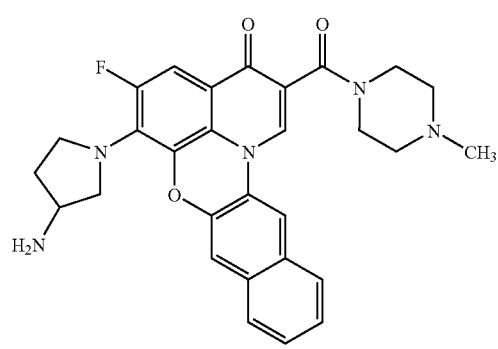
1265
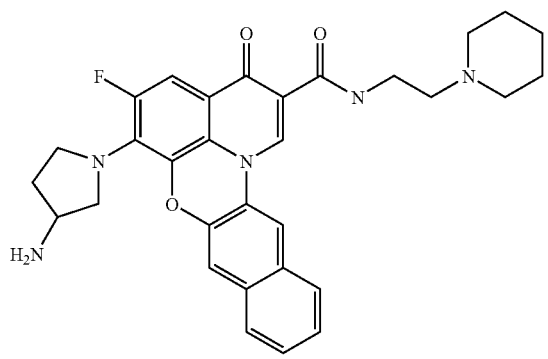

TABLE 3-continued
1266
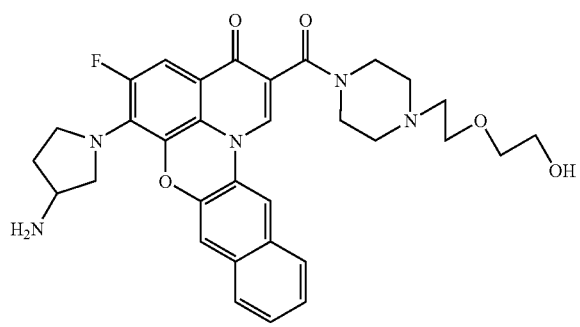
1267 Chiral
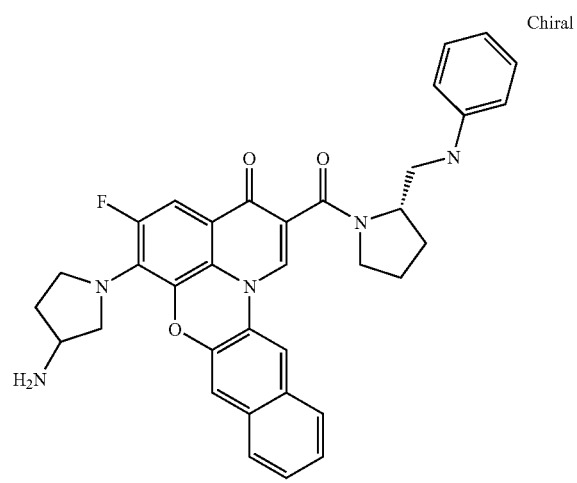
1268
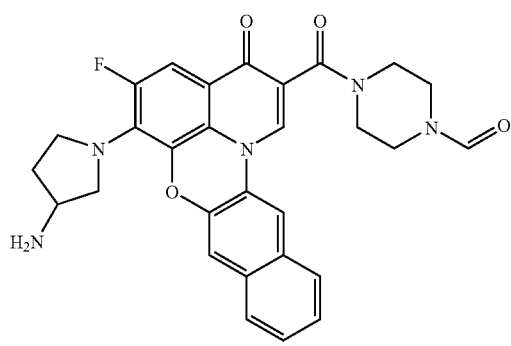
1269 Chiral
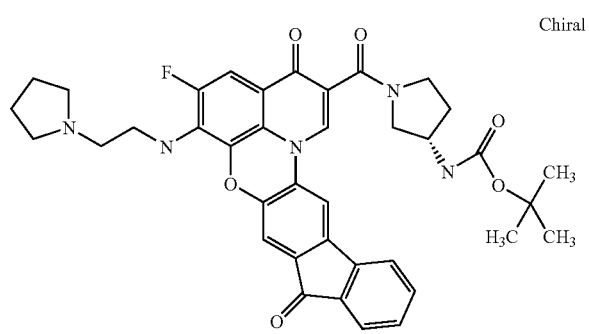

TABLE 3-continued
1270 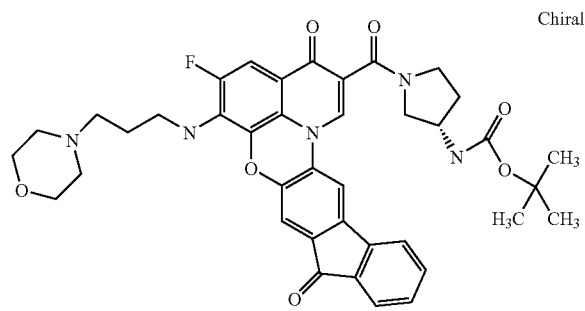 Chiral
1271 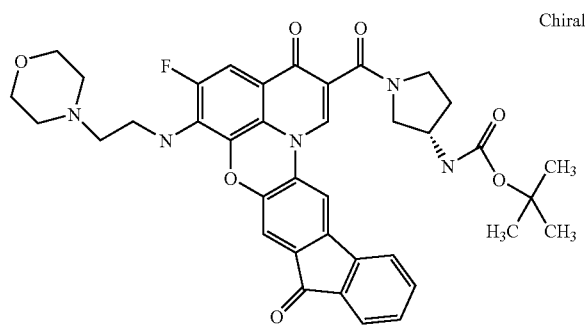 Chiral
1272 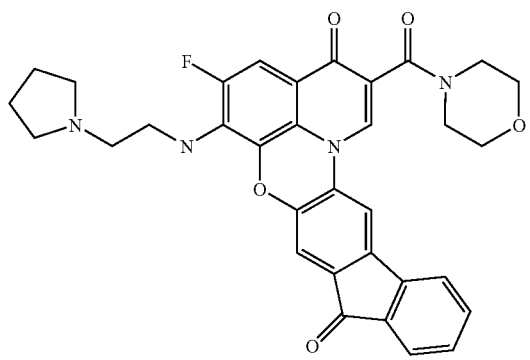
1273 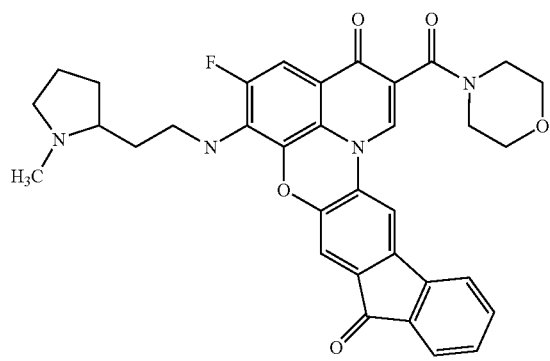

TABLE 3-continued
1274
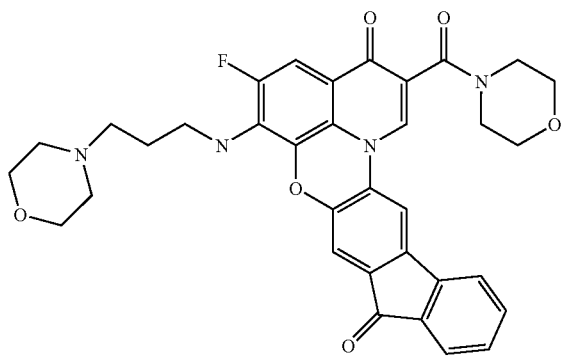
1275
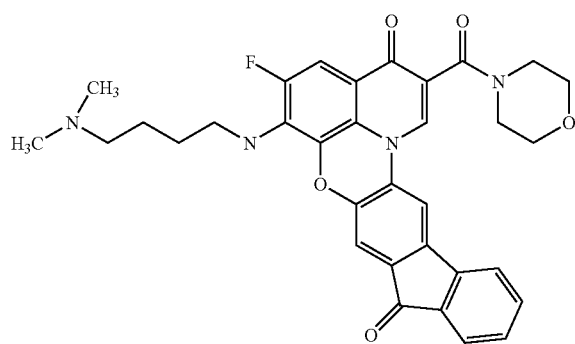
1276
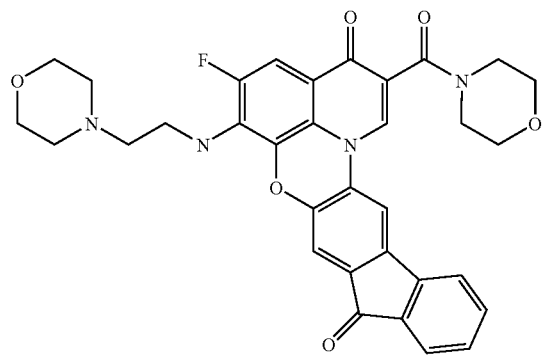
1277
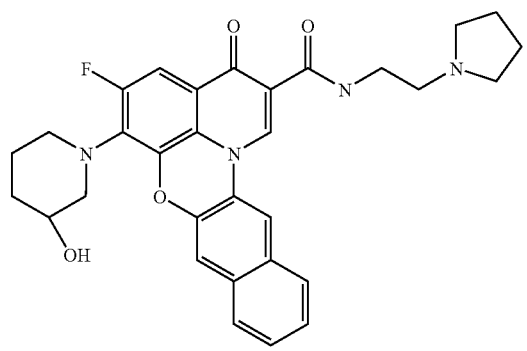

TABLE 3-continued
1278
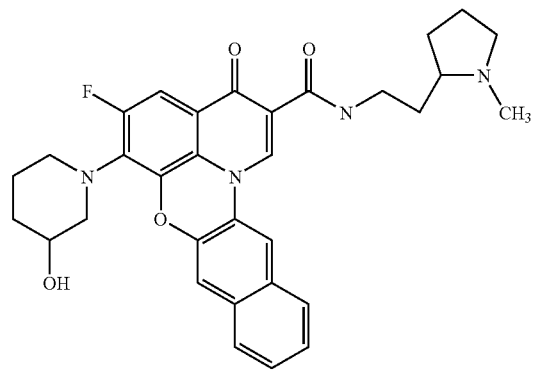
1279
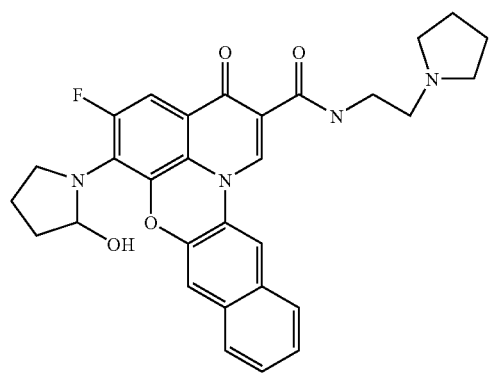
1280
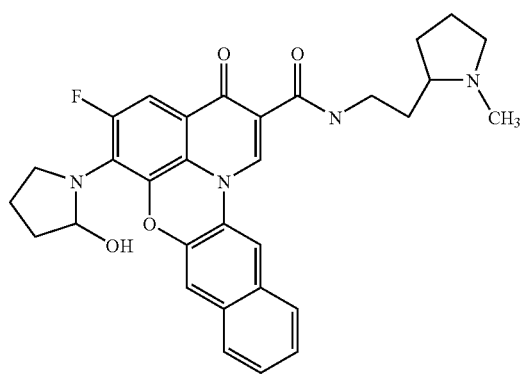
1281
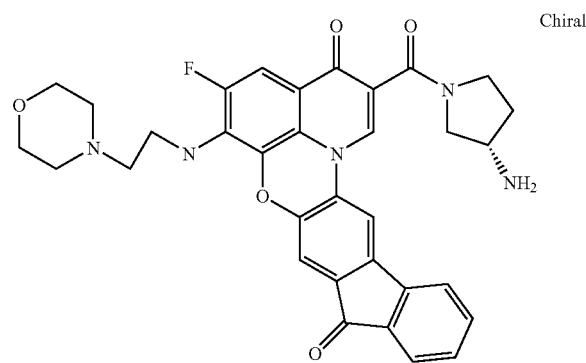

TABLE 3-continued
1282 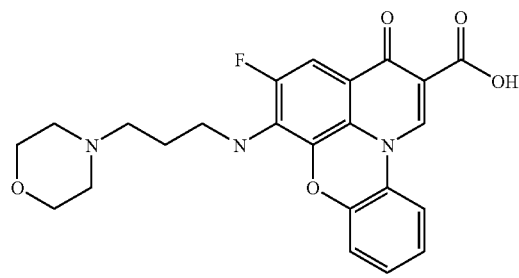
1283 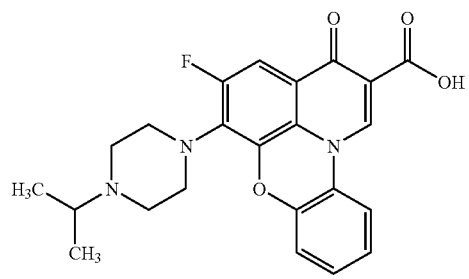
1284 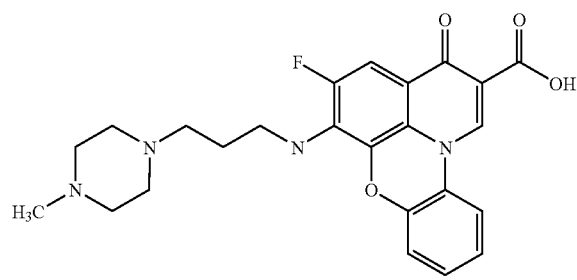
1285 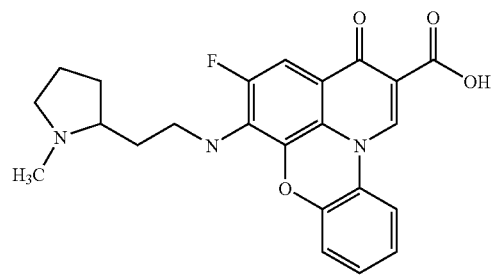
1286 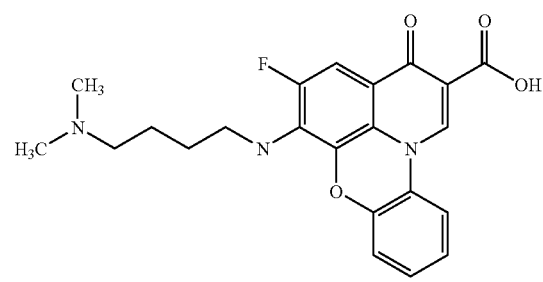

TABLE 3-continued
1287 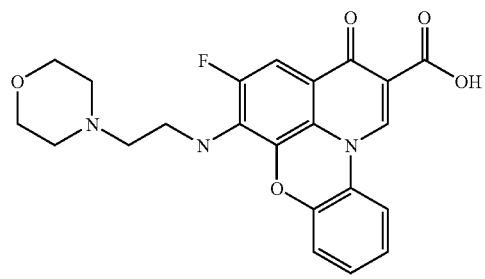
1288 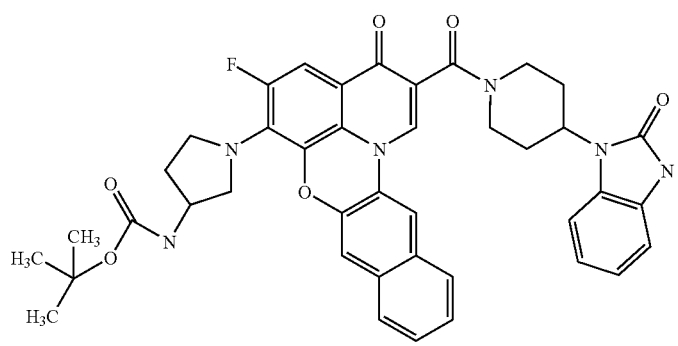
1289 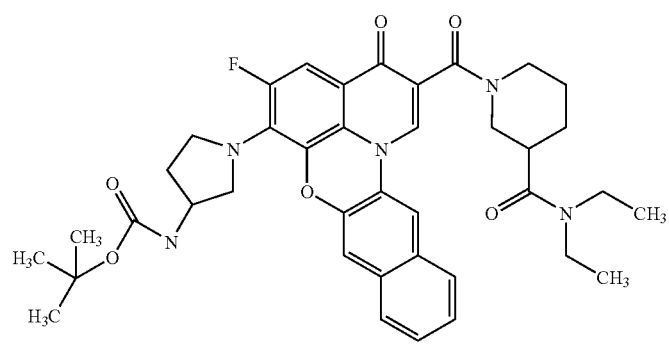
1290 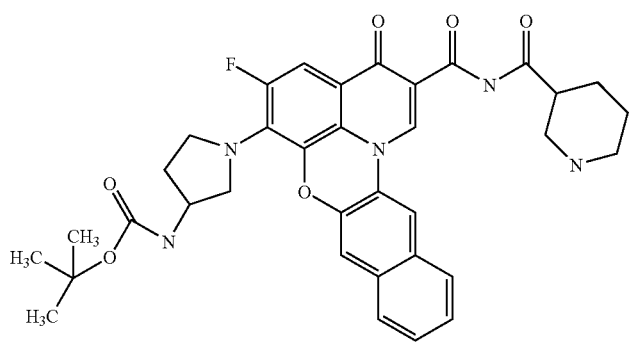

TABLE 3-continued
1291
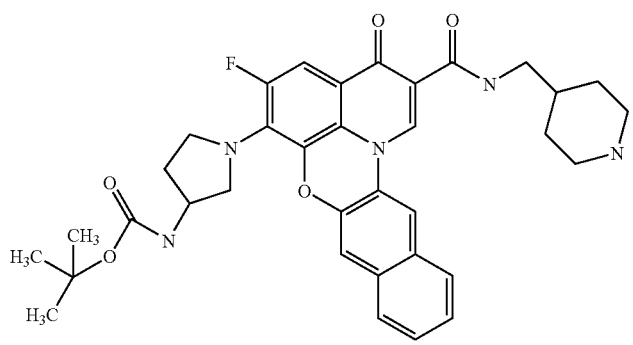
1292
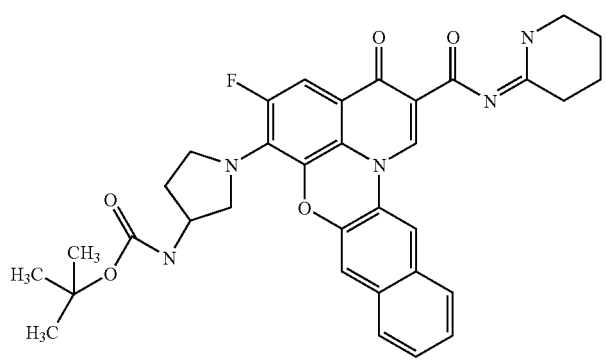
1293
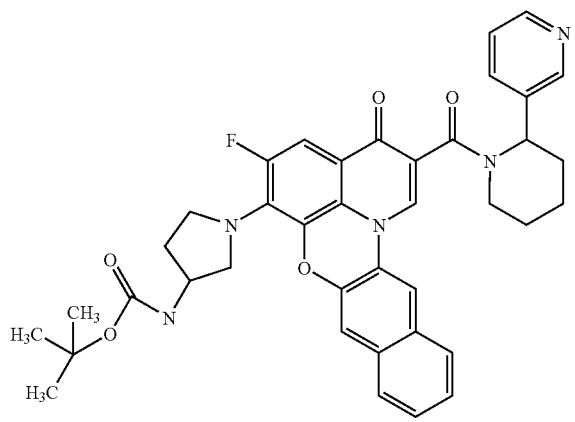
1294
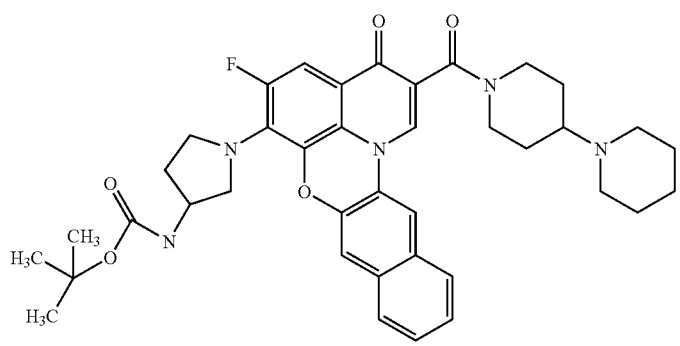

TABLE 3-continued
1295
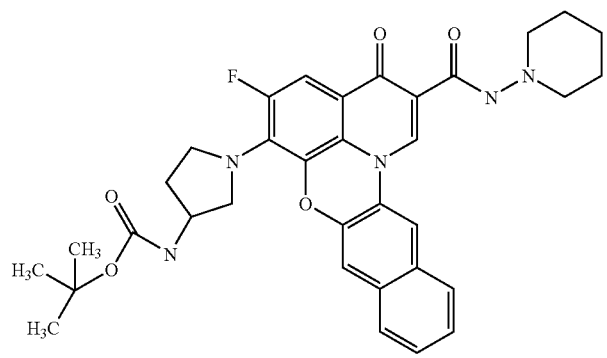
1296
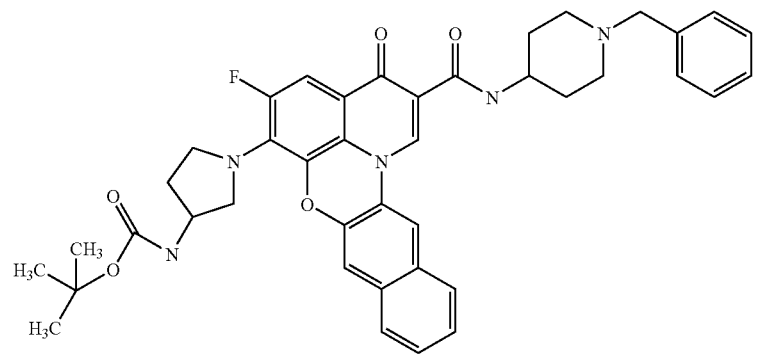
1297
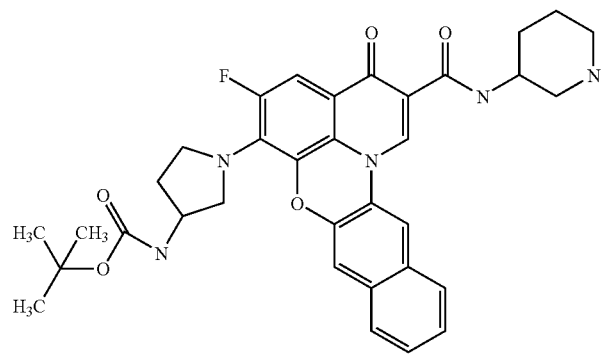
1298
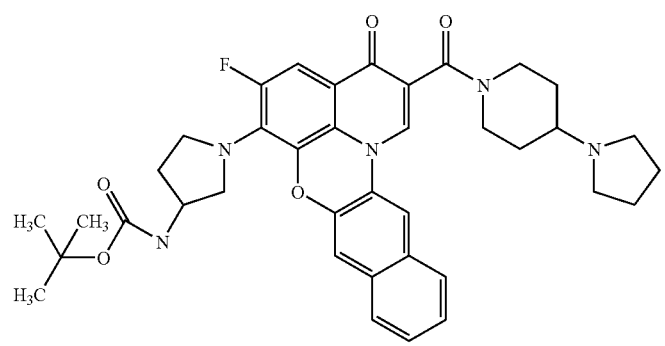

TABLE 3-continued
1299
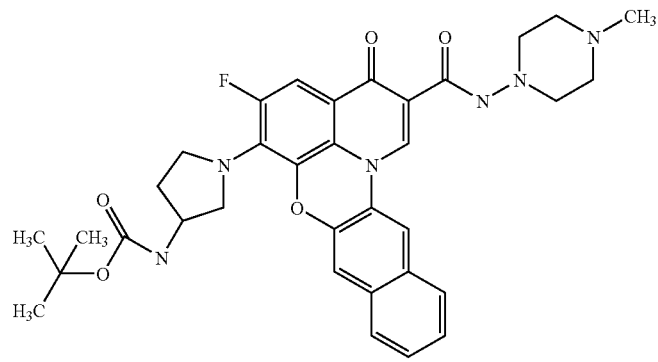
1300
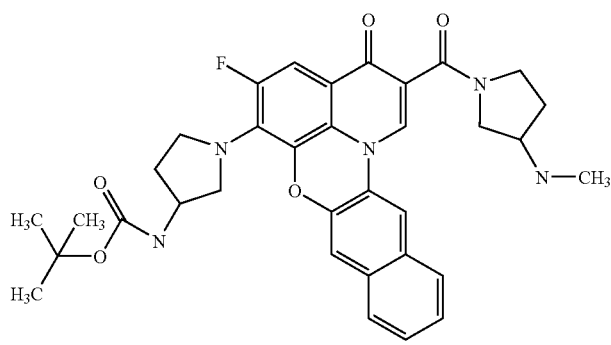
1301
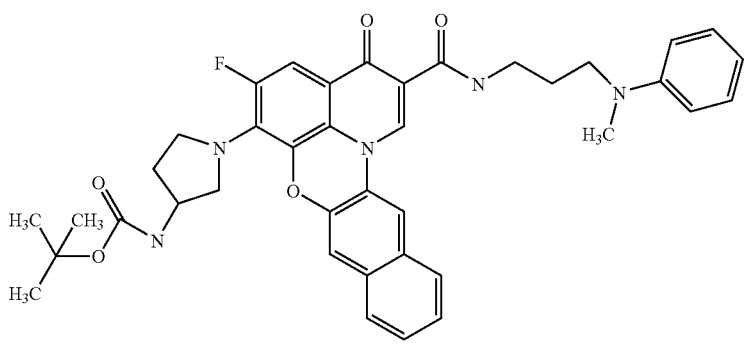
1302
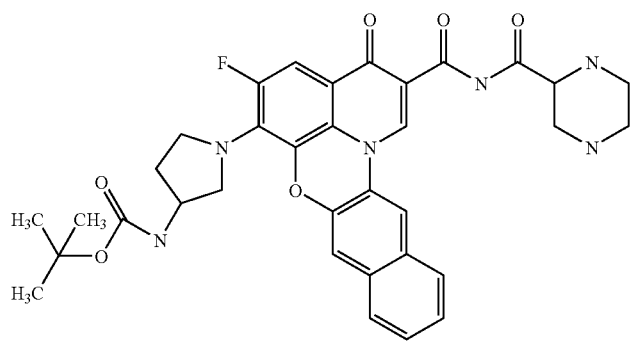

TABLE 3-continued
1303 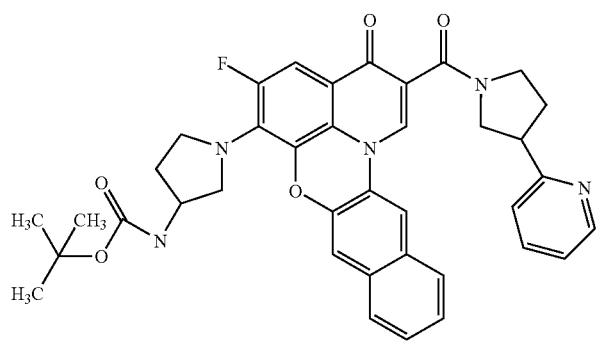
1304 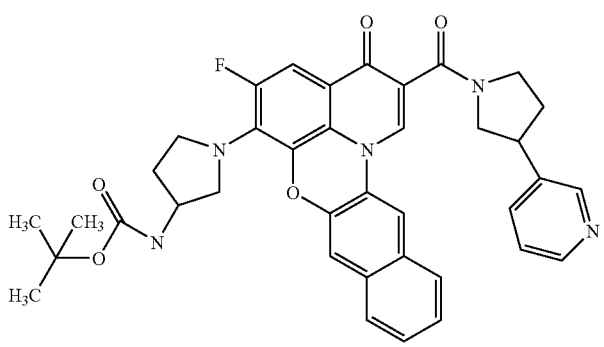
1305 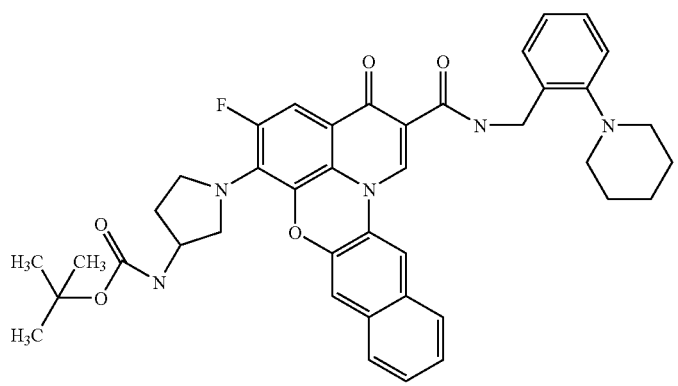
1306 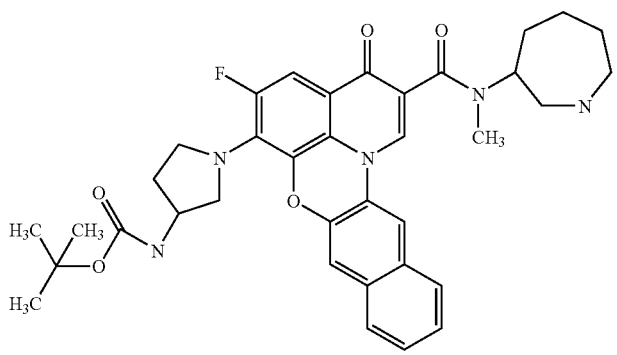

TABLE 3-continued
1307 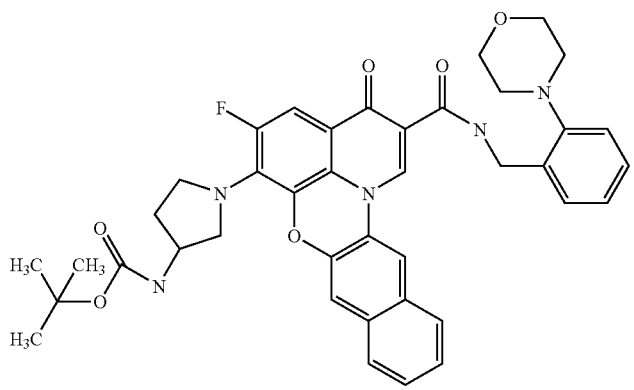
1308 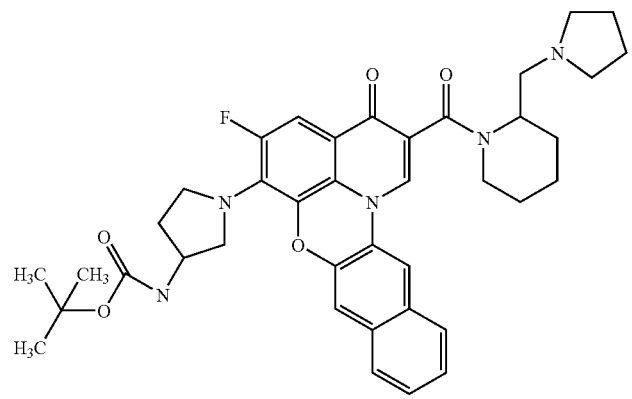
1309 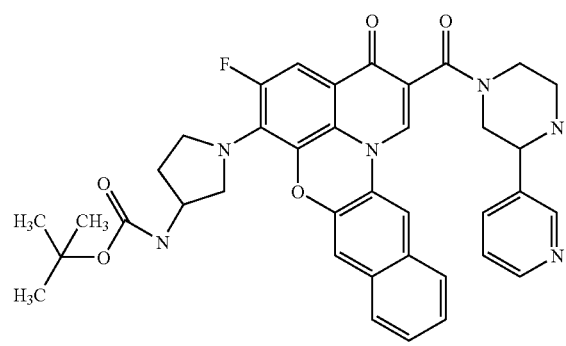
1310 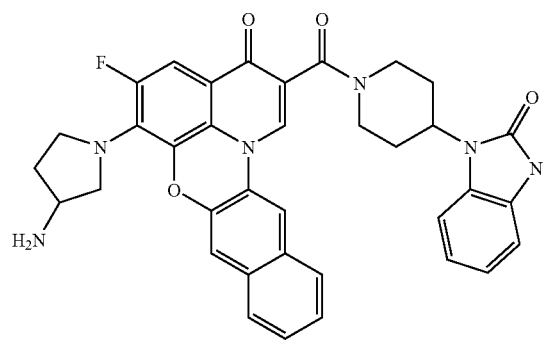

TABLE 3-continued
1311
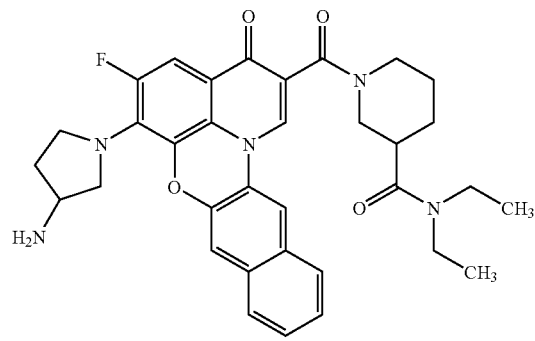
1312
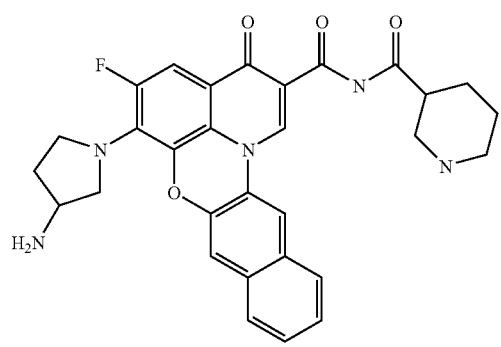
1313
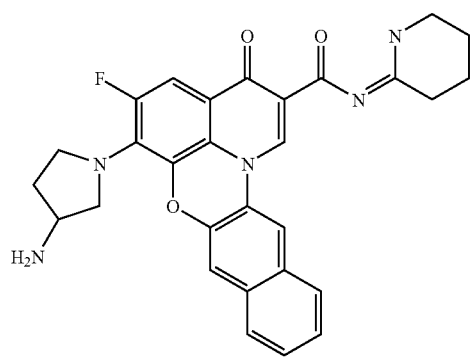
1314
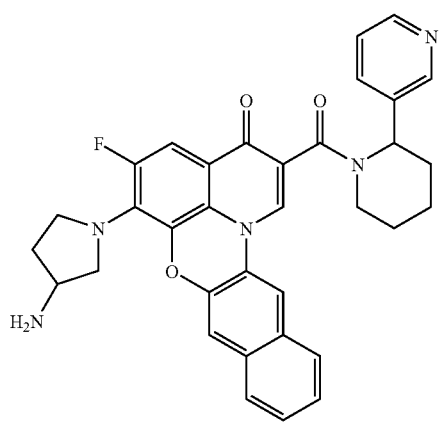

TABLE 3-continued
| 1315 | 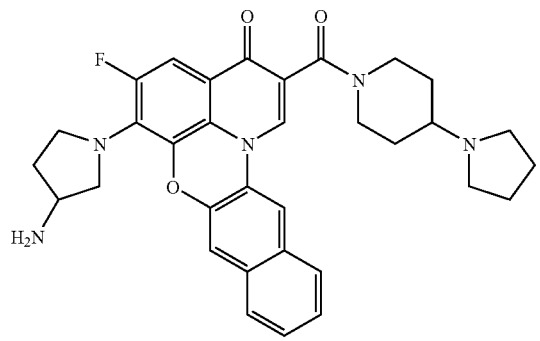 |
| 1316 | 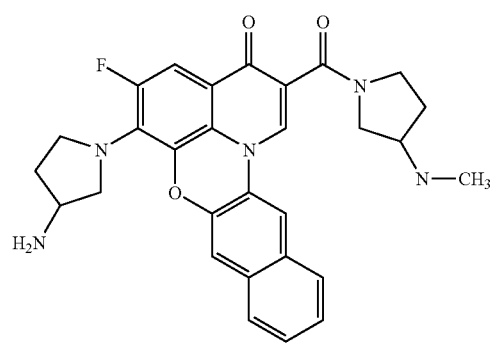 |
| 1317 | 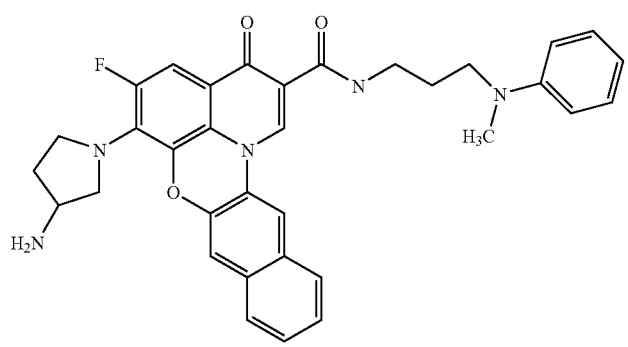 |
| 1318 | 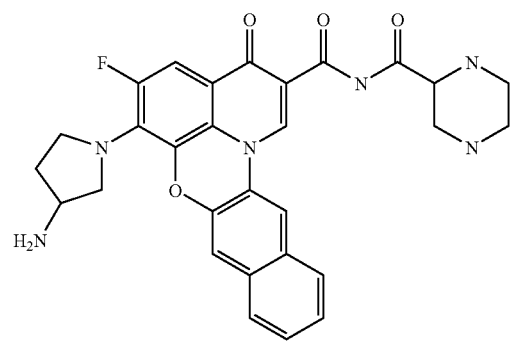 |

TABLE 3-continued
1319 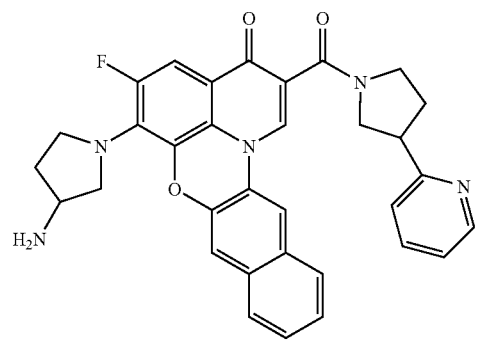
1320 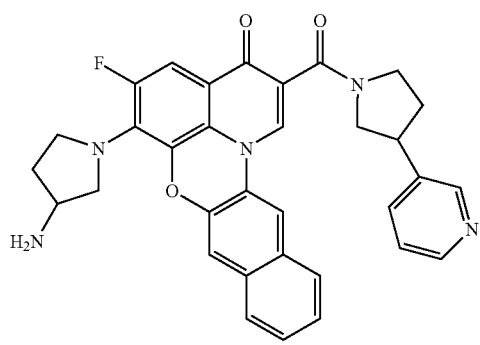
1321 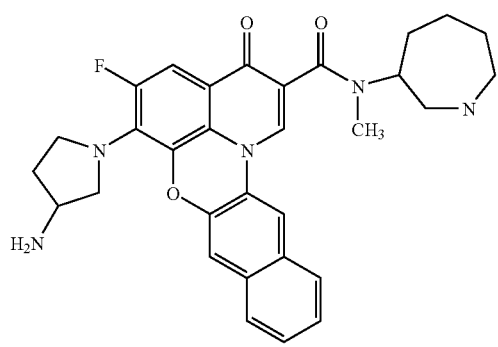
1322 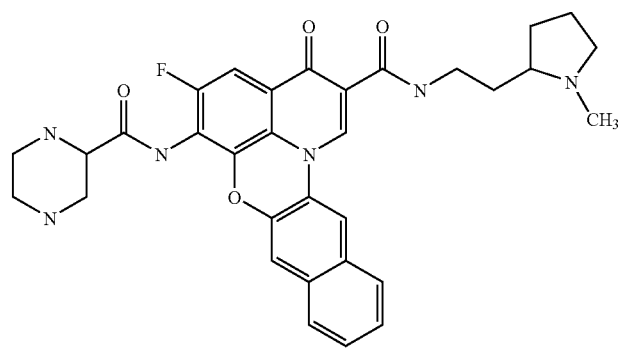

TABLE 3-continued
1323 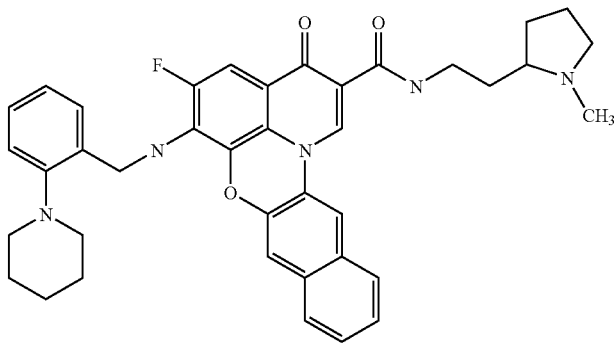
1324 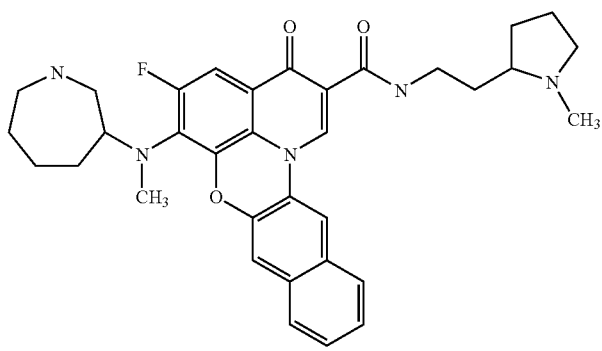
1325 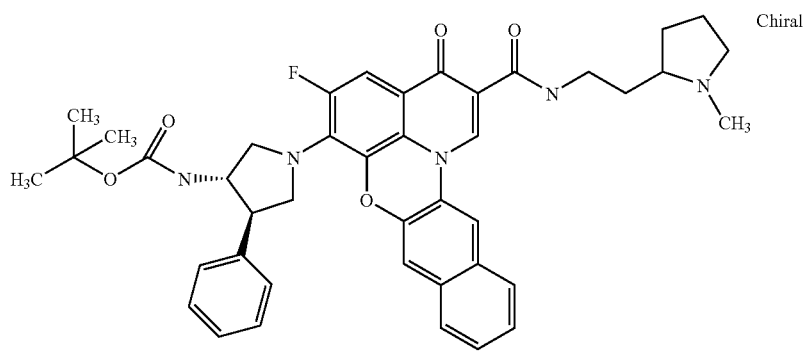
Chiral
1326 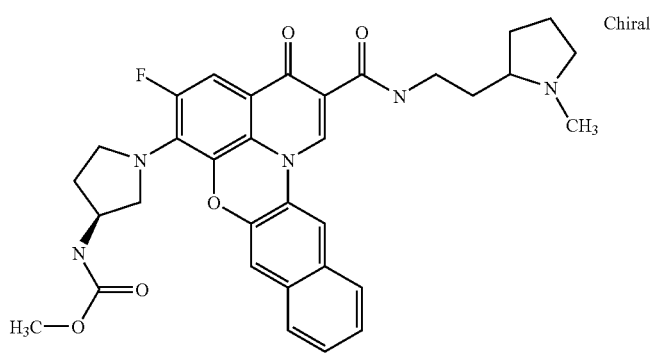
Chiral TABLE 3-continued
1327 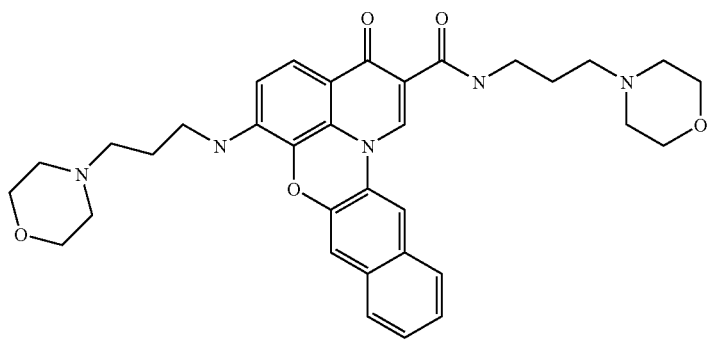
1328 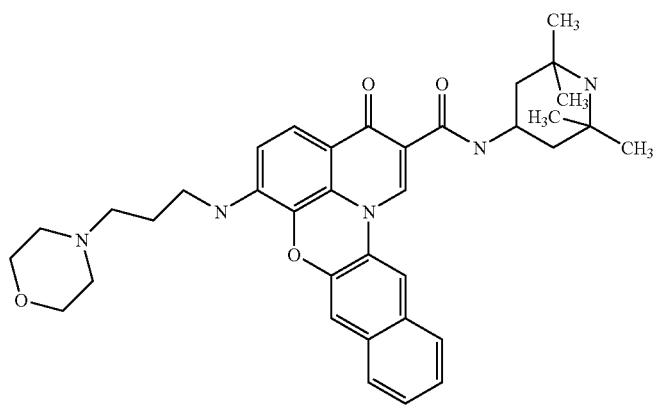
1329 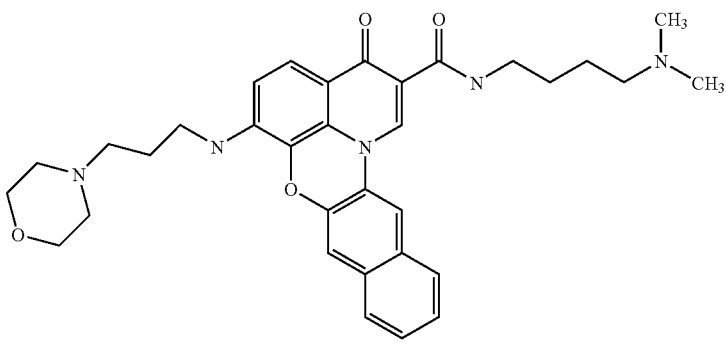
1330 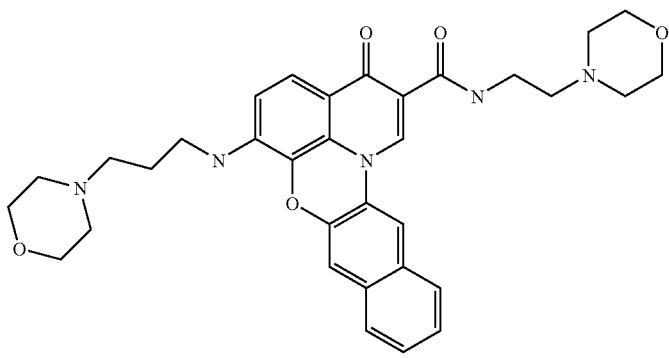

TABLE 3-continued
1331 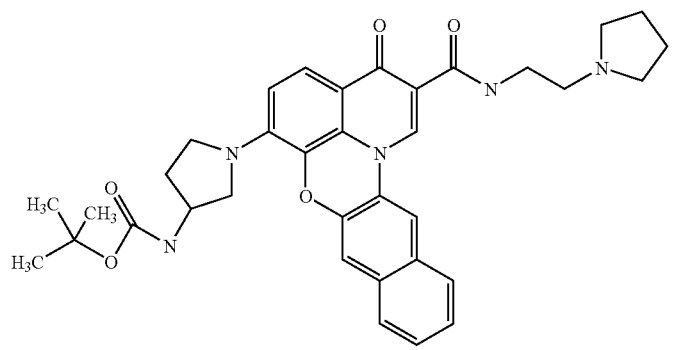
1332 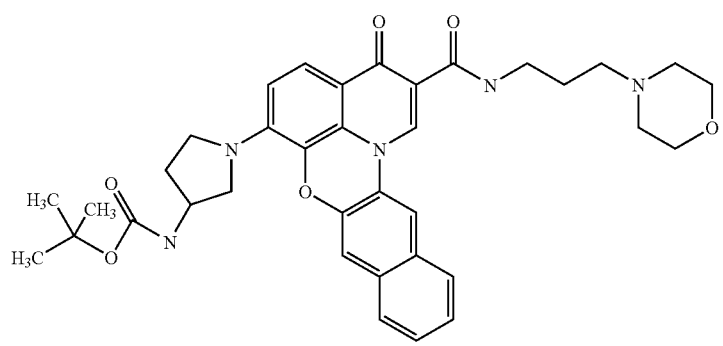
1333 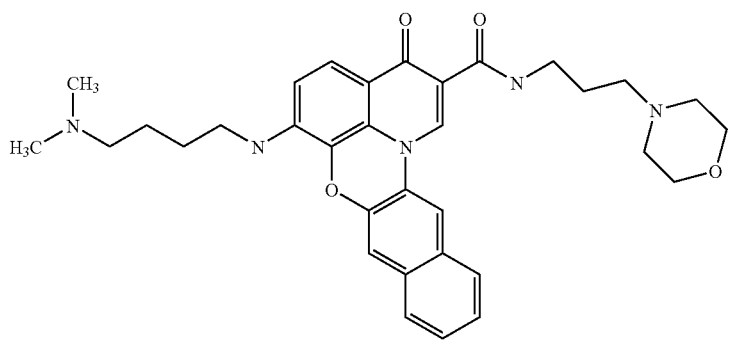
1334 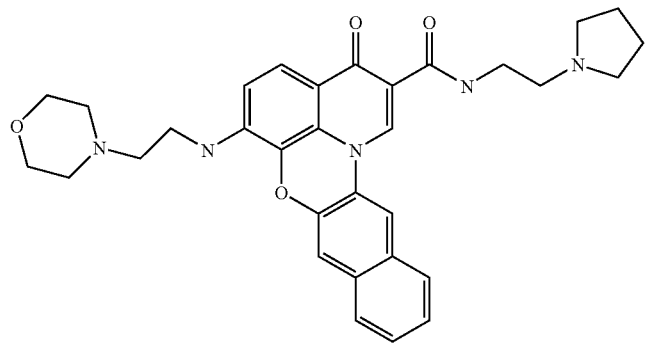

TABLE 3-continued
1335 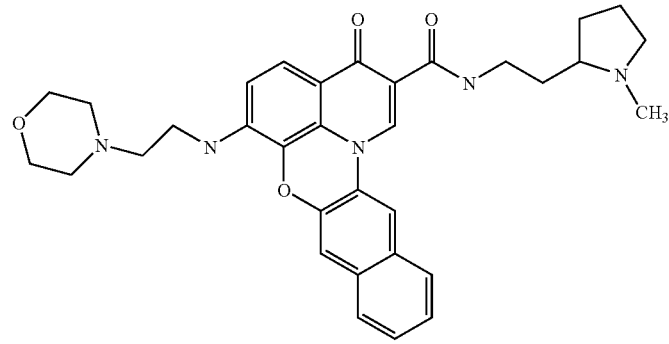
1336 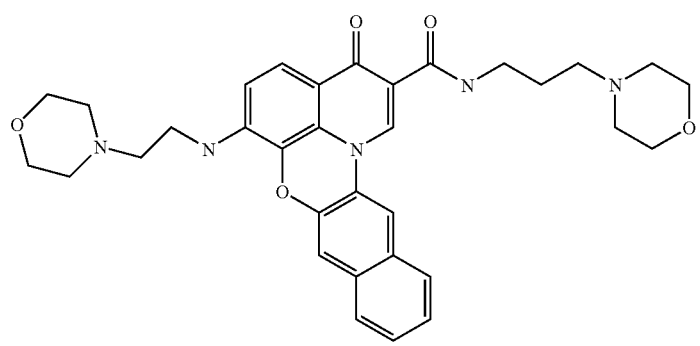
1337 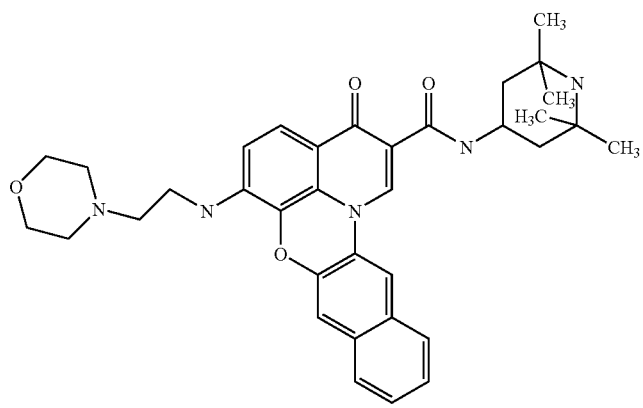
1338 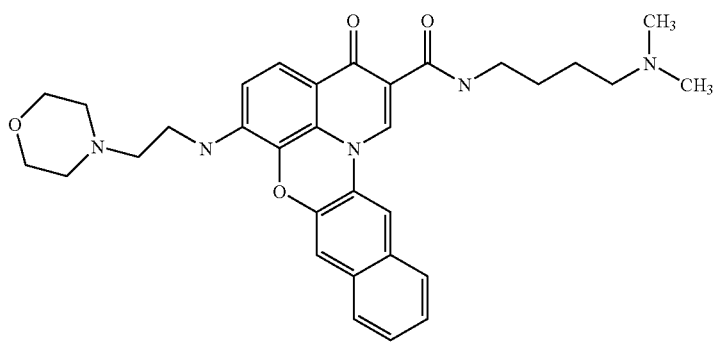

TABLE 3-continued
1339 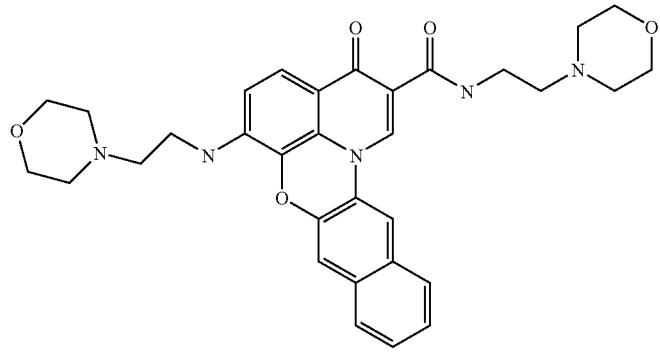
1340 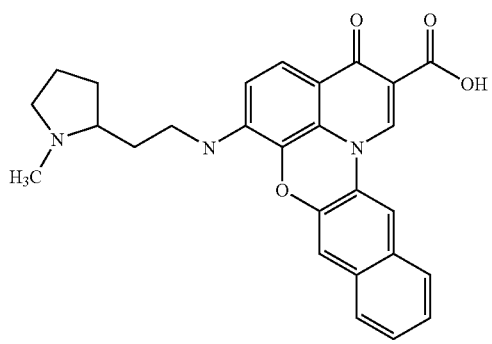
1341 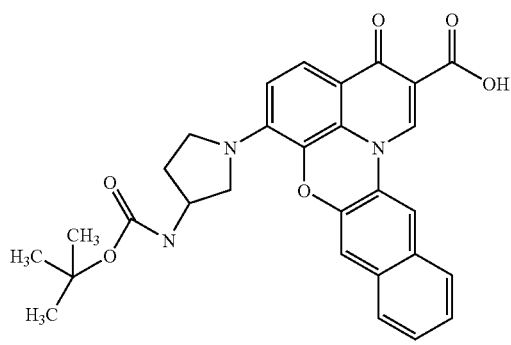
1342 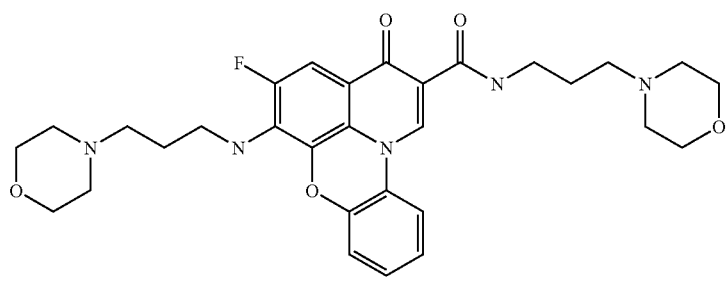
1343 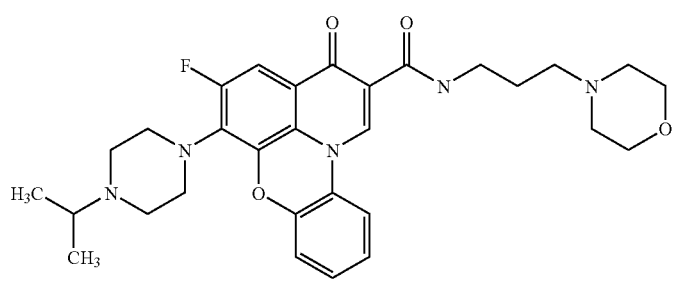

TABLE 3-continued
1344
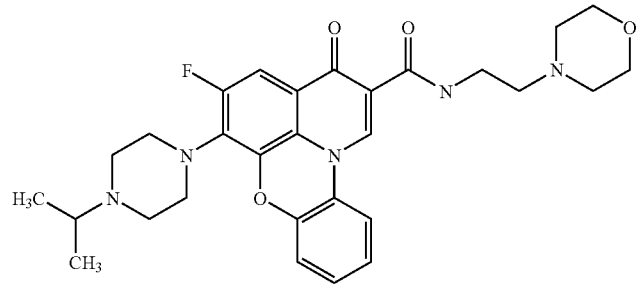
1345
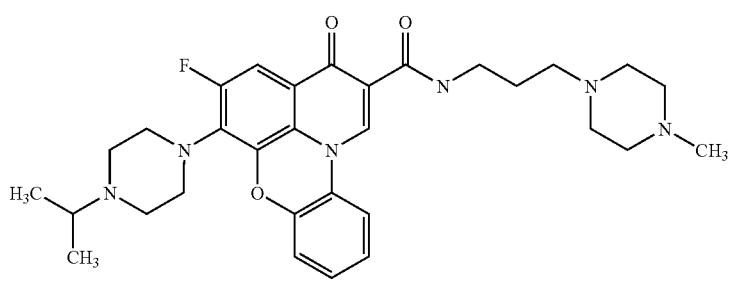
1346
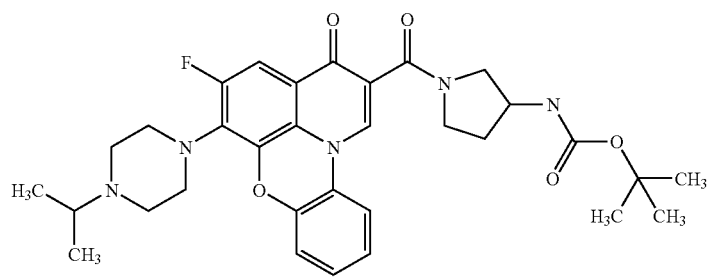
1347
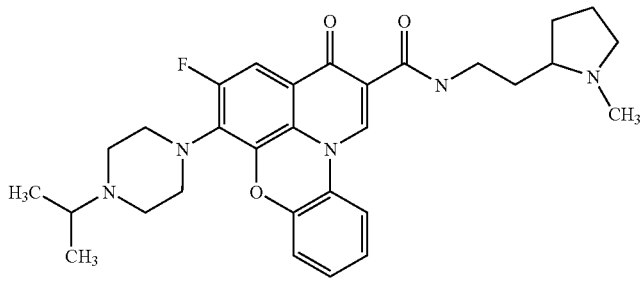
1348
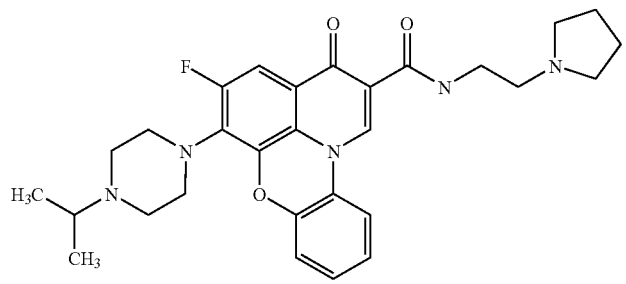

TABLE 3-continued
1349 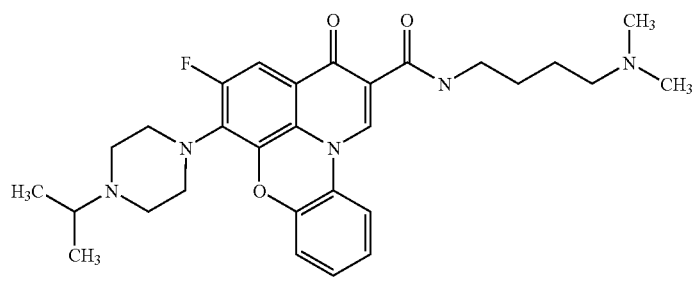
1350 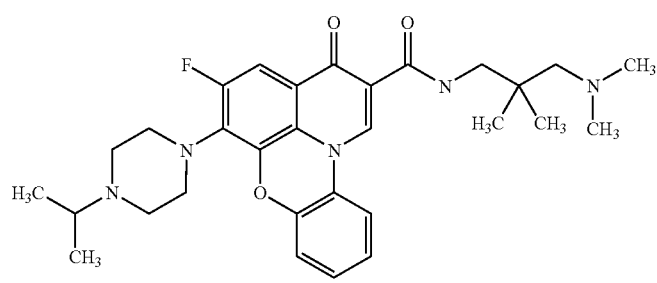
1351 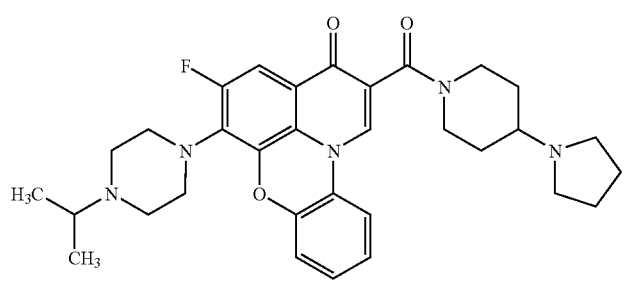
1352 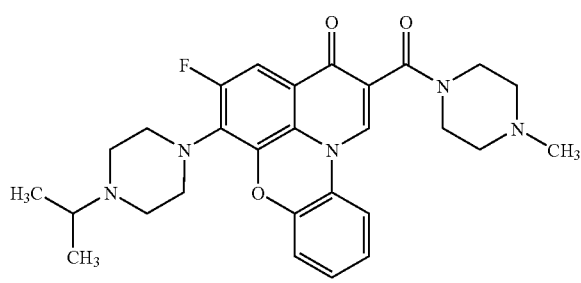
1353 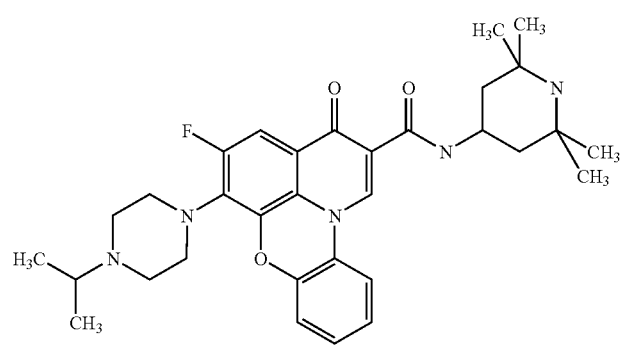

TABLE 3-continued
1354 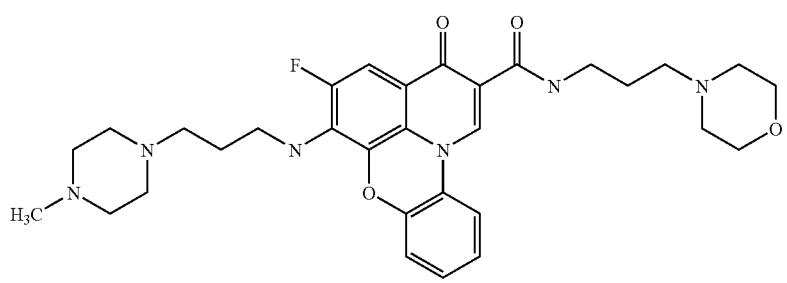
1355 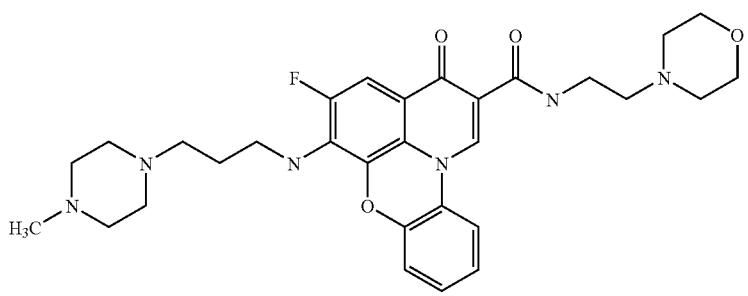
1356 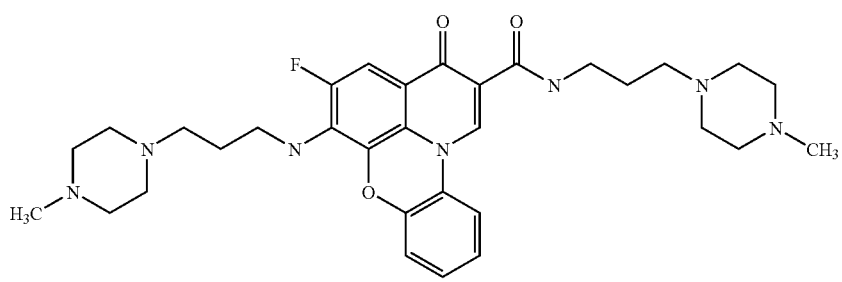
1357 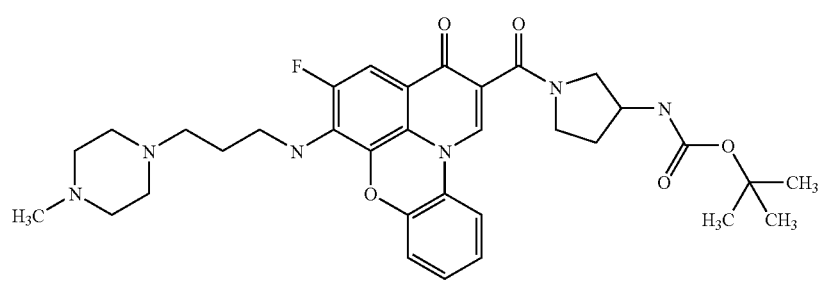
1358 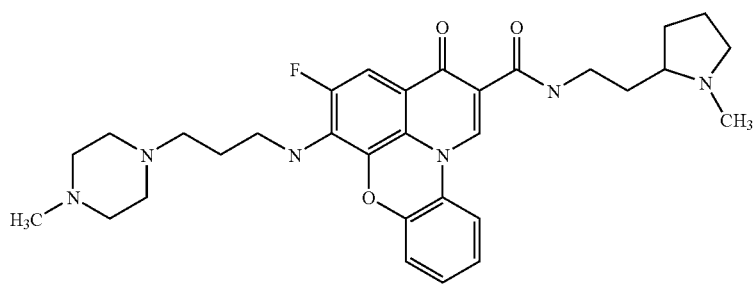

TABLE 3-continued
1359 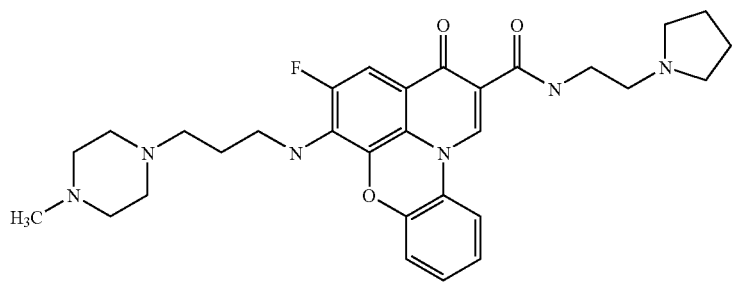
1360 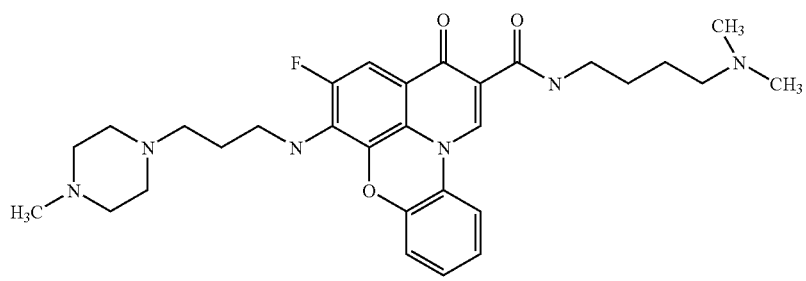
1361 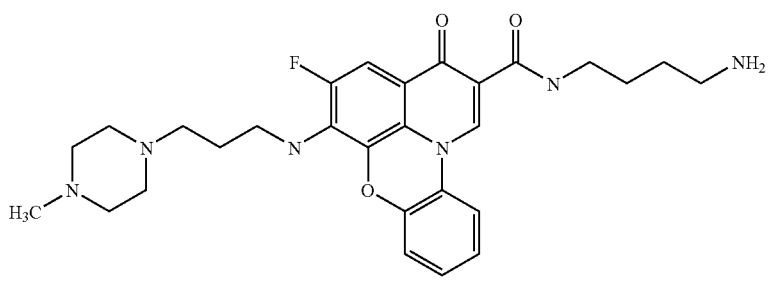
1362 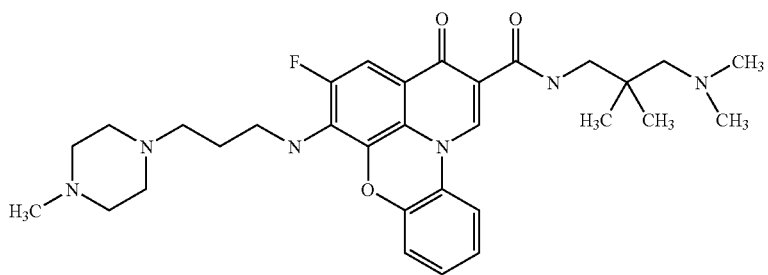
1363 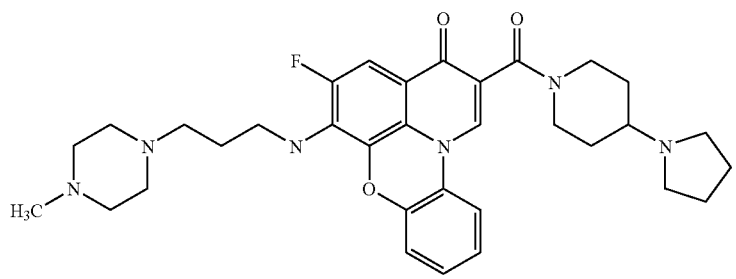

TABLE 3-continued
1364 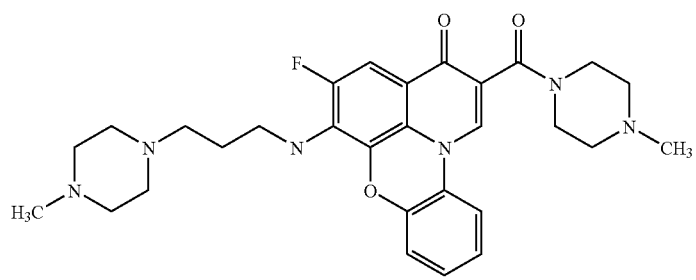
1365 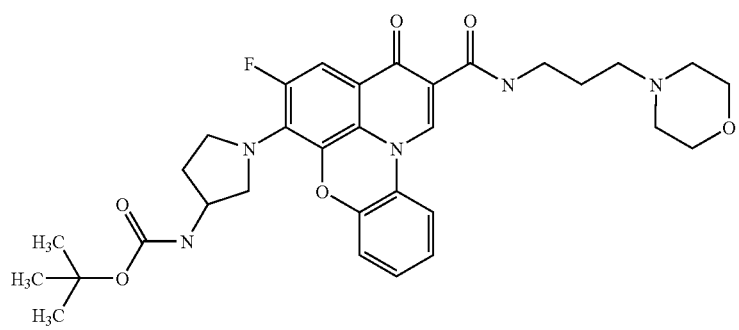
1366 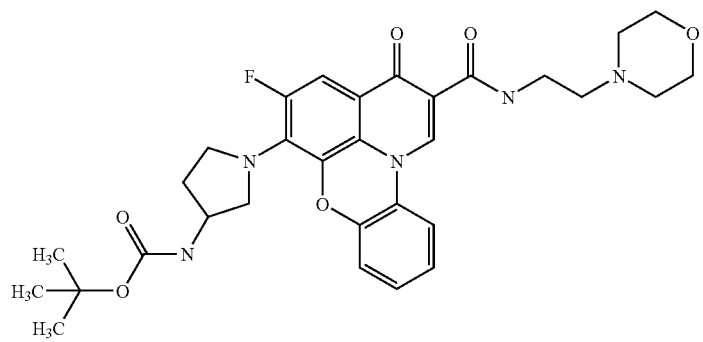
1367 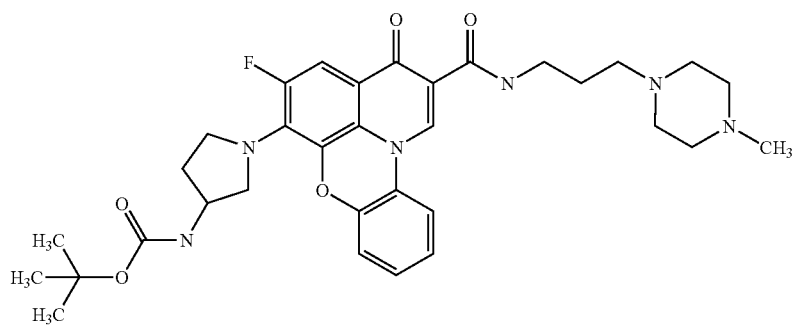
1368 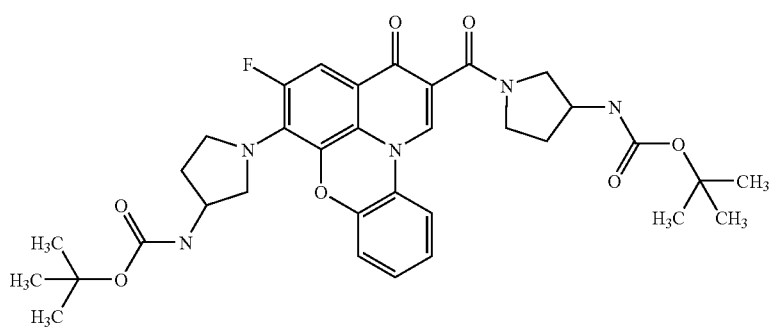

TABLE 3-continued
1369
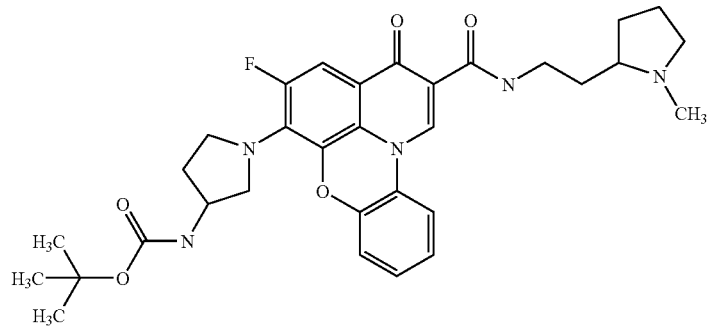
1370
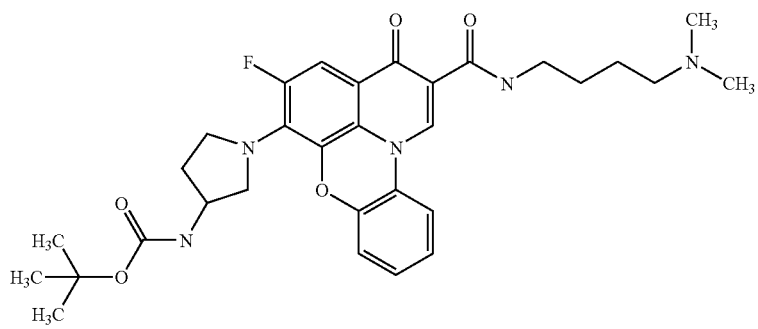
1371
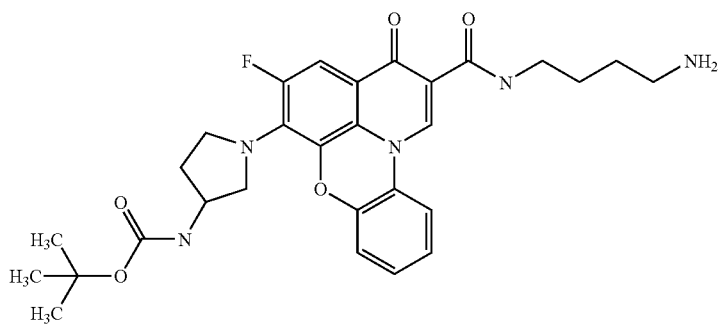
1372
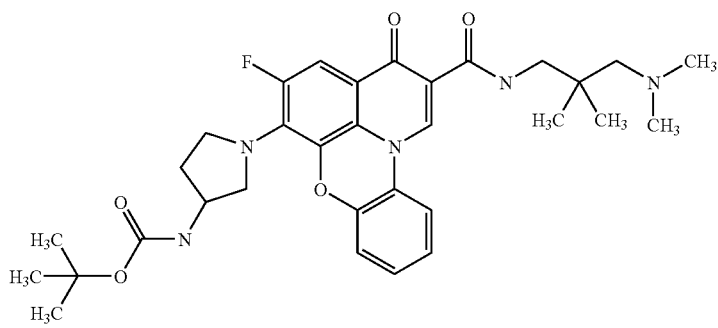

TABLE 3-continued
1373
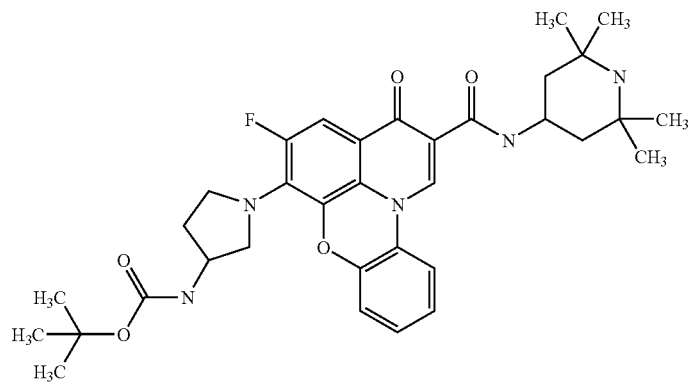
1374
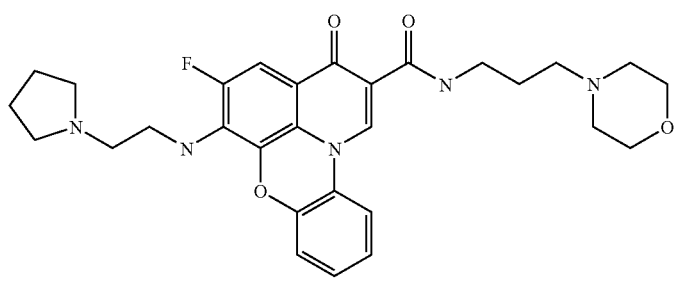
1375
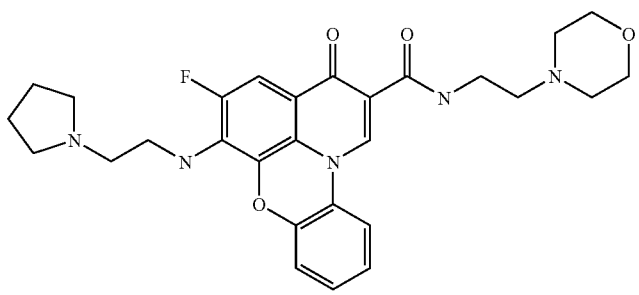
1376
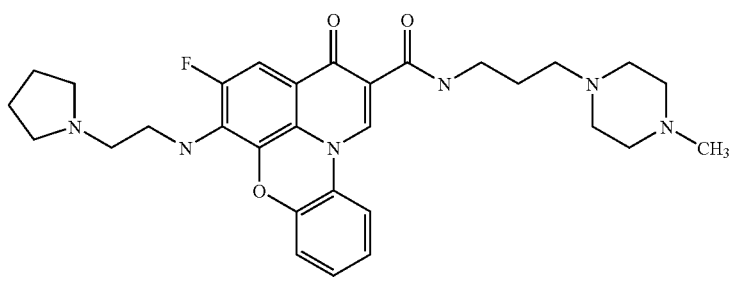
1377
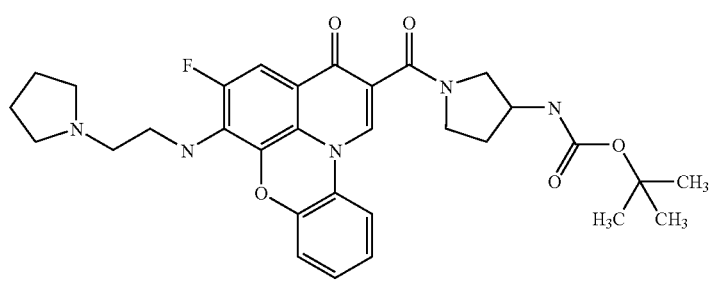

TABLE 3-continued
1378 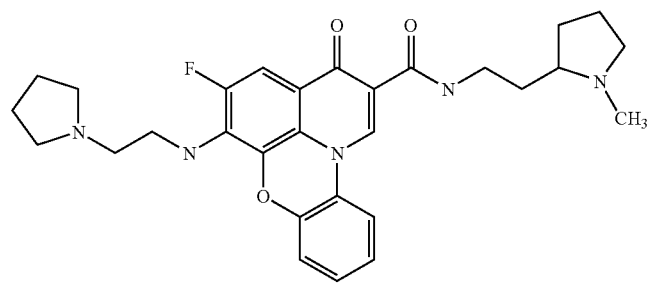
1379 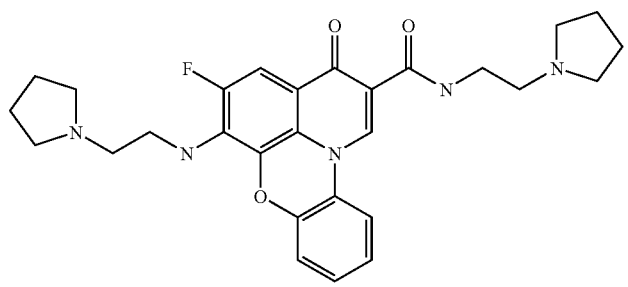
1380 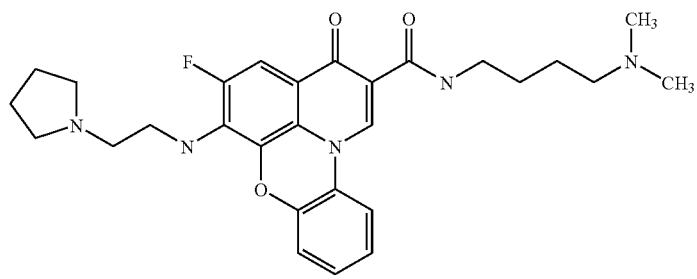
1381 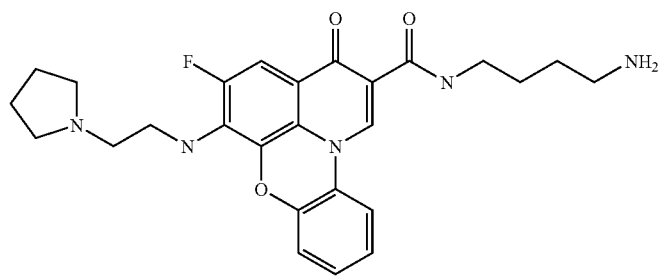
1382 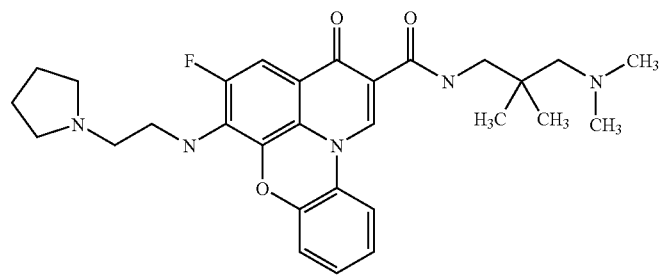

TABLE 3-continued
1383 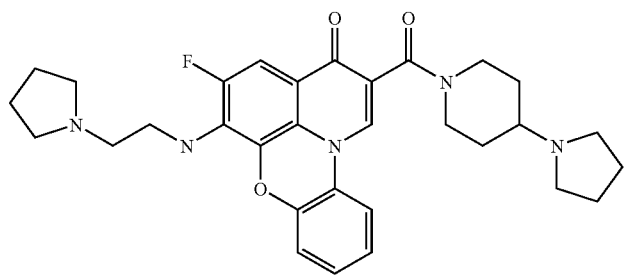
1384 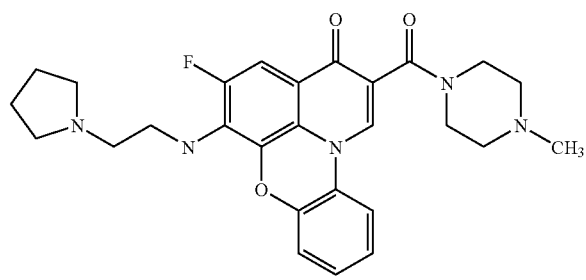
1385 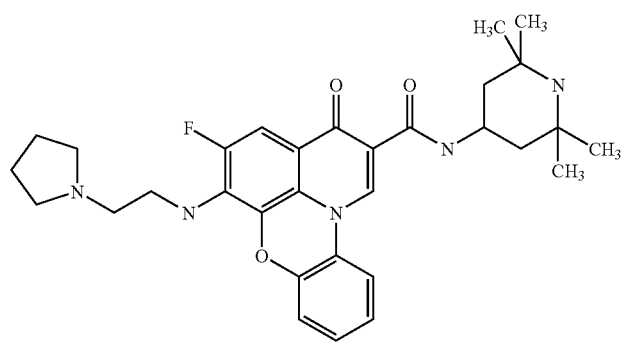
1386 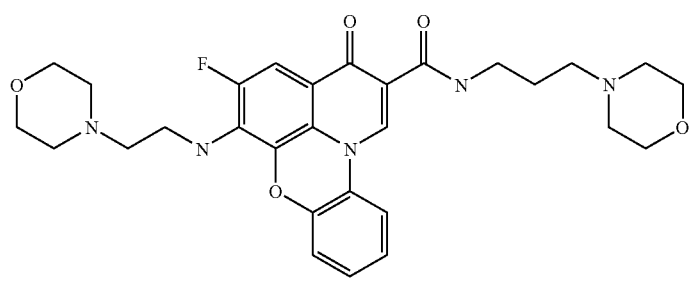
1387 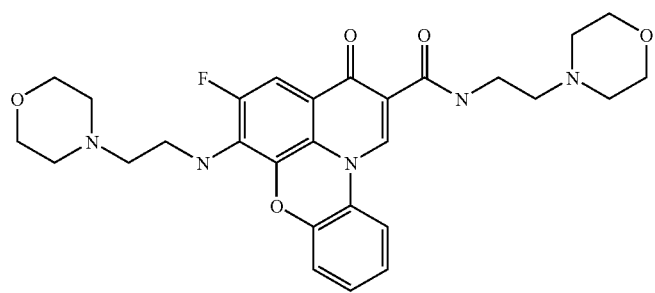

TABLE 3-continued
1388
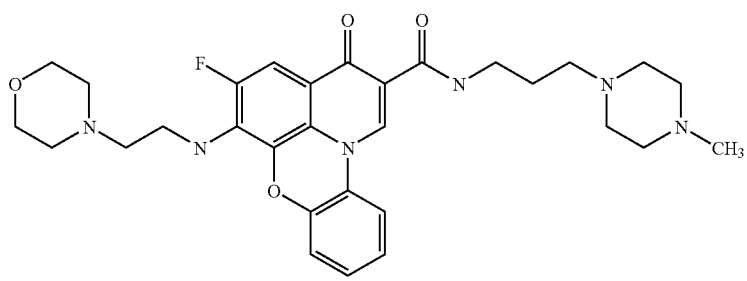
1389
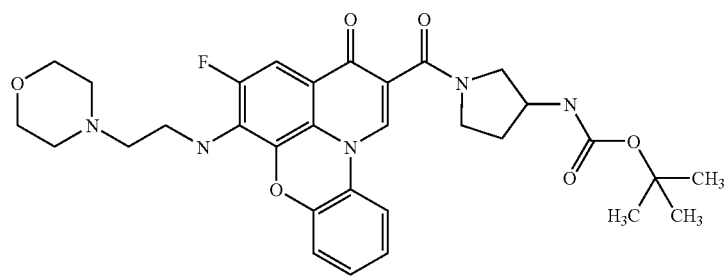
1390
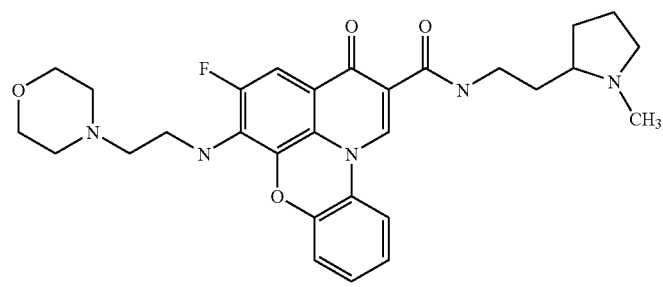
1391
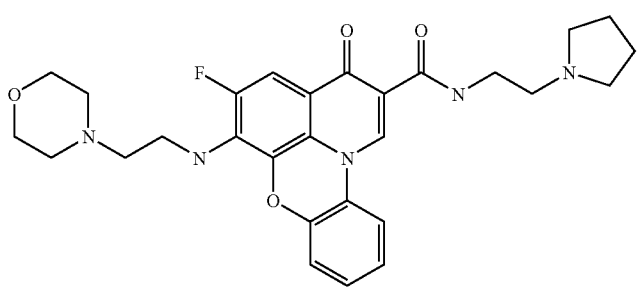
1392
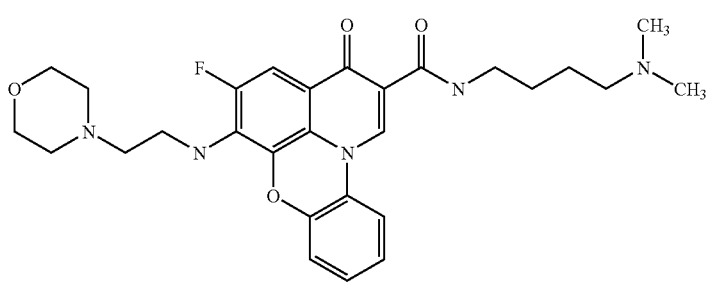

TABLE 3-continued
1393 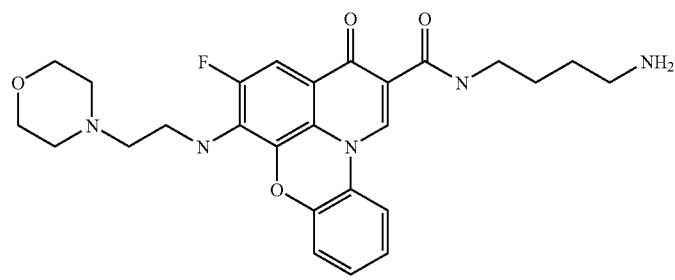
1394 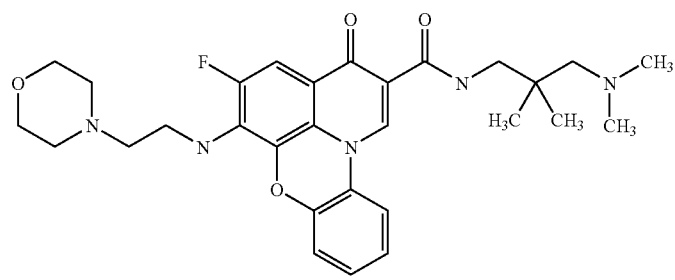
1395 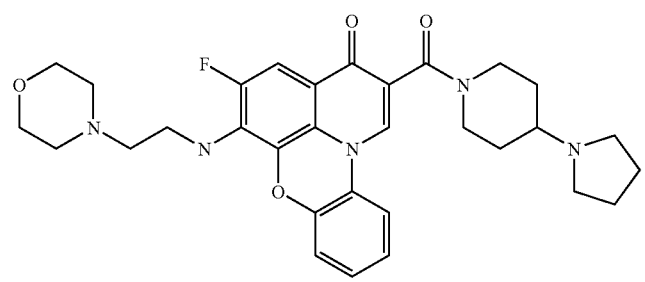
1396 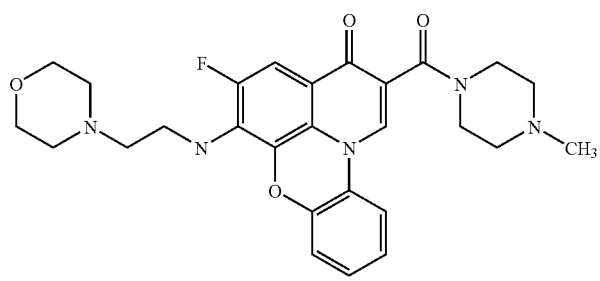
1397 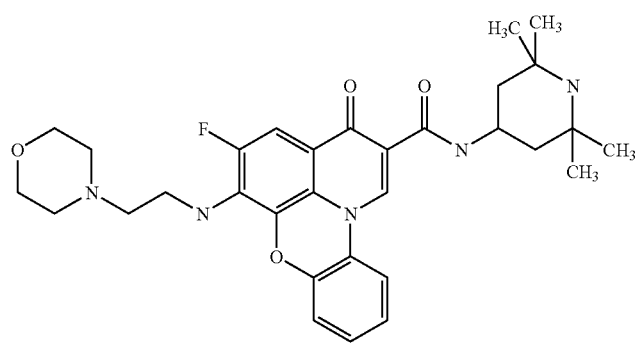

TABLE 3-continued
1398 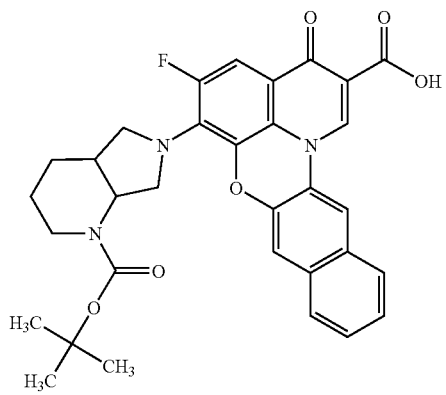
1399 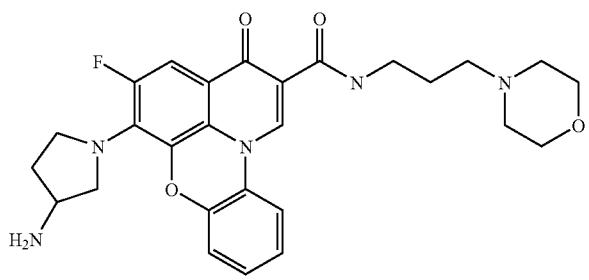
1400 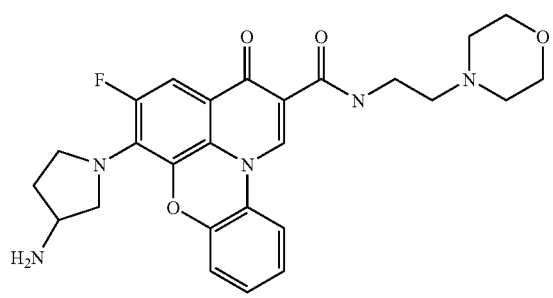
1401 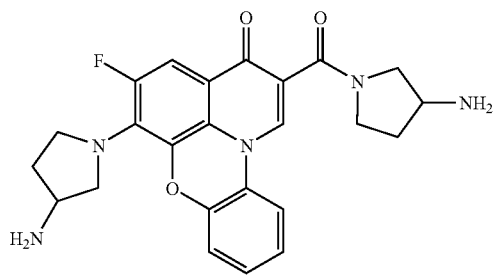
1402 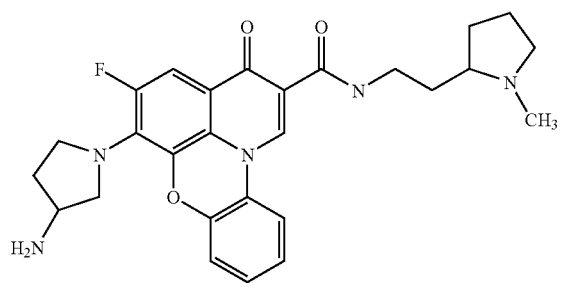

TABLE 3-continued
1403 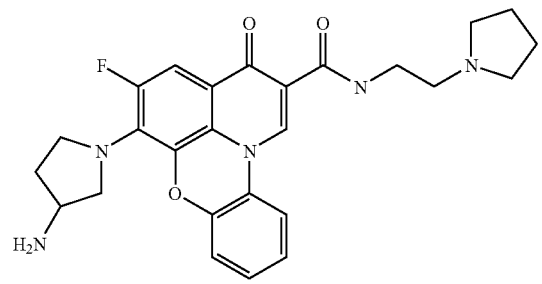
1404 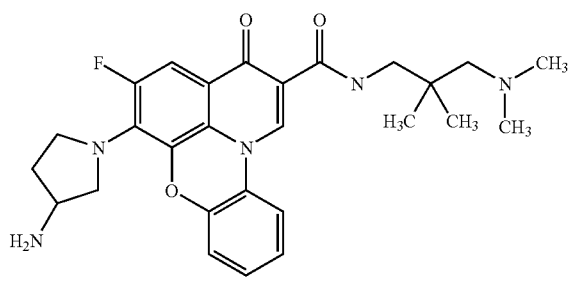
1405 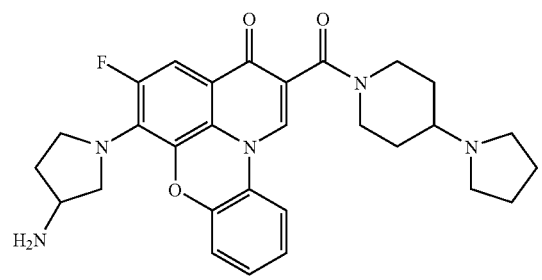
1406 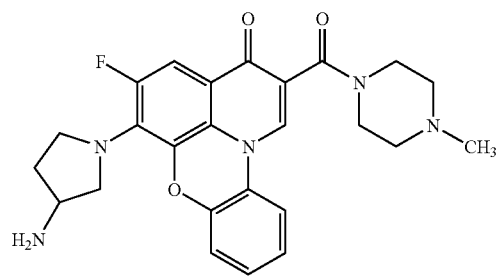
1407 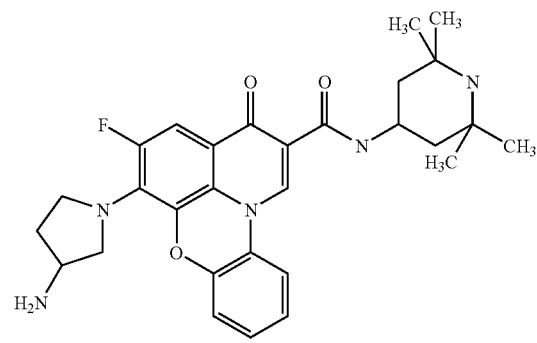

TABLE 3-continued
1408 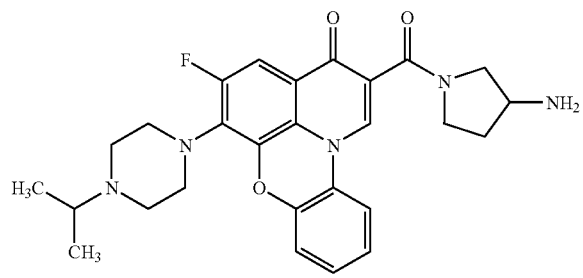
1409 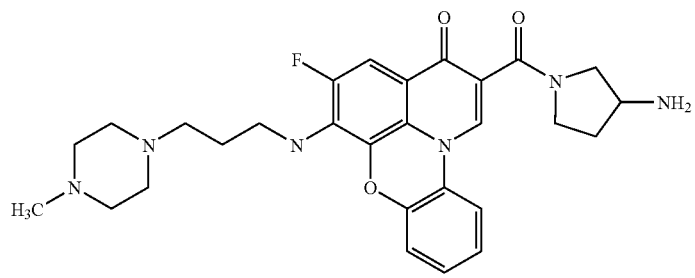
1410 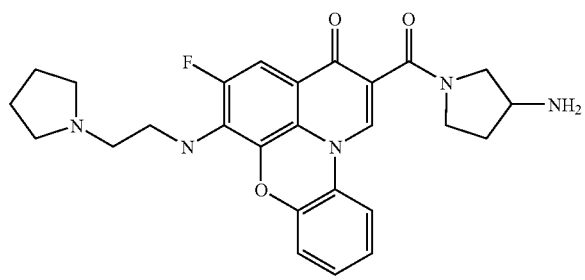
1411 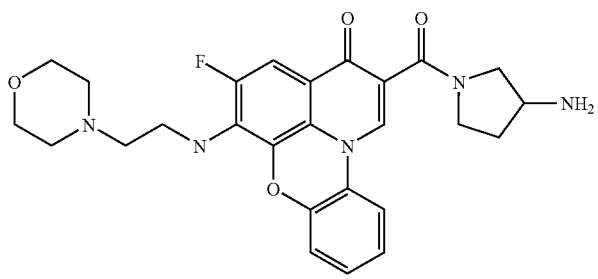
1412 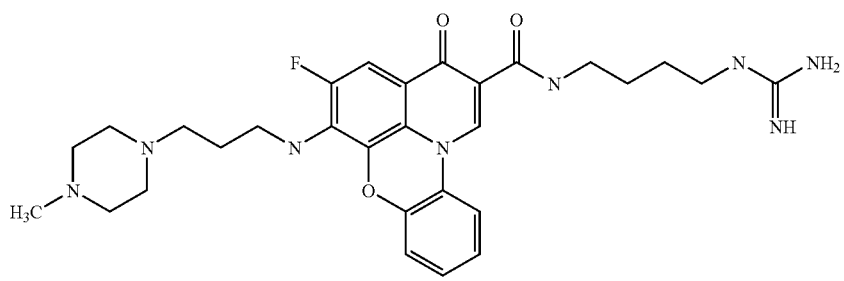

TABLE 3-continued
1413 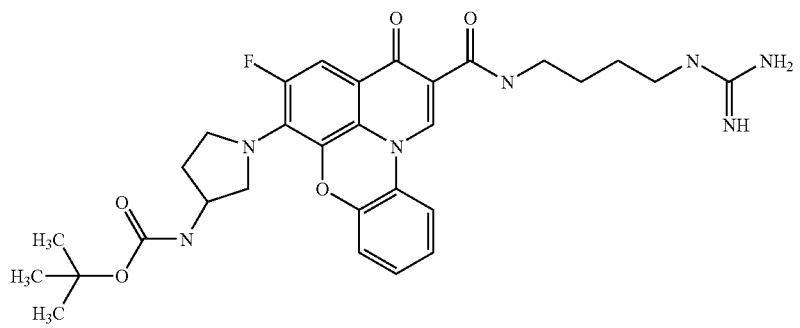
1414 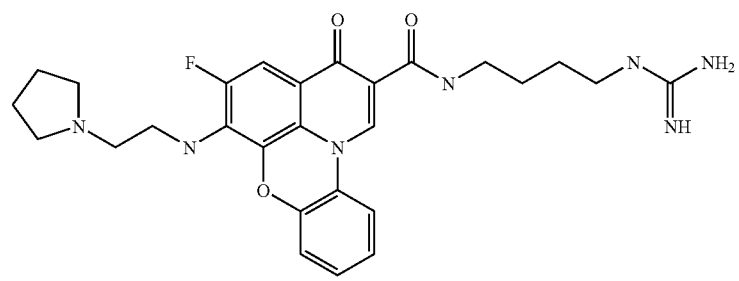
1415 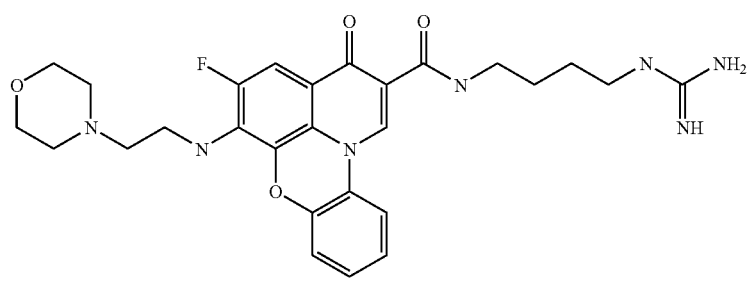
1416 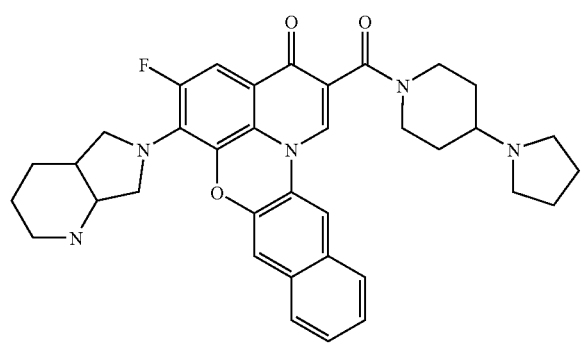
1417 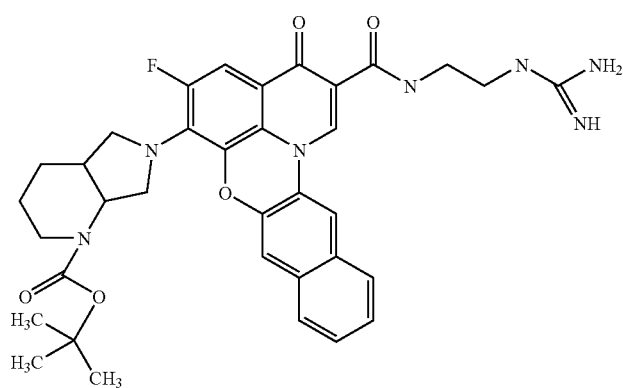

TABLE 3-continued
1418
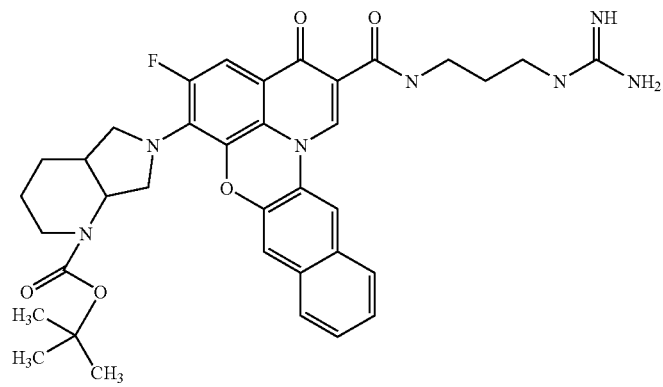
1419
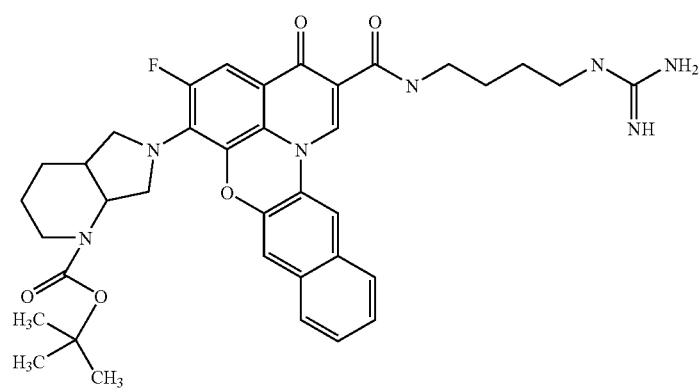
1420
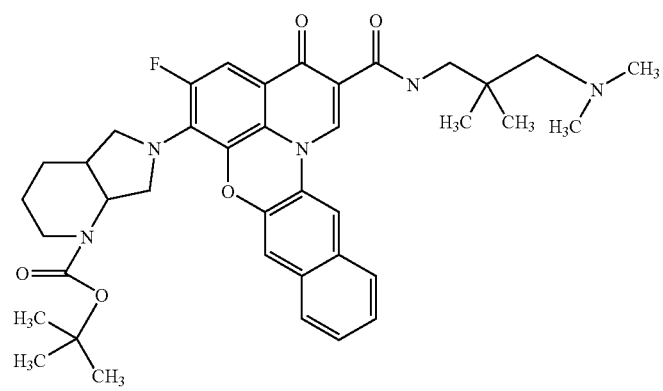
1421
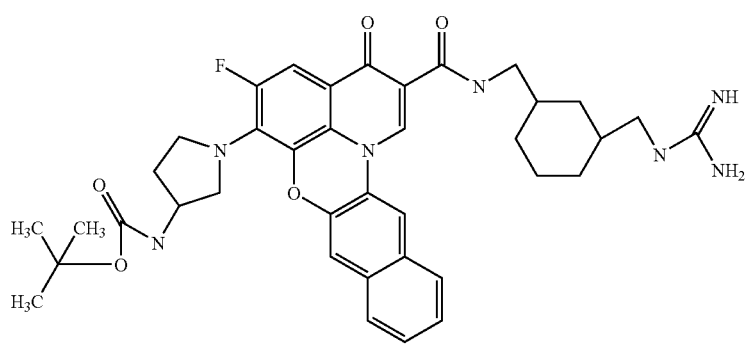

TABLE 3-continued
1422
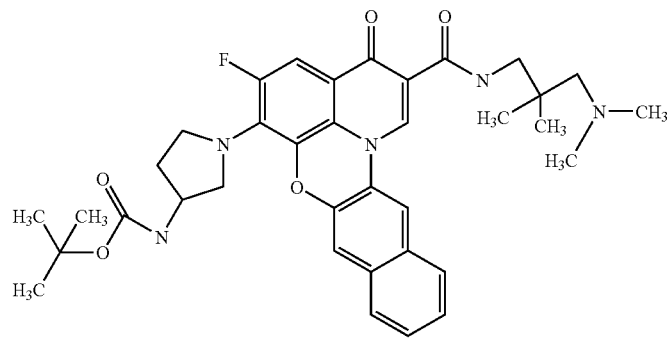
1423
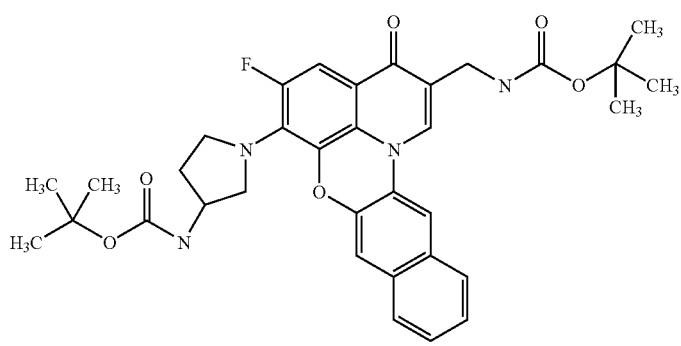
1424
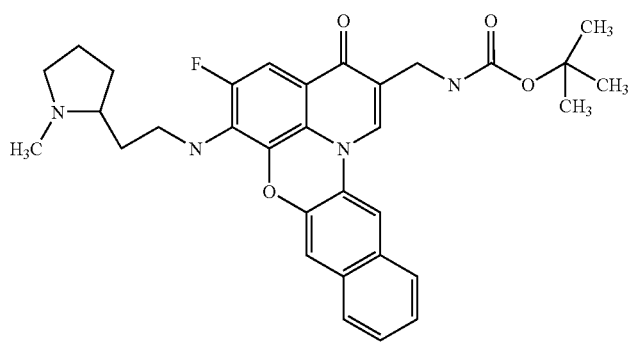
1425
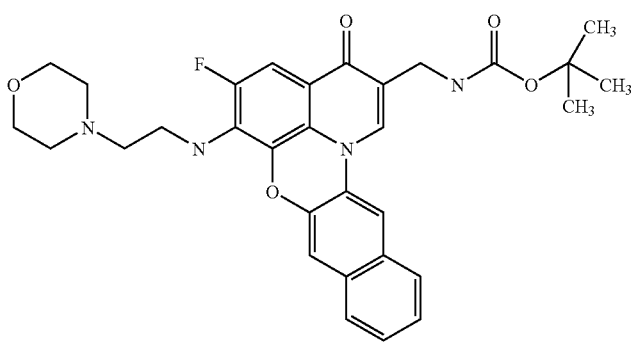

TABLE 3-continued
1426 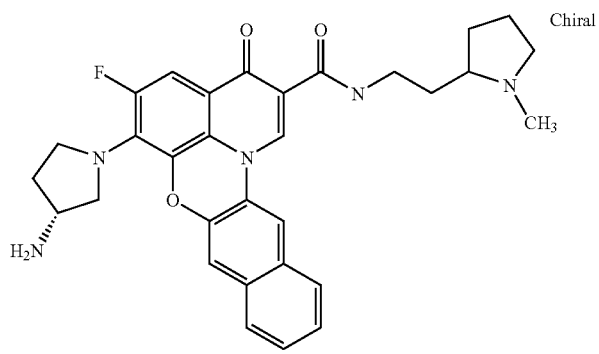
1427 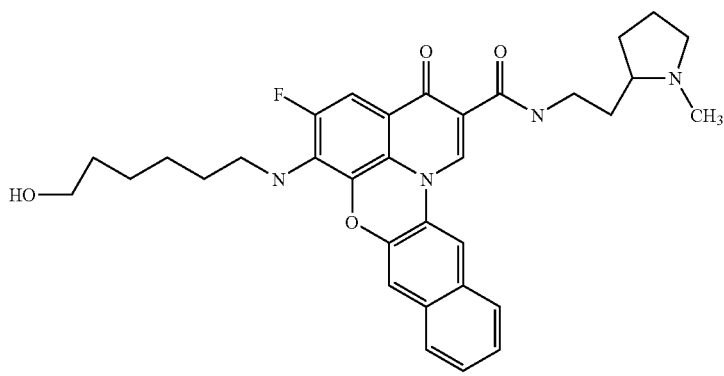
1428 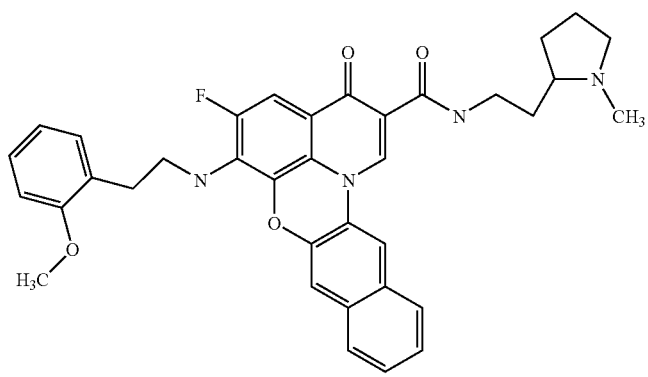
1429 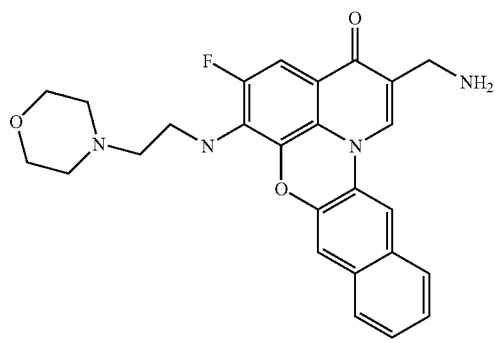

TABLE 3-continued
1430
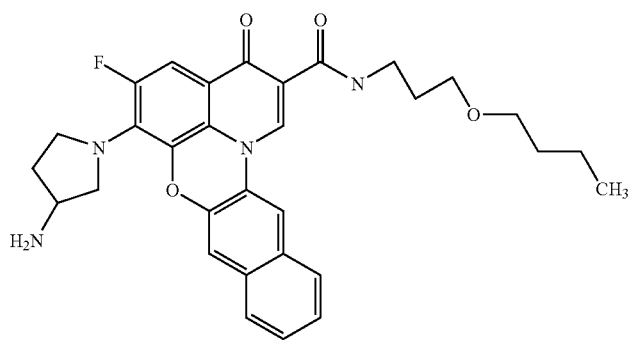
1431
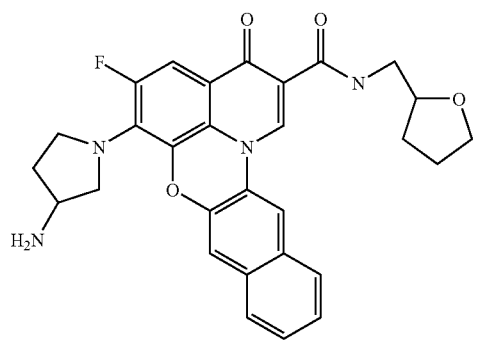
1432
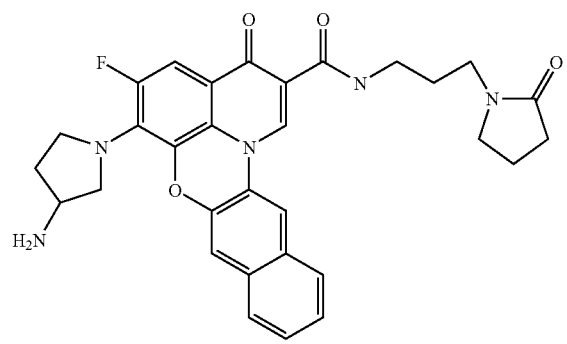
1433
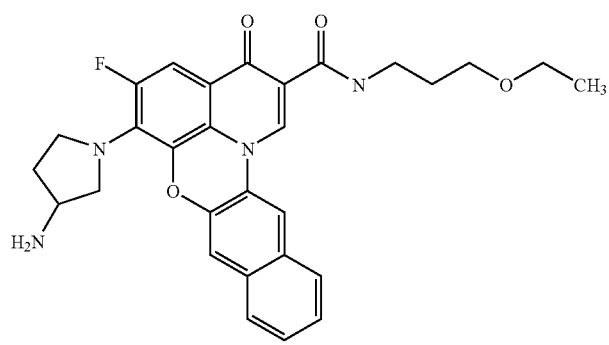

TABLE 3-continued
1434 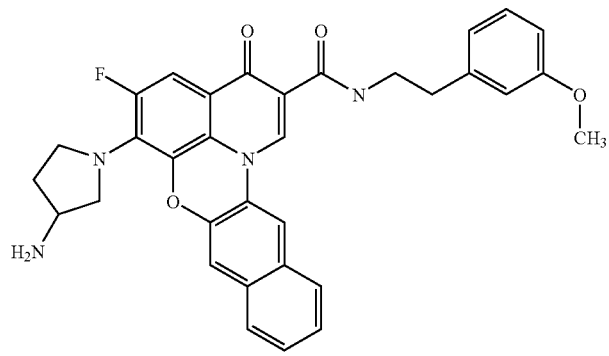
1435 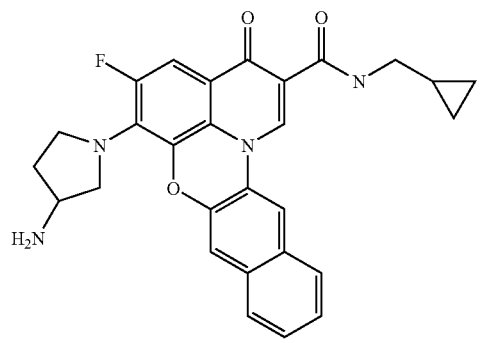
1436 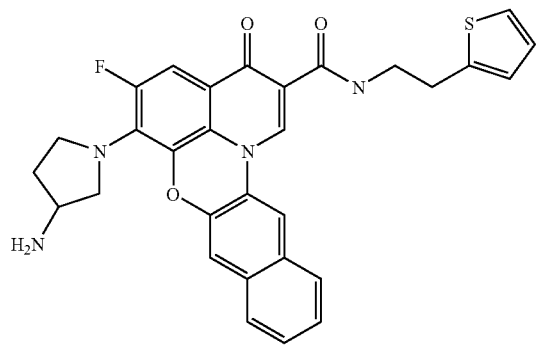
1437 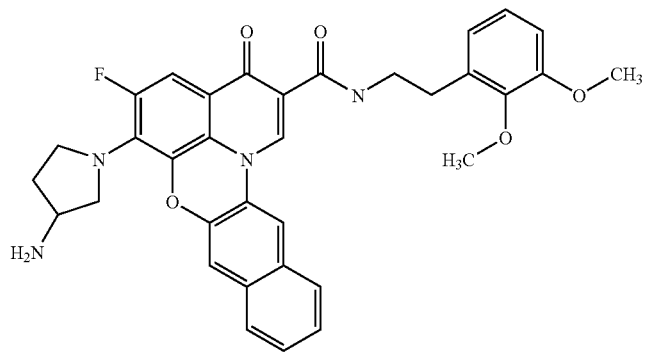

TABLE 3-continued
1438 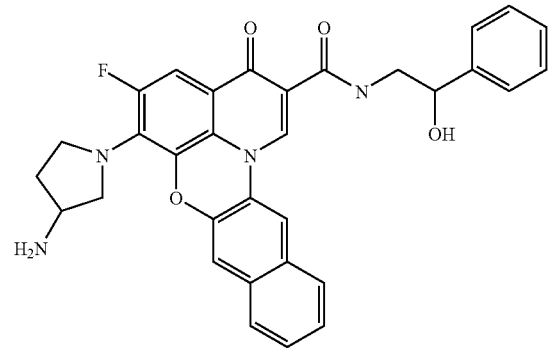
1439 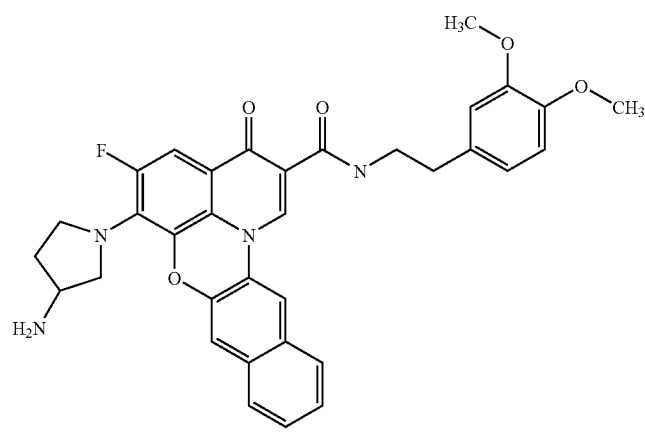
1440 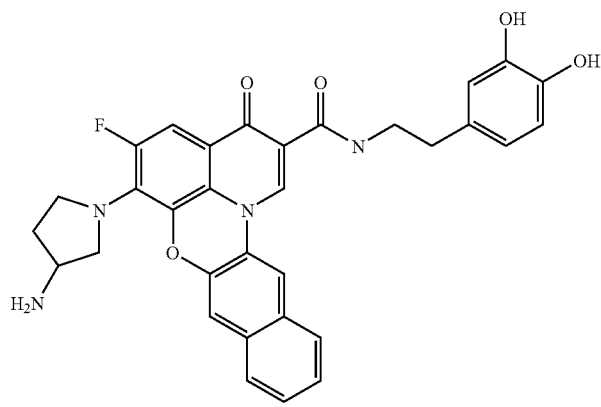
1441 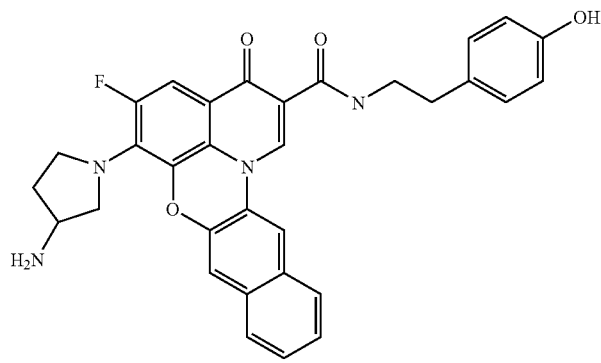

TABLE 3-continued
1442
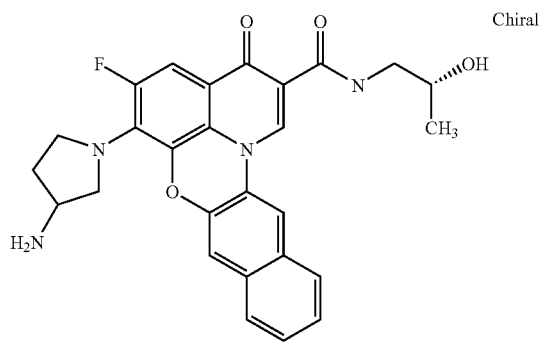
Chiral
1443
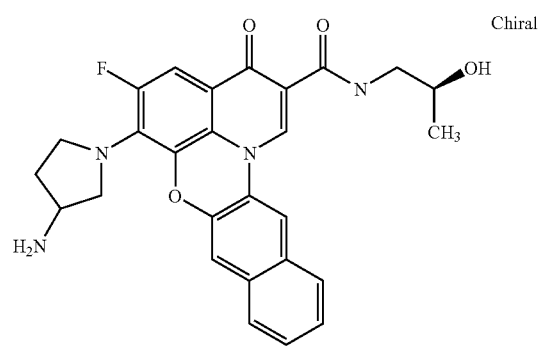
Chiral
1444
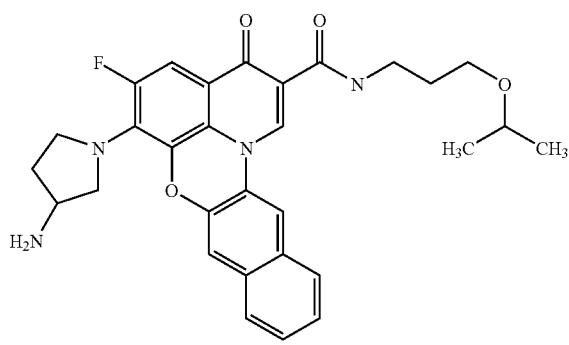
1445
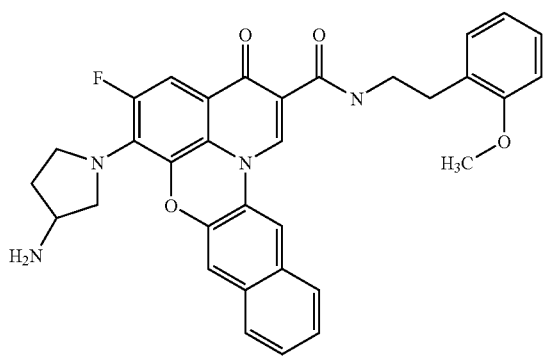

TABLE 3-continued
1446 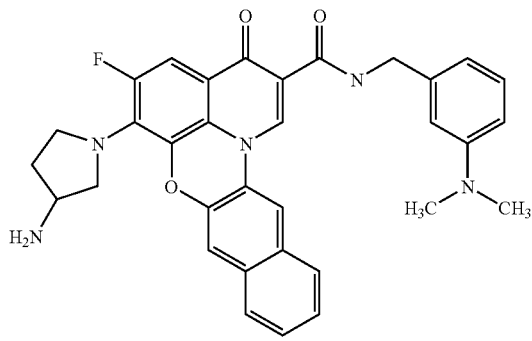
1447 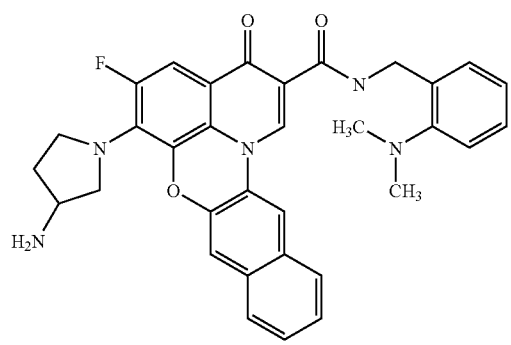
1448 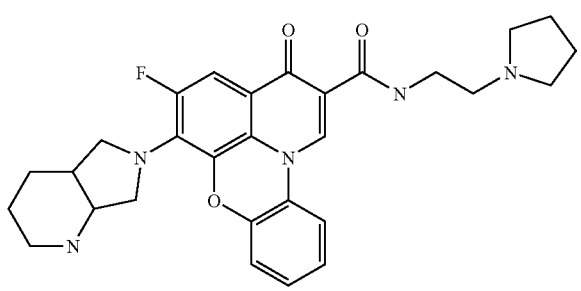
1449 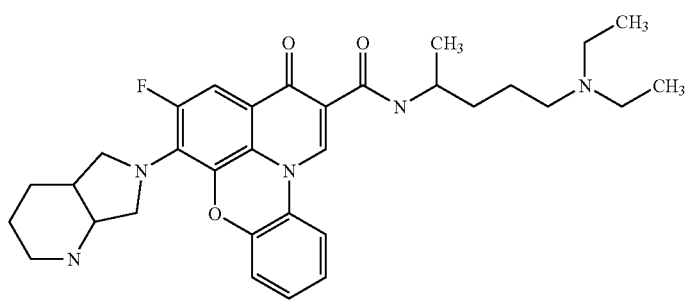
1450 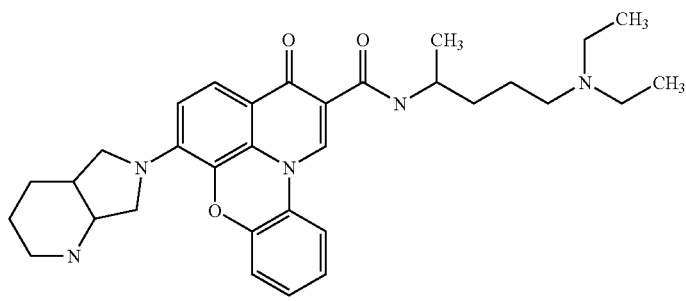

TABLE 3-continued
| 1451 | 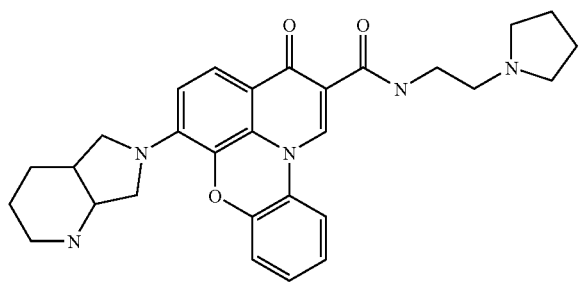 |
| --- | --- |
| 1452 | 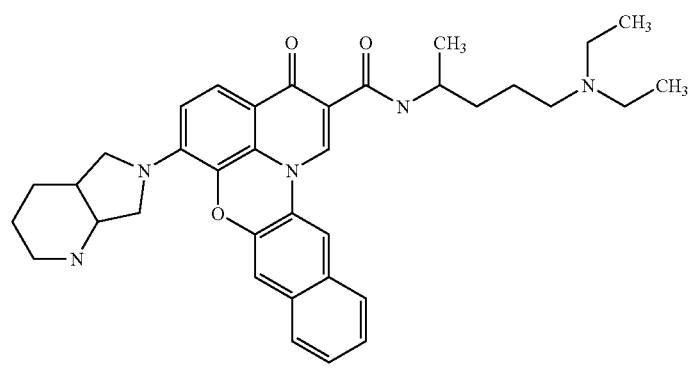 |
| 1453 | 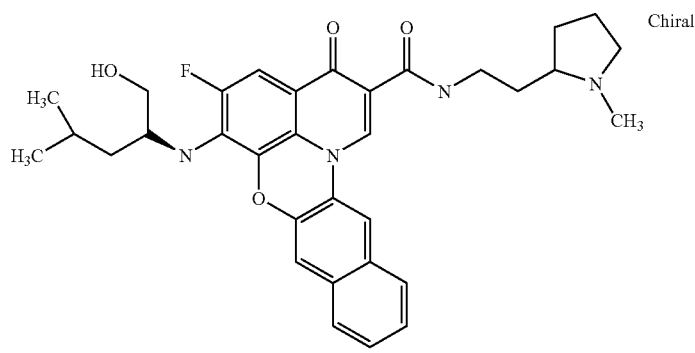 |
| 1454 | 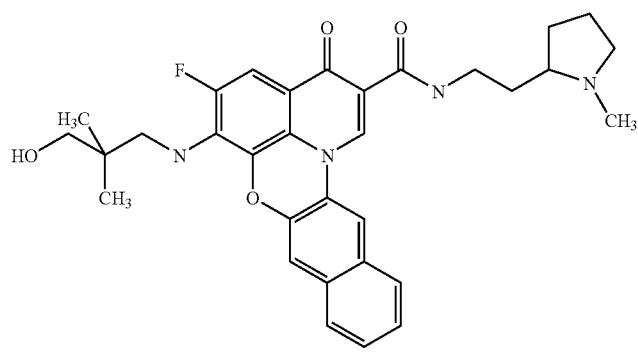 |

TABLE 3-continued
| 1455 | 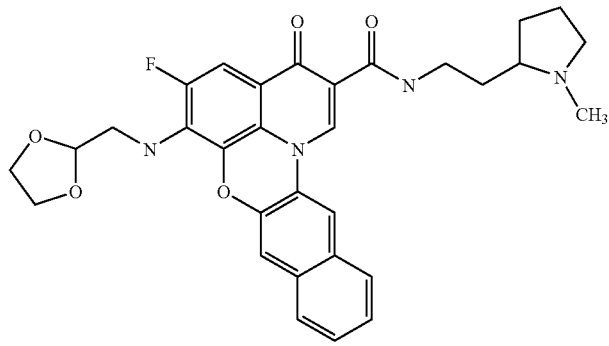 |
| --- | --- |
| 1456 | 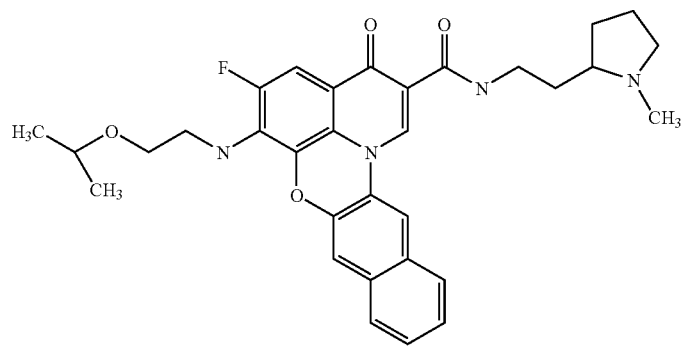 |
| 1457 | 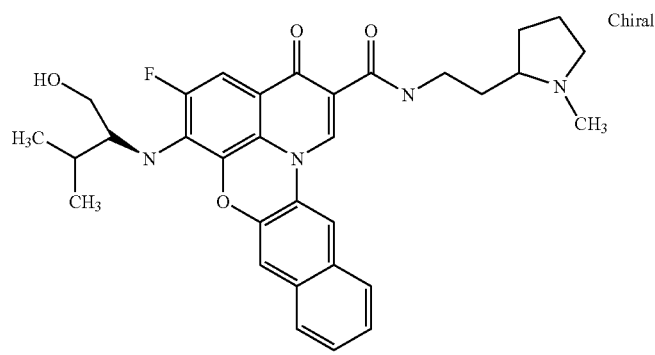 |
| 1458 | 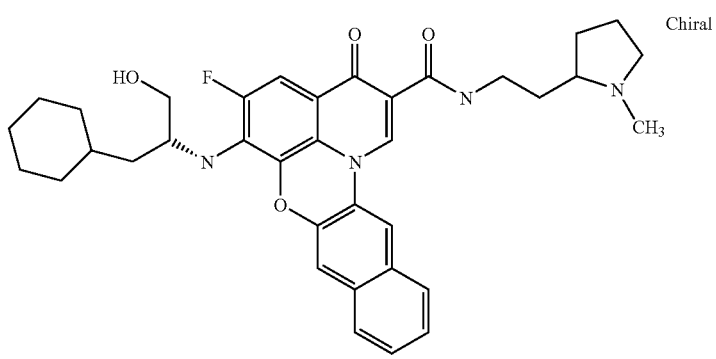 |

TABLE 3-continued
1459 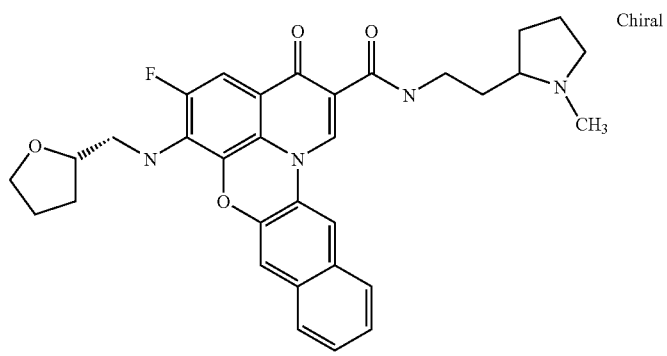 Chiral
1460 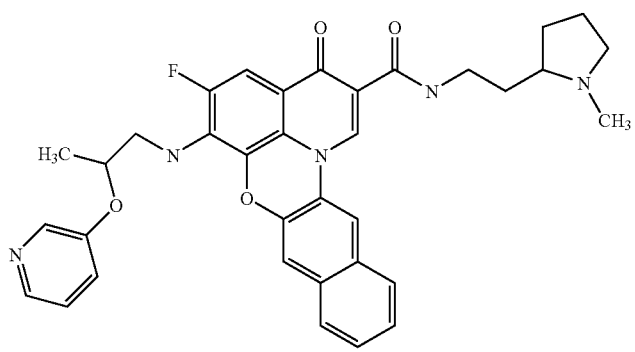
1461 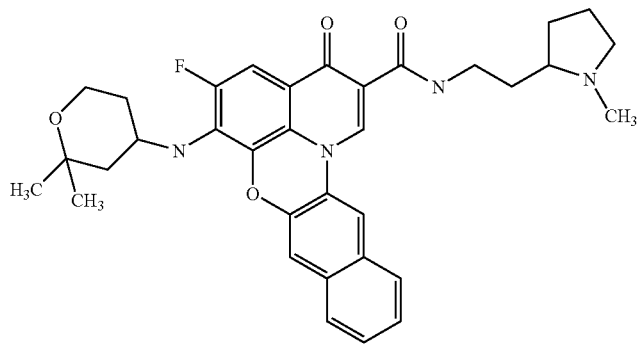
1462 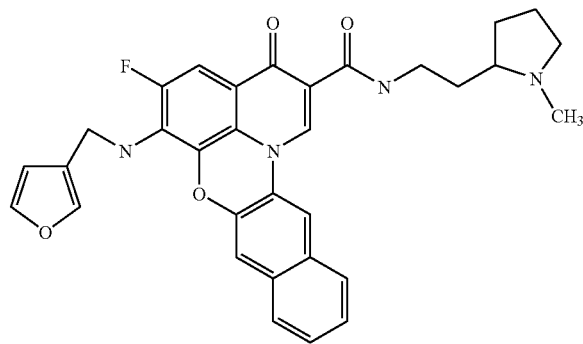

TABLE 3-continued
1463
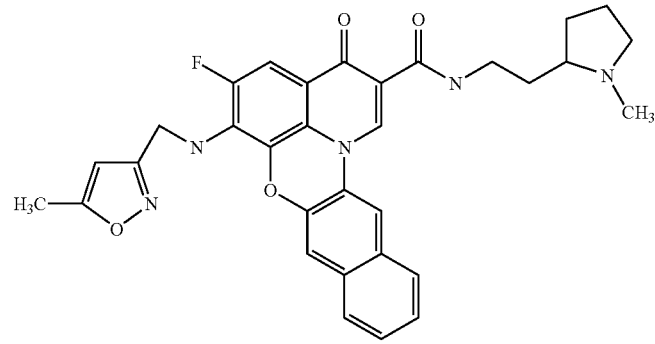
1464
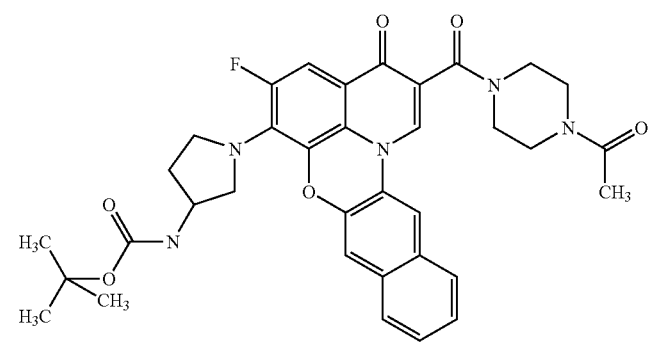
1465
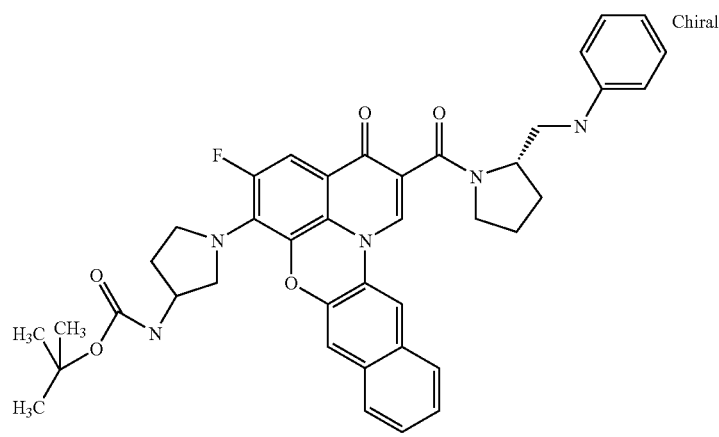
1466
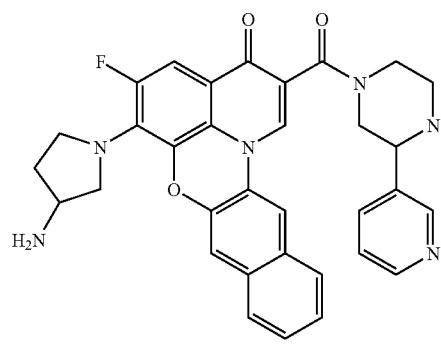

What is claimed is:

1. A method for treating or ameliorating a cell proliferative disorder, comprising administering to a subject in need thereof an effective amount of a compound of formula 1

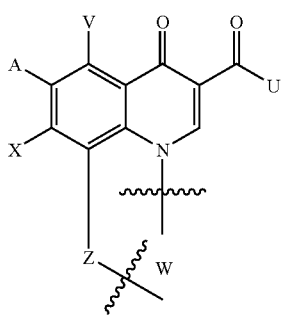

(1)

or a pharmaceutically acceptable salt or a pharmaceutical composition thereof, wherein:

V is H, halo, $NR^1R^2$, $NH_2$, or $NR^1$—$(CR^1{}_2)_n$—$NR^3R^4$;

A is H, fluoro, or $NR^1{}_2$;

Z is O;

U is selected from the group consisting of $NR^1$—$(CR^1{}_2)_n$—$NR^3R^4$ and $NR^1R$;

X is $OR^2$, $NR^1R^2$, halo, azido, or $SR^2$;

n is 1-6;

R is an optionally substituted 5-14 membered heterocyclic ring containing one or more N, O or S; or R is a $C_{1-10}$ alkyl or $C_{2-10}$ alkenyl optionally containing one or more non-adjacent heteroatoms selected from N, O, and S, and optionally substituted with an optionally substituted carbocyclic or heterocyclic ring;

$R^1$ and $R^3$ are independently H or an optionally substituted $C_{1-6}$ alkyl, said alkyl optionally containing one or more non-adjacent heteroatoms selected from N, O, and S;

$R^2$ and $R^4$ are independently H or a $C_{1-10}$ alkyl or $C_{2-10}$ alkenyl optionally containing one or more non-adjacent heteroatoms selected from N, O, and S, and optionally substituted with an optionally substituted carbocyclic or heterocyclic ring; and wherein said $C_{1-10}$ alkyl may be optionally substituted by one or more OH, $C_{1-6}$ alkoxy, amino, amido, halo, =O, aryl or heterocyclic groups;

or R² is an optionally substituted heterocyclic ring, aryl or heteroaryl;

wherein R¹ and R² together with N in NR¹R², and/or R³ and R⁴ together with N in NR³R⁴, and/or R¹ and R together with N in NR¹R may independently form an optionally substituted 5-6 membered ring containing N, and optionally O or S;

W is selected from the group consisting of

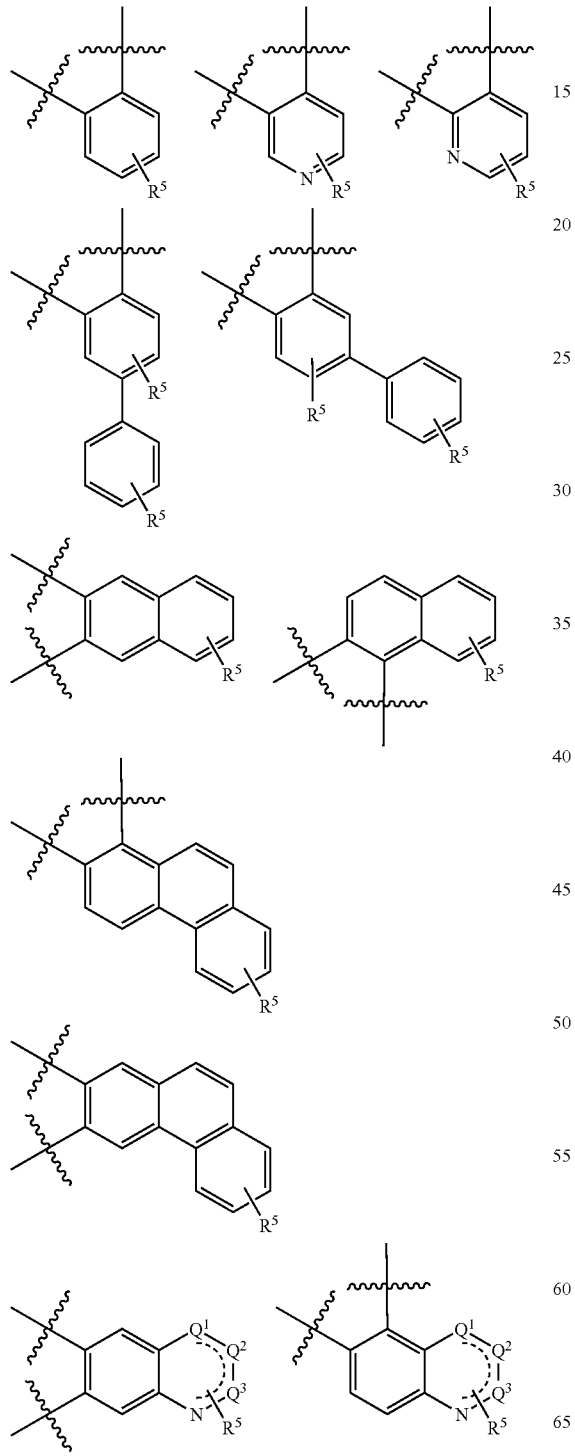

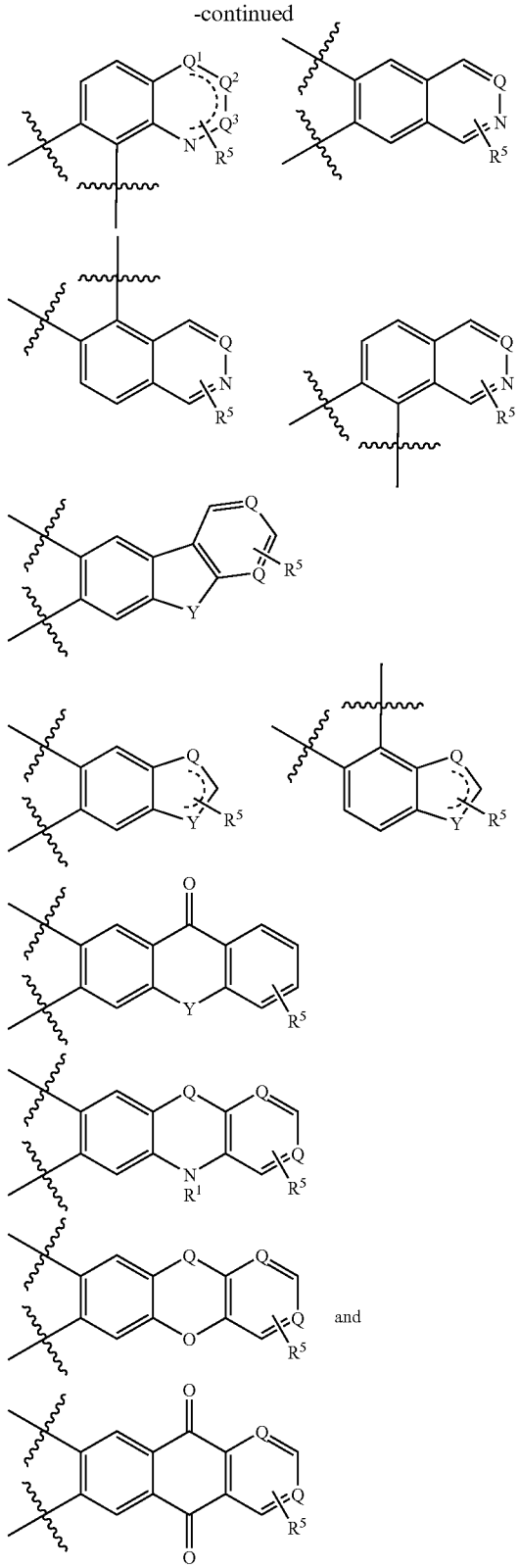

wherein Q, Q¹, Q², and Q³ are independently CH or N;
Y is independently O, CH, =O or NR¹;
and R⁵ is a substituent at any position on the fused ring;
and is H, OR², $C_{1-6}$ alkyl, or $C_{2-6}$ alkenyl, each optionally substituted by halo, =O or one or more heteroatoms; or R⁵ is an inorganic substituent; or two adjacent R⁵ are linked to obtain a 5-6 membered optionally substituted carbocyclic or heterocyclic ring, optionally fused to an additional optionally substituted carbocyclic or heterocyclic ring;

provided that U is not morpholinyl or 2,4-difluoroaniline when X is F or pyrrolidinyl; A is F; and W is phenylene;

wherein said cell proliferative disorder is a cancer selected from colorectal cancer, breast cancer, lung cancer, liver cancer, pancreatic cancer, prostate cancer, brain cancer, skin cancer, renal cancer, ovarian cancer, cervical cancer, leukemia, and lymphoma;

thereby treating or ameliorating said cell-proliferative disorder.

2. The method of claim 1, wherein said subject is human or an animal.

3. The method of claim 1, wherein V is H.

4. The method of claim 1, wherein A is fluoro.

5. The method of claim 1, wherein W is naphthalenyl.

6. The method of claim 1, wherein U is NR¹R and X is NR¹R².

7. The method of claim 6, wherein R¹ is H and R is a $C_{1-10}$ alkyl optionally containing one or more non-adjacent heteroatoms selected from N, O and S, and optionally substituted with a $C_{3-6}$ cycloalkyl, aryl or a 5-14 membered heterocyclic ring containing one or more N, O or S, each of which is optionally substituted.

8. The method of claim 7, wherein said 5-14 membered heterocyclic ring is selected from the group consisting of tetrahydrofuran, 1,3-dioxolane, 2,3-dihydrofuran, tetrahydropyran, benzofuran, isobenzofuran, 1,3-dihydro-isobenzofuran, isoxazole, 4,5-dihydroisoxazole, piperidine, pyrrolidine, pyrrolidin-2-one, pyrrole, pyridine, pyrimidine, octahydro-pyrrolo[3,4-b]pyridine, piperazine, pyrazine, morpholine, thiomorpholine, imidazole, imidazolidine-2,4-dione, benzimidazole, 1,3-dihydrobenzimidazol-2-one, indole, thiazole, benzothiazole, thiadiazole, thiophene, tetrahydro-thiophene 1,1-dioxide, diazepine, triazole, guanidine, diazabicyclo[2.2.1]heptane, 2,5-diazabicyclo[2.2.1]heptane, and 2,3,4,4a,9,9a-hexahydro-1H-β-carboline.

9. The method of claim 6, wherein R¹ and R² together with N in NR¹R² form an optionally substituted 5-14 membered ring containing one or more N, O or S.

10. The method of claim 9, where NR¹R² is morpholine, thiomorpholine, imidazole, pyrrolidine, piperazine, pyridine, piperidine or diazepine, each of which is optionally substituted.

11. The method of claim 1, wherein U is NR¹R, where R is a $C_{1-10}$ alkyl or $C_{2-10}$ alkenyl optionally containing one or more non-adjacent heteroatoms selected from N, O, and S, and optionally substituted with an optionally substituted carbocyclic or heterocyclic ring.

12. The method of claim 1, wherein X is NR¹R², wherein R¹ and R² together with N in NR¹R form an optionally substituted 5-6 membered ring containing one or more N, and optionally O or S.

13. The method of claim 12, wherein said optionally substituted 5-6 membered ring is selected from the group consisting of morpholine, thiomorpholine, imidazole, pyrrolidine, piperazine, pyridine and piperidine.

14. The method of claim 1, wherein W is optionally substituted naphthalenyl.

15. The method of claim 1, wherein X is NR¹R²; and U has the formula $$NR^1-(CR^1{}_2)_n-NR^3R^4 \qquad (2)$$

wherein R¹ and R² are as defined in claim 1;

R³ is H or $C_{1-6}$ alkyl;

n is 1-6; and

R⁴ is H or a $C_{1-10}$ alkyl or $C_{2-10}$ alkenyl optionally containing one or more non-adjacent heteroatoms selected from N, O and S, and optionally substituted with an optionally substituted carbocyclic or heterocyclic ring; and wherein R¹ and R² together with N in NR¹R²; and R³ and R⁴ together with N in NR³R⁴ each independently may form an optionally substituted 5-14 membered ring containing N, and optionally O or S.

16. The method of claim 1, wherein W is benzene, pyridine, biphenyl, naphthalene, phenanthrene, quinoline, isoquinoline, quinazoline, cinnoline, phthalazine, quinoxaline, indole, benzimidazole, benzoxazole, benzthiazole, benzofuran, anthrone, xanthone, acridone, fluorenone, carbazolyl, pyrimido[4,3-b]furan, pyrido[4,3-b]indole, pyrido[2,3-b]indole, dibenzofuran, acridine or acridizine, each of which may be optionally substituted.

17. The method of claim 1, wherein each optionally substituted moiety is substituted with one or more halo, OR², NR¹R², carbamate, $C_{1-10}$ alkyl, $C_{2-10}$ alkenyl, each optionally substituted by halo, =O, aryl or one or more heteroatoms; inorganic substituents, aryl, carbocyclic or a heterocyclic ring.

18. The method of claim 1, wherein V is NH₂ or NR¹—$(CR^1{}_2)_n$—NR³R⁴;

wherein R¹ and R³ are independently H or $C_{1-6}$ alkyl;

n is 1-6; and

R⁴ is H, $C_{1-6}$ alkyl optionally substituted with a carbocyclic or heterocyclic ring, or aryl; and wherein R³ and R⁴ in NR³R⁴ may form an optionally substituted ring.

19. The method of claim 1, wherein said compound is a compound having formula (1A)

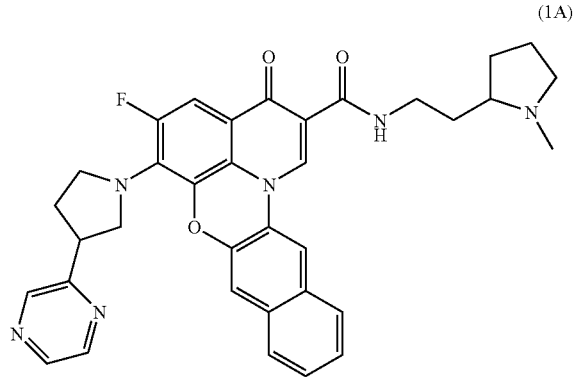

(1A)

or a pharmaceutically acceptable salt or pharmaceutical composition thereof, and optionally with a chemotherapeutic agent.

20. The method of claim 1, wherein said compound is a compound having formula

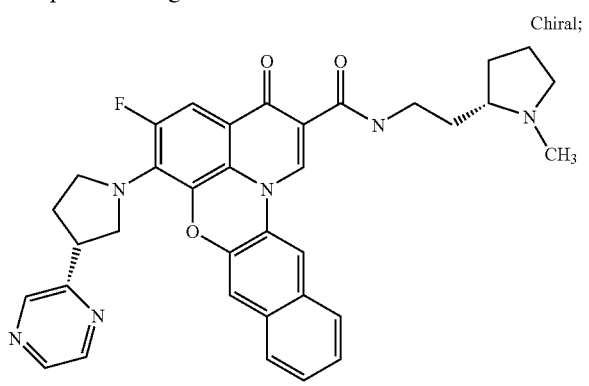

or a pharmaceutically acceptable salt or pharmaceutical composition thereof.

21. The method of claim 1, wherein said compound is a compound having formula

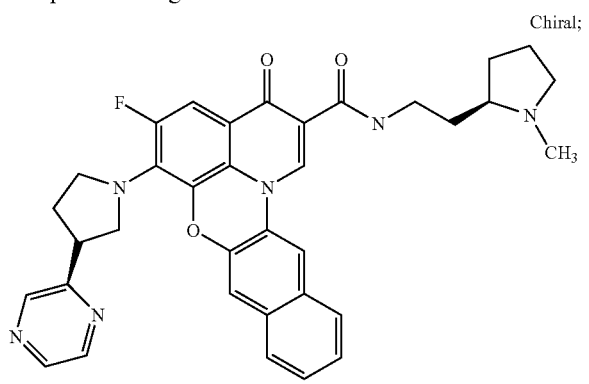

or a pharmaceutically acceptable salt or pharmaceutical composition thereof.

22. The method of claim 1, wherein said compound is a compound having formula

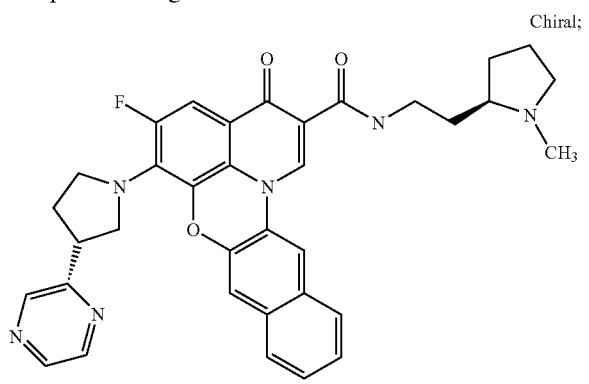

or a pharmaceutically acceptable salt or pharmaceutical composition thereof.

23. The method of claim 1, wherein said compound is a compound having formula

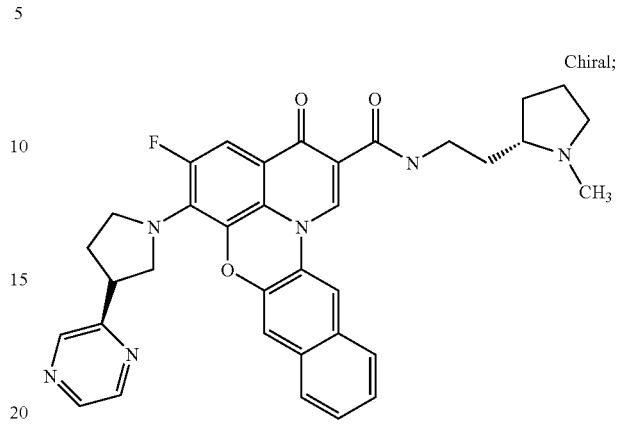

or a pharmaceutically acceptable salt or pharmaceutical composition thereof.

24. The method of claim 1, wherein said compound is a compound having formula (1A)

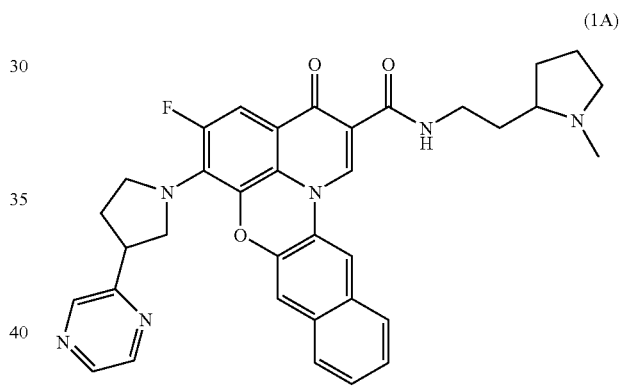

or a pharmaceutically acceptable salt or pharmaceutical composition thereof, which has a 50:50 ratio of RS and SS isomers.

25. The method of claim 1, wherein said cancer is prostate cancer.

26. The method of claim 1, wherein said cancer is colorectal cancer.

27. The method of claim 1, wherein said cancer is pancreatic cancer.

28. The method of claim 1, wherein said cancer is leukemia.

* * * * *